US008486967B2

(12) United States Patent
Baumann et al.

(10) Patent No.: US 8,486,967 B2

(45) Date of Patent: Jul. 16, 2013

(54) HETEROARYL SUBSTITUTED PIPERIDINES

(75) Inventors: Karlheinz Baumann, Efringen-Kirchen (DE); Alexander Flohr, Loerrach (DE); Erwin Goetschi, Reinach BL (CH); Luke Green, Basel (CH); Synese Jolidon, Blauen (CH); Henner Knust, Rheinfelden (DE); Anja Limberg, Basel (CH); Thomas Luebbers, Loerrach (DE); Andrew Thomas, Binningen (CH)

(73) Assignee: Hoffmann-La Roche Inc., Nutley, NJ (US)

(*) Notice: Subject to any disclaimer, the term of this patent is extended or adjusted under 35 U.S.C. 154(b) by 14 days.

(21) Appl. No.: 13/023,563

(22) Filed: Feb. 9, 2011

(65) Prior Publication Data

US 2011/0201605 A1 Aug. 18, 2011

(30) Foreign Application Priority Data

Feb. 17, 2010 (EP) .................................... 10153843

(51) Int. Cl.

| | |
|---|---|
| ***A01N 43/42*** | (2006.01) |
| ***A61K 31/44*** | (2006.01) |
| ***C07D 513/02*** | (2006.01) |
| ***C07D 515/02*** | (2006.01) |

(52) U.S. Cl.

USPC .......................................... 514/303; 546/119

(58) Field of Classification Search

None

See application file for complete search history.

(56) References Cited

U.S. PATENT DOCUMENTS

| | | | |
|---|---|---|---|
| 5,686,070 | A | 11/1997 | Doerschuk et al. |
| 6,399,773 | B1 | 6/2002 | Liu et al. |
| 2003/0176454 | A1 | 9/2003 | Yamada et al. |
| 2004/0034008 | A1 | 2/2004 | Stamford et al. |
| 2005/0176772 | A1 | 8/2005 | Calabrese et al. |
| 2006/0004013 | A1 | 1/2006 | Kimura et al. |
| 2006/0014958 | A1 | 1/2006 | Chen et al. |
| 2007/0117798 | A1 | 5/2007 | Kimura et al. |
| 2007/0117839 | A1 | 5/2007 | Kimura et al. |
| 2007/0219181 | A1 | 9/2007 | Kimura et al. |
| 2008/0280948 | A1 | 11/2008 | Baumann et al. |
| 2009/0023713 | A1 | 1/2009 | Aebi et al. |
| 2009/0163485 | A1 | 6/2009 | Knust et al. |
| 2009/0181965 | A1 | 7/2009 | Baumann et al. |
| 2009/0215759 | A1 | 8/2009 | Baumann et al. |

FOREIGN PATENT DOCUMENTS

| | | |
|---|---|---|
| EP | 0233461 | 8/1987 |
| EP | 1201661 | 5/2002 |
| EP | 1479397 | 11/2004 |
| EP | 1947098 | 7/2008 |
| EP | 1950211 | 7/2008 |
| EP | 2243785 | 10/2010 |
| WO | 1993/19050 | 9/1993 |
| WO | 94/04487 | 3/1994 |
| WO | 97/21704 | 6/1997 |
| WO | 99/65884 | 12/1999 |
| WO | 00/25780 | 5/2000 |
| WO | 00/027842 | 5/2000 |
| WO | 00/78731 | 12/2000 |
| WO | 01/47897 | 7/2001 |
| WO | 01/87845 | 11/2001 |
| WO | 02/057240 | 7/2002 |
| WO | 03/002561 | 1/2003 |
| WO | 03/040141 A1 | 5/2003 |
| WO | 2003/044014 | 5/2003 |
| WO | 03/047512 | 6/2003 |
| WO | 03/053939 | 7/2003 |
| WO | 2004/046118 | 6/2004 |
| WO | 2004/069185 | 8/2004 |
| WO | 2004/087699 | 10/2004 |
| WO | 2004/110350 | 12/2004 |
| WO | 2005/003103 | 1/2005 |
| WO | 2005/013996 | 2/2005 |
| WO | 2005/040120 | 5/2005 |
| WO | 2005/044785 | 5/2005 |
| WO | 2005/063022 | 7/2005 |
| WO | 2005/115990 | 12/2005 |
| WO | 2006/040192 | 4/2006 |
| WO | 2006/058905 | 6/2006 |
| WO | 2006/111549 | 10/2006 |
| WO | 2006/112550 | 10/2006 |
| WO | 2006/112551 | 10/2006 |
| WO | 2006/113704 | 10/2006 |
| WO | 2007/013673 | 2/2007 |
| WO | 2007/051333 | 5/2007 |

(Continued)

OTHER PUBLICATIONS

Wilkins et al., Science of Synthesis 13:277-295 ( 2004).

(Continued)

*Primary Examiner* — Jeffrey Murray

(57) ABSTRACT

The invention relates to compounds of formula

I

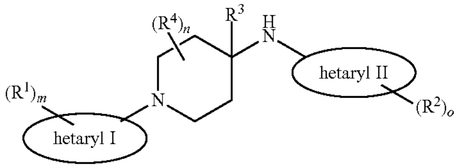

where hetaryl I, hetaryl II,
$R^1$,
$R^2$,
$R^3$, $R^4$, m, n, and o are as defined in the specification
or to pharmaceutically active acid addition salts thereof. The compounds of formula I are modulators for amyloid beta and thus may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

8 Claims, No Drawings

FOREIGN PATENT DOCUMENTS

| | | |
|---|---|---|
| WO | 2007/053452 | 5/2007 |
| WO | 2007/054480 | 5/2007 |
| WO | 2007/058304 | 5/2007 |
| WO | 2007/058305 | 5/2007 |
| WO | 2007/060810 | 5/2007 |
| WO | 2007/060821 | 5/2007 |
| WO | 2007/076161 | 5/2007 |
| WO | 2007/102580 | 9/2007 |
| WO | 2007/120333 | 10/2007 |
| WO | 2007/125405 | 11/2007 |
| WO | 2007/131953 | 11/2007 |
| WO | 2007/135969 | 11/2007 |
| WO | 2007/135970 | 11/2007 |
| WO | 2007/139149 | 12/2007 |
| WO | 2008/006103 | 1/2008 |
| WO | 2008/013213 | 1/2008 |
| WO | 2008/065626 | 6/2008 |
| WO | 2008/097538 | 8/2008 |
| WO | 2008/099210 | 8/2008 |
| WO | 2008/107096 | 9/2008 |
| WO | 2008/138753 | 11/2008 |
| WO | 2008/156580 | 12/2008 |
| WO | 2019093 | 1/2009 |
| WO | 2009/032277 | 2/2009 |
| WO | 2010/027500 | 2/2009 |
| WO | 2009/032861 | 3/2009 |
| WO | 2009/064388 | 5/2009 |
| WO | 2009/076337 | 6/2009 |
| WO | 2008/100412 | 8/2009 |
| WO | 2009/103652 | 8/2009 |
| WO | 2009/155551 | 12/2009 |
| WO | 2010/010184 | 1/2010 |
| WO | 2010/010188 | 1/2010 |
| WO | 2010/098487 | 9/2010 |
| WO | 2010/0119881 | 10/2010 |

OTHER PUBLICATIONS

Delecea et al., Proc. Natl. Acad. Sci. USA 95:322-327 ( 1998).
Sakamoto et al., Regul. Pept. 118:183-191 ( 2004).
Kumita et al., Nippon Noyaku Gakkaishi 26(1):60-66 ( 2001).
Dhar et al., Bioorganic & Medicinal Chemistry Letters (XP002522864), 12(12):3125-3128 ( 2002).
Suzuki et al., Brain Research 1044:116-121 ( 2005).
Yang et al., Org. Chem. vol. 67(21):7429-7431 ( 2002).
(Office Action in copending U.S. Appl. No. 12/114,852 Jun. 28, 2010).
Kidwai et al., Chemical Papers:231-234 ( 2000).
Cai et al., Expert Opin. Ther. Patents 16(5):631-646 ( 2006).
Albaneze-Walker et al., Tetrahedron 61:6330-6336 ( 2005).
Piper et al., Eur. J. Neuroscience 12:726-730 ( 2000).
Winsky Sommerer et al., J. Neuroscience 24:11439-11448 ( 2004).
Menicagli et al., Synth. Commun. 24:2153-2158 ( 1994).
Ida et al., Biochem. Biophys. Res. Comm. 270:318-323 ( 2000).
Sakurai et al., Cell 92:573-585 ( 1998).
Patrick, Graham An Introduction to Medicinal Chemistry "10.3. 9"Oxford, vol. 3rd edition:210-212.
Cooke et al., Tetrahedron 57:2787-2789 ( 2001).
Kuru et al., Neuroreport 11:1977-1980 ( 2000).
(EPO Communication in EP Appl. 09713519.8 Dec. 30, 2011).
Ringold et al., Am. Chem. Soc. 78:2477-2479 ( 1956).
Schulte et al., Synlett:2331-2336 ( 2007).
Reinke, A. et al., Chem. Biol. Drug Des. 70:206-215 ( 2007).
(International Search Report PCT/EP 2008/055290 Oct. 8, 2008).
Siegel, Annu. Rev. Psychol. 55:125-148 ( 2004).
(Translation of Israeli Off Act in Corres Israeli App 206945 dated Feb. 29, 2012).
Iwanowicz et al., Bioorg. Med. Chem. Lett. 13:2059-2063 ( 2003).
Grundmann et al., Am. Chem. Soc. 79:944-948 ( 1957).
Tilley et al., Helv. Chim. Acta 63:832-840 ( 1980).
Pitts et al., Bioorganic & Medicinal Chemistry Letters 12(16):2137-2140 ( 2002).
Chang et al., Neurosci. Res. 56:356-362 ( 2006).
Nishino et al., Lancet 355:39-40 ( 2000).
(International Search Report PCT/EP2009/064497 Apr. 8, 2010).
(International Search Report for PCT/EP2008/067273 May 15, 2009).
Paul et al., Jour. of Medicinal Chemistry (XP002522865), 36(19):2716-2725 ( 1999).
Caubere et al., Bull. Soc. Chim. Fr.:2112-2115 ( 1973).
Chemelli et al., Cell 98:437-451 ( 1999).
Malherbe et al., Mol. Pharmacol. 64:823-832 ( 2003).
McPhee et al., Med. Chem. Soc. 66:1132-1136 ( 1944).
Bingham et al., Current Opinion in Drug Discovery & Development 9(5):551-559 ( 2006).
Olson, R. et al., Current Topics in Medicinal Chemistry 8:17-33 ( 2008).
Lin et al., Cell 98:365-376 ( 1999).
(International Search Report for PCT/EP2009/062570 Dec. 4, 2009).
Dorwald F. A. Side Reactions in Organic Systhesis "1 & Preface"Wiley,:1-16 ( 2005).
Peyron et al., Nature Medicine 6:991-997 ( 2000).
Bourgin et al., J. Neurosci. 20(20):7760-7765 ( 2000).
(Office Action in copending U.S. Appl. No. 12/334,559 Sep. 30, 2009).
(International Search Report for PCT/EP2009/051613 Apr. 22, 2004).
Hirt et al., Helv. 33:1365-1369 ( 1950).
Kubinyi 3D QSAR in Drug Design: Ligand Protein Interactions & Molecular SimilaritySpringer, vol. 2-3:243-244 ( 1998).
Mignot et al., Sleep 11:1012-1020 ( 1997).
Sakurai, Regulatory Peptides 126:3-10 ( 2005).
(Office Action in copending U.S. Appl. No. 12/334,559 May 20, 2010).
Peyron et al., Neurosci. 18:9996-10015 ( 1998).
Nambu et al., Brain Res. 18:243-260 ( 1999).
Bessard et al., Tetrahedron 55:405-412 ( 1999).
Smith et al., Neurosci. Lett. 341(3):256-258 ( 2003).
Schaeffer et al., Am. Chem. Soc. 73:2990-2992 ( 1951).
Digby et al., J. Endocrinol. 191:129-136 ( 2006).
Wu et al., Tet. Lett. 49:2869-2871 ( 2008).
Nettekoven et al., Synthesis 11:1649-1652 ( 2003).
Maiti et al., JOC Note 75:1791-1794 ( 2010).
Nilsson et al., J. Med. Chem. 46:3985-4001 ( 2003).
Jantzen et al., Neuroscience 22:226-254 ( 2002).
Takahashi et al., Biol. Chem. 278:18644-18670 ( 2003).
Perretto et al., Med. Chem. 48:5705-5720 ( 2005).
Clarke et al., Biol. Chem. 281:31279-31289 ( 2006).
Narlawar et al., Med. Chem. 49:7588-7591 ( 2006).
Beher et al., Biol. Chem. 279:43419-43426 ( 2004).
Morihara et al., Neurochem. 83:1009-1012 ( 2002).
Kukar et al., Nature Med. 11:545-550 ( 2005).
Lleo et al., Nature Med. 10:1065-1066 ( 2004).
Weggen et al., Nature 414:212-216 ( 2001).
Stock et al., Bioorg. Med. Chem. Lett. 16:2219-2223 ( 2006).
CAS Registry Database, RN 1157514-34-5, 1157480-39-1, 1157167-60-6, 1157158-89-8, 1157149-17-1, (XP000002657208) Jun. 14, 2009.
CAS Registry Database, RN 1152960-43-4, (XP000002657204) Jun. 7, 2009.
CAS Registry Database, RN 27891-70-1, (XP000002657200) Jul. 20, 2000.
CAS Registry Database, 2010:1317052, RN 1251940-78-9 (XP002630973).
CAS Registry Database, RN 1158058-30-0, 1158029-75-4, 1157826-03-3, 1157745-38-4, (XP000002657209) Jun. 15, 2009.
CAS Registry Database, RN 1186620-93-8, (XP000002657212) Sep. 30, 2009.
CAS Registry Database, RN 1179662-24-8, (XP000002657211) Sep. 3, 2009.
(International Search Report for PCT/EP2011/052101 Sep 1,2011).
Van Viel et al., Journal of Med. Chem. 42:2987-2104 (1999).
CAS Registry Database, RN 1134777-36-8, (XP000002657203) Apr. 15, 2009.
CAS Registry Database, RN 1179176-65-8, (XP000002657210) Sep. 2, 2009.
CAS Registry Database, RN 1154176-44-9, 1154720-00-9, (XP000002657206) Jun. 9, 2009.

CAS Registry Database, RN 1155577-98-2, (XP000002657207) Jun. 11, 2009.
CAS Registry Database, RN 1153747-25-1, (XP000002657205) Jun. 8, 2009.
CAS Registry Database, RN 1097071-40-3, 1096954-43-6, (XP000002657202) Jan. 28, 2009.
CAS Registry Database, RN 909673-09-2, 909673-06-09, 909656-26-4, 909646-91-9, 909646-89-5, (XP000002657201) Oct. 5, 2006.

HETEROARYL SUBSTITUTED PIPERIDINES

PRIORITY TO RELATED APPLICATION(S)

This application claims the benefit of European Patent Application No. 10153843.7, filed Feb. 17, 2010, which is hereby incorporated by reference in its entirety.

BACKGROUND OF THE INVENTION

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be nicastrin and the products of the aph1 and pen-2 genes. Proven substrates for γ-secretase are the APP and the proteins of the Notch receptor family, however, γ-secretase has loose substrate specificity and may cleave further membrane proteins unrelated to APP and Notch.

The γ-secretase activity is absolutely required for the production of Aβ peptides. This has been shown both by genetic means, i.e., ablation of the presenilin genes and by low-molecular-weight inhibitory compounds. Since according to the amyloid hypothesis for AD the production and deposition of Aβ is the ultimate cause for the disease, it is thought that selective and potent inhibitors of γ-secretase will be useful for the prevention and treatment of AD.

An alternative mode of treatment is the modulation of the γ-secretase activity which results in a selective reduction of the Aβ42 production. This will result in an increase of shorter Aβ isoforms, such as Aβ38, Aβ37 or others, which have reduced capability for aggregation and plaque formation, and are less neurotoxic. Compounds which show this effect on modulating γ-secretase activity include certain non-steroidal anti-inflammatory drugs (NSAIDs) and related analogues (Weggen et al. Nature, 414 (2001) 212-16).

Numerous documents describe the current knowledge on γ-secretase modulation, for example the following publications:

Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91

SUMMARY OF THE INVENTION

The invention provides compounds of formula

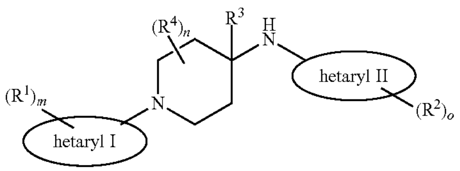

I hetaryl I is a five or six membered heteroaryl group, containing 1 to 3 heteroatoms, selected from O, S and N;

hetaryl II is a five or six membered heteroaryl group, containing 1 to 3 heteroatoms, selected from O, S and N, or is a two membered ring system containing 1 to 4 heteroatoms selected from S, O and N, wherein at least one ring is aromatic in nature;

$R^1$ is lower alkyl, lower alkoxy, lower alkyl substituted by halogen, or halogen;

$R^2$ is halogen, lower alkyl, lower alkoxy, hydroxy, lower alkyl substituted by halogen, lower alkyl substituted by hydroxy or benzo[1,3]dioxolyl, or
- is —$(CHR)_p$-phenyl, optionally substituted by halogen, lower alkyl, lower alkoxy, $S(O)_2$-lower alkyl, cyano, nitro, lower alkoxy substituted by halogen, dimethylamino, —$(CH_2)$p-NHC(O)O-lower alkyl, or lower alkyl substituted by halogen, and R is hydrogen, halogen, hydroxy or lower alkoxy, or
- is cycloalkenyl or cycloalkyl, each of which is optionally substituted by hydroxy or lower alkyl substituted by halogen, or
- is a five or six membered heteroaryl group, containing 1 to 3 heteroatoms, selected from O, S and N, which is optionally substituted by halogen, lower alkyl, lower alkoxy or dimethylamino, or
- is O-phenyl, optionally substituted by halogen, or
- is heterocycloalkyl, optionally substituted by halogen, hydroxy, lower alkyl substituted by halogen or C(O)O-lower alkyl;

$R^3$ is hydrogen, lower alkyl, cyano or phenyl;

$R^4$ is lower alkoxy, lower alkyl or halogen;

p is 0 or 1;

n is 0, 1 or 2; when n is 2 then each $R^4$ is the same or different;

m is 0, 1 or 2; when m is 2 then each $R^1$ is the same or different;

o is 0, 1, 2 or 3, when o is 2 or 3 then each $R^2$ is the same or different;

or pharmaceutically active acid addition salts thereof.

The present invention provides compounds of formula I per se and pharmaceutically active acid addition salts thereof. The invention also provides pharmaceutical compositions containing the compounds of the invention. The invention further provides methods for the production of compounds and compositions of the invention.

The invention provides all forms of optically pure enantiomers, racemates or diastereomeric mixtures for compounds of formula I.

The present compounds of formula I are modulators for amyloid beta and thus, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

DETAILED DESCRIPTION OF THE INVENTION

The following definitions for compounds of formula I are used:

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CF_2CHF_2$, $CH_2CF_2CF_3$ and the like.

As used herein, the term "lower alkyl substituted by hydroxy" denotes an alkyl group as defined above, wherein at least one hydrogen atom is replaced by hydroxy, for example $CH_2OH$, $CHCH_3OH$ or $C(CH_3)_2OH$.

As used herein, the term "lower alkoxy" denotes an alkyl group as defined above, which is bonded via an O-atom.

As used herein, the term "lower alkoxy substituted by halogen" denotes an alkoxy group as defined above, wherein at least one hydrogen atom is replaced by halogen, for example $OCF_3$, $OCHF_2$, $OCH_2F$, $OCH_2CF_3$, $OCH_2CH_2CF_3$, $OCF_2CHF_2$, $OCH_2CF_2CF_3$ and the like.

The term "halogen" denotes chlorine, iodine, fluorine and bromine.

The term "a five or six membered heteroaryl group, containing 1 to 3 heteroatoms, selected from O, S and N" denotes one of the following groups

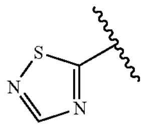 , 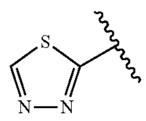 , 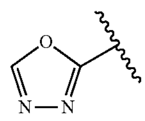 ,

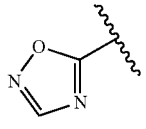 , 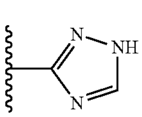 , 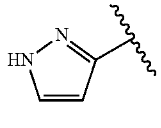 ,

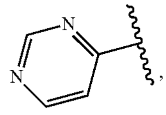 , 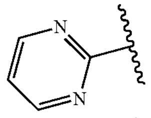 , 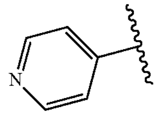 or

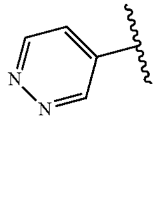 ;

The term "a two membered ring system containing 1 to 4 heteroatoms selected from S, O and N, wherein at least one ring is aromatic in nature" denotes one of the following groups

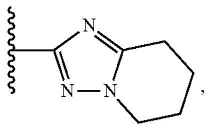 , 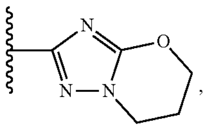 ,

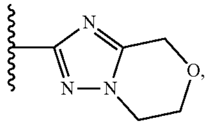 , 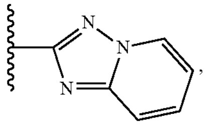 ,

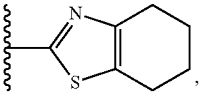 , 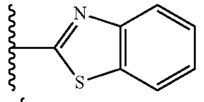 or

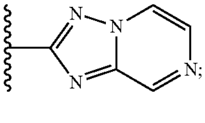 ; 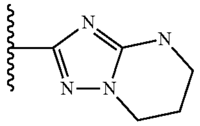

As used herein, the term "heterocycloalkyl" denotes a saturated or partially unsaturated ring, containing heteroatoms such as O, S and N, which groups are selected from morpholinyl, di-hydropyridinyl, dihydropyranyl, piperidinyl or 6-aza-spiro[2,5]octanyl.

The term "cycloalkyl" denotes a saturated alkyl ring with 3-6 carbon atoms, such as cyclopropyl, cyclobutyl, cyclopentyl or cyclohexyl.

The term "cycloalkenyl" denotes a partially unsaturated alkyl ring with 3-6 carbon atoms, for example cyclohexenyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

One embodiment of the invention provides compounds of formula I, wherein hetaryl I is

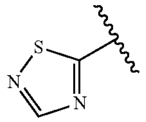 [SMILES: *c1ncns1]

and hetaryl II is a two membered ring system containing 1 to 4 heteroatoms, for example the following compounds

[8-(4-fluoro-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(4-fluoro-phenyl)-[1,2,4]triazolo[1,5-a]pyridin-2-yl]-[1-(3-methyl-[1,2,4]thiadiazol-5-yl)-piperidin-4-yl]-amine;

[5-(4-fluoro-phenyl)-[1,2,4]triazolo[1,5-a]pyridin-2-yl]-[1-(3-methyl-[1,2,4]thiadiazol-5-yl)-piperidin-4-yl]-amine;

[1-(3-methyl-[1,2,4]thiadiazol-5-yl)-piperidin-4-yl]-(4-phenyl-4,5,6,7-tetrahydro-benzothiazol-2-yl)-amine;

[8-(2-chloro-4-fluoro-phenyl)-[1,2,4]triazolo[1,5-a]pyridin-2-yl]-[1-(3-methyl-[1,2,4]thiadiazol-5-yl)-piperidin-4-yl]-amine;

[8-(2,4-difluoro-phenyl)-[1,2,4]triazolo[1,5-a]pyridin-2-yl]-[1-(3-methyl-[1,2,4]thiadiazol-5-yl)-piperidin-4-yl]-amine;

[8-(4-chloro-phenyl)-[1,2,4]triazolo[1,5-a]pyridin-2-yl]-[1-(3-methyl-[1,2,4]thiadiazol-5-yl)-piperidin-4-yl]-amine;

[8-(3-chloro-4-fluoro-phenyl)-6-methyl-[1,2,4]triazolo[1,5-a]pyridin-2-yl]-[1-(3-methyl-[1,2,4]thiadiazol-5-yl)-piperidin-4-yl]-amine;

[8-(2-chloro-4-fluoro-phenyl)-6-methyl-[1,2,4]triazolo[1,5-a]pyridin-2-yl]-[1-(3-methyl-[1,2,4]thiadiazol-5-yl)-piperidin-4-yl]-amine;

[8-(3,4-difluoro-phenyl)-6-methyl-[1,2,4]triazolo[1,5-a]pyridin-2-yl]-[1-(3-methyl-[1,2,4]thiadiazol-5-yl)-piperidin-4-yl]-amine;

[8-(3,4-difluoro-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(4-fluoro-2-methoxy-phenyl)-[1,2,4]triazolo[1,5-a]pyridin-2-yl]-[1-(3-methyl-[1,2,4]thiadiazol-5-yl)-piperidin-4-yl]-amine;

[8-(4-fluoro-3-trifluoromethyl-phenyl)-[1,2,4]triazolo[1,5-a]pyridin-2-yl]-[1-(3-methyl-[1,2,4]thiadiazol-5-yl)-piperidin-4-yl]-amine;

[8-(2,4-difluoro-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(4-fluoro-3-trifluoromethyl-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(2-fluoro-4-methanesulfonyl-phenyl)-[1,2,4]triazolo[1,5-a]pyridin-2-yl]-[1-(3-methyl-[1,2,4]thiadiazol-5-yl)-piperidin-4-yl]-amine;

[8-(3,4-difluoro-phenyl)-6-fluoro-[1,2,4]triazolo[1,5-a]pyridin-2-yl]-[1-(3-methyl-[1,2,4]thiadiazol-5-yl)-piperidin-4-yl]-amine;

[8-(2,4-dichloro-phenyl)-[1,2,4]triazolo[1,5-a]pyridin-2-yl]-[1-(3-methyl-[1,2,4]thiadiazol-5-yl)-piperidin-4-yl]-amine;

[8-(2-fluoro-4-trifluoromethyl-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[1-(3-methyl-[1,2,4]thiadiazol-5-yl)-piperidin-4-yl]-[8-(2,3,4-trifluoro-phenyl)-[1,2,4]triazolo[1,5-a]pyridin-2-yl]-amine;

[8-(3,4-difluoro-phenyl)-6-fluoro-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(3,4-difluoro-phenyl)-5-trifluoromethyl-[1,2,4]triazolo[1,5-a]pyridin-2-yl]-[1-(3-methyl-[1,2,4]thiadiazol-5-yl)-piperidin-4-yl]-amine;

[8-(6-methoxy-pyridin-3-yl)-[1,2,4]triazolo[1,5-a]pyridin-2-yl]-[1-(3-methyl-[1,2,4]thiadiazol-5-yl)-piperidin-4-yl]-amine;

[8-(3-chloro-4-fluoro-phenyl)-6-fluoro-[1,2,4]triazolo[1,5-a]pyridin-2-yl]-[1-(3-methyl-[1,2,4]thiadiazol-5-yl)-piperidin-4-yl]-amine;

[8-(6-fluoro-pyridin-3-yl)-[1,2,4]triazolo[1,5-a]pyridin-2-yl]-[1-(3-methyl-[1,2,4]thiadiazol-5-yl)-piperidin-4-yl]-amine;

[8-(2-fluoro-pyridin-3-yl)-[1,2,4]triazolo[1,5-a]pyridin-2-yl]-[1-(3-methyl-[1,2,4]thiadiazol-5-yl)-piperidin-4-yl]-amine;

[1-(3-methyl-[1,2,4]thiadiazol-5-yl)-piperidin-4-yl]-[8-(3,4,5-trifluoro-phenyl)-[1,2,4]triazolo[1,5-a]pyridin-2-yl]-amine;

[1-(3-methyl-[1,2,4]thiadiazol-5-yl)-piperidin-4-yl]-[8-(2,3,4-trifluoro-phenyl)-5,6,7,8-tetrahydro-[1,2,4]triazolo[1,5-a]pyridin-2-yl]-amine;

[8-(3,4-difluoro-phenyl)-6-trifluoromethyl-[1,2,4]triazolo[1,5-a]pyridin-2-yl]-[1-(3-methyl-[1,2,4]thiadiazol-5-yl)-piperidin-4-yl]-amine;

[8-(3,4-difluoro-phenyl)-5-trifluoromethyl-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(3,4-difluoro-phenyl)-6-trifluoromethyl-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[1-(3-methyl-[1,2,4]thiadiazol-5-yl)-piperidin-4-yl]-(8-phenoxy-[1,2,4]triazolo[1,5-a]pyridin-2-yl)-amine;

3-(2-(1-(2-chloropyridin-4-yl)piperidin-4-ylamino)-[1,2,4]triazolo[1,5-a]pyridin-8-yl)benzonitrile;

N-(1-(3-methyl-1,2,4-thiadiazol-5-yl)piperidin-4-yl)-8-(3-(trifluoromethoxy)phenyl)-[1,2,4]triazolo[1,5-a]pyridin-2-amine;

8-(2,3-dichlorophenyl)-N-(1-(3-methyl-1,2,4-thiadiazol-5-yl)piperidin-4-yl)-[1,2,4]triazolo[1,5-a]pyridin-2-amine;

8-(3,4-dichlorophenyl)-N-(1-(3-methyl-1,2,4-thiadiazol-5-yl)piperidin-4-yl)-[1,2,4]triazolo[1,5-a]pyridin-2-amine;

8-(3-chlorophenyl)-N-(1-(3-methyl-1,2,4-thiadiazol-5-yl)piperidin-4-yl)-[1,2,4]triazolo[1,5-a]pyridin-2-amine;

[8-(5-dimethylamino-2-nitro-phenyl)-[1,2,4]triazolo[1,5-a]pyridin-2-yl]-[1-(3-methyl-[1,2,4]thiadiazol-5-yl)-piperidin-4-yl]-amine;

[8-(3,5-bis-trifluoromethyl-phenyl)-[1,2,4]triazolo[1,5-a]pyridin-2-yl]-[1-(3-methyl-[1,2,4]thiadiazol-5-yl)-piperidin-4-yl]-amine;

N-(1-(3-methyl-1,2,4-thiadiazol-5-yl)piperidin-4-yl)-8-(4-(trifluoromethoxy)phenyl)-[1,2,4]triazolo[1,5-a]pyridin-2-amine;

[8-(3-methoxy-phenyl)-[1,2,4]triazolo[1,5-a]pyridin-2-yl]-[1-(3-methyl-[1,2,4]thiadiazol-5-yl)-piperidin-4-yl]-amine;

[8-(3-chloro-phenoxy)-[1,2,4]triazolo[1,5-a]pyridin-2-yl]-[1-(3-methyl-[1,2,4]thiadiazol-5-yl)-piperidin-4-yl]-amine;

[8-(5-chloro-2-fluoro-phenyl)-[1,2,4]triazolo[1,5-a]pyridin-2-yl]-[1-(3-methyl-[1,2,4]thiadiazol-5-yl)-piperidin-4-yl]-amine;

[8-(2-chloro-phenyl)-[1,2,4]triazolo[1,5-a]pyridin-2-yl]-[1-(3-methyl-[1,2,4]thiadiazol-5-yl)-piperidin-4-yl]-amine;

[8-(3-dimethylamino-phenyl)-[1,2,4]triazolo[1,5-a]pyridin-2-yl]-[1-(3-methyl-[1,2,4]thiadiazol-5-yl)-piperidin-4-yl]-amine;

[8-(2-fluoro-pyridin-4-yl)-[1,2,4]triazolo[1,5-a]pyridin-2-yl]-[1-(3-methyl-[1,2,4]thiadiazol-5-yl)-piperidin-4-yl]-amine;

(8-benzo[1,3]dioxol-5-yl-[1,2,4]triazolo[1,5-a]pyridin-2-yl)-[1-(3-methyl-[1,2,4]thiadiazol-5-yl)-piperidin-4-yl]-amine;

[8-(2-chloro-5-trifluoromethyl-phenyl)-[1,2,4]triazolo[1,5-a]pyridin-2-yl]-[1-(3-methyl-[1,2,4]thiadiazol-5-yl)-piperidin-4-yl]-amine;

[8-(3,5-bis-trifluoromethyl-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(4-dimethylamino-phenyl)-[1,2,4]triazolo[1,5-a]pyridin-2-yl]-[1-(3-methyl-[1,2,4]thiadiazol-5-yl)-piperidin-4-yl]-amine;

(cis, rac)-N-(3-fluoro-1-(3-methyl-1,2,4-thiadiazol-5-yl)piperidin-4-yl)-8-(2,3,4-trifluorophenyl)-[1,2,4]triazolo[1,5-a]pyridin-2-amine;

(3S,4R)— and (3R,4S)—N-(3-fluoro-1-(3-methyl-1,2,4-thiadiazol-5-yl)piperidin-4-yl)-8-(2,3,4-trifluorophenyl)-[1,2,4]triazolo[1,5-a]pyridin-2-amine;

(cis, rac)-[3-fluoro-1-(3-methyl-[1,2,4]thiadiazol-5-yl)-piperidin-4-yl]-[8-(4-fluoro-phenyl)-[1,2,4]triazolo[1,5-a]pyridin-2-yl]-amine;

(cis, rac)-[3,4-difluoro-1-(3-methyl-[1,2,4]thiadiazol-5-yl)-piperidin-4-yl]-[8-(4-fluoro-phenyl)-[1,2,4]triazolo[1,5-a]pyridin-2-yl]-amine;

N-(3,3-difluoro-1-(3-methyl-1,2,4-thiadiazol-5-yl)piperidin-4-yl)-8-(2,3,4-trifluorophenyl)-[1,2,4]triazolo[1,5-a]pyridin-2-amine;

4-chloro-3-(2-(1-(3-methyl-1,2,4-thiadiazol-5-yl)piperidin-4-ylamino)-[1,2,4]triazolo[1,5-a]pyridin-8-yl)benzonitrile;

(4-fluorophenyl)(2-(1-(3-methyl-1,2,4-thiadiazol-5-yl)piperidin-4-ylamino)-[1,2,4]triazolo[1,5-a]pyridin-8-yl)methanol; and N-((3S,5S)-3,5-dimethyl-1-(3-methyl-1,2,4-thiadiazol-5-yl)piperidin-4-yl)-8-(2,3,4-trifluorophenyl)-[1,2,4]triazolo[1,5-a]pyridin-2-amine.

A further embodiment of the invention provides compounds of formula I, wherein hetaryl I is

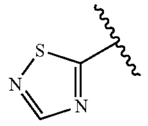 [SMILES: *c1ncns1]

and hetaryl II is a five or six membered heteroaryl group, containing 1 to 3 heteroatoms, selected from O, S and N, for example the following compounds

[1-(3,5-dichloro-benzyl)-1H-[1,2,4]triazol-3-yl]-[1-(3-methyl-[1,2,4]thiadiazol-5-yl)-piperidin-4-yl]-amine;

[1-(3-chloro-benzyl)-1H-[1,2,4]triazol-3-yl]-[1-(3-methyl-[1,2,4]thiadiazol-5-yl)-piperidin-4-yl]-amine;

2-[2-[1-(3-methyl-[1,2,4]thiadiazol-5-yl)-piperidin-4-ylamino]-6-(4-trifluoromethyl-phenyl)-pyrimidin-4-yl]-propan-2-ol;

2-{6-(4-chloro-phenyl)-2-[1-(3-methyl-[1,2,4]thiadiazol-5-yl)-piperidin-4-ylamino]-pyrimidin-4-yl}-propan-2-ol and 2-{6-(4-chloro-benzyl)-2-[1-(3-methyl-[1,2,4]thiadiazol-5-yl)-piperidin-4-ylamino]-pyrimidin-4-yl}-propan-2-ol.

A further embodiment of the invention provides compounds of formula I, wherein hetaryl I is

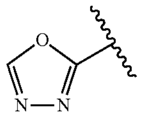

and hetaryl II is a two membered ring system containing 1 to 4 heteroatoms, for example the following compounds

[1-(5-methyl-[1,3,4]oxadiazol-2-yl)-piperidin-4-yl]-(4-phenyl-4,5,6,7-tetrahydro-benzothiazol-2-yl)-amine;

[8-(2-chloro-4-fluoro-phenyl)-[1,2,4]triazolo[1,5-a]pyridin-2-yl]-[1-(5-methyl-[1,3,4]oxadiazol-2-yl)-piperidin-4-yl]-amine;

[8-(4-fluoro-3-trifluoromethyl-phenyl)-[1,2,4]triazolo[1,5-a]pyridin-2-yl]-[1-(5-methyl-[1,3,4]oxadiazol-2-yl)-piperidin-4-yl]-amine;

[8-(4-fluoro-3-trifluoromethyl-phenyl)-5,6,7,8-tetrahydro-[1,2,4]triazolo[1,5-a]pyridin-2-yl]-[1-(5-methyl-[1,3,4]oxadiazol-2-yl)-piperidin-4-yl]-amine;

[1-(5-methyl-[1,3,4]oxadiazol-2-yl)-piperidin-4-yl]-[8-(2,3,4-trifluoro-phenyl)-[1,2,4]triazolo[1,5-a]pyridin-2-yl]-amine;

[8-(2,3-dichloro-phenyl)-[1,2,4]triazolo[1,5-a]pyridin-2-yl]-[1-(5-methyl-[1,3,4]oxadiazol-2-yl)-piperidin-4-yl]-amine;

[8-(3-chloro-phenyl)-[1,2,4]triazolo[1,5-a]pyridin-2-yl]-[1-(5-methyl-[1,3,4]oxadiazol-2-yl)-piperidin-4-yl]-amine;

3-(2-(1-(3-methyl-1,2,4-thiadiazol-5-yl)piperidin-4-ylamino)-[1,2,4]triazolo[1,5-a]pyridin-8-yl)benzonitrile;

[8-(3,4-dichloro-phenyl)-[1,2,4]triazolo[1,5-a]pyridin-2-yl]-[1-(5-methyl-[1,3,4]oxadiazol-2-yl)-piperidin-4-yl]-amine;

3-(2-(1-(5-methyl-1,3,4-oxadiazol-2-yl)piperidin-4-ylamino)-[1,2,4]triazolo[1,5-a]pyridin-8-yl)benzonitrile;

N-(1-(5-methyl-1,3,4-oxadiazol-2-yl)piperidin-4-yl)-8-(3-(trifluoromethoxy)phenyl)-[1,2,4]triazolo[1,5-a]pyridin-2-amine and

[8-(3,5-bis-trifluoromethyl-phenyl)-[1,2,4]triazolo[1,5-a]pyridin-2-yl]-[1-(5-methyl-[1,3,4]oxadiazol-2-yl)-piperidin-4-yl]-amine.

A further embodiment of the invention provides compounds of formula I, wherein hetaryl I is

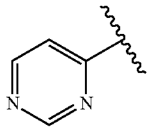 [SMILES: *c1ccncn1]

and hetaryl II is a two membered ring system containing 1 to 4 heteroatoms, for example the following compounds 2-{8-(4-chloro-phenyl)-2-[1-(6-methyl-pyrimidin-4-yl)-piperidin-4-ylamino]-[1,2,4]triazolo[1,5-a]pyridin-5-yl}-propan-2-ol;

8-(2-chloro-4-fluorophenyl)-N-(1-(6-methylpyrimidin-4-yl)piperidin-4-yl)-[1,2,4]triazolo[1,5-a]pyridin-2-amine;

8-(3,4-difluorophenyl)-N-(1-(6-methylpyrimidin-4-yl)piperidin-4-yl)-[1,2,4]triazolo[1,5-a]pyridin-2-amine;

8-(3,4-difluorophenyl)-6-methyl-N-(1-(6-methylpyrimidin-4-yl)piperidin-4-yl)-[1,2,4]triazolo[1,5-a]pyridin-2-amine;

8-(3,4-difluorophenyl)-6-fluoro-N-(1-(6-methylpyrimidin-4-yl)piperidin-4-yl)-[1,2,4]triazolo[1,5-a]pyridin-2-amine;

8-(2-chloro-4-fluorophenyl)-N-(1-(pyrimidin-4-yl)piperidin-4-yl)-[1,2,4]triazolo[1,5-a]pyridin-2-amine;

8-(2-chloro-4-fluorophenyl)-N-(1-(2-methylpyrimidin-4-yl)piperidin-4-yl)-[1,2,4]triazolo[1,5-a]pyridin-2-amine;

8-(2-chloro-4-fluorophenyl)-6-methyl-N-(1-(6-methylpyrimidin-4-yl)piperidin-4-yl)-[1,2,4]triazolo[1,5-a]pyridin-2-amine;

[8-(2-fluoro-4-trifluoromethyl-phenyl)-5,6,7,8-tetrahydro-[1,2,4]triazolo[1,5-a]pyridin-2-yl]-[1-(6-methyl-pyrimidin-4-yl)-piperidin-4-yl]-amine;
[8-(6-fluoro-pyridin-3-yl)-[1,2,4]triazolo[1,5-a]pyridin-2-yl]-[1-(6-methyl-pyrimidin-4-yl)-piperidin-4-yl]-amine;
[8-(4-fluoro-3-trifluoromethyl-phenyl)-[1,2,4]triazolo[1,5-a]pyridin-2-yl]-[1-(6-methyl-pyrimidin-4-yl)-piperidin-4-yl]-amine;
[8-(2-chloro-thiophen-3-yl)-[1,2,4]triazolo[1,5-a]pyridin-2-yl]-[1-(6-methyl-pyrimidin-4-yl)-piperidin-4-yl]-amine;
[1-(6-methyl-pyrimidin-4-yl)-piperidin-4-yl]-[8-(2,3,4-trifluoro-phenyl)-[1,2,4]triazolo[1,5-a]pyridin-2-yl]-amine;
[8-(6-methoxy-pyridin-3-yl)-[1,2,4]triazolo[1,5-a]pyridin-2-yl]-[1-(6-methyl-pyrimidin-4-yl)-piperidin-4-yl]-amine;
[8-(3,4-difluoro-phenyl)-5,6,7,8-tetrahydro-[1,2,4]triazolo[1,5-a]pyridin-2-yl]-[1-(6-methyl-pyrimidin-4-yl)-piperidin-4-yl]-amine;
[8-(3-chloro-4-fluoro-phenyl)-6-fluoro-[1,2,4]triazolo[1,5-a]pyridin-2-yl]-[1-(6-methyl-pyrimidin-4-yl)-piperidin-4-yl]-amine;
[8-(3,4-dichloro-phenyl)-[1,2,4]triazolo[1,5-a]pyridin-2-yl]-[1-(6-methyl-pyrimidin-4-yl)-piperidin-4-yl]-amine;
[1-(6-methyl-pyrimidin-4-yl)-piperidin-4-yl]-[8-(3,4,5-trifluoro-phenyl)-[1,2,4]triazolo[1,5-a]pyridin-2-yl]-amine;
[8-(3-chloro-phenyl)-[1,2,4]triazolo[1,5-a]pyridin-2-yl]-[1-(6-methyl-pyrimidin-4-yl)-piperidin-4-yl]-amine;
3-{2-[1-(6-methyl-pyrimidin-4-yl)-piperidin-4-ylamino]-[1,2,4]triazolo[1,5-a]pyridin-8-yl}-benzonitrile;
[8-(4-tert-butyl-phenyl)-[1,2,4]triazolo[1,5-a]pyridin-2-yl]-[1-(6-methyl-pyrimidin-4-yl)-piperidin-4-yl]-amine;
[8-(3-chloro-phenyl)-[1,2,4]triazolo[1,5-a]pyridin-2-yl]-[1-(6-methyl-pyrimidin-4-yl)-piperidin-4-yl]-amine;
[8-(3-dimethylamino-phenyl)-[1,2,4]triazolo[1,5-a]pyridin-2-yl]-[1-(6-methyl-pyrimidin-4-yl)-piperidin-4-yl]-amine;
tert-butyl 4-(6-methyl-2-(1-(6-methylpyrimidin-4-yl)piperidin-4-ylamino)-[1,2,4]triazolo[1,5-a]pyridin-8-yl)-5,6-dihydropyridine-1(2H)-carboxylate;
8-(3,4-difluorophenyl)-N-(1-(6-methoxypyrimidin-4-yl)piperidin-4-yl)-[1,2,4]triazolo[1,5-a]pyridin-2-amine;
8-(2-chloro-4-fluorophenyl)-N-(1-(6-ethoxypyrimidin-4-yl)piperidin-4-yl)-[1,2,4]triazolo[1,5-a]pyridin-2-amine;
8-(3,4-difluorophenyl)-N-(1-(6-methylpyridazin-4-yl)piperidin-4-yl)-[1,2,4]triazolo[1,5-a]pyridin-2-amine;
8-(3,4-difluorophenyl)-N-(1-(pyrimidin-4-yl)piperidin-4-yl)-[1,2,4]triazolo[1,5-a]pyridin-2-amine;
8-(3,4-difluorophenyl)-6-methyl-N-(1-(pyrimidin-4-yl)piperidin-4-yl)-[1,2,4]triazolo[1,5-a]pyridin-2-amine;
8-(2-chloro-4-fluorophenyl)-6-methyl-N-(1-(pyrimidin-4-yl)piperidin-4-yl)-[1,2,4]triazolo[1,5-a]pyridin-2-amine;
8-(2-chloro-4-fluorophenyl)-N-(1-(2-chloropyrimidin-4-yl)piperidin-4-yl)-[1,2,4]triazolo[1,5-a]pyridin-2-amine;
2-{8-(3,4-difluoro-phenyl)-2-[1-(6-methyl-pyrimidin-4-yl)-piperidin-4-ylamino]-[1,2,4]triazolo[1,5-a]pyridin-5-yl}-propan-2-ol;
4-(3-chloro-4-fluorophenyl)-6-methyl-N-(1-(6-methylpyrimidin-4-yl)piperidin-4-yl)benzo[d]thiazol-2-amine;
[4-(3,4-difluoro-phenyl)-4,5,6,7-tetrahydro-[1,2,4]triazolo[1,5-a]pyrimidin-2-yl]-[1-(6-methyl-pyrimidin-4-yl)-piperidin-4-yl]-amine;
(cis, rac)-[8-(3,4-difluoro-phenyl)-[1,2,4]triazolo[1,5-a]pyridin-2-yl]-[3-fluoro-1-(6-methyl-pyrimidin-4-yl)-piperidin-4-yl]-amine;
(cis, rac)-N-(3-fluoro-1-(6-methylpyrimidin-4-yl)piperidin-4-yl)-8-(2,3,4-trifluorophenyl)-[1,2,4]triazolo[1,5-a]pyridin-2-amine;

2-{8-(4-fluoro-phenyl)-2-[1-(6-methyl-pyrimidin-4-yl)-piperidin-4-ylamino]-[1,2,4]triazolo[1,5-a]pyridin-5-yl}-propan-2-ol;
2-{8-(3,4-difluoro-phenyl)-2-[1-(6-methyl-pyrimidin-4-yl)-piperidin-4-ylamino]-[1,2,4]triazolo[1,5-a]pyridin-5-yl}-propan-2-ol and
N-(3,3-difluoro-1-(6-methylpyrimidin-4-yl)piperidin-4-yl)-8-(2,3,4-trifluorophenyl)-[1,2,4]triazolo[1,5-a]pyridin-2-amine.

A further embodiment of the invention provides compounds of formula I, wherein hetaryl I is

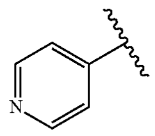

and hetaryl II is a two membered ring system containing 1 to 4 heteroatoms, for example the following compounds 8-(2-chloro-4-fluorophenyl)-N-(1-(2-chloropyridin-4-yl)piperidin-4-yl)-[1,2,4]triazolo[1,5-a]pyridin-2-amine;
8-(3,5-bis(trifluoromethyl)phenyl)-N-(1-(2-chloropyridin-4-yl)piperidin-4-yl)-[1,2,4]triazolo[1,5-a]pyridin-2-amine;
N-(1-(2-chloropyridin-4-yl)piperidin-4-yl)-8-(3-methoxyphenyl)-[1,2,4]triazolo[1,5-a]pyridin-2-amine;
8-(3-chlorophenoxy)-N-(1-(2-chloropyridin-4-yl)piperidin-4-yl)-[1,2,4]triazolo[1,5-a]pyridin-2-amine;
(2'-chloro-3,4,5,6-tetrahydro-2H-[1,4]bipyridinyl-4-yl)-[8-(4-trifluoromethoxy-phenyl)-[1,2,4]triazolo[1,5-a]pyridin-2-yl]-amine;
3-(2-(1-(2-chloropyridin-4-yl)piperidin-4-ylamino)-[1,2,4]triazolo[1,5-a]pyridin-8-yl)benzonitrile;
N-(1-(2-chloropyridin-4-yl)piperidin-4-yl)-8-(3,4-difluorophenyl)-[1,2,4]triazolo[1,5-a]pyridin-2-amine;
8-(3,4-difluorophenyl)-N-(1-(2-methoxypyridin-4-yl)piperidin-4-yl)-[1,2,4]triazolo[1,5-a]pyridin-2-amine;
8-(2-chloro-4-fluorophenyl)-N-(1-(2-methoxypyridin-4-yl)piperidin-4-yl)-[1,2,4]triazolo[1,5-a]pyridin-2-amine;
N-(1-(2-chloropyridin-4-yl)piperidin-4-yl)-8-(3,4-difluorophenyl)-6-methyl-[1,2,4]triazolo[1,5-a]pyridin-2-amine;
N-(1-(2-chloropyridin-4-yl)piperidin-4-yl)-8-(3,4-difluorophenyl)-6-fluoro-[1,2,4]triazolo[1,5-a]pyridin-2-amine;
8-(2-chloro-4-fluorophenyl)-N-(1-(2-chloropyridin-4-yl)piperidin-4-yl)-6-methyl-[1,2,4]triazolo[1,5-a]pyridin-2-amine;
6-chloro-N-(1-(2-chloropyridin-4-yl)piperidin-4-yl)-8-(3,4-difluorophenyl)-[1,2,4]triazolo[1,5-a]pyridin-2-amine;
N-(1-(2-chloropyridin-4-yl)piperidin-4-yl)-6,8-bis(3,4-difluorophenyl)-[1,2,4]triazolo[1,5-a]pyridin-2-amine;
8-(2-chloro-4-ethoxyphenyl)-N-(1-(2-ethoxypyridin-4-yl)piperidin-4-yl)-[1,2,4]triazolo[1,5-a]pyridin-2-amine;
8-(3,4-difluorophenyl)-N-(1-(2-ethoxypyridin-4-yl)piperidin-4-yl)-[1,2,4]triazolo[1,5-a]pyridin-2-amine;
8-(3,4-difluorophenyl)-N-(1-(2-(trifluoromethyl)pyridin-4-yl)piperidin-4-yl)-[1,2,4]triazolo[1,5-a]pyridin-2-amine;
8-(2-chloro-4-fluorophenyl)-N-(1-(2-(trifluoromethyl)pyridin-4-yl)piperidin-4-yl)-[1,2,4]triazolo[1,5-a]pyridin-2-amine;
4-(3-chloro-4-fluorophenyl)-N-(1-(2-chloropyridin-4-yl)piperidin-4-yl)-6-methylbenzo[d]thiazol-2-amine;

N-(1-(2-chloropyridin-4-yl)piperidin-4-yl)-4-(3,4-difluorophenyl)-6-methylbenzo[d]thiazol-2-amine;

4-(2-chloro-4-fluorophenyl)-N-(1-(2-chloropyridin-4-yl)piperidin-4-yl)-6-methylbenzo[d]thiazol-2-amine;

N-(1-(2-chloropyridin-4-yl)piperidin-4-yl)-8-(4-fluoropiperidin-1-yl)-[1,2,4]triazolo[1,5-a]pyridin-2-amine;

N-(1-(2-chloropyridin-4-yl)piperidin-4-yl)-8-(4,4-difluoropiperidin-1-yl)-[1,2,4]triazolo[1,5-a]pyridin-2-amine;

8-(2-chloro-4-fluorophenyl)-2-(1-(2-chloropyridin-4-yl)piperidin-4-ylamino)-5,6,7,8-tetrahydro-[1,2,4]triazolo[1,5-a]pyridin-6-ol;

N-(1-(2-methoxypyridin-4-yl)piperidin-4-yl)-8-(2,3,4-trifluorophenyl)-5,6,7,8-tetrahydro-[1,2,4]triazolo[1,5-a]pyridin-2-amine;

[8-(3,5-bis-trifluoromethyl-phenyl)-5,6,7,8-tetrahydro-[1,2,4]triazolo[1,5-a]pyridin-2-yl]-(2'-methoxy-3,4,5,6-tetrahydro-2H-[1,4']bipyridinyl-4-yl)-amine;

1-(2-chloropyridin-4-yl)-4-(8-(3,4-difluorophenyl)-[1,2,4]triazolo[1,5-a]pyridin-2-ylamino)piperidine-4-carbonitrile;

(cis, rac)-N-(1-(2-chloropyridin-4-yl)-3-fluoropiperidin-4-yl)-8-(3,4-difluorophenyl)-[1,2,4]triazolo[1,5-a]pyridin-2-amine;

(cis, rac)-N-(3-fluoro-1-(2-methoxypyridin-4-yl)piperidin-4-yl)-8-(2,3,4-trifluorophenyl)-[1,2,4]triazolo[1,5-a]pyridin-2-amine;

N-(1-(2-chloropyridin-4-yl)-4-phenylpiperidin-4-yl)-8-(3,4-difluorophenyl)-[1,2,4]triazolo[1,5-a]pyridin-2-amine;

8-(2-chloro-4-fluorophenyl)-6-methyl-N-(1-(2-(trifluoromethyl)pyridin-4-yl)piperidin-4-yl)-[1,2,4]triazolo[1,5-a]pyridin-2-amine;

N-(1-(2-(trifluoromethyl)pyridin-4-yl)piperidin-4-yl)-8-(2,3,4-trifluorophenyl)-[1,2,4]triazolo[1,5-a]pyridin-2-amine;

8-(2,4-difluorophenyl)-N-(1-(2-(trifluoromethyl)pyridin-4-yl)piperidin-4-yl)-[1,2,4]triazolo[1,5-a]pyridin-2-amine;

8-(3,5-bis(trifluoromethyl)phenyl)-N-(1-(2-(trifluoromethyl)pyridin-4-yl)piperidin-4-yl)-[1,2,4]triazolo[1,5-a]pyridin-2-amine and 4-(8-(2-chloro-4-fluorophenyl)-[1,2,4]triazolo[1,5-a]pyridin-2-ylamino)-1-(2-(trifluoromethyl)pyridin-4-yl)piperidine-4-carbonitrile.

A further embodiment of the invention provides compounds of formula I, wherein hetaryl I is

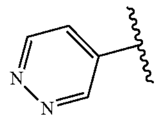 [SMILES: *c1ccnnc1]

and hetaryl II is a two membered ring system containing 1 to 4 heteroatoms, for example the following compounds 8-(3,4-difluorophenyl)-6-fluoro-N-(1-(6-methylpyridazin-4-yl)piperidin-4-yl)-[1,2,4]triazolo[1,5-a]pyridin-2-amine;

8-(3,4-difluorophenyl)-6-methyl-N-(1-(6-methylpyridazin-4-yl)piperidin-4-yl)-[1,2,4]triazolo[1,5-a]pyridin-2-amine;

8-(2-chloro-4-fluorophenyl)-N-(1-(6-methylpyridazin-4-yl)piperidin-4-yl)-[1,2,4]triazolo[1,5-a]pyridin-2-amine;

6-chloro-8-(3,4-difluorophenyl)-N-(1-(6-methylpyridazin-4-yl)piperidin-4-yl)-[1,2,4]triazolo[1,5-a]pyridin-2-amine and 8-(2-chloro-4-fluorophenyl)-6-methyl-N-(1-(6-methylpyridazin-4-yl)piperidin-4-yl)-[1,2,4]triazolo[1,5-a]pyridin-2-amine.

An embodiment of the invention further provides compounds of formula

I-1

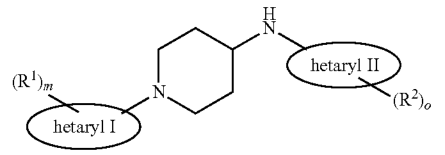

wherein hetaryl I is a five or six membered heteroaryl group, containing 1 to 3 heteroatoms, selected from O, S and N;

hetaryl II is a five or six membered heteroaryl group, containing 1 to 3 heteroatoms, selected from O, S and N, or is a two membered ring system containing 1 to 4 heteroatoms selected from S or N, wherein at least one ring is aromatic in nature;

$R^1$ is lower alkyl or halogen;

$R^2$ is lower alkyl, lower alkyl substituted by hydroxy or is $—(CH_2)_p$-phenyl, optionally substituted by halogen, lower alkyl or lower alkyl substituted by halogen; if o is 2 or 3 then $R^2$ may be the same or different;

p is 0 or 1;

m is 0, 1 or 2;

o is 0, 1, 2 or 3;

or to pharmaceutically active acid addition salts thereof.

The present compounds of formula I and their pharmaceutically acceptable salts can be prepared by methods known in the art, for example, by processes described below, which processes comprise a) reacting a compound of formula

2

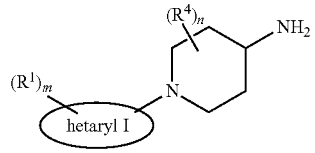

with a compound of formula

3

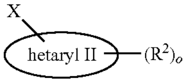

to produce a compound of formula

I

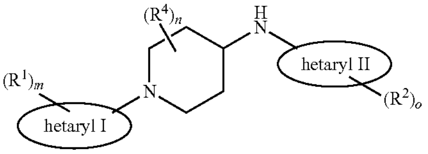

wherein X is halogen and the further groups have the meaning as described above and, if desired, converting the compounds obtained into pharmaceutically acceptable acid addition salts;

or b) reacting a compound of formula

6

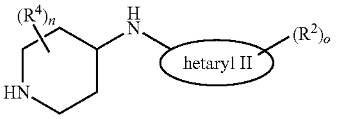

with a compound of formula

7

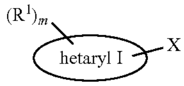

to produce a compound of formula

I

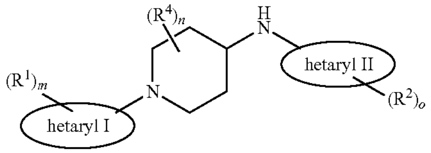

wherein X is halogen and the further groups have the meaning as described above, or c) reacting a compound of formula

8

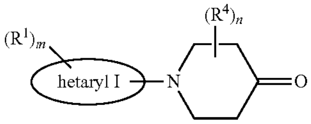

with a compound of formula

9

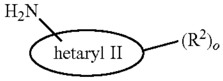

to produce a compound of formula

I

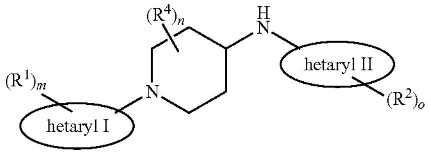

wherein the groups have the meaning as described above and $R^3$ is hydrogen, and, if desired converting the compounds obtained into pharmaceutically acceptable acid addition salts.

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

Scheme 1

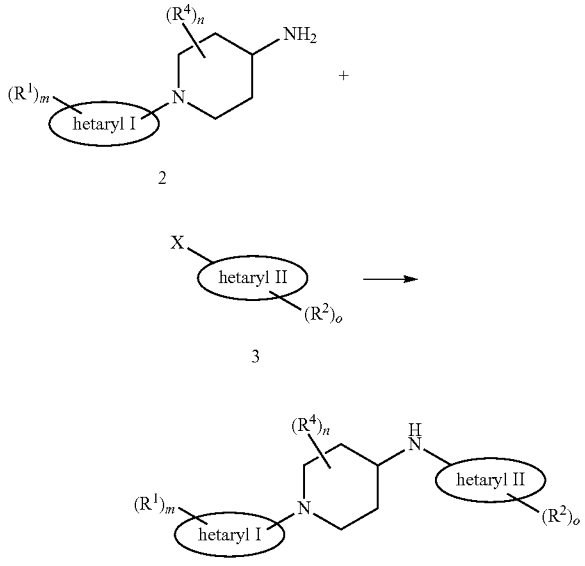

2

3

I

The present compounds of formula I and their pharmaceutically acceptable salts can be prepared by coupling of amines of general formula 2 and halides of general formula 3 (see Scheme 1). This reaction can be accomplished using generally known procedures, e.g. displacement reactions under catalytic conditions (like e.g. palladium(0) or copper(II) catalysis) or under thermal conditions or under basic conditions.

Alternatively halides 3 can be coupled under conditions as described above with amines of general formula 4 which bear a protective group PG, e.g. Boc, on the piperidine nitrogen (see Scheme 2). After deprotection with e.g. trifluoro acetic acid, the piperidines 6 can be coupled with a hetaryl I halides of formula 7 to provide compounds of formula I.

Scheme 3

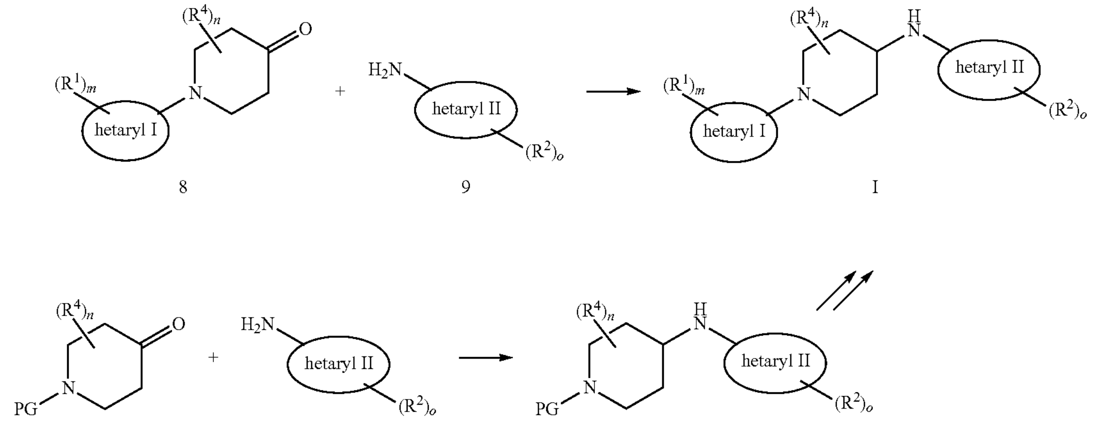

8 9 I 10 9 5

Scheme 2

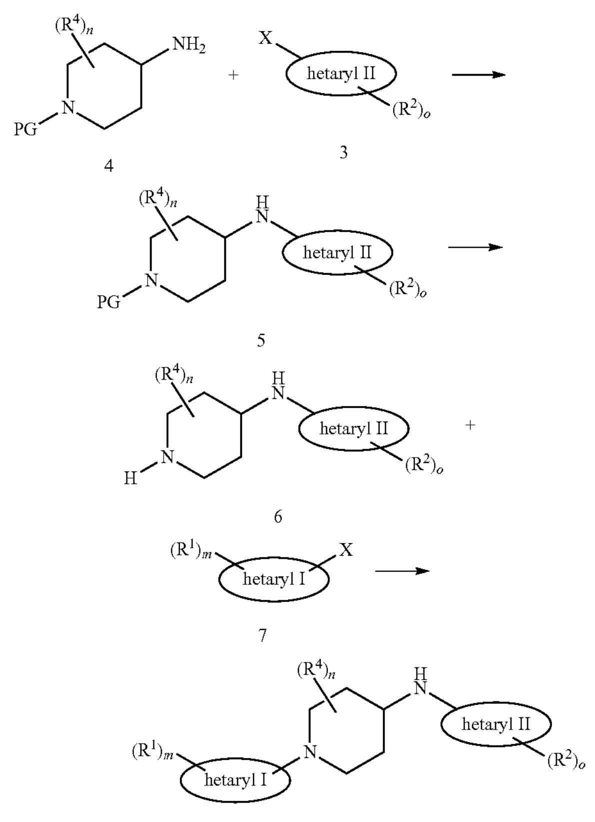

4 3 5 6 7 I $R^1$ is hydrogen.

Alternatively anilines of general formula 9 can be employed in a reductive amination reaction with ketones of general formula 8 or 10 (see Scheme 3) providing compounds I either directly or after cleavage of protective group PG of 5, followed by coupling with heteroaryl I halide 7 as described in Scheme 2. The reductive amination can be accomplished by methods known to one skilled in the art of organic synthesis, for example by heating the amine and the ketone in an appropriate solvent (e.g. toluene, dichloroethane, THF) possibly in the presence of an acid (e.g. acetic acid, tetraisopropyl-orthotitanate) and reduction of the intermediary imine with an appropriate reducing agent (e.g. sodium triacetoxyborohydride, sodium cyanoborohydride, sodium borohydride, hydrogen in the presence paladium on charcoal).

Anilines of general formula 9, which can be used as starting materials for the preparation of compounds of formula I can be prepared as described in the following schemes.

Scheme 4

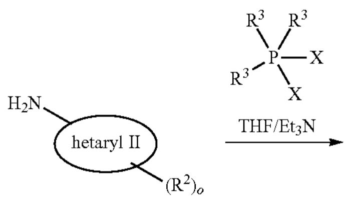

9

-continued

-continued

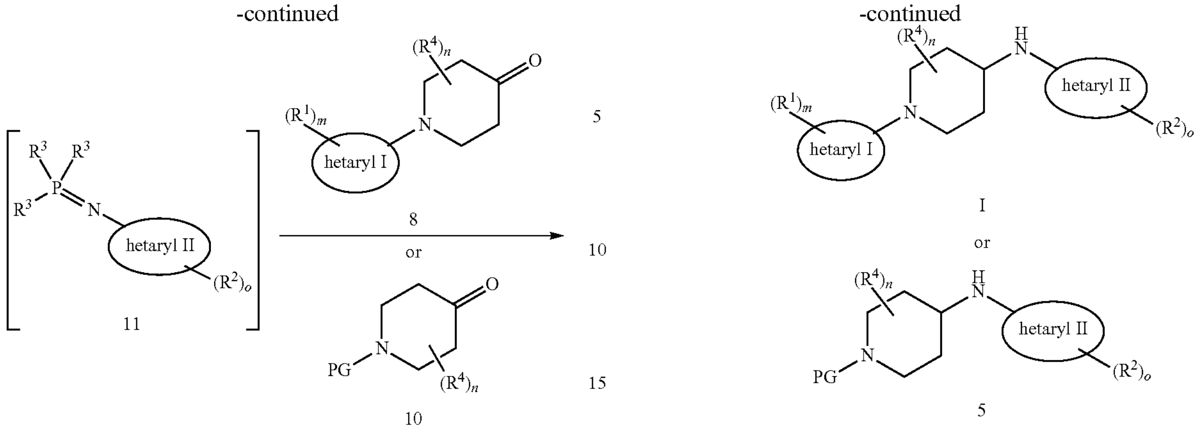

11

10

I or

5

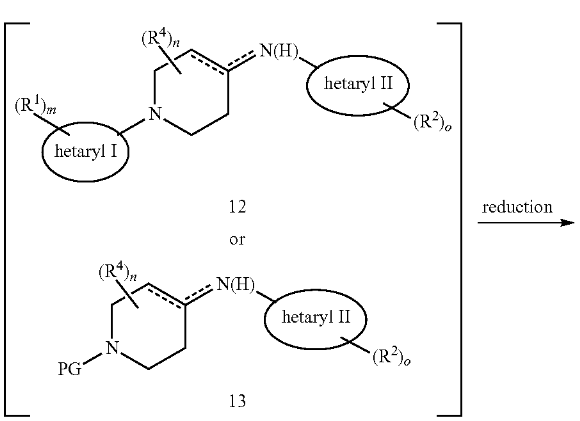

12 or

13

The coupling of anilines of general formula 9 with ketones of general formula 8 or 10 can alternatively be accomplished by following an aza-Wittig/reduction protocol (see Scheme 4). Anilines of general formula 9 can be first converted to their corresponding trialkylphosphazenes 11 by reaction with trialkyldihalophosphorane (e.g. dichlorotrimethylphosphorane, prepared by reaction of trimethylphosphine with hexachloroethane in THF or dichloromethane) and an organic amine base (e.g. triethylamine, di-isopropylethylamine) in a suitable solvent (e.g. THF, dichloromethane). Ketones of general formula 8 or 10 are then added to the reaction mixture containing the in situ prepared phosphazenes 11 and the mixture is heated. The resulting imine/enamines 12 or 13 are then treated with an appropriate reducing agent (e.g. sodium triacetoxyborohydride, sodium cyanoborohydride, sodium borohydride, decaborane, borane-THF complex, hydrogen in the presence palladium on charcoal) in the appropriate solvent (THF, DCM, MeOH and mixtures thereof) with or without acid catalysis (e.g. acetic acid) at ambient or elevated temperatures to provide compounds of general formula 5 or I (for R3 being hydrogen).

Scheme 5

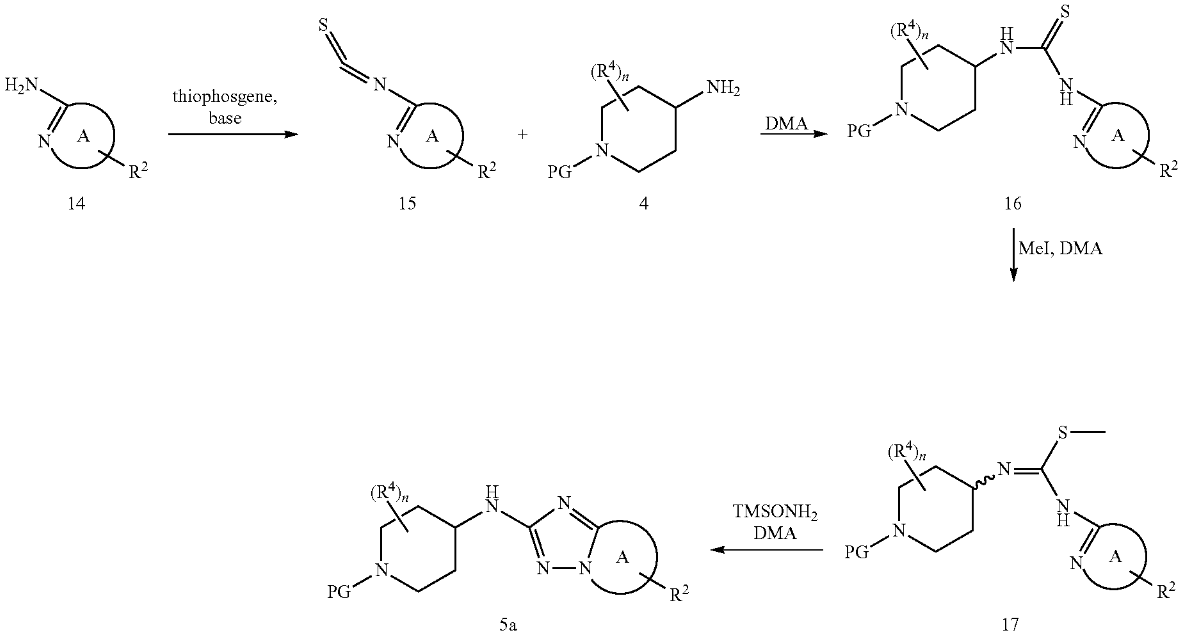

14 15 4 16

5a 17

A represents

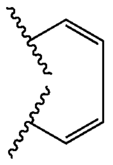
or
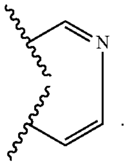
.

Triazolopyridines of general formula 5a can alternatively be constructed by converting amines of general formula 14 into their corresponding isothiocyanates 15 (e.g. by reaction with thiosphosgene or 1,1'-thiocarbonyldiimidazole in dichloromethane in the presence of an organic or aqueous inorganic base) and reaction with amines of general formula 4 (see Scheme 5). The resulting thioureas 16 can be activated by alkylation with iodomethane and subsequently cyclised to triazolopyridines 5a by strong heating (>130° C.) in the presence of a suitably functionalised hydroxylamine derivative e.g. O-(trimethlysilyl)-hydroxylamine in a polar solvent e.g. dimethylacetamide.

Scheme 6

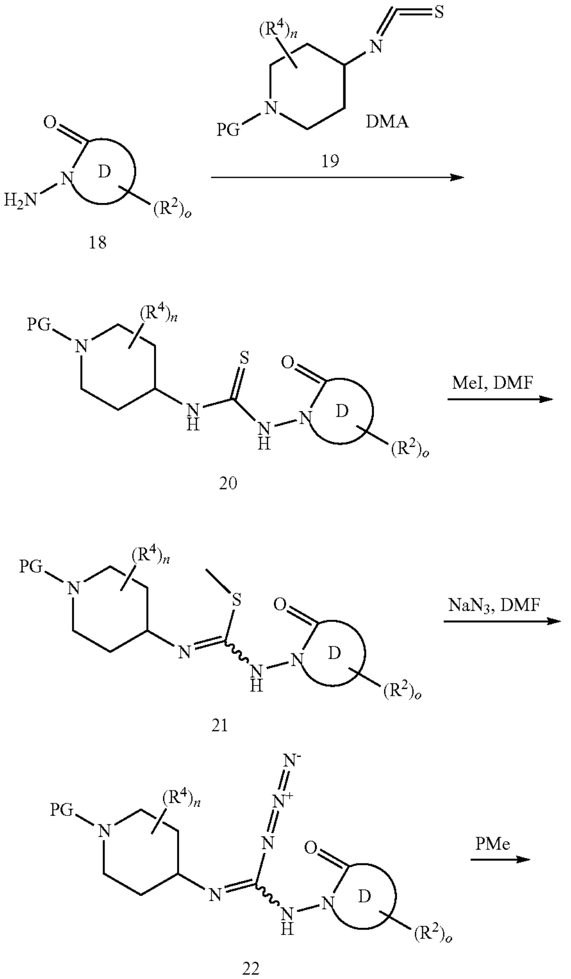

18
19
20
21
22

-continued

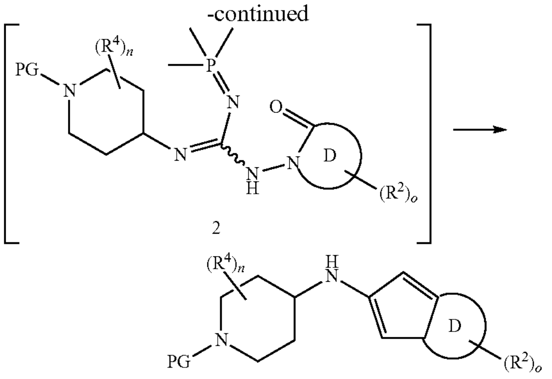
2
5

D represents a carbocyclic ring, preferrably

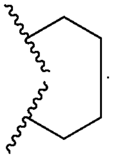 [SMILES: *CCCC*]
.

Triazolopyridines of general formula 5b can be prepared by first condensing cyclic hydrazides 18 and isothiocyanates 19 (prepared by known methods to those skilled in the art) to form thiourea 20 (see Scheme 6). Activation of the sulphur group by alkylation (e.g. iodomethane in DMF at elevated temperatures) allows its displacement by an azide (e.g. sodium azide in DMF at elevated temperatures) to afford azidoguanidine 22. Staudinger reduction with trimethylphosphine generates an intermediate phosphazene 23 which cyclises on heating to generate triazolopyridine 5b.

Anilines of general formula 9, which can be used as starting materials for the preparation of compounds of formula I may be prepared as described in the following schemes.

Scheme 7

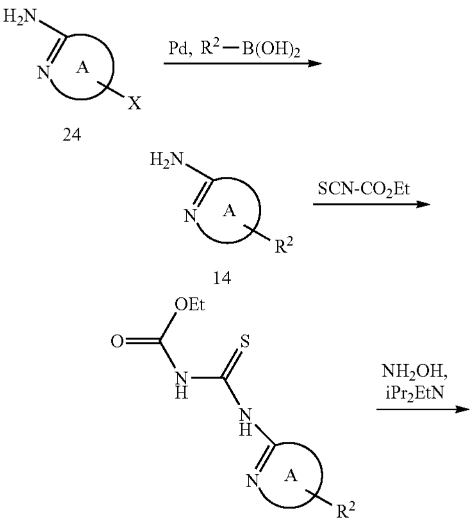

24
14
25

-continued

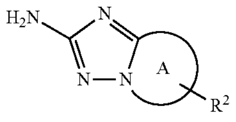

9a

A represents

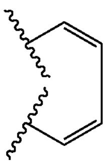

or

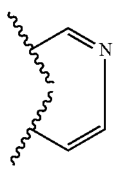

and X represents Cl or Br.

Anilines 9a in which heteroaryl II is an annelated triazole moiety (see Scheme 7) can be constructed from the corresponding amino derivatives 14, which are either commercially available or can be obtained from the corresponding halides 24 by palladium catalyzed Suzuki coupling with boronic acids or boronic esters (e.g. pinacol ester). Amines 14 can be reacted with ethoxycarbonyl isothiocyanate to yield thiourea derivatives 25 which undergo a cyclization reaction upon treatment with hydroxylamine in the presence of a base under liberation of carbon dioxide to yield annelated triazoles 9a (as e.g. described by M. Nettekoven et al., Synthesis 2003, 11, 1649-1652).

Scheme 8

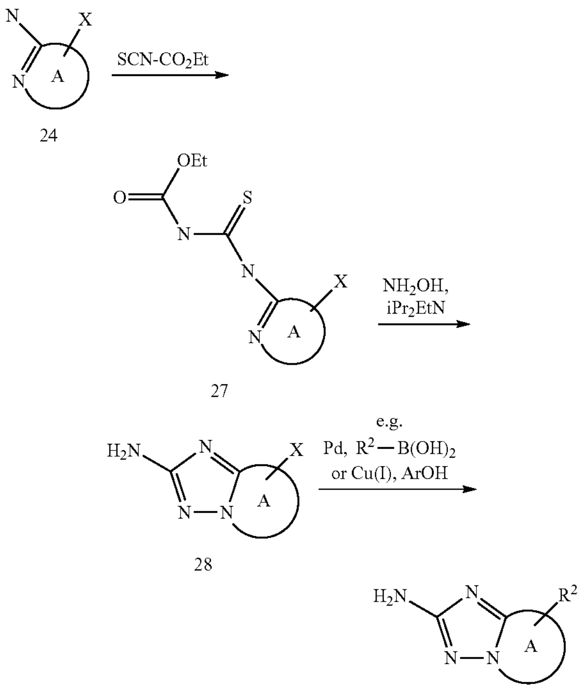

9a

Alternatively the order of steps in Scheme 7 can be changed (see Scheme 8). Halides 24 (which are either commercially available or can be synthesized by methods known in the art) can be reacted with ethoxycarbonyl isothiocyanate followed by treatment with hydroxylamine to provide annelated triazoles 28. These halides can then be subjected e.g. to palladium catalyzed Suzuki coupling with boronic acids or copper (I) catalyzed coupling with phenols (e.g. according to D. Maiti et al. JOC 2010, 75, 1791-1794) to provide substituted aminotriazoles 9a.

Scheme 9

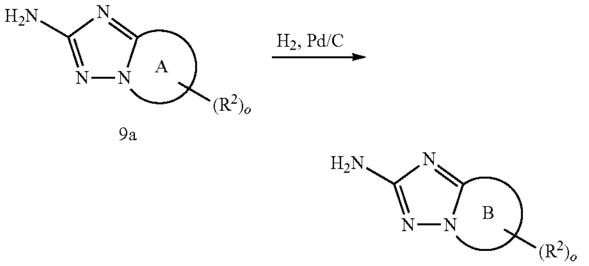

9b

A is

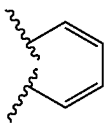

or

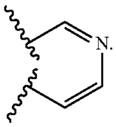

B is

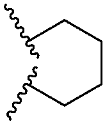

or

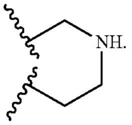

Compounds 9a can be hydrogenated with palladium on charcoal as catalyst to yield the corresponding partly saturated compounds 9b (see Scheme 9). Depending on the nature of ring A this reaction may require elevated temperature or hydrogen pressure or the presence of acid (e.g. HCl). Alternatively compounds 9a can be reduced with metals e.g. magnesium in alcoholic solution (like ethanol) with or without activation of the metal (e.g. activation with catalytic amounts of iodine).

If ring B of compound 9b contains a NH group this can be modified e.g. by reductive amination with aldehydes or ketones in the presence of a reducing agent like sodium triacetoxy borohydride to give the alkylated amines, by acylation with anhydrides or acid chlorides in the presence of a base to give the amides, by reaction with sulfonylchlorides to give the sulfonamides, by reaction with carbonyldiimidazole or triphosgene and alcohols or an amines to give the carbamates or ureas, respectively.

To accomplish these modifications it might be necessary to protect the amino group on the triazole 9a prior to the hydrogenation step e.g. by protection with Boc group which can be introduced e.g. with Boc anhydride and can be cleaved after hydrogenation and the modifications with e.g. trifluoroacetic acid.

Scheme 10

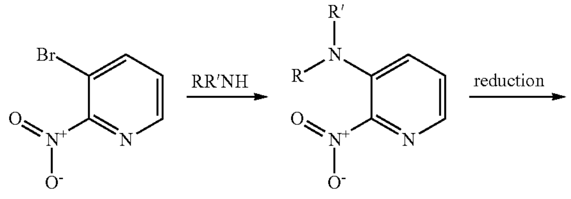

29

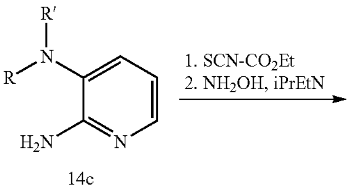

14c

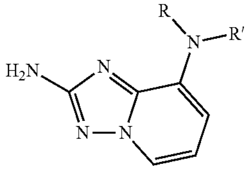

9c

Introduction of an amine substituent ($R^2$=RR'N) (R and R' are preferably methyl) in 8-position of triazolopyridine 9c (see Scheme 10) can be accomplished by treating the 3-bromo-2-nitropyridine with an amine RR'NH in the presence of a base (e.g. potassium carbonate), a catalyst (e.g. TBAI) at ambient to higher temperature in a polar solvent (e.g. DMSO). Reduction of the nitro group either by metal, metal salts or hydrogen in the presence of a catalyst (e.g. Pd on carbon) yields the aminopyridine 14c which can be converted according to Scheme 7 to the corresponding aminotriazole derivative 9c.

Scheme 11

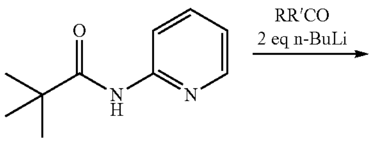

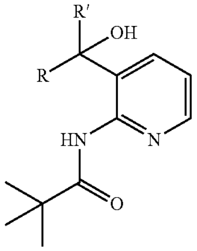

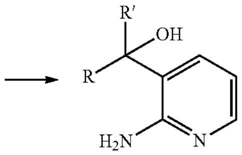

30 31

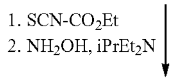

-continued

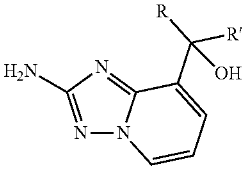

9d

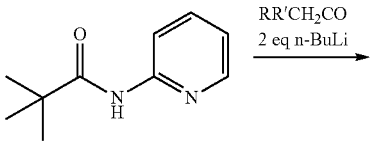

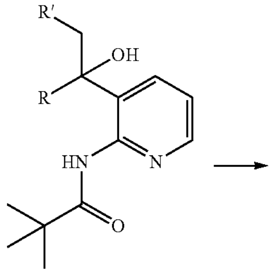

32

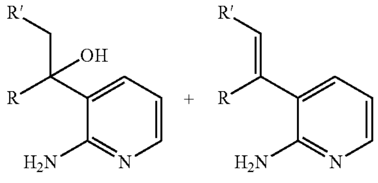

33 34

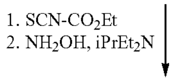

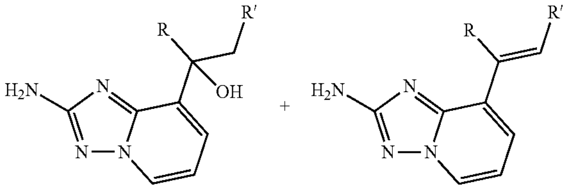

9e 9f

R and R' are lower alkyl.

8-Alkyl or 8-cycloalkyl substituted triazolopyridines can be obtained via directed ortho-metallation of a suitable protected aminopyridine (e.g. pivaloyl derivative) by double deprotonation with n-butyl lithium (Scheme 11). Reacting the resulting dianion at low temperature with an aldehyde or with a ketone yields the 3-carbinole pyridine derivative 30 or 32. The pivaloyl directing group can be cleaved off under basic condition with for example potassium hydroxide at elevated temperature. If an alpha-hydrogen atom is available next to the alcohol elimination of water may occur to yield the corresponding olefin 34. The obtained aminopyridines 31, 33 or 34 can be converted according to Scheme 7 to the corresponding aminotriazole derivatives 9d, 9e or 9f.

Scheme 12

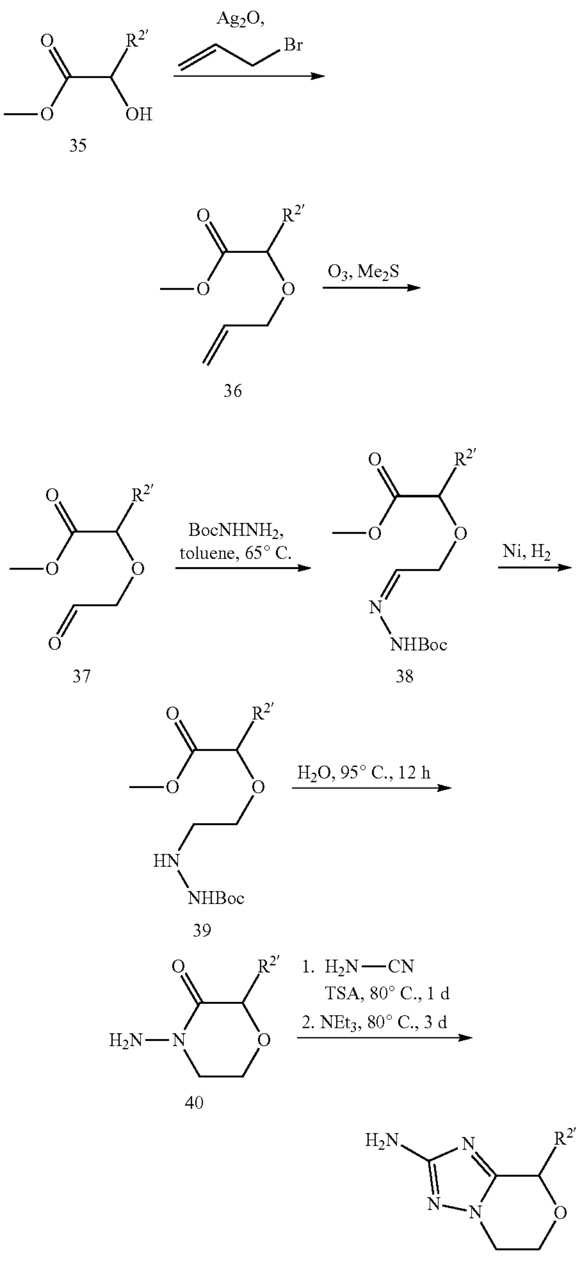

35

36

37

38

39

40

9g $R^{2'}$ is phenyl optionally substituted by halogen or lower alkyl.

Aminotriazoles of general formula 9g can be prepared starting from mandelate derivative 35 (see Scheme 12). Allylation followed by ozonolysis of the double bond provides aldehyde 37 which forms hydrazone 38 upon treatment with Boc-protected hydrazine. Catalytic hydrogenation in the presence of Nickel gives compound 39. Heating in water causes lactamization and deprotection (in analogy to J. W. Nilsson et al. J. Med. Chem. 2003, 46, 3985-4001). Hydrazide 40 undergoes a cyclization reaction with cyanamide by heating under acidic conditions first followed by heating under basic conditions (in analogy to WO2010/098487, Preparation Example 2-7) to provide aniline 9g.

Scheme 13

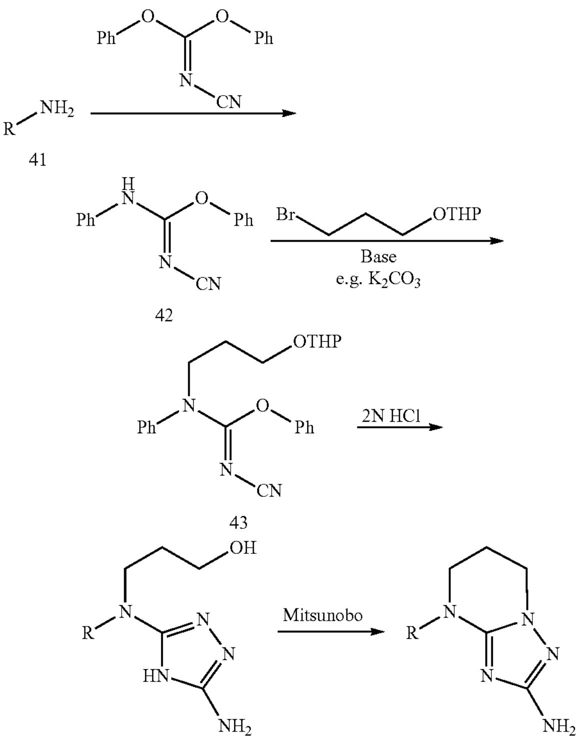

41

42

43

44

9h

Amines 41 can be acylated with N-cyanodiphenoxyimidocarbonate (see Scheme 13) and alkylated with a suitable protected 3-halo-propanol (e.g. bromo-alcohol protected with a THP ether) in the presence of a base (e.g. potassium carbonate) at ambient or higher temperature in a polar solvent (e.g. DMF). After deprotection of the alcohol the compound 44 is cyclized for example under Mitsunobo conditions or with tetrabromomethane and triphenylphosphine to yield the amine 9h.

Scheme 14

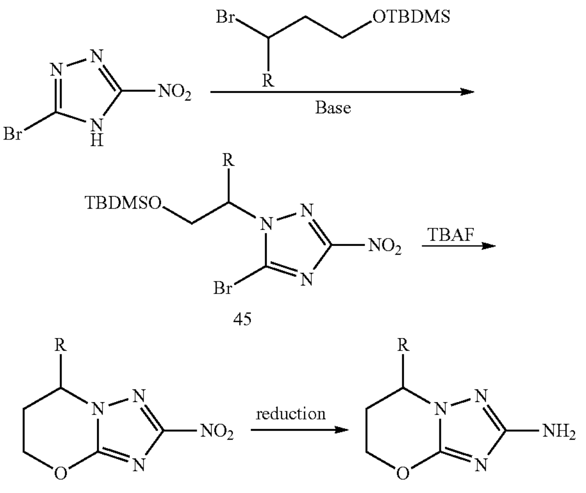

45

46

9i

3-Bromo-5-nitro-4H-[1,2,4]triazole can be alkylated with a suitable protected bromo-alcohol (e.g. with the tert.-butyldimethylsilyl group) in the presence of base (e.g. potassium carbonate). Deprotection of the protected alcohol 45 may lead to spontaneous cyclization of the liberated alcohol onto the bromide or may be catalyzed by a base to yield the bicyclic derivative 46. Reduction of the nitro-group by hydrogen catalyzed by a metal catalyst (e.g. Pd on carbon) or by metal salts or metals provides the amine 91 (see Scheme 14).

Scheme 15

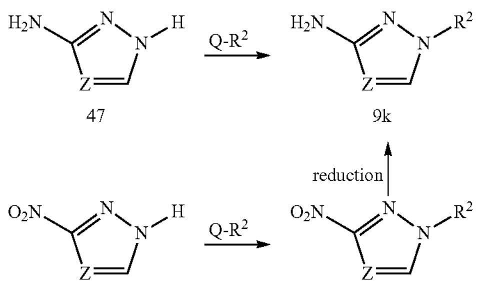

47 9k 48 49

Z represents C or N, Q represents a leaving group.

Anilines 9k in which heteroaryl II is a substituted triazole or pyrazole moiety (see Scheme 15) can be prepared for example by deprotonation of 47 or 48 with sodium hydride in DMF and subsequent alkylation with Q-$R^2$. Q represents a leaving group (e.g. Cl, Br, I, tosylate, mesylate). Nitro compounds 49 can be reduced to amines 9k using generally known procedures, e.g. catalytic hydrogenation in the presence of a catalyst such as palladium on carbon or, by metal reduction e.g. with stannous chloride in HCl or, by hydrazine in the presence of palladium on carbon.

The starting materials 47, 48 are either commercially available or readily prepared by methods known to one skilled in the art of organic synthesis. Examples for 47 are, but not limited to, 1H-[1,2,4]triazol-3-ylamine and 1H-pyrazol-3-ylamine. Examples for 48 are, but not limited to, 4-nitro-1H-pyrazole.

Scheme 16

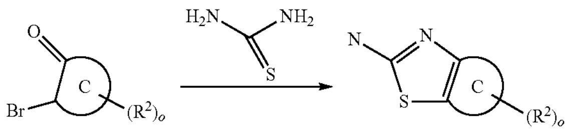

50 91

C represents a carbocyclic ring, preferrably

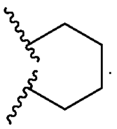 [SMILES: *CCCC*]

Anilines 91 in which heteroaryl II is a an annelated thiazole (see Scheme 16) can be prepared by condensation of α-bromoketones 50 with thiourea (for example by heating in an appropriate solvent, e.g. ethanol). α-Bromoketones are either commercially available or readily prepared by methods known to one skilled in the art of organic synthesis, e.g. by reaction of an appropriate ketone with bromine in chloroform.

Halides of general formula 3, which can be used as starting materials for the preparation of compounds of formula I may be prepared as described in the following schemes.

Scheme 17

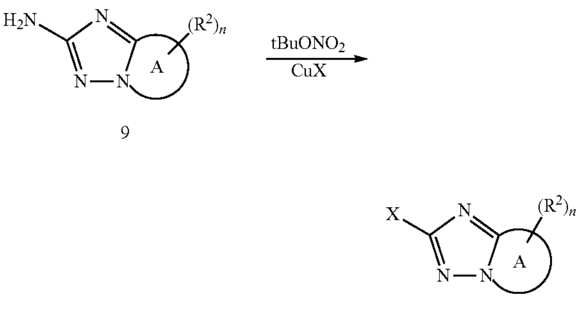

9 3

The halotriazole 3 can be prepared from the aniline 9 (see Scheme 17) via formation of the corresponding diazonium salt and subsequent decomposition in the presence of a halide source like copper (I) halide or hydrogenhalide (X=chlorine or bromine).

Scheme 18

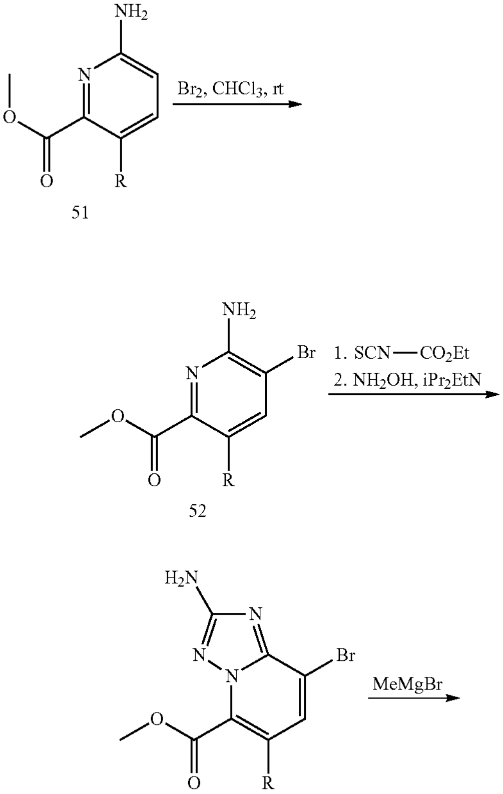

51 52 53

-continued

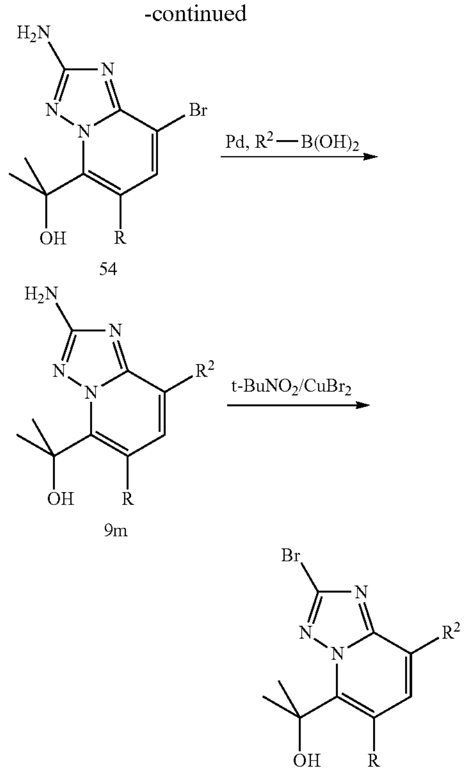

54

9m

3m

R = H or lower alkyl

Anilines of general formula 9m or the corresponding bromides 3m with an 2-propan-2-ol group in 5-position of the triazolopyridine (see Scheme 18) can be prepared starting from ester 51 by bromination in chloroform followed by cyclization as already described in Scheme 8 to give 2-amino-triazolopyridine 53. The ester 53 can then be treated with methyl magnesium bromide to provide the tertiary alcohol 54. Conversion of the bromide by e.g. Suzuki reaction gives aniline 9m or after Sandmeyer reaction bromide 3m. The starting material 51 is either commercially available or can be synthesized by methods known in the art, e.g for R=Me, 51 can be prepared from the corresponding bromide by reaction with trimethyl boroxine in the presence of a palladium catalyst.

Scheme 19

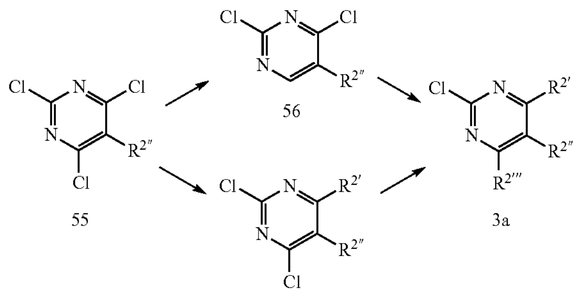

55

56

57

3a $R^{2'}$, $R^{2''}$ and $R^{2'''}$ is lower alkyl, lower alkyl substituted by hydroxy, —$(CH_2)_p$-phenyl, optionally substituted by halogen, lower alkyl or lower alkyl substituted by halogen.

Halides 3a in which heteroaryl II is a pyrimidine (see Scheme 19) can be prepared as e.g. described in K. Baumann et al., WO2009103652 by reduction of trichloro-pyrimidines 55 to give dichloro-derivative 56, e.g. by treatment with zink in aquous ammonia at 0° C. Subsequently, the 4-chloro substituent of 56 can be replaced in a nucleophilic substitution reaction (like reaction with a Grignard reagent $R^{2'}$MgX, e.g. benzylmagnesium chloride in tetrahydrofuran at −80 to +20° C.) or, by a metal catalyst assisted displacement reaction (e.g. using palladium acetate, 2-(dicyclohexylphosphino-biphenyl, tetrahydrofuran, microwave oven, 30 min, 200° C.). Alternatively, one of the reactive chloro atoms of 55 is first replaced by a group $R^{2'}$, followed by replacement of a second chloro-substituent in the intermediate 57 bya group $R^{2'''}$, to afford 3a.

Scheme 20

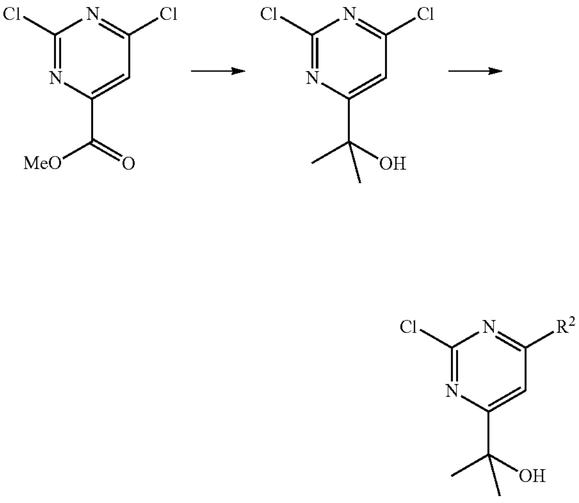

3b $R^2$ is —$(CH_2)_p$-phenyl, optionally substituted by halogen, lower alkyl or lower alkyl substituted by halogen.

Halides 3b in which heteroaryl II is a pyrimidine (see Scheme 20) can be prepared from 2,6-dichloro-pyrimidine-4-carboxylic acid methyl ester by reaction with e.g. methylmagnesium chloride in THF at −78° C. to 0° C. which provides 2-(2,6-dichloro-pyrimidin-4-yl)-propan-2-ol. The chloride in 4-position of 2-(2,6-dichloro-pyrimidin-4-yl)-propan-2-ol can be replaced by a substituent $R^2$ for example in a Suzuki coupling reaction with an aryl/heteroaryl boronic acid/ester $R^2$—B(OH/OR')$_2$ in the presence of a palladium catalyst and a base (e.g. sodium carbonate) in e.g. dimethoxyethane as solvent to provide chloride 3b. Alternatively the 4-chloro substituent can be reacted with an organo zinc chloride $R^2$ZnCl, e.g. benzylzinc chloride in the presence of a palladium catalyst to provide chloride 3b. To accomplish these modifications it might be necessary to protect the alcohol group of 2-(2,6-dichloro-pyrimidin-4-yl)-propan-2-ol prior to the second step e.g. by protection with trimethylsilyl group which can be introduced e.g. with bis(trimethylsilyl) acetamide and can be cleaved after the modifications with e.g. p-TsOH in THF/water.

Scheme 21

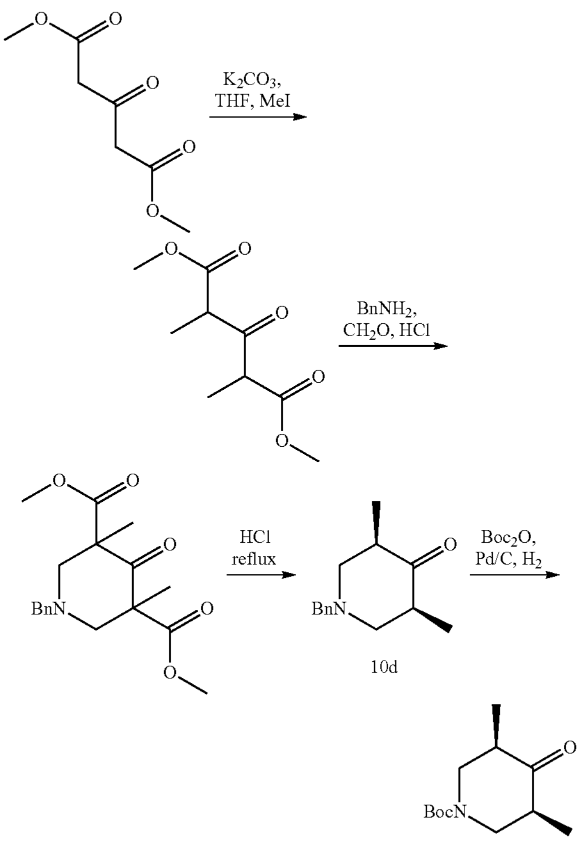

10d

10e

Ketones 10d can be prepared according to A. A. Calabrese et al., US20050176772 starting from dimethyl 3-oxopentanedioate by dimethylation with methyl iodide, followed by cyclization with benzylamine and formaldehyde. Ester hydrolysis and decarboxylation takes place in refluxing aqueous HCl solution to yield ketone 10d. A protective group exchange from benzyl to boc group can be accomplished by hydrogenation in the presence of boc anhydride to provide ketone 10e (see Scheme 21). Ketone 10e can be subjected to an aza-Wittig/reduction protocol with an amine of general formula 9 as described in Scheme 4.

Ketones of general formula 8, which can be used as starting materials for the preparation of compounds of formula I may be prepared as described in the following schemes.

Scheme 22

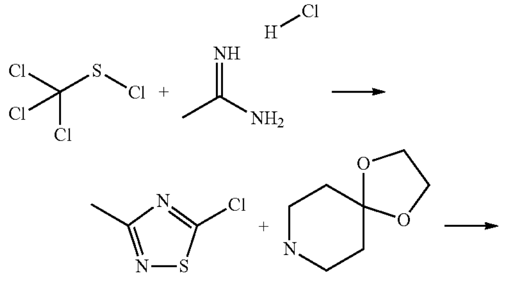

-continued

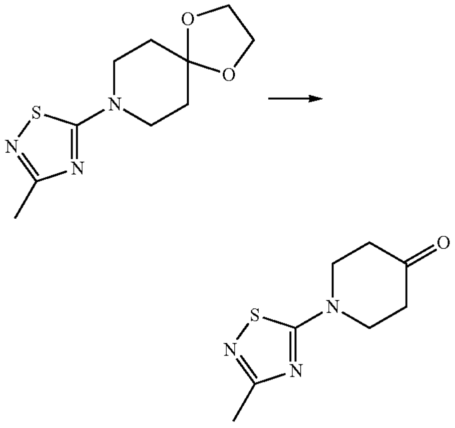

8a

Ketone 8a in which heteroaryl I is a 3-methyl-[1,2,4]thiadiazole (see Scheme 22) can be prepared starting from 5-chloro-3-methyl-[1,2,4]thiadiazole which can be obtained by condensation of acetamidine with perchloromethyl mercaptan in the presence sodium hydroxide. The chloride can be coupled with 1,4-dioxa-8-azaspiro(4,5)decane in the presence of a palladium catalyst and a base (e.g. sodium tert-butoxide). Acid (e.g. HCl) catalyzed cleavage of the ketal then provides ketone 8a.

Scheme 23

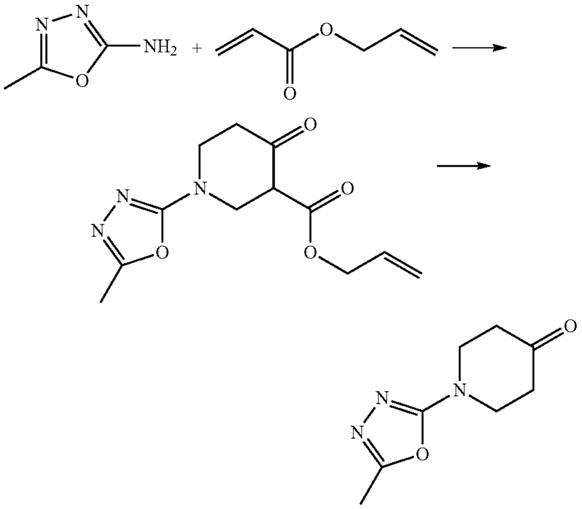

8b

Ketone 8b in which heteroaryl I is a [1,3,4]oxadiazole (see Scheme 23) can be prepared starting from 5-methyl-[1,3,4]oxadiazol-2-ylamine by a base catalysed condensation with an acrylic ester. Decarboxylation to the ketone 8b can be accomplished in the case of an allylic ester through palladium (0) catalyzed deallylation in the presence of a trapping agent e.g. formic acid or amine etc. In case of an alkoxyester standard decarboxylation methods can be applied.

Amines of general formula 2, which can be used as starting materials for the preparation of compounds of formula I may be prepared as described in the following schemes.

Scheme 24

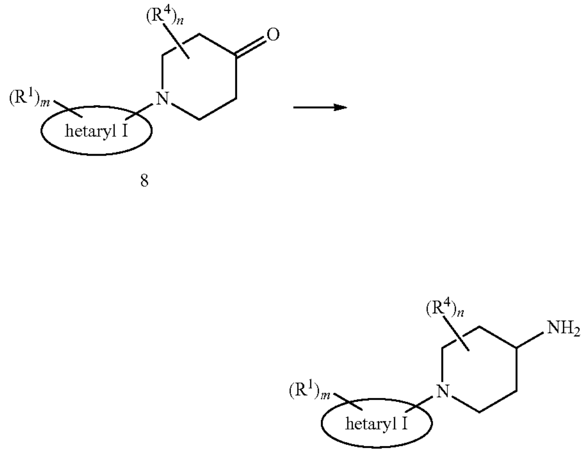

8

2

The ketones 8 can be easily converted into the amines 2 via reductive amination with ammonia, or hydroxylamine or other suitable amine precursor (see Scheme 24).

Scheme 25

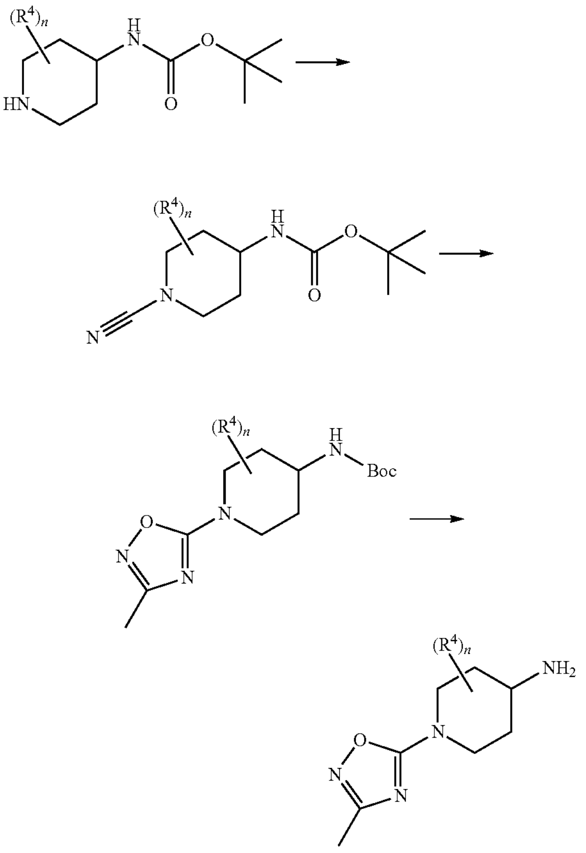

2a

Amines 2a in which heteroaryl I is a [1,2,4]oxadiazole (see Scheme 25) can be prepared starting from the N-Boc protected aminopiperidines by reaction with bromocyan and subsequent cyclization with acetamidoxime in the presence of an lewis acid like zinc(II) chloride to yield after deprotection the amines 2a.

Scheme 26

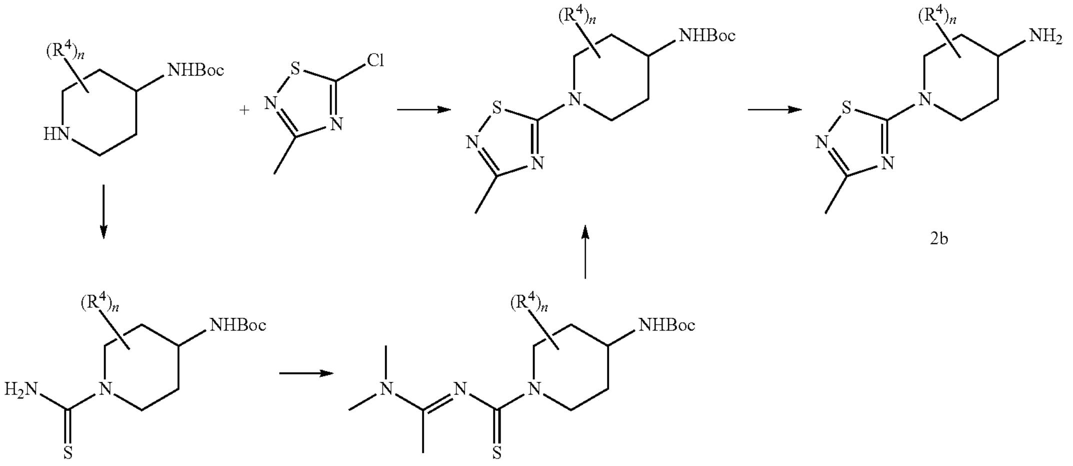

2b

Amines 2b in which heteroaryl I is a 3-methyl-[1,2,4]thiadiazole (see Scheme 26) can e.g. be prepared by palladium catalyzed coupling of 5-chloro-3-methyl-[1,2,4]thiadiazole with piperidin-4-yl-carbamic acid tert-butyl esters and subsequent cleavage of the Boc protective group in the presence of an acid. Alternatively amines 2b can be prepared from the Boc-protected aminopiperidines by reaction with an isothiocyanate source like benzoylisothiocyanate, metal isothiocyanate, thiophosgen or an activated thiourea derivative to give the corresponding thiourea derivatives. Condensation with 1,1-dimethoxy-ethyl)-dimethyl-amine and subsequent cyclization with hydroxylamine-O-sulfonic acid in the presence of a base like pyridine yields after deprotection the amines 2b.

Amines of formula 4a and 4b and ketones of formula 10a, 10b, 10c (possibly existing preferably as their hydrates depending on the nature of the ketones), which can be used as starting materials for the preparation of compounds of formula I may be prepared as described in the following schemes.

Scheme 27

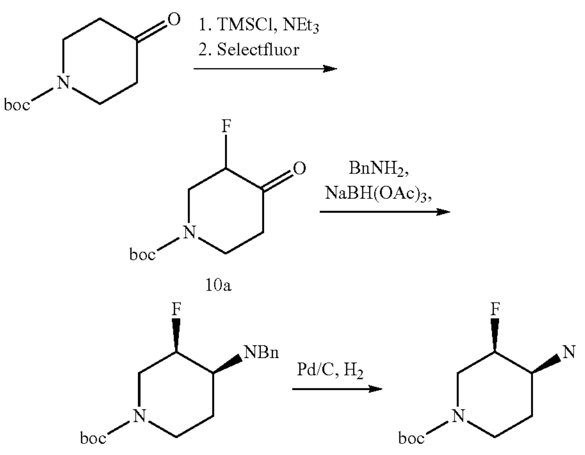

10a

4a

α-Fluorination of N-protected 4-piperidinone can be accomplished e.g. following procedures of M. van Niel et al. J. Med. Chem. 1999, 42, 2987-2104 by reaction of the corresponding silyl enol ether with an electrophilic fluorination reagent like selectfluor. Reductive amination of ketone 10a with benzylamine and sodium triacetoxy borohydride provides predominantly cis isomer of the 4-amino-3-fluoropiperidine (~5:1 cis:trans ratio). The two isomers can be separated by silica gel chromatography. Cleavage of the benzyl group by e.g. hydrogenation yields amine 4a (see Scheme 27).

Scheme 28

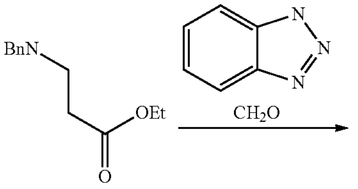

-continued

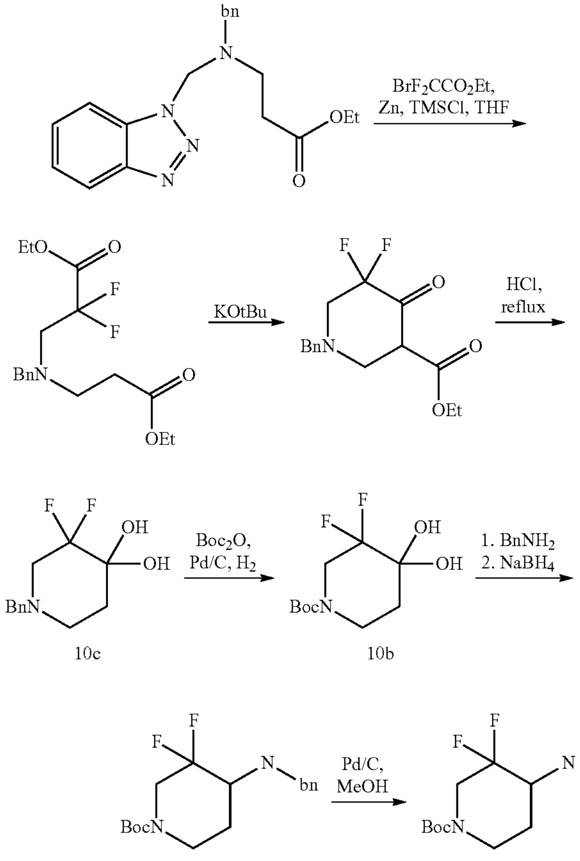

10c

10b

4b

Difluoro derivatives 10b, 10c and 4b can be prepared starting from 3-benzylamino-propionic ester (see Scheme 28). Reaction with formaldehyde and benzotriazole followed by a Reformatsky type reaction provides the corresponding acyclic di-fluoro derivative (as described by O. Bezencon et al. WO2005040120). Diekmann cyclization can e.g. be accomplished with potassium tert-butoxide in NMP. Ester hydrolysis and decarboxylation by heating in aqueous HCl solution provides 3,3-difluoropiperidone 10c as its hydrate. A protective group exchange from benzyl to boc group can be accomplished by hydrogenation in the presence on boc anhydride. Reductive amination with benzylamine and e.g. sodium borohydride followed by cleavage of benzyl group yield 3,3-difluororo-4-aminopiperidine 4b.

Scheme 29

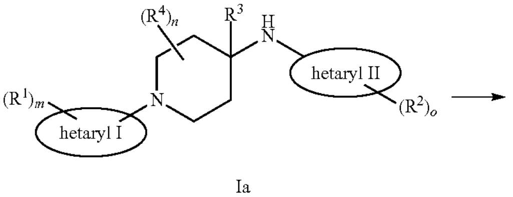

Ia
$R^1$ is Cl

-continued

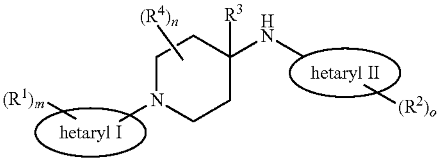

Ib
$R^1$ is OMe or OEt

Compounds of general formula Ia where $R^1$ is a halogen such as Cl can be converted into compounds of general formula Ib where $R^1$ is alkoxy, such as OMe, OEt upon treatment with the appropriate sodium salt (NaOMe or NaOEt) in a suitable alcohol solvent such as methanol or ethanol respectively (see Scheme 29).

Scheme 30

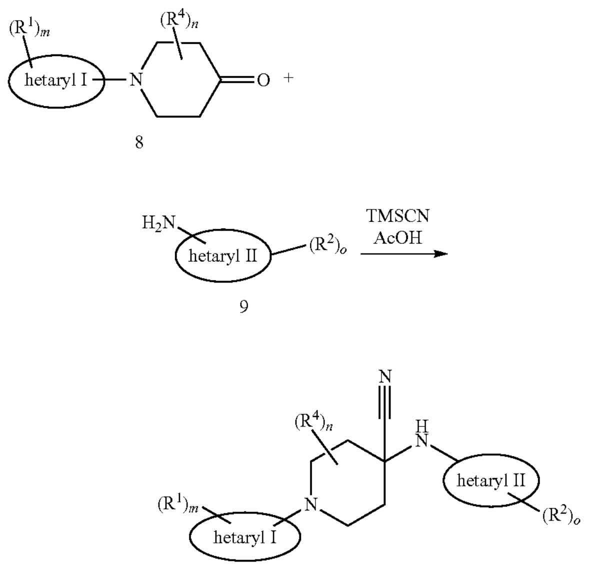

8

9

Ic

Compounds of general formula Ic with $R^3$=cyano can be prepared by reaction of compounds of general formula 8 with compounds of general formula 9 in the presence of a cyanating agent, such as trimethylsilyl cyanide, in the presence of acetic acid (see Scheme 30).

Scheme 31

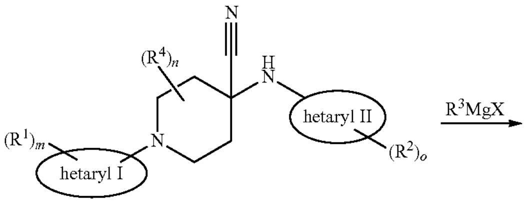

Ic

-continued

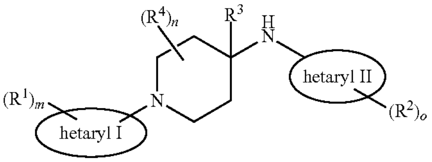

Id
$R^3$ is phenyl or methyl

Compounds of general formula Id can be prepared by reaction of compounds of general formula Ic with Grignard reagents in a suitable solvent such as THF (see Scheme 31).

Scheme 32

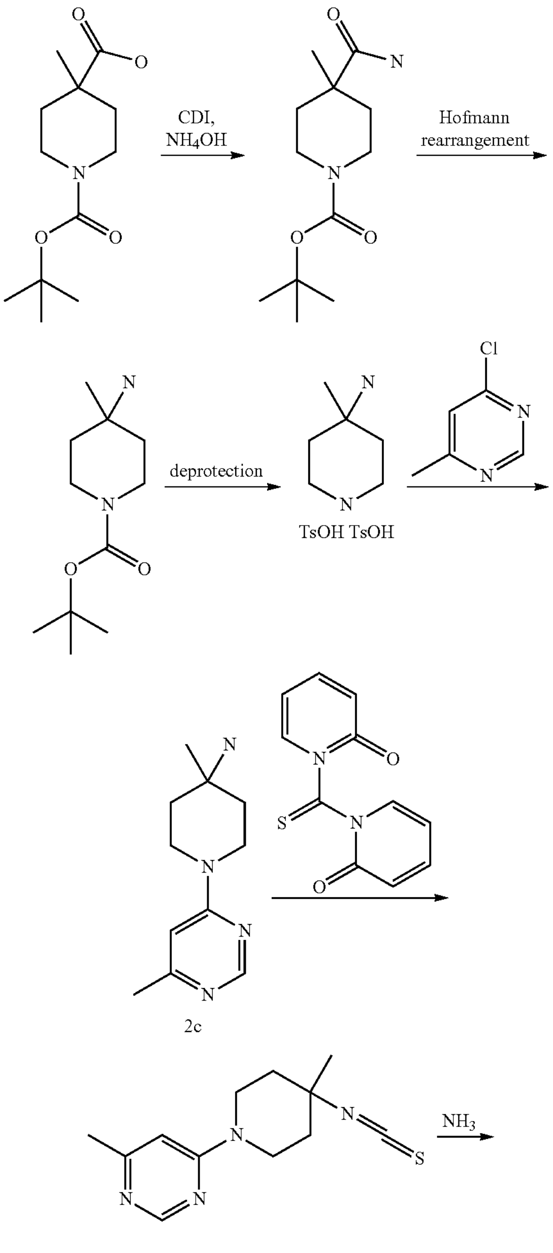

2c

-continued

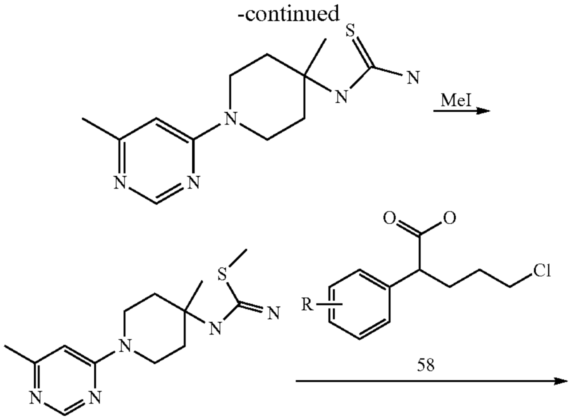

I

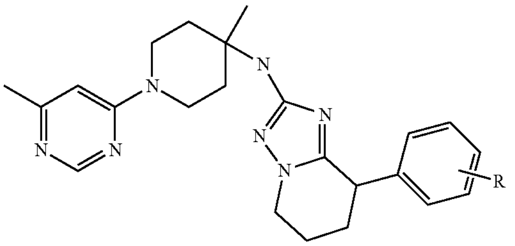

Ie

Compounds of general formula Ie can be prepared staring from N-Boc protected 4-methyl-piperidine-4-carboxylic acid (see Scheme 32) which can be treated with an activating agent such as CDI in the presence of ammonium hydroxide to form the corresponding amide. The amide can be converted to the amine upon treatment with 1,3-dibromo-5,5-dimethylhydantoin in potassium hydroxide with sodium sulfite. Cleavage of the Boc protective group provides 4-methyl-piperidin-4-ylamine which can in turn be converted to compound 2c upon reaction with 4-chloro-6-methyl-pyrimidine in the presence of potassium phosphate in a suitable solvent such as NMP. Compound 2c can be converted to the isothiocyanate by reaction with 1,1'-thiocarbonyldipyridin-2(1H)-one in a suitable solvent such as DCM. Treatment with ammonia provides the corresponding thiourea. Treatment with methyliodide in a suitable solvent such as ethanol gives the methylisothiourea which undergoes a cyclization reaction with (3-chloropropyl)-phenyl-acetic acids of formula 58 in the presence of EDCI, HOBt, DIPEA and hydrazine to yield compounds of general formula Ie.

The compounds were investigated in accordance with the test given hereinafter.

Description of γ-Secretase Assay

Cellular γ-Secretase Assay

Human neuroglioma H4 cells overexpressing human APP were plated at 30,000 cells/well/200 μL in 96-well plates in IMDM media containing 10% FCS, 0.2 mg/L Hygromycin B and incubated for 2 hours at 37° C., 5% $CO_2$ prior to adding test compounds.

Compounds for testing were dissolved in 100% $Me_2SO$ yielding in a 10 mM stock solution. Typically 12 μL of these solutions were further diluted in 1000 μL of IMDM media (w/o FCS). Subsequent 1:1 dilutions gave a ten point dose response curve. 100 μL of each dilution was added to the cells in 96-well plates. Appropriate controls using vehicle only and reference compound were applied to this assay. The final concentration of $Me_2SO$ was 0.4%.

After incubation for 22 hours at 37° C., 5% $CO_2$, 50 μL supernatant was transferred into round-bottom 96-well polypropylene plates for detection of Aβ42. 50 μL assay buffer (50 mM Tris/Cl, pH 7.4, 60 mM NaCl, 0.5% BSA, 1% TWEEN 20) was added to the wells followed by the addition of 100 μL of detection antibody (ruthenylated BAP15 0.0625 μg/mL in assay buffer). 50 μL of a premix of capture antibody (biotinylated 6E10 antibody, 1 μg/mL) and Steptavidin-coated magnetic beads (Dynal M-280, 0.125 mg/mL) were preincubated for 1 hour at room temperature before adding the assay plates. Assay plates were incubated on a shaker for 3 hours at room temperature and finally read in the Bioveris M8 Analyser according to the manufacturer's instructions (Bioveris).

Toxicity of compounds was monitored by a cell viability test of the compound-treated cells using a colorimetric assay (CellTiter 96™ AQ assay, Promega) according to the manufacturer's instructions. Briefly, after removal of 50 μL cell culture supernatant for detection of Aβ42, 20 μL of 1×MTS/PES solution was added to the cells and incubated for 30 minutes at 37° C., 5% $CO_2$. Optical density was then recorded at 490 nm.

$IC_{50}$ values for inhibition of Aβ42 secretion were calculated by nonlinear regression fit analysis using XLfit 4.0 software (IDBS).

The preferred compounds show a $IC_{50}$<0.5 (μM). In the list below are described the data for inhibition of Aβ42 secretion:

| Example No. | $EC_{50}$ Aβ42 (μM) |
|---|---|
| 1 | 0.37 |
| 2 | 0.22 |
| 3 | 0.55 |
| 4 | 0.26 |
| 5 | 0.31 |
| 6 | 0.65 |
| 7 | 1.29 |
| 8 | 0.75 |
| 9 | 1.86 |
| 10 | 0.72 |
| 11 | 0.61 |
| 12 | 1.25 |
| 13 | 0.26 |
| 14 | 1.39 |
| 15 | 0.72 |
| 16 | 0.77 |
| 17 | 0.71 |
| 18 | 0.76 |
| 19 | 1.31 |
| 20 | 1.43 |
| 21 | 0.86 |
| 22 | 2.18 |
| 23 | 0.22 |
| 24 | 1.82 |
| 25 | 0.27 |
| 26 | 1.47 |
| 27 | 4.17 |
| 28 | 0.86 |
| 29 | 0.86 |
| 30 | 0.75 |
| 31 | 0.55 |
| 32 | 1.34 |
| 33 | 6.88 |
| 34 | 1.97 |
| 35 | 1.49 |
| 36 | 0.68 |
| 37 | 0.16 |
| 38 | 0.29 |
| 39 | 0.09 |

-continued

| Example No. | $EC_{50}$ Aβ42 (μM) |
|---|---|
| 40 | 0.96 |
| 41 | 1.38 |
| 42 | 0.68 |
| 43 | 1.48 |
| 44 | 3.31 |
| 45 | 1.11 |
| 46 | 0.14 |
| 47 | 0.17 |
| 48 | 1.061 |
| 49 | 0.300 |
| 50 | 0.591 |
| 51 | 0.896 |
| 52 | 0.213 |
| 53 | 0.228 |
| 54 | 0.285 |
| 55 | 0.360 |
| 56 | 0.521 |
| 57 | 2.052 |
| 58 | 0.158 |
| 59 | 0.843 |
| 60 | 0.258 |
| 61 | 0.278 |
| 62 | 0.889 |
| 63 | 0.382 |
| 64 | 0.138 |
| 65 | 0.155 |
| 66 | 0.247 |
| 67 | 0.245 |
| 68 | 0.257 |
| 69 | 0.272 |
| 70 | 0.235 |
| 71 | 0.255 |
| 72 | 0.231 |
| 73 | 0.328 |
| 74 | 0.180 |
| 75 | 1.104 |
| 76 | 0.279 |
| 77 | 0.172 |
| 78 | 0.221 |
| 79 | 0.259 |
| 80 | 0.143 |
| 81 | 0.231 |
| 82 | 0.293 |
| 83 | 1.142 |
| 84 | 0.306 |
| 85 | 0.272 |
| 86 | 0.180 |
| 87 | 0.551 |
| 88 | 0.148 |
| 89 | 0.204 |
| 90 | 0.523 |
| 91 | 0.243 |
| 92 | 0.254 |
| 93 | 0.357 |
| 94 | 0.348 |
| 95 | 0.843 |
| 96 | 0.232 |
| 97 | 0.727 |
| 98 | 0.410 |
| 99 | 0.500 |
| 100 | 0.912 |
| 101 | 0.399 |
| 102 | 0.164 |
| 103 | 0.780 |
| 104 | 0.519 |
| 105 | 0.360 |
| 106 | 0.470 |
| 107 | 0.707 |
| 108 | 2.516 |
| 109 | 0.285 |
| 110 | 0.804 |
| 111 | 0.492 |
| 112 | 0.448 |
| 113 | 0.736 |
| 114 | 0.270 |
| 115 | 0.328 |
| 116 | 0.111 |

-continued

| Example No. | $EC_{50}$ Aβ42 (μM) |
|---|---|
| 117 | 0.368 |
| 118 | 0.338 |
| 119 | 0.169 |
| 120 | 0.255 |
| 121 | 0.621 |
| 122 | 0.786 |
| 123 | 0.210 |
| 124 | 0.109 |
| 125 | 0.348 |
| 126 | 0.368 |
| 127 | 0.851 |
| 128 | 0.115 |
| 129 | 0.597 |
| 130 | 0.226 |
| 131 | 0.467 |
| 132 | 0.280 |
| 133 | 0.376 |
| 134 | 0.187 |
| 135 | 0.196 |
| 136 | 0.192 |
| 137 | 0.769 |
| 138 | 0.097 |
| 139 | 0.165 |
| 140 | 0.157 |
| 141 | 0.160 |
| 142 | 0.333 |
| 143 | 1.735 |
| 144 | 0.126 |
| 145 | 0.443 |
| 146 | 0.404 |
| 147 | 0.155 |
| 148 | 0.177 |
| 149 | 0.394 |
| 150 | 0.422 |
| 151 | 0.191 |
| 152 | 0.325 |
| 153 | 0.572 |
| 154 | 1.208 |
| 155 | 0.380 |
| 156 | 0.187 |
| 157 | 0.361 |
| 158 | 0.545 |
| 159 | 0.578 |
| 160 | 1.134 |
| 161 | 0.450 |
| 162 | 0.645 |
| 163 | 0.827 |
| 164 | 0.786 |
| 165 | 0.758 |
| 166 | 0.841 |
| 167 | 1.926 |
| 168 | 1.431 |
| 169 | 0.051 |
| 170 | 0.393 |
| 171 | 0.501 |
| 172 | 0.480 |
| 173 | 0.867 |
| 174 | 0.564 |
| 175 | 0.659 |
| 176 | 0.542 |
| 177 | 0.722 |
| 178 | 1.181 |
| 179 | 1.474 |
| 180 | 0.056 |
| 181 | 0.129 |
| 182 | 0.180 |
| 183 | 0.174 |
| 184 | 0.279 |
| 185 | 0.285 |
| 186 | 0.186 |
| 187 | 0.312 |
| 188 | 0.463 |
| 189 | 0.410 |
| 190 | 0.497 |
| 191 | 0.042 |
| 192 | 0.408 |
| 193 | 0.519 |

-continued

| Example No. | $EC_{50}$ Aβ42 (μM) |
|---|---|
| 194 | 1.118 |
| 195 | 0.727 |
| 196 | 0.379 |
| 197 | 0.941 |
| 198 | 0.535 |
| 199 | 0.157 |
| 200 | 0.411 |
| 201 | 0.455 |
| 202 | 0.283 |
| 203 | 0.259 |
| 204 | 0.220 |
| 205 | 0.332 |
| 206 | 0.246 |
| 207 | 0.457 |
| 208 | 0.318 |
| 209 | 0.796 |
| 210 | 0.186 |
| 211 | 0.872 |
| 212 | 0.161 |
| 213 | 0.455 |
| 214 | 0.512 |
| 215 | 0.488 |
| 216 | 0.334 |
| 217 | 0.190 |
| 218 | 0.506 |
| 219 | 0.155 |
| 220 | 0.276 |
| 221 | 0.185 |
| 222 | 0.301 |
| 223 | 0.205 |
| 224 | 0.506 |
| 225 | 0.174 |
| 226 | 0.170 |
| 227 | 1.571 |
| 228 | 0.131 |
| 229 | 0.185 |
| 230 | 0.311 |
| 231 | 0.694 |
| 232 | 0.484 |
| 233 | 1.495 |
| 234 | 1.162 |
| 235 | 1.156 |
| 236 | 1.067 |
| 237 | 0.723 |
| 238 | 0.253 |
| 239 | 0.284 |
| 240 | 0.215 |
| 241 | 0.246 |
| 242 | 0.377 |
| 243 | 0.166 |
| 244 | 0.385 |
| 245 | 0.321 |
| 246 | 0.423 |
| 247 | 0.233 |
| 248 | 0.363 |
| 249 | 0.965 |
| 250 | 0.075 |
| 251 | 0.205 |
| 252 | 0.434 |
| 253 | 0.285 |
| 254 | 0.496 |
| 255 | 0.67 |
| 256 | 0.256 |
| 257 | 0.798 |
| 258 | 0.21 |
| 259 | 0.818 |
| 260 | 1.934 |
| 261 | 1.68 |
| 262 | 0.265 |
| 263 | 0.624 |
| 264 | 0.945 |
| 265 | 2.77 |
| 266 | 1.404 |
| 267 | 0.487 |
| 268 | 1.447 |
| 269 | 0.595 |
| 270 | 1.063 |

-continued

| Example No. | $EC_{50}$ Aβ42 (μM) |
|---|---|
| 271 | 1.107 |
| 272 | 1.127 |
| 273 | 1.11 |
| 274 | 1.356 |
| 275 | 0.424 |
| 276 | 0.558 |
| 277 | 0.416 |
| 278 | 1.539 |
| 279 | — |
| 280 | — |
| 281 | — |
| 282 | — |
| 283 | — |

The present invention provides pharmaceutical compositions containing compounds of formula I and/or pharmaceutically acceptable salts of the compounds of formula I in conjunction with a pharmaceutically acceptable acid addition salt. Such compositions can be administered orally, e.g. in the form of tablets, coated tablets, dragées, hard and soft gelatin capsules, solutions, emulsions or suspensions. The administration can, however, also be effected rectally, e.g. in the form of suppositories, parenterally, e.g. in the form of injection solutions.

The pharmaceutical compositions of the invention can contain pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| | | Tablet Formulation (Wet Granulation) mg/tablet | | | |
|---|---|---|---|---|---|
| Item | Ingredients | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
|---|---|---|---|---|---|
| Item | Ingredients | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

Example 1

[8-(4-Fluoro-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine

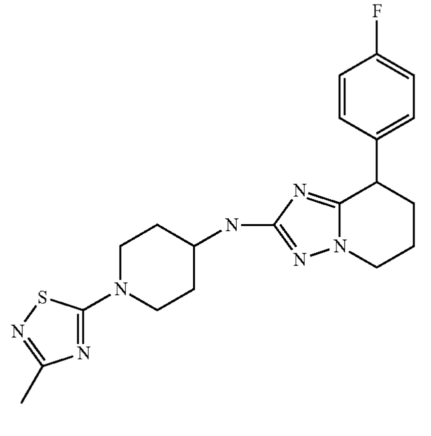 [SMILES: Cc1nsc(N2CCC(Nc3nc4n(n3)CCCC4c3ccc(F)cc3)CC2)n1]

a) 5-Chloro-3-methyl-[1,2,4]thiadiazole

To a suspension of acetamidine hydrochloride (7 g, 0.07 mol) in dichloromethane (75 mL) was added perchloromethyl mercaptan (12 g, 0.063 mol) at room temperature under an argon atmosphere. After cooling to −10° C. a solution of sodium hydroxide (14 g, 0.348 mol) in water (22.5 mL) was added slowly. The reaction mixture was stirred at 0° C. for 12 hours. Water was added, the aqueous phase was extracted with dichloromethane, the combined organic phases were dried over sodium sulfate and the solvent was evaporated. The residue was purified by short-path vacuum distillation (75° C., 30 mbar) to give the title compound as a colorless liquid.

$^1$H NMR ($CDCl_3$, 300 MHz): (ppm)=2.64 (s, 3H).

b) 8-(3-Methyl-[1,2,4]thiadiazol-5-yl)-1,4-dioxa-8-aza-spiro[4.5]decane

To a prestirred solution (10 minutes at room temperature) of palladium(II) acetate (180 mg, 0.001 mmol) and 2-(dicyclohexylphosphino)biphenyl (572 mg, 0.002 mmol) in dioxane (10 mL) were added 1,4-dioxa-8-azaspiro(4,5)decane (1.3 mL, 10 mmol), 5-chloro-3-methyl-[1,2,4]thiadiazole (1.48 g, 11 mmol) and sodium tert-butylate (1.47 g, 15 mmol) and heated in the microwave at 130° C. for 15 minutes. The reaction mixture was diluted with half saturated brine, the aqueous phase was extracted with ethyl acetate, the combined organic phases were dried over sodium sulfate, the solvent was evaporated and the residue was purified by silica gel chromatography using ethyl acetate as eluent. The title compound was obtained as a light yellow solid (1.87 g, 77%).

MS ISP (m/e): 242.4 (23) [$(M+H)^+$].

$^1$H NMR ($CDCl_3$, 300 MHz): (ppm)=4.00 (s, 4H), 3.64-3.60 (m, 4H), 2.40 (s, 3H), 1.83-1.79 (m, 4H).

c) 1-(3-Methyl-[1,2,4]thiadiazol-5-yl)-piperidin-4-one

To a solution of 8-(3-methyl-[1,2,4]thiadiazol-5-yl)-1,4-dioxa-8-aza-spiro[4.5]decane (1.75 g, 7 mmol) in acetone (15 mL) was added 2 N aqueous HCl solution (50 mL) and stirred at 50° C. for 3 hours. The reaction mixture was cooled to 0° C. and saturated aqueous $NaHCO_3$ solution was added dropwise until pH 7. The aqueous phase was extracted three times with dichloromethane, the combined organic phases were dried over sodium sulfate and the solvent was evaporated to give the title compound as a light brown solid (1.29 g, 90%).

MS ISP (m/e): 198.3 (100) [$(M+H)^+$].

$^1$H NMR ($CDCl_3$, 300 MHz): (ppm)=3.88-3.84 (m, 4H), 2.64-2.60 (m, 4H), 2.44 (s, 3H).

d) 3-(4-Fluoro-phenol)-pyridin-2-ylamine

A mixture of 2-amino-3-bromopyridine (2.0 g, 11.2 mmol), 4-fluorophenyl boronic acid (3.23 g, 22.4 mmol), dichloro[1,1'-bis(diphenylphosphino)-ferrocene]palladium (II) dichloromethane adduct (733 mg, 0.001 mmol) and an aqueous solution of $Na_2CO_3$ (2 N, 11.2 mL, 22.4 mmol) in dioxane (30 mL) was heated to 110° C. for 2 hours. The reaction mixture was diluted with water and extracted with diethyl ether, the combined organic phases were dried over sodium sulfate, the solvent was evaporated and the residue purified by silica gel chromatography using n-heptane/diethyl ether as eluent. The title compound was obtained as a light yellow solid (1.95 g, 92%).

MS ISP (m/e): 189.3 (100) [$(M+H)^+$].

$^1H$ NMR ($CDCl_3$, 300 MHz): (ppm)=8.08-8.06 (m, 1H), 7.44-7.39 (m, 2H), 7.34-7.31 (m, 1H), 7.17-7.12 (m, 2H), 6.76-6.72 (m, 1H), 4.57 (bs, 2H).

e) N-(3-(4-Fluoro-phenyl)-pyridin-2-yl)-N'-ethoxy-carbonyl-thiourea

To a solution of 3-(4-fluoro-phenyl)-pyridin-2-ylamine (200 mg, 1.06 mmol) in dioxane (10 mL) was added ethoxy-carbonyl isothiocyanate (141 μL, 1.17 mmol) and stirred at room temperature for 12 hours. The solvent was evaporated and the residue was used for the next step without purification. The title compound was obtained as a light yellow solid (340 mg, 100%).

MS ISP (m/e): 320.1 (100) $[(M+H)^+]$.

f) 8-(4-Fluoro-phenyl)-[1,2,4]triazolo[1,5-a]pyridin-2-ylamine

To a solution of hydroxylamine hydrochloride (370 mg, 5.32 mmol) and N,N-diisopropylethylamine (543 μL, 3.19 mmol) in MeOH (2 mL) and EtOH (2 mL) was added a solution of N-(3-(4-fluoro-phenyl)-pyridin-2-yl)-N'-ethoxy-carbonyl-thiourea (340 mg, 1.06 mmol) in MeOH (2 mL) and EtOH (2 mL). The reaction mixture was stirred at room temperature for 1 hour and then at 60° C. for 3 hours. The solvents were evaporated and saturated aqueous $NaHCO_3$ solution was added to the residue. The aqueous phase was extracted with $CH_2Cl_2$, the combined organic phases were dried over sodium sulfate, the solvent was evaporated and the residue purified by silica gel chromatography using dichloromethane/methanol (with 10% ammonia) as eluent. The title compound was obtained as a white solid (205 mg, 84%).

MS ISP (m/e): 229.2 (100) $[(M+H)^+]$.

$^1H$ NMR ($CDCl_3$, 300 MHz): (ppm)=8.31-8.28 (m, 1H), 7.96-7.91 (m, 2H), 7.50-7.47 (m, 1H), 7.22-7.16 (m, 2H), 6.94-6.89 (m, 1H), 4.51 (bs, 2H).

g) 8-(4-Fluoro-phenyl)-5,6,7,8-tetrahydro-[1,2,4]triazolo[1,5-a]pyridin-2-ylamine 8-(4-Fluoro-phenyl)-[1,2,4]triazolo[1,5-a]pyridin-2-ylamine (232 mg, 1.02 mmol) in EtOH (10 mL) and aqueous HCl solution (25%, 162 L, 1.12 mmol) was hydrogenated in the presence of palladium on charcoal (10%, 232 mg, 0.22 mmol) at 50 bar and 50° C. for 18 hours. The catalyst was filtered off, washed thoroughly with EtOH and the solvent was removed from the combined filtrates. Saturated aqueous $NaHCO_3$ solution was added to the residue. The aqueous phase was extracted with $CH_2Cl_2$, the combined organic phases were dried over sodium sulfate, the solvent was evaporated and the residue purified by silica gel chromatography using dichloromethane/methanol (with 10% ammonia) as eluent. The title compound was obtained as a white solid (174 mg, 74%).

MS ISP (m/e): 233.1 (100) $[(M+H)^+]$.

$^1H$ NMR ($CDCl_3$, 300 MHz): (ppm)=7.14-7.09 (m, 2H), 7.04-6.98 (m, 2H), 4.14-4.03 (m, 5H), 2.30-2.24 (m, 1H), 2.15-1.90 (m, 3H).

h) [8-(4-Fluoro-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine To a solution of 8-(4-fluoro-phenyl)-5,6,7,8-tetrahydro-[1,2,4]triazolo[1,5-a]pyridin-2-ylamine (60 mg, 0.258 mmol) and 1-(3-methyl-[1,2,4]thiadiazol-5-yl)-piperidin-4-one (76 mg, 0.387 mmol) in dry dichloroethane (3 mL) was added tetraisopropyl-orthotitanate (236 μL, 0.775 mmol) under an argon atmosphere and heated to 85° C. for 12 hours. The reaction mixture was cooled to room temperature, sodium borohydride (20 mg, 0.517 mmol) and ethanol (1.5 mL) were added and stirred at room temperature for 3 hour and at 50° C. for 30 minutes. The reaction mixture was cooled to room temperature and evaporated. An aqueous solution of $Na_2CO_3$ (2M) was added to the residue. The aqueous phase was extracted with ethyl acetate, the combined organic phases were dried over sodium sulfate, the solvent was evaporated and the residue purified by silica gel chromatography using dichloromethane/methanol (with 10% ammonia) as eluent. The title compound was obtained as a white solid (28.8 mg, 27%).

MS ISP (m/e): 414.3 (100) $[(M+H)^+]$.

$^1H$ NMR ($CDCl_3$, 300 MHz): (ppm)=7.13-7.09 (m, 2H), 7.04-6.98 (m, 2H), 4.14-4.01 (m, 4H), 3.86-3.68 (m, 3H), 3.35-3.25 (m, 2H), 2.40 (s, 3H), 2.31-1.91 (m, 6H), 1.64-1.51 (m, 2H).

Example 2

[8-(4-Fluoro-phenyl)-[1,2,4]triazolo[1,5-a]pyridin-2-yl]-[1-(3-methyl-[1,2,4]thiadiazol-5-yl)-piperidin-4-yl]-amine

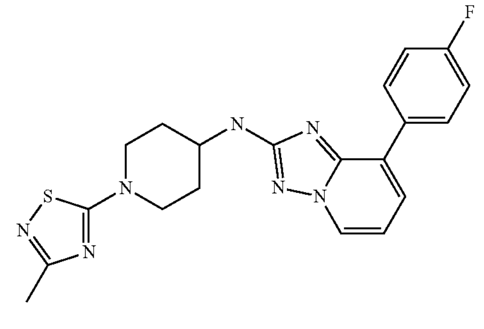 [SMILES: Cc1nsc(N2CCC(Nc3nc4c(-c5ccc(F)cc5)cccn4n3)CC2)n1]

Prepared in analogy to example 1 step h) starting with 1-(3-methyl-[1,2,4]thiadiazol-5-yl)-piperidin-4-one (example 1c) and 8-(4-fluoro-phenyl)-[1,2,4]triazolo[1,5-a]pyridin-2-ylamine (example 1f). The title compound was obtained as a white solid (yield=28%).

MS ISP (m/e): 410.2 (100) $[(M+H)^+]$.

$^1H$ NMR ($CDCl_3$, 300 MHz): (ppm)=8.32-8.30 (m, 1H), 7.96-7.91 (m, 2H), 7.50-7.47 (m, 1H), 7.21-7.15 (m, 2H), 6.92-6.87 (m, 1H), 4.53-4.51 (m, 1H), 3.99-3.86 (m, 3H), 3.40-3.31 (m, 2H), 2.42 (s, 3H), 2.29-2.24 (m, 2H), 1.73-1.60 (m, 2H).

Example 3

[5-(4-Fluoro-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine

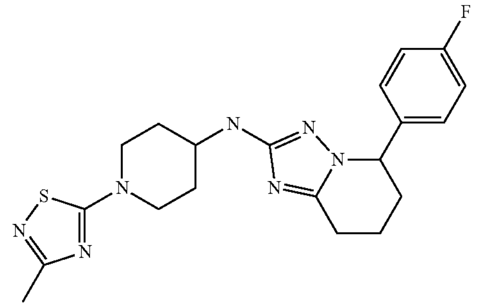 [SMILES: Cc1nsc(N2CCC(Nc3nc4n(n3)C(c3ccc(F)cc3)CCC4)CC2)n1]

Prepared in analogy to example 1 step h) starting from 1-(3-methyl-[1,2,4]thiadiazol-5-yl)-piperidin-4-one (example 1c) and 5-(4-fluoro-phenyl)-5,6,7,8-tetrahydro-[1,2,4]triazolo[1,5-a]pyridin-2-ylamine. The latter compound can be prepared in analogy to example 1 steps d-g) starting from 2-amino-6-bromo-pyridine. The title compound was obtained as a white solid (yield=30%).

MS ISP (m/e): 414.4 (100) [(M+H)$^+$].

$^1$H NMR ($CDCl_3$, 300 MHz): (ppm)=7.06-6.94 (m, 4H), 5.28-5.24 (m, 1H), 4.00-3.97 (m, 1H), 3.87-3.69 (m, 3H), 3.31-3.21 (m, 2H), 2.92-2.85 (m, 2H), 2.40 (s, 3H), 2.38-2.32 (m, 1H), 2.18-1.83 (m, 5H), 1.53-1.49 (m, 2H).

Example 4

[5-(4-Fluoro-phenyl)-[1,2,4]triazolo[1,5-a]pyridin-2-yl]-[1-(3-methyl-[1,2,4]thiadiazol-5-yl)-piperidin-4-yl]-amine

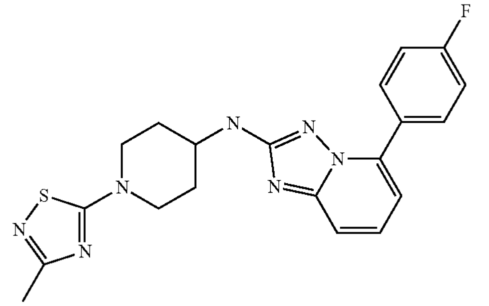 [SMILES: Cc1nsc(N2CCC(Nc3nc4cccc(-c5ccc(F)cc5)n4n3)CC2)n1]

Prepared in analogy to example 1 step h) starting from 1-(3-methyl-[1,2,4]thiadiazol-5-yl)-piperidin-4-one (example 1c) and 5-(4-fluoro-phenyl)-[1,2,4]triazolo[1,5-a]pyridin-2-ylamine. The latter compound can be prepared in analogy to example 1 steps d-f) starting from 2-amino-6-bromo-pyridine. The title compound was obtained as a white solid.

MS ISP (m/e): 410.2 (100) [(M+H)$^+$].

$^1$H NMR ($CDCl_3$, 300 MHz): (ppm)=7.95-7.90 (m, 2H), 7.49-7.39 (m, 2H), 7.23-7.18 (m, 2H), 6.90-6.87 (m, 1H), 4.47-4.44 (m, 1H), 4.04-3.87 (m, 3H), 3.39-3.30 (m, 2H), 2.41 (s, 3H), 2.27-2.21 (m, 2H), 1.71-1.59 (m, 2H).

Example 5

[1-(3,5-Dichloro-benzyl)-1H-[1,2,4]triazol-3-yl]-[1-(3-methyl-[1,2,4]thiadiazol-5-yl)-piperidin-4-yl]-amine

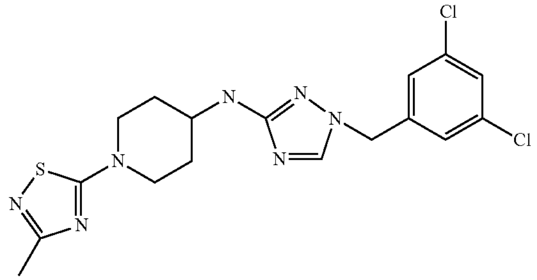 [SMILES: Cc1nsc(N2CCC(Nc3ncn(Cc4cc(Cl)cc(Cl)c4)n3)CC2)n1]

a) 1-(3,5-Dichloro-benzyl)-1H-[1,2,4]triazol-3-ylamine

3-Amino-1,2,4-triazole (420 mg, 5.0 mmol) was dissolved in DMF (3 mL) under argon atmosphere, sodium hydride (55%, 218 mg, 5.0 mmol) was added at room temperature in small portions and stirred at room temperature for 1 hour. The reaction mixture was cooled to 0° C., 3,5-dichlorobenzyl chloride (977 mg, 5.0 mmol) was added and the reaction mixture was stirred at room temperature for 3 hours. The reaction mixture was poured onto water and the aqueous phase extracted with ethyl acetate. The combined organic phases were dried over $Na_2SO_4$, filtered, the solvents were evaporated and the residue purified by silica gel chromatography using dichloromethane/methanol as eluent. The title compound was obtained as a white solid (357 mg, 29%).

MS ISP (m/e): 243.2 (100) [(M+H)$^+$].

$^1$H NMR ($CDCl_3$, 300 MHz): (ppm)=7.75 (s, 1H), 7.34-7.32 (m, 1H), 7.13-7.12 (m, 2H), 5.07 (s, 2H).

b) [1-(3,5-Dichloro-benzyl)-1H-[1,2,4]triazol-3-yl]-[1-(3-methyl-[1,2,4]thiadiazol-5-yl)-piperidin-4-yl]-amine Prepared in analogy to example 1 step h) starting from 1-(3-methyl-[1,2,4]thiadiazol-5-yl)-piperidin-4-one (example 1c) and 1-(3,5-dichloro-benzyl)-1H-[1,2,4]triazol-3-ylamine. The title compound was obtained as a white solid (yield=27%).

MS ISP (m/e): 424.2 (100) [(M+H)$^+$].

$^1$H NMR ($CDCl_3$, 300 MHz): (ppm)=7.75 (s, 1H), 7.34-7.33 (m, 1H), 7.13-7.12 (m, 2H), 5.09 (s, 2H), 4.12-4.10 (m, 1H), 3.91-3.70 (m, 3H), 3.35-3.26 (m, 2H), 2.41 (s, 3H), 2.23-2.15 (m, 2H), 1.65-1.52 (m, 2H).

Example 6

[1-(4-Methyl-benzyl)-1H-[1,2,4]triazol-3-yl]-[1-(3-methyl-[1,2,4]thiadiazol-5-yl)-piperidin-4-yl]-amine

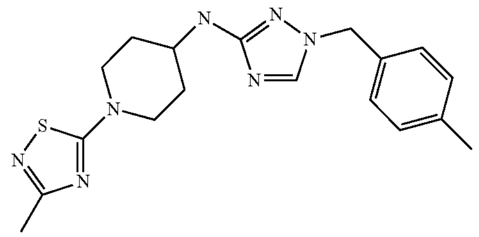 [SMILES: Cc1ccc(Cn2cnc(NC3CCN(c4nc(C)ns4)CC3)n2)cc1]

Prepared in analogy to example 1 step h) starting from 1-(3-methyl-[1,2,4]thiadiazol-5-yl)-piperidin-4-one (example 1c) and 1-(4-methyl-benzyl)-1H-[1,2,4]triazol-3-ylamine. The title compound was obtained as a white solid.

MS ISP (m/e): 370.2 (100) [(M+H)$^+$].

$^1$H NMR ($CDCl_3$, 300 MHz): (ppm)=7.61 (s, 1H), 7.17 (m, 4H), 5.09 (s, 2H), 4.13-4.11 (m, 1H), 3.89-3.70 (m, 3H), 3.34-3.25 (m, 2H), 2.40 (s, 3H), 2.35 (s, 3H), 2.21-2.16 (m, 2H), 1.64-1.51 (m, 2H).

Example 7

[1-(3-Fluoro-benzyl)-1H-[1,2,4]triazol-3-yl]-[1-(3-methyl-[1,2,4]thiadiazol-5-yl)-piperidin-4-yl]-amine

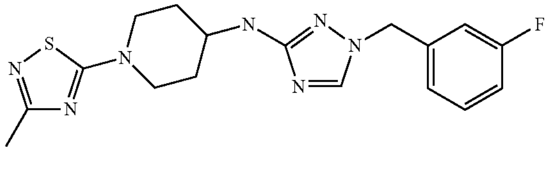 [SMILES: Cc1nsc(N2CCC(Nc3ncn(Cc4cccc(F)c4)n3)CC2)n1]

Prepared in analogy to example 1 step h) starting from 1-(3-methyl-[1,2,4]thiadiazol-5-yl)-piperidin-4-one (example 1c) and 1-(3-fluoro-benzyl)-1H-[1,2,4]triazol-3-ylamine. The title compound was obtained as a colorless oil.

MS ISP (m/e): 374.1 (100) [(M+H)$^+$].

$^1$H NMR ($CDCl_3$, 300 MHz): (ppm)=7.70 (s, 1H), 7.36-7.30 (m, 1H), 7.05-6.92 (m, 3H), 5.13 (s, 2H), 4.19-4.17 (m, 1H), 3.88-3.69 (m, 3H), 3.34-3.24 (m, 2H), 2.40 (s, 3H), 2.21-2.15 (m, 2H), 1.64-1.51 (m, 2H).

Example 8

[1-(3-Methyl-[1,2,4]thiadiazol-5-yl)-piperidin-4-yl]-[1-(3-trifluoromethyl-benzyl)-1H-[1,2,4]triazol-3-yl]-amine

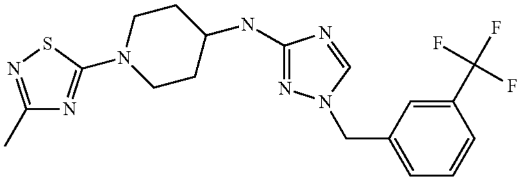 [SMILES: Cc1nsc(N2CCC(Nc3ncn(Cc4cccc(C(F)(F)F)c4)n3)CC2)n1]

Prepared in analogy to example 1 step h) starting from 1-(3-methyl-[1,2,4]thiadiazol-5-yl)-piperidin-4-one (example 1c) and 1-(3-trifluoromethyl-benzyl)-1H-[1,2,4]triazol-3-ylamine. The title compound was obtained as a white solid.

MS ISP (m/e): 424.3 (100) [(M+H)$^+$].

$^1$H NMR ($CDCl_3$, 300 MHz): (ppm)=7.73 (s, 1H), 7.61-7.58 (m, 1H), 7.52-7.41 (m, 3H), 5.19 (s, 2H), 4.20-4.18 (m, 1H), 3.89-3.70 (m, 3H), 3.33-3.24 (m, 2H), 2.40 (s, 3H), 2.21-2.15 (m, 2H), 1.64-1.51 (m, 2H).

Example 9

[1-(4-Fluoro-benzyl)-1H-[1,2,4]triazol-3-yl]-[1-(3-methyl-[1,2,4]thiadiazol-5-yl)-piperidin-4-yl]-amine

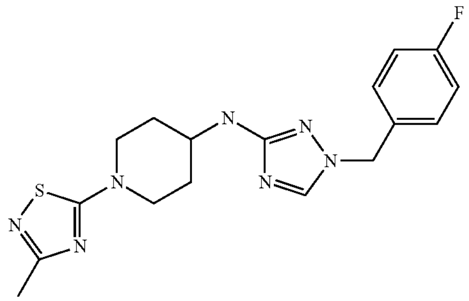 [SMILES: Cc1nsc(N2CCC(Nc3ncn(Cc4ccc(F)cc4)n3)CC2)n1]

Prepared in analogy to example 1 step h) starting from 1-(3-methyl-[1,2,4]thiadiazol-5-yl)-piperidin-4-one (example 1c) and 1-(4-fluoro-benzyl)-1H-[1,2,4]triazol-3-ylamine. The title compound was obtained as a white solid.

MS ISP (m/e): 374.2 (100) [(M+H)$^+$].

$^1$H NMR ($CDCl_3$, 300 MHz): (ppm)=7.65 (s, 1H), 7.27-7.22 (m, 2H), 7.09-7.02 (m, 2H), 5.10 (s, 2H), 4.17-4.14 (m, 1H), 3.88-3.69 (m, 3H), 3.34-3.24 (m, 2H), 2.40 (s, 3H), 2.20-2.15 (m, 2H), 1.64-1.51 (m, 2H).

Example 10

[1-(4-Chloro-benzyl)-1H-[1,2,4]triazol-3-yl]-[1-(3-methyl-[1,2,4]thiadiazol-5-yl)-piperidin-4-yl]-amine

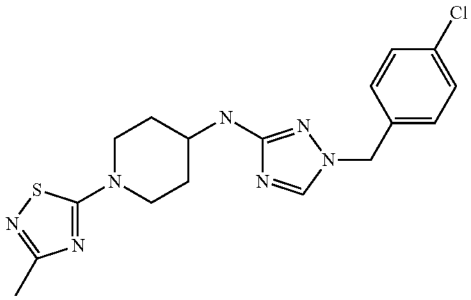 [SMILES: Cc1nsc(N2CCC(Nc3ncn(Cc4ccc(Cl)cc4)n3)CC2)n1]

Prepared in analogy to example 1 step h) starting from 1-(3-methyl-[1,2,4]thiadiazol-5-yl)-piperidin-4-one (example 1c) and 1-(4-chloro-benzyl)-1H-[1,2,4]triazol-3-ylamine. The title compound was obtained as a white solid.

MS ISP (m/e): 390.2 (100) [(M+H)$^+$].

$^1$H NMR ($CDCl_3$, 300 MHz): (ppm)=7.65 (s, 1H), 7.36-7.33 (m, 2H), 7.20-7.17 (m, 2H), 5.11 (s, 2H), 4.13-4.11 (m, 1H), 3.88-3.67 (m, 3H), 3.34-3.25 (m, 2H), 2.40 (s, 3H), 2.21-2.15 (m, 2H), 1.64-1.52 (m, 2H).

Example 11

[1-(3-Methyl-[1,2,4]thiadiazol-5-yl)-piperidin-4-yl]-[1-(3,4,5-trifluoro-benzyl)-1H-[1,2,4]triazol-3-yl]-amine

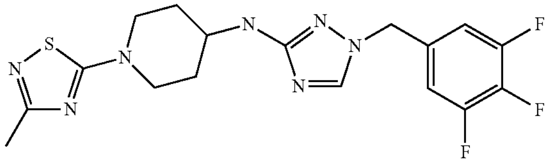 [SMILES: Cc1nsc(N2CCC(Nc3ncn(Cc4cc(F)c(F)c(F)c4)n3)CC2)n1]

Prepared in analogy to example 1 step h) starting from 1-(3-methyl-[1,2,4]thiadiazol-5-yl)-piperidin-4-one (example 1c) and 1-(3,4,5-trifluoro-benzyl)-1H-[1,2,4]triazol-3-ylamine. The title compound was obtained as a yellow solid.

MS ISP (m/e): 410.3 (100) [(M+H)$^+$].

$^1$H NMR ($CDCl_3$, 300 MHz): (ppm)=7.75 (s, 1H), 6.90-6.85 (m, 2H), 5.07 (s, 2H), 4.17-4.14 (m, 1H), 3.90-3.66 (m, 3H), 3.35-3.25 (m, 2H), 2.41 (s, 3H), 2.21-2.16 (m, 2H), 1.64-1.53 (m, 2H).

Example 12

[1-(2-Chloro-benzyl)-1H-[1,2,4]triazol-3-yl]-[1-(3-methyl-[1,2,4]thiadiazol-5-yl)-piperidin-4-yl]-amine

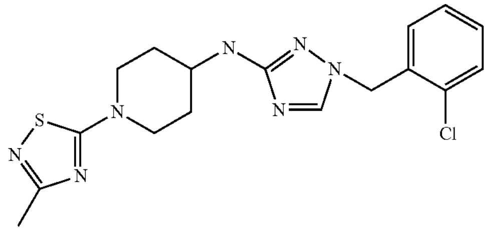 [SMILES: Cc1nsc(N2CCC(Nc3ncn(Cc4ccccc4Cl)n3)CC2)n1]

Prepared in analogy to example 1 step h) starting from 1-(3-methyl-[1,2,4]thiadiazol-5-yl)-piperidin-4-one (example 1c) and 1-(3-chloro-benzyl)-1H-[1,2,4]triazol-3-ylamine. The title compound was obtained as a yellow solid.

MS ISP (m/e): 390.3 (100) [(M+H)$^+$].

$^1$H NMR ($CDCl_3$, 300 MHz): (ppm)=7.73 (s, 1H), 7.43-7.15 (m, 4H), 5.26 (s, 2H), 4.17-4.14 (m, 1H), 3.90-3.70 (m, 3H), 3.34-3.25 (m, 2H), 2.40 (s, 3H), 2.21-2.16 (m, 2H), 1.65-1.52 (m, 2H).

Example 13

[1-(3-Chloro-benzyl)-1H-[1,2,4]triazol-3-yl]-[1-(3-methyl-[1,2,4]thiadiazol-5-yl)-piperidin-4-yl]-amine

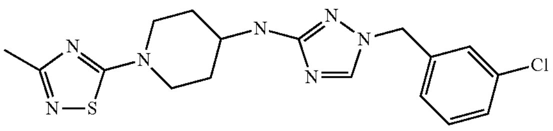 [SMILES: Cc1nsc(N2CCC(Nc3ncn(Cc4cccc(Cl)c4)n3)CC2)n1]

Prepared in analogy to example 1 step h) starting from 1-(3-methyl-[1,2,4]thiadiazol-5-yl)-piperidin-4-one (example 1c) and 1-(3-chloro-benzyl)-1H-[1,2,4]triazol-3-ylamine. The title compound was obtained as a colorless oil.

MS ISP (m/e): 390.2 (100) [(M+H)$^+$].

$^1$H NMR ($CDCl_3$, 300 MHz): (ppm)=7.71 (s, 1H), 7.32-7.30 (m, 2H), 7.25-7.24 (m, 1H), 7.14-7.11 (m, 1H), 5.12 (s, 2H), 4.14-4.12 (m, 1H), 3.89-3.72 (m, 3H), 3.35-3.26 (m, 2H), 2.41 (s, 3H), 2.22-2.16 (m, 2H), 1.66-1.52 (m, 2H).

Example 14

[1-(2,4-Dichloro-benzyl)-1H-pyrazol-3-yl]-[1-(3-methyl-[1,2,4]thiadiazol-5-yl)-piperidin-4-yl]-amine

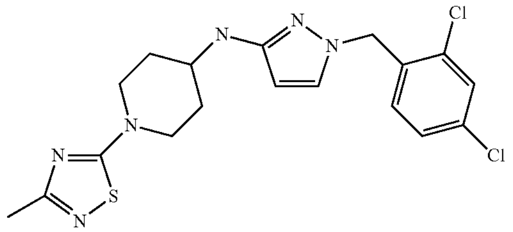 [SMILES: Cc1nsc(N2CCC(Nc3ccn(Cc4ccc(Cl)cc4Cl)n3)CC2)n1]

a) 1-(2,4-Dichloro-benzol)-1H-pyrazol-3-ylamine

3-Aminopyrazole (506 mg, 5.8 mmol) was dissolved in DMF (2 mL) under argon atmosphere, sodium hydride (55%, 241 mg, 5.5 mmol) was added at room temperature in small portions and stirred at room temperature for 1 hour. The reaction mixture was cooled to 0° C., 2,4-dichlorobenzyl chloride (1100 mg, 5.5 mmol) was added and the reaction mixture was stirred at room temperature for 3 hours. The reaction mixture was poured onto water and the aqueous phase extracted with ethyl acetate. The combined organic phases were dried over $Na_2SO_4$, filtered, the solvents were evaporated and the residue purified by silica gel chromatography using dichloromethane/methanol as eluent. The title compound was obtained as a white solid (700 mg, 52%).

MS ISP (m/e): 242.2 (100) $[(M+H)^+]$.

$^1H$ NMR ($CDCl_3$, 300 MHz): (ppm)=7.39-7.38 (m, 1H), 7.21-7.20 (m, 1H), 7.17 (m, 1H), 6.90-6.87 (m, 1H), 5.65-5.64 (m, 1H), 5.16 (s, 2H), 3.66 (bs, 2H).

b) [1-(2,4-Dichloro-benzyl)-1H-pyrazol-3-yl]-[1-(3-methyl-[1,2,4]thiadiazol-5-yl)-piperidin-4-yl]-amine Prepared in analogy to example 1 step h) starting from 1-(3-methyl-[1,2,4]thiadiazol-5-yl)-piperidin-4-one (example 1c) and 1-(2,4-dichloro-benzyl)-1H-pyrazol-3-ylamine. The title compound was obtained as a colorless oil (yield=56%).

MS ISP (m/e): 423.1 (100) $[(M+H)^+]$.

$^1H$ NMR ($CDCl_3$, 300 MHz): (ppm)=7.40-7.39 (m, 1H), 7.24-7.23 (m, 1H), 7.20-7.17 (m, 1H), 6.87-6.84 (m, 1H), 5.62-5.61 (m, 1H), 5.18 (s, 2H), 3.90-3.83 (m, 2H), 3.60-3.51 (m, 2H), 3.33-3.23 (m, 2H), 2.41 (s, 3H), 2.21-2.15 (m, 2H), 1.61-1.48 (m, 2H).

Example 15

[1-(4-Fluoro-benzyl)-1H-pyrazol-3-yl]-[1-(3-methyl-[1,2,4]thiadiazol-5-yl)-piperidin-4-yl]-amine

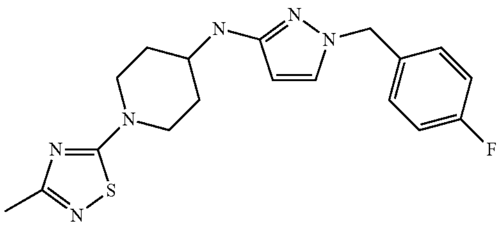 [SMILES: Cc1nsc(N2CCC(Nc3ccn(Cc4ccc(F)cc4)n3)CC2)n1]

Prepared in analogy to example 1 step h) starting from 1-(3-methyl-[1,2,4]thiadiazol-5-yl)-piperidin-4-one (example 1c) and 1-(4-fluoro-benzyl)-1H-pyrazol-3-ylamine. The title compound was obtained as a colorless oil.

MS ISP (m/e): 373.2 (100) $[(M+H)^+]$.

$^1H$ NMR ($CDCl_3$, 300 MHz): (ppm)=7.18-7.13 (m, 3H), 7.03-6.98 (m, 2H), 5.58-5.57 (m, 1H), 5.07 (s, 2H), 3.89-3.82 (m, 2H), 3.58-3.48 (m, 2H), 3.32-3.23 (m, 2H), 2.40 (s, 3H), 2.18-2.14 (m, 2H), 1.60-1.47 (m, 2H).

Example 16

[1-(4-Chloro-benzyl)-1H-pyrazol-3-yl]-[1-(3-methyl-[1,2,4]thiadiazol-5-yl)-piperidin-4-yl]-amine

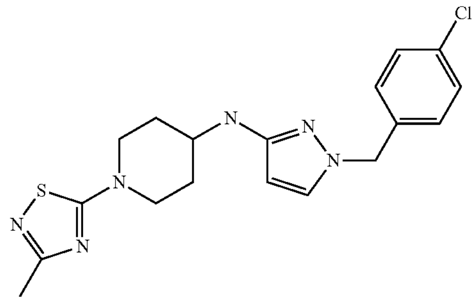

Prepared in analogy to example 1 step h) starting from 1-(3-methyl-[1,2,4]thiadiazol-5-yl)-piperidin-4-one (example 1c) and 1-(4-chloro-benzyl)-1H-pyrazol-3-ylamine. The title compound was obtained as a white solid (yield=70%).

MS ISP (m/e): 389.3 (100) $[(M+H)^+]$.

$^1H$ NMR ($CDCl_3$, 300 MHz): (ppm)=7.31-7.28 (m, 2H), 7.16-7.15 (m, 1H), 7.12-7.09 (m, 2H), 5.59-5.58 (m, 1H), 5.07 (s, 2H), 3.89-3.82 (m, 2H), 3.59-3.49 (m, 2H), 3.32-3.23 (m, 2H), 2.41 (s, 3H), 2.19-2.14 (m, 2H), 1.61-1.49 (m, 2H).

Example 17

[1-(3-Chloro-benzyl)-1H-pyrazol-3-yl]-[1-(3-methyl-[1,2,4]thiadiazol-5-yl)-piperidin-4-yl]-amine

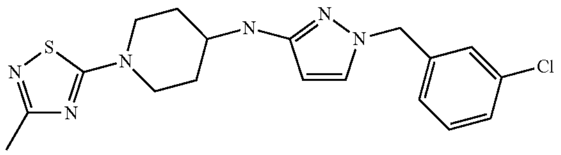 [SMILES: Cc1nsc(N2CCC(Nc3ccn(Cc4cccc(Cl)c4)n3)CC2)n1]

Prepared in analogy to example 1 step h) starting from 1-(3-methyl-[1,2,4]thiadiazol-5-yl)-piperidin-4-one (example 1c) and 1-(3-chloro-benzyl)-1H-pyrazol-3-ylamine. The title compound was obtained as a white solid.

MS ISP (m/e): 389.2 (100) [(M+H)$^+$].

$^1$H NMR ($CDCl_3$, 300 MHz): (ppm)=7.27-7.25 (m, 2H), 7.19-7.18 (m, 1H), 7.17-7.15 (m, 1H), 7.07-7.04 (m, 1H), 5.61-5.60 (m, 1H), 5.08 (s, 2H), 3.90-3.83 (m, 2H), 3.62-3.50 (m, 2H), 3.33-3.24 (m, 2H), 2.41 (s, 3H), 2.21-2.15 (m, 2H), 1.61-1.49 (m, 2H).

Example 18

[1-(3,4,5-Trifluoro-benzyl)-1H-pyrazol-3-yl]-[1-(3-methyl-[1,2,4]thiadiazol-5-yl)-piperidin-4-yl]-amine

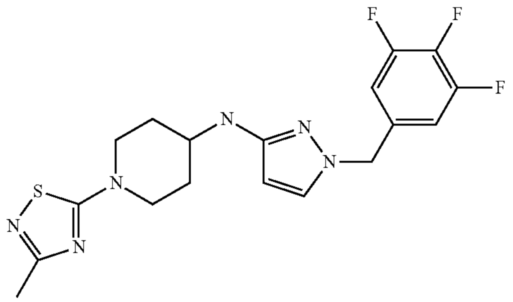 [SMILES: Cc1nsc(N2CCC(Nc3ccn(Cc4cc(F)c(F)c(F)c4)n3)CC2)n1]

Prepared in analogy to example 1 step h) starting from 1-(3-methyl-[1,2,4]thiadiazol-5-yl)-piperidin-4-one (example 1c) and 1-(3,4,5-trifluoro-benzyl)-1H-pyrazol-3-ylamine. The title compound was obtained as a colorless oil (yield=42%).

MS ISP (m/e): 409.3 (100) [(M+H)$^+$].

$^1$H NMR ($CDCl_3$, 300 MHz): (ppm)=7.21-7.20 (m, 2H), 6.79-6.75 (m, 2H), 5.62 (m, 1H), 5.03 (s, 2H), 3.90-3.83 (m, 2H), 3.59-3.51 (m, 2H), 3.33-3.24 (m, 2H), 2.41 (s, 3H), 2.21-2.15 (m, 2H), 1.61-1.48 (m, 2H).

Example 19

[1-(3-Fluoro-benzyl)-1H-pyrazol-3-yl]-[1-(3-methyl-[1,2,4]thiadiazol-5-yl)-piperidin-4-yl]-amine

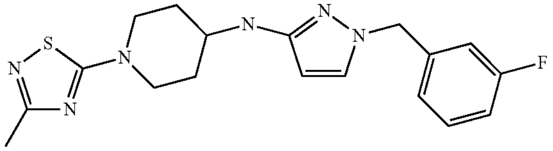 [SMILES: Cc1nsc(N2CCC(Nc3ccn(Cc4cccc(F)c4)n3)CC2)n1]

Prepared in analogy to example 1 step h) starting from 1-(3-methyl-[1,2,4]thiadiazol-5-yl)-piperidin-4-one (example 1c) and 1-(3-fluoro-benzyl)-1H-pyrazol-3-ylamine. The title compound was obtained as a yellow oil (yield=73%).

MS ISP (m/e): 373.2 (100) [(M+H)$^+$].

$^1$H NMR ($CDCl_3$, 300 MHz): (ppm)=7.30-7.27 (m, 1H), 7.19-7.18 (m, 1H), 7.00-6.94 (m, 2H), 6.87-6.82 (m, 1H), 5.61-5.60 (m, 1H), 5.11 (s, 2H), 3.90-3.83 (m, 2H), 3.64-3.50 (m, 2H), 3.33-3.24 (m, 2H), 2.40 (s, 3H), 2.21-2.14 (m, 2H), 1.62-1.48 (m, 2H).

Example 20

[1-(2,4-Dichloro-phenyl)-5-methyl-1H-[1,2,4]triazol-3-yl]-[1-(3-methyl-[1,2,4]thiadiazol-5-yl)-piperidin-4-yl]-amine

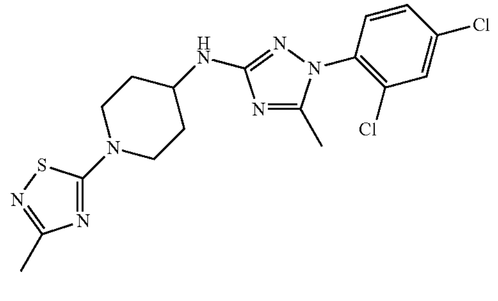 [SMILES: Cc1nsc(N2CCC(Nc3nc(C)n(-c4ccc(Cl)cc4Cl)n3)CC2)n1]

a) 4-[1-(2,4-Dichloro-phenyl)-5-methyl-1H-[1,2,4]triazol-3-ylamino]-piperidine-1-carboxylic acid tert-butyl ester Prepared in analogy to example 1 step h) starting from 4-oxo-piperidine-1-carboxylic acid tert-butyl ester and 1-(2,4-dichloro-phenyl)-5-methyl-1H-[1,2,4]triazol-3-ylamine. The title compound was obtained as a light yellow solid (yield=34%).

MS ISP (m/e): 426.1 (100) [(M+H)$^+$].

$^1$H NMR (DMSO-$D_6$, 300 MHz): (ppm)=7.91 (s, 1H), 7.65-7.55 (m, 2H), 5.99 (d, 1H), 3.80-3.70 (m, 2H), 3.50-3.40 (m, 1H), 2.90-2.75 (m, 2H), 2.17 (s, 3H), 1.87 (d, 2H), 1.39 (s, 9H), 1.20-1.35 (m, 2H).

b) [1-(2,4-Dichloro-phenyl)-5-methyl-1H-[1,2,4]triazol-3-yl]-piperidin-4-yl-amine hydrochloride 4-[1-(2,4-Dichloro-phenyl)-5-methyl-1H-[1,2,4]triazol-3-ylamino]-piperidine-1-carboxylic acid tert-butyl ester (120 mg, 0.28 mmol) was dissolved in dioxane (2 ml) saturated with HCl gas. The mixture was stirred overnight at room temperature, concentrated and the residue triturated with diethyl ether to yield the title compound as a brownish solid (57 mg, 56%).

MS ISP (m/e): 326.1 (100) $[(M+H)^+]$.

$^1$H NMR (DMSO-$D_6$, 300 MHz): (ppm)=9.22 (s broad, 1H), 9.00 (s broad, 1H), 8.82 (s broad, 1H), 7.93 (s, 1H), 7.70-7.60 (m, 2H), 3.60-3.55 (m, 1H), 3.23 (d, 2H), 2.94 (qa, 2H), 2.15 (s, 3H), 2.05 (d, 2H), 1.68 (qa, 2H).

c) [1-(2,4-Dichloro-phenyl)-5-methyl-1H-[1,2,4]triazol-3-yl]-[1-(3-methyl-[1,2,4]thiadiazol-5-yl)-piperidin-4-yl]-amine Prepared in analogy to example 1 step b) starting from [1-(2,4-dichloro-phenyl)-5-methyl-1H-[1,2,4]triazol-3-yl]-piperidin-4-yl-amine hydrochloride and 5-chloro-3-methyl-[1,2,4]thiadiazole (example 1 step a)). The title compound was obtained as slightly yellow solid (yield=10%).

MS ISP (m/e): 424.1/426.0 (100/72) $[(M+H)^+]$.

$^1$H NMR (DMSO-$D_6$, 300 MHz): (ppm)=7.91 (s, 1H), 7.65-7.55 (m, 2H), 6.10 (d, 1H), 3.76 (s broad, 2H), 3.65-3.55 (m, 1H), 3.27 (t, 2H), 2.27 (s, 3H), 2.12 (s, 3H), 2.00 (d, 2H), 1.50 (qa, 2H).

Example 21

[1-(6-Methyl-pyrimidin-4-yl)-piperidin-4-yl]-(4-phenyl-4,5,6,7-tetrahydro-benzothiazol-2-yl)-amine

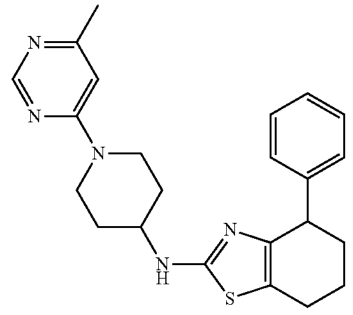 [SMILES: Cc1cc(N2CCC(Nc3nc4c(s3)CCCC4c3ccccc3)CC2)ncn1]

a) 2-Bromo-6-phenyl-cyclohexanone

To a solution of 2-phenyl-cyclohexanone (10.0 g, 57 mmol) in $CHCl_3$ (20 mL) at −10° C. a solution of bromine (9.6 g, 3.1 mL, 60 mmol) in $CHCl_3$ (10 mL) was added and the reaction mixture was allowed to warm to 0° C. After for 2 hours the solvent was evaporated, methanol (30 mL) was added to the residue, cooled to 0° C., stirred for 30 minutes and the white solid was filtered off to give the title compound as a white solid (5.48 g, 38%).

MS ISP (m/e): 253.0/255.1 (31/32) $[(M+H)^+]$, 270.1/272.1 (100/95) $[(M+NH_4)^+]$.

$^1$H NMR ($CDCl_3$, 300 MHz): (ppm)=7.37-7.28 (m, 3H), 7.16-7.13 (m, 2H), 4.83-4.76 (m, 1H), 3.74-3.68 (m, 1H), 2.80-2.75 (m, 1H), 2.36-2.19 (m, 2H), 2.13-1.93 (m, 3H).

b) 4-Phenyl-4,5,6,7-tetrahydro-benzothiazol-2-ylamine

A solution of 2-bromo-6-phenyl-cyclohexanone (4.32 g, 17 mmol) and thiourea (1.18 g, 16 mmol) in EtOH (150 mL) was heated to reflux for 12 hours. The solvent was evaporated, diethyl ether was added to the residue and stirred at room temperature for 1 hour, the solid filtered off and washed with diethylether. The solid was dissolved in ethyl acetate and the organic phase was washed three times with sodium carbonate solution. The organic phase was dried over sodium sulfate, the solvent was evaporated to give the title compound as a white solid (3.46 g, 88%). MS ISP (m/e): 231.1 $[(M+H)^+]$.

$^1$H NMR (DMSO-$D_6$, 300 MHz): (ppm, HBr salt)=8.91 (bs, 2H), 7.39-7.26 (m, 3H), 7.15-7.13 (m, 2H), 4.02 (m, 1H), 2.63-2.57 (m, 2H), 2.15-2.05 (m, 1H), 1.73-1.66 (m, 3H).

c) 4-(4-Phenyl-4,5,6,7-tetrahydro-benzothiazol-2-ylamino)-piperidine-1-carboxylic acid tert-butyl ester To a solution of 4-phenyl-4,5,6,7-tetrahydro-benzothiazol-2-ylamine (1.15 mg, 5 mmol) in dichloroethane (15 mL) was added at room temperature under stirring 1-Boc-4-piperidone (1.57 g, 7.5 mmol) and tetraisopropyl-orthotitanate (4.44 mL, 15 mmol). The reaction was stirred over night at 85° C. in a sealed tube. At room temperature ethanol (15 mL) and sodium borohydride (378 mg, 10 mmol) were added and the reaction was stirred at 85° C. for 4.5 hours. Water was added, the reaction stirred for 30 minutes and the precipitate was filtered off and washed with ethanol. The filtrate was concentrated under reduced pressure. Water was added and the reaction was extracted twice with ethyl acetate. The combined organic layers were washed with concentrated aqueous sodium chloride solution, dried over sodium sulfate, filtered and concentrated under reduced pressure. The residue was purified by column chromatography on silica gel using a gradient from n-heptane/EtOAc 9:1 to 1:1 (v/v) as eluent to yield the title compound as a light yellow viscous oil (1.58 g, 76%).

MS ISP (m/e): 414.4 (100) $[(M+H)^+]$, 358.3 (34) $[(M-isobutene+H)^+]$.

$^1$H NMR (DMSO-$D_6$, 300 MHz): (ppm)=7.26 (t, 2H), 7.16 (t, 1H), 7.06 (d, 2H), 3.88 (m, 2H), 3.27 (m, 2H), 2.94 (m, 2H), 2.59 (m, 1H), 2.05 (m, 1H), 1.82 (m, 2H), 1.65 (m, 3H), 1.38 (s, 9H), 1.25 (m, 3H).

d) (4-Phenyl-4,5,6,7-tetrahydro-benzothiazol-2-yl)-piperidin-4-yl-amine dihydrochloride To a solution of 4-(4-phenyl-4,5,6,7-tetrahydro-benzothiazol-2-ylamino)-piperidine-1-carboxylic acid tert-butyl ester (1.575 g, 3.8 mmol) in methylene chloride (13.8 mL) was added 2 M HCl solution in diethyl ether (6.9 mL). The reaction was stirred at room temperature over the weekend. The solvent was removed under reduced pressure and the residue was treated with diethyl ether and evaporated. The title compound was obtained as a light yellow solid (1.32 g, 90%).

MS ISP (m/e): 314.2 (100) $[(M+H)^+]$, 231.2 (34) $[(M+H)^+]$.

$^1$H NMR (DMSO-$D_6$, 300 MHz): (ppm)=9.08 (br m, 2H), 7.36 (t, 2H), 7.25 (t, 1H), 7.10 (d, 2H), 4.15 (m, 1H), 3.85 (m, 1H), 3.27 (m, 2H), 2.90 (m, 2H), 2.64 (m, 1H), 2.07 (m, 3H), 1.80 (m, 3H), 1.60 (m, 1H).

e) [1-(6-Methyl-pyrimidin-4-yl)-piperidin-4-yl]-(4-phenyl-4,5,6,7-tetrahydro-benzothiazol-2-yl)-amine (4-Phenyl-4,5,6,7-tetrahydro-benzothiazol-2-yl)-piperidin-4-yl-amine dihydrochloride (77.3 mg, 0.2 mmol) was suspended in tetrahydrofurane (2 mL). At 0° C. N,N-diisopropylethylamine (110 1, 0.64 mmol) was added at room temperature under nitrogen and stirring. To the yellow solution 4-chloro-6-methylpyrimidine (28.9 mg, 0.22 mmol) was added and the reaction was stirred at room temperature over night. The reaction was heated to reflux over night and then heated with N-methylpyrrolidone in a microwave oven to 200° C. for 30 minutes. Water was added and the reaction was extracted twice with diethyl ether. The combined organic layers were washed with water, dried over sodium sulfate, filtered and concentrated under reduced pressure. The residue was purified by column chromatography on silica gel using a gradient from EtOAc to EtOAc/EtOH 9:1 (v/v) as eluent. The title compound was obtained as a light yellow solid (55 mg, 68%).

MS ISP (m/e): 406.3 (100) [$(M+H)^+$].

$^1$H NMR (DMSO-$D_6$, 300 MHz): (ppm)=8.34 (s, 1H), 7.31-7.24 (m, 3H), 7.26 (t, 1H), 7.06 (d, 2H), 6.70 (s, 1H), 4.17 (m, 2H), 3.89 (m, 1H), 3.06 (m, 2H), 2.58 (m, 1H), 2.23 (s, 3H), 2.04 (m, 1H), 1.99 (m, 2H), 1.68 (m, 3H), 1.25 (m, 3H).

Example 22

[1-(2-Methyl-pyrimidin-4-yl)-piperidin-4-yl]-(4-phenyl-4,5,6,7-tetrahydro-benzothiazol-2-yl)-amine

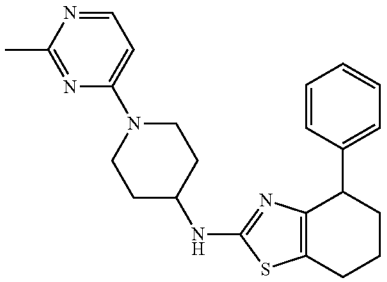 [SMILES: Cc1nccc(N2CCC(Nc3nc4c(s3)CCCC4c3ccccc3)CC2)n1]

(4-Phenyl-4,5,6,7-tetrahydro-benzothiazol-2-yl)-piperidin-4-yl-amine dihydrochloride (115.9 mg, 0.3 mmol) was dissolved in N-methylpyrrolidone (3 mL). N,N-diisopropylethylamine (165 1, 0.96 mmol) and 4-chloro-2-methylpyrimidine (44.7 mg, 0.33 mmol) were added at room temperature under nitrogen and stirring. The reaction was heated in a microwave oven to 200° C. for 30 minutes. Water was added and the reaction was extracted twice with diethyl ether. The combined organic layers were washed with water, dried over sodium sulfate, filtered and concentrated under reduced pressure. The residue was purified by column chromatography on silica gel using a gradient from EtOAc to EtOAc/EtOH 9:1 (v/v) as eluent. The title compound was obtained as a light yellow viscous oil (34 mg, 28%).

MS ISP (m/e): 406.4 (100) [$(M+H)^+$].

$^1$H NMR (DMSO-$D_6$, 300 MHz): (ppm)=8.03 (d, 1H), 7.31-7.24 (m, 3H), 7.16 (t, 1H), 7.06 (d, 2H), 6.61 (d, 1H), 4.07 (m, 2H), 3.89 (m, 1H), 3.59 (m, 1H), 3.04 (m, 2H), 2.58 (m, 1H), 2.04 (m, 1H), 1.90 (m, 2H), 1.68 (m, 3H), 1.30 (m, 3H).

Example 23

[1-(3-Methyl-[1,2,4]thiadiazol-5-yl)-piperidin-4-yl]-(4-phenyl-4,5,6,7-tetrahydro-benzothiazol-2-yl)-amine

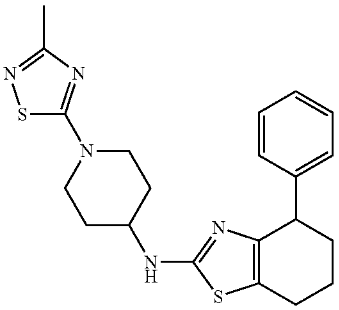 [SMILES: Cc1nsc(N2CCC(Nc3nc4c(s3)CCCC4c3ccccc3)CC2)n1]

Palladium (II) acetate (3.6 mg, 0.016 mmol) and 2-(dicyclohexylphosphino)biphenyl (11.6 mg, 0.032 mmol) were stirred under nitrogen at room temperature in dioxane (1.8 mL) for 10 minutes. Sodium tert.-butylat (29 mg, 0.3 mmol), (4-phenyl-4,5,6,7-tetrahydro-benzothiazol-2-yl)-piperidin-4-yl-amine dihydrochloride (77.3 mg, 0.2 mmol), N,N-diisopropylethylamine (69 L, 0.4 mmol) and 5-chloro-3-methyl-[1,2,4]thiadiazole (29.6 mg; 0.22 mmol) were added and the reaction was heated to 200° C. for 30 minutes in a microwave oven. The reaction was diluted with water and extracted twice with ethyl acetate. The combined organic layers were washed with water, dried over sodium sulfate, filtered and concentrated under reduced pressure. The residue was purified by column chromatography on silica gel using heptane/EtOAc 4:1 to 1:4 (v/v) as eluent. The title compound was obtained as a white solid (55 mg, 67%).

MS ISP (m/e): 412.2 (100) [$(M+H)^+$].

$^1$H NMR (DMSO-$D_6$, 300 MHz): (ppm)=7.29 (d, 1H), 7.26 (t, 2H), 7.16 (t, 1H), 7.06 (d, 2H), 3.89 (m, 1H), 3.65 (m, 3H), 3.25 (m, 1H), 2.60 (m, 1H), 2.26 (s, 3H), 2.04 (m, 2H), 1.68 (m, 3H), 1.49 (m, 2H), 1.85 (m, 3H).

Example 24

[1-(5-Methyl-[1,3,4]thiadiazol-2-yl)-piperidin-4-yl]-(4-phenyl-4,5,6,7-tetrahydro-benzothiazol-2-yl)-amine

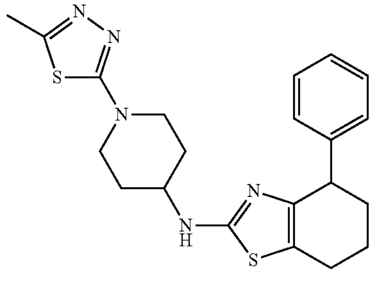 [SMILES: Cc1nnc(N2CCC(Nc3nc4c(s3)CCCC4c3ccccc3)CC2)o1]

Palladium (II) acetate (3.6 mg, 0.016 mmol) and 2-(dicyclohexylphosphino)biphenyl (11.6 mg, 0.032 mmol) were stirred under nitrogen at room temperature in dioxane (1.8 mL) for 10 minutes. Sodium tert-butylat (29 mg, 0.3 mmol), (4-phenyl-4,5,6,7-tetrahydro-benzothiazol-2-yl)-piperidin-4-yl-amine dihydrochloride (77.3 mg, 0.2 mmol), N,N-diisopropylethylamine (69 L, 0.4 mmol) and 2-bromo-5-methyl-1,3,4-thiadiazole (40.2 mg; 0.22 mmol) were added and the reaction was heated to 200° C. for 30 minutes in a microwave oven. The reaction was diluted with water and extracted twice with ethyl acetate. The combined organic layers were washed with water, dried over sodium sulfate, filtered and concentrated under reduced pressure. The residue was purified by column chromatography on silica gel using EtOAc as eluent. The title compound was obtained as a yellow solid (23 mg, 28%).

MS ISP (m/e): 412.2 (100) [$(M+H)^+$].

$^1$H NMR (DMSO-$D_6$, 300 MHz): (ppm)=7.33 (d, 1H), 7.26 (d, 2H), 7.16 (t, 1H), 7.06 (d, 2H), 3.89 (m, 1H), 3.67 (m, 2H), 3.52 (m, 1H), 3.17 (m, 2H), 2.59 (m, 1H), 2.04 (m, 1H), 1.92 (m, 3H), 1.68 (m, 3H), 1.46 (m, 2H).

Example 25

[1-(5-Methyl-[1,3,4]oxadiazol-2-yl)-piperidin-4-yl]-(4-phenyl-4,5,6,7-tetrahydro-benzothiazol-2-yl)-amine

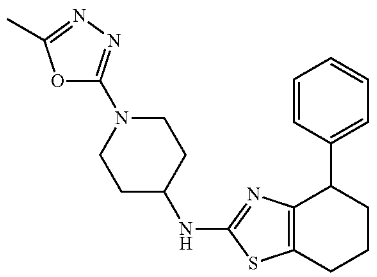

a) 4-Hydroxy-1-(5-methyl-[1,3,4]oxadiazol-2-yl)-1,2,5,6-tetrahydro-pyridine-3-carboxylic acid allyl ester potassium salt To a solution of 5-methyl-1,3,4-oxadiazol-2-ylamine (198.2 mg, 2 mmol) and allyl acrylate (851 L, 6 mmol) in N-methylpyrrolidone (4 mL) was added at room temperature under stirring and nitrogen potassium tert-butylat (359.1 mg, 3.2 mmol). The reaction was stirred over night. To the formed suspension tetrahydrofurane was added and the title compound was filtered off, washed with tetrahydrofurane, dried and the title compound was obtained as white solid crystals (255 mg, 42%).

MS ISP (m/e): 266.1 (84) [$(M-K+H)^+$], 208.2 (100).

$^1$H NMR (DMSO-$D_6$, 300 MHz): (ppm)=5.90 (m, 1H), 5.25 (d, 1H), 5.06 (d, 1H), 4.37 (d, 2H), 4.13 (s, 2H), 3.43 (t, 2H), 2.31 (s, 3H), 2.03 (t, 2H).

b) 1-(5-Methyl-[1,3,4]oxadiazol-2-yl)-piperidin-4-one

4-Hydroxy-1-(5-methyl-[1,3,4]oxadiazol-2-yl)-1,2,5,6-tetrahydro-pyridine-3-carboxylic acid allyl ester potassium salt (163 mg, 0.54 mmol) was dissolved in little 25% aqueous HCl solution and the solvent was removed under reduced pressure. The residue was evaporated twice with toluene/tetrahydrofurane. The residue was suspended in tetrahydrofurane (0.26 mL). To a solution of triethyl amine (263 L, 1.88 mmol) and formic acid (42 L, 1.08 mmol) in tetrahydrofurane (0.51 mL) was added under nitrogen and stirring a solution of palladium (II) acetate (3.0 mg, 0.013 mmol) and triphenylphosphine (7.3 mg, 0.027 mmol) in tetrahydrofurane (0.77 mL). After stirring for 5 minutes at room temperature the prepared catalyst solution was added to the suspension. The reaction was stirred at room temperature for 1 hour, poured onto water and extracted twice with ethyl acetate. The combined organic layers were washed with saturated aqueous NaCl solution, dried over sodium sulfate, filtered and the solvent was evaporated under reduced pressure. The title compound was obtained as a yellow viscous oil (54 mg, 55%).

MS ISP (m/e): 279.1 (100) [$(M+H)^+$], 182.1 (36), 222.1 (21).

$^1$H NMR (DMSO-$D_6$, 300 MHz): (ppm)=3.72 (t, 4H), 2.47 (t, 4H), 2.35 (s, 3H).

c) [1-(5-Methyl-[1,3,4]oxadiazol-2-yl)-piperidin-4-yl]-(4-phenyl-4,5,6,7-tetrahydro-benzothiazol-2-yl)-amine To a solution of 4-phenyl-4,5,6,7-tetrahydro-benzothiazol-2-ylamine (46 mg, 0.2 mmol) in dichloroethane (0.6 mL) was added at room temperature under stirring 1-(5-methyl-[1,3,4]oxadiazol-2-yl)-piperidin-4-one (50 mg, 0.28 mmol) and tetraisopropyl-orthotitanate (178 L, 0.6 mmol). The reaction was stirred over night at 90° C. in a sealed tube under nitrogen. At room temperature ethanol (0.6 mL) and sodium borohydride (15 mg, 0.4 mmol) were added and the reaction was stirred at 85° C. for 4.5 hours. Water was added, the reaction stirred for 30 minutes and the precipitate was filtered off and washed with ethanol. The filtrate was concentrated under reduced pressure. Water was added and the reaction was extracted twice with ethyl acetate. The combined organic layers were washed with concentrated aqueous sodium chloride solution, dried over sodium sulfate, filtered and concentrated under reduced pressure. The residue was purified twice by column chromatography on silica gel using $CH_2Cl_2$/MeOH 19:1 (v/v) and then a gradient from AcOEt to AcOEt/EtOH 1:9 (v/v) as eluents to yield the title compound as a light yellow viscous oil (28 mg, 35%).

MS ISP (m/e): 396.1 (100) [$(M+H)^+$].

$^1$H NMR (DMSO-$D_6$, 300 MHz): (ppm)=7.32 (d, 1H), 7.26 (d, 2H), 7.15 (t, 1H), 7.05 (d, 2H), 3.89 (m, 1H), 3.67 (m, 2H), 3.52 (m, 1H), 3.09 (m, 2H), 2.59 (m, 1H), 2.31 (s, 3H), 2.04 (m, 1H), 1.94 (m, 3H), 1.68 (m, 3H), 1.38 (m, 2H).

Example 26

[1-(3-Chloro-benzyl)-1H-[1,2,4]triazol-3-yl]-[1-(5-methyl-[1,3,4]oxadiazol-2-yl)-piperidin-4-yl]-amine

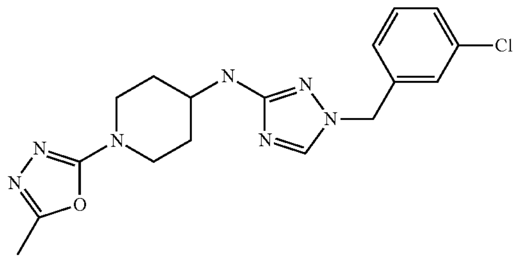 [SMILES: Cc1nnc(N2CCC(Nc3ncn(Cc4cccc(Cl)c4)n3)CC2)o1]

A solution of 1-(5-methyl-[1,3,4]oxadiazol-2-yl)-piperidin-4-one (91 mg, 0.5 mmol) and 1-(3-chloro-benzyl)-1H-[1,2,4]triazol-3-ylamine (104 mg, 0.5 mmol) in dry toluene (8 mL) and acetic acid (0.4 mL) was heated under reflux at a Dean-Stark trap for 12 hours. The reaction mixture was cooled to room temperature, ethanol (5 mL) was added, followed by sodium borohydride (19 mg, 0.5 mmol) and stirred at room temperature overnight. The reaction mixture was extracted with water and ethyl acetate, the organic layers were combined, dried over $Na_2SO_4$, filtered and the solvents were evaporated. The residue was purified by silica gel chromatography using dichloromethane/methanol as eluent. The title compound was obtained as a white solid (91 mg, 49%).

MS ISP (m/e): 374.2 (100) [(M+H)$^+$].

$^1$H NMR ($CDCl_3$, 300 MHz): (ppm)=7.70 (s, 1H), 7.31-7.29 (m, 2H), 7.24-7.23 (m, 1H), 7.14-7.11 (m, 1H), 5.11 (s, 2H), 4.12-4.09 (m, 1H), 3.96-3.89 (m, 2H), 3.75-3.65 (m, 1H), 3.22-3.12 (m, 2H), 2.38 (s, 3H), 2.20-2.12 (m, 2H), 1.60-1.47 (m, 2H).

Example 27

(4-Benzyl-6-methyl-pyrimidin-2-yl)-(3,4,5,6-tetrahydro-2H-[1,4']bipyridinyl-4-yl)-amine dihydrochloride

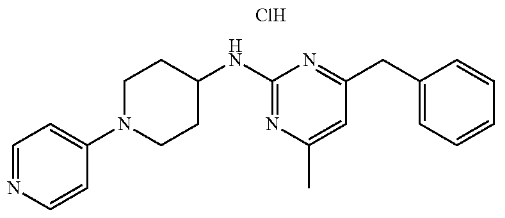 [SMILES: Cl ; Cc1cc(Cc2ccccc2)nc(NC2CCN(c3ccncc3)CC2)n1]

To a suspension of 4-benzyl-2-chloro-6-methyl-pyrimidine (WO2009103652; 70 mg, 0.32 mmol) and 4-(4-aminopiperidino)pyridine dihydrochloride (ABCR; 80 mg, 0.32 mmol) in dioxane (2 mL) was added potassium carbonate (885 mg, 6.4 mmol), palladium(II) acetate (3 mg, 0.013 mmol) and 2-(dicyclohexylphosphino)biphenyl (11 mg, 0.031 mmol). The reaction mixture was refluxed overnight, concentrated, hydrolyzed and extracted with ethyl acetate. Chromatography on Si-Amine (Silicycle, 10 g) using cyclohexane/ethyl acetate as eluent gave a gummy solid which was dissolved in dioxane and treated with a few drops of dioxane saturated with HCl gas to yield the title compound as a slightly yellow solid (70 mg, 51%).

MS ISP (m/e): 360.3 (100) [(M+H)$^+$].

$^1$H NMR ($CDCl_3$, 300 MHz): (ppm)=8.25 (t, 2H), 7.40-7.20 (m, 7H), 6.62 (s, 1H), 4.40-4.25 (m, 1H), 4.17 (d, 2H), 3.96 (s, 2H), 3.50-3.35 (m, 2H), 2.34 (s, 3H), 2.03 (d, 2H), 1.55 (q, 2H).

Example 28

(4-Benzyl-6-methyl-pyrimidin-2-yl)-[1-(2-methyl-pyrimidin-4-yl)-piperidin-4-yl]-amine

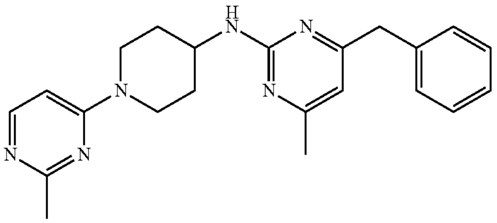 [SMILES: Cc1cc(Cc2ccccc2)nc(NC2CCN(c3ccnc(C)n3)CC2)n1]

a) [1-(2-Methyl-pyrimidin-4-yl)-piperidin-4-yl]-carbamic acid tert-butyl ester

A suspension of Boc-4-aminopiperidine (715.3 mg, 3.5 mmol), 4-chloro-2-methylpyrimidine (521 mg, 3.85 mmol) and N,N-diisopropylethyl amine (899 L, 5.25 mmol) in dioxane (14 mL) was heated to 150° C. in the microwave for 30 minutes. The reaction was diluted with water and extracted twice with ethyl acetate. The combined organic layers were washed with water, dried over sodium sulfate, filtered and concentrated under reduced pressure. The title compound was obtained after stirring of the crude product with diethyl ether and drying as white crystals (649.5 mg, 64%).

MS ISP (m/e): 293.2 (100) [(M+H)$^+$], 237.1 (37) [(M−isobutene+H)$^+$].

$^1$H NMR ($CDCl_3$, 300 MHz): (ppm)=8.11 (d, 1H), 6.33 (d, 1H), 4.46 (m, 1H), 4.32 (m, 2H), 3.72 (s, 1H), 3.00 (m, 2H), 2.50 (s, 3H), 2.03 (m, 2H), 1.46 (s, 9H), 1.38 (m, 2H).

b) 1-(2-Methyl-pyrimidin-4-yl)-piperidin-4-ylamine dihydrochloride

To a solution of [1-(2-methyl-pyrimidin-4-yl)-piperidin-4-yl]-carbamic acid tert-butyl ester (818.7 mg, 2.8 mmol) in $CH_2Cl_2$ (14 mL) was added at room temperature under stirring a 2 M HCl solution in diethyl ether (7 mL) and was stirred at room temperature over the weekend. The solvent was removed under reduced pressure and the residue was treated twice with diethyl ether. The title compound was obtained after removal of the solvent under reduced pressure as a light brown solid (869 mg, 100%)

MS ISP (m/e): 193.2 (100) [(M+H)$^+$].

$^1$H NMR (DMSO-$D_6$, 300 MHz): (ppm)=8.44 (br s, 2H), 8.31 (d, 1H), 7.14 (d, 1H), 4.92 (m, 1H), 4.28 (m, 1H), 3.38 (m, 2H), 3.18 (m, 1H), 2.54 (s, 3H), 2.09 (m, 2H), 1.60 (m, 2H).

c) (4-Benzyl-6-methyl-pyrimidin-2-yl)-[1-(2-methyl-pyrimidin-4-yl)-piperidin-4-yl]-amine A solution of 1-(2-methyl-pyrimidin-4-yl)-piperidin-4-ylamine dihydrochloride (53 mg, 0.2 mmol), 4-benzyl-2-chloro-6-methylpyrimidin (48.1 mg, 0.22 mmol) and N,N-diisopropylethyl amine (120 L, 0.7 mmol) in N-methylpyrrolidinone (1 mL) was heated at 200° C. in a microwave oven for 1 hour. The reaction was diluted with water and extracted twice with ethyl acetate. The combined organic layers were washed with water, dried over sodium sulfate, filtered and concentrated under reduced pressure. The residue was purified by column chromatography on silica gel with AcOEt/EtOH 9:1 (v/v) as eluent. The title compound was obtained as a light yellow solid (16 mg, 21%).

MS ISP (m/e): 375.4 (100) [$(M+H)^+$].

$^1$H NMR ($CDCl_3$, 300 MHz): (ppm)=8.11 (d, 1H), 7.28 (m, 5H), 6.34 (d, 1H), 6.24 (s, 1H), 4.91 (d, 1H), 4.32 (m, 2H), 4.15 (m, 1H), 3.86 (s, 2H), 3.13 (m, 2H), 2.50 (s, 3H), 2.25 (s, 3H), 2.12 (m, 2H), 1.46 (m, 2H).

Example 29

2-[2-[1-(2-Methyl-pyrimidin-4-yl)-piperidin-4-ylamino]-6-(4-trifluoromethyl-phenyl)-pyrimidin-4-yl]-propan-2-ol

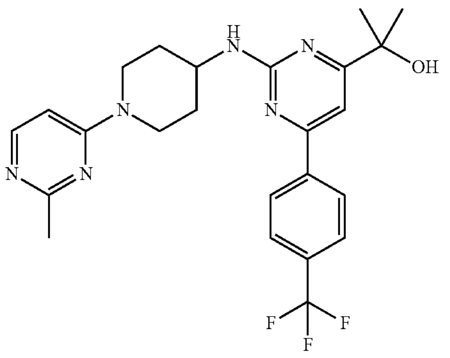 [SMILES: Cc1nccc(N2CCC(Nc3nc(-c4ccc(C(F)(F)F)cc4)cc(C(C)(C)O)n3)CC2)n1]

A mixture of palladium (II) acetate (2.7 mg, 0.012 mmol) and 2-(dicyclohexylphosphino)-biphenyl (8.4 mg, 0.024 mmol) in dioxane (1 mL) was stirred under argon at 20° C. for 10 minutes. The resulting catalyst solution was added to a suspension of potassium carbonate (692 mg, 5.0 mmol), 1-(2-methyl-pyrimidin-4-yl)-piperidin-4-ylamine dihydrochloride (80 mg, 0.3 mmol), and 2-[2-chloro-6-(4-trifluoromethyl-phenyl)-pyrimidin-4-yl]-propan-2-ol (95 mg, 0.3 mmol) in dioxane (1.7 mL). The reaction mixture was heated to 170° C. in a microwave oven for 30 minutes. The reaction mixture was cooled, diluted with water and extracted twice with ethyl acetate. The organic layer was washed with brine, dried over sodium sulfate, and concentrated under reduced pressure. The crude product was purified by column chromatography on silica gel using $CH_2Cl_2$/0-10% MeOH as eluent. The title compound was obtained as a light yellow solid (9 mg, 6%).

MS ISP (m/e): 473.2 (100) [$(M+H)^+$].

$^1$H NMR ($CDCl_3$, 300 MHz): (ppm)=8.14 (d, 2H), 8.11 (d, 1H), 7.75 (d, 2H), 7.06 (s, 1H), 6.39 (d, 1H), 5.20 (d, 1H), 4.35-4.50 (m, 3H), 4.25 (br s, 1H), 3.18 (m, 2H), 2.52 (s, 3H), 2.22 (m, 2H), 1.60 (m, 2H), 1.55 (s, 6H).

Example 30

2-[2-[1-(6-Methyl-pyrimidin-4-yl)-piperidin-4-ylamino]-6-(4-trifluoromethyl-phenyl)-pyrimidin-4-yl]-propan-2-ol

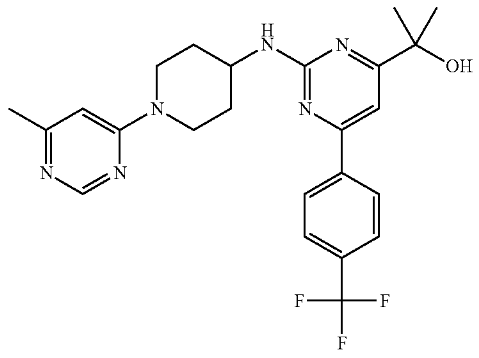 [SMILES: Cc1cc(N2CCC(Nc3nc(-c4ccc(C(F)(F)F)cc4)cc(C(C)(C)O)n3)CC2)ncn1]

a) [1-(6-Methyl-pyrimidin-4-yl)-piperidin-4-yl]-carbamic acid tert-butyl ester

A suspension of Boc-4-aminopiperidine (613 mg, 3 mmol), 4-chloro-6-methylpyrimidine (433 mg, 3.3 mmol) and N,N-diisopropylethyl amine (771 L, 4.5 mmol) in dioxane (12 mL) was heated to 150° C. in the microwave for 30 minutes. The reaction was diluted with water and extracted twice with ethyl acetate. The combined organic layers were washed with water, dried over sodium sulfate, filtered and concentrated under reduced pressure. The crude product was purified by column chromatography on silica gel using a gradient from AcOEt to AcOEt/EtOH 9:1 as eluent. The title compound was obtained as a light yellow solid (693 mg, 79%).

MS ISP (m/e): 293.2 (100) [$(M+H)^+$], 237.1 (58) [$(M-isobutene+H)^+$].

$^1$H NMR ($CDCl_3$, 300 MHz): (ppm)=8.50 (s, 1H), 6.38 (s, 1H), 4.45 (m, 1H), 4.32 (m, 2H), 3.73 (m, 1H), 3.02 (m, 2H), 2.35 (s, 3H), 2.04 (m, 2H), 1.45 (s, 9H), 1.35 (m, 2H).

b) 1-(6-Methyl-pyrimidin-4-yl)-piperidin-4-ylamine dihydrochloride

To a solution of [1-(6-methyl-pyrimidin-4-yl)-piperidin-4-yl]-carbamic acid tert-butyl ester (686 mg, 2.3 mmol) in $CH_2Cl_2$ (12 mL) was added at room temperature under stirring a 2 M HCl solution in diethyl ether (6 mL) and was stirred at room temperature over night. The precipitate was filtered off, washed with $CH_2Cl_2$ and diethyl ether and dried to yield the title compound as a light yellow solid (610 mg, 98%)

MS ISP (m/e): 193.2 (100) [$(M+H)^+$].

$^1$H NMR (DMSO-$D_6$, 300 MHz): (ppm)=8.77 (s, 1H), 8.42 (br s, 2H), 7.20 (s, 1H), 3.45 (m under water peak, 3H), 2.42 (s, 3H), 2.08 (m, 2H), 1.59 (m, 2H).

c) 2-[2-[1-(6-Methyl-pyrimidin-4-yl)-piperidin-4-ylamino]-6-(4-trifluoromethyl-phenyl)-pyrimidin-4-yl]-propan-2-ol A solution of 1-(6-methyl-pyrimidin-4-yl)-piperidin-4-ylamine dihydrochloride (53 mg, 0.2 mmol), 2-[2-chloro-6-

(4-trifluoromethyl-phenyl)-pyrimidin-4-yl]-propan-2-ol (69.7 mg, 0.22 mmol)) and N,N-diisopropylethyl amine (120 L, 0.7 mmol) in N-methyl-pyrrolidinone (1 mL) was heated at 160° C. in a microwave oven for 5 hours. The reaction was diluted with water and extracted twice with ethyl acetate. The combined organic layers were washed with water, dried over sodium sulfate, filtered and concentrated under reduced pressure. The residue was purified by column chromatography on silica gel using a gradient from AcOEt to AcOEt/EtOH 9:1 (v/v) as eluent. The title compound was obtained as a white solid (36 mg, 38%).

MS ISP (m/e): 473.2 (100) [(M+H)$^+$].

$^1$H NMR ($CDCl_3$, 300 MHz): (ppm)=8.53 (s, 1H), 8.12 (d, 2H), 7.73 (d, 2H), 7.06 (s, 1H), 6.43 (s, 1H), 5.22 (d, 1H), 4.37 (m, 2H), 4.26 (m, 1H), 3.20 (m, 2H), 2.38 (s, 3H), 2.24 (m, 2H), 1.60 (m, 2H), 1.55 (s, 6H).

Example 31

2-{6-(4-Chloro-benzyl)-2-[1-(6-methyl-pyrimidin-4-yl)-piperidin-4-ylamino]-pyrimidin-4-yl}-propan-2-ol

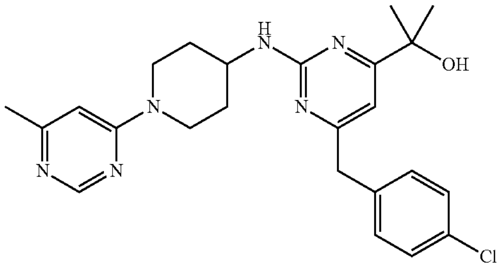 [SMILES: Cc1cc(N2CCC(Nc3nc(Cc4ccc(Cl)cc4)cc(C(C)(C)O)n3)CC2)ncn1]

To a solution of 1-(6-methyl-pyrimidin-4-yl)-piperidin-4-ylamine dihydrochloride (53 mg, 0.2 mmol) and N,N-diisopropylethyl amine (120 L, 0.7 mmol) in N-methyl-pyrrolidinone (0.5 mL) was added a solution of 2-[2-chloro-6-(4-chloro-benzyl)-pyrimidin-4-yl]-propan-2-ol (65.4 mg, 0.22 mmol)) in dioxane (1.5 mL). The reaction was heated at 160° C. in a microwave oven for 5 hours. The reaction was diluted with water and extracted twice with ethyl acetate. The combined organic layers were washed with water, dried over sodium sulfate, filtered and concentrated under reduced pressure. The residue was purified by column chromatography on silica gel using a gradient from AcOEt to AcOEt/EtOH 9:1 (v/v) as eluent. The title compound was obtained as a white solid (27 mg, 30%).

MS ISP (m/e): 453.3/455.2 (100/39) [(M+H)$^+$].

$^1$H NMR ($CDCl_3$, 300 MHz): (ppm)=8.52 (s, 1H), 7.29 (d, 2H), 7.20 (d, 2H), 6.41 (s, 1H), 5.10 (m, 1H), 4.52 (m, 1H), 4.30 (m, 2H), 4.11 (m, 1H), 3.87 (s, "H), 3.14 (m, "H), 2.37 (s, 3H), 2.06 (m, 2H), 1.52 (m, 2H), 1.43 (s, 6H).

Example 32

(2'-Chloro-3,4,5,6-tetrahydro-2H-[1,4']bipyridinyl-4-yl)-(4,6-dimethyl-pyrimidin-2-yl)-amine

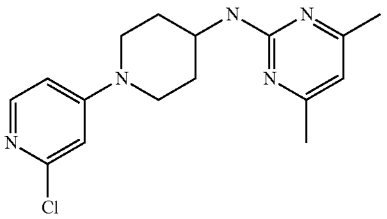 [SMILES: Cc1cc(C)nc(NC2CCN(c3ccnc(Cl)c3)CC2)n1]

a) 4-(4,6-Dimethyl-pyrimidin-2-ylamino)-piperidine-1-carboxylic acid tert-butyl ester To a mixture of 2-chloro-4,6-dimethylpyrimidine (5.00 g, 0.035 mol), 4-amino-1-Boc-piperidine (7.023 g, 0.035 mol), sodium tert-butoxide (5.055 g, 0.53 mol) in dioxane (120 mL) was added under an argon atmosphere palladium(II) acetate (0.630 g, 0.003 mol) and 2-(dicyclohexylphospino)biphenyl (1.966 g, 0.006 mmol). The reaction mixture was stirred for 5 hours at 130° C. It was diluted with ethyl acetate (400 mL) and washed with aqueous sodium carbonate (1M, 200 mL), water (200 mL) and brine (150 mL). The combined aqueous layers were extracted with ethyl acetate (400 mL) and the combined organic layers were dried over sodium sulfate. Concentration and purification by chromatography ($SiO_2$, n-heptane/ethyl acetate=2:1 to 1:1) afforded the title compound (5.44 g, 51%) as an orange oil.

MS ISP (m/e): 307.1 (100) [(M+H)$^+$].

$^1$H NMR ($CDCl_3$, 300 MHz): (ppm)=1.30-1.45 (m, 2H), 1.47 (s, 9H), 1.95-2.05 (m, 2H), 2.27 (s, 6H), 2.90-3.05 (m, 2H), 3.95-4.10 (m, 3H), 4.75 (d br, 1H), 6.31 (s, 1H).

b) (4,6-Dimethyl-pyrimidin-2-yl)-piperidin-4-yl-amine

To a solution of 4-(4,6-dimethyl-pyrimidin-2-ylamino)-piperidine-1-carboxylic acid tert-butyl ester in THF (50 mL) was added dropwise at 0° C. hydrochloric acid (4 M in dioxane, 44.3 mL) and the reaction mixture was stirred for 22 hours at ambient temperature. The resulting suspension was filtered and dried. The residue was diluted with water (160 mL) and washed with ethyl acetate (130 mL). To the aqueous layer were added ethyl acetate (160 mL) and sodium carbonate (28.5 g) and it was extracted with ethyl acetate (160 mL). Drying of the combined organic layers over sodium sulfate afforded the title compound (2.15 g, 59%) as a light yellow solid.

MS ISP (m/e): 207.3 (100) [(M+H)$^+$].

$^1$H NMR ($CDCl_3$, 300 MHz): (ppm)=1.30-1.45 (m, 2H), 1.60 (s br, 1H), 2.00-2.10 (m, 2H), 2.27 (s, 6H), 2.75 (“td”, 2H), 3.10 (“dt”, 2H), 3.90-4.05 (m, 1H), 4.85 (d br, 1H), 6.29 (s, 1H).

c) (2'-Chloro-3,4,5,6-tetrahydro-2H-[1,4']bipyridinyl-4-yl)-(4,6-dimethyl-pyrimidin-2-yl)-amine To a solution of 4,6-dimethyl-pyrimidin-2-yl)-piperidin-4-yl-amine (100 mg, 0.49 mmol) in DMF (1.0 mL) was added 2-chloro-4-fluoropyridine (57 μL, 0.63 mmol) and N,N-diisopropylethylamine (117 μL, 0.68 mmol). Under an argon atmosphere the reaction mixture was heated to 150° C. for 30 minutes in a microwave oven. It was diluted with ethyl acetate (15 mL) and washed with water (15 mL) and brine (10 mL). The aqueous layers were extracted with ethyl acetate (15 mL) and the combined organic layers were dried over sodium sulfate. Purification by chromatography ($SiO_2$, heptane/ethyl acetate/methanol=100:0:0 to 0:90:10) afforded the title compound (121 mg, 79%) as a white solid.

MS ISP (m/e): 318.1 (100) [$(M+H)^+$].

$^1$H NMR ($CDCl_3$, 300 MHz): (ppm)=1.40-1.60 (m, 2H), 2.10-2.20 (m, 2H), 2.28 (s, 6H), 3.10 ("td", 2H), 3.80 ("dt", 2H), 4.05-4.20 (m, 2H), 4.75 (d br, 1H), 6.33 (s, 1H), 6.07 (dd, 1H), 6.15 (d, 1H), 8.00 (d, 1H).

Example 33

(4,6-Dimethyl-pyrimidin-2-yl)-[1-(6-methyl-pyrimidin-4-yl)-piperidin-4-yl]-amine

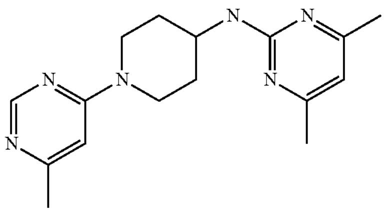 [SMILES: Cc1cc(N2CCC(Nc3nc(C)cc(C)n3)CC2)ncn1]

In analogy to the procedure described for the synthesis of example 32 (step c), the title compound (4,6-dimethyl-pyrimidin-2-yl)-[1-(6-methyl-pyrimidin-4-yl)-piperidin-4-yl]-amine was prepared from 4,6-dimethyl-pyrimidin-2-yl)-piperidin-4-yl-amine using 4-chloro-6-methylpyrimidine instead of 2-chloro-4-fluoropyridine and was obtained as a colorless oil.

MS ISP (m/e): 299.4 (100) [$(M+H)^+$].

$^1$H NMR ($CDCl_3$, 300 MHz): (ppm)=1.40-1.52 (m, 2H), 2.10-2.20 (m, 2H), 2.29 (s, 6H), 2.36 (s, 3H), 3.10-3.25 (m, 2H), 4.10-4.20 (m, 1H), 4.25-4.40 (m, 2H), 4.95 (d br, 1H), 6.32 (s, 1H), 6.39 (s, 1H), 8.51 (s, 1H).

Example 34

2-[6-(4-Chloro-benzyl)-2-(2',5'-dimethyl-3,4,5,6-tetrahydro-2H-[1,4']bipyridinyl-4-ylamino)-pyrimidin-4-yl]-propan-2-ol

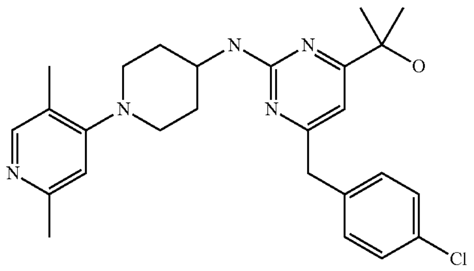 [SMILES: Cc1cc(N2CCC(Nc3nc(Cc4ccc(Cl)cc4)cc(C(C)(C)O)n3)CC2)c(C)cn1]

a) 4-Chloro-2,5-dimethyl-pyridine 1-oxide

A mixture of 2,5-dimethyl-1-oxy-pyridin-4-ol bromide (5.00 g, 22.7 mmol) in phosphorus oxychloride (4.15 mL, 45.5 mmol) was stirred for 3 hours at 130° C. After cooling to ambient temperature it was poured carefully onto aqueous sodium carbonate (1 M, 100 mL). After stirring for 15 minutes tert-butylmethylether (50 mL) was added and the resulting mixture was stirred for 18 hours at ambient temperature. The aqueous layer was separated and extracted with tert-butylmethylether (50 mL). The combined organic layers were dried over sodium sulfate and concentrated in vacuo to afford a brown oil. Further extensive extraction of the aqueous layer with ethyl acetate (50 mL) and drying over sodium sulfate afforded the title compound (1.32 g, 41%) as a white solid.

MS ISP (m/e): 157.0 (100) [$(M+H)^+$].

$^1$H NMR ($CDCl_3$, 300 MHz): (ppm)=2.26 (s, 6H), 2.45 (s, 3H), 7.21 (s, 1H), 8.12 (s, 1H).

b) 2',5'-Dimethyl-3,4,5,6-tetrahydro-2H-[1,4']bipyridinyl-4-ylamine

A mixture 4-chloro-2,5-dimethyl-pyridine 1-oxide (200 mg, 1.41 mmol), Boc-4-aminopiperidine (311 mg, 1.55 mmol) and N,N-diisopropyl ethyl amine (484 μL, 2.82 mmol) in sulfolane (1 mL) was heated to 160° C. for 30 minutes in a microwave oven followed by heating to 220° C. for 30 minutes. After the addition of aqueous hydrochloric acid (25% in water, 0.5 mL) the mixture was stirred for 18 h at ambient temperature. It was treated with ammonia in methanol and concentrated. Purification by chromatography ($SiO_2$, dichloromethane/methanol/ammonia=95:4.5:0.5 to 90:9:1) afforded the title compound (99 mg, 40%) as a light brown oil.

MS ISP (m/e): 206.3 (100) [$(M+H)^+$].

$^1$H NMR ($CDCl_3$, 300 MHz): (ppm)=1.45-1.60 (m, 2H), 1.63 (s br, 2H), 1.85-1.95 (m, 2H), 2.17 (s, 3H), 2.43 (s, 3H), 2.65-2.75 (m, 2H), 2.75-2.90 (m, 1H), 3.20-3.35 (m, 2H), 6.65 (s, 1H), 8.11 (s, 1H).

c) 2-[6-(4-Chloro-benzyl)-2-(2',5'-dimethyl-3,4,5,6-tetrahydro-2H-[1,4']bipyridinyl-4-ylamino)-pyrimidin-4-yl]-propan-2-ol To a mixture of 2',5'-dimethyl-3,4,5,6-tetrahydro-2H-[1,4]bipyridinyl-4-ylamine (143 mg, 0.48 mmol), 2-[2-chloro-6-(4-chloro-benzyl)-pyrimidin-4-yl]-propan-2-ol (99 mg, 0.48 mmol), finely milled potassium carbonate (100 mg, 0.72 mmol) in dioxane (2 mL) was added under an argon atmosphere palladium(II) acetate (5 mg, 0.02 mmol) and 2-(dicyclohexylphosphino)biphenyl (17 mg, 0.05 mmol) and the reaction mixture was heated at 150° C. for 30 minutes. Concentration and purification by chromatography ($SiO_2$, n-heptane/ethyl acetate/(ethyl acetate/triethylamine=95:5)=50:50:0 to 0:80:20) afforded the title compound (67 mg, 30%) as a light brown foam.

MS EI (m/e): 466.3 (100) [$(M+H)^+$].

$^1$H NMR ($CDCl_3$, 300 MHz): (ppm)=1.43 (s, 3H), 1.56 (s, 3H), 1.60-1.71 (m, 2H), 2.10-2.25 (m, 2H), 2.20 (s, 3H), 2.47 (s, 3H), 2.75-2.90 (m, 2H), 3.22-3.35 (m, 2H), 3.87 (s, 2H), 3.90-4.15 (m, 1H), 4.57 (s, 1H), 5.30 (s br, 1H), 6.39 (s, 1H), 6.68 (s, 1H), 7.18-7.35 (m, 4H), 8.16 (s, 1H).

Example 35

2-[6-(4-Chloro-benzyl)-2-(2'-methyl-3,4,5,6-tetrahydro-2H-[1,4']bipyridinyl-4-ylamino)-pyrimidin-4-yl]-propan-2-ol

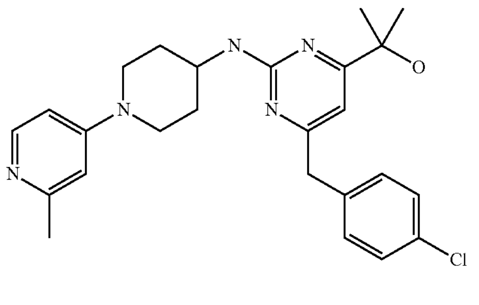 [SMILES: Cc1cc(N2CCC(Nc3nc(Cc4ccc(Cl)cc4)cc(C(C)(C)O)n3)CC2)ccn1]

4-[4-(4-Chloro-benzyl)-6-(1-hydroxy-1-methyl-ethyl)-pyrimidin-2-ylamino]-piperidine-1-carboxylic acid tert-butyl ester To a mixture of 2-[2-chloro-6-(4-chloro-benzyl)-pyrimidin-4-yl]-propan-2-ol (500 mg, 1.68 mmol), 4-amino-1-Boc-piperidine (404 mg, 2.02 mmol), sodium tert-butoxide (243 mg, 2.52 mmol) in dioxane (2.5 mL) was added under an argon atmosphere palladium(II) acetate (30 mg, 0.14 mmol) and 2-(dicyclohexylphosphino)biphenyl (94 mg, 0.27 mmol) and the reaction mixture was heated to 150° C. for 30 minutes in a microwave oven. It was diluted with ethyl acetate (15 mL) and washed with water (15 mL) and brine (15 mL). The aqueous layers were extracted with ethyl acetate (15 mL) and dried over sodium sulfate. Purification by chromatography ($SiO_2$, heptane:ethyl acetate=80:20 to 60:40) afforded the title compound (230 mg, 30%) as a light brown oil.

MS ISP (m/e): 461.3 (100) $[(M+H)^+]$.

$^1H$ NMR ($CDCl_3$, 300 MHz): (ppm)=1.41 (s, 3H), 1.47 (s, 9H), 1.55 (s, 3H), 1.50-1.70 (m, 2H), 1.95-2.10 (m, 2H), 2.80-3.00 (m, 2H), 3.85 (s, 2H), 3.90-4.10 (m, 3H), 4.50-4.55 (s, 1H), 4.95-5.05 (s br, 1H), 6.38 (s, 1H), 7.17-7.29 (m, 4H)

b) 2-[6-(4-Chloro-benzyl)-2-(piperidin-4-ylamino)-pyrimidin-4-yl]-propan-2-ol

To a solution of 4-[4-(4-chloro-benzyl)-6-(1-hydroxy-1-methyl-ethyl)-pyrimidin-2-ylamino]-piperidine-1-carboxylic acid tert-butyl ester (220 mg, 0.447 mmol) in dichloromethane (5 mL) was added at 0° C. trifluoroacetic acid (365 μL, 4.77 mmol) and the mixture was stirred for 18 hours while allowing to warm to ambient temperature. It was basified by addition of 1 M aqueous sodium carbonate solution (5 mL) and extracted with dichloromethane (15 mL). The organic layers were washed with 1 M aqueous sodium carbonate solution (15 mL) and dried over sodium sulfate. Concentration afforded the title compound (192 mg, 99%) as a brown semi-solid.

MS ISP (m/e): 361.2 (100) $[(M+H)^+]$.

$^1H$ NMR ($CDCl_3$, 300 MHz): (ppm)=1.30-1.40 (m, 2H), 1.40 (s, 3H), 1.41 (s, 3H), 1.95-2.10 (m, 2H), 2.65-2.80 (m, 2H), 3.05-3.20 (m, 2H), 3.89 (s, 1H), 3.80-4.00 (m, 1H), 3.85 (s, 2H), 5.03 (s br, 1H), 5.29 (s, 1H), 6.35 (s, 1H), 7.18-7.29 (m, 4H).

c) 2-[6-(4-Chloro-benzyl)-2-(2'-methyl-3,4,5,6-tetrahydro-2H-[1,4']bipyridinyl-4-ylamino)-pyrimidin-4-yl]-propan-2-ol A solution of 2-[6-(4-chloro-benzyl)-2-(piperidin-4-ylamino)-pyrimidin-4-yl]-propan-2-ol (76 mg, 0.19 mmol), 4-chloro-2-picoline (24 mg, 0.19 mmol) and triethylamine (53 μL, 0.38 mmol) in sulfolane (0.76 mL) was stirred in a preheated oil bath at 150° C. for 30 minutes. After further addition of 4-chloro-2-picoline (24 mg, 0.19 mmol) and triethylamine (53 μL, 0.38 mmol) the solution was stirred for further 60 minutes at 150° C. It was diluted with ethyl acetate (15 mL) and was washed with 1 M aqueous sodium carbonate solution (20 mL), water (15 mL) and brine (15 mL). The combined aqueous layers were extracted with ethyl acetate (15 mL). The organic layer was dried over sodium sulfate. Concentration and purification by chromatography ($SiO_2$, dichloromethane/methanol/triethylamine=95:4.5:0.5) afforded the title compound (34 mg, 40%) as an off-white foam.

MS ISP (m/e): 452.2 (100) $[(M+H)^+]$.

$^1H$ NMR ($CDCl_3$, 300 MHz): (ppm)=1.41)s, 3H), 1.42 (s, 3H), 1.45-1.60 (m, 2H), 2.05-2.20 (m, 2H), 2.46 (s, 3H), 2.95-3.10 (m, 2H), 3.75-3.90 (m, 2H), 3.86 (s, 2H), 4.00-4.10 (m, 1H), 4.50 (s br, 1H), 5.02 (s br, 1H), 6.41 (s, 1H), 6.50-6.55 (m, 1H), 6.55-6.60 (m, 1H), 7.18-7.35 (m, 4H), 8.15 (d, 1H).

Example 36

(4-Benzyl-6-methyl-pyrimidin-2-yl)-[1-(3-methyl-[1,2,4]thiadiazol-5-yl)-piperidin-4-yl]-amine

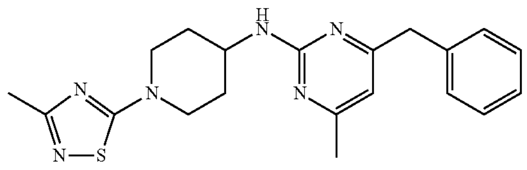 [SMILES: Cc1cc(Cc2ccccc2)nc(NC2CCN(c3nc(C)ns3)CC2)n1]

a) [1-(3-Methyl-[1,2,4]thiadiazol-5-yl)-piperidin-4-yl]-carbamic acid tert-butyl ester Palladium (II) acetate (5.4 mg, 0.024 mmol) and 2-(dicyclohexylphosphino)biphenyl (17.4 mg, 0.048 mmol) were stirred under nitrogen at room temperature in dioxane (1.7 mL) for 10 minutes. Sodium tert-butylat (44 mg, 0.33 mmol), Boc-4-aminopiperidine (61.3 mg, 0.3 mmol), and 5-chloro-3-methyl-[1,2,4]-thiadiazole (44.4 mg; 0.33 mmol) were added and the reaction was heated to 150° C. for 30 minutes in a microwave oven. The reaction was diluted with water and extracted twice with ethyl acetate. The combined organic layers were washed with saturated aqueous NaCl solution, dried over sodium sulfate, filtered and concentrated under reduced pressure. The residue was purified by column chromatography on silica gel using a gradient from n-heptane/EtOAc 9:1 to 1:1 (v/v) as eluent. The title compound was obtained as a yellow solid (39 mg, 44%).

MS ISP (m/e): 299.2 (43) $[(M+H)^+]$, 243.2 (100) $[(M-isobutene+H)^+]$.

$^1H$ NMR (DMSO-$D_6$, 300 MHz): (ppm)=6.92 (br d, 1H), 3.72 (m, 2H), 3.03 (m, 1H), 3.25 (m, 2H), 2.27 (s, 3H), 1.83 (m, 2H), 1.44 (m, 2H), 1.38 (s, 9H).

b) 1-(3-Methyl-[1,2,4]thiadiazol-5-yl)-piperidin-4-ylamine dihydrochloride

To a solution of [1-(3-methyl-[1,2,4]thiadiazol-5-yl)-piperidin-4-yl]-carbamic acid tert-butyl ester (256 mg, 0.86 mmol) in $CH_2Cl_2$ (8.6 mL) was added at room temperature under stirring a 2 M HCl solution in diethyl ether (4.3 mL) and was stirred at room temperature over night. The solvent was removed under reduced pressure. The crude product was treated twice with diethyl ether to yield the title compound as a yellow semi-solid (260 mg, 100%)

MS ISP (m/e): 199.1 (100) [$(M+H)^+$], 182.1 (52).

$^1$H NMR (DMSO-$D_6$, 300 MHz): (ppm)=8.26 (br s, 3H), 3.81 (m, 2H), 3.29-3.20 (m, 3H), 2.28 (s, 3H), 2.02 (m, 2H), 1.59 (m, 2H).

c) (4-Benzyl-6-methyl-pyrimidin-2-yl)-[(R)-1-(3-methyl-[1,2,4]thiadiazol-5-yl)-pyrrolidin-3-yl]-amine A solution of 1-(3-methyl-[1,2,4]thiadiazol-5-yl)-piperidin-4-ylamine dihydrochloride (54.2 mg, 0.2 mmol), 4-benzyl-2-chloro-6-methyl-pyrimidine (48.1 mg, 0.22 mmol)) and N,N-diisopropylethyl amine (120 L, 0.7 mmol) in dioxane (0.6 mL) was heated at 200° C. in a microwave oven for 1 hour. The reaction was diluted with water and extracted twice with ethyl acetate. The combined organic layers were washed with saturated aqueous NaCl solution, dried over sodium sulfate, filtered and concentrated under reduced pressure. The residue was purified by column chromatography on silica gel with EtOAc as eluent. The title compound was obtained as a yellow viscous oil (22 mg, 29%).

MS ISP (m/e): 381.3 (100) [$(M+H)^+$].

$^1$H NMR ($CDCl_3$, 300 MHz): (ppm)=7.32-7.21 (m, 5H), 6.26 (s, 1H), 5.27 (m, 1H), 4.13 (m, 1H), 3.86 (m, 4H), 3.33 (m, 2H), 2.42 (s, 3H), 2.26 (s, 3H), 2.13 (m, 2H), 1.62 (m, 2H).

Example 37

2-[2-[1-(3-Methyl-[1,2,4]thiadiazol-5-yl)-piperidin-4-ylamino]-6-(4-trifluoromethyl-phenyl)-pyrimidin-4-yl]-propan-2-ol

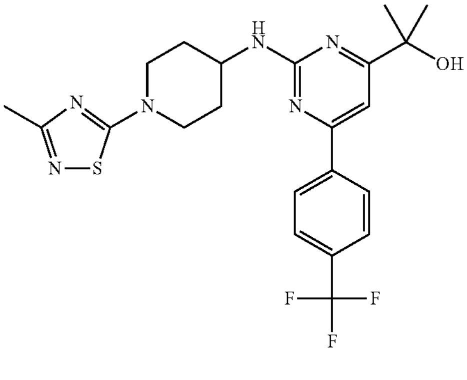 [SMILES: Cc1nsc(N2CCC(Nc3nc(-c4ccc(C(F)(F)F)cc4)cc(C(C)(C)O)n3)CC2)n1]

A solution of 1-(3-methyl-[1,2,4]thiadiazol-5-yl)-piperidin-4-ylamine dihydrochloride (54.2 mg, 0.2 mmol), 2-[2-chloro-6-(4-trifluoromethyl-phenyl)-pyrimidin-4-yl]-propan-2-ol (69.7 mg, 0.22 mmol) and N,N-diisopropylethyl amine (120 L, 0.7 mmol) in dioxane (2 mL) was heated at 200° C. in a microwave oven for 2 hours. The reaction was concentrated under reduced pressure and the residue was purified by column chromatography on silica gel with $CH_2Cl_2$/MeOH 19:1 (v/v) as eluent. The title compound was obtained as a brown viscous oil (26 mg, 27%). MS ISP (m/e): 479.1 (100) [$(M+H)^+$].

$^1$H NMR ($CDCl_3$, 300 MHz): (ppm)=8.12 (d, 2H), 7.73 (d, 2H), 7.08 (s, 1H), 5.21 (br d, 1H), 4.37 (s, 1H), 4.25 (m, 1H), 3.90 (m, 2H), 3.38 (m, 2H), 2.43 (s, 3H), 2.23 (m, 2H), 1.70 (m, 2H), 1.55 (s, 6H).

Example 38

2-{6-(4-Chloro-phenyl)-2-[1-(3-methyl-[1,2,4]thiadiazol-5-yl)-piperidin-4-ylamino]-pyrimidin-4-yl}-propan-2-ol

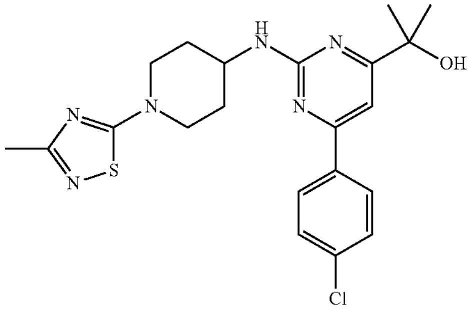 [SMILES: Cc1nsc(N2CCC(Nc3nc(-c4ccc(Cl)cc4)cc(C(C)(C)O)n3)CC2)n1]

In analogy to example 29, 1-(3-methyl-[1,2,4]thiadiazol-5-yl)-piperidin-4-ylamine (59.5 mg, 0.3 mmol) was reacted with 2-[2-chloro-6-(4-chloro-phenyl)-pyrimidin-4-yl]-propan-2-ol (85 mg, 0.3 mmol) to give the title compound (55 mg, 41%) as off-white foam.

MS ISP (m/e): 445.2 (98) [$(M+H)^+$].

$^1$H NMR ($CDCl_3$, 300 MHz): (ppm)=7.96 (d, 2H), 7.45 (d, 2H), 7.02 (s, 1H), 5.18 (d, 1H), 4.45 (s, 1H), 4.22 (br s, 1H), 3.92 (m, 2H), 3.38 (m, 2H), 2.43 (s, 3H), 2.24 (m, 2H), 1.70 (m, 2H), 1.54 (s, 6H).

Example 39

2-{6-(4-Chloro-benzyl)-2-[1-(3-methyl-[1,2,4]thiadiazol-5-yl)-piperidin-4-ylamino]-pyrimidin-4-yl}-propan-2-ol

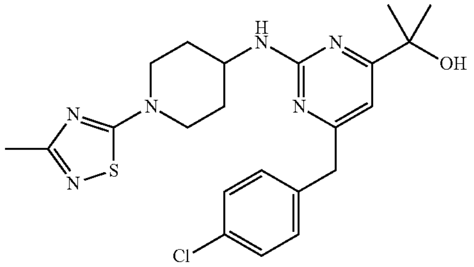 [SMILES: Cc1nsc(N2CCC(Nc3nc(Cc4ccc(Cl)cc4)cc(C(C)(C)O)n3)CC2)n1]

a) 2-(2,6-Dichloro-pyrimidin-4-yl)-propan-2-ol

To a stirred solution of methyl 2,6-dichloro-pyrimidine-4-carboxylate (1.03 g, 5.0 mmol) in tetrahydrofuran (40 mL) was added at −75° C. over 10 minutes a 3 M solution of methylmagnesium chloride in tetrahydrofuran (3.66 mL, 11.0 mmol). The solution was stirred at −78° C. for 30 min, then warmed up to 0° C. over 10 min, and stirring was continued for 2 h at 0° C. The reaction was stopped by the addition of saturated ammonium chloride solution (40 mL) and the mixture was extracted with ethyl acetate (100 mL). The organic layer was separated, washed with brine, dried over sodium sulfate, and evaporated under reduced pressure. The remaining oil was purified by chromatography on silica gel using heptane/0-20% ethyl acetate as eluent to give the title compound (0.76 g, 73%) as light yellow oil.

$^1$H NMR ($CDCl_3$, 300 MHz): (ppm)=7.53 (s, 1H), 2.85 (s, 1H), 1.58 (s, 6H).

b) 2,4-Dichloro-6-(1-methyl-1-trimethylsilanyloxy-ethyl)-pyrimidine

A mixture of 2-(2,6-dichloro-pyrimidin-4-yl)-propan-2-ol (1.04 g, 5.0 mmol) and N,O-bis(trimethyl-silyl)acetamide (1.49 mL, 6.0 mmol) was stirred at 100° C. for 4 h. The reaction mixture was cooled to 20° C. and purified by chromatography on silica gel using heptane/0-10% ethyl acetate as eluent to afford the title compound (1.16 g, 83%) as a colorless oil.

$^1$H NMR ($CDCl_3$, 300 MHz): (ppm)=7.60 (s, 1H), 1.57 (s, 6H), 0.21 (s, 9H).

c) 2-Chloro-4-(4-chloro-benzyl)-6-(1-methyl-1-trimethylsilanyloxy-ethyl)-pyrimidine To a solution of 2,4-dichloro-6-(1-methyl-1-trimethylsilanyloxy-ethyl)-pyrimidine (5.02 g, 18.0 mmol) in THF (60 mL) was added $Pd(TPP)_4$ (0.83 g, 0.72 mmol). The solution was flushed with argon, and subsequently, a 0.5 M solution of 4-chloro-benzylzinc chloride in tetrahydrofuran (36 mL, 18.0 mmol) was added at 20° C. over 1-3 minutes. The reaction mixture was heated to 50° C. for 3 h under an atmosphere of argon. After cooling the mixture to 20° C., saturated aqueous ammonium chloride solution (30 mL) was added to quench the reaction. The mixture was extracted with ethyl acetate (2×30 mL) and the organic layers were washed with brine (2×30 mL), dried over sodium sulfate, and evaporated under reduced pressure. The residual oil was purified by chromatography on silica gel using heptane/0-30% ethyl acetate as eluent to afford the title compound (4.72 g, 71%) as a colorless oil.

MS ISP (m/e): 369.0 (54) [$(M+H)^+$].

d) 2-[2-Chloro-6-(4-chloro-benzyl)-pyrimidin-4-yl]-propan-2-ol

A solution of 2-chloro-4-(4-chloro-benzyl)-6-(1-methyl-1-trimethylsilanyloxy-ethyl)-pyrimidine (3.69 g, 10.0 mmol) and toluene-4-sulfonic acid monohydrate (0.19 g, 1.0 mmol) in 90% aqueous tetrahydrofuran (40 mL) was stirred at 20° C. for 2 h. The solution was diluted with ethyl acetate and washed successively with saturated sodium hydrogencarbonate solution and with brine. The organic layer was dried over sodium sulfate and evaporated under reduced pressure. The residual oil was crystallized from cyclohexane to give the title compound (2.28 g, 77%) as a white solid.

$^1$H NMR ($CDCl_3$, 300 MHz): (ppm)=7.31 (d, 2H), 7.21 (d, 2H), 7.18 (s, 1H), 4.07 (s, 2H), 3.12 (s, 1H), 1.51 (s, 6H).

e) 2-{6-(4-Chloro-benzyl)-2-[1-(3-methyl-[1,2,4]thiadiazol-5-yl)-piperidin-4-ylamino]-pyrimidin-4-yl}-propan-2-ol In analogy to example 29, 1-(3-methyl-[1,2,4]thiadiazol-5-yl)-piperidin-4-ylamine (65 mg, 0.33 mmol) was reacted with 2-[2-chloro-6-(4-chloro-benzyl)-pyrimidin-4-yl]-propan-2-ol (98 mg, 0.33 mmol) to give the title compound (55 mg, 36%) as yellow foam.

MS ISP (m/e): 459.4 (100) [$(M+H)^+$].

$^1$H NMR ($CDCl_3$, 300 MHz): (ppm)=7.28 (d, 2H), 7.19 (d, 2H), 6.43 (s, 1H), 5.02 (d, 1H), 4.42 (s, 1H), 4.12 (br s, 1H), 3.88 (m, 2H), 3.87 (s, 2H), 3.32 (m, 2H), 2.42 (s, 3H), 2.16 (m, 2H), 1.62 (m, 2H), 1.43 (s, 6H).

Example 40

2-[2-[1-(5-Methyl-[1,3,4]oxadiazol-2-yl)-piperidin-4-ylamino]-6-(4-trifluoromethyl-phenyl)-pyrimidin-4-yl]-propan-2-ol

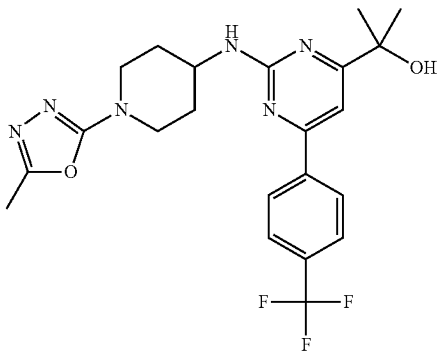 [SMILES: Cc1nnc(N2CCC(Nc3nc(-c4ccc(C(F)(F)F)cc4)cc(C(C)(C)O)n3)CC2)o1]

a) 1-(5-Methyl-[1,3,4]oxadiazol-2-yl)-piperidin-4-one O-benzyl-oxime

A solution of 1-(5-methyl-[1,3,4]oxadiazol-2-yl)-piperidin-4-one (1.52 g, 8.39 mmol), O-benzylhydroxylamine hydrochloride (1.50 g, 9.23 mmol) and ammonium acetate (1.62 g, 21.0 mmol) in MeOH (34.5 mL) was heated to reflux for 2 hours under nitrogen. The solvent was removed under reduced pressure and the residue was purified by column chromatography on silica gel using a gradient from AcOEt to AcOEt/EtOH 9:1 (v/v) as eluent to yield the title compound as a light yellow viscous oil (2.32 g, 96%).

MS ISP (m/e): 287.3 (35) [$(M+H)^+$], 309.4 (10) [$(M+Na)^+$].

$^1$H NMR (DMSO-$D_6$, 300 MHz): (ppm)=7.35 (m, 5H), 5.03 (s, 2H), 3.51 (sept, 4H), 2.64 (t, 2H), 2.37 (t, 2H), 2.33 (s, 3H).

b) 1-(5-Methyl-[1,3,4]oxadiazol-2-yl)-piperidin-4-ylamine

To a solution of 1-(5-methyl-[1,3,4]oxadiazol-2-yl)-piperidin-4-one O-benzyl-oxime (2.32 g, 8.1 mmol)) in 7 M $NH_3$ solution in MeOH (40.5 mL) was hydrogenated under an atmosphere of hydrogen in the presence of Palladium on charcoal (10%, 464 mg). The catalyst was filtered off and washed with MeOH. The filtrate was concentrated under reduced pressure to yield the title compound (1.61 g, 100%) as a yellow solid.

MS ISP (m/e): 183.1 (100) [$(M+H)^+$], 166.2 (46) [$(M-NH_3+H)^+$].

$^1$H NMR (DMSO-$D_6$, 300 MHz): (ppm)=3.68 (m, 2H), 3.01 (m, 2H), 2.75 (m, 1H), 2.31 (s, 3H), 1.73 (m, 2H), 1.25 (m, 2H).

c) 2-[2-[1-(5-Methyl-[1,3,4]oxadiazol-2-yl)-piperidin-4-ylamino]-6-(4-trifluoromethyl-phenyl)-pyrimidin-4-yl]-propan-2-ol A solution of 1-(5-methyl-[1,3,4]oxadiazol-2-yl)-piperidin-4-ylamine (36.5 mg, 0.2 mmol), 2-[2-chloro-6-(4-trifluoromethyl-phenyl)-pyrimidin-4-yl]-propan-2-ol (69.1 mg, 0.22 mmol)) and N,N-diisopropylethylamine (52 L, 0.3 mmol) in dioxane (2 mL) was heated at 160° C. in a microwave oven for 5.5 hours. The reaction was diluted with water and extracted twice with ethyl acetate. The combined organic layers were washed with saturated aqueous NaCl solution, dried over sodium sulfate, filtered and concentrated under reduced pressure. The residue was purified by column chromatography on silica gel with EtOAc/EtOH 9:1 (v/v) as eluent. The title compound was obtained as a white solid (29 mg, 31%).

MS ISP (m/e): 463.2 (100) [$(M+H)^+$], 445.1 (32) [$(M-H_2O+H)^+$], 485.3 (11) [$(M+Na)^+$].

$^1$H NMR ($CDCl_3$, 300 MHz): (ppm)=8.11 (d, 2H), 7.74 (d, 2H), 7.07 (s, 1H), 5.22 (m, 1H), 4.41 (m, 1H), 4.19 (m, 1H), 4.00 (m, 2H), 3.26 (m, 2H), 2.41 (s, 3H), 2.20 (m, 2H), 1.65 8m, 2H), 1.55 (s, 6H).

Example 41

(4-Benzyl-6-methyl-pyrimidin-2-yl)-[1-(3-bromo-[1,2,4]thiadiazol-5-yl)-piperidin-4-yl]-amine

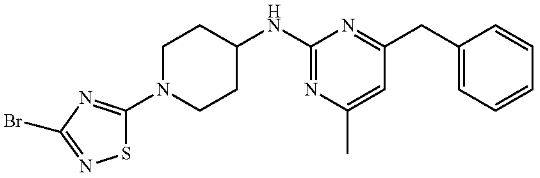

A solution of (4-benzyl-6-methyl-pyrimidin-2-yl)-piperidin-4-yl-amine hydrochloride (125 mg, 0.39 mmol), 3-bromo-5-chloro-[1,2,4]thiadiazol (39 mg, 0.19 mmol) and N,N-diisopropylethyl amine (66 L, 0.39 mmol) in tetrahydrofurane (3 mL) was heated to 95° C. 4.5 hours. The reaction was diluted with water and extracted twice with ethyl acetate. The combined organic layers were washed with saturated aqueous NaCl solution, dried over sodium sulfate, filtered and concentrated under reduced pressure. The residue was purified by column chromatography on silica gel using a gradient from $CH_2Cl_2$ to $CH_2Cl_2$/MeOH 19:1 (v/v) as eluent. The title compound was obtained as a colorless oil (84 mg, 96%).

MS ISP (m/e): 447.2/445.2 (100/90) [$(M+H)^+$].

$^1$H NMR ($CDCl_3$, 300 MHz): (ppm)=7.31-7.23 (m, 5H), 6.27 (s, 1H), 4.92 (d, 1H), 4.12 (m, 1H), 3.86 (m, 4H), 3.39 (m, 2H), 2.26 (s, 3H), 2.17 (m, 2H), 1.60 (m, 2H).

Example 42

2-{6-(4-Chloro-benzyl)-2-[1-(5-methyl-[1,3,4]oxadiazol-2-yl)-piperidin-4-ylamino]-pyrimidin-4-yl}-propan-2-ol

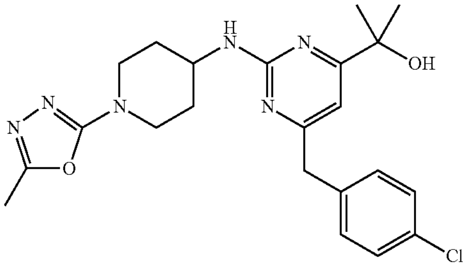 [SMILES: Cc1nnc(N2CCC(Nc3nc(Cc4ccc(Cl)cc4)cc(C(C)(C)O)n3)CC2)o1]

A solution of 1-(5-methyl-[1,3,4]oxadiazol-2-yl)-piperidin-4-ylamine (50 mg, 0.27 mmol), 2-[2-chloro-6-(4-chloro-benzyl)-pyrimidin-4-yl]-propan-2-ol (81.5 mg, 0.27 mmol)) and N,N-diisopropylethylamine (71 L, 0.41 mmol) in dioxane (2.8 mL) was heated at 160° C. in a microwave oven for 6 hours. The reaction was diluted with water and extracted twice with ethyl acetate. The combined organic layers were washed with saturated aqueous NaCl solution, dried over sodium sulfate, filtered and concentrated under reduced pressure. The residue was purified by column chromatography on silica gel using a gradient from $CH_2Cl_2$ to $CH_2Cl_2$/MeOH 19:1 (v/v) as eluent. The title compound was obtained as a colorless foam (31 mg, 26%).

MS ISP (m/e): 443.4/445.2 (100/29) [$(M+H)^+$].

$^1$H NMR ($CDCl_3$, 300 MHz): (ppm)=7.28 (d, 2H), 7.19 (d, 2H), 6.41 (s, 1H), 5.04 (m, 1H), 4.03 (m, 1H), 3.96 (m, 2H), 3.87 (s, 2H), 3.20 (m, 2H), 2.40 (s, 3H), 2.22 (m, 2H), 1.57 (m, 2H), 1.42 (s, 6H).

Example 43

(4-Benzyl-6-methyl-pyrimidin-2-yl)-[1-(3-chloro-[1,2,4]thiadiazol-5-yl)-piperidin-4-yl]-amine

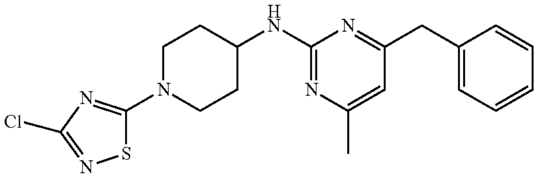 [SMILES: Cc1cc(Cc2ccccc2)nc(NC2CCN(c3nc(Cl)ns3)CC2)n1]

A solution of (4-benzyl-6-methyl-pyrimidin-2-yl)-piperidin-4-yl-amine hydrochloride (159 mg, 0.5 mmol), 3,5-dichloro-[1,2,4]thiadiazol (39 mg, 0.25 mmol) and N,N-diisopropylethylamine (85 L, 0.5 mmol) in tetrahydrofurane (2 mL) was heated to 95° C. 4 hours under nitrogen. The reaction was diluted with water and extracted twice with ethyl acetate. The combined organic layers were washed with saturated aqueous NaCl solution, dried over sodium sulfate, filtered and concentrated under reduced pressure. The residue was purified by column chromatography on silica gel using $Et_2O$ as eluent. The title compound was obtained as a colorless oil (52 mg, 52%).

MS ISP (m/e): 401.3/403.4 (100/45) [$(M+H)^+$].

$^1$H NMR ($CDCl_3$, 300 MHz): (ppm)=7.31-7.23 (m, 5H), 6.27 (s, 1H), 5.00 (d, 1H), 4.14 (m, 1H), 3.86 (s, 2H), 3.85 (m, 2H), 3.39 (m, 2H), 2.25 (s, 3H), 2.16 (m, 2H), 1.59 (m, 2H).

Example 44

(4-Benzyl-6-methyl-pyrimidin-2-yl)-[1-(3-methyl-[1,2,4]oxadiazol-5-yl)-piperidin-4-yl]-amine

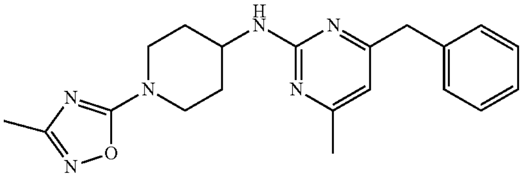 [SMILES: Cc1cc(Cc2ccccc2)nc(NC2CCN(c3nc(C)no3)CC2)n1]

a) 4-(4-Benzyl-6-methyl-pyrimidin-2-ylamino)-piperidine-1-carbonitrile

To a solution of (4-benzyl-6-methyl-pyrimidin-2-yl)-piperidin-4-yl-amine hydrochloride (255 mg, 0.8 mmol) in $CH_2Cl_2$ (1.5 mL) was added at 0° C. a suspension of sodium hydrogencarbonate (202 mg, 2.49 mmol) in water (0.5 mL) and then within 1 minute a solution of bromocyan (106 mg, 0.97 mmol) in $CH_2Cl_2$ (1 mL). The reaction was stirred at 0° C. for 45 minutes and then at room temperature over night. The reaction was diluted with $CH_2Cl_2$, washed with saturated aqueous $NaHCO_3$ solution and with saturated aqueous NaCl solution, dried over sodium sulfate, filtered and the solvent was evaporated under reduced pressure. The residue was purified by column chromatography using a gradient from $CH_2Cl_2$ to $CH_2Cl_2$/MeOH 19:1 (v/v) as eluent. The title compound was obtained as a colorless oil (135 mg, 55%).

MS ISP (m/e): 308.3 (100) [$(M+H)^+$].

$^1$H NMR ($CDCl_3$, 300 MHz): (ppm)=7.31-7.22 (m, 5H), 6.26 (s, 1H), 4.87 (d, 1H), 3.95 (m, 1H), 3.85 (s, 2H), 3.45 (dt, 2H), 3.18 (dt, 2H), 2.24 (s, 3H), 2.06 (m, 2H), 1.58 (ddt, 2H).

b) (4-Benzyl-6-methyl-pyrimidin-2-yl)-[1-(3-methyl-[1,2,4]oxadiazol-5-yl)-piperidin-4-yl]-amine To a solution of 4-(4-benzyl-6-methyl-pyrimidin-2-ylamino)-piperidine-1-carbonitrile (135 mg, 0.44 mmol) and acetamidoxime (39 mg, 0.53 mmol) in EtOAc (1 mL) and THF (1 mL) was added within 10 minutes a solution of zinc chloride (73 mg, 0.53 mmol) in EtOAc (1 mL). After stirring at room temperature for 4 hours the reaction was heated to reflux over night under nitrogen. The reaction was diluted with water and extracted twice with ethyl acetate. The combined organic layers were washed with saturated aqueous NaCl solution, dried over sodium sulfate, filtered and concentrated under reduced pressure. The residue was purified by column chromatography on silica gel using $CH_2Cl_2$/MeOH 19:1 (v/v) as eluent. The title compound was obtained as a colorless gum (98 mg, 61%).

MS ISP (m/e): 365.3 (100) [$(M+H)^+$].

$^1$H NMR ($CDCl_3$, 300 MHz): (ppm)=7.31-7.24 (m, 5H), 6.25 (s, 1H), 4.87 (d, 1H), 4.07 (m, 3H), 3.85 (s, 2H), 3.29 (m, 2H), 2.25 (s, 3H), 2.22 (s, 3H), 2.13 (m, 2H), 1.53 (m, 2H).

Example 45

5-(4-Fluorophenyl)-N-(1-(3-methyl-1,2,4-thiadiazol-5-yl)piperidin-4-yl)-[1,2,4]triazolo[1,5-a]pyrazin-2-amine

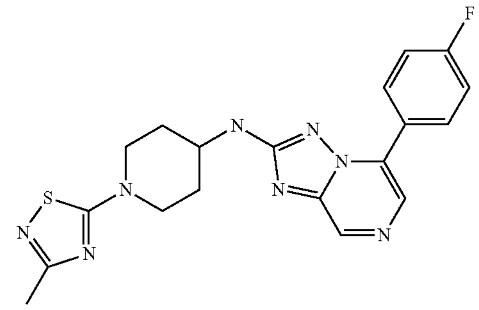 [SMILES: Cc1nsc(N2CCC(Nc3nc4cncc(-c5ccc(F)cc5)n4n3)CC2)n1]

a) 6-(4-Fluoro-phenyl)-pyrazin-2-ylamine

Prepared in analogy to example 1d, starting from 2-amino-6-chloropyrazine and 4-fluorobenzeneboronic acid. The title compound was obtained as a slightly brown solid (yield: 91%).

MS ISP (m/e): 190.3 (100) [$(M+H)^+$].

$^1$H NMR (DMSO-$D_6$, 300 MHz): (ppm)=8.27 (s, 1H), 8.04 (dd, 2H), 7.84 (s, 1H), 7.30 (t, 2H), 6.52 (br s, 2H).

b) N-(6-(4-Fluoro-phenyl)-pyrazin-2-yl)-N'-ethoxycarbonyl-thiourea

Prepared in analogy to example 1e, starting from 6-(4-fluoro-phenyl)-pyrazin-2-ylamine. The title compound precipitated from the reaction, was filtered and washed with n-heptane, dried and was obtained as white crystals (yield: 80%).

MS ISP (m/e): 321.2 (100) [$(M+H)^+$], 232.2 (34), 275.2 (25).

$^1$H NMR (DMSO-$D_6$, 300 MHz): (ppm)=12.18 (br s, 1H), 11.92 (br s, 1H), 9.56 (br s, 1H), 9.10 (s, 1H), 8.19 (dd, 2H), 7.40 (t, 2H), 4.25 (q, 2H), 1.28 (t, 3H).

c) 5-(4-Fluoro-phenyl)-[1,2,4]triazolo[1,5-a]pyrazin-2-ylamine

Prepared in analogy to example 1f, starting from N-(6-(4-fluoro-phenyl)-pyrazin-2-yl)-N'-ethoxycarbonyl-thiourea. The reaction was diluted with water and the title compound was filtered and washed with MeOH/$Et_2O$ 4:1 and then with $Et_2O$. The product was purified by column chromatography on silica gel using $CH_2Cl_2$/MeOH (v/v=19:1) as eluent to yield the title compound as white crystals (yield: 73%).

MS ISP (m/e): 230.3 (100) [$(M+H)^+$].

$^1$H NMR (DMSO-$D_6$, 300 MHz): (ppm)=8.83 (s, 1H), 8.19 (s, 1H), 8.12 (dd, 2H), 7.43 (t, 2H), 6.54 (br s, 2H).

d) 5-(4-Fluorophenyl)-N-(1-(3-methyl-1,2,4-thiadiazol-5-yl)piperidin-4-yl)-[1,2,4]triazolo[1,5-a]pyrazin-2-amine Prepared in analogy to example 1h, starting from 5-(4-fluoro-phenyl)-[1,2,4]triazolo[1,5-a]pyrazin-2-ylamine and 1-(3-methyl-[1,2,4]thiadiazol-5-yl)-piperidin-4-one. The title compound was obtained as a white solid.

MS ISP (m/e): 411.3 (67) [(M+H)$^+$].

$^1$H NMR ($CDCl_3$, 300 MHz): (ppm)=8.87 (s, 1H), 8.12 (s, 1H), 8.01-7.96 (m, 2H), 7.29-7.23 (m, 2H), 4.78-4.76 (m, 1H), 4.07-3.88 (m, 3H), 3.40-3.31 (m, 2H), 2.42 (s, 3H), 2.27-2.22 (m, 2H), 1.74-1.61 (m, 2H).

Example 46

[8-(3,4-Difluoro-phenyl)-[1,2,4]triazolo[1,5-a]pyridin-2-yl]-[1-(3-methyl-[1,2,4]thiadiazol-5-yl)-piperidin-4-yl]-amine

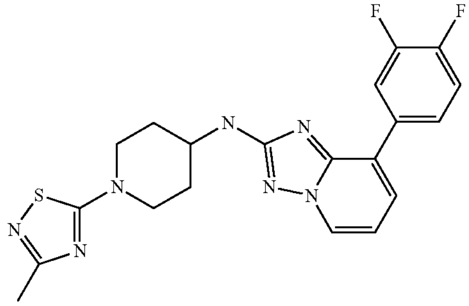 [SMILES: Cc1nsc(N2CCC(Nc3nc4c(-c5ccc(F)c(F)c5)cccn4n3)CC2)n1]

Prepared in analogy to example 1h, starting from 8-(3,4-difluoro-phenyl)-[1,2,4]triazolo[1,5-a]pyridin-2-ylamine and 1-(3-methyl-[1,2,4]thiadiazol-5-yl)-piperidin-4-one. The title compound was obtained as a white solid.

MS ISP (m/e): 428.3 (100) [(M+H)$^+$].

$^1$H NMR ($CDCl_3$, 300 MHz): (ppm)=8.34-8.32 (m, 1H), 7.96-7.88 (m, 1H), 7.72-7.67 (m, 1H), 7.52-7.49 (m, 1H), 7.31-7.22 (m, 1H), 6.93-6.88 (m, 1H), 4.56-4.53 (m, 1H), 3.98-3.89 (m, 3H), 3.41-3.32 (m, 2H), 2.42 (s, 3H), 2.31-2.24 (m, 2H), 1.70-1.61 (m, 2H).

Example 47

8-(3-Chloro-4-fluorophenyl)-N-(1-(3-methyl-1,2,4-thiadiazol-5-yl)piperidin-4-yl)-[1,2,4]triazolo[1,5-a]pyridin-2-amine

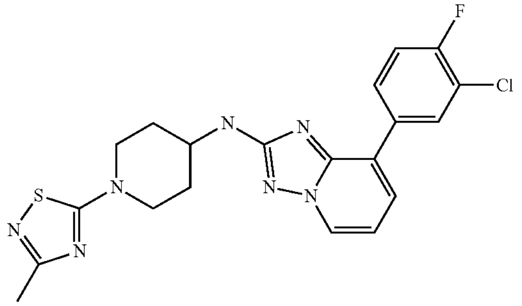

Prepared in analogy to example 1h, starting from 8-(3-Chloro-4-fluoro-phenyl)-[1,2,4]triazolo[1,5-a]pyridin-2-ylamine and 1-(3-methyl-[1,2,4]thiadiazol-5-yl)-piperidin-4-one. The title compound was obtained as a white solid.

MS ISP (m/e): 444.2 (100) [(M+H)$^+$].

$^1$H NMR ($CDCl_3$, 300 MHz): (ppm)=8.34-8.32 (m, 1H), 8.11-8.07 (m, 1H), 7.88-7.83 (m, 1H), 7.51-7.49 (m, 1H), 7.28-7.22 (m, 1H), 6.93-6.88 (m, 1H), 4.54-4.51 (m, 1H), 4.00-3.88 (m, 3H), 3.41-3.32 (m, 2H), 2.42 (s, 3H), 2.30-2.24 (m, 2H), 1.74-1.61 (m, 2H).

Example 48

[8-(4-Chloro-phenyl)-6-cyclopropyl-[1,2,4]triazolo[1,5-a]pyridin-2-yl]-[1-(6-methyl-pyrimidin-4-yl)-piperidin-4-yl]-amine

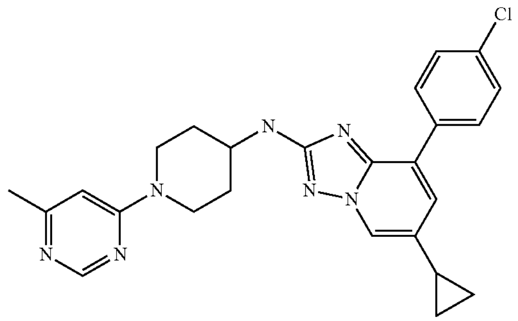 [SMILES: Cc1cc(N2CCC(Nc3nc4c(-c5ccc(Cl)cc5)cc(C5CC5)cn4n3)CC2)ncn1]

a) 5-Cyclopropyl-pyridin-2-ylamine

To a solution of 5-bromo-pyridin-2-ylamine (2 g, 11.55 mmol) and cyclopropyl boronic acid (2.98 g, 34.68 mmol) in toluene (40 mL) and water (2 mL) was added $K_3PO_4$ (8.59 g, 40.46 mmol) under an argon atmosphere. To this were added $Pd(OAc)_2$ (259.52 mg, 1.16 mmol) and tricyclohexylphosphene (647.3 mg, 2.3 mmol) and stirred at 80° C. for 16 hours. The reaction mixture was cooled to room temperature and water was added. The aqueous phase was extracted with ethyl acetate, the combined organic phases were dried over sodium sulfate, the solvent was evaporated and the residue purified by silica gel chromatography using ethyl acetate/hexane as eluent. The title compound was obtained as an off white solid (1.1 g, 71%).

$^1$H NMR (DMSO-$D_6$, 400 MHz): δ (ppm)=7.73 (s, 1H), 7.04-7.02 (dd, J=8.48 & 2.04 Hz, 1H), 6.34 (d, J=8.48 & 2.04 Hz, 1H), 5.60 (s, 2H), 1.78-1.66 (m, 1H), 0.82-0.77 (m, 2H), 0.52-0.31 (m, 2H)

b) 3-Bromo-5-cyclopropyl-pyridin-2-ylamine

To a solution of 5-cyclopropyl-pyridin-2-ylamine (1.1 g, 8.19 mmol) in dry chloroform (100 mL) was added bromine (0.42 mL, 8.2 mmol) in chloroform (11 mL) at room temperature and stirred for 18 hours. An aqueous solution of sodium thiosulfate was added, the aqueous phase was extracted with dichloromethane, the combined organic phases were dried over sodium sulfate, the solvent was evaporated and the residue purified by silica gel chromatography using ethyl acetate/hexane as eluent. The title compound was obtained as light yellow oil (1.0 g, 57%).

MS ESI (m/z): 213.0 [(M+H)$^+$].

$^1$H NMR (DMSO-$D_6$, 400 MHz): δ (ppm)=7.77 (d, J=1.44 Hz, 1H), 7.39 (d, J=1.44 Hz, 1H), 5.9 (s, 2H), 1.79-1.74 (m, 1H), 0.85-0.80 (m, 2H), 0.59-0.55 (m, 2H).

c) N-(3-Bromo-5-cyclopropyl-pyridin-2-yl)-N'-ethoxycarbonyl-thiourea

To a solution of 3-bromo-5-cyclopropyl-pyridin-2-ylamine (1.0 g, 4.69 mmol) in dry 1,4-dioxane (20 mL) was added ethoxy carbonyl isothiocyanate (0.55 mL, 5.16 mmol) under an argon atmosphere and stirred at room temperature for 6 hours. The solvent was evaporated and the title compound was obtained as light yellow oil (1.5 g, 98%).

MS ESI (m/z): 346.2 [(M+H)$^+$].

$^1$H NMR (DMSO-$D_6$, 400 MHz): δ (ppm)=11.41 (s, 1H), 11.32 (s, 1H), 8.29 (s, 1H), 7.80 (s, 1H), 4.24-4.19 (q, J=7.08, 2H), 2.03-1.97 (m, 1H), 1.28-1.24 (t, J=7.12 Hz, 3H), 1.06-0.97 (m, 2H), 0.84-0.81 (m, 2H).

d) 8-Bromo-6-cyclopropyl-[1,2,4]triazolo[1,5-a]pyridin-2-ylamine

To a solution of N-(3-bromo-5-cyclopropyl-pyridin-2-yl)-N'-ethoxycarbonyl-thiourea (1.5 g, 4.36 mmol) in dry methanol (20 mL) were added hydroxylamine hydrochloride (1.41 g, 21.8 mmol) and diisopropyl ethylamine (12.14 mL, 13.08 mmol) under an argon atmosphere and stirred at room temperature for 6 hours. Methanol was evaporated and the residue purified by silica gel chromatography using ethyl acetate/hexane as eluent. The title compound was obtained as off white solid (910 mg, 82%).

MS ESI (m/z): 252.6 [(M+H)$^+$].

$^1$H NMR (DMSO-$D_6$, 400 MHz): δ (ppm)=8.41 (s, 1H), 7.48 (s, 1H), 6.12 (s, 2H), 1.99-1.90 (m, 1H), 0.93-0.84 (m, 2H), 0.80-0.75 (m, 2H).

e) 8-(4-Chloro-phenyl)-6-cyclopropyl-[1,2,4]triazolo[1,5-a]pyridin-2-ylamine

To a solution of 8-bromo-6-cyclopropyl-[1,2,4]triazolo[1,5-a]pyridin-2-ylamine (300 mg, 1.29 mmol) and 4-chlorophenyl boronic acid (463 mg, 2.96 mmol) in dioxane (15 mL) was added an aqueous solution of $Na_2CO_3$ (2 M, 2 mL) and degassed with argon for 5 minutes. $PdCl_2$ (dppf)$_2$.$CH_2Cl_2$ (30.34 mg, 0.04 mmol) was added and stirred at 80° C. for 90 minutes. The reaction mixture was cooled to room temperature and water (20 mL) was added. The aqueous phase was extracted with ethyl acetate, the combined organic phases were dried over sodium sulfate, the solvent was evaporated and the residue purified by silica gel chromatography using ethyl acetate/hexane as eluent. The title compound was obtained as an off white solid (252 mg, 75%).

MS ESI (m/z): 284.8 [(M+H)$^+$].

$^1$H NMR (DMSO-$D_6$, 400 MHz): δ (ppm)=8.39 (s, 1H), 8.18 (d, 2H), 7.54 (d, 2H), 7.45 (s, 1H), 2.05-2.01 (m, 1H), 0.97-0.92 (m, 2H), 0.84-0.82 (m, 2H).

f) 2-Bromo-8-(4-chloro-phenyl)-6-cyclopropyl-[1,2,4]triazolo[1,5-a]pyridine

To a solution of tert-butylnitrite (0.18 mL, 1.05 mmol) in dry acetonitrile (7 mL) was added copper(II) bromide (234 mg, 1.05 mmol) under an argon atmosphere and heated to 60° C. for 0.1 hour. 8-(4-Chloro-phenyl)-6-cyclopropyl-[1,2,4]triazolo[1,5-a]pyridin-2-ylamine (200 mg, 0.7 mmol) in acetonitrile (5 mL) was added at 60° C. The reaction mixture was stirred at 75° C. for 3 hours and then cooled to room temperature. Water (10 mL) was added. The aqueous phase was extracted with dichloromethane, the combined organic phases were dried over sodium sulfate, the solvent was evaporated and the residue purified by silica gel chromatography using ethyl acetate/hexane as eluent. The title compound was obtained as off white solid (150 mg, 61%).

MS ESI (m/z): 348.2 [(M+H)$^+$].

$^1$H NMR (DMSO-$D_6$, 400 MHz): (ppm)=8.81 (s, 1H), 8.14 (d, J=8.52 Hz, 2H), 7.72 (s, 1H), 7.62 (d, J=8.4 Hz, 2H), 2.12-2.10 (m, 1H), 1.03-0.93 (m, 4H).

g) [8-(4-Chloro-phenyl)-6-cyclopropyl-[1,2,4]triazolo[1,5-a]pyridin-2-yl]-[1-(6-methyl-pyrimidin-4-yl)-piperidin-4-yl]-amine A solution of 2-bromo-8-(4-chloro-phenyl)-6-cyclopropyl-[1,2,4]triazolo[1,5-a]pyridine (50 mg, 0.14 mmol), 1-(6-methyl-pyrimidin-4-yl)-piperidin-4-ylamine (see example 94a, 23 mg, 0.12 mmol) and sodium phenoxide (21 mg, 0.2 mmol) in dry 1,4-dioxane (3 mL) in a sealed tube was purged with argon for 10 minutes. $Pd_2(dba)_3$.$CHCl_3$ (8 mg, 0.01 mmol) and xanthphos (2 mg) were added to the solution and stirred at 160° C. for 15 hours. The reaction mixture was cooled to room temperature and water (10 mL) was added. The aqueous phase was extracted with ethyl acetate, the combined organic phases were dried over sodium sulfate, the solvent was evaporated and the residue purified by silica gel chromatography using dichloromethane/methanol as eluent. The title compound was obtained as a light brown solid (5 mg, 8%).

MS ESI (m/z): 460.0 [(M+H)$^+$].

Example 49

2-[8-(4-Chloro-phenyl)-2-[1-(6-methyl-pyrimidin-4-yl)-piperidin-4-ylamino]-[1,2,4]triazolo[1,5-a]pyridin-5-yl]-propan-2-ol

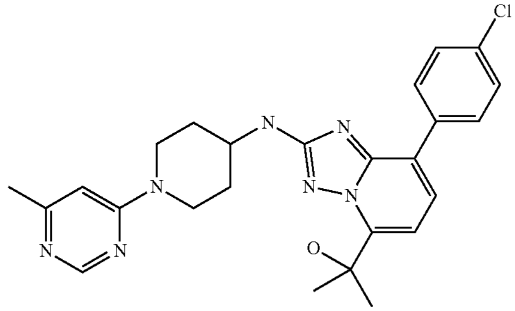 [SMILES: Cc1cc(N2CCC(Nc3nc4c(-c5ccc(Cl)cc5)ccc(C(C)(C)O)n4n3)CC2)ncn1]

a) N-(6-Methyl-pyridin-2-yl)-acetamide

To a solution of 6-methyl-pyridin-2-ylamine (50 g, 0.462 mol) in acetic anhydride (200 mL) was heated to 90° C. for 90 minutes. The reaction mixture was cooled to room temperature and evaporated. An aqueous saturated solution of $NaHCO_3$ was added to the residue until pH 8. The aqueous phase was extracted with ethyl acetate, the combined organic phases were dried over sodium sulfate, and the solvent was evaporated. The title compound was obtained as a white solid (68 g, 98%).

MS ESI (m/e): 151.2 [(M+H)$^+$].

$^1$H NMR (DMSO-$D_6$, 400 MHz): (ppm)=10.38 (s, 1H), 7.86 (d, J=8.2 Hz, 2H), 7.62 (t, J=7.8 Hz, 1H), 6.92 (d, J=7.4 Hz, 1H), 2.38 (s, 3H), 2.06 (s, 3H).

b) 6-Acetylamino-pyridine-2-carboxylic acid

A solution of N-(6-methyl-pyridin-2-yl)-acetamide (10 g, 0.067 mmol) in water (100 mL) was heated to 75° C. Potassium permanganate (37 g, 233 mmol) was added portion-wise at 75° C. After 4 hours at 75° C. for the reaction mixture was cooled to room temperature and the solid was filtered. The aqueous layer was evaporated to half of its original volume and acidified with HCl (12 N) to pH 4-5. The precipitate was filtered and dried. The title compound was obtained as off white solid (4.5 g, 37%).

MS ESI (m/z): 181.2 [$(M+H)^+$].

$^1$H NMR (DMSO-$D_6$, 400 MHz): (ppm)=13.0 (s, 1H), 10.78 (s, 1H), 8.26 (d, J=8.28 Hz, 1H), 7.92 (t, J=7.8 Hz, 1H), 7.72 (d, J=7.1 Hz, 1H), 2.10 (s, 3H).

c) 6-Amino-pyridine-2-carboxylic acid methyl ester

A solution of 6-acetylamino-pyridine-2-carboxylic acid (16 g, 0.088 mol) in methanolic hydrochloride (4N, 50 mL) was heated to reflux for 18 hours. The reaction mixture was cooled to room temperature and evaporated. Water was added to the residue and alkalized with solid $NaHCO_3$. The aqueous phase was extracted with ethyl acetate, the combined organic phases were dried over sodium sulfate, and the solvent was evaporated. The title compound was obtained as a white solid (8 g, 59%).

MS ESI (m/z): 153.0 [$(M+H)^+$].

$^1$H NMR (DMSO-$D_6$, 400 MHz): (ppm)=7.53 (t, J=7.52 Hz, 1H), 7.48 (d, J=7.28 Hz, 2H), 6.66 (d, J=8.04 Hz, 1H), 4.71 (s, 2H), 3.94 (s, 3H).

d) 6-Amino-5-bromo-pyridine-2-carboxylic acid methyl ester

To a solution of 6-amino-pyridine-2-carboxylic acid methyl ester (10 g, 66.0 mmol) in chloroform (450 mL) was added bromine (3.4 mL, 66.0 mmol) in $CHCl_3$ (100 mL) at room temperature and stirred for 40 hours. The reaction mixture was diluted with $CHCl_3$ and washed with saturated sodium thiosulfate solution and water. The organic phase was dried over sodium sulfate, the solvent was evaporated and the residue purified by silica gel column chromatography using ethyl acetate/hexane as eluent. The title compound obtained as yellow solid (3.3 g, 22%).

MS ESI (m/e): 231.0 [$(M+H)^+$].

$^1$H NMR ($CDCl_3$, 400 MHz): δ (ppm)=7.76 (d, J=7.88 Hz, 1H), 7.34 (d, J=7.92 Hz, 1H), 5.23 (s, 2H), 3.94 (s, 3H).

d') 6-Amino-3-bromo-pyridine-2-carboxylic acid methyl ester

In step d) the isomeric 6-amino-3-bromo-pyridine-2-carboxylic acid methyl ester (3.0 g, 19%) was isolated as side product.

MS ESI (m/e): 231.2 [$(M+H)^+$].

$^1$H NMR ($CDCl_3$, 400 MHz): δ (ppm)=7.60 (d, J=8.72 Hz, 1H), 6.47 (d, J=7.88 Hz, 1H), 4.71 (s, 2H), 3.94 (s, 3H).

e) N-(3-Bromo-6-ethoxycarbonyl-pyridin-2-yl)-N'-ethoxycarbonyl-thiourea

To a solution of 6-amino-5-bromo-pyridine-2-carboxylic acid methyl ester (3.3 g, 14.28 mmol) in dry 1,4-dioxane (20 mL) was added ethoxy carbonyl isothiocyanate (1.8 mL, 15.7 mmol) under an argon atmosphere and stirred at room temperature for 16 hours. The solvent was evaporated and the title compound was obtained as yellow solid (4.9 g, 95%).

MS ESI (m/e): 362.0 [$(M+H)^+$].

$^1$HNMR (DMSO-$D_6$, 400 MHz): δ (ppm)=1.54 (s, 1H), 11.46 (s, 1H), 8.36 (d, J=8.16 Hz, 1H), 7.92 (d, J=8.16 Hz, 1H), 4.27-4.23 (m, 2H), 3.89 (s, 3H), 1.36-1.26 (m, 3H).

f) 2-Amino-8-bromo-[1,2,4]triazolo[1,5-a]pyridine-5-carboxylic acid methyl ester To a solution of N-(3-bromo-6-ethoxycarbonyl-pyridin-2-yl)-N'-ethoxycarbonyl-thiourea (2 g, 5.52 mmol) in dry methanol (10 mL) were added hydroxylamine hydrochloride (1.92 g, 27.62 mmol) and diisopropyl ethylamine (2.98 mL, 16.57 mmol) under an argon atmosphere and stirred at room temperature for 4 hours. The solid was filtered and methanol (40 mL) was added to residue. The reaction mixture was heated to reflux for 12 hours. The solvent was evaporated and the title compound was obtained as off white solid (800 mg, 53%).

MS ESI (m/e): 270.8 [$(M+H)^+$].

$^1$H NMR (DMSO-$D_6$, 400 MHz): δ (ppm)=7.66 (d, J=8.04 Hz, 1H), 7.43 (d, J=8.12 Hz, 1H), 4.9 (s, 2H), 4.02 (s, 3H).

g) 2-(2-Amino-8-bromo-[1,2,4]triazolo[1,5-a]pyridin-5-yl)-propan-2-ol

To a solution of 2-amino-8-bromo-[1,2,4]triazolo[1,5-a]pyridine-5-carboxylic acid methyl ester (900 mg, 3.32 mmol) in tetrahydrofuran was added methyl magnesium bromide (1.4 M solution in toluene/tetrahydrofuran; 75/25) (9.49 mL, 13.28 mmol) at −40° C. and stirred at −30° C. for 1 hour. The reaction mixture was warmed to room temperature and quenched with saturated aqueous $NH_4Cl$ solution. The aqueous phase was extracted with ethyl acetate, the combined organic phases were dried over sodium sulfate, the solvent was evaporated and the residue was purified by silica gel column chromatography using ethyl acetate/hexane as eluent. The title compound was obtained as yellow solid (400 mg, 44%) which was contaminated with 1-(2-amino-8-bromo-[1,2,4]triazolo[1,5-a]pyridin-5-yl)-ethanone.

MS ESI (m/e): 273.2 [$(M+H)^+$].

h) 2-[2-Amino-8-(4-chloro-phenyl)-[1,2,4]triazolo[1,5-a]pyridin-5-yl]-propan-2-ol To a solution of 2-(2-amino-8-bromo-[1,2,4]triazolo[1,5-a]pyridin-5-yl)-propan-2-ol (contaminated with ketone) (120 mg, 0.443 mmol) and 4-chlorophenyl boronic acid (155 mg, 0.987 mmol) in dioxane (6 mL) was added aqueous solution of $Na_2CO_3$ (2 M, 0.72 mL) and degassed with argon for 5 minute. To this was added $PdCl_2$ $(dppf)_2.CH_2Cl_2$ (30.34 mg, 0.04 mmol) and stirred at 90° C. for 90 minutes. The reaction mixture was cooled to room temperature and water (20 mL) was added. The aqueous phase was extracted with ethyl acetate, the combined organic phases were dried over sodium sulfate, the solvent was evaporated and the residue was purified by silica gel chromatography using ethyl acetate/hexane as eluent. The title compound was obtained as an off white solid (65 mg, 48%) which was contaminated with 1-[2-amino-8-(4-chloro-phenyl)-[1,2,4]triazolo[1,5-a]pyridin-5-yl]-ethanone.

MS ESI (m/e): 273.2 [$(M+H)^+$].

i) 2-[2-Bromo-8-(4-chloro-phenyl)-[1,2,4]triazolo[1,5-a]pyridin-5-yl]-propan-2-ol To a solution of tert-butylnitrite (0.06 mL, 0.47 mmol) in dry acetonitrile (5 mL) was added Cu(II) bromide (105 mg, 0.47 mmol) under an argon atmosphere and heated to 60° C. for 0.1 hour. 2-[2-Amino-8-(4-chloro-phenyl)-[1,2,4]triazolo[1,5-a]pyridin-5-yl]-propan-2-ol (mixture of alcohol and ketone) (90 mg, 0.32 mmol) in acetonitrile (5 mL) was added at 60° C. and stirred at 75° C. for 3 hour. The reaction mixture was cooled to room temperature and water (10 mL) was added. The aqueous phase was extracted with dichloromethane, the combined organic phases were dried over sodium sulfate, the solvent was evaporated and the residue was purified by silica gel chromatography using ethyl acetate/hexane as eluent. The title compound was obtained as off white solid (20 mg, 48%).

MS ESI (m/e): 368.0 [(M+H)$^+$].

k) 2-{8-(4-Chloro-phenyl)-2-[1-(6-methyl-pyrimidin-4-yl)-piperidin-4-ylamino]-[1,2,4]triazolo[1,5-a]pyridin-5-yl}-propan-2-ol A solution of 2-[2-bromo-8-(4-chloro-phenyl)-[1,2,4]triazolo[1,5-a]pyridin-5-yl]-propan-2-ol (42 mg, 0.11 mmol), 1-(6-methyl-pyrimidin-4-yl)-piperidin-4-ylamine (18 mg, 0.1 mmol) and sodium phenoxide (17 mg, 0.15 mmol) in dry 1,4-dioxane (6 mL) in a sealed tube was purged with argon for 10 minutes. $Pd_2(dba)_3.CHCl_3$ (8 mg, 0.012 mmol) and xanthphos (2 mg) were added to the solution and degassing continued for another 5 minutes before the reaction mixture was heated to 160° C. for 15 hours. The reaction mixture was cooled to room temperature and water (10 mL) was added. The aqueous phase was extracted with ethyl acetate, the combined organic phases were dried over sodium sulfate, the solvent was evaporated and the residue purified by silica gel chromatography using dichloromethane/methanol as eluent. The title compound was obtained as a white solid (7 mg, 13%). MS ESI (m/e): 478.0 [(M+H)$^+$].

Example 50

[6-Cyclopropyl-8-(4-fluoro-phenyl)-[1,2,4]triazolo[1,5-a]pyridin-2-yl]-[1-(6-methyl-pyrimidin-4-yl)-piperidin-4-yl]-amine

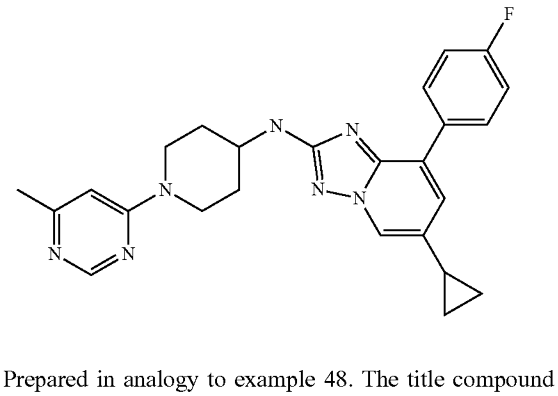

Prepared in analogy to example 48. The title compound was obtained as a brown solid.

MS ESI (m/z): 444.3 [(M+H)$^+$].

$^1$H NMR (DMSO-$D_6$, 400 MHz): δ (ppm)=8.46 (s, 1H), 8.36 (s, 1H), 8.19-8.16 (m, 2H), 7.45 (s, 1H), 7.31 (t, J=8.88 Hz, 2H), 6.73-6.69 (m, 2H), 4.3 (m, 2H), 3.10 (t, J=11.64 Hz, 2H), 2.5 (s, 3H), 2.04-1.99 (m, 3H), 1.44 (m, 2H), 0.97-0.93 (m, 2H), 0.85-0.83 (m, 2H).

Example 51

[8-(3-Chloro-4-fluoro-phenyl)-6-cyclopropyl-[1,2,4]triazolo[1,5-a]pyridin-2-yl]-[1-(6-methyl-pyrimidin-4-yl)-piperidin-4-yl]-amine

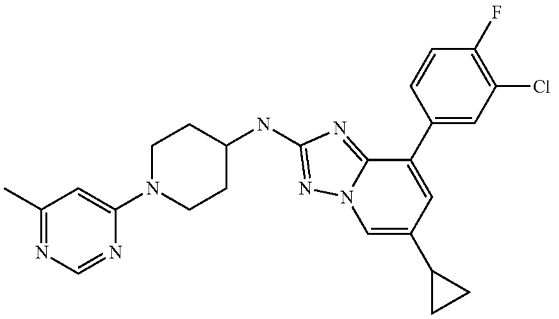 [SMILES: Cc1cc(N2CCC(Nc3nc4c(-c5ccc(F)c(Cl)c5)cc(C5CC5)cn4n3)CC2)ncn1]

To a solution of dibutyl tin chloride (10 mg, 0.03 mmol) and 8-(3-chloro-4-fluoro-phenyl)-6-cyclopropyl-[1,2,4]triazolo[1,5-a]pyridin-2-ylamine (prepared in analogy to example 48a-e, 100 mg, 0.33 mmol) in dry THF (1.5 mL) were added 1-(6-methyl-pyrimidin-4-yl)-piperidin-4-one (example 93b, 63 mg, 0.33 mmol) and phenyl silane (0.016 mL, 0.4 mmol) under an argon atmosphere and heated to 100° C. in the microwave for 40 minutes. The reaction mixture was cooled to room temperature, the solvent was evaporated and the residue was purified by prep-HPLC (acetonitrile/$H_2O$). The title compound was obtained as a white solid (20 mg, 13%). MS ESI (m/z): 477.8 [(M+H)$^+$].

$^1$H NMR (DMSO-$D_6$, 400 MHz): δ (ppm)=8.5 (s, 1H), 8.34 (s, 1H), 7.6-7.55 (m, 2H), 7.34-7.3 (m, 1H), 7.17 (s, 1H), 6.71 (s, 1H), 6.63 (d, 1H), 4.24 (d, 2H), 3.08 (t, J=11.32 Hz, 2H), 2.23 (s, 3H), 2.00-1.94 (m, 3H), 1.4-1.32 (m, 2H), 0.94-0.9 (m, 2H), 0.77-0.75 (m, 2H).

Example 52

8-(2-Chloro-4-fluorophenyl)-N-(1-(6-methylpyrimidin-4-yl)piperidin-4-yl)-[1,2,4]triazolo[1,5-a]pyridin-2-amine

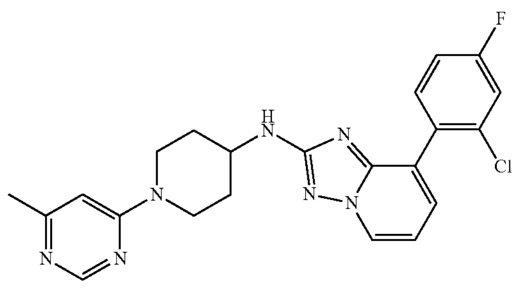 [SMILES: Cc1cc(N2CCC(Nc3nc4c(-c5ccc(F)cc5Cl)cccn4n3)CC2)ncn1]

1-(6-Methylpyrimidin-4-yl)piperidin-4-amine dihydrochloride (133 mg, 0.5 mmol) was suspended in dichloromethane (15 mL) and then extracted with aqueous sodium hydroxide (2 M, 10 mL). The aqueous layer was extracted with dichloromethane (15 mL) and the organic layers were combined, dried over sodium sulfate and evaporated carefully. After addition of 2-bromo-8-(2-chloro-4-fluorophenyl)-[1,2,4]triazolo[1,5-a]pyridine (180 mg, 0.55 mmol), 4,5-bis(diphenylphosphino)-9,9-dimethylxanthene (23.1 mg, 0.04 mmol), tris(dibenzylideneacetone)dipalladium(o) chloroform adduct (21 mg, 0.02 mmol) and sodium phenoxide (87 mg, 0.75 mmol) in dry 1,4-dioxane (4 mL) the reaction mixture was stirred under an argon atmosphere for 60 minutes at 130° C. in the microwave. Concentration and purification of the residue by chromatography (SiO2, heptane:ethyl acetate 3:1 to 0:1) afforded the title compound as yellow foam (97 mg, 44%).

MS ISP (m/e): 438.3 and 440.4 [(M+H)$^+$].

$^1$H NMR ($CDCl_3$, 300 MHz): δ (ppm)=8.50 (s, 1H), 8.36 (d, 1H), 7.50 (dd, 1H), 7.37 (d, 1H), 7.26 (dd, 1H), 7.10 (dt, 1H), 6.59 (dd, 1H), 6.39 (s, 1H), 4.53 (d, 1H), 4.35-4.20 (m, 2H), 3.98-3.75 (m, 1H), 3.17 (dt, 2H), 2.35 (s, 3H), 2.28-2.15 (m, 2H), 1.55-1.40 (m, 2H).

Example 53

8-(3,4-Difluorophenyl)-N-(1-(6-methylpyrimidin-4-yl)piperidin-4-yl)-[1,2,4]triazolo[1,5-a]pyridin-2-amine

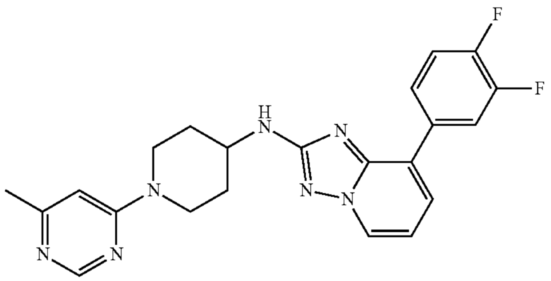 [SMILES: Cc1cc(N2CCC(Nc3nc4c(-c5ccc(F)c(F)c5)cccn4n3)CC2)ncn1]

Prepared in analogy to example 52 employing 2-bromo-8-(3,4-difluorophenyl)-[1,2,4]triazolo[1,5-a]pyridine instead of 2-bromo-8-(2-chloro-4-fluorophenyl)-[1,2,4]triazolo[1,5-a]pyridine. The title compound was obtained as yellow foam.

MS ISP (m/e): 422.2 [(M+H)$^+$].

$^1$H NMR ($CDCl_3$, 300 MHz): δ (ppm)=8.52 (s, 1H), 8.33 (d, 1H), 7.92 (ddd, 1H), 7.70 (m, 1H), 7.50 (d, 1H), 7.35 (m, 1H), 6.89 (dd, 1H), 6.41 (s, 1H), 4.57 (d, 1H), 4.40-4.35 (m, 2H), 4.00-3.90 (m, 1H), 3.19 (dt, 2H), 2.37 (s, 3H), 2.28-2.15 (m, 2H), 1.60-1.40 (m, 2H).

Example 54

8-(3,4-Difluorophenyl)-6-methyl-N-(1-(6-methylpyrimidin-4-yl)piperidin-4-yl)-[1,2,4]triazolo[1,5-a]pyridin-2-amine

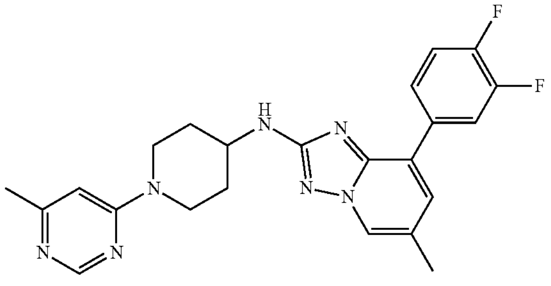 [SMILES: Cc1cc(-c2ccc(F)c(F)c2)c2nc(NC3CCN(c4cc(C)ncn4)CC3)nn2c1]

Prepared in analogy to example 52 employing 2-bromo-8-(3,4-difluorophenyl)-6-methyl-[1,2,4]triazolo[1,5-a]pyridine instead of 2-bromo-8-(2-chloro-4-fluorophenyl)-[1,2,4]triazolo[1,5-a]pyridine. The title compound was obtained as yellow oil.

MS ISP (m/e): 436.3 [(M+H)$^+$].

$^1$H NMR ($CDCl_3$, 300 MHz): δ (ppm)=8.51 (s, 1H), 8.15 (d, 1H), 7.90 (ddd, 1H), 7.70 (m, 1H), 7.35 (s, 1H), 7.35 (m, 1H), 6.41 (s, 1H), 4.50 (d, 1H), 4.40-4.35 (m, 2H), 4.00-3.90 (m, 1H), 3.18 (dt, 2H), 2.40 (s, 3H), 2.36 (s, 3H), 2.30-2.17 (m, 2H), 1.60-1.40 (m, 2H).

Example 55

8-(3,4-Difluorophenyl)-6-fluoro-N-(1-(6-methylpyrimidin-4-yl)piperidin-4-yl)-[1,2,4]triazolo[1,5-a]pyridin-2-amine

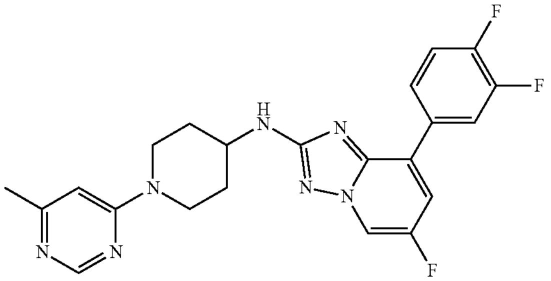 [SMILES: Cc1cc(N2CCC(Nc3nc4c(-c5ccc(F)c(F)c5)cc(F)cn4n3)CC2)ncn1]

Prepared in analogy to example 52 employing 2-bromo-8-(3,4-difluorophenyl)-6-fluoro-[1,2,4]triazolo[1,5-a]pyridine instead of 2-bromo-8-(2-chloro-4-fluorophenyl)-[1,2,4]triazolo[1,5-a]pyridine. The title compound was obtained as orange viscous oil.

MS ISP (m/e): 440.4 [(M+H)$^+$].

$^1$H NMR ($CDCl_3$, 300 MHz): δ (ppm)=8.52 (s, 1H), 8.30 (dd, 1H), 7.95 (ddd, 1H), 7.70 (m, 1H), 7.44 (dd, 1H), 7.35 (m, 1H), 6.41 (s, 1H), 4.55 (d, 1H), 4.40-4.35 (m, 2H), 4.00-3.90 (m, 1H), 3.18 (dt, 2H), 2.37 (s, 3H), 2.30-2.17 (m, 2H), 1.60-1.40 (m, 2H). 1H), 6.41 (s, 1H), 4.55 (d, 1H), 4.40-4.35 (m, 2H), 4.00-3.90 (m, 1H), 3.18 (dt, 2H), 2.37 (s, 3H), 2.30-2.17 (m, 2H), 1.60-1.40 (m, 2H).

Example 56

8-(3,4-Difluorophenyl)-6-chloro-N-(1-(6-methylpyrimidin-4-yl)piperidin-4-yl)-[1,2,4]triazolo[1,5-a]pyridin-2-amine

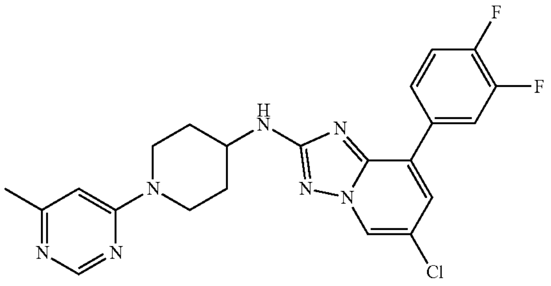 [SMILES: Cc1cc(N2CCC(Nc3nc4c(-c5ccc(F)c(F)c5)cc(Cl)cn4n3)CC2)ncn1]

Prepared in analogy to example 52 employing 2-bromo-8-(3,4-difluorophenyl)-6-chloro-[1,2,4]triazolo[1,5-a]pyridine instead of 2-bromo-8-(2-chloro-4-fluorophenyl)-[1,2,4]triazolo[1,5-a]pyridine. The title compound was obtained as orange viscous oil.

MS ISP (m/e): 440.4 [(M+H)$^+$].

$^1$H NMR ($CDCl_3$, 300 MHz): δ (ppm)=8.51 (s, 1H), 8.37 (d, 1H), 7.90 (dt, 1H), 7.70 (m, 1H), 7.50 (d, 1H), 7.30 (m, 1H), 6.41 (s, 1H), 4.57 (d, 1H), 4.40-4.30 (m, 2H), 4.00-3.90 (m, 1H), 3.18 (dt, 2H), 2.37 (s, 3H), 2.30-2.17 (m, 2H), 1.60-1.40 (m, 2H).

Example 57

8-(2-Chloro-4-fluorophenyl)-N-(1-(2-methylpyridin-4-yl)piperidin-4-yl)-[1,2,4]triazolo[1,5-a]pyridin-2-amine

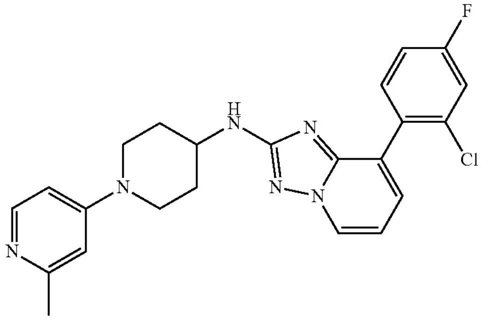 [SMILES: Cc1cc(N2CCC(Nc3nc4c(-c5ccc(F)cc5Cl)cccn4n3)CC2)ccn1]

a) tert-Butyl 4-(8-(2-chloro-4-fluorophenyl)-[1,2,4]triazolo[1,5-a]pyridin-2-ylamino)piperidine-1-carboxylate Prepared in analogy to example 52 employing tert-butyl 4-aminopiperidine-1-carboxylate instead of 1-(6-methylpyrimidin-4-yl)piperidin-4-amine. The title compound was obtained as yellow foam.

MS ISP (m/e): 446.3 and 448.3 [(M+H)$^+$].

$^1$H NMR ($CDCl_3$, 300 MHz): δ (ppm)=8.35 (d, 1H), 7.51 (dd, 1H), 7.37 (d, 1H), 7.28 (dd, 1H), 7.09 (ddd, 1H), 6.87 (dd, 1H), 4.49 (d, 1H), 4.05-3.90 (m, 2H), 3.82-3.70 (m, 1H), 2.98 (dt, 2H), 2.15-2.02 (m, 2H), 1.65-1.55 (m, 2H), 1.46 (s, 9H).

b) 8-(2-Chloro-4-fluorophenyl)-N-(piperidin-4-yl)-[1,2,4]triazolo[1,5-a]pyridin-2-amine To a solution of tert-butyl 4-(8-(2-chloro-4-fluorophenyl)-[1,2,4]triazolo[1,5-a]pyridin-2-ylamino)piperidine-1-carboxylate (810 mg, 1.82 mmol) in tetrahydrofuran (8 mL) and methanol (6 mL) was added hydrogen chloride solution (4.0 M in dioxane, 2.3 mL, 9.1 mmol). The reaction mixture was stirred for 1.5 hours at 60° C. and then concentrated in vacuo. The residue was diluted with ethyl acetate (40 mL) and washed with aqueous sodium carbonate (1 M, 30 mL), water (30 mL) and brine (30 mL). The aqueous layers were extracted with further ethyl acetate (40 mL). The organic layers were combined, dried over magnesium sulfate and filtered off. Concentration afforded the title compound as yellow foam (639 mg, 98%).

MS ISP (m/e): 346.2 and 348.3 [(M+H)$^+$].

$^1$H NMR ($CDCl_3$, 300 MHz): δ (ppm)=8.35 (d, 1H), 7.51 (dd, 1H), 7.37 (d, 1H), 7.28 (dd, 1H), 7.09 (ddd, 1H), 6.87 (dd, 1H), 4.54 (d, 1H), 3.70-3.65 (m, 1H), 3.25-3.10 (m, 2H), 2.80 (dt, 2H), 2.15-2.02 (m, 2H), 1.65-1.55 (m, 2H).

c) 8-(2-Chloro-4-fluorophenyl)-N-(1-(2-methylpyridin-4-yl)piperidin-4-yl)-[1,2,4]triazolo[1,5-a]pyridin-2-amine A mixture of 8-(2-chloro-4-fluorophenyl)-N-(piperidin-4-yl)-[1,2,4]triazolo[1,5-a]pyridin-2-amine (69 mg, 2 mmol), 4-bromo-2-methylpyridine (34 mg, 0.2 mmol) and N,N-diisopropylethylamine (40 mg, 0.3 mmol) in 1,4-dioxane (0.8 mL) was stirred for 30 minutes at 150° C. in the microwave. Purification by chromatography of the reaction mixture ($SiO_2$, heptane:ethyl acetate 1:1 to ethyl acetate:methanol: ammoniumhydroxide 80:18:2 afforded the title compound as yellow semisolid (21 mg, 24%).

MS ISP (m/e): 437.3 and 439.3 [(M+H)$^+$].

$^1$H NMR ($CDCl_3$, 300 MHz): δ (ppm)=8.35 (m, 2H), 7.50 (dd, 1H), 7.37 (dd, 1H), 7.26 (dd, 1H), 7.10 (dt, 1H), 6.86 (m, 1H), 6.55 (m, 1H), 5.30 (s, 1H), 4.53 (m, 1H), 3.90-3.80 (m, 1H), 3.75-3.60 (m, 1H), 3.57 (m, 2H), 3.17 (dt, 2H), 2.46 (s, 3H), 2.30-2.10 (m, 2H), 1.55-1.40 (m, 2H).

Example 58

8-(2-Chloro-4-fluorophenyl)-N-(1-(2-chloropyridin-4-yl)piperidin-4-yl)-[1,2,4]triazolo[1,5-a]pyridin-2-amine

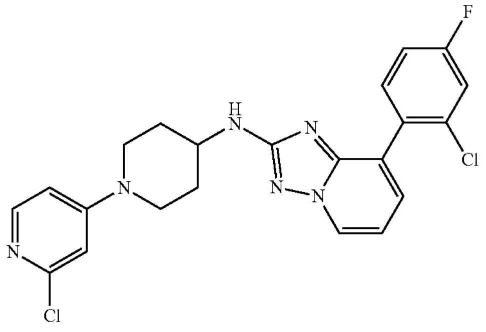 [SMILES: Fc1ccc(-c2cccn3nc(NC4CCN(c5ccnc(Cl)c5)CC4)nc23)c(Cl)c1]

Prepared in analogy to example 57c) employing 4-bromo-2-chloropyridine instead of 4-bromo-2-methylpyridine. The title compound was obtained as a yellow solid.

MS ISP (m/e): 457.3, 459.3 and 461.3 [(M+H)$^+$].

$^1$H NMR ($CDCl_3$, 300 MHz): δ (ppm)=8.36 (d, 1H), 8.00 (d, 1H), 7.65 (d, 1H), 7.50 (dd, 1H), 7.37 (dd, 1H), 7.26 (dd, 1H), 7.10 (dt, 1H), 6.89 (dd, 1H), 6.66 (d, 1H), 6.59 (dd, 1H), 4.51 (m, 1H), 3.95-3.85 (m, 1H), 3.85-3.75 (m, 2H), 3.12 (dt, 2H), 2.21 (m, 2H), 1.55-1.40 (m, 2H).

Example 59

8-(2-Chloro-4-fluorophenyl)-N-(1-(5-fluoro-2-methylpyridin-4-yl)piperidin-4-yl)-[1,2,4]triazolo[1,5-a]pyridin-2-amine

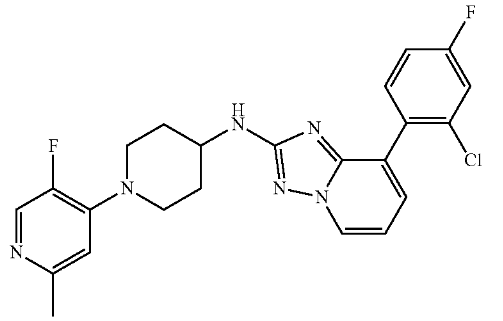 [SMILES: Cc1cc(N2CCC(Nc3nc4c(-c5ccc(F)cc5Cl)cccn4n3)CC2)c(F)cn1]

Prepared in analogy to example 57c) employing 4-chloro-5-fluoro-2-methylpyridine instead of 4-bromo-2-methylpyridine. The title compound was obtained as a yellow solid.

MS ISP (m/e): 455.3 and 457.3 [(M+H)$^+$].

$^1$H NMR ($CDCl_3$, 300 MHz): δ (ppm)=8.35 (d, 1H), 8.08 (d, 1H), 7.65 (d, 1H), 7.50 (m, 1H), 7.37 (dd, 1H), 7.26 (dd, 1H), 6.89 (dd, 1H), 6.60 (dd, 1H), 4.65 (m, 1H), 3.95-3.85 (m, 1H), 3.85-3.75 (m, 2H), 3.12 (dt, 2H), 2.45 (s, 3H), 2.21 (m, 2H), 1.55-1.40 (m, 2H).

Example 60

8-(2-Chloro-4-fluorophenyl)-N-(1-(pyrimidin-4-yl)piperidin-4-yl)-[1,2,4]triazolo[1,5-a]pyridin-2-amine

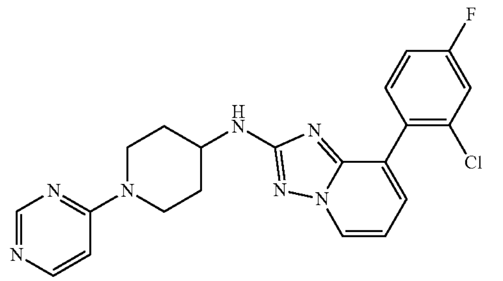 [SMILES: Fc1ccc(-c2cccn3nc(NC4CCN(c5ccncn5)CC4)nc23)c(Cl)c1]

Prepared in analogy to example 57c) employing 4-chloropyrimidine instead of 4-bromo-2-methylpyridine. The title compound was obtained as an orange semisolid.

MS ISP (m/e): 424.2 and 426.1 [(M+H)$^+$].

$^1$H NMR ($CDCl_3$, 300 MHz): δ (ppm)=8.36 (d, 1H), 8.10 (d, 1H), 7.50 (dd, 1H), 7.39 (d, 1H), 7.28 (dd, 1H), 7.09 (ddd, 1H), 6.86 (dd, 1H), 6.33 (d, 1H), 4.54 (d, 1H), 4.40-4.35 (m, 2H), 3.95-3.85 (m, 1H), 3.17 (dt, 2H), 2.50 (s, 3H), 2.20 (m, 2H), 1.55-1.40 (m, 2H).

Example 61

8-(2-Chloro-4-fluorophenyl)-N-(1-(2-methylpyrimidin-4-yl)piperidin-4-yl)-[1,2,4]triazolo[1,5-a]pyridin-2-amine

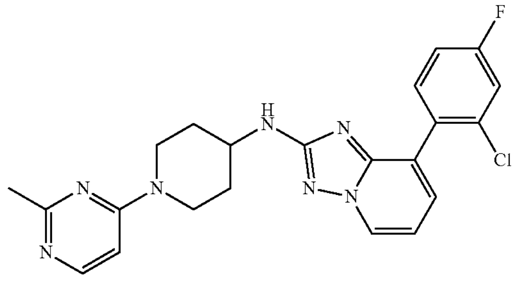 [SMILES: Cc1nccc(N2CCC(Nc3nc4c(-c5ccc(F)cc5Cl)cccn4n3)CC2)n1]

Prepared in analogy to example 57c) employing 4-chloro-2-methylpyrimidine instead of 4-bromo-2-methylpyridine. The title compound was obtained as a yellow semisolid.

MS ISP (m/e): 438.3 and 440.3 [(M+H)$^+$].

$^1$H NMR ($CDCl_3$, 300 MHz): δ (ppm)=8.36 (d, 1H), 8.10 (d, 1H), 7.50 (dd, 1H), 7.39 (d, 1H), 7.28 (dd, 1H), 7.09 (ddd, 1H), 6.86 (dd, 1H), 6.33 (d, 1H), 4.54 (d, 1H), 4.40-4.35 (m, 2H), 3.95-3.85 (m, 1H), 3.17 (dt, 2H), 2.50 (s, 3H), 2.20 (m, 2H), 1.55-1.40 (m, 2H).

Example 62

8-(2-Chloro-4-fluorophenyl)-N-(1-(2,6-dimethylpyrimidin-4-yl)piperidin-4-yl)-[1,2,4]triazolo[1,5-a]pyridin-2-amine

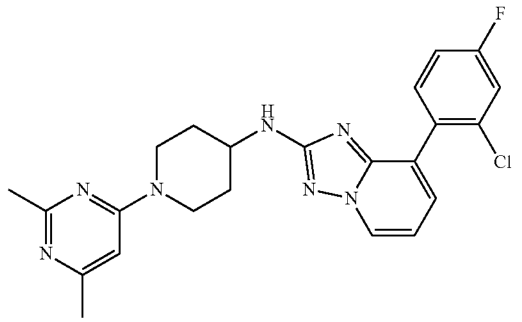 [SMILES: Cc1cc(N2CCC(Nc3nc4c(-c5ccc(F)cc5Cl)cccn4n3)CC2)nc(C)n1]

Prepared in analogy to example 57c) employing 4-chloro-2,6-dimethylpyrimidine instead of 4-bromo-2-methylpyridine. The title compound was obtained as a yellow semisolid.

MS ISP (m/e): 452.2 and 454.3 [(M+H)$^+$].

$^1$H NMR ($CDCl_3$, 300 MHz): δ (ppm)=8.37 (d, 1H), 7.47 (dd, 1H), 7.39 (d, 1H), 7.28 (dd, 1H), 7.10 (ddd, 1H), 6.89 (dd, 1H), 6.22 (d, 1H), 4.38 (d, 1H), 4.45-4.35 (m, 2H), 3.95-3.85 (m, 1H), 3.15 (dt, 2H), 2.48 (s, 3H), 2.33 (s, 3H), 2.20 (m, 2H), 1.55-1.40 (m, 2H).

Example 63

8-(2-Chloro-4-fluorophenyl)-6-methyl-N-(1-(6-methylpyrimidin-4-yl)piperidin-4-yl)-[1,2,4]triazolo[1,5-a]pyridin-2-amine

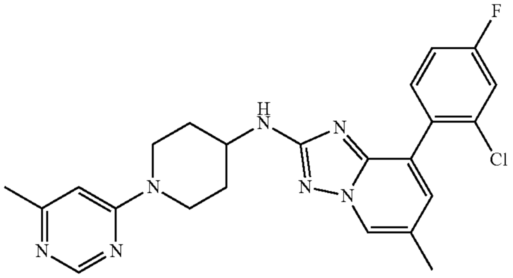 [SMILES: Cc1cc(-c2ccc(F)cc2Cl)c2nc(NC3CCN(c4cc(C)ncn4)CC3)nn2c1]

Prepared in analogy to example 52 employing 2-bromo-8-(2-chloro-4-fluorophenyl)-6-methyl-[1,2,4]triazolo[1,5-a]pyridine instead of 2-bromo-8-(2-chloro-4-fluorophenyl)-[1,2,4]triazolo[1,5-a]pyridine. The title compound was obtained as a yellow foam.

MS ISP (m/e): 452.2 and 454.2 [(M+H)$^+$].

$^1$H NMR ($CDCl_3$, 300 MHz): δ (ppm)=8.50 (s, 1H), 8.18 (s, 1H), 7.48 (dd, 1H), 7.7 (m, 1H), 7.23 (m, 1H), 7.08 (ddd, 1H), 6.39 (d, 1H), 4.45 (d, 1H), 4.35-4.25 (m, 2H), 3.95-3.85 (m, 1H), 3.15 (dt, 2H), 2.39 (s, 3H), 2.36 (s, 3H), 2.18 (m, 2H), 1.55-1.40 (m, 2H).

Example 64

[8-(2-Chloro-4-fluoro-phenyl)-[1,2,4]triazolo[1,5-a]pyridin-2-yl]-[1-(3-methyl-[1,2,4]thiadiazol-5-yl)-piperidin-4-yl]-amine

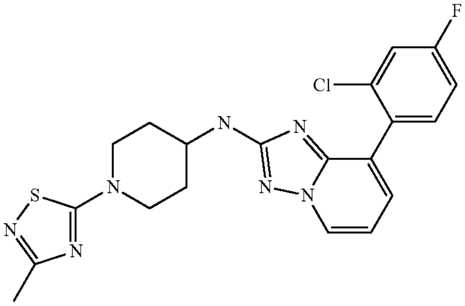 [SMILES: Cc1nsc(N2CCC(Nc3nc4c(-c5ccc(F)cc5Cl)cccn4n3)CC2)n1]

Prepared in analogy to example 1h, employing 8-(2-chloro-4-fluoro-phenyl)-[1,2,4]triazolo[1,5-a]pyridin-2-ylamine (prepared in analogy to example 1a-f). The title compound was obtained as a yellow solid.

MS ISP (m/e): 444.2/446.1 (100/30) [(M+H)$^+$].

$^1$H NMR ($CDCl_3$, 300 MHz): (ppm)=8.38-8.35 (m, 1H), 7.52-7.47 (m, 1H), 7.40-7.37 (m, 1H), 7.29-7.26 (m, 1H), 7.13-7.06 (m, 1H), 6.93-6.88 (m, 1H), 4.74-4.71 (m, 1H), 3.92-3.85 (m, 3H), 3.40-3.30 (m, 2H), 2.41 (s, 3H), 2.27-2.21 (m, 2H), 1.72-1.58 (m, 2H).

Example 65

[8-(2,4-Difluoro-phenyl)-[1,2,4]triazolo[1,5-a]pyridin-2-yl]-[1-(3-methyl-[1,2,4]thiadiazol-5-yl)-piperidin-4-yl]-amine

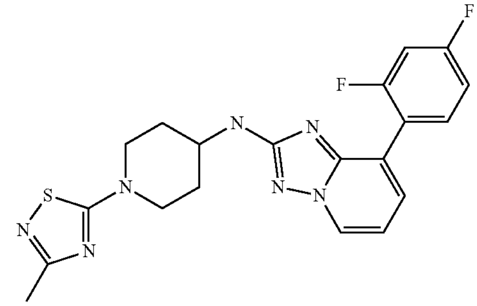 [SMILES: Cc1nsc(N2CCC(Nc3nc4c(-c5ccc(F)cc5F)cccn4n3)CC2)n1]

Prepared in analogy to example 1h, employing 8-(2,4-difluoro-phenyl)-[1,2,4]triazolo[1,5-a]pyridin-2-ylamine (prepared in analogy to example 1a-f). The title compound was obtained as a white solid.

MS ISP (m/e): 428.3 (100) [(M+H)$^+$].

$^1$H NMR ($CDCl_3$, 300 MHz): (ppm)=8.35-8.33 (m, 1H), 7.85-7.77 (m, 1H), 7.50-7.47 (m, 1H), 7.04-6.87 (m, 3H), 4.60-4.57 (m, 1H), 3.90-3.86 (m, 3H), 3.39-3.29 (m, 2H), 2.41 (s, 3H), 2.27-2.21 (m, 2H), 1.70-1.57 (m, 2H).

Example 66

[8-(4-Chloro-phenyl)-[1,2,4]triazolo[1,5-a]pyridin-2-yl]-[1-(3-methyl-[1,2,4]thiadiazol-5-yl)-piperidin-4-yl]-amine

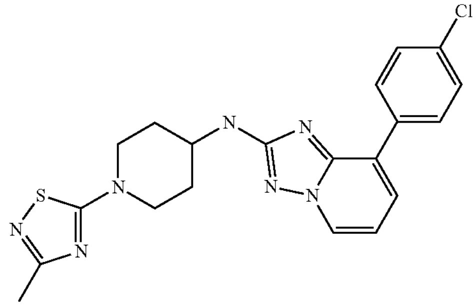 [SMILES: Cc1nsc(N2CCC(Nc3nc4c(-c5ccc(Cl)cc5)cccn4n3)CC2)n1]

a) N-(3-Bromo-pyridin-2-yl)-N'-ethoxycarbonyl-thiourea

3-Bromopyridin-2-amine (30 g, 168 mmol) and ethoxycarbonyl isothiocyanate (24.8 g, 21.3 mL, 185 mmol) were dissolved in dioxane (300 mL) and stirred at room temperature. After 4 hours further ethoxycarbonyl isothiocyanate (1 mL, 8.4 mmol) was added. After 1 hour the solvent was evaporated and the residue dried in high vacuum for 12 hours. The title compound was obtained as a light yellow solid (51.2 g, 100%) and was used crude for the next step.

MS ISP (m/e): 304.0/305.9 (100/73) [(M+H)$^+$].

$^1$H NMR ($CDCl_3$, 300 MHz): δ (ppm)=8.41 (m, 1H) 7.99-7.96 (m, 1H), 7.11-7.07 (m, 1H), 4.32 (q, 2H), 1.36 (t, 3H).

b) 8-Bromo-[1,2,4]-triazolo[1,5-a]pyridin-2-amine

Hydroxylamine (58.5 g, 842 mmol) and N,N-diisopropylethylamine (65.3 g, 86.3 mL, 505 mmol) were dissolved in methanol (200 mL) and ethanol (200 mL). N-(3-Bromo-pyridin-2-yl)-N'-ethoxycarbonyl-thiourea (51.2 g, 168 mmol) was added and the reaction mixture was stirred at room temperature for 1 hour and then at 60° C. for 3 hours. The white precipitate was filtered off and triturated with water for 25 minutes, filtered and triturated two times with diethylether. The solid was dried by co-evaporation with toluene and dried in vacuum. The title compound was obtained as a white solid (27.9 g, 78%).

MS ISP (m/e): 213.0/215.1 (86/95) [(M+H)$^+$].

$^1$H NMR ($CDCl_3$, 300 MHz): δ (ppm)=8.28 (dd, 1H) 7.62 (dd, 1H), 6.73 (t, 1H), 4.66 (bs, 2H).

c) 8-(4-Chloro-phenyl)-[1,2,4]triazolo[1,5-a]pyridin-2-ylamine

A mixture of 8-bromo-[1,2,4]triazolo[1,5-a]pyridin-2-amine (500 mg, 2.35 mmol), 4-chlorophenyl boronic acid (757 mg, 4.69 mmol), dichloro[1,1'-bis(diphenylphosphino)-ferrocene]palladium(II) dichloromethane adduct (153 mg, 0.188 mmol) and an aqueous solution of $Na_2CO_3$ (2 N, 2.35 mL, 4.69 mmol) in dioxane (10 mL) was stirred at 110° C. for 2 hours. The reaction mixture was diluted with a 2 N aqueous solution of sodium carbonate and extracted with diethyl ether, the combined organic phases were dried over sodium sulfate, the solvent was evaporated and the residue purified by silica gel chromatography using pentane/diethyl ether as eluent. The title compound was obtained as a white solid (572 mg, 99%).

MS ISP (m/e): 245.3/247.2 (100/38) [(M+H)$^+$].

$^1$H NMR ($CDCl_3$, 300 MHz): δ (ppm)=8.30 (dd, 1H) 7.93-7.88 (m, 2H), 7.52-7.45 (m, 3H), 6.92 (t, 1H), 4.51 (bs, 2H).

d) 2-Bromo-8-(4-chloro-phenyl)-[1,2,4]-triazolo[1,5-a]pyridine

A mixture of copper(II) bromide (150.6 mg, 0.674 mmol) and tert-butyl nitrite (89 L, 0.674 mmol) in acetonitrile (5 ml) was heated to 60° C. and 8-(4-chloro-phenyl)-[1,2,4]triazolo[1,5-a]pyridin-2-ylamine (150 mg, 0.613 mmol) was added in small portions. After complete addition, the reactuion mixture was heated to 75° C. for 1 hour. Further copper(II) bromide (150.6 mg, 0.674 mmol) and tert-butyl nitrite (89 L, 0.674 mmol) were added add the mixture heated to 75° C. for an additional hour. The reaction mixture was cooled to room temperature and water was added. The aqueous phase was extracted three times with dichloromethane, the combined organic phases were dried over sodium sulfate, the solvent was evaporated and the residue purified by silica gel chromatography using pentane/diethyl ether as eluent. The title compound was obtained as a white solid (165 mg, 87%).

MS ISP (m/e): 308.0/310.0/312.1 (85/100/31) [(M+H)$^+$].

$^1$H NMR ($CDCl_3$, 300 MHz): δ (ppm)=8.54-8.51 (m, 1H), 7.97-7.94 (m, 2H), 7.70-7.67 (m, 1H), 7.51-7.48 (m, 2H), 7.17-7.12 (m, 1H).

e) 1-(3-Methyl-1,2,4-thiadiazol-5-yl)piperidin-4-amine 1-(3-Methyl-1,2,4-thiadiazol-5-yl)piperidin-4-amine dihydrochloride (see example 36b, 2.3 g, 8.48 mmol) was neutralized with 2 N NaOH solution, The water layer was extracted three times with $CH_2Cl_2$ and three times with ethyl acetate, the combined organic phases were dried over $Na_2SO_4$, filtered and the solvents were evaporated. The crude product was purified by flash chromatography with $CH_2Cl_2$ and MeOH over a 50 g Si—$NH_2$ column. The title compound was isolated as a light yellow oil (1.2 g, 71%).

$^1$H NMR ($CDCl_3$, 300 MHz): δ (ppm)=3.89-3.84 (m, 2H), 3.24-3.14 (m, 2H), 3.02-2.93 (m, 1H), 2.40 (s, 3H), 1.95-1.89 (m, 2H), 1.51-1.38 (m, 2H).

f)[8-(4-Chloro-phenyl)-[1,2,4]triazolo[1,5-a]pyridin-2-yl]-[1-(3-methyl-[1,2,4]thiadiazol-5-yl)-piperidin-4-yl]-amine Through a suspension of 1-(3-methyl-1,2,4-thiadiazol-5-yl)piperidin-4-amine (40 mg, 202 μmol), 2-bromo-8-(4-chlorophenyl)-[1,2,4]triazolo[1,5-a]pyridine (74.7 mg, 242 μmol), 4,5-bis(diphenylphosphino)-9,9-dimethylxanthene (9.34 mg, 16.1 μmol), tris(dibenzylideneacetone)dipalladium (0) chloroform adduct (8.35 mg, 8.07 μmol) and sodium phenoxide (35.1 mg, 303 μmol) in dry dioxane (3 mL) was bubbled argon for 5 minutes. The mixture was then irradiated at 150° C. for 60 minutes. The crude material was purified by flash chromatography (silica gel, 70 g, 0% to 15% MeOH/$NH_4OH$ (9:1) in dichloromethane). The title compound was obtained as an off-white foam (42 mg, 49%).

MS ISP (m/e): 426.1/428.3 (100/39) [(M+H)$^+$].

$^1$H NMR ($CDCl_3$, 300 MHz): δ (ppm)=8.33-8.31 (m, 1H), 7.92-7.89 (m, 2H), 7.52-7.44 (m, 3H), 6.93-6.88 (m, 1H), 4.52-4.50 (m, 1H), 3.99-3.87 (m, 3H), 3.41-3.31 (m, 2H), 2.42 (s, 3H), 2.29-2.23 (m, 2H), 1.73-1.60 (m, 2H).

Example 67

[8-(3-Chloro-4-fluoro-phenyl)-6-methyl-[1,2,4]triazolo[1,5-a]pyridin-2-yl]-[1-(3-methyl-[1,2,4]thiadiazol-5-yl)-piperidin-4-yl]-amine

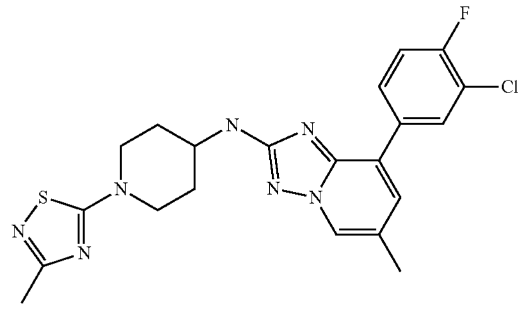 [SMILES: Cc1cc(-c2ccc(F)c(Cl)c2)c2nc(NC3CCN(c4nc(C)ns4)CC3)nn2c1]

Prepared in analogy to example 66. The title compound was obtained as light yellow foam. MS ISP (m/e): 458.2/460.2 (100/34) [(M+H)$^+$].

$^1$H NMR ($CDCl_3$, 300 MHz): δ (ppm)=8.15-8.13 (m, 1H), 8.09-8.06 (m, 1H), 7.89-7.84 (m, 1H), 7.35 (m, 1H), 7.27-7.26 (m, 1H), 4.47-4.44 (m, 1H), 3.94-3.86 (m, 3H), 3.40-3.31 (m, 2H), 2.42 (s, 3H), 2.40 (s, 3H), 2.31-2.24 (m, 2H), 1.73-1.60 (m, 2H).

Example 68

[8-(2-Chloro-4-fluoro-phenyl)-6-methyl-[1,2,4]triazolo[1,5-a]pyridin-2-yl]-[1-(3-methyl-[1,2,4]thiadiazol-5-yl)-piperidin-4-yl]-amine

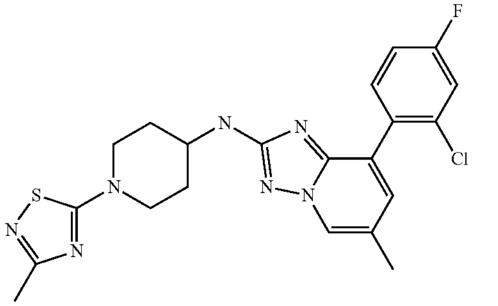 [SMILES: Cc1cc(-c2ccc(F)cc2Cl)c2nc(NC3CCN(c4nc(C)ns4)CC3)nn2c1]

Prepared in analogy to example 66. The title compound was obtained as white foam.

MS ISP (m/e): 458.2/460.2 (100/40) [(M+H)$^+$].

$^1$H NMR ($CDCl_3$, 300 MHz): δ (ppm)=8.18 (m, 1H), 7.49-7.44 (m, 1H), 7.29-7.24 (m, 2H), 7.12-7.05 (m, 1H), 4.82-4.79 (m, 1H), 3.89-3.84 (m, 3H), 3.39-3.30 (m, 2H), 2.41 (s, 3H), 2.40 (s, 3H), 2.25-2.20 (m, 2H), 1.71-1.58 (m, 2H).

Example 69

[8-(3,4-Difluoro-phenyl)-6-methyl-[1,2,4]triazolo[1,5-a]pyridin-2-yl]-[1-(3-methyl-[1,2,4]thiadiazol-5-yl)-piperidin-4-yl]-amine

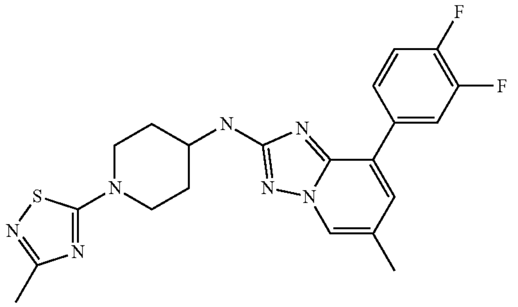 [SMILES: Cc1cc(-c2ccc(F)c(F)c2)c2nc(NC3CCN(c4nc(C)ns4)CC3)nn2c1]

Prepared in analogy to example 66. The title compound was obtained as off-white solid.

MS ISP (m/e): 442.2 (100) [(M+H)$^+$].

$^1$H NMR ($CDCl_3$, 300 MHz): δ (ppm)=8.14 (m, 1H), 7.94-7.87 (m, 1H), 7.72-7.67 (m, 1H), 7.35 (m, 1H), 7.28-7.24 (m, 1H), 4.47-4.44 (m, 1H), 3.94-3.87 (m, 3H), 3.40-3.31 (m, 2H), 2.42 (s, 3H), 2.40 (s, 3H), 2.29-2.22 (m, 2H), 1.72-1.60 (m, 2H).

Example 70

[8-(3,4-Difluoro-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine

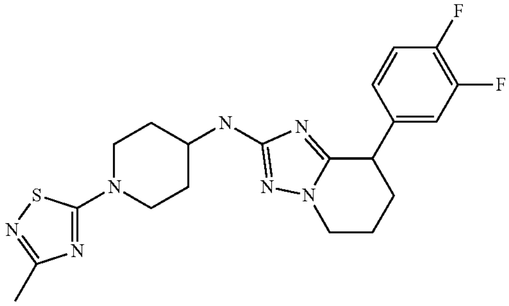 [SMILES: Cc1nsc(N2CCC(Nc3nc4n(n3)CCCC4c3ccc(F)c(F)c3)CC2)n1]

Prepared in analogy to example 1. The title compound was obtained as white foam.

MS ISP (m/e): 432.3 (100) [(M+H)$^+$].

$^1$H NMR ($CDCl_3$, 300 MHz): δ (ppm)=7.16-7.07 (m, 1H), 7.00-6.93 (m, 1H), 6.91-6.87 (m, 1H), 4.12-4.02 (m, 4H), 3.87-3.68 (m, 3H), 3.35-3.25 (m, 2H), 2.40 (s, 3H), 2.31-1.91 (m, 6H), 1.64-1.51 (m, 2H).

Example 71

[8-(4-Fluoro-2-methoxy-phenyl)-[1,2,4]triazolo[1,5-a]pyridin-2-yl]-[1-(3-methyl-[1,2,4]thiadiazol-5-yl)-piperidin-4-yl]-amine

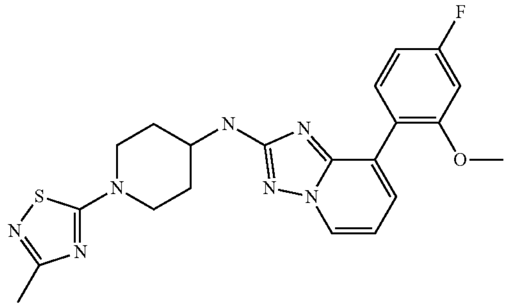 [SMILES: COc1cc(F)ccc1-c1cccn2nc(NC3CCN(c4nc(C)ns4)CC3)nc12]

Prepared in analogy to example 66. The title compound was obtained as white foam.

MS ISP (m/e): 440.2 (100) [(M+H)$^+$].

$^1$H NMR ($CDCl_3$, 300 MHz): δ (ppm)=8.31-8.29 (m, 1H), 7.58-7.53 (m, 1H), 7.46-7.44 (m, 1H), 6.88-6.84 (m, 1H), 6.80-6.72 (m, 2H), 4.53-4.50 (m, 1H), 3.91-3.85 (m, 3H), 3.79 (s, 3H), 3.39-3.29 (m, 2H), 2.41 (s, 3H), 2.26-2.21 (m, 2H), 1.69-1.56 (m, 2H).

Example 72

[8-(4-Fluoro-3-trifluoromethyl-phenyl)-[1,2,4]triazolo[1,5-a]pyridin-2-yl]-[1-(3-methyl-[1,2,4]thiadiazol-5-yl)-piperidin-4-yl]-amine

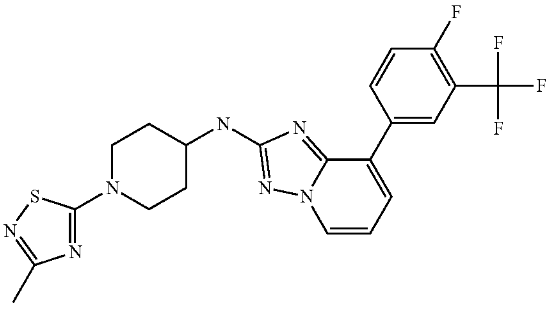 [SMILES: Cc1nsc(N2CCC(Nc3nc4c(-c5ccc(F)c(C(F)(F)F)c5)cccn4n3)CC2)n1]

Prepared in analogy to example 66. The title compound was obtained as light brown foam. MS ISP (m/e): 478.1 (100) [$(M+H)^+$].

$^1H$ NMR ($CDCl_3$, 300 MHz): δ (ppm)=8.36-8.29 (m, 2H), 8.20-8.15 (m, 1H), 7.55-7.52 (m, 1H), 7.35-7.29 (m, 1H), 6.96-6.91 (m, 1H), 4.66-4.63 (m, 1H), 3.96-3.89 (m, 3H), 3.41-3.31 (m, 2H), 2.42 (s, 3H), 2.30-2.25 (m, 2H), 1.75-1.62 (m, 2H).

Example 73

[8-(2,4-Difluoro-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine

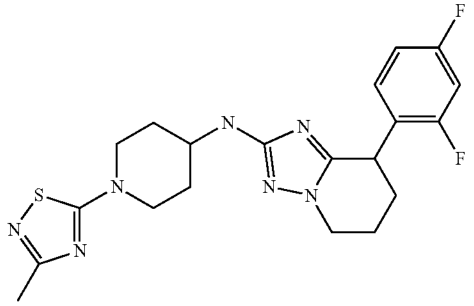 [SMILES: Cc1nsc(N2CCC(Nc3nc4n(n3)CCCC4c3ccc(F)cc3F)CC2)n1]

Prepared in analogy to example 1. The title compound was obtained as white foam.

MS ISP (m/e): 432.3 (100) [$(M+H)^+$].

$^1H$ NMR ($CDCl_3$, 300 MHz): δ (ppm)=7.02-6.91 (m, 1H), 6.86-6.79 (m, 2H), 4.37-4.33 (m, 1H), 4.11-4.07 (m, 2H), 4.02-3.99 (m, 1H), 3.87-3.81 (m, 2H), 3.76-3.66 (m, 1H), 3.35-3.25 (m, 2H), 2.40 (s, 3H), 2.31-1.90 (m, 6H), 1.64-1.49 (m, 2H).

Example 74

[8-(4-Fluoro-3-trifluoromethyl-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine

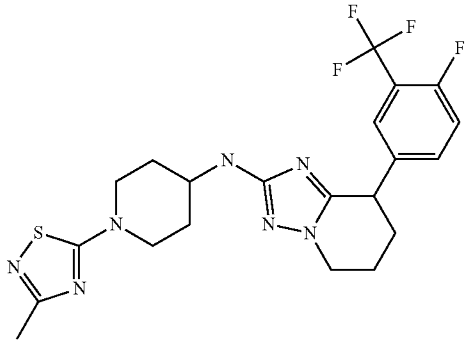 [SMILES: Cc1nsc(N2CCC(Nc3nc4n(n3)CCCC4c3ccc(F)c(C(F)(F)F)c3)CC2)n1]

Prepared in analogy to example 1. The title compound was obtained as white solid.

MS ISP (m/e): 482.3 (100) [$(M+H)^+$].

$^1H$ NMR ($CDCl_3$, 300 MHz): δ (ppm)=7.44-7.41 (m, 1H), 7.36-7.30 (m, 1H), 7.22-7.13 (m, 1H), 4.18-4.08 (m, 3H), 4.03-4.00 (m, 1H), 3.88-3.67 (m, 3H), 3.35-3.25 (m, 2H), 2.40 (s, 3H), 2.35-1.90 (m, 6H), 1.65-1.50 (m, 2H).

Example 75

[8-(2-Fluoro-4-methanesulfonyl-phenyl)-[1,2,4]triazolo[1,5-a]pyridin-2-yl]-[1-(3-methyl-[1,2,4]thiadiazol-5-yl)-piperidin-4-yl]-amine

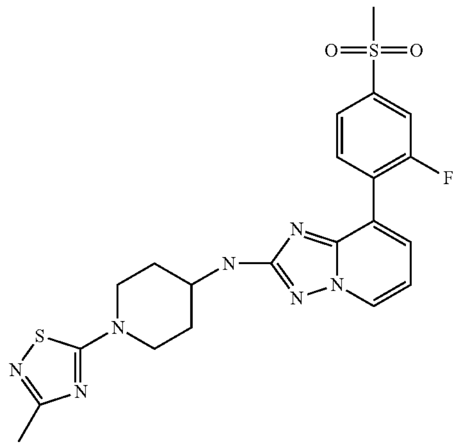 [SMILES: Cc1nsc(N2CCC(Nc3nc4c(-c5ccc(S(C)(=O)=O)cc5F)cccn4n3)CC2)n1]

Prepared in analogy to example 66. The title compound was obtained as orange solid.

MS ISP (m/e): 488.2 (100) [$(M+H)^+$].

$^1H$ NMR ($CDCl_3$, 300 MHz): δ (ppm)=8.42-8.39 (m, 1H), 8.14-8.09 (m, 1H), 7.87-7.78 (m, 2H), 7.61-7.58 (m, 1H), 6.98-6.93 (m, 1H), 4.54-4.52 (m, 1H), 3.94-3.87 (m, 3H), 3.40-3.31 (m, 2H), 3.11 (s, 3H), 2.42 (s, 3H), 2.28-2.23 (m, 2H), 1.72-1.59 (m, 2H).

Example 76

[8-(2-Fluoro-4-methanesulfonyl-phenyl)-[1,2,4]triazolo[1,5-a]pyridin-2-yl]-[1-(3-methyl-[1,2,4]thiadiazol-5-yl)-piperidin-4-yl]-amine

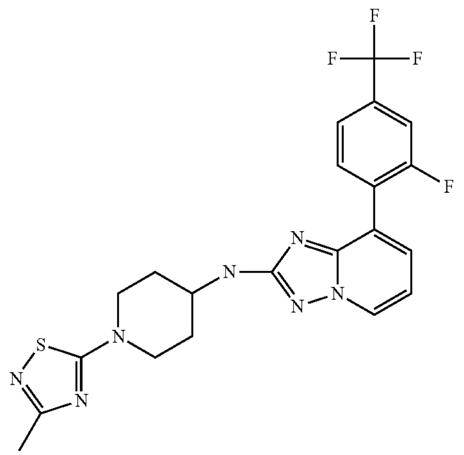 [SMILES: Cc1nsc(N2CCC(Nc3nc4c(-c5ccc(C(F)(F)F)cc5F)cccn4n3)CC2)n1]

Prepared in analogy to example 66. The title compound was obtained as orange solid.

MS ISP (m/e): 478.1 (100) [(M+H)$^+$].

$^1$H NMR ($CDCl_3$, 300 MHz): δ (ppm)=8.40-8.37 (m, 1H), 8.01-7.96 (m, 1H), 7.56-7.54 (m, 2H), 7.50-7.47 (m, 1H), 6.96-6.91 (m, 1H), 4.56-4.53 (m, 1H), 3.93-3.87 (m, 3H), 3.40-3.31 (m, 2H), 2.41 (s, 3H), 2.28-2.23 (m, 2H), 1.72-1.59 (m, 2H).

Example 77

[8-(3,4-Difluoro-phenyl)-6-fluoro-[1,2,4]triazolo[1,5-a]pyridin-2-yl]-[1-(3-methyl-[1,2,4]thiadiazol-5-yl)-piperidin-4-yl]-amine

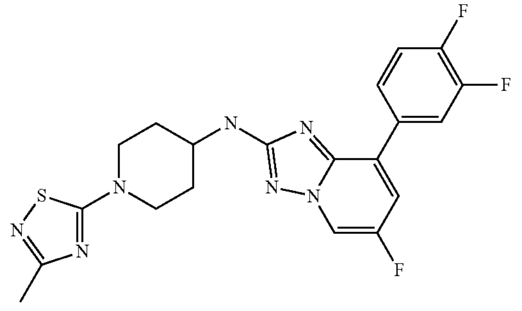

Prepared in analogy to example 66 starting with 3-bromo-5-fluoropyridin-2-amine instead of 3-bromopyridin-2-amine in step a). The title compound was obtained as white foam.

MS ISP (m/e): 446.3 (100) [(M+H)$^+$].

$^1$H NMR ($CDCl_3$, 300 MHz): δ (ppm)=8.30-8.29 (m, 1H), 8.01-7.93 (m, 1H), 7.74-7.69 (m, 1H), 7.45-7.42 (m, 1H), 7.33-7.24 (m, 1H), 4.54-4.51 (m, 1H), 3.94-3.89 (m, 3H), 3.41-3.31 (m, 2H), 2.42 (s, 3H), 2.28-2.23 (m, 2H), 1.73-1.60 (m, 2H).

Example 78

[8-(2,4-Dichloro-phenyl)-[1,2,4]triazolo[1,5-a]pyridin-2-yl]-[1-(3-methyl-[1,2,4]thiadiazol-5-yl)-piperidin-4-yl]-amine

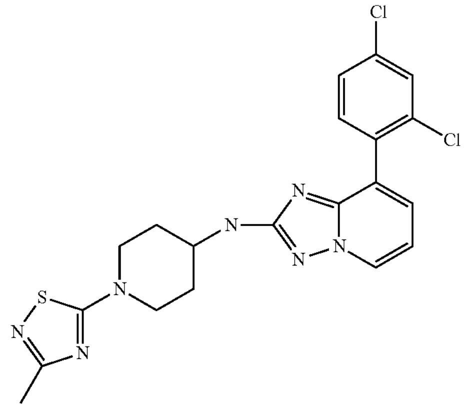 [SMILES: Cc1nsc(N2CCC(Nc3nc4c(-c5ccc(Cl)cc5Cl)cccn4n3)CC2)n1]

Prepared in analogy to example 66. The title compound was obtained as white foam.

MS ISP (m/e): 460.2/462.2/464.1 (100/70/14) [(M+H)$^+$].

$^1$H NMR ($CDCl_3$, 300 MHz): δ (ppm)=8.37-8.35 (m, 1H), 7.54 (m, 1H), 7.49-7.46 (m, 1H), 7.40-7.33 (m, 2H), 6.92-6.87 (m, 1H), 4.56-4.54 (m, 1H), 3.91-3.85 (m, 3H), 3.38-3.29 (m, 2H), 2.41 (s, 3H), 2.26-2.21 (m, 2H), 1.69-1.57 (m, 2H).

Example 79

[8-(2-Fluoro-4-trifluoromethyl-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine

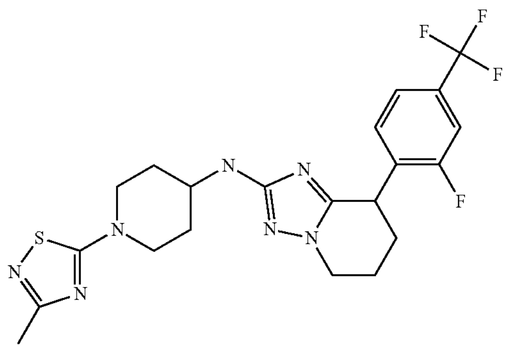 [SMILES: Cc1nsc(N2CCC(Nc3nc4n(n3)CCCC4c3ccc(C(F)(F)F)cc3F)CC2)n1]

Prepared in analogy to example 1. The title compound was obtained as white foam.

MS ISP (m/e): 482.3 (100) [(M+H)$^+$].

$^1$H NMR ($CDCl_3$, 300 MHz): δ (ppm)=7.38-7.33 (m, 2H), 7.19-7.14 (m, 1H), 4.46-4.41 (m, 1H), 4.16-4.09 (m, 3H), 3.87-3.81 (m, 2H), 3.76-3.67 (m, 1H), 3.35-3.25 (m, 2H), 2.40 (s, 3H), 2.36-1.95 (m, 6H), 1.65-1.50 (m, 2H).

Example 80

[1-(3-Methyl-[1,2,4]thiadiazol-5-yl)-piperidin-4-yl]-[8-(2,3,4-trifluoro-phenyl)-[1,2,4]triazolo[1,5-a]pyridin-2-yl]-amine

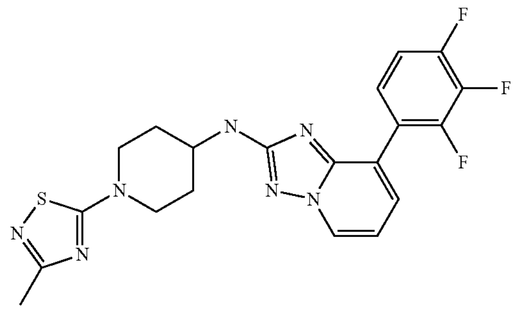 [SMILES: Cc1nsc(N2CCC(Nc3nc4c(-c5ccc(F)c(F)c5F)cccn4n3)CC2)n1]

Prepared in analogy to example 66. The title compound was obtained as brown solid.

MS ISP (m/e): 446.3 (100) [(M+H)$^+$].

$^1$H NMR (CDCl$_3$, 300 MHz): δ (ppm)=8.38-8.35 (m, 1H), 7.61-7.48 (m, 2H), 7.14-7.05 (m, 1H), 6.94-6.89 (m, 1H), 4.55-4.53 (m, 1H), 3.93-3.86 (m, 3H), 3.40-3.30 (m, 2H), 2.41 (s, 3H), 2.28-2.21 (m, 2H), 1.72-1.62 (m, 2H).

Example 81

[8-(3,4-Difluoro-phenyl)-6-fluoro-5,6,7,8-tetrahydro-[1,2,4]triazolo[1,5-a]pyridin-2-yl]-[1-(3-methyl-[1,2,4]thiadiazol-5-yl)-piperidin-4-yl]-amine

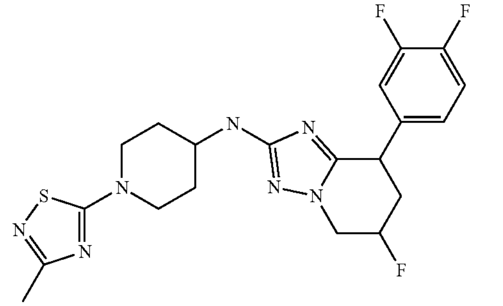 [SMILES: Cc1nsc(N2CCC(Nc3nc4n(n3)CC(F)CC4c3ccc(F)c(F)c3)CC2)n1]

a) 8-(3,4-Difluoro-phenyl)-6-fluoro-5,6,7,8-tetrahydro-[1,2,4]triazolo[1,5-a]pyridin-2-ylamine A solution of 8-(3,4-difluorophenyl)-6-fluoro-[1,2,4]triazolo[1,5-a]pyridin-2-amine (prepared in analogy to example 66a-c starting with 3-bromo-5-fluoropyridin-2-amine, 237 mg, 897 μmol) in ethanol (8 mL) and HCl (25% in water, 144 mg, 120 μL, 987 μmol) was hydrogenated at 80° C. and 80 bar for 18 hours in the presence of Pd/C (237 mg, 222 μmol). The catalyst was filtered off, washed thoroughly with MeOH and the solvents were evaporated. The crude material was purified by flash chromatography (silica gel, 50 g, 0% to 15% MeOH/$NH_4OH$ (9:1) in dichloromethane). The title compound was obtained as white foam (76 mg, 32%). MS ISP (m/e): 269.2 (100) [(M+H)$^+$].

b) [8-(3,4-Difluoro-phenyl)-6-fluoro-5,6,7,8-tetrahydro-[1,2,4]triazolo[1,5-a]pyridin-2-yl]-[1-(3-methyl-[1,2,4]thiadiazol-5-yl)-piperidin-4-yl]-amine A solution of 8-(3,4-difluorophenyl)-6-fluoro-5,6,7,8-tetrahydro-[1,2,4]triazolo[1,5-a]pyridin-2-amine (74 mg, 276 μmol), 1-(3-methyl-1,2,4-thiadiazol-5-yl)piperidin-4-one (82 mg, 414 μmol) and titanium(IV) isopropoxide (240 mg, 253 μL, 828 μmol) dissolved in dichloroethane (6 mL) was heated to 85° C. for 12 hours. Further 1-(3-methyl-1,2,4-thiadiazol-5-yl)piperidin-4-one (54 mg, 276 μmol) was added and stirred at 85° C. for another two hours. The reaction mixture was cooled to 50° C., sodium borohydride (41.7 mg, 1.1 mmol) and ethanol (3 mL) were added and stirred at 50° C. for one hour. The solvent was evaporated, the residue extracted with 2 N $Na_2CO_3$ solution and ethyl acetate. The organic layers were combined, dried over $Na_2SO_4$, filtered and the solvent was evaporated. The residue was purified by flash chromatography (silica gel, 70 g, 0% to 15% MeOH/$NH_4OH$ (9:1) in dichloromethane) and then by preparative HPLC. The title compound was obtained as light green foam (37.1 mg, 30%).

MS ISP (m/e): 450.2 (100) [(M+H)$^+$].

$^1$H NMR (CDCl$_3$, 300 MHz): δ (ppm)=7.14-7.08 (m, 1H), 7.02-6.98 (m, 1H), 6.93-6.91 (m, 1H), 5.32-5.27 & 5.20-5.15 (m, 1H), 4.36-4.33 (m, 1H), 4.31-4.29 (m, 1H), 4.26-4.23 (m, 1H), 4.18-4.16 (m, 1H), 3.86-3.83 (m, 2H), 3.75-3.67 (m, 1H), 3.33-3.27 (m, 2H), 2.63-2.43 (m, 2H), 2.40 (s, 3H), 2.20-2.16 (m, 2H), 1.64-1.52 (m, 2H).

Example 82

[8-(3,4-Difluoro-phenyl)-5-trifluoromethyl-[1,2,4]triazolo[1,5-a]pyridin-2-yl]-[1-(3-methyl-[1,2,4]thiadiazol-5-yl)-piperidin-4-yl]-amine

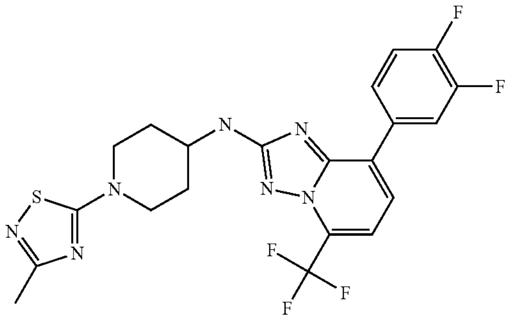 [SMILES: Cc1nsc(N2CCC(Nc3nc4c(-c5ccc(F)c(F)c5)ccc(C(F)(F)F)n4n3)CC2)n1]

a) 3-Bromo-6-(trifluoromethyl)pyridin-2-amine

A solution of 6-(trifluoromethyl)pyridin-2-amine (200 mg, 1.23 mmol) in dichlormethane (2.47 mL) was cooled to 0° C. and bromine (197 mg, 63.4 μL, 1.23 mmol) was slowly added within 30 minutes. After 25 hours at 0° C. the reaction mixture was extracted with saturated $Na_2S_2O_3$ solution, water and brine, dried over $Na_2SO_4$ and concentrated in vacuo. The crude material was purified by flash chromatography over silica gel using $CH_2Cl_2$/MeOH (with 10% ammonia) as eluent. The title compound was obtained as a white solid (711 mg, 24%).

$^1$H NMR ($CDCl_3$, 300 MHz): δ (ppm)=7.80-7.77 (m, 1H), 6.91-6.89 (m, 1H).

b) [8-(3,4-Difluoro-phenyl)-5-trifluoromethyl-[1,2,4]triazolo[1,5-a]pyridin-2-yl]-[1-(3-methyl-[1,2,4]thiadiazol-5-yl)-piperidin-4-yl]-amine Prepared in analogy to example 66 starting with 3-bromo-6-(trifluoromethyl)pyridin-2-amine instead of 3-bromopyridin-2-amine in step a). The title compound was obtained as light yellow solid.

MS ISP (m/e): 496.3 (53) [(M+H)$^+$].

$^1$H NMR ($CDCl_3$, 300 MHz): δ (ppm)=8.01-7.94 (m, 1H), 7.78-7.71 (m, 1H), 7.57-7.55 (m, 1H), 7.35-7.29 (m, 2H), 4.73-4.71 (m, 1H), 3.93-3.89 (m, 3H), 3.43-3.34 (m, 2H), 2.42 (s, 3H), 2.30-2.25 (m, 2H), 1.75-1.60 (m, 2H).

Example 83

[8-(2-Methyl-pyrimidin-5-yl)-[1,2,4]triazolo[1,5-a]pyridin-2-yl]-[1-(3-methyl-[1,2,4]thiadiazol-5-yl)-piperidin-4-yl]-amine

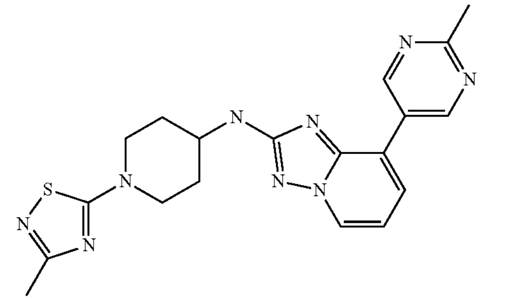

Prepared in analogy to example 66. The title compound was obtained as light yellow solid. MS ISP (m/e): 408.3 (100) [(M+H)$^+$].

$^1$H NMR ($CDCl_3$, 300 MHz): δ (ppm)=9.28 (s, 2H), 8.38-8.36 (m, 1H), 7.58-7.56 (m, 1H), 6.96-6.93 (m, 1H), 4.59-4.57 (m, 1H), 3.99-3.89 (m, 3H), 3.39-3.32 (m, 2H), 2.81 (s, 3H), 2.42 (s, 3H), 2.28-2.24 (m, 2H), 1.72-1.62 (m, 2H).

Example 84

[8-(6-Methoxy-pyridin-3-yl)-[1,2,4]triazolo[1,5-a]pyridin-2-yl]-[1-(3-methyl-[1,2,4]thiadiazol-5-yl)-piperidin-4-yl]-amine

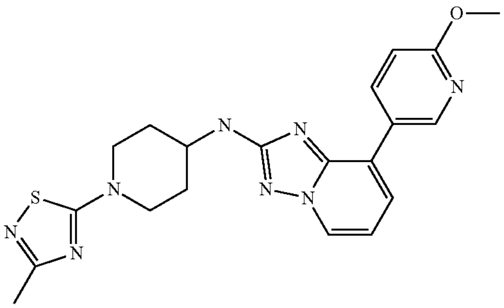 [SMILES: COc1ccc(-c2cccn3nc(NC4CCN(c5nc(C)ns5)CC4)nc23)cn1]

Prepared in analogy to example 66. The title compound was obtained as light yellow solid. MS ISP (m/e): 423.2 (100) [(M+H)$^+$].

$^1$H NMR ($CDCl_3$, 300 MHz): δ (ppm)=8.73 (m, 1H), 8.31-8.29 (m, 1H), 8.25-8.22 (m, 1H), 7.49-7.47 (m, 1H), 6.92-6.85 (m, 2H), 4.56-4.55 (m, 1H), 4.03-3.88 (m, 3H), 4.00 (s, 3H), 3.39-3.32 (m, 2H), 2.42 (s, 3H), 2.28-2.24 (m, 2H), 1.71-1.61 (m, 2H).

Example 85

[8-(2-Chloro-4-fluoro-phenyl)-[1,2,4]triazolo[1,5-a]pyridin-2-yl]-[1-(5-methyl-[1,3,4]oxadiazol-2-yl)-piperidin-4-yl]-amine

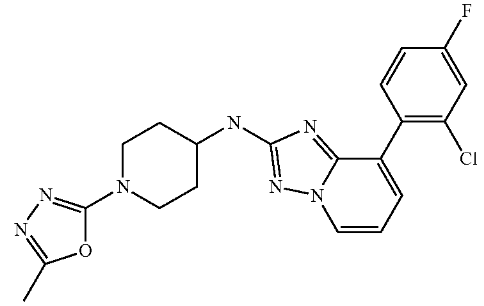 [SMILES: Cc1nnc(N2CCC(Nc3nc4c(-c5ccc(F)cc5Cl)cccn4n3)CC2)o1]

Prepared in analogy to example 66a-d and f employing 1-(5-methyl-[1,3,4]oxadiazol-2-yl)-piperidin-4-ylamine (see example 40b) instead of 1-(3-methyl-1,2,4-thiadiazol-5-yl)piperidin-4-amine in step f. The title compound was obtained as white solid.

MS ISP (m/e): 428.3/430.3 (100/41) [(M+H)$^+$].

$^1$H NMR ($CDCl_3$, 300 MHz): δ (ppm)=8.38-8.35 (m, 1H), 7.53-7.48 (m, 1H), 7.40-7.37 (m, 1H), 7.29-7.26 (m, 1H), 7.13-7.07 (m, 1H), 6.91-6.87 (m, 1H), 4.53-4.50 (m, 1H), 3.97-3.80 (m, 3H), 3.27-3.18 (m, 2H), 2.39 (s, 3H), 2.24-2.19 (m, 2H), 1.66-1.53 (m, 2H).

Example 86

[8-(3-Chloro-4-fluoro-phenyl)-6-fluoro-[1,2,4]triazolo[1,5-a]pyridin-2-yl]-[1-(3-methyl-[1,2,4]thiadiazol-5-yl)-piperidin-4-yl]-amine

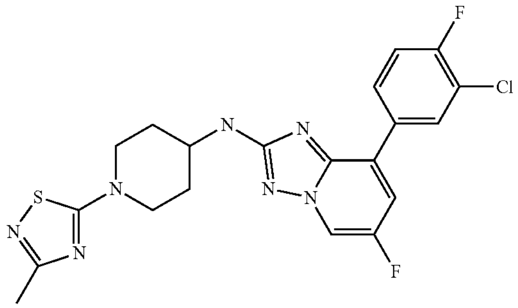

Prepared in analogy to example 66 starting with 3-bromo-5-fluoropyridin-2-amine instead of 3-bromopyridin-2-amine in step a). The title compound was obtained as off-white solid. MS ISP (m/e): 462.2/464.3 (100/33) [(M+H)$^+$].

$^1$H NMR ($CDCl_3$, 300 MHz): δ (ppm)=8.30-8.29 (m, 1H), 8.15-8.12 (m, 1H), 7.90-7.85 (m, 1H), 7.45-7.41 (m, 1H), 7.30-7.24 (m, 1H), 4.54-4.52 (m, 1H), 3.94-3.89 (m, 3H), 3.40-3.31 (m, 2H), 2.42 (s, 3H), 2.29-2.23 (m, 2H), 1.73-1.60 (m, 2H).

Example 87

N-(1-(3,4-Dichlorobenzyl)-1H-1,2,4-triazol-3-yl)-1-(3-methyl-1,2,4-thiadiazol-5-yl)piperidin-4-amine

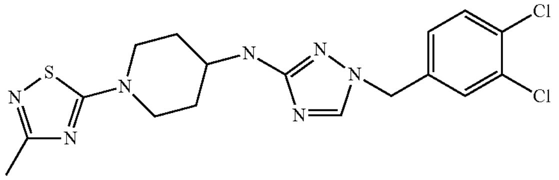 [SMILES: Cc1nsc(N2CCC(Nc3ncn(Cc4ccc(Cl)c(Cl)c4)n3)CC2)n1]

Prepared in analogy to example 5. The title compound was obtained as white foam.

MS ISP (m/e): 424.2/426.0 (100/66) [(M+H)$^+$].

$^1$H NMR ($CDCl_3$, 300 MHz): (ppm)=7.73 (s, 1H), 7.46-7.43 (m, 1H), 7.35 (m, 1H), 7.10-7.07 (m, 1H), 5.09 (s, 2H), 4.14-4.11 (m, 1H), 3.89-3.70 (m, 3H), 3.34-3.25 (m, 2H), 2.41 (s, 3H), 2.21-2.16 (m, 2H), 1.65-1.52 (m, 2H).

Example 88

[8-(6-Fluoro-pyridin-3-yl)-[1,2,4]triazolo[1,5-a]pyridin-2-yl]-[1-(3-methyl-[1,2,4]thiadiazol-5-yl)-piperidin-4-yl]-amine

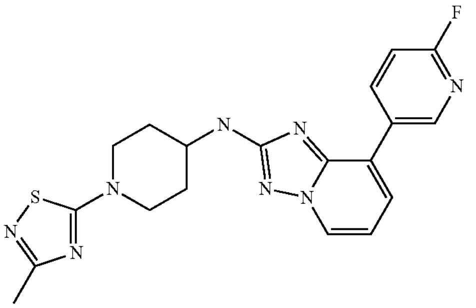 [SMILES: Cc1nsc(N2CCC(Nc3nc4c(-c5ccc(F)nc5)cccn4n3)CC2)n1]

Prepared in analogy to example 66. The title compound was obtained as off-white foam.

MS ISP (m/e): 411.2 (100) [(M+H)$^+$].

$^1$H NMR ($CDCl_3$, 300 MHz): δ (ppm)=8.77-8.76 (m, 1H), 8.53-8.47 (m, 1H), 8.37-8.35 (m, 1H), 7.56-7.53 (m, 1H), 7.09-7.05 (m, 1H), 6.96-6.91 (m, 1H), 4.52-4.49 (m, 1H), 4.00-3.88 (m, 3H), 3.41-3.31 (m, 2H), 2.42 (s, 3H), 2.30-2.24 (m, 2H), 1.74-1.61 (m, 2H).

Example 89

[8-(2-Fluoro-pyridin-3-yl)-[1,2,4]triazolo[1,5-a]pyridin-2-yl]-[1-(3-methyl-[1,2,4]thiadiazol-5-yl)-piperidin-4-yl]-amine

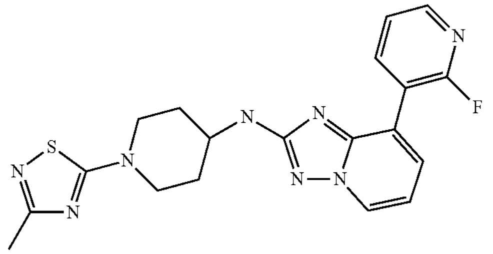 [SMILES: Cc1nsc(N2CCC(Nc3nc4c(-c5cccnc5F)cccn4n3)CC2)n1]

Prepared in analogy to example 66. The title compound was obtained as brown oil.

MS ISP (m/e): 411.3 (81) [(M+H)$^+$].

$^1$H NMR ($CDCl_3$, 300 MHz): δ (ppm)=8.50-8.43 (m, 1H), 8.38-8.36 (m, 1H), 8.27-8.25 (m, 1H), 7.67-7.64 (m, 1H), 7.37-7.34 (m, 1H), 6.96-6.91 (m, 1H), 4.54-4.51 (m, 1H), 3.96-3.88 (m, 3H), 3.40-3.31 (m, 2H), 2.42 (s, 3H), 2.29-2.23 (m, 2H), 1.72-1.61 (m, 2H).

Example 90

[8-(3-Methanesulfonyl-phenyl)-[1,2,4]triazolo[1,5-a]pyridin-2-yl]-[1-(3-methyl-[1,2,4]thiadiazol-5-yl)-piperidin-4-yl]-amine

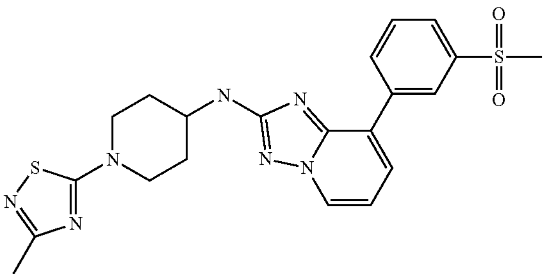 [SMILES: Cc1nsc(N2CCC(Nc3nc4c(-c5cccc(S(C)(=O)=O)c5)cccn4n3)CC2)n1]

Prepared in analogy to example 66. The title compound was obtained as light yellow foam. MS ISP (m/e): 470.3 (100) [(M+H)$^+$].

$^1$H NMR ($CDCl_3$, 300 MHz): δ (ppm)=8.60 (m, 1H), 8.38-8.30 (m, 2H), 7.99-7.96 (m, 1H), 7.73-7.68 (m, 1H), 7.63. 7.61 (m, 1H), 6.98-6.93 (m, 1H), 4.67-4.64 (m, 1H), 3.98-3.89 (m, 3H), 3.41-3.32 (m, 2H), 3.11 (s, 3H), 2.42 (s, 3H), 2.31-2.25 (m, 2H), 1.75-1.61 (m, 2H).

Example 91

[1-(3-Methyl-[1,2,4]thiadiazol-5-yl)-piperidin-4-yl]-[8-(3,4,5-trifluoro-phenyl)-[1,2,4]triazolo[1,5-a]pyridin-2-yl]-amine

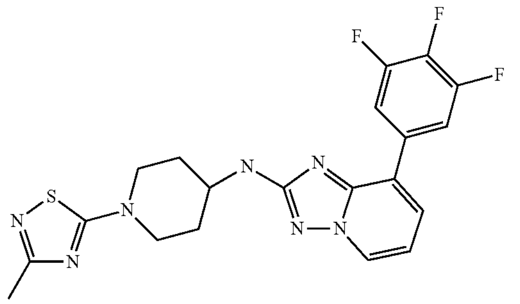 [SMILES: Cc1nsc(N2CCC(Nc3nc4c(-c5cc(F)c(F)c(F)c5)cccn4n3)CC2)n1]

Prepared in analogy to example 66. The title compound was obtained as light yellow foam. MS ISP (m/e): 446.3 (100) [(M+H)$^+$].

$^1$H NMR ($CDCl_3$, 300 MHz): δ (ppm)=8.36-8.33 (m, 1H), 7.76-7.70 (m, 2H), 7.52-7.49 (m, 1H), 6.94-6.89 (m, 1H), 4.57-4.54 (m, 1H), 3.97-3.89 (m, 3H), 3.41-3.32 (m, 2H), 2.42 (s, 3H), 2.30-2.25 (m, 2H), 1.74-1.61 (m, 2H).

Example 92

[1-(3-Methyl-[1,2,4]thiadiazol-5-yl)-piperidin-4-yl]-[8-(2,3,4-trifluoro-phenyl)-5,6,7,8-tetrahydro-[1,2,4]triazolo[1,5-a]pyridin-2-yl]-amine

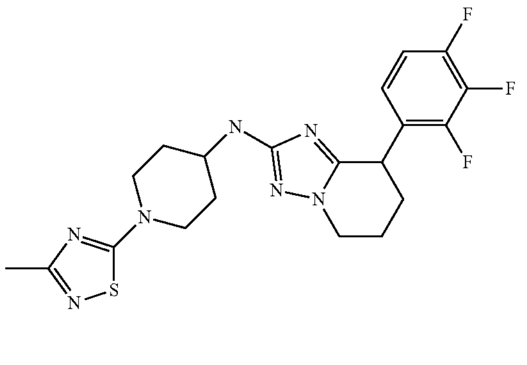 [SMILES: Cc1nsc(N2CCC(Nc3nc4n(n3)CCCC4c3ccc(F)c(F)c3F)CC2)n1]

Prepared in analogy to example 1. The title compound was obtained as yellow oil.

MS ISP (m/e): 450.2 (100) [(M+H)$^+$].

$^1$H NMR ($CDCl_3$, 300 MHz): δ (ppm)=6.96-6.87 (m, 1H), 6.78-6.70 (m, 1H), 4.38-4.33 (m, 1H), 4.11-4.05 (m, 3H), 3.86-3.81 (m, 2H), 3.76-3.66 (m, 1H), 3.34-3.24 (m, 2H), 2.40 (s, 3H), 2.33-1.93 (m, 6H), 1.64-1.50 (m, 2H).

Example 93

[8-(2-Fluoro-4-trifluoromethyl-phenyl)-5,6,7,8-tetrahydro-[1,2,4]triazolo[1,5-a]pyridin-2-yl]-[1-(6-methyl-pyrimidin-4-yl)-piperidin-4-yl]-amine

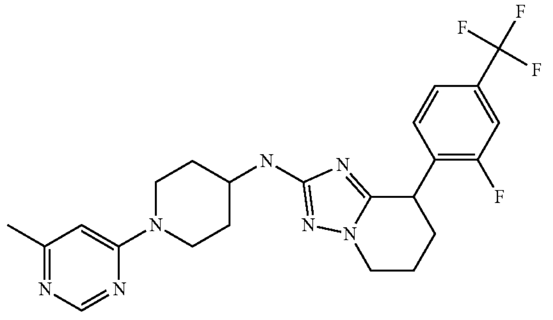 [SMILES: Cc1cc(N2CCC(Nc3nc4n(n3)CCCC4c3ccc(C(F)(F)F)cc3F)CC2)ncn1]

a) 8-(6-Methylpyrimidin-4-yl)-1,4-dioxa-8-azaspiro[4.5]decane

A solution of 1,4-dioxa-8-azaspiro[4.5]decane (3.04 g, 2.72 mL, 21.2 mmol), 4-chloro-6-methylpyrimidine (3.00 g, 23.4 mmol) and N,N-diisopropylethylamine (4.12 g, 5.56 mL, 31.8 mmol) in dioxane (50 mL) was heated to 140° C. in the microwave for 40 minutes. The reaction mixture was concentrated, then directly purified by flash chromatography (silica gel, 70 g, 0% to 15% MeOH/$NH_4OH$ (9:1) in dichloromethane). The title compound was obtained as orange oil (4.64 g, 93%).

MS ISP (m/e): 236.2 (100) [(M+H)$^+$].

$^1$H NMR ($CDCl_3$, 300 MHz): δ (ppm)=8.52-8.51 (m, 1H), 6.42 (m, 1H), 4.01 (s, 4H), 3.83-3.79 (m, 4H), 2.45 (s, 3H), 1.79-1.75 (m, 4H).

b) 1-(6-Methylpyrimidin-4-yl)piperidin-4-one

To a solution of 8-(6-methylpyrimidin-4-yl)-1,4-dioxa-8-azaspiro[4.5]decane (4.64 g, 19.7 mmol) in acetone (45 mL) was added 2 N HCl (180 g, 150 mL, 4.94 mol) and stirred at 50° C. for 2 hours. The reaction mixture was cooled to room temperature, then adjusted to pH 7 with $NaHCO_3$ solution. The aqueous phase was extracted 4 times with $CH_2Cl_2$, the organic layers were combined, dried over $Na_2SO_4$ and the solvent was evaporated. The title compound was obtained as light brown liquid (2.7 g, 72%).

MS ISP (m/e): 192.3 (100) [(M+H)$^+$].

$^1$H NMR ($CDCl_3$, 300 MHz): δ (ppm)=8.57 (m, 1H), 6.48 (m, 1H), 3.99-3.95 (m, 4H), 2.57-2.53 (m, 4H), 2.41 (s, 3H).

c) [8-(2-Fluoro-4-trifluoromethyl-phenyl)-5,6,7,8-tetrahydro-[1,2,4]triazolo[1,5-a]pyridin-2-yl]-[1-(6-methyl-pyrimidin-4-yl)-piperidin-4-yl]-amine Prepared in analogy to example 1h employing 1-(6-methylpyrimidin-4-yl)piperidin-4-one and 8-(2-fluoro-4-trifluoromethyl-phenyl)-5,6,7,8-tetrahydro-[1,2,4]triazolo[1,5-a]pyridin-2-ylamine (prepared in analogy to example 1d-g). The title compound was obtained as light yellow foam. MS ISP (m/e): 476.2 (100) [(M+H)$^+$].

$^1$H NMR ($CDCl_3$, 300 MHz): δ (ppm)=8.49 (m, 1H), 7.38-7.32 (m, 2H), 7.19-7.14 (m, 1H), 6.38 (m, 1H), 4.46-4.42 (m, 1H), 4.30-4.24 (m, 2H), 4.13-3.95 (m, 3H), 3.78-3.69 (m, 1H), 3.17-3.08 (m, 2H), 2.35 (s, 3H), 2.38-2.29 (m, 1H), 2.18-1.93 (m, 5H), 1.50-1.35 (m, 2H).

Example 94

[8-(6-Fluoro-pyridin-3-yl)-[1,2,4]triazolo[1,5-a]pyridin-2-yl]-[1-(6-methyl-pyrimidin-4-yl)-piperidin-4-yl]-amine

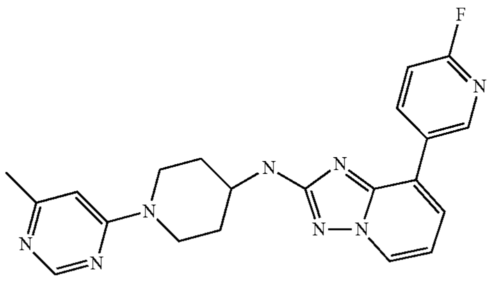 [SMILES: Cc1cc(N2CCC(Nc3nc4c(-c5ccc(F)nc5)cccn4n3)CC2)ncn1]

a) 1-(6-Methyl-pyrimidin-4-yl)-piperidin-4-ylamine 1-(6-Methylpyrimidin-4-yl)piperidin-4-amine dihydrochloride (see example 30b, 2 g, 7.54 mmol) was neutralized with 2 N NaOH solution and $CH_2Cl_2$, the aqueous layers were extracted three times with $CH_2Cl_2$, the combines organic layers were dried over $Na_2SO_4$, filtered and the solvent was evaporated. The title compound was obtained as a brown oil (1.31 g, 90%).

$^1$H NMR ($CDCl_3$, 300 MHz): δ (ppm)=8.50 (m, 1H), 6.39 (m, 1H), 4.35-4.31 (m, 2H), 3.02-2.93 (m, 3H), 2.35 (s, 3H), 1.94-1.89 (m, 2H), 1.37-1.29 (m, 4H).

b) [8-(6-Fluoro-pyridin-3-yl)-[1,2,4]triazolo[1,5-a]pyridin-2-yl]-[1-(6-methyl-pyrimidin-4-yl)-piperidine-4-yl]-amine Prepared in analogy to example 66a-d and f. In step f) 1-(6-methyl-pyrimidin-4-yl)-piperidin-4-ylamine was employed instead of 1-(3-methyl-1,2,4-thiadiazol-5-yl)piperidin-4-amine. The title compound was obtained as light brown foam.

MS ISP (m/e): 405.5 (100) [(M+H)$^+$].

$^1$H NMR ($CDCl_3$, 300 MHz): δ (ppm)=8.77-8.76 (m, 1H), 8.54-8.47 (m, 2H), 8.38-8.35 (m, 1H), 7.55-7.52 (m, 1H), 7.08-7.05 (m, 1H), 6.95-6.91 (m, 1H), 6.41 (m, 1H), 4.53-4.51 (m, 1H), 4.37-4.33 (m, 2H), 4.02-3.92 (m, 1H), 3.23-3.14 (m, 2H), 2.37 (s, 3H), 2.27-2.22 (m, 2H), 1.59-1.46 (m, 2H).

Example 95

[8-(5-Chloro-thiophen-2-yl)-[1,2,4]triazolo[1,5-a]pyridin-2-yl]-[1-(6-methyl-pyrimidin-4-yl)-piperidin-4-yl]-amine

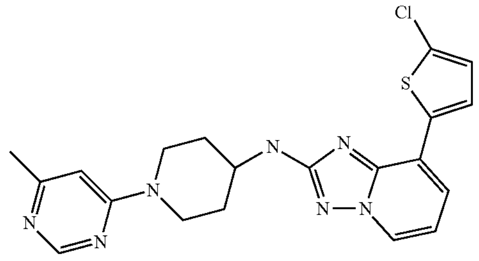 [SMILES: Cc1cc(N2CCC(Nc3nc4c(-c5ccc(Cl)s5)cccn4n3)CC2)ncn1]

Prepared in analogy to example 94. The title compound was obtained as yellow oil.

MS ISP (m/e): 426.1/428.2 (90/36) [(M+H)$^+$].

$^1$H NMR ($CDCl_3$, 300 MHz): δ (ppm)=8.52 (m, 1H), 8.26-8.23 (m, 1H), 7.76-7.74 (m, 1H), 7.56-7.53 (m, 1H), 6.97-6.96 (m, 1H), 6.86-6.81 (m, 1H), 6.42 (m, 1H), 4.61-4.58 (m, 1H), 4.37-4.33 (m, 2H), 4.03-3.94 (m, 1H), 3.24-3.15 (m, 2H), 2.37 (s, 3H), 2.29-2.23 (m, 2H), 1.61-1.48 (m, 2H).

Example 96

[8-(4-Fluoro-3-trifluoromethyl-phenyl)-[1,2,4]triazolo[1,5-a]pyridin-2-yl]-[1-(6-methyl-pyrimidin-4-yl)-piperidin-4-yl]-amine

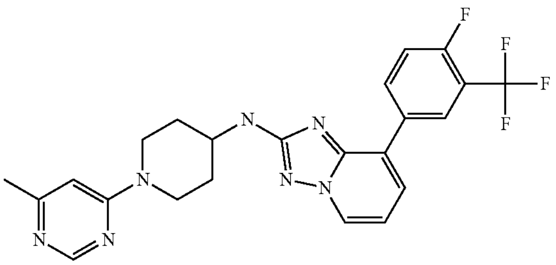 [SMILES: Cc1cc(N2CCC(Nc3nc4c(-c5ccc(F)c(C(F)(F)F)c5)cccn4n3)CC2)ncn1]

Prepared in analogy to example 94. The title compound was obtained as light yellow foam. MS ISP (m/e): 472.2 (100) [(M+H)$^+$].

$^1$H NMR ($CDCl_3$, 300 MHz): δ (ppm)=8.52 (m, 1H), 8.37-8.30 (m, 2H), 8.22-8.18 (m, 1H), 7.55-7.52 (m, 1H), 7.35-7.29 (m, 1H), 6.95-6.90 (m, 1H), 6.42 (m, 1H), 4.53-4.50 (m, 1H), 4.38-4.34 (m, 2H), 4.02-3.92 (m, 1H), 3.23-3.13 (m, 2H), 2.37 (s, 3H), 2.29-2.23 (m, 2H), 1.60-1.47 (m, 2H).

Example 97

[8-(6-Dimethylamino-pyridin-3-yl)-[1,2,4]triazolo[1,5-a]pyridin-2-yl]-[1-(6-methyl-pyrimidin-4-yl)-piperidin-4-yl]-amine

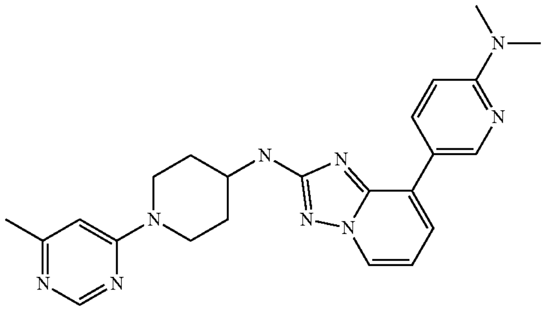

Prepared in analogy to example 94. The title compound was obtained as light yellow foam. MS ISP (m/e): 430.5 (100) $[(M+H)^+]$.

$^1$H NMR ($CDCl_3$, 300 MHz): δ (ppm)=8.74 (m, 1H), 8.52 (m, 1H), 8.26-8.17 (m, 2H), 7.46-7.43 (m, 1H), 6.88-6.84 (m, 1H), 6.64-6.61 (m, 1H), 6.41 (m, 1H), 4.46-4.43 (m, 1H), 4.36-4.31 (m, 2H), 4.03-3.94 (m, 1H), 3.24-3.15 (m, 2H), 3.15 (s, 6H), 2.38 (s, 3H), 2.27-2.22 (m, 2H), 1.59-1.46 (m, 2H).

Example 98

[8-(2-Chloro-thiophen-3-yl)-[1,2,4]triazolo[1,5-a]pyridin-2-yl]-[1-(6-methyl-pyrimidin-4-yl)-piperidin-4-yl]-amine

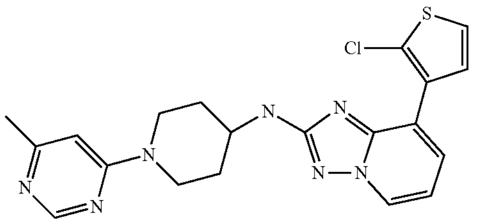 [SMILES: Cc1cc(N2CCC(Nc3nc4c(-c5ccsc5Cl)cccn4n3)CC2)ncn1]

Prepared in analogy to example 94. The title compound was obtained as light yellow solid. MS ISP (m/e): 426.1/428.3 (100/44) $[(M+H)^+]$.

$^1$H NMR ($CDCl_3$, 300 MHz): δ (ppm)=8.51 (m, 1H), 8.35-8.32 (m, 1H), 7.76-7.64 (m, 1H), 7.50-7.48 (m, 1H), 7.23-7.21 (m, 1H), 6.92-6.87 (m, 1H), 6.41 (m, 1H), 4.55-4.52 (m, 1H), 4.34-4.30 (m, 2H), 4.00-3.90 (m, 1H), 3.23-3.14 (m, 2H), 2.36 (s, 3H), 2.26-2.20 (m, 2H), 1.57-1.44 (m, 2H).

Example 99

[8-(4-Fluoro-3-trifluoromethyl-phenyl)-5,6,7,8-tetrahydro-[1,2,4]triazolo[1,5-a]pyridin-2-yl]-[1-(6-methyl-pyrimidin-4-yl)-piperidin-4-yl]-amine

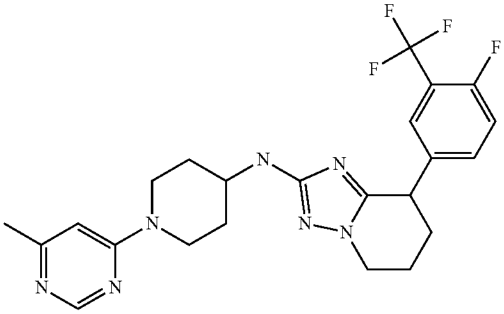 [SMILES: Cc1cc(N2CCC(Nc3nc4n(n3)CCCC4c3ccc(F)c(C(F)(F)F)c3)CC2)ncn1]

Prepared in analogy to example 93. The title compound was obtained as light yellow foam. MS ISP (m/e): 476.3 (100) $[(M+H)^+]$.

$^1$H NMR ($CDCl_3$, 300 MHz): δ (ppm)=8.49 (m, 1H), 7.43-7.41 (m, 1H), 7.35-7.32 (m, 1H), 7.18-7.14 (m, 1H), 6.38 (m, 1H), 4.29-4.25 (m, 2H), 4.17-4.09 (m, 3H), 4.01-3.99 (m, 1H), 3.77-3.69 (m, 1H), 3.17-3.10 (m, 2H), 2.36 (s, 3H), 2.37-2.28 (m, 1H), 2.18-1.89 (m, 5H), 1.49-1.37 (m, 2H).

Example 100

[8-(3,4-Difluoro-phenyl)-6-trifluoromethyl-[1,2,4]triazolo[1,5-a]pyridin-2-yl]-[1-(6-methyl-pyrimidin-4-yl)-piperidin-4-yl]-amine

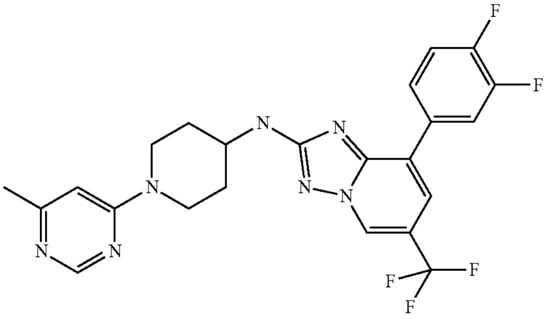 [SMILES: Cc1cc(N2CCC(Nc3nc4c(-c5ccc(F)c(F)c5)cc(C(F)(F)F)cn4n3)CC2)ncn1]

Prepared in analogy to example 66a-d and f, employing 3-bromo-5-(trifluoromethyl)pyridin-2-amine instead of 3-bromopyridin-2-amine in step a) and 1-(6-methyl-pyrimidin-4-yl)-piperidin-4-ylamine (see example 94a) instead of 1-(3-methyl-1,2,4-thiadiazol-5-yl)piperidin-4-amine in step f). The title compound was obtained as brown foam.

MS ISP (m/e): 490.2 (100) $[(M+H)^+]$.

$^1$H NMR ($CDCl_3$, 300 MHz): δ (ppm)=8.66 (m, 1H), 8.52 (m, 1H), 7.99-7.93 (m, 1H), 7.74-7.70 (m, 1H), 7.64 (m, 1H), 7.33-7.29 (m, 1H), 6.42 (m, 1H), 4.69-4.67 (m, 1H), 4.37-4.34 (m, 2H), 4.00-3.93 (m, 1H), 3.22-3.15 (m, 2H), 2.37 (s, 3H), 2.26-2.22 (m, 2H), 1.59-1.49 (m, 2H).

Example 101

[8-(3,4-Difluoro-phenyl)-6-trifluoromethyl-[1,2,4]triazolo[1,5-a]pyridin-2-yl]-[1-(3-methyl-[1,2,4]thiadiazol-5-yl)-piperidin-4-yl]-amine

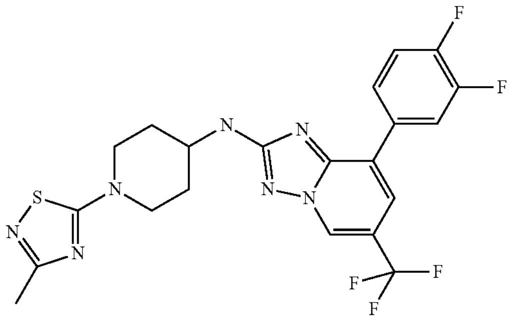 [SMILES: Cc1nsc(N2CCC(Nc3nc4c(-c5ccc(F)c(F)c5)cc(C(F)(F)F)cn4n3)CC2)n1]

Prepared in analogy to example 66 employing 3-bromo-5-(trifluoromethyl)pyridin-2-amine instead of 3-bromopyridin-2-amine in step a). The title compound was obtained as light brown foam. MS ISP (m/e): 496.3 (100) [(M+H)$^+$].

$^1$H NMR ($CDCl_3$, 300 MHz): δ (ppm)=8.65 (m, 1H), 7.98-7.93 (m, 1H), 7.73-7.69 (m, 1H), 7.65 (m, 1H), 7.34-7.27 (m, 1H), 4.69-4.67 (m, 1H), 3.98-3.90 (m, 3H), 3.40-3.33 (m, 2H), 2.42 (s, 3H), 2.29-2.24 (m, 2H), 1.73-1.64 (m, 2H).

Example 102

[1-(6-Methyl-pyrimidin-4-yl)-piperidin-4-yl]-[8-(2,3,4-trifluoro-phenyl)-[1,2,4]triazolo[1,5-a]pyridin-2-yl]-amine

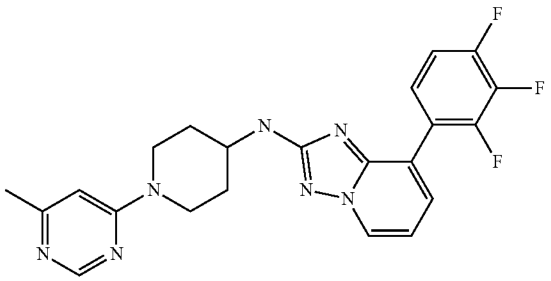 [SMILES: Cc1cc(N2CCC(Nc3nc4c(-c5ccc(F)c(F)c5F)cccn4n3)CC2)ncn1]

Prepared in analogy to example 94. The title compound was obtained as white foam.

MS ISP (m/e): 440.3 (100) [(M+H)$^+$].

$^1$H NMR ($CDCl_3$, 300 MHz): δ (ppm)=8.51 (m, 1H), 8.38-8.36 (m, 1H), 7.61-7.55 (m, 1H), 7.50-7.48 (m, 1H), 7.14-7.05 (m, 1H), 6.93-6.86 (m, 1H), 6.41 (m, 1H), 4.51-4.49 (m, 1H), 4.35-4.30 (m, 2H), 3.99-3.89 (m, 1H), 3.23-3.13 (m, 2H), 2.37 (s, 3H), 2.26-2.20 (m, 2H), 1.57-1.45 (m, 2H).

Example 103

[8-(2-Fluoro-pyridin-3-yl)-[1,2,4]triazolo[1,5-a]pyridin-2-yl]-[1-(6-methyl-pyrimidin-4-yl)-piperidin-4-yl]-amine

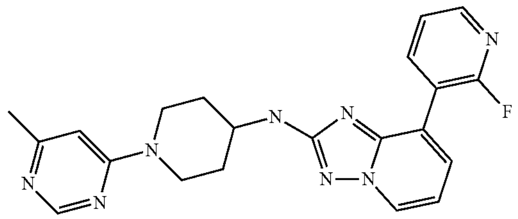 [SMILES: Cc1cc(N2CCC(Nc3nc4c(-c5cccnc5F)cccn4n3)CC2)ncn1]

Prepared in analogy to example 94. The title compound was obtained as brown solid.

MS ISP (m/e): 405.3 (15) [(M+H)$^+$].

$^1$H NMR ($CDCl_3$, 300 MHz): δ (ppm) 8.51-8.44 (m, 2H), 8.39-8.36 (m, 1H), 8.26-8.24 (m, 1H), 7.66-7.63 (m, 1H), 7.36-7.33 (m, 1H), 6.95-6.90 (m, 1H), 6.41 (m, 1H), 4.57-4.54 (m, 1H), 4.35-4.31 (m, 2H), 4.00-3.90 (m, 1H), 3.22-3.13 (m, 2H), 2.36 (s, 3H), 2.26-2.20 (m, 2H), 1.58-1.45 (m, 2H).

Example 104

[8-(2,6-Dimethoxy-pyridin-3-yl)-[1,2,4]triazolo[1,5-a]pyridin-2-yl]-[1-(6-methyl-pyrimidin-4-yl)-piperidin-4-yl]-amine

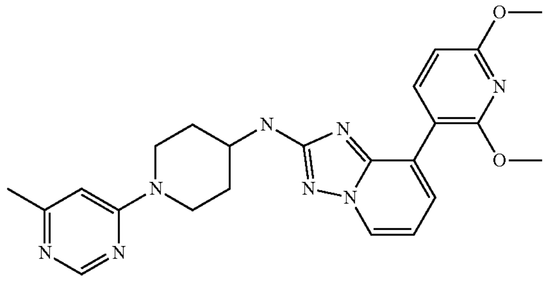

Prepared in analogy to example 94. The title compound was obtained as yellow oil.

MS ISP (m/e): 447.4 (100) [(M+H)$^+$].

$^1$H NMR ($CDCl_3$, 300 MHz): δ (ppm)=8.50 (m, 1H), 8.28-8.26 (m, 1H), 8.08-8.05 (m, 1H), 7.62-7.59 (m, 1H), 6.88-6.83 (m, 1H), 6.46-6.43 (m, 1H), 6.40 (m, 1H), 4.51-4.48 (m, 1H), 4.33-4.29 (m, 2H), 3.98-3.91 (m, 1H), 3.96 (s, 3H), 3.95 (s, 3H), 3.22-3.13 (m, 2H), 2.36 (s, 3H), 2.25-2.19 (m, 2H), 1.56-1.43 (m, 2H).

Example 105

[8-(6-Methoxy-pyridin-3-yl)-[1,2,4]triazolo[1,5-a]pyridin-2-yl]-[1-(6-methyl-pyrimidin-4-yl)-piperidin-4-yl]-amine

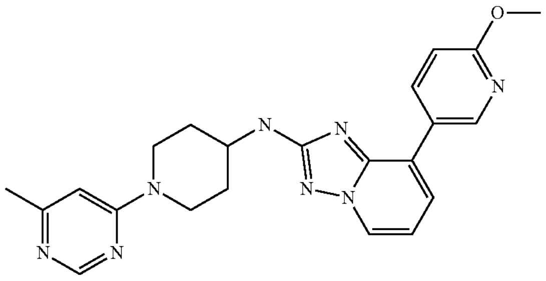

Prepared in analogy to example 94. The title compound was obtained as yellow oil.

MS ISP (m/e): 417.4 (35) [(M+H)$^+$].

$^1$H NMR ($CDCl_3$, 300 MHz): δ (ppm)=8.73 (m, 1H), 8.51 (m, 1H), 8.32-8.30 (m, 1H), 8.26-8.23 (m, 1H), 7.49-7.46 (m, 1H), 6.92-6.85 (m, 2H), 6.41 (m, 1H), 4.52-4.49 (m, 1H), 4.36-4.31 (m, 2H), 4.02-3.96 (m, 1H), 4.00 (s, 3H), 3.23-3.14 (m, 2H), 2.36 (s, 3H), 2.26-2.21 (m, 2H), 1.58-1.45 (m, 2H).

Example 106

[8-(3,4-Difluoro-phenyl)-5,6,7,8-tetrahydro-[1,2,4]triazolo[1,5-a]pyridin-2-yl]-[1-(6-methyl-pyrimidin-4-yl)-piperidin-4-yl]-amine

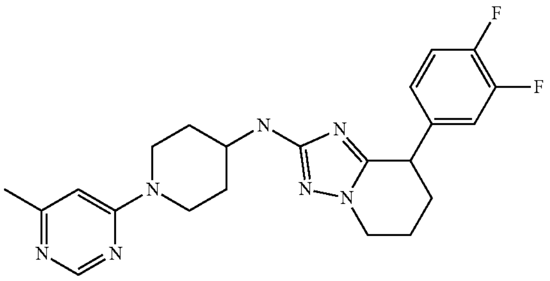 [SMILES: Cc1cc(N2CCC(Nc3nc4n(n3)CCCC4c3ccc(F)c(F)c3)CC2)ncn1]

Prepared in analogy to example 93. The title compound was obtained as light yellow oil.

MS ISP (m/e): 426.2 (100) [(M+H)$^+$].

$^1$H NMR ($CDCl_3$, 300 MHz): δ (ppm)=8.49 (m, 1H), 7.15-7.07 (m, 1H), 6.99-6.93 (m, 1H), 6.91-6.87 (m, 1H), 6.38 (m, 1H), 4.29-4.24 (m, 2H), 4.12-4.04 (m, 4H), 3.78-3.68 (m, 1H), 3.17-3.09 (m, 2H), 2.35 (s, 3H), 2.30-2.25 (m, 1H), 2.17-1.88 (m, 5H), 1.50-1.35 (m, 2H).

Example 107

[8-(6-Methoxy-pyridin-3-yl)-[1,2,4]triazolo[1,5-a]pyridin-2-yl]-[1-(5-methyl-[1,3,4]oxadiazol-2-yl)-piperidin-4-yl]-amine

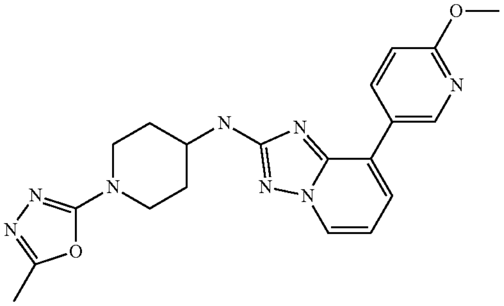 [SMILES: COc1ccc(-c2cccn3nc(NC4CCN(c5nnc(C)o5)CC4)nc23)cn1]

Prepared in analogy to example 85. The title compound was obtained as light yellow foam. MS ISP (m/e): 407.4 (100) [(M+H)$^+$].

$^1$H NMR ($CDCl_3$, 300 MHz): δ (ppm)=8.73-8.72 (m, 1H), 8.32-8.29 (m, 1H), 8.26-8.22 (m, 1H), 7.49-7.46 (m, 1H), 6.92-6.85 (m, 2H), 4.51-4.49 (m, 1H), 4.01-3.93 (m, 3H), 4.00 (s, 3H), 3.28-3.19 (m, 2H), 2.40 (s, 3H), 2.26-2.21 (m, 2H), 1.68-1.55 (m, 2H).

Example 108

[8-(6-Fluoro-pyridin-3-yl)-[1,2,4]triazolo[1,5-a]pyridin-2-yl]-[1-(5-methyl-[1,3,4]oxadiazol-2-yl)-piperidin-4-yl]-amine

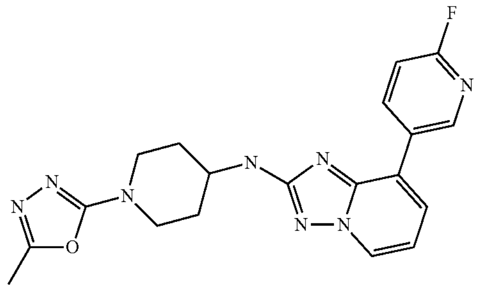 [SMILES: Cc1nnc(N2CCC(Nc3nc4c(-c5ccc(F)nc5)cccn4n3)CC2)o1]

Prepared in analogy to example 85. The title compound was obtained as brown solid.

MS ISP (m/e): 395.2 (51) [(M+H)$^+$].

$^1$H NMR ($CDCl_3$, 300 MHz): δ (ppm)=8.76-8.75 (m, 1H), 8.53-8.47 (m, 1H), 8.37-8.35 (m, 1H), 7.55-7.52 (m, 1H), 7.09-7.05 (m, 1H), 6.95-6.91 (m, 1H), 4.58-4.55 (m, 1H), 4.01-3.83 (m, 3H), 3.28-3.19 (m, 2H), 2.40 (s, 3H), 2.26-2.21 (m, 2H), 1.68-1.56 (m, 2H).

Example 109

[8-(4-Fluoro-3-trifluoromethyl-phenyl)-[1,2,4]triazolo[1,5-a]pyridin-2-yl]-[1-(5-methyl-[1,3,4]oxadiazol-2-yl)-piperidin-4-yl]-amine

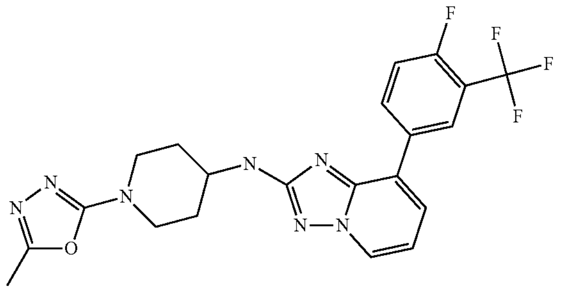 [SMILES: Cc1nnc(N2CCC(Nc3nc4c(-c5ccc(F)c(C(F)(F)F)c5)cccn4n3)CC2)o1]

Prepared in analogy to example 85. The title compound was obtained as light brown foam. MS ISP (m/e): 462.3 (100) [(M+H)$^+$].

$^1$H NMR ($CDCl_3$, 300 MHz): δ (ppm)=8.36-8.34 (m, 1H), 8.32-8.29 (m, 1H), 8.21-8.16 (m, 1H), 7.55-7.52 (m, 1H), 7.35-7.29 (m, 1H), 6.95-6.90 (m, 1H), 4.57-4.54 (m, 1H), 4.01-3.81 (m, 3H), 3.28-3.19 (m, 2H), 2.40 (s, 3H), 2.28-2.22 (m, 2H), 1.70-1.57 (m, 2H).

Example 110

[8-(3-Chloro-4-fluoro-phenyl)-6-fluoro-[1,2,4]triazolo[1,5-a]pyridin-2-yl]-[1-(5-methyl-[1,3,4]oxadiazol-2-yl)-piperidin-4-yl]-amine

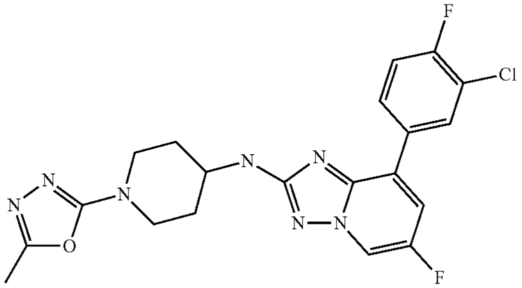 [SMILES: Cc1nnc(N2CCC(Nc3nc4c(-c5ccc(F)c(Cl)c5)cc(F)cn4n3)CC2)o1]

Prepared in analogy to example 66a-d and f starting with 3-bromo-5-fluoropyridin-2-amine instead of 3-bromopyridin-2-amine in step a and employing 1-(5-methyl-[1,3,4]oxadiazol-2-yl)-piperidin-4-ylamine (see example 40b) instead of 1-(3-methyl-1,2,4-thiadiazol-5-yl)piperidin-4-amine in step f. The title compound was obtained as light brown foam.

MS ISP (m/e): 446.1/448.1 (100/35) [(M+H)$^+$].

$^1$H NMR ($CDCl_3$, 300 MHz): δ (ppm)=8.30-8.28 (m, 1H), 8.15-8.12 (m, 1H), 7.90-7.85 (m, 1H), 7.44-7.41 (m, 1H), 7.30-7.24 (m, 1H), 4.55-4.53 (m, 1H), 3.99-3.81 (m, 3H), 3.28-3.19 (m, 2H), 2.40 (s, 3H), 2.26-2.20 (m, 2H), 1.69-1.56 (m, 2H).

Example 111

[8-(3-Chloro-4-fluoro-phenyl)-6-fluoro-[1,2,4]triazolo[1,5-a]pyridin-2-yl]-[1-(6-methyl-pyrimidin-4-yl)-piperidin-4-yl]-amine

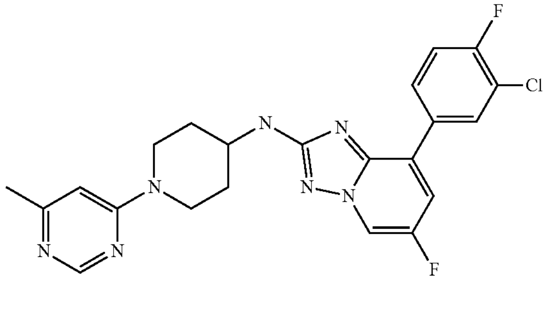 [SMILES: Cc1cc(N2CCC(Nc3nc4c(-c5ccc(F)c(Cl)c5)cc(F)cn4n3)CC2)ncn1]

Prepared in analogy to example 66a-d and f starting with 3-bromo-5-fluoropyridin-2-amine instead of 3-bromopyridin-2-amine in step a and employing 1-(6-methyl-pyrimidin-4-yl)-piperidin-4-ylamine (see example 94a) instead of 1-(3-methyl-1,2,4-thiadiazol-5-yl)piperidin-4-amine in step f. The title compound was obtained as light yellow foam.

MS ISP (m/e): 456.3/458.3 (100/34) [(M+H)$^+$].

$^1$H NMR ($CDCl_3$, 300 MHz): δ (ppm)=8.52 (m, 1H), 8.31-8.29 (m, 1H), 8.15-8.12 (m, 1H), 7.90-7.85 (m, 1H), 7.45-7.41 (m, 1H), 7.30-7.24 (m, 1H), 6.41 (m, 1H), 4.53-4.51 (m, 1H), 4.37-4.33 (m, 2H), 3.99-3.89 (m, 1H), 3.23-3.14 (m, 2H), 2.37 (s, 3H), 2.27-2.21 (m, 2H), 1.59-1.46 (m, 2H).

Example 112

[8-(4-Fluoro-3-trifluoromethyl-phenyl)-5,6,7,8-tetrahydro-[1,2,4]triazolo[1,5-a]pyridin-2-yl]-[1-(5-methyl-[1,3,4]oxadiazol-2-yl)-piperidin-4-yl]-amine

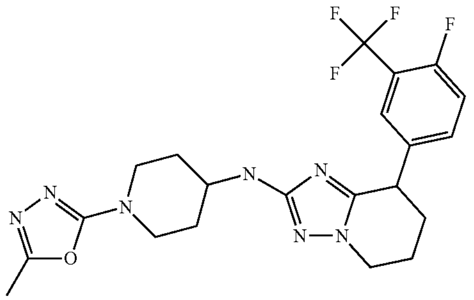 [SMILES: Cc1nnc(N2CCC(Nc3nc4n(n3)CCCC4c3ccc(F)c(C(F)(F)F)c3)CC2)o1]

Prepared in analogy to example 1h employing 1-(5-methyl-[1,3,4]oxadiazol-2-yl)-piperidin-4-one (see example 25b) and 8-(4-fluoro-3-trifluoromethyl-phenyl)-5,6,7,8-tetrahydro-[1,2,4]triazolo[1,5-a]pyridin-2-ylamine (prepared in analogy to example 1d-g). The title compound was obtained as brown solid.

MS ISP (m/e): 466.3 (71) [(M+H)$^+$].

$^1$H NMR ($CDCl_3$, 300 MHz): δ (ppm)=7.43-7.41 (m, 1H), 7.36-7.31 (m, 1H), 7.19-7.13 (m, 1H), 4.17-4.02 (m, 4H), 3.93-3.87 (m, 2H), 3.70-3.58 (m, 1H), 3.23-3.13 (m, 2H), 2.38 (s, 3H), 2.35-2.26 (m, 1H), 2.16-1.90 (m, 5H), 1.60-1.49 (m, 2H).

Example 113

[8-(2-Methyl-pyridin-4-yl)-[1,2,4]triazolo[1,5-a]pyridin-2-yl]-[1-(6-methyl-pyrimidin-4-yl)-piperidin-4-yl]-amine

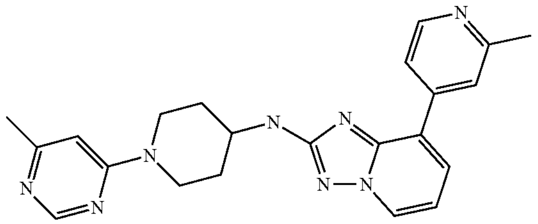

Prepared in analogy to example 94. The title compound was obtained as light yellow oil.

MS ISP (m/e): 401.4 (100) [(M+H)$^+$].

$^1$H NMR ($CDCl_3$, 300 MHz): δ (ppm)=8.73-8.60 (m, 1H), 8.52 (m, 1H), 8.39-8.37 (m, 1H), 7.80 (m, 1H), 7.72-7.70 (m, 1H), 7.63-7.61 (m, 1H), 6.95-6.90 (m, 1H), 6.41 (m, 1H), 4.63-4.61 (m, 1H), 4.36-4.32 (m, 2H), 4.02-3.93 (m, 1H), 3.24-3.14 (m, 2H), 2.65 (s, 3H), 2.37 (s, 3H), 2.27-2.22 (m, 2H), 1.60-1.47 (m, 2H).

Example 114 & 115

[8-(3,4-Difluoro-phenyl)-5-trifluoromethyl-5,6,7,8-tetrahydro-[1,2,4]triazolo[1,5-a]pyridin-2-yl]-[1-(3-methyl-[1,2,4]thiadiazol-5-yl)-piperidin-4-yl]-amine

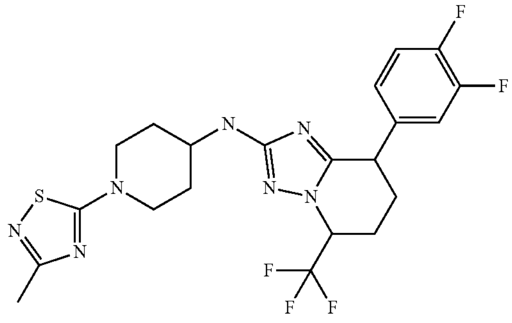 [SMILES: Cc1nsc(N2CCC(Nc3nc4n(n3)C(C(F)(F)F)CCC4c3ccc(F)c(F)c3)CC2)n1]

a) 8-(3,4-Difluoro-phenyl)-5-trifluoromethyl-[1,2,4]triazolo[1,5-a]pyridin-2-ylamine Prepared in analogy to example 66 steps a-c starting with 3-bromo-6-(trifluoromethyl)pyridin-2-amine (see example 82a) in step a. The title compound was obtained as an off-white solid. MS ISP (m/e): 315.1 (100) [(M+H)$^+$].

$^1$H NMR ($CDCl_3$, 300 MHz): δ (ppm)=7.97-7.90 (m, 1H), 7.76-7.70 (m, 1H), 7.57-7.55 (m, 1H), 7.36-7.30 (m, 2H), 4.75 (bs, 2H).

b) 8-(3,4-Difluoro-phenyl)-5-trifluoromethyl-5,6,7,8-tetrahydro-[1,2,4]triazolo[1,5-a]pyridin-2-ylamine Prepared in analogy to example 81a employing 8-(3,4-difluoro-phenyl)-5-trifluoromethyl-[1,2,4]triazolo[1,5-a]pyridin-2-ylamine. The title compound was obtained as mixture of racemic diastereomers as white solid.

MS ISP (m/e): 319.2 (100) [(M+H)$^+$].

$^1$H NMR ($CDCl_3$, 300 MHz): δ (ppm)=7.19-7.10 (m, 1H), 7.02-6.96 (m, 1H), 6.93-6.89 (m, 1H), 4.72-4.67 (m, 1H), 4.18 (bs, 2H), 4.12-4.07 (m, 1H), 2.47-2.39 (m, 1H), 2.29-2.12 (m, 3H).

c) 2-Bromo-8-(3,4-difluoro-phenyl)-5-trifluoromethyl-5,6,7,8-tetrahydro-[1,2,4]triazolo[1,5-a]pyridine Prepared in analogy to example 66d employing 8-(3,4-difluoro-phenyl)-5-trifluoromethyl-5,6,7,8-tetrahydro-[1,2,4]triazolo[1,5-a]pyridin-2-ylamine. The title compound was obtained as mixture of racemic diastereomers as yellow oil.

$^1$H NMR ($CDCl_3$, 300 MHz): δ (ppm)=7.20-7.11 (m, 1H), 7.01-6.94 (m, 1H), 6.91-6.87 (m, 1H), 4.92-4.86 (m, 1H), 4.22-4.17 (m, 1H), 2.53-2.46 (m, 1H), 2.37-2.19 (m, 3H).

d) [8-(3,4-Difluoro-phenyl)-5-trifluoromethyl-5,6,7,8-tetrahydro-[1,2,4]triazolo[1,5-a]pyridin-2-yl]-[1-(3-methyl-[1,2,4]thiadiazol-5-yl)-piperidin-4-yl]-amine Prepared in analogy to example 66f employing 2-bromo-8-(3,4-difluoro-phenyl)-5-trifluoromethyl-5,6,7,8-tetrahydro-[1,2,4]triazolo[1,5-a]pyridine. Both diastereomers were separated by preparative HPLC (without assignment of configuration to the diastereomers).

Example 114

Diastereomer A (rac). Retention time 3.13 minutes (Gemini NX 3u 50×4.6 mm)

White solid.

MS ISP (m/e): 499.9 (100) [(M+H)$^+$].

$^1$H NMR ($CDCl_3$, 300 MHz): δ (ppm)=7.18-7.09 (m, 1H), 6.95-6.89 (m, 1H), 6.86-6.82 (m, 1H), 4.74-4.68 (m, 1H), 4.20-4.15 (m, 2H), 3.90-3.70 (m, 3H), 3.35-3.25 (m, 2H), 2.40 (s, 3H), 2.47-2.13 (m, 5H), 1.99-1.89 (m, 1H), 1.66-1.46 (m, 2H).

Example 115

Diastereomer B (rac). Retention Time 3.57 Minutes (Gemini NX 3u 50×4.6 mm)

White solid. MS ISP (m/e): 500.0 (100) [(M+H)$^+$].

$^1$H NMR ($CDCl_3$, 300 MHz): δ (ppm)=7.18-7.09 (m, 1H), 7.02-6.95 (m, 1H), 6.93-6.88 (m, 1H), 4.74-4.67 (m, 1H), 4.22-4.14 (m, 1H), 4.12-4.03 (m, 1H), 3.88-3.67 (m, 3H), 3.34-3.27 (m, 2H), 2.40 (s, 3H), 2.46-2.12 (m, 6H), 1.66-1.48 (m, 2H).

Example 116 & 117

[8-(3,4-Difluoro-phenyl)-6-trifluoromethyl-5,6,7,8-tetrahydro-[1,2,4]triazolo[1,5-a]pyridin-2-yl]-[1-(3-methyl-[1,2,4]thiadiazol-5-yl)-piperidin-4-yl]-amine

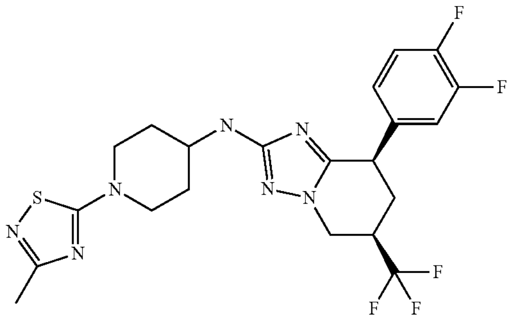

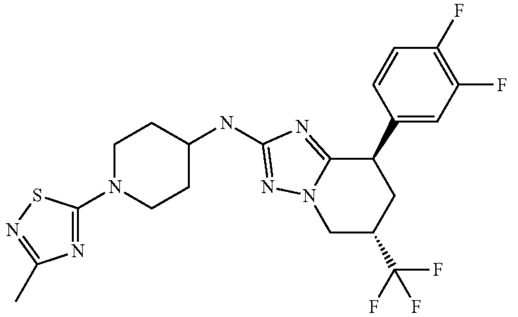

a) 8-(3,4-Difluoro-phenyl)-6-trifluoromethyl-[1,2,4]triazolo[1,5-a]pyridin-2-ylamine Prepared in analogy to example 66a-c starting from 3-bromo-5-trifluoromethyl-pyridin-2-ylamine. The title compound was obtained as an light grey solid.

MS ISP (m/e): 315.1 (84) [(M+H)$^+$].

$^1$H NMR ($CDCl_3$, 300 MHz): δ (ppm)=8.63 (m, 1H), 7.98-7.91 (m, 1H), 7.75-7.70 (m, 1H), 7.65-7.64 (m, 1H), 7.36-7.30 (m, 1H), 4.67 (bs, 2H).

b) 8-(3,4-Difluoro-phenyl)-6-trifluoromethyl-5,6,7,8-tetrahydro-[1,2,4]triazolo[1,5-a]pyridin-2-ylamine To a solution of 8-(3,4-difluorophenyl)-6-(trifluoromethyl)-[1,2,4]triazolo[1,5-a]pyridin-2-amine (500 mg, 1.59 mmol) and magnesium (309 mg, 12.7 mmol) in methanol (80 mL) and THF (40 mL) was added iodine (2 mg, 7.88 μmol), stirred for 10 minutes at room temperature, then sonicated for 30 minutes. The reaction mixture was concentrated in vacuo. The residue was dissolved in THF and dried over $Na_2SO_4$, then filtered off, washed thoroughly with THF and the solvents were evaporated. The crude material was purified by flash chromatography (silica gel, 70 g, 0% to 15% MeOH/$NH_4OH$ (9:1) in dichloromethane). The title compound was obtained as mixture of racemic diastereomers as white solid (324 mg, 64%).

$^1$H NMR ($CDCl_3$, 300 MHz): δ (ppm)=7.21-7.12 (m, 1H), 7.10-7.03 (m, 1H), 7.01-6.96 (m, 1H), 4.38-4.32 (m, 1H), 4.15 (br, 2H), 4.13-4.04 (m, 2H), 3.06-2.93 (m, 1H), 2.57-2.50 (m, 1H), 2.04-1.91 (m, 1H).

c) [8-(3,4-Difluoro-phenyl)-6-trifluoromethyl-5,6,7,8-tetrahydro-[1,2,4]triazolo[1,5-a]pyridin-2-yl]-[1-(3-methyl-[1,2,4]thiadiazol-5-yl)-piperidin-4-yl]-amine Prepared in analogy to example 1h employing 8-(3,4-difluoro-phenyl)-6-trifluoromethyl-5,6,7,8-tetrahydro-[1,2,4]triazolo[1,5-a]pyridin-2-ylamine. Cis and trans isomer were separated by preparative HPLC.

Example 116

(6R,8R)/(6S,8S) racemate. Retention time 3.2 minutes (Gemini NX 3u 50×4.6 mm). White foam. MS ISP (m/e): 500.0 (100) [(M+H)$^+$].

$^1$H NMR ($CDCl_3$, 600 MHz): δ (ppm)=7.18-7.15 (m, 1H), 7.08-7.05 (m, 1H), 7.00-6.98 (m, 1H), 4.40-4.37 (m, 1H), 4.12-4.04 (m, 3H), 3.85-3.82 (m, 2H), 3.71-3.66 (m, 1H), 3.32-3.27 (m, 2H), 3.03-2.97 (m, 1H), 2.55-2.52 (m, 1H), 2.40 (s, 3H), 2.18-2.15 (m, 2H), 2.02-1.95 (m, 1H), 1.61-1.52 (m, 2H).

Example 117

(6R,8S)/(6S,8R) racemate. Retention time 3.4 minutes (Gemini NX 3u 50×4.6 mm). White foam. MS ISP (m/e): 500.0 (100) [(M+H)$^+$].

$^1$H NMR ($CDCl_3$, 600 MHz): δ (ppm)=7.19-7.13 (m, 1H), 6.91-6.86 (m, 1H), 6.81 (m, 1H), 4.39-4.33 (m, 2H), 4.19-4.04 (m, 2H), 3.88-3.84 (m, 2H), 3.73 (m, 1H), 3.34-3.27 (m, 2H), 2.94 (m, 1H), 2.41 (s, 3H), 2.32-2.18 (m, 4H), 1.62-1.57 (m, 2H).

Example 118

[1-(5-Methyl-[1,3,4]oxadiazol-2-yl)-piperidin-4-yl]-[8-(2,3,4-trifluoro-phenyl)-[1,2,4]triazolo[1,5-a]pyridin-2-yl]-amine

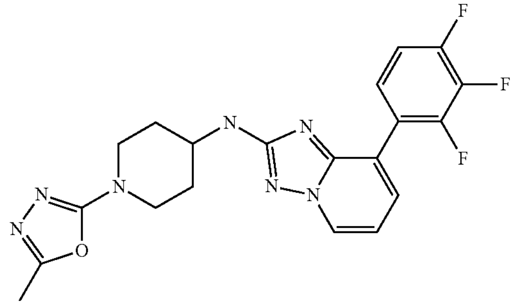 [SMILES: Cc1nnc(N2CCC(Nc3nc4c(-c5ccc(F)c(F)c5F)cccn4n3)CC2)o1]

Prepared in analogy to example 85. The title compound was obtained as white foam.

MS ISP (m/e): 430.0 (100) [(M+H)$^+$].

$^1$H NMR ($CDCl_3$, 300 MHz): δ (ppm)=8.38-8.35 (m, 1H), 7.60-7.52 (m, 1H), 7.50-7.47 (m, 1H), 7.13-7.05 (m, 1H), 6.93-6.88 (m, 1H), 4.57 (m, 1H), 3.98-3.92 (m, 2H), 3.87-3.83 (m, 1H), 3.28-3.19 (m, 2H), 2.39 (s, 3H), 2.25-2.19 (m, 2H), 1.64-1.55 (m, 2H).

Example 119

[8-(3,4-Dichloro-phenyl)-[1,2,4]triazolo[1,5-a]pyridin-2-yl]-[1-(6-methyl-pyrimidin-4-yl)-piperidin-4-yl]-amine

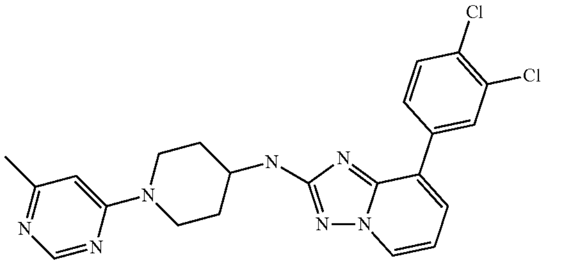 [SMILES: Cc1cc(N2CCC(Nc3nc4c(-c5ccc(Cl)c(Cl)c5)cccn4n3)CC2)ncn1]

Prepared in analogy to example 94. The title compound was obtained as light brown oil.

MS ISP (m/e): 454.3/456.3 (100/78) [(M+H)$^+$].

$^1$H NMR ($CDCl_3$, 300 MHz): δ (ppm)=8.51 (m, 1H), 8.35-8.33 (m, 1H), 8.15 (m, 1H), 7.86-7.82 (m, 1H), 7.56-7.51 (m, 2H), 6.92-6.88 (m, 1H), 6.41 (m, 1H), 4.55-4.52 (m, 1H), 4.37-4.32 (m, 2H), 4.01-3.92 (m, 1H), 3.23-3.14 (m, 2H), 2.37 (s, 3H), 2.27-2.22 (m, 2H), 1.57-1.47 (m, 2H).

Example 120

[1-(6-Methyl-pyrimidin-4-yl)-piperidin-4-yl]-[8-(3,4,5-trifluoro-phenyl)-[1,2,4]triazolo[1,5-a]pyridin-2-yl]-amine

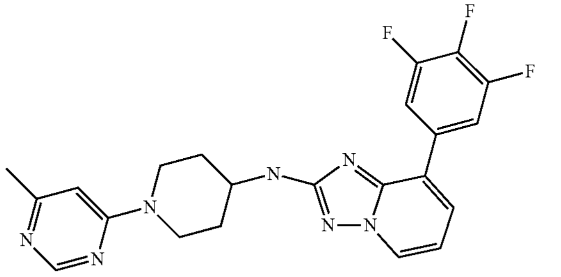 [SMILES: Cc1cc(N2CCC(Nc3nc4c(-c5cc(F)c(F)c(F)c5)cccn4n3)CC2)ncn1]

Prepared in analogy to example 94. The title compound was obtained as white foam.

MS ISP (m/e): 440.3 (75) [(M+H)$^+$].

$^1$H NMR ($CDCl_3$, 300 MHz): δ (ppm)=8.52-8.51 (m, 1H), 8.36-8.34 (m, 1H), 7.76-7.71 (m, 2H), 7.51-7.49 (m, 1H), 6.93-6.88 (m, 1H), 6.42 (m, 1H), 4.57-4.54 (m, 1H), 4.37-4.33 (m, 2H), 4.02-3.92 (m, 1H), 3.24-3.14 (m, 2H), 2.37 (s, 3H), 2.28-2.22 (m, 2H), 1.60-1.47 (m, 2H).

Example 121

[8-(2-Fluoro-pyridin-4-yl)-[1,2,4]triazolo[1,5-a]pyridin-2-yl]-[1-(6-methyl-pyrimidin-4-yl)-piperidin-4-yl]-amine

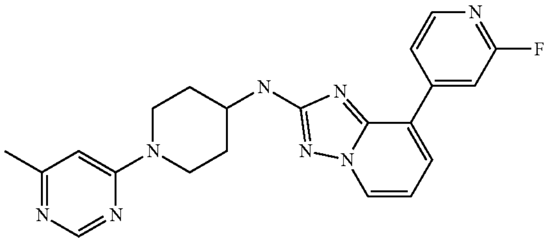 [SMILES: Cc1cc(N2CCC(Nc3nc4c(-c5ccnc(F)c5)cccn4n3)CC2)ncn1]

Prepared in analogy to example 94. The title compound was obtained as yellow foam.

MS ISP (m/e): 405.4 (59) [(M+H)$^+$].

$^1$H NMR ($CDCl_3$, 300 MHz): δ (ppm)=8.52 (m, 1H), 8.42-8.40 (m, 1H), 8.34-8.32 (m, 1H), 7.84-7.82 (m, 1H), 7.73 (m, 1H), 7.69-7.66 (m, 1H), 6.97-6.92 (m, 1H), 6.42 (m, 1H), 4.59-4.56 (m, 1H), 4.37-4.33 (m, 2H), 4.03-3.92 (m, 1H), 3.23-3.15 (m, 2H), 2.37 (s, 3H), 2.28-2.22 (m, 2H), 1.60-1.49 (m, 2H).

Example 122

[8-(2-Fluoro-pyridin-4-yl)-[1,2,4]triazolo[1,5-a]pyridin-2-yl]-[1-(6-methyl-pyrimidin-4-yl)-piperidin-4-yl]-amine

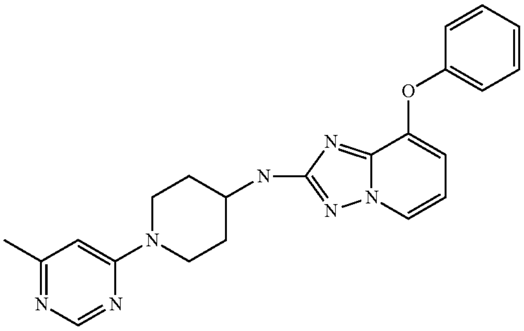 [SMILES: Cc1cc(N2CCC(Nc3nc4c(Oc5ccccc5)cccn4n3)CC2)ncn1]

a) 8-Phenoxy-[1,2,4]triazolo[1,5-a]pyridin-2-ylamine

A mixture of 8-bromo-[1,2,4]triazolo[1,5-a]pyridin-2-amine (see example 66b, 500 mg, 2.35 mmol), phenol (442 mg, 4.69 mmol), copper(I) iodide (44.7 mg, 235 μmol), picolinic acid (57.8 mg, 469 μmol) and potassium phosphate tribasic (1.49 g, 7.04 mmol) in DMSO (10 mL) was heated to 120° C. After 12 hours further phenol (442 mg, 4.69 mmol), copper(I) iodide (44.7 mg, 235 μmol), picolinic acid (57.8 mg, 469 μmol) and potassium phosphate tribasic (1.49 g, 7.04 mmol) were added and stirred at 120° C. for another 18 hours. Water was added to the reaction mixture and the aqueous phase was extracted with ethyl acetate. The combined organic phases were dried over sodium sulfate and the solvent was evaporated. The crude material was purified by prep. HPLC. The title compound was obtained as off-white solid (200 mg, 38%).

MS ISP (m/e): 227.2 (100) [(M+H)$^+$].

$^1$H NMR ($CDCl_3$, 300 MHz): δ (ppm)=8.10-8.07 (m, 1H), 7.42-7.37 (m, 2H), 7.22-7.17 (m, 1H), 7.14-7.11 (2H), 6.78-6.67 (m, 2H), 4.53 (bs, 2H).

b) [8-(2-Fluoro-pyridin-4-yl)-[1,2,4]triazolo[1,5-a]pyridin-2-yl]-[1-(6-methyl-pyrimidin-4-yl)-piperidin-4-yl]-amine A solution of 8-phenoxy-[1,2,4]triazolo[1,5-a]pyridin-2-amine (80 mg, 354 μmol), 1-(6-methylpyrimidin-4-yl)piperidin-4-one (see example 93b, 101 mg, 530 μmol) and titanium (IV) isopropoxide (302 mg, 314 μL, 1.06 mmol) in 1,2 dichloroethane (5 mL) was heated to 85° C. for 12 hours. Further titanium(IV) isopropoxide (302 mg, 314 μL, 1.06 mmol) was added and the mixture stirred at 85° C. for another 8 hours. The reaction mixture was cooled to 50° C., $NaBH_4$ (53.5 mg, 1.41 mmol) and ethanol (3 mL) were added and the reaction mixture was stirred at 50° C. for one hour. The solvent was evaporated, the residue extracted with 2 N $Na_2CO_3$ solution and ethyl acetate. The organic layers were combined, dried over $Na_2SO_4$, filtered and the solvent was evaporated. The residue was purified by flash chromatography (silica gel, 70 g, 0% to 15% MeOH/$NH_4$OH (9:1) in dichloromethane). The title compound was obtained as white solid (27 mg, 19%). MS ISP (m/e): 402.4 (100) [(M+H)$^+$].

$^1$H NMR ($CDCl_3$, 300 MHz): δ (ppm)=8.51 (m, 1H), 8.11-8.09 (m, 1H), 7.42-7.37 (m, 2H), 7.23-7.18 (m, 1H), 7.15-7.12 (m, 2H), 6.75-6.64 (m, 2H), 6.41 (m, 1H), 4.51-4.48 (m, 1H), 4.35-4.31 (m, 2H), 4.05-3.96 (m, 1H), 3.21-3.13 (m, 2H), 2.36 (s, 3H), 2.26-2.22 (m, 2H), 1.57-1.45 (m, 2H).

Example 123

[8-(3-Chloro-phenyl)-[1,2,4]triazolo[1,5-a]pyridin-2-yl]-[1-(6-methyl-pyrimidin-4-yl)-piperidin-4-yl]-amine

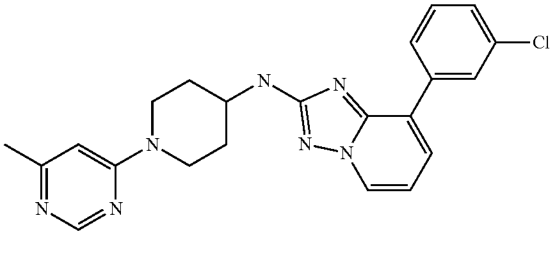 [SMILES: Cc1cc(N2CCC(Nc3nc4c(-c5cccc(Cl)c5)cccn4n3)CC2)ncn1]

Prepared in analogy to example 94. The title compound was obtained as orange foam.

MS ISP (m/e): 420.3/422.3 (100/38) [(M+H)$^+$].

$^1$H NMR ($CDCl_3$, 300 MHz): δ (ppm)=8.52 (m, 1H), 8.35-8.32 (m, 1H), 7.99 (m, 1H), 7.87-7.84 (m, 1H), 7.53-7.51 (m, 1H), 7.45-7.36 (m, 2H), 6.92-6.87 (m, 1H), 6.41 (m, 1H), 4.54-4.51 (m, 1H), 4.36-4.31 (m, 2H), 4.02-3.92 (m, 1H), 3.23-3.14 (m, 2H), 2.36 (s, 3H), 2.27-2.22 (m, 2H), 1.56-1.47 (m, 2H).

Example 124

3-{2-[1-(6-Methyl-pyrimidin-4-yl)-piperidin-4-ylamino]-[1,2,4]triazolo[1,5-a]pyridin-8-yl}-benzonitrile

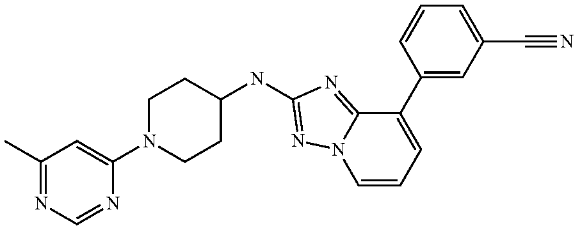 [SMILES: Cc1cc(N2CCC(Nc3nc4c(-c5cccc(C#N)c5)cccn4n3)CC2)ncn1]

Prepared in analogy to example 94. The title compound was obtained as orange foam.

$^1$H NMR ($CDCl_3$, 300 MHz): δ (ppm)=8.51 (m, 1H), 8.37-8.36 (m, 1H), 8.22-8.19 (m, 2H), 7.70-7.67 (m, 1H), 7.59-7.53 (m, 2H), 6.95-6.91 (m, 1H), 6.41 (m, 1H), 4.55-4.53 (m, 1H), 4.37-4.32 (m, 2H), 4.01-3.92 (m, 1H), 3.23-3.15 (m, 2H), 2.36 (s, 3H), 2.27-2.23 (m, 2H), 1.60-1.48 (m, 2H).

Example 125

[8-(4-tert-Butyl-phenyl)-[1,2,4]triazolo[1,5-a]pyridin-2-yl]-[1-(6-methyl-pyrimidin-4-yl)-piperidin-4-yl]-amine

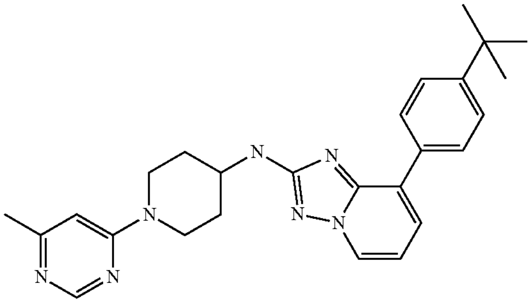 [SMILES: Cc1cc(N2CCC(Nc3nc4c(-c5ccc(C(C)(C)C)cc5)cccn4n3)CC2)ncn1]

Prepared in analogy to example 94. The title compound was obtained as orange foam.

$^1$H NMR ($CDCl_3$, 300 MHz): δ (ppm)=8.51 (m, 1H), 8.31-8.29 (m, 1H), 7.88-7.85 (m, 2H), 7.53-7.49 (m, 3H), 6.90-6.85 (m, 1H), 6.40 (m, 1H), 4.52-4.49 (m, 1H), 4.34-4.29 (m, 2H), 3.99-3.95 (m, 1H), 3.23-3.15 (m, 2H), 2.36 (s, 3H), 2.26-2.21 (m, 2H), 1.55-1.45 (m, 2H), 1.35 (s, 9H).

Example 126

[1-(3-Methyl-[1,2,4]thiadiazol-5-yl)-piperidin-4-yl]-(8-phenoxy-[1,2,4]triazolo[1,5-a]pyridin-2-yl)-amine

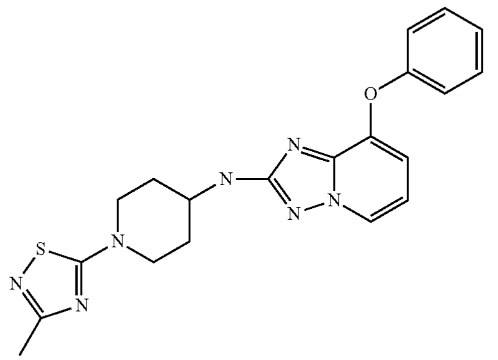 [SMILES: Cc1nsc(N2CCC(Nc3nc4c(Oc5ccccc5)cccn4n3)CC2)n1]

Prepared in analogy to example 122 employing 1-(3-methyl-[1,2,4]thiadiazol-5-yl)-piperidin-4-one (see example 1c) in step b). The title compound was obtained as white solid.

MS ISP (m/e): 408.3 (100) [(M+H)$^+$].

$^1$H NMR ($CDCl_3$, 300 MHz): δ (ppm)=8.10-8.08 (m, 1H), 7.42-7.37 (m, 2H), 7.23-7.18 (m, 1H), 7.14-7.12 (m, 2H), 6.75-6.65 (m, 2H), 4.52-4.49 (m, 1H), 4.04-3.95 (m, 1H), 3.91-3.87 (m, 2H), 3.39-3.30 (m, 2H), 2.42 (s, 3H), 2.28-2.23 (m, 2H), 1.72-1.60 (m, 2H).

Example 127

N-(1-(2-Chloropyridin-4-yl)piperidin-4-yl)-8-(5-fluoropyridin-2-yl)-[1,2,4]triazolo[1,5-a]pyridin-2-amine

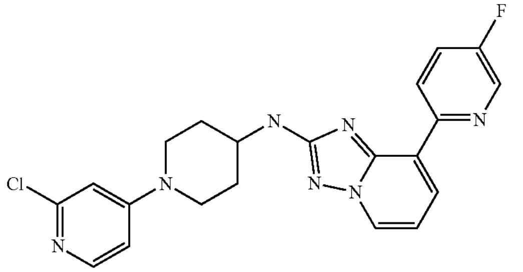 [SMILES: Fc1ccc(-c2cccn3nc(NC4CCN(c5ccnc(Cl)c5)CC4)nc23)nc1]

Prepared in analogy to example 66 employing 1-(2-chloropyridin-4-yl)piperidin-4-amine dihydrochloride (see example 169b) in step e). The title compound was obtained as light yellow oil. MS ISP (m/e): 424.2/426.3 (100/27) [(M+H)$^+$].

$^1$H NMR ($CDCl_3$, 300 MHz): δ (ppm)=8.93-8.87 (m, 1H), 8.58-8.57 (m, 1H), 8.39-8.35 (m, 2H), 8.05-8.02 (m, 1H), 7.57-7.50 (m, 1H), 7.01-6.95 (m, 1H), 6.70-6.69 (m, 1H), 6.62-6.59 (m, 1H), 4.56-4.53 (m, 1H), 4.02-3.93 (m, 1H), 3.88-3.83 (m, 2H), 3.20-3.11 (m, 2H), 2.30-2.26 (m, 2H), 1.69-1.57 (m, 2H).

Example 128

8-(3,5-Bis(trifluoromethyl)phenyl)-N-(1-(2-chloropyridin-4-yl)piperidin-4-yl)-[1,2,4]triazolo[1,5-a]pyridin-2-amine

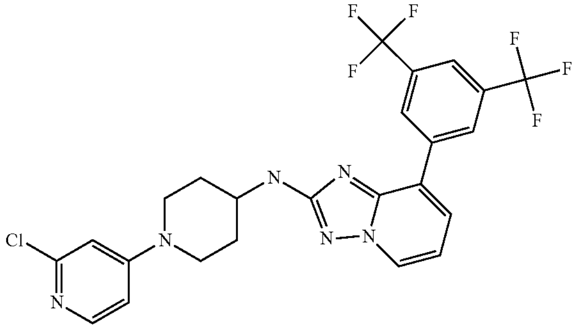 [SMILES: FC(F)(F)c1cc(-c2cccn3nc(NC4CCN(c5ccnc(Cl)c5)CC4)nc23)cc(C(F)(F)F)c1]

Prepared in analogy to example 127. The title compound was obtained as orange solid.

MS ISP (m/e): 541.3/543.3 (100/39) [(M+H)$^+$]. $^1$H NMR ($CDCl_3$, 300 MHz): δ (ppm)=8.56 (m, 2H), 8.41-8.38 (m, 1H), 8.04-8.02 (m, 1H), 7.90 (m, 1H), 7.66-7.64 (m, 1H), 6.99-6.94 (m, 1H), 6.69 (m, 1H), 6.62-6.59 (m, 1H), 4.59-4.56 (m, 1H), 4.00-3.92 (m, 1H), 3.89-3.84 (m, 2H), 3.17-3.08 (m, 2H), 2.31-2.25 (m, 2H), 1.65-1.60 (m, 2H).

Example 129

4-(2-(1-(2-Chloropyridin-4-yl)piperidin-4-ylamino)-[1,2,4]triazolo[1,5-a]pyridin-8-yl)benzonitrile

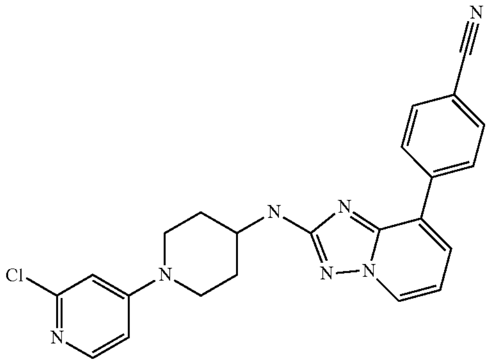 [SMILES: N#Cc1ccc(-c2cccn3nc(NC4CCN(c5ccnc(Cl)c5)CC4)nc23)cc1]

Prepared in analogy to example 127. The title compound was obtained as light yellow solid. MS ISP (m/e): 430.3/432.3 (100/35) [(M+H)$^+$].

$^1$H NMR ($CDCl_3$, 300 MHz): δ (ppm)=8.39-8.36 (m, 1H), 8.13-8.10 (m, 2H), 8.03-8.01 (m, 1H), 7.79-7.76 (m, 2H), 7.59-7.56 (m, 1H), 6.97-6.92 (m, 1H), 6.68 (m, 1H), 6.61-6.58 (m, 1H), 4.57-4.55 (m, 1H), 3.99-3.91 (m, 1H), 3.86-3.81 (m, 2H), 3.18-3.09 (m, 2H), 2.28-2.22 (m, 2H), 1.66-1.55 (m, 2H).

Example 130

[8-(2,3-Dichloro-phenyl)-[1,2,4]triazolo[1,5-a]pyridin-2-yl]-[1-(5-methyl-[1,3,4]oxadiazol-2-yl)-piperidin-4-yl]-amine

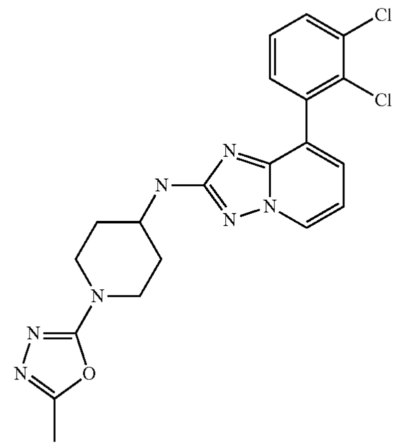 [SMILES: Cc1nnc(N2CCC(Nc3nc4c(-c5cccc(Cl)c5Cl)cccn4n3)CC2)o1]

Prepared in analogy to example 85. The title compound was obtained as yellow foam.

MS ISP (m/e): 444.2/446.1 (100/49) [(M+H)$^+$].

$^1$H NMR ($CDCl_3$, 300 MHz): δ (ppm)=8.39-8.37 (m, 1H), 7.55-7.52 (m, 1H), 7.41-7.36 (m, 2H), 7.33-7.28 (m, 1H), 6.92-6.88 (m, 1H), 4.53-4.50 (m, 1H), 3.97-3.90 (m, 2H), 3.88-3.78 (m, 1H), 3.27-3.18 (m, 2H), 2.39 (s, 3H), 2.24-2.19 (m, 2H), 1.65-1.53 (m, 2H).

Example 131

[8-(3-Chloro-phenyl)-[1,2,4]triazolo[1,5-a]pyridin-2-yl]-[1-(6-methyl-pyrimidin-4-yl)-piperidin-4-yl]-amine

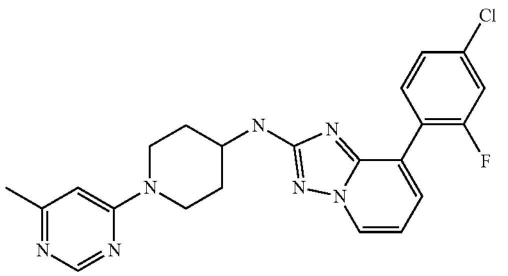 [SMILES: Cc1cc(N2CCC(Nc3nc4c(-c5ccc(Cl)cc5F)cccn4n3)CC2)ncn1]

Prepared in analogy to example 94. The title compound was obtained as yellow foam.

MS ISP (m/e): 438.2/440.3 (100/37) [(M+H)$^+$].

$^1$H NMR ($CDCl_3$, 300 MHz): δ (ppm)=8.51 (m, 1H), 8.37-8.34 (m, 1H), 7.83-7.77 (m, 1H), 7.51-7.49 (m, 1H), 7.28-7.22 (m, 2H), 6.92-6.87 (m, 1H), 6.40 (m, 1H), 4.51-4.49 (m, 1H), 4.34-4.28 (m, 2H), 3.99-3.88 (m, 1H), 3.22-3.13 (m, 2H), 2.36 (s, 3H), 2.26-2.20 (m, 2H), 1.57-1.46 (m, 2H).

Example 132

N-(1-(2-Chloropyridin-4-yl)piperidin-4-yl)-8-(3-methoxyphenyl)-[1,2,4]triazolo[1,5-a]pyridin-2-amine

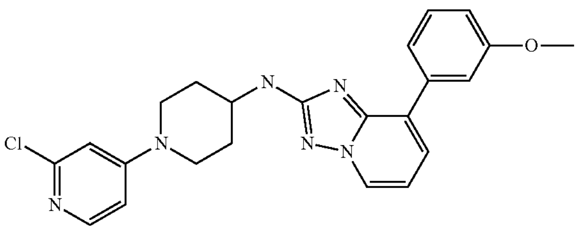 [SMILES: COc1cccc(-c2cccn3nc(NC4CCN(c5ccnc(Cl)c5)CC4)nc23)c1]

Prepared in analogy to example 127. The title compound was obtained as yellow foam.

MS ISP (m/e): 435.3/437.3 (100/31) [(M+H)$^+$].

$^1$H NMR ($CDCl_3$, 300 MHz): δ (ppm)=8.33-8.30 (m, 1H), 8.03-8.01 (m, 1H), 7.56-7.49 (m, 3H), 7.43-7.37 (m, 1H), 6.97-6.93 (m, 1H), 6.92-6.87 (m, 1H), 6.68-6.67 (m, 1H), 6.61-6.58 (m, 1H), 4.54-4.52 (m, 1H), 3.99-3.91 (m, 1H), 3.87 (s, 3H), 3.85-3.79 (m, 2H), 3.18-3.09 (m, 2H), 2.28-2.22 (m, 2H), 1.65-1.53 (m, 2H).

Example 133

8-(3-Chlorophenoxy)-N-(1-(2-chloropyridin-4-yl)piperidin-4-yl)-[1,2,4]triazolo[1,5-a]pyridin-2-amine

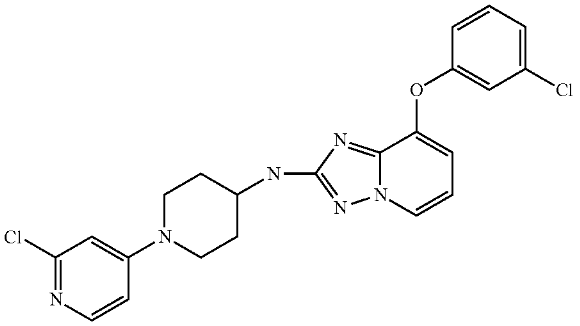 [SMILES: Clc1cccc(Oc2cccn3nc(NC4CCN(c5ccnc(Cl)c5)CC4)nc23)c1]

Prepared in analogy to example 122 employing 1-(2-chloropyridin-4-yl)piperidin-4-one (see example 232b) in step b). The title compound was obtained as white foam.

MS ISP (m/e): 454.8 (100) [(M+H)$^+$].

$^1$H NMR ($CDCl_3$, 300 MHz): δ (ppm)=8.17-8.15 (m, 1H), 8.03-8.01 (m, 1H), 7.33-7.28 (m, 1H), 7.18-7.15 (m, 1H), 7.09-7.08 (m, 1H), 7.02-6.98 (m, 1H), 6.90-6.88 (m, 1H), 6.77-6.72 (m, 1H), 6.68-6.67 (m, 1H), 6.61-6.58 (m, 1H), 5.12-5.10 (m, 1H), 3.98-3.89 (m, 1H), 3.83-3.79 (m, 2H), 3.19-3.10 (m, 2H), 2.25-2.19 (m, 2H), 1.67-1.55 (m, 2H).

Example 134

(2'-Chloro-3,4,5,6-tetrahydro-2H-[1,4']bipyridinyl-4-yl)-[8-(4-trifluoromethoxy-phenyl)-[1,2,4]triazolo[1,5-a]pyridin-2-yl]-amine

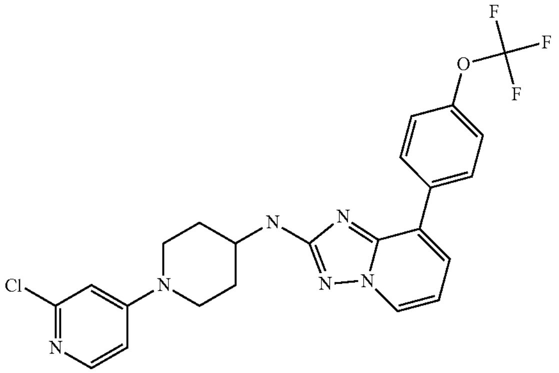 [SMILES: FC(F)(F)Oc1ccc(-c2cccn3nc(NC4CCN(c5ccnc(Cl)c5)CC4)nc23)cc1]

Prepared in analogy to example 127. The title compound was obtained as off-white solid. MS ISP (m/e): 489.2/491.2 (100/42) [$(M+H)^+$]. $^1H$ NMR ($CDCl_3$, 300 MHz): δ (ppm)=8.36-8.33 (m, 1H), 8.04-8.02 (m, 1H), 7.96-7.93 (m, 2H), 7.52-7.50 (m, 1H), 7.35-7.32 (m, 2H), 6.95-6.91 (m, 1H), 6.68 (m, 1H), 6.62-6.59 (m, 1H), 4.94-4.91 (m, 1H), 3.98-3.90 (m, 1H), 3.86-3.79 (m, 2H), 3.21-3.12 (m, 2H), 2.27-2.22 (m, 2H), 1.68-1.55 (m, 2H).

Example 135

3-(2-(1-(2-Chloropyridin-4-yl)piperidin-4-ylamino)-[1,2,4]triazolo[1,5-a]pyridin-8-yl)benzonitrile

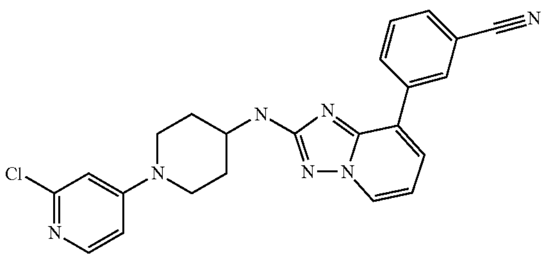 [SMILES: N#Cc1cccc(-c2cccn3nc(NC4CCN(c5ccnc(Cl)c5)CC4)nc23)c1]

Prepared in analogy to example 127. The title compound was obtained as light yellow solid. MS ISP (m/e): 430.3/432.4 (100/31) [$(M+H)^+$]. $^1H$ NMR ($CDCl_3$, 300 MHz): δ (ppm)=8.38-8.36 (m, 2H), 8.22-8.19 (m, 1H), 8.03-8.01 (m, 1H), 7.70-7.67 (m, 1H), 7.62-7.54 (m, 2H), 6.96-6.91 (m, 1H), 6.69-6.68 (m, 1H), 6.61-6.59 (m, 1H), 4.59-4.56 (m, 1H), 4.00-3.90 (m, 1H), 3.86-3.82 (m, 2H), 3.19-3.10 (m, 2H), 2.28-2.23 (m, 2H), 1.64-1.55 (m, 2H).

Example 136

[8-(4-Chloro-phenoxy)-[1,2,4]triazolo[1,5-a]pyridin-2-yl]-[1-(3-methyl-[1,2,4]thiadiazol-5-yl)-piperidin-4-yl]-amine

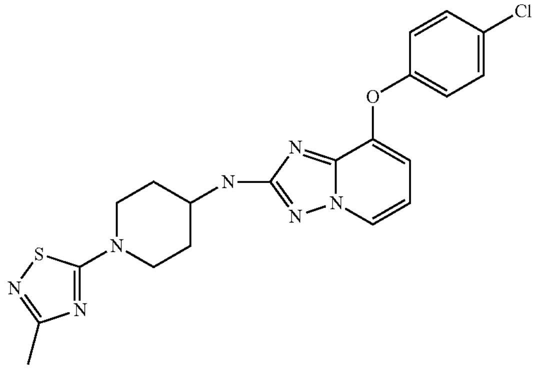 [SMILES: Cc1nsc(N2CCC(Nc3nc4c(Oc5ccc(Cl)cc5)cccn4n3)CC2)n1]

Prepared in analogy to example 126. The title compound was obtained as white solid.

MS ISP (m/e): 442.3/444.2 (100/44) [$(M+H)^+$].

$^1H$ NMR ($CDCl_3$, 300 MHz): δ (ppm)=8.13-8.11 (m, 1H), 7.36-7.33 (m, 2H), 7.07-7.04 (m, 2H), 6.80-6.77 (m, 1H), 6.72-6.67 (m, 1H), 4.54-4.51 (m, 1H), 4.01-3.87 (m, 3H), 3.39-3.29 (m, 2H), 2.42 (s, 3H), 2.27-2.22 (m, 2H), 1.71-1.62 (m, 2H).

Example 137

4-(2-(1-(6-Methylpyrimidin-4-yl)piperidin-4-ylamino)-[1,2,4]triazolo[1,5-a]pyridin-8-yl)benzonitrile

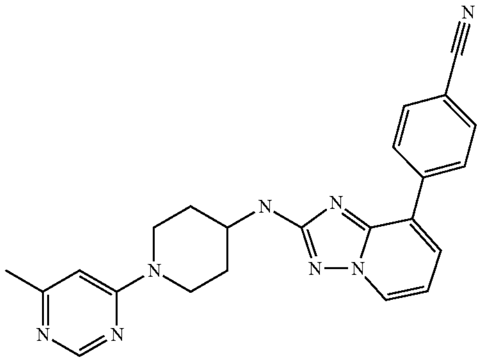 [SMILES: Cc1cc(N2CCC(Nc3nc4c(-c5ccc(C#N)cc5)cccn4n3)CC2)ncn1]

Prepared in analogy to example 94. The title compound was obtained as yellow foam.

MS ISP (m/e): 411.2 (100) [$(M+H)^+$]. $^1H$ NMR ($CDCl_3$, 300 MHz): δ (ppm)=8.51 (m, 1H), 8.39-8.37 (m, 1H), 8.13-8.11 (m, 2H), 7.79-7.76 (m, 2H), 7.59-7.50 (m, 1H), 6.96-6.91 (m, 1H), 6.41 (m, 1H), 4.58-4.55 (m, 1H), 4.36-4.32 (m, 2H), 4.01-3.92 (m, 1H), 3.23-3.14 (m, 2H), 2.37 (s, 3H), 2.27-2.21 (m, 2H), 1.58-1.46 (m, 2H).

Example 138

N-(1-(3-Methyl-1,2,4-thiadiazol-5-yl)piperidin-4-yl)-8-(3-(trifluoromethoxy)phenyl)-[1,2,4]triazolo[1,5-a]pyridin-2-amine

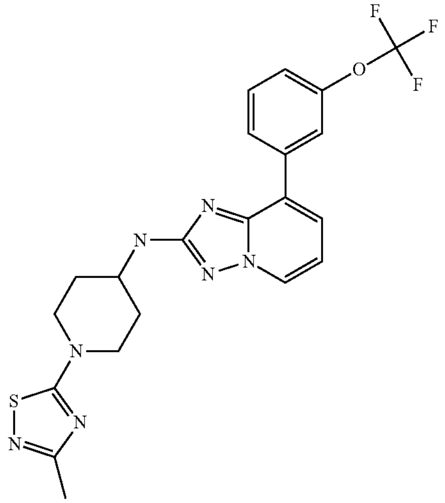 [SMILES: Cc1nsc(N2CCC(Nc3nc4c(-c5cccc(OC(F)(F)F)c5)cccn4n3)CC2)n1]

Prepared in analogy to example 66. The title compound was obtained as yellow solid.

MS ISP (m/e): 476.2 (56) [(M+H)$^+$]. $^1$H NMR ($CDCl_3$, 300 MHz): δ (ppm)=8.35-8.33 (m, 1H), 7.93-7.89 (m, 2H), 7.57-7.51 (m, 2H), 7.25 (m, 1H), 6.94-6.90 (m, 1H), 4.55-4.53 (m, 1H), 4.01-3.89 (m, 3H), 3.40-3.31 (m, 2H), 2.42 (s, 3H), 2.30-2.25 (m, 2H), 1.74-1.62 (m, 2H).

Example 139

8-(2,3-Dichlorophenyl)-N-(1-(3-methyl-1,2,4-thiadiazol-5-yl)piperidin-4-yl)-[1,2,4]triazolo[1,5-a]pyridin-2-amine

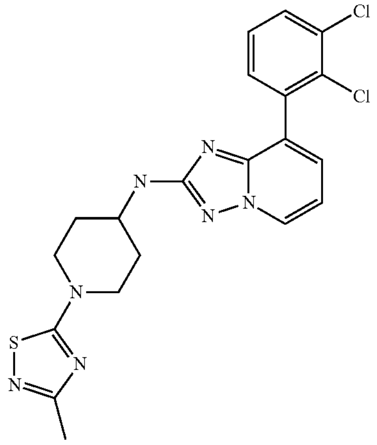 [SMILES: Cc1nsc(N2CCC(Nc3nc4c(-c5cccc(Cl)c5Cl)cccn4n3)CC2)n1]

Prepared in analogy to example 66. The title compound was obtained as yellow solid.

MS ISP (m/e): 460.2/462.2/464.2 (100/71/13) [(M+H)$^+$]. $^1$H NMR ($CDCl_3$, 300 MHz): δ (ppm)=8.39-8.37 (m, 1H), 7.56-7.52 (m, 1H), 7.40-7.36 (m, 2H), 7.33-7.28 (m, 1H), 6.93-6.88 (m, 1H), 4.57-4.54 (m, 1H), 3.95-3.84 (m, 3H), 3.39-3.30 (m, 2H), 2.41 (s, 3H), 2.27-2.21 (m, 2H), 1.70-1.61 (m, 2H).

Example 140

8-(3,4-Dichlorophenyl)-N-(1-(3-methyl-1,2,4-thiadiazol-5-yl)piperidin-4-yl)-[1,2,4]triazolo[1,5-a]pyridin-2-amine

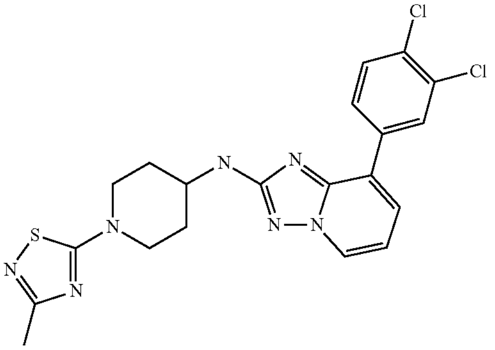 [SMILES: Cc1nsc(N2CCC(Nc3nc4c(-c5ccc(Cl)c(Cl)c5)cccn4n3)CC2)n1]

Prepared in analogy to example 66. The title compound was obtained as yellow oil.

MS ISP (m/e): 460.3/462.2 (100/68) [(M+H)$^+$].

$^1$H NMR ($CDCl_3$, 300 MHz): δ (ppm)=8.35-8.33 (m, 1H), 8.15-8.14 (m, 1H), 7.85-7.82 (m, 1H), 7.56-7.51 (m, 2H), 6.93-6.89 (m, 1H), 4.58-4.55 (m, 1H), 3.99-3.89 (m, 3H), 3.41-3.32 (m, 2H), 2.42 (s, 3H), 2.30-2.24 (m, 2H), 1.74-1.64 (m, 2H).

Example 141

8-(3-Chlorophenyl)-N-(1-(3-methyl-1,2,4-thiadiazol-5-yl)piperidin-4-yl)-[1,2,4]triazolo[1,5-a]pyridin-2-amine

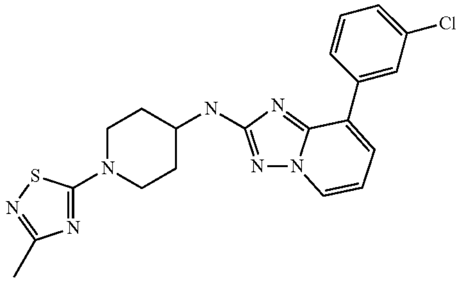 [SMILES: Cc1nsc(N2CCC(Nc3nc4c(-c5cccc(Cl)c5)cccn4n3)CC2)n1]

Prepared in analogy to example 66. The title compound was obtained as yellow oil.

MS ISP (m/e): 426.2/428.3 (100/42) [(M+H)$^+$].

$^1$H NMR ($CDCl_3$, 300 MHz): δ (ppm)=8.34-8.32 (m, 1H), 7.99 (m, 1H), 7.87-7.84 (m, 1H), 7.54-7.51 (m, 1H), 7.45-7.36 (m, 2H), 6.93-6.88 (m, 1H), 4.56-4.53 (m, 1H), 4.00-3.88 (m, 3H), 3.41-3.32 (m, 2H), 2.42 (s, 3H), 2.30-2.24 (m, 2H), 1.74-1.61 (m, 2H).

Example 142

[8-(3-Chloro-phenyl)-[1,2,4]triazolo[1,5-a]pyridin-2-yl]-[1-(5-methyl-[1,3,4]oxadiazol-2-yl)-piperidin-4-yl]-amine

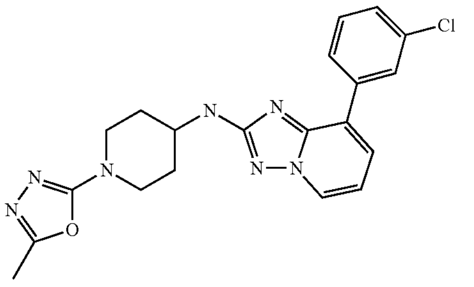 [SMILES: Cc1nnc(N2CCC(Nc3nc4c(-c5cccc(Cl)c5)cccn4n3)CC2)o1]

Prepared in analogy to example 85. The title compound was obtained as light brown oil.

MS ISP (m/e): 410.2/412.3 (100/33) [(M+H)$^+$].

$^1$H NMR ($CDCl_3$, 300 MHz): δ (ppm)=8.34-8.32 (m, 1H), 7.99 (m, 1H), 7.87-7.84 (m, 1H), 7.54-7.51 (m, 1H), 7.42-7.36 (m, 2H), 6.92-6.88 (m, 1H), 4.55-4.53 (m, 1H), 4.00-3.81 (m, 3H), 3.29-3.20 (m, 2H), 2.40 (s, 3H), 2.27-2.22 (m, 2H), 1.69-1.57 (m, 2H).

Example 143

[8-(3,4-Difluoro-phenyl)-5,6,7,8-tetrahydro-[1,2,4]triazolo[1,5-a]pyridin-2-yl]-[1-(5-methyl-[1,3,4]oxadiazol-2-yl)-piperidin-4-yl]-amine

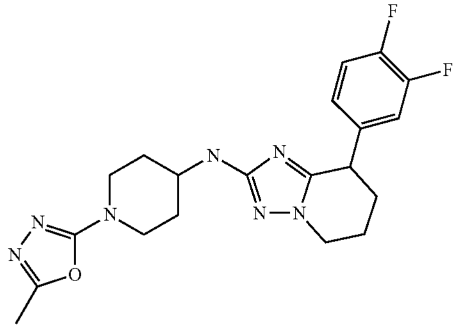 [SMILES: Cc1nnc(N2CCC(Nc3nc4n(n3)CCCC4c3ccc(F)c(F)c3)CC2)o1]

a) 8-(3,4-Difluorophenyl)-5,6,7,8-tetrahydro-[1,2,4]triazolo[1,5-a]pyridin-2-amine To a solution of 8-(3,4-difluorophenyl)-[1,2,4]triazolo[1,5-a]pyridin-2-amine (prepared in analogy to example 66a-c, 500 mg, 2.03 mmol) in methanol (60 mL) and THF (30 mL) magnesium (395 mg, 16.2 mmol) and iodine (3 mg) were added. After 1.5 hours at room temperature further magnesium (395 mg, 16.2 mmol) was added and the reaction mixture was stirred at 50° C. for 1 hour. Further magnesium (148 mg, 6.09 mmol) was added again and stirred at room temperature for 4 hours. The solvent was evaporated, the residue was dissolved in THF and dried over $Na_2SO_4$. The solvent was evaporated and the residue was purified by flash chromatography (silica gel, 100 g, 0% to 15% MeOH/$NH_3$ (9:1) in dichloromethane, 45 minutes). The title compound was obtained as white solid (226 mg, 45%).

MS ISP (m/e): 251.3 (100) [(M+H)$^+$].

$^1$H NMR ($CDCl_3$, 300 MHz): δ (ppm)=7.16-7.07 (m, 1H), 7.01-6.94 (m, 1H), 6.91-6.87 (m, 1H), 4.12-4.05 (m, 5H), 2.33-2.24 (m, 1H), 2.20-1.86 (m, 3H).

b)[8-(3,4-Difluoro-phenyl)-5,6,7,8-tetrahydro-[1,2,4]triazolo[1,5-a]pyridin-2-yl]-[1-(5-methyl-[1,3,4]oxadiazol-2-yl)-piperidin-4-yl]-amine A solution of 1-(5-methyl-1,3,4-oxadiazol-2-yl)piperidin-4-one (79.6 mg, 440 μmol) and 8-(3,4-difluorophenyl)-5,6,7,8-tetrahydro-[1,2,4]triazolo[1,5-a]pyridin-2-amine (110 mg, 440 mmol) in toluene (5 mL) and acetic acid (280 μL) was heated to reflux at a Dean-Stark trap. The reaction mixture was cooled to room temperature and ethanol (3 mL) was added followed by sodium borohydride (66.5 mg, 61.9 μL, 1.76 mmol). The reaction mixture was stirred at 50° C. for 3 hours. Further sodium borohydride (66.5 mg, 61.9 μL, 1.76 mmol) was added and stirred at 50° C. for 3 hours. Water was added to the reaction mixture and the aqueous phase was extracted with ethyl acetate. The combined organic layers were dried over $Na_2SO_4$ and the solvent was evaporated. The residue was purified by flash chromatography (silica gel, 100 g, 0% to 15% MeOH in dichloromethane, 40 minutes). The title compound was obtained as a white solid (32.8 mg, 18%). MS ISP (m/e): 416.3 (69) [(M+H)$^+$]. $^1$H NMR ($CDCl_3$, 300 MHz): δ (ppm)=7.16-7.07 (m, 1H), 7.00-6.93 (m, 1H), 6.91-6.87 (m, 1H), 4.12-4.01 (m, 4H), 3.93-3.87 (m, 2H), 3.72-3.60 (m, 1H), 3.23-3.13 (m, 2H), 2.38 (s, 3H), 2.32-2.23 (m, 1H), 2.18-1.88 (m, 5H), 1.58-1.48 (m, 2H).

Example 144

3-(2-(1-(3-Methyl-1,2,4-thiadiazol-5-yl)piperidin-4-ylamino)-[1,2,4]triazolo[1,5-a]pyridin-8-yl)benzonitrile

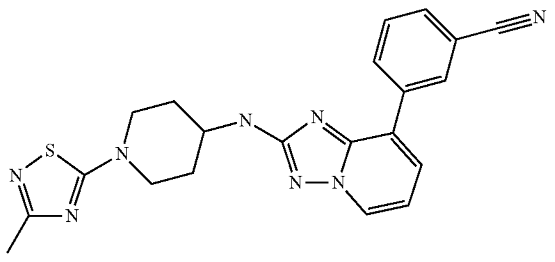 [SMILES: Cc1nsc(N2CCC(Nc3nc4c(-c5cccc(C#N)c5)cccn4n3)CC2)n1]

Prepared in analogy to example 66. The title compound was obtained as yellow foam.

MS ISP (m/e): 417.3 (100) [(M+H)$^+$].

$^1$H NMR ($CDCl_3$, 300 MHz): δ (ppm)=8.38-8.36 (m, 2H), 8.22-8.19 (m, 1H), 7.71-7.67 (m, 1H), 7.62-7.54 (m, 2H), 6.97-6.92 (m, 1H), 4.56-4.54 (m, 1H), 4.00-3.89 (m, 3H), 3.41-3.32 (m, 2H), 2.42 (s, 3H), 2.30-2.25 (m, 2H), 1.74-1.62 (m, 2H).

Example 145

[8-(3,4-Dichloro-phenyl)-[1,2,4]triazolo[1,5-a]pyridin-2-yl]-[1-(5-methyl-[1,3,4]oxadiazol-2-yl)-piperidin-4-yl]-amine

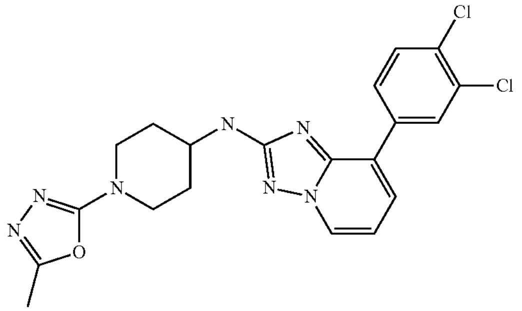 [SMILES: Cc1nnc(N2CCC(Nc3nc4c(-c5ccc(Cl)c(Cl)c5)cccn4n3)CC2)o1]

Prepared in analogy to example 85. The title compound was obtained as yellow solid.

MS ISP (m/e): 444.3/446.2 (100/54) [(M+H)$^+$].

$^1$H NMR ($CDCl_3$, 300 MHz): δ (ppm)=8.35-8.32 (m, 1H), 8.15 (m, 1H), 7.85-7.82 (m, 1H), 7.56-7.51 (m, 2H), 6.92-6.88 (m, 1H), 4.59-4.57 (m, 1H), 3.99-3.83 (m, 3H), 3.28-3.20 (m, 2H), 2.40 (s, 3H), 2.26-2.22 (m, 2H), 1.69-1.57 (m, 2H).

Example 146

[8-(5-Dimethylamino-2-nitro-phenyl)-[1,2,4]triazolo[1,5-a]pyridin-2-yl]-[1-(3-methyl-[1,2,4]thiadiazol-5-yl)-piperidin-4-yl]-amine

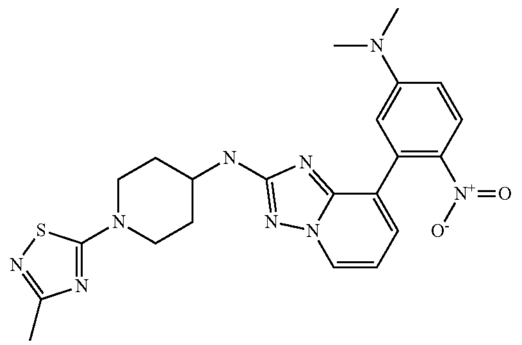 [SMILES: Cc1nsc(N2CCC(Nc3nc4c(-c5cc(N(C)C)ccc5[N+](=O)[O-])cccn4n3)CC2)n1]

Prepared in analogy to example 66. The title compound was obtained as light yellow oil.

MS ISP (m/e): 480.3 (80) [(M+H)$^+$].

$^1$H NMR ($CDCl_3$, 300 MHz): δ (ppm)=8.33-8.31 (m, 1H), 8.18-8.14 (m, 1H), 7.33-7.31 (m, 1H), 6.90-6.85 (m, 1H), 6.70-6.66 (m, 1H), 6.54-6.53 (m, 1H), 4.49-4.47 (m, 1H), 3.87-3.84 (m, 3H), 3.37-3.28 (m, 2H), 3.10 (s, 6H), 2.41 (s, 3H), 2.23-2.18 (m, 2H), 1.66-1.53 (m, 2H).

Example 147

[8-(3,5-Bis-trifluoromethyl-phenyl)-[1,2,4]triazolo[1,5-a]pyridin-2-yl]-[1-(3-methyl-[1,2,4]thiadiazol-5-yl)-piperidin-4-yl]-amine

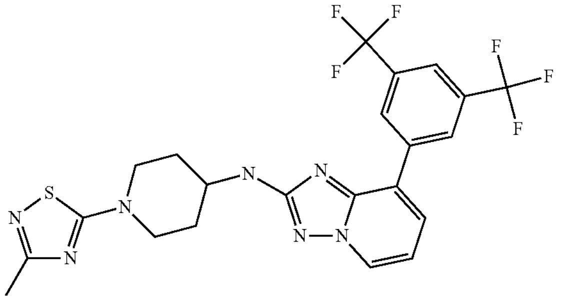 [SMILES: Cc1nsc(N2CCC(Nc3nc4c(-c5cc(C(F)(F)F)cc(C(F)(F)F)c5)cccn4n3)CC2)n1]

Prepared in analogy to example 66. The title compound was obtained as light yellow foam. MS ISP (m/e): 528.2 (100) [(M+H)$^+$].

$^1$H NMR ($CDCl_3$, 300 MHz): δ (ppm)=8.56 (s, 2H), 8.40-8.38 (m, 1H), 7.90 (m, 1H), 7.66-7.64 (m, 1H), 6.99-6.94 (m, 1H), 4.58-4.55 (m, 1H), 4.00-3.91 (m, 3H), 3.40-3.31 (m, 2H), 2.42 (s, 3H), 2.32-2.27 (m, 2H), 1.76-1.63 (m, 2H).

Example 148

N-(1-(3-Methyl-1,2,4-thiadiazol-5-yl)piperidin-4-yl)-8-(4-(trifluoromethoxy)phenyl)-[1,2,4]triazolo[1,5-a]pyridin-2-amine

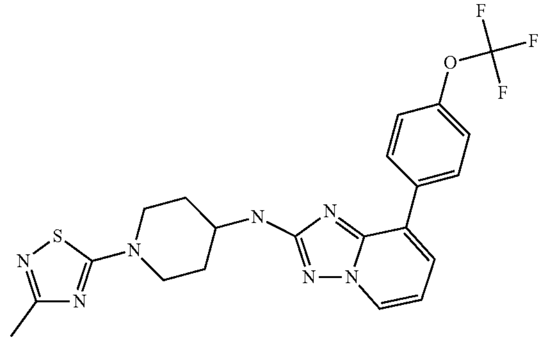 [SMILES: Cc1nsc(N2CCC(Nc3nc4c(-c5ccc(OC(F)(F)F)cc5)cccn4n3)CC2)n1]

Prepared in analogy to example 66. The title compound was obtained as light yellow foam. MS ISP (m/e): 476.2 (100) [(M+H)$^+$].

$^1$H NMR ($CDCl_3$, 300 MHz): δ (ppm)=8.35-8.32 (m, 1H), 8.01-7.98 (m, 2H), 7.53-7.50 (m, 1H), 7.35-7.32 (m, 2H), 6.94-6.89 (m, 1H), 4.54-4.51 (m, 1H), 4.00-3.88 (m, 3H), 3.41-3.32 (m, 2H), 2.42 (s, 3H), 2.29-2.24 (m, 2H), 1.73-1.60 (m, 2H).

Example 149

3-(2-(1-(5-Methyl-1,3,4-oxadiazol-2-yl)piperidin-4-ylamino)-[1,2,4]triazolo[1,5-a]pyridin-8-yl)benzonitrile

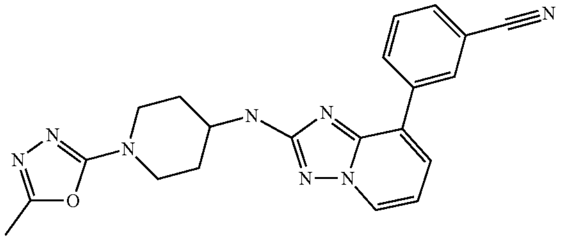 [SMILES: Cc1nnc(N2CCC(Nc3nc4c(-c5cccc(C#N)c5)cccn4n3)CC2)o1]

Prepared in analogy to example 85. The title compound was obtained as light yellow foam. MS ISP (m/e): 401.3 (100) $[(M+H)^+]$.

$^1$H NMR ($CDCl_3$, 300 MHz): δ (ppm)=8.38-8.36 (m, 2H), 8.23-8.19 (m, 1H), 7.70-7.67 (m, 1H), 7.62-7.52 (m, 2H), 6.96-6.91 (m, 1H), 4.55-4.52 (m, 1H), 4.01-3.83 (m, 3H), 3.29-3.20 (m, 2H), 2.40 (s, 3H), 2.27-2.22 (m, 2H), 1.70-1.61 (m, 2H).

Example 150

N-(1-(5-Methyl-1,3,4-oxadiazol-2-yl)piperidin-4-yl)-8-(3-(trifluoromethoxy)phenyl)-[1,2,4]triazolo[1,5-a]pyridin-2-amine

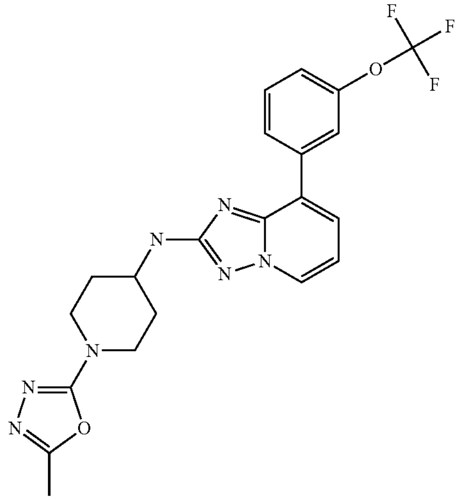 [SMILES: Cc1nnc(N2CCC(Nc3nc4c(-c5cccc(OC(F)(F)F)c5)cccn4n3)CC2)o1]

Prepared in analogy to example 85. The title compound was obtained as light yellow foam. MS ISP (m/e): 460.3 (100) $[(M+H)^+]$.

$^1$H NMR ($CDCl_3$, 300 MHz): δ (ppm)=8.35-8.33 (m, 1H), 7.93-7.90 (m, 2H), 7.56-7.49 (m, 2H), 7.24 (m, 1H), 6.94-6.89 (m, 1H), 4.53-4.50 (m, 1H), 4.01-3.84 (m, 3H), 3.28-3.19 (m, 2H), 2.40 (s, 3H), 2.28-2.22 (m, 2H), 1.69-1.56 (m, 2H).

Example 151

[8-(3-Methoxy-phenyl)-[1,2,4]triazolo[1,5-a]pyridin-2-yl]-[1-(3-methyl-[1,2,4]thiadiazol-5-yl)-piperidin-4-yl]-amine

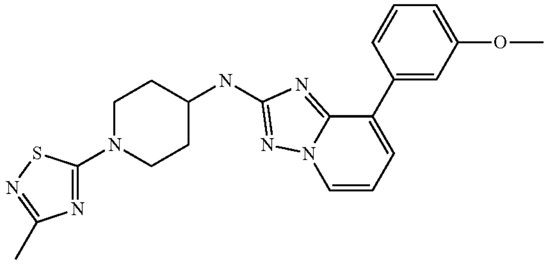 [SMILES: COc1cccc(-c2cccn3nc(NC4CCN(c5nc(C)ns5)CC4)nc23)c1]

Prepared in analogy to example 66. The title compound was obtained as yellow foam.

MS ISP (m/e): 422.2 (100) $[(M+H)^+]$. $^1$H NMR ($CDCl_3$, 300 MHz): δ (ppm)=8.32-8.30 (m, 1H), 7.55-7.49 (m, 3H), 7.43-7.37 (m, 1H), 6.97-6.93 (m, 1H), 6.92-6.87 (m, 1H), 4.55-4.52 (m, 1H), 4.00-3.86 (m, 3H), 3.87 (s, 3H), 3.40-3.31 (m, 2H), 2.42 (s, 3H), 2.29-2.24 (m, 2H), 1.73-1.60 (m, 2H).

Example 152

[8-(3-Chloro-phenoxy)-[1,2,4]triazolo[1,5-a]pyridin-2-yl]-[1-(3-methyl-[1,2,4]thiadiazol-5-yl)-piperidin-4-yl]-amine

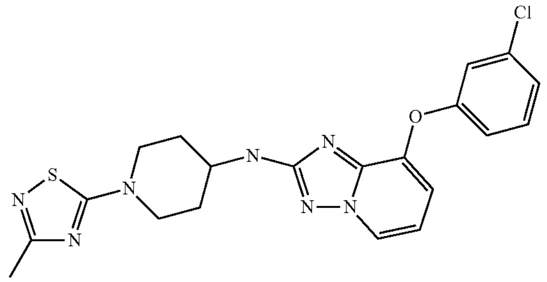 [SMILES: Cc1nsc(N2CCC(Nc3nc4c(Oc5cccc(Cl)c5)cccn4n3)CC2)n1]

a) 2-Bromo-8-(3-chlorophenoxy)-[1,2,4]triazolo[1,5-a]pyridine

Copper(II) bromide (365 mg, 1.63 mmol) and tert-butyl nitrite (168 mg, 195 μL, 1.63 mmol) were dissolved in acetonitril (8.0 mL) and heated to 60° C. 8-(3-Chlorophenoxy)-[1,2,4]triazolo[1,5-a]pyridin-2-amine (prepared in analogy to example 122a, 387 mg, 1.48 mmol) was added in small portions, heated to 75° C. and stirred for 2 hours.

Water was added to the reaction mixture and the aqueous phase was extracted with metyhlene chloride. The combined organic layers were dried over $Na_2SO_4$. The solvent was evaporated and the residue was purified by flash chromatography (silica gel, 70 g, 0% to 100% ethyl acetate in toluene, 35 minutes). The title compound was obtained as a light red solid (142 mg, 30%). MS ISP (m/e): 324.2/326.1 (77/100) [(M+H)$^+$].

$^1$H NMR ($CDCl_3$, 300 MHz): δ (ppm)=8.34-8.32 (m, 1H), 7.38-7.33 (m, 1H), 7.25-7.21 (m, 1H), 7.16-7.14 (m, 1H), 7.07-7.03 (m, 1H), 6.96-6.90 (m, 2H).

b) [8-(3-Chloro-phenoxy)-[1,2,4]triazolo[1,5-a]pyridin-2-yl]-[1-(3-methyl-[1,2,4]thiadiazol-5-yl)-piperidin-4-yl]-amine Prepared in analogy to example 66f employing 2-bromo-8-(3-chlorophenoxy)-[1,2,4]triazolo[1,5-a]pyridine. The title compound was obtained as white foam.

MS ISP (m/e): 442.3/444.3 (100/40) [(M+H)$^+$].

$^1$H NMR ($CDCl_3$, 300 MHz): δ (ppm)=8.17-8.14 (m, 1H), 7.33-7.27 (m, 1H), 7.17-7.14 (m, 1H), 7.09-7.08 (m, 1H), 7.02-6.98 (m, 1H), 6.88-6.85 (m, 1H),6.75-6.70 (m, 1H), 4.62-4.60 (m, 1H), 4.00-3.86 (m, 3H), 3.38-3.29 (m, 2H), 2.41 (s, 3H), 2.27-2.22 (m, 2H), 1.72-1.59 (m, 2H).

Example 153

N-(1-(6-Methylpyrimidin-4-yl)piperidin-4-yl)-8-(2,3,4-trifluorophenyl)-5,6,7,8-tetrahydro-[1,2,4]triazolo[1,5-a]pyridin-2-amine

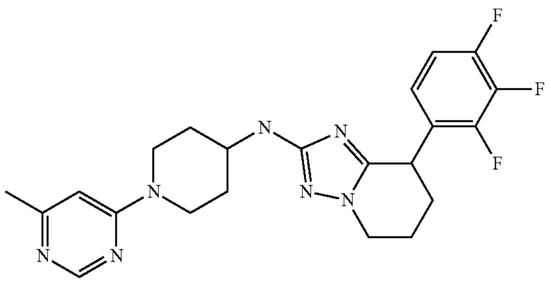 [SMILES: Cc1cc(N2CCC(Nc3nc4n(n3)CCCC4c3ccc(F)c(F)c3F)CC2)ncn1]

Prepared in analogy to example 143 employing 1-(6-methylpyrimidin-4-yl)piperidin-4-one (see example 93b). The title compound was obtained as light yellow foam.

MS ISP (m/e): 444.3 (64) [(M+H)$^+$].

$^1$H NMR ($CDCl_3$, 300 MHz): δ (ppm)=8.49 (m, 1H), 6.96-6.87 (m, 1H), 6.78-6.70 (m, 1H), 6.38 (m, 1H), 4.38-4.34 (m, 1H), 4.30-4.24 (m, 2H), 4.12-4.07 (m, 2H), 4.01-3.98 (m, 1H), 3.79-3.67 (m, 1H), 3.17-3.08 (m, 2H), 2.35 (s, 3H), 2.32-2.25 (m, 1H), 2.18-1.91 (m, 5H), 1.50-1.35 (m, 2H).

Example 154

[8-(3-Chloro-phenoxy)-[1,2,4]triazolo[1,5-a]pyridin-2-yl]-[1-(5-methyl-[1,3,4]oxadiazol-2-yl)-piperidin-4-yl]-amine

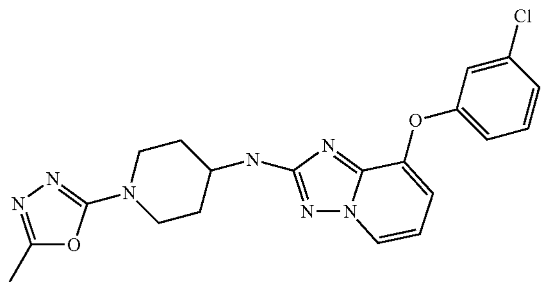 [SMILES: Cc1nnc(N2CCC(Nc3nc4c(Oc5cccc(Cl)c5)cccn4n3)CC2)o1]

Prepared in analogy to example 66f employing 2-bromo-8-(3-chlorophenoxy)-[1,2,4]triazolo[1,5-a]pyridine (see example 152a) and 1-(5-methyl-[1,3,4]oxadiazol-2-yl)-piperidin-4-ylamine (see example 40b). The title compound was obtained as yellow oil.

MS ISP (m/e): 426.1 (59) [(M+H)$^+$].

$^1$H NMR ($CDCl_3$, 300 MHz): δ (ppm)=8.16-8.14 (m, 1H), 7.33-7.27 (m, 1H), 7.17-7.14 (m, 1H), 7.09-7.08 (m, 1H), 7.02-6.98 (m, 1H), 6.88-6.85 (m, 1H), 6.75-6.70 (m, 1H), 4.58-4.55 (m, 1H), 3.98-3.85 (m, 3H), 3.26-3.17 (m, 2H), 2.39 (s, 3H), 2.24-2.19 (m, 2H), 1.67-1.54 (m, 2H).

Example 155

[8-(3,5-Bis-trifluoromethyl-phenyl)-[1,2,4]triazolo[1,5-a]pyridin-2-yl]-[1-(5-methyl-[1,3,4]oxadiazol-2-yl)-piperidin-4-yl]-amine

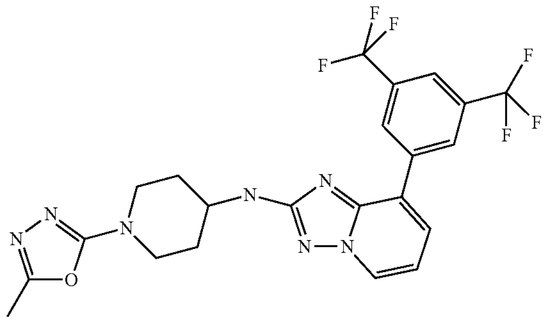 [SMILES: Cc1nnc(N2CCC(Nc3nc4c(-c5cc(C(F)(F)F)cc(C(F)(F)F)c5)cccn4n3)CC2)o1]

Prepared in analogy to example 85. The title compound was obtained as light yellow foam. MS ISP (m/e): 512.4 (100) [(M+H)$^+$].

$^1$H NMR ($CDCl_3$, 300 MHz): δ (ppm)=8.57 (m, 2H), 8.40-8.39 (m, 1H), 7.91 (m, 1H), 7.66-7.64 (m, 1H), 6.99-6.94 (m, 1H), 4.58-4.56 (m, 1H), 4.03-3.85 (m, 3H), 3.27-3.19 (m, 2H), 2.41 (s, 3H), 2.29-2.25 (m, 2H), 1.71-1.64 (m, 2H).

Example 156

[8-(5-Chloro-2-fluoro-phenyl)-[1,2,4]triazolo[1,5-a]pyridin-2-yl]-[1-(3-methyl-[1,2,4]thiadiazol-5-yl)-piperidin-4-yl]-amine

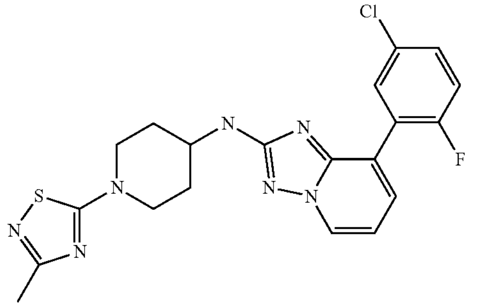 [SMILES: Cc1nsc(N2CCC(Nc3nc4c(-c5cc(Cl)ccc5F)cccn4n3)CC2)n1]

Prepared in analogy to example 66. The title compound was obtained as yellow foam.

MS ISP (m/e): 444.3/446.2 (100/27) [$(M+H)^+$].

$^1H$ NMR ($CDCl_3$, 300 MHz): δ (ppm)=8.37-8.34 (m, 1H), 7.86-7.83 (m, 1H), 7.54-7.50 (m, 1H), 7.37-7.32 (m, 1H), 7.18-7.12 (m, 1H), 6.93-6.88 (m, 1H), 4.55-4.52 (m, 1H), 3.98-3.87 (m, 3H), 3.40-3.31 (m, 2H), 2.42 (s, 3H), 2.29-2.24 (m, 2H), 1.72-1.59 (m, 2H).

Example 157

[8-(3-Dimethylamino-phenyl)-[1,2,4]triazolo[1,5-a]pyridin-2-yl]-[1-(6-methyl-pyrimidin-4-yl)-piperidin-4-yl]-amine

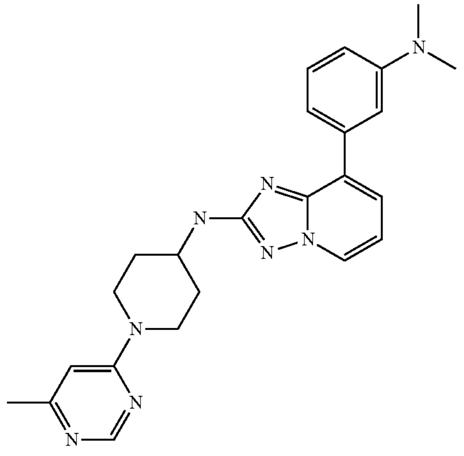

Prepared in analogy to example 1h employing 1-(6-methylpyrimidin-4-yl)piperidin-4-one (see example 93b) and 8-(3-dimethylamino-phenyl)-[1,2,4]triazolo[1,5-a]pyridin-2-ylamine (prepared in analogy to example 66a-c). The title compound was obtained as white foam.

MS ISP (m/e): 429.3 (100) [$(M+H)^+$]. $^1H$ NMR ($CDCl_3$, 300 MHz): δ (ppm)=8.51 (m, 1H), 8.31-8.29 (m, 1H), 7.54-7.52 (m, 1H), 7.37-7.32 (m, 2H), 7.23-7.21 (m, 1H), 6.90-6.85 (m, 1H), 6.81-6.78 (m, 1H), 6.41 (m, 1H), 4.50-4.47 (m, 1H), 4.35-4.31 (m, 2H), 4.04-3.93 (m, 1H), 3.77-3.73 (m, 2H), 3.21-3.13 (m, 2H), 3.01 (s, 6H), 2.36 (s, 3H), 2.27-2.22 (m, 2H).

Example 158

N-(1-(3-Methyl-1,2,4-thiadiazol-5-yl)piperidin-4-yl)-8-(6-methylpyridin-3-yl)-[1,2,4]triazolo[1,5-a]pyridin-2-amine

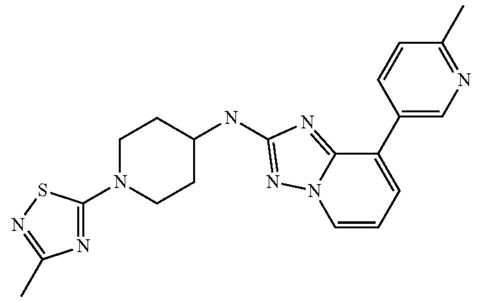 [SMILES: Cc1ccc(-c2cccn3nc(NC4CCN(c5nc(C)ns5)CC4)nc23)cn1]

Prepared in analogy to example 66. The title compound was obtained as light yellow foam. MS ISP (m/e): 407.4 (100) [$(M+H)^+$].

$^1H$ NMR ($CDCl_3$, 300 MHz): δ (ppm)=9.01-9.00 (m, 1H), 8.34-8.32 (m, 1H), 8.28-8.24 (m, 1H), 7.55-7.53 (m, 1H), 7.30-7.26 (m, 1H), 6.94-6.90 (m, 1H), 4.52-4.49 (m, 1H), 4.01-3.88 (m, 3H), 3.40-3.31 (m, 2H), 2.62 (s, 3H), 2.42 (s, 3H), 2.29-2.24 (m, 2H), 1.73-1.61 (m, 2H).

Example 159

7-Methoxy-N-(1-(6-methylpyrimidin-4-yl)piperidin-4-yl)-4-phenylbenzo[d]thiazol-2-amine

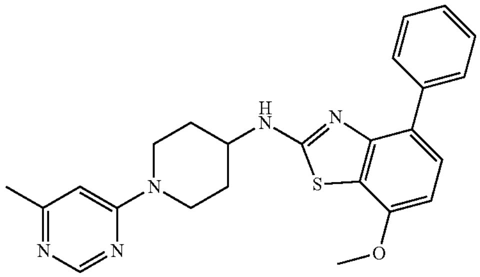 [SMILES: COc1ccc(-c2ccccc2)c2nc(NC3CCN(c4cc(C)ncn4)CC3)sc12]

a) 2-Chloro-7-methoxy-4-phenylbenzo[d]thiazole

A solution of copper(II) chloride (78.7 mg, 585 μmol) and tert-butyl nitrite (67.1 mg, 77.6 μL, 585 μmol) dissolved in acetonitrile (5 mL) was heated to 60° C. 7-Methoxy-4-phenylbenzo[d]thiazol-2-amine (100 mg, 390 μmol) was added in small portions. After complete addition the reaction mixture was heated to 60° C. for three hours. The reaction mixture was cooled to room temperature, water was added and extracted with diethyl ether. The organic layers were combined, dried over sodium sulfate, filtered and the solvents were evaporated under reduced pressure to yield the title compound as a light brown oil (100 mg, 93%).

$^1H$ NMR (DMSO-$D_6$, 300 MHz): (ppm)=7.72 (d, 2H), 7.65 (d, 1H), 7.49 (t, 2H), 7.39 (t, 1H), 7.25 (d, 1H), 4.02 (s, 3H).

b) 7-Methoxy-N-(1-(6-methylpyrimidin-4-yl)piperidin-4-yl)-4-phenylbenzo[d]thiazol-2-amine A solution of 2-chloro-7-methoxy-4-phenylbenzo[d]thiazole (100 mg, 363 μmol), 1-(6-methylpyrimidin-4-yl)piperidin-4-amine dihydrochloride (115 mg, 435 μmol) and Hunig's base (187 mg, 253 μL, 1.45 mmol) in dioxane (2 mL) was heated to 160° C. in a microwave oven for 30 minutes. N-Methyl-2-pyrrolidinone (0.5 mL) was added and the reaction was heated to 200° C. in a microwave oven for 2 hours. Water was added and the reaction was extracted twice with dichloromethane. The combined organic layers were washed with water and with saturated aqueous sodium chloride solution, dried over sodium sulfate and filtered. The solvent was evaporated in vacuo and the residue was purified by column chromatography on silica gel using a gradient from dichloromethane to dichloromethane/methanol 9:1 (v/v) as eluent to yield the title compound as a light brown solid (40 mg, 25%). MS ISP (m/e): 432.4 (100) [(M+H)$^+$].

$^1H$ NMR ($CDCl_3$, 300 MHz): (ppm)=8.51 (s, 1H), 7.77 (d, 2H), 7.43-7.29 (m, 4H), 6.72 (d, 1H), 6.39 (s, 1H), 5.53 (br s, 1H), 4.31 (br d, 2H), 3.98 (s, 3H), 3.79 (m, 1H), 3.10 (m, 2H), 2.36 (s, 3H), 2.20 (br d, 2H), 1.50 (m, 2H).

Example 160

N-(1-(6-Methylpyrimidin-4-yl)piperidin-4-yl)-8-morpholino-[1,2,4]triazolo[1,5-a]pyridin-2-amine

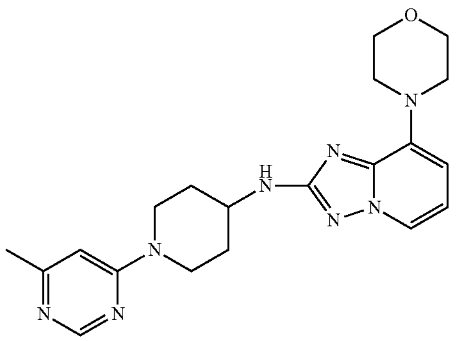 [SMILES: Cc1cc(N2CCC(Nc3nc4c(N5CCOCC5)cccn4n3)CC2)ncn1]

4-(2-Nitropyridin-3-yl)morpholine

To a solution of 3-bromo-2-nitropyridine (207 mg, 1 mmol) in DMSO (2 mL) was added at room temperature under stirring and under an atmosphere of nitrogen morpholine (95.8 mg, 95.8 μL, 1.1 mmol), tetrabutyl ammonium iodide (18.5 mg, 50.0 μmol) and potassium carbonate (152 mg, 1.1 mmol). The reaction was stirred at 80° C. over night. Water was added and the aqueous phase was extracted twice with diethyl ether. The combined organic layers were washed with water and with saturated aqueous sodium chloride solution, dried over sodium sulfate, filtered and the solvent was evaporated under reduced pressure. The title compound was obtained as a yellow oil (57 mg, 27%) after column chromatography on silica gel using a gradient from heptane/ethyl acetate 4:1 to 1:1 (v/v) as eluent.

$^1H$ NMR (DMSO-$D_6$, 300 MHz): δ (ppm)=8.45 (d, 1H), 7.96 (d, 1H), 7.71 (dd, 1H), 3.67 (t, 4H), 3.00 (t, 4H).

b) 3-Morpholinopyridin-2-amine

To a solution of 4-(2-nitropyridin-3-yl)morpholine (155 mg, 741 μmol) in ethyl acetate was added Pd/C 10% (15.5 mg, 146 μmol) and the reaction was hydrogenated under an atmosphere of hydrogen for 3 hours at room temperature. The catalyst was filtered off, washed with ethyl acetate and the solvent was evaporated under reduced pressure. The title compound was obtained as a purple solid (128 mg, 96%).

MS ISP (m/e): 180.1 (100) [(M+H)$^+$].

$^1H$ NMR (DMSO-$D_6$, 300 MHz): δ (ppm)=7.66 (d, 1H), 7.14 (d, 1H), 6.54 (dd, 1H), 5.59 (br s, 2H), 3.75 (t, 4H), 2.79 (t, 4H).

c) 8-Morpholin-4-yl-[1,2,4]triazolo[1,5-a]pyridin-2-ylamine

Prepared in analogy to example 1e-f), starting from 3-morpholinopyridin-2-amine. The crude product was purified by column chromatography on silica gel using ethyl acetate as eluent. The title compound was obtained as a light brown solid (yield: 85% over 2 steps).

MS ISP (m/e): 220.2 (100) [(M+H)$^+$].

$^1H$ NMR (DMSO-$D_6$, 300 MHz): δ (ppm)=8.10 (d, 1H), 6.76 (t, 1H), 6.68 (d, 1H), 5.92 (br s, 2H), 3.77 (t, 4H), 3.38 (t, 4H).

d) N-(1-(6-Methylpyrimidin-4-yl)piperidin-4-yl)-8-morpholino-[1,2,4]triazolo[1,5-a]pyridin-2-amine Prepared in analogy to example 1h, starting from 8-morpholin-4-yl-[1,2,4]triazolo[1,5-a]pyridin-2-ylamine and 1-(6-methylpyrimidin-4-yl)piperidin-4-one (see example 93b). The title compound was obtained as a white solid (yield: 34%) after column chromatography on silica gel using a gradient from methylene chloride to methylene chloride/methanol 19:1 (v/v) as eluent.

MS ISP (m/e): 395.2 (100) [(M+H)$^+$].

$^1H$ NMR (DMSO-$D_6$, 300 MHz): (ppm)=8.36 (s, 1H), 8.18 (d, 1H), 6.77-6.71 (m, 3H), 6.60 (d, 1H), 4.27 (br d, 2H), 3.77 (br s, 5H), 3.39 (br s, 4H), 3.10 (t, 2H), 2.25 (s, 3H), 1.97 (br d, 2H), 1.42 (br q, 2H).

Example 161 tert-Butyl 4-(6-methyl-2-(1-(6-methylpyrimidin-4-yl)piperidin-4-ylamino)-[1,2,4]triazolo[1,5-a]pyridin-8-yl)-5,6-dihydropyridine-1(2H)-carboxylate

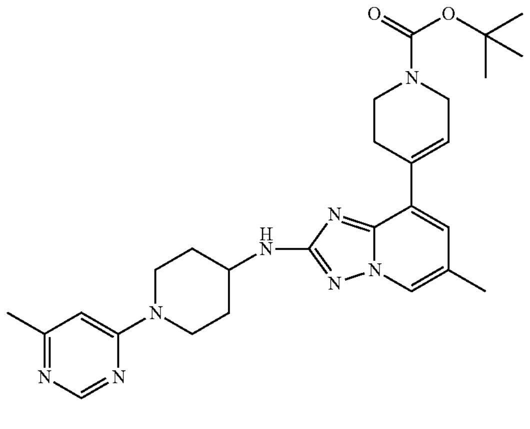 [SMILES: Cc1cc(C2=CCN(C(=O)OC(C)(C)C)CC2)c2nc(NC3CCN(c4cc(C)ncn4)CC3)nn2c1]

a) 8-Bromo-6-methyl-[1,2,4]triazolo[1,5-a]pyridin-2-ylamine

Prepared in analogy to example 1e-f, starting from 2-amino-3-bromo-5-methylpyridine. The crude product was purified by crystallization from hot EtOAc. Most of the product was not soluble and precipitated during work-up. This material was filtered off, washed with water and $CH_2Cl_2$, dried and combined with the other material. The title compound was obtained as a white solid (yield: 73% over two steps). MS ISP (m/e): 227.1/229.2 (100/84) [$(M+H)^+$].

$^1$H NMR (DMSO-$D_6$, 300 MHz): δ (ppm)=8.43 (s, 1H), 7.63 (s, 1H), 6.13 (br s, 2H), 2.27 (s, 3H).

b) tert-Butyl 4-(2-amino-6-methyl-[1,2,4]triazolo[1,5-a]pyridin-8-yl)-5,6-dihydropyridine-1(2H)-carboxylate A mixture of 8-bromo-6-methyl-[1,2,4]triazolo[1,5-a]pyridin-2-ylamine (1.14 g, 5 mmol), tert-butyl 4-(4,4,5,5-tetramethyl-1,3,2-dioxaborolan-2-yl)-5,6-dihydropyridine-1(2H)-carboxylate (2.39 g, 7.5 mmol), dichloro[1,1'-bis(diphenylphosphino)-ferrocene]palladium(II) dichloromethane adduct (204 mg, 250 μmol) and an aqueous solution of $Na_2CO_3$ (2 N, 12.5 mL, 25 mmol) in dioxane (50 mL) was stirred at 110° C. over night. The reaction mixture was diluted with water and extracted twice with EtOAc. The combined organic phases were washed with saturated aqueous sodium chloride solution, dried over sodium sulfate, the solvent was evaporated under reduced pressure and the residue purified by silica gel chromatography using EtOAc as eluent. The title compound was obtained after stirring with diethyl ether, filtration and drying as a light yellow crystalline solid (1.54 g, 93%).

MS ISP (m/e): 330.1 (100) [$(M+H)^+$], 274.1 (87), 230.3 (23), 201.3 (20).

c) tert-Butyl 4-(6-methyl-2-(1-(6-methylpyrimidin-4-yl)piperidin-4-ylamino)-[1,2,4]triazolo[1,5-a]pyridin-8-yl)-5,6-dihydropyridine-1(2H)-carboxylate Prepared in analogy to example 1h, starting from tert-butyl 4-(2-amino-6-methyl-[1,2,4]triazolo[1,5-a]pyridin-8-yl)-5,6-dihydropyridine-1(2H)-carboxylate and 1-(6-methylpyrimidin-4-yl)piperidin-4-one (see example 93b). The title compound was obtained as a light yellow solid (yield: 32%) after column chromatography on silica gel using a gradient from methylene chloride to methylene chloride/methanol 19:1 (v/v) as eluent.

MS ISP (m/e): 505.3 (100) [$(M+H)^+$].

$^1$H NMR (DMSO-$D_6$, 300 MHz): (ppm)=8.37 (s, 2H), 7.26 (br s, 2H), 6.74 (s, 1H), 6.60 (d, 1H), 4.28 (br d, 2H), 4.07 (br s, 2H), 3.79 (br m, 1H), 3.56 (t, 2H), 3.11 (t, 2H), 2.57 (br s, 2H), 2.28 (s, 3H), 2.25 (s, 3H), 1.97 (br d, 2H), 1.43 (br s, 11H).

Example 162

8-Cyclohexenyl-6-methyl-N-(1-(6-methylpyrimidin-4-yl)piperidin-4-yl)-[1,2,4]triazolo[1,5-a]pyridin-2-amine

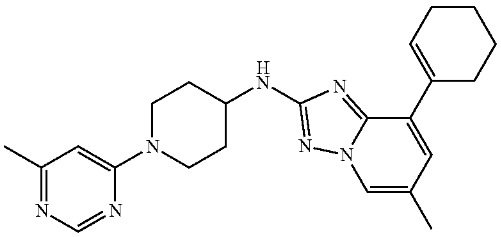 [SMILES: Cc1cc(C2=CCCCC2)c2nc(NC3CCN(c4cc(C)ncn4)CC3)nn2c1]

a) 8-Cyclohexenyl-6-methyl-[1,2,4]triazolo[1,5-a]pyridin-2-amine

Prepared in analogy to example 160b, starting from 8-bromo-6-methyl-[1,2,4]triazolo[1,5-a]pyridin-2-ylamine and tert-butyl 4-(4,4,5,5-tetramethyl-1,3,2-dioxaborolan-2-yl)-5,6-dihydropyridine-1(2H)-carboxylate. The title compound was obtained a light brown solid (yield: 63%) after column chromatography on silica gel using ethyl acetate as eluent.

MS ISP (m/e): 229.3 (100) [$(M+H)^+$].

b) 8-Cyclohexenyl-6-methyl-N-(1-(6-methylpyrimidin-4-yl)piperidin-4-yl)-[1,2,4]triazolo[1,5-a]pyridin-2-amine Prepared in analogy to example 1h, starting from 8-cyclohexenyl-6-methyl-[1,2,4]triazolo[1,5-a]pyridin-2-amine and 1-(6-methylpyrimidin-4-yl)piperidin-4-one (see example 93b). The title compound was obtained as a yellow viscous oil (yield: 17%) after column chromatography on silica gel using a gradient from methylene chloride to methylene chloride/methanol 19:1 (v/v) as eluent. MS ISP (m/e): 404.6 (100) [$(M+H)^+$].

$^1$H NMR ($CDCl_3$, 300 MHz): (ppm)=8.51 (s, 1H), 8.00 (s, 1H), 7.12 (s, 1H), 7.04 (t, 1H), 6.41 (s, 1H), 4.43-4.29 (m, 2H), 3.95 (m, 1H), 3.21 (t, 2H), 2.54 (br s, 2H), 2.39 (s, 3H), 2.32 (s, 3H), 2.28 (m, 2H), 1.83 (m, 2H), 1.45-1.78 (m, 6H).

Example 163 tert-Butyl 3-(6-methyl-2-(1-(6-methylpyrimidin-4-yl)piperidin-4-ylamino)-[1,2,4]triazolo[1,5-a]pyridin-8-yl)benzylcarbamate

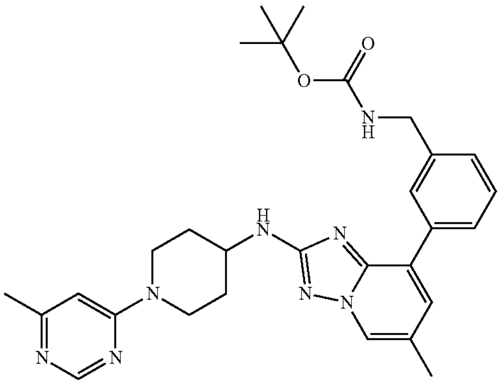 [SMILES: Cc1cc(-c2cccc(CNC(=O)OC(C)(C)C)c2)c2nc(NC3CCN(c4cc(C)ncn4)CC3)nn2c1]

a) [3-(2-Amino-6-methyl-[1,2,4]triazolo[1,5-a]pyridin-8-yl)-benzyl]-carbamic acid tert-butyl ester Prepared in analogy to example 160b, starting from 8-bromo-6-methyl-[1,2,4]triazolo[1,5-a]pyridin-2-amine and 3-((tert-butoxycarbonylamino)methyl)phenylboronic acid. The title compound was obtained as an off-white solid (yield: 99%) after precipitation from diethyl ether. MS ISP (m/e): 354.4 (80) [(M+H)$^+$], 298.4 (100), 237.2 (99).

b) tert-Butyl 3-(2-bromo-6-methyl-[1,2,4]triazolo[1,5-a]pyridin-8-yl)benzylcarbamate A solution of copper(II) bromide (213 mg, 955 μmol) and tert-butyl nitrite (109 mg, 127 μL, 955 μmol) dissolved in acetonitrile (3.2 mL) was heated to 60° C. tert-Butyl 3-(2-amino-6-methyl-[1,2,4]triazolo[1,5-a]pyridin-8-yl)benzylcarbamate (225 mg, 637 μmol) was added in small portions. After complete addition the reaction mixture was heated to 75° C. for two hours. The reaction mixture was cooled to room temperature, water was added and extracted with methylene chloride. The organic layers were combined, washed with saturated sodium chloride solution, dried over sodium sulfate, filtered and the solvents were evaporated under reduced pressure to yield the title compound as a light yellow solid (114 mg, 43%) after column chromatography on silica gel using a gradient from heptane to a mixture of heptane/ethyl acetate 1:1 (v/v) as eluent. MS ISP (m/e): 417.2/419.1 (75/87) [(M+H)$^+$], 361.1/363.0 (94/100).

c) tert-Butyl 3-(6-methyl-2-(1-(6-methylpyrimidin-4-yl)piperidin-4-ylamino)-[1,2,4]triazolo[1,5-a]pyridin-8-yl)benzylcarbamate A solution of 1-(6-methylpyrimidin-4-yl)piperidin-4-amine (52.5 mg, 273 μmol), tert-butyl 3-(2-bromo-6-methyl-[1,2,4]triazolo[1,5-a]pyridin-8-yl)benzylcarbamate (114 mg, 273 mmol), 4,5-bis(diphenylphosphino)-9,9-dimethylxanthene (12.6 mg, 21.9 μmol), tris(dibenzylideneacetone)dipalladium(0) chloroform adduct (11.3 mg, 10.9 μmol) and sodium phenoxide (50.1 mg, 410 μmol) in dioxane (3 mL) was degassed three times and reacted at 140° C. under an atmosphere of nitrogen in a microwave oven for 1 hour. The title compound was obtained a light yellow solid (46 mg, 32%) after column chromatography on silica gel using a gradient from methylenechloride to a mixture of methylenechlorid/methanol 19:1 (v/v) as eluent.

MS ISP (m/e): 529.3 (100) [(M+H)$^+$].

$^1$H NMR ($CDCl_3$, 300 MHz): (ppm)=8.51 (s, 1H), 8.13 (s, 1H), 7.85 (d, 1H), 7.82 (s, 1H), 7.42 (t, 1H), 7.36 (s, 1H), 7.33 (d, 1H), 6.41 (s, 1H), 4.92 (br s, 1H), 4.47 (d, 1H), 4.40-4.25 (m, 4H), 3.95 (m, 1H), 3.19 (t, 2H), 2.39 (s, 3H), 2.37 (s, 3H), 2.25 (br d, 2H), 1.70-1.46 (m, 2H), 1.46 (s, 9H).

Example 164

Ethyl 3-(6-methyl-2-(1-(6-methylpyrimidin-4-yl)piperidin-4-ylamino)-[1,2,4]triazolo[1,5-a]pyridin-8-yl)benzylcarbamate

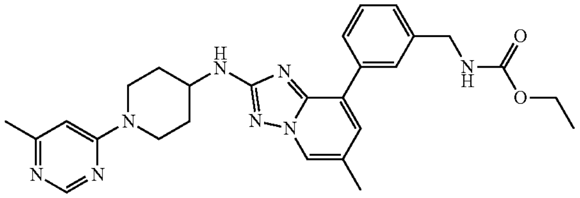 [SMILES: CCOC(=O)NCc1cccc(-c2cc(C)cn3nc(NC4CCN(c5cc(C)ncn5)CC4)nc23)c1]

a) 8-(3-(Aminomethyl)phenyl)-6-methyl-N-(1-(6-methylpyrimidin-4-yl)piperidin-4-yl)-[1,2,4]triazolo[1,5-a]pyridin-2-amine dihydrochloride To a solution of tert-butyl 3-(6-methyl-2-(1-(6-methylpyrimidin-4-yl)piperidin-4-ylamino)-[1,2,4]triazolo[1,5-a]pyridin-8-yl)benzylcarbamate (46 mg, 87.0 μmol) in methylene chloride (1 mL) was added 2 M solution of HCl in Ether (500 μL). The suspension was stirred at room temperature over night. The solvent was decanted and the residue was digerated with diethyl ether three times. The title compound was dried under reduced pressure and was obtained as a yellow solid (39 mg, 89%). MS ISP (m/e): 429.3 (100) [(M+H)$^+$], 412.4 (57).

b) Ethyl 3-(6-methyl-2-(1-(6-methylpyrimidin-4-yl)piperidin-4-ylamino)-[1,2,4]triazolo[1,5-a]pyridin-8-yl)benzylcarbamate To a suspension of 8-(3-(aminomethyl)phenyl)-6-methyl-N-(1-(6-methylpyrimidin-4-yl)piperidin-4-yl)-[1,2,4]triazolo[1,5-a]pyridin-2-amine dihydrochloride (37 mg, 73.8 μmol) in dichloromethane (0.75 mL) was added N,N-diisopropylethylamine (38.1 mg, 51.5 μL, 295 mmol). To the resulting yellow solution was added ethyl chloroformate (8.99 mg, 7.89 μL, 81.2 mmol) and the reaction was stirred at room temperature over night. The title compound was obtained as a light yellow solid (35 mg, 95%) after column chromatography on silica gel using a gradient from methylene chloride to a mixture of methylene chloride/methanol 19:1 (v/v) as eluent. MS ISP (m/e): 501.2 (100) [(M+H)$^+$]. $^1$H NMR ($CDCl_3$, 300 MHz): (ppm)=8.51 (s, 1H), 8.13 (s, 1H), 7.83 (br s, 2H), 7.44 (t, 1H), 7.36 (s, 1H), 7.33 (d, 1H), 6.41 (s, 1H), 5.08 (br m, 1H), 4.53 (br d, 1H), 4.44 (d, 2H), 4.32 (br d, 2H), 4.15 (q, 2H), 3.96 (m, 1H), 3.69 (m, 1H), 3.20 (t, 2H), 3.10 (m, 1H), 2.40 (s, 3H), 2.38 (s, 3H), 2.22 (br d, 2H), 1.25 (t, 3H).

Example 165

Ethyl 4-(6-methyl-2-(1-(6-methylpyrimidin-4-yl)piperidin-4-ylamino)-[1,2,4]triazolo[1,5-a]pyridin-8-yl)-5,6-dihydropyridine-1(2H)-carboxylate

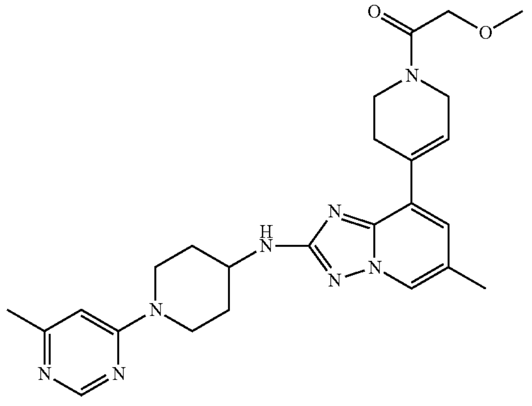

a) 6-Methyl-N-(1-(6-methylpyrimidin-4-yl)piperidin-4-yl)-8-(1,2,3,6-tetrahydropyridin-4-yl)-[1,2,4]triazolo[1,5-a]pyridin-2-amine Prepared in analogy to example 164a, starting from tert-butyl 4-(6-methyl-2-(1-(6-methylpyrimidin-4-yl)piperidin-4-ylamino)-[1,2,4]triazolo[1,5-a]pyridin-8-yl)-5,6-dihydropyridine-1(2H)-carboxylate. Since the product did not precipitated out from the reaction it was diluted with water and extracted twice with methylene chloride. The aqueous layer was set basic with 1 N aqueous sodium hydroxide solution and extracted 4 times with methylene chloride. The combined organic layers were dried over sodium sulfate, filtered and the solvent was evaporated to yield the title compound as a yellow solid (194 mg, 77%).

MS ISP (m/e): 405.5 (53) [(M+H)$^+$], 376.4 (100).

b) Ethyl 4-(6-methyl-2-(1-(6-methylpyrimidin-4-yl)piperidin-4-ylamino)-[1,2,4]triazolo[1,5-a]pyridin-8-yl)-5,6-dihydropyridine-1(2H)-carboxylate Prepared in analogy to example 164b, starting from 6-methyl-N-(1-(6-methylpyrimidin-4-yl)piperidin-4-yl)-8-(1,2,3,6-tetrahydropyridin-4-yl)-[1,2,4]triazolo[1,5-a]pyridin-2-amine and ethyl chloroformate. The title compound was obtained as a light yellow solid (yield: 36%) after column chromatography on silica gel using a gradient from methylene chloride to a mixture of methylene chloride/methanol 19:1 (v/v) as eluent.

MS ISP (m/e): 477.3 (100) [(M+H)$^+$].

$^1$H NMR ($CDCl_3$, 300 MHz): (ppm)=8.51 (s, 1H), 8.04 (s, 1H), 7.18 (br s, 1H), 7.11 (s, 1H), 6.41 (s, 1H), 4.41 (br d, 1H), 4.22-4.15 (m, 4H), 3.96 (m, 1H), 3.73 (t, 1H), 3.17 (t, 2H), 2.64 (br s, 2H), 2.36 (s, 3H), 2.34 (s, 3H), 2.21 (br d, 2H), 1.50 (m, 2H), 1.31-1.25 (m, 5H).

Example 166

Isopropyl 4-(6-methyl-2-(1-(6-methylpyrimidin-4-yl)piperidin-4-ylamino)-[1,2,4]triazolo[1,5-a]pyridin-8-yl)-5,6-dihydropyridine-1(2H)-carboxylate

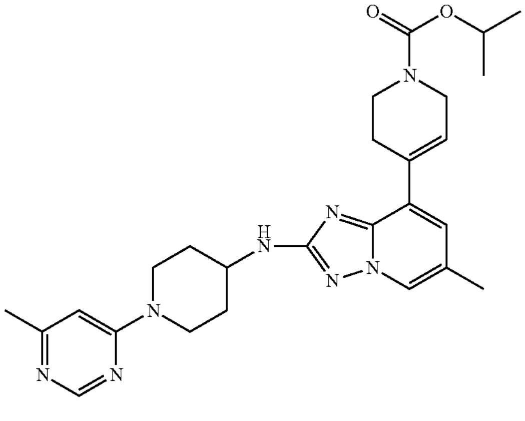 [SMILES: Cc1cc(C2=CCN(C(=O)OC(C)C)CC2)c2nc(NC3CCN(c4cc(C)ncn4)CC3)nn2c1]

Prepared in analogy to example 164b, starting from 6-methyl-N-(1-(6-methylpyrimidin-4-yl)piperidin-4-yl)-8-(1,2,3,6-tetrahydropyridin-4-yl)-[1,2,4]triazolo[1,5-a]pyridin-2-amine and isopropyl chloroformate. The title compound was obtained as a colorless solid (yield: 32%) after column chromatography on silica gel using a gradient from methylene chloride to a mixture of methylene chloride/methanol 19:1 (v/v) as eluent. MS ISP (m/e): 491.3 (100) [(M+H)$^+$]. $^1$H NMR ($CDCl_3$, 300 MHz): (ppm)=8.51 (s, 1H), 8.04 (s, 1H), 7.16 (br s, 1H), 7.11 (s, 1H), 6.41 (s, 1H), 4.97 (sept, 1H), 4.39 (d, 1H), 4.31 (br d, 2H), 4.21 (br s, 2H), 3.96 (m, 1H), 3.72 (t, 1H), 3.18 (t, 2H), 2.63 (br s, 2H), 2.37 (s, 3H), 2.34 (s, 3H), 2.21 (br d, 2H), 1.53 (m, 2H), 1.26 (d, 6H).

Example 167

N-(1-(6-Methylpyrimidin-4-yl)piperidin-4-yl)-7-phenyl-6,7-dihydro-5H-[1,2,4]triazolo[5,1-b][1,3]oxazin-2-amine

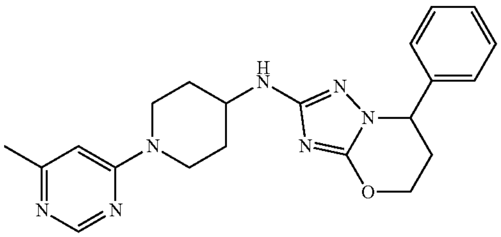 [SMILES: Cc1cc(N2CCC(Nc3nc4n(n3)C(c3ccccc3)CCO4)CC2)ncn1]

(3-Bromo-3-phenylpropoxy)(tert-butyl)dimethylsilane

A suspension of tert-butyldimethyl(3-phenylpropoxy)silane (2.22 g, 8.86 mmol), N-bromosuccinimide (1.58 g, 8.86 mmol) and benzoyl peroxide (66.4 mg, 266 μmol) in carbon tetrachloride (17.8 mL) was heated to reflux for 3 hours. The reaction was filtered, the precipitate washed with carbon tetrachloride and the solvent was evaporated. Water was added and the reaction was extracted twice with diethyl ether. The combined organic layers were washed with saturated aqueous sodium chloride solution, dried over sodium sulfate, filtered and the solvent was evaporated under reduced pressure. The title compound was obtained as a light yellow oil (1.63 g, 55%) after column chromatography on silica gel using heptane/ethyl acetate 19:1 (v/v) as eluent. $^1$H NMR ($CDCl_3$, 300 MHz): δ (ppm)=7.42-7.26 (m, 5H), 5.42 (dd, 1H), 3.76 (m, 1H), 3.68 (m, 1H), 2.48 (m, 1H), 2.28 (m, 1H), 0.90 (s, 9H), 0.06 (s, 3H), 0.03 (s, 3H).

b) 5-Bromo-1-(3-(tert-butyldimethylsilyloxy)-1-phenylpropyl)-3-nitro-1H-1,2,4-triazole A solution of (3-bromo-3-phenylpropoxy)(tert-butyl)dimethylsilane (934 mg, 2.84 mmol) in acetonitrile (27 mL) was stirred at room temperature under an atmosphere of nitrogen with sodium iodide (425 mg, 2.84 mmol) for 15 minutes. Potassium carbonate (560 mg, 4.05 mmol) was added and the reaction was heated 60° C. At this temperature 5-bromo-3-nitro-1H-1,2,4-triazole (532 mg, 2.7 mmol) dissolved in acetonitrile (5.3 mL) was added within 30 minutes. The reaction was stirred for 2 hours at 85° C. Water was added and the aqueous phase was extracted twice with ethyl acetate. The combined organic layers were washed with saturated aqueous sodium chloride solution, dried over sodium sulfate, filtered and the solvent was evaporated under reduced pressure. The title compound was obtained as a colorless viscous oil (510 mg, 42%) after column chromatography on silica gel using a gradient from heptane to heptane/ethyl acetate 4:1 (v/v) as eluent. $^1$H NMR ($CDCl_3$, 300 MHz): δ (ppm)=7.42-7.36 (m, 5H), 5.91 (dd, 1H), 3.58 (m, 1H), 3.48 (m, 1H), 2.72 (m, 1H), 2.39 (m, 1H), 0.91 (s, 9H), 0.00 (s, 6H).

c) 2-Nitro-7-phenyl-6,7-dihydro-5H-[1,2,4]triazolo[5,1-b][1,3]oxazine

To a solution of 5-bromo-1-(3-(tert-butyldimethylsilyloxy)-1-phenylpropyl)-3-nitro-1H-1,2,4-triazole (510 mg, 1.16 mmol) in tetrahydrofurane (11.6 mL) was added under an atmosphere of nitrogen at room temperature 1 M tetrabutyl ammonium fluoride solution in tetrahydrofurane (3.47 mL, 3.47 mmol). The yellow solution was stirred at room temperature over night. Water was added and the aqueous phase was extracted twice with ethyl acetate. The combined organic layers were washed with saturated aqueous sodium bicarbonate solution and brine, dried over sodium sulfate, filtered and the solvent was evaporated under reduced pressure. The title compound was obtained as a light yellow solid (174 mg, 61%) after column chromatography on silica gel using a gradient from heptane/ethyl acetate 4:1 to 1:1 (v/v) as eluent. MS ISP (m/e): 247.2 (100) [$(M+H)^+$], 264.1 (36). $^1$H NMR ($CDCl_3$, 300 MHz): δ (ppm)=7.42-7.38 (m, 3H), 7.09 (d, 2H), 5.61 (t, 1H), 4.56 (m, 2H), 2.77 (m, 1H), 2.42 (m, 1H).

d) 7-Phenyl-6,7-dihydro-5H-[1,2,4]triazolo[5,1-b][1,3]oxazin-2-ylamine

To a solution of 2-nitro-7-phenyl-6,7-dihydro-5H-[1,2,4]triazolo[5,1-b][1,3]oxazine (174 mg, 707 μmol) in ethyl acetate (7 mL) was added 10% Pd on carbon (17.4 mg, 164 μmol). The reaction was hydrogenated at room temperature under an atmosphere of hydrogen over night. The catalyst was filtered off and washed with ethyl acetate. The title compound was obtained as a white solid (143.3 mg, 94%) after stirring with diethyl ether.

MS ISP (m/e): 217.3 (100) [$(M+H)^+$].

$^1$H NMR (DMSO-$D_6$, 300 MHz): δ (ppm)=7.39-7.29 (m, 3H), 7.16 (d, 2H), 5.22 (t, 1H), 5.15 (br s, 2H), 4.35 (m, 1H), 4.21 (m, 1H), 2.50 (m, 1H), 2.15 (m, 1H).

e) N-(1-(6-Methylpyrimidin-4-yl)piperidin-4-yl)-7-phenyl-6,7-dihydro-5H-[1,2,4]triazolo[5,1-b][1,3]oxazin-2-amine Prepared in analogy to example 1h, starting from 7-phenyl-6,7-dihydro-5H-[1,2,4]triazolo[5,1-b][1,3]oxazin-2-amine and 1-(6-methylpyrimidin-4-yl)piperidin-4-one (see example 93b). The title compound was obtained as a light yellow solid (yield: 17%) after column chromatography on silica gel using a gradient from methylene chloride to methylene chloride/methanol 19:1 (v/v) as eluent. MS ISP (m/e): 392.3 (100) [$(M+H)^+$].

$^1$H NMR ($CDCl_3$, 300 MHz): (ppm)=8.49 (s, 1H), 7.38-7.31 (m, 3H), 7.12 (d, 2H), 6.37 (s, 1H), 4.44-4.20 (m, 4H), 3.97 (br d, 1H), 4.25 (m, 1H), 3.09 (m, 1H), 2.65 (m, 1H), 2.34 (s, 3H), 2.25-2.10 (m, 3H), 1.41 (m, 2H).

Example 168

8-(3,6-dihydro-2H-pyran-4-yl)-6-methyl-N-(1-(6-methylpyrimidin-4-yl)piperidin-4-yl)-[1,2,4]triazolo[1,5-a]pyridin-2-amine

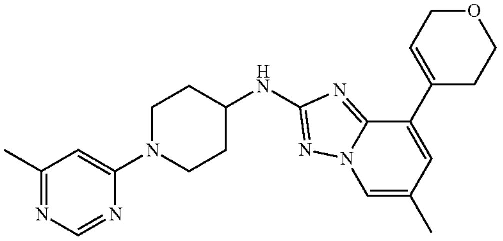 [SMILES: Cc1cc(C2=CCOCC2)c2nc(NC3CCN(c4cc(C)ncn4)CC3)nn2c1]

a) 8-(3,6-Dihydro-2H-pyran-4-yl)-6-methyl-[1,2,4]triazolo[1,5-a]pyridin-2-amine

Prepared in analogy to example 160b, starting from 8-bromo-6-methyl-[1,2,4]triazolo[1,5-a]pyridin-2-ylamine and 2-(3,6-dihydro-2H-pyran-4-yl)-4,4,5,5-tetramethyl-1,3,2-dioxaborolane. The title compound was obtained a light brown solid (yield: 55%) after column chromatography on silica gel using ethyl acetate as eluent.

MS ISP (m/e): 231.2 (50) [$(M+H)^+$], 201.2 (100) [$(M-CH_2CO+H)^+$].

b) 8-(3,6-Dihydro-2H-pyran-4-yl)-6-methyl-N-(1-(6-methylpyrimidin-4-yl)piperidin-4-yl)-[1,2,4]triazolo[1,5-a]pyridin-2-amine Prepared in analogy to example 1h, starting from 8-(3,6-dihydro-2H-pyran-4-yl)-6-methyl-[1,2,4]triazolo[1,5-a]pyridin-2-amine and 1-(6-methylpyrimidin-4-yl)piperidin-4-one (see example 93b). The title compound was obtained as a yellow oil (yield: 5%) after column chromatography on silica gel using a gradient from methylene chloride to methylene chloride/methanol 19:1 (v/v) as eluent. MS ISP (m/e): 406.5 (100) [$(M+H)^+$].

$^1$H NMR ($CDCl_3$, 300 MHz): δ (ppm)=8.51 (s, 1H), 8.04 (s, 1H), 7.34 (s, 1H), 7.13 (s, 1H), 6.41 (s, 1H), 4.42 (br s, 2H), 4.34 (br d, 2H), 3.98 (t, 2H), 3.96 (m, 1H), 3.17 (t, 2H), 2.61 (br s, 2H), 2.36 (s, 3H), 2.34 (s, 3H), 2.21 (br d, 2H), 1.52 (br d, 2H).

Example 169

N-(1-(2-Chloropyridin-4-yl)piperidin-4-yl)-8-(3,4-difluorophenyl)-[1,2,4]triazolo[1,5-a]pyridin-2-amine

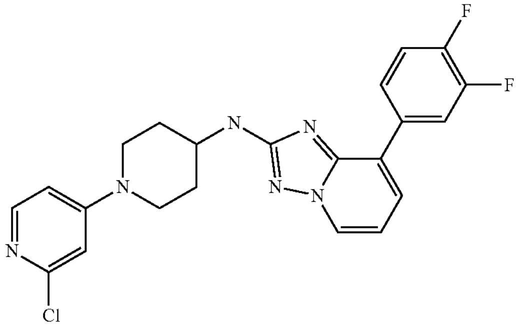 [SMILES: Fc1ccc(-c2cccn3nc(NC4CCN(c5ccnc(Cl)c5)CC4)nc23)cc1F]

a) tert-Butyl 1-(2-chloropyridin-4-yl)piperidin-4-ylcarbamate

To a mixture of 2-chloro-4-fluoropyridine (1.00 g, 7.60 mmol) and Boc-4-aminopiperidine (1.98 g, 9.09 mmol) in NMP (10 mL) was added DIPEA (1.86 mL, 10.6 mmol). Argon was bubbled through the cloudy solution for 5 minutes before the reaction mixture was heated in the microwave for 2×30 minutes to 150° C. The mixture was then poured into water and extracted with ethyl acetate. The combined organic phases were dried over sodium sulfate, filtered and evaporated. Purification by chromatography (silica gel, 50 g, 0 to 50% ethyl acetate in heptane) afforded the title compound (1.47 g, 62%) as a white solid.

MS ISP (m/e): 312.1 [$(M+H)^+$].

b) 1-(2-Chloropyridin-4-yl)piperidin-4-amine dihydrochloride

To a solution of tert-butyl 1-(2-chloropyridin-4-yl)piperidin-4-ylcarbamate (1.00 g, 3.21 mmol) in dichloromethane (16 mL) was added HCl (2 M in diethylether, 8.02 mL, 16.0 mmol) and the reaction mixture was stirred at room temperature over night for 18 hours. The mixture was then filtered off and the white precipitate washed with dichloromethane and diethylether and dried to afford the title compound (913 mg, 99%) as a white solid. MS ISP (m/e): 212.1/214.1 [$(M+H)^+$].

c) N-(1-(2-Chloropyridin-4-yl)piperidin-4-yl)-8-(3,4-difluorophenyl)-[1,2,4]triazolo[1,5-a]pyridin-2-amine A suspension of 1-(2-chloropyridin-4-yl)piperidin-4-amine dihydrochloride (142 mg, 0.50 mmol) in dichloromethane was washed with 2 N NaOH, the aqueous layer extracted with dichloromethane, the combined organic layers dried over sodium sulfate and evaporated. The "free-base" residue was dissolved in dioxane (4 mL), 2-bromo-8-(3,4-difluorophenyl)-[1,2,4]triazolo[1,5-a]pyridine (prepared in analogy to example 66a-d) (170 mg, 0.55 mmol), 4,5-bis(diphenylphosphino)-9,9-dimethylxanthene (23 mg, 8 mol %), tris(dibenzylideneacetone)dipalladium chloroform complex (21 mg, 4 mol %) and sodium phenoxide (87 mg, 0.75 mmol) were added, Ar was bubbled through the reaction mixture for 5 minutes and then irradiated at 130° C. in the microwave for 1 hour. The crude material was purified by flash chromatography (silica-$NH_2$, 20 g, 0 to 100% ethyl acetate in heptane). The title compound was obtained as a yellow solid (103 mg, 47%).

MS ISP (m/e): 232.1 [$(M+H)^+$].

Example 170

8-(3,4-Difluorophenyl)-N-(1-(6-methoxypyrimidin-4-yl)piperidin-4-yl)-[1,2,4]triazolo[1,5-a]pyridin-2-amine

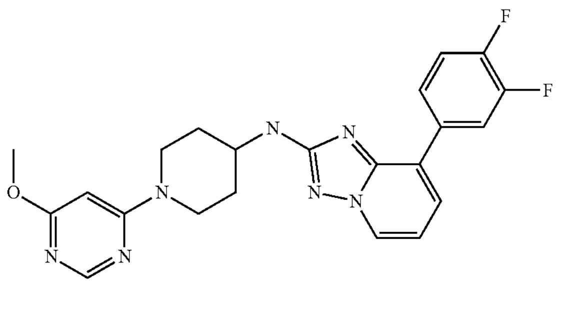 [SMILES: COc1cc(N2CCC(Nc3nc4c(-c5ccc(F)c(F)c5)cccn4n3)CC2)ncn1]

Prepared in analogy to example 169c, employing 1-(6-methoxypyrimidin-4-yl)piperidin-4-amine (122 mg, 0.43 mmol) instead of 1-(2-chloropyridin-4-yl)piperidin-4-amine.

The title compound was obtained as a light yellow foam (90 mg, 47%).

MS ISP (m/e): 438.3 [$(M+H)^+$].

Example 171

8-(2-Chloro-4-fluorophenyl)-N-(1-(6-methoxypyrimidin-4-yl)piperidin-4-yl)-[1,2,4]triazolo[1,5-a]pyridin-2-amine

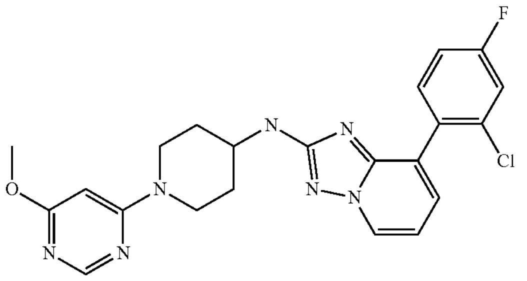 [SMILES: COc1cc(N2CCC(Nc3nc4c(-c5ccc(F)cc5Cl)cccn4n3)CC2)ncn1]

Prepared in analogy to example 170, employing 2-bromo-8-(2-chloro-4-fluorophenyl)-[1,2,4]triazolo[1,5-a]pyridine (180 mg, 0.55 mmol) instead of 2-bromo-8-(3,4-difluorophenyl)-[1,2,4]triazolo[1,5-a]pyridine. The title compound was obtained as a light yellow foam (71 mg, 31%). MS ISP (m/e): 454.2 [$(M+H)^+$].

Example 172

8-(2-Chloro-4-fluorophenyl)-N-(1-(6-ethoxypyrimidin-4-yl)piperidin-4-yl)-[1,2,4]triazolo[1,5-a]pyridin-2-amine

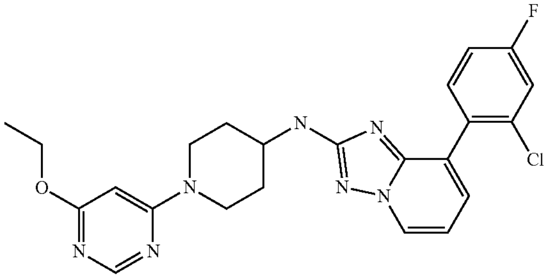 [SMILES: CCOc1cc(N2CCC(Nc3nc4c(-c5ccc(F)cc5Cl)cccn4n3)CC2)ncn1]

Prepared in analogy to example 171, employing 1-(6-ethoxypyrimidin-4-yl)piperidin-4-amine (100 mg, 0.34 mmol) instead of 1-(6-methoxypyrimidin-4-yl)piperidin-4-amine.

The title compound was obtained as a light yellow foam (78 mg, 49%).

MS ISP (m/e): 468.3/470.3 [$(M+H)^+$].

Example 173

8-(3,4-Difluorophenyl)-N-(1-(6-ethoxypyrimidin-4-yl)piperidin-4-yl)-[1,2,4]triazolo[1,5-a]pyridin-2-amine

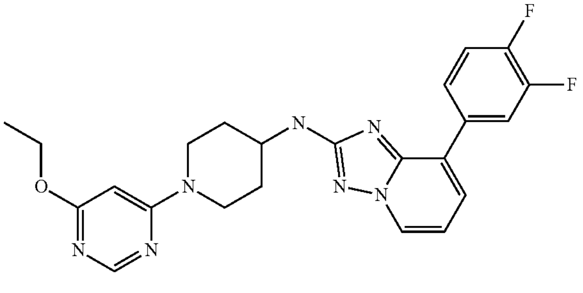 [SMILES: CCOc1cc(N2CCC(Nc3nc4c(-c5ccc(F)c(F)c5)cccn4n3)CC2)ncn1]

Prepared in analogy to example 172, employing 2-bromo-8-(3,4-difluorophenyl)-[1,2,4]triazolo[1,5-a]pyridine (116 mg, 0.37 mmol)) instead of 2-bromo-8-(2-chloro-4-fluorophenyl)-[1,2,4]triazolo[1,5-a]pyridine.

The title compound was obtained as a light yellow foam (71 mg, 46%).

MS ISP (m/e): 452.2 [(M+H)$^+$].

Example 174

8-(3,4-Difluorophenyl)-N-(1-(6-(trifluoromethyl)pyrimidin-4-yl)piperidin-4-yl)-[1,2,4]triazolo[1,5-a]pyridin-2-amine

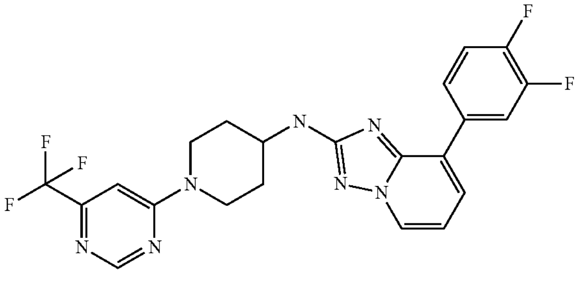 [SMILES: Fc1ccc(-c2cccn3nc(NC4CCN(c5cc(C(F)(F)F)ncn5)CC4)nc23)cc1F]

a) tert-Butyl 1-(6-(trifluoromethyl)pyrimidin-4-yl)piperidin-4-ylcarbamate

To a mixture of 4-chloro-6-(trifluoromethyl)pyrimidine (0.82 g, 4.49 mmol) and Boc-4-aminopiperidine (1.17 g, 5.84 mmol) in NMP (5.7 mL) was added DIPEA (1.10 mL, 6.29 mmol) and after 30 minutes the mixture was poured into water and extracted with ethyl acetate. The combined organic phases were dried over sodium sulfate, filtered and evaporated. Purification by chromatography (silica gel, 70 g, 0 to 50% ethyl acetate in heptane) afforded the title compound (1.43 g, 92%) as a white solid. MS ISP (m/e): 347.2 [(M+H)$^+$].

b) 1-(6-(Trifluoromethyl)pyrimidin-4-yl)piperidin-4-amine dihydrochloride

To a solution of tert-butyl 1-(6-(trifluoromethyl)pyrimidin-4-yl)piperidin-4-ylcarbamate (1.42 g, 4.1 mmol) in dichloromethane (20 mL) was added HCl (2 M in diethylether, 10.2 mL, 20.5 mmol) and the reaction mixture was stirred at room temperature for 18 hours. The mixture was filtered and the white precipitate was washed with dichloromethane and diethylether and dried to afford the title compound (1.27 g, 97%) as a white solid.

MS ISP (m/e): 247.2 [(M+H)$^+$].

c) 8-(3,4-Difluorophenyl)-N-(1-(6-(trifluoromethyl)pyrimidin-4-yl)piperidin-4-yl)-[1,2,4]triazolo[1,5-a]pyridin-2-amine Prepared in analogy to example 173, employing 1-(6-(trifluoromethyl)pyrimidin-4-yl)piperidin-4-amine dihydrochloride (116 mg, 0.37 mmol)) instead of 1-(6-ethoxypyrimidin-4-yl)piperidin-4-amine. The title compound was obtained as an off white foam (93 mg, 49%).

MS ISP (m/e): 476.2 [(M+H)$^+$].

Example 175

8-(2-Chloro-4-fluorophenyl)-6-methyl-N-(1-(6-(trifluoromethyl)pyrimidin-4-yl)piperidin-4-yl)-[1,2,4]triazolo[1,5-a]pyridin-2-amine

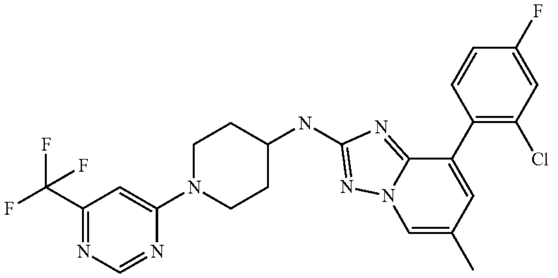 [SMILES: Cc1cc(-c2ccc(F)cc2Cl)c2nc(NC3CCN(c4cc(C(F)(F)F)ncn4)CC3)nn2c1]

Prepared in analogy to example 174c, employing 2-bromo-8-(2-chloro-4-fluorophenyl)-6-methyl-[1,2,4]triazolo[1,5-a]pyridine (150 mg, 0.44 mmol) instead of 2-bromo-8-(3,4-difluorophenyl)-[1,2,4]triazolo[1,5-a]pyridine. The title compound was obtained as an off white foam (103 mg, 51%).

MS ISP (m/e): 506.2/508.3 [(M+H)$^+$].

Example 176

8-(2-Chloro-4-fluorophenyl)-N-(1-(6-(trifluoromethyl)pyrimidin-4-yl)piperidin-4-yl)-[1,2,4]triazolo[1,5-a]pyridin-2-amine

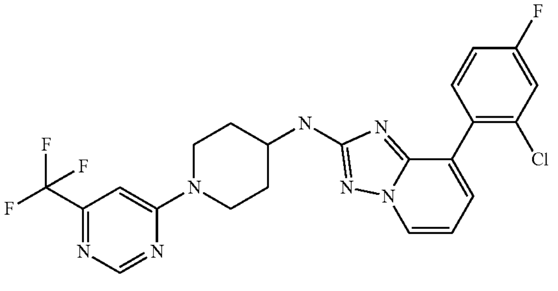 [SMILES: Fc1ccc(-c2cccn3nc(NC4CCN(c5cc(C(F)(F)F)ncn5)CC4)nc23)c(Cl)c1]

Prepared in analogy to example 174c, employing 2-bromo-8-(2-chloro-4-fluorophenyl)-[1,2,4]triazolo[1,5-a]pyridine (144 mg, 0.44 mmol) instead of 2-bromo-8-(3,4-difluorophenyl)-[1,2,4]triazolo[1,5-a]pyridine. The title compound was obtained as an off white foam (88 mg, 45%). MS ISP (m/e): m/e=492.2/494.2 [$(M+H)^+$].

Example 177

8-(3,4-Difluorophenyl)-6-methyl-N-(1-(6-(trifluoromethyl)pyrimidin-4-yl)piperidin-4-yl)-[1,2,4]triazolo[1,5-a]pyridin-2-amine

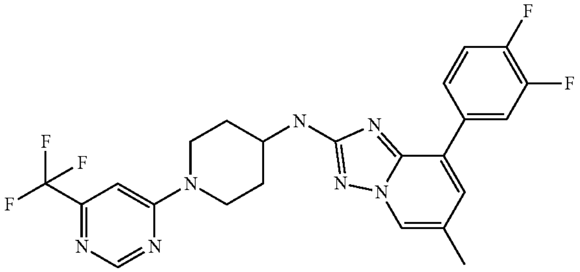 [SMILES: Cc1cc(-c2ccc(F)c(F)c2)c2nc(NC3CCN(c4cc(C(F)(F)F)ncn4)CC3)nn2c1]

Prepared in analogy to example 174c, employing 2-bromo-8-(3,4-difluorophenyl)-6-methyl-[1,2,4]triazolo[1,5-a]pyridine (143 mg, 0.44 mmol) instead of 2-bromo-8-(3,4-difluorophenyl)-[1,2,4]triazolo[1,5-a]pyridine. The title compound was obtained as a light yellow foam (89 mg, 46%). MS ISP (m/e): m/e=490.2 [$(M+H)^+$].

Example 178

8-(3,4-Difluorophenyl)-6-fluoro-N-((6-(trifluoromethyl)pyrimidin-4-yl)piperidin-4-yl)-[1,2,4]triazolo[1,5-a]pyridin-2-amine

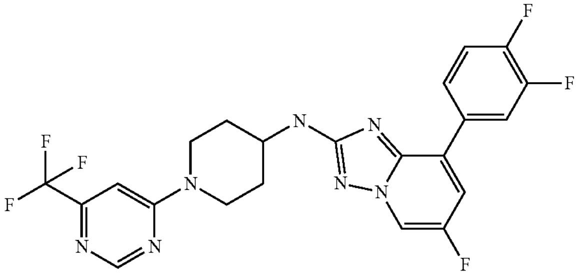 [SMILES: Fc1cc(-c2ccc(F)c(F)c2)c2nc(NC3CCN(c4cc(C(F)(F)F)ncn4)CC3)nn2c1]

Prepared in analogy to example 174c, employing 2-bromo-8-(3,4-difluorophenyl)-6-fluoro-[1,2,4]triazolo[1,5-a]pyridine (144 mg, 0.44 mmol) instead of 2-bromo-8-(3,4-difluorophenyl)-[1,2,4]triazolo[1,5-a]pyridine. The title compound was obtained as an off white foam (50 mg, 25%). MS ISP (m/e): m/e=494.2 [$(M+H)^+$].

Example 179

6-Chloro-8-(3,4-difluorophenyl)-N-(1-(6-(trifluoromethyl)pyrimidin-4-yl)piperidin-4-yl)-[1,2,4]triazolo[1,5-a]pyridin-2-amine

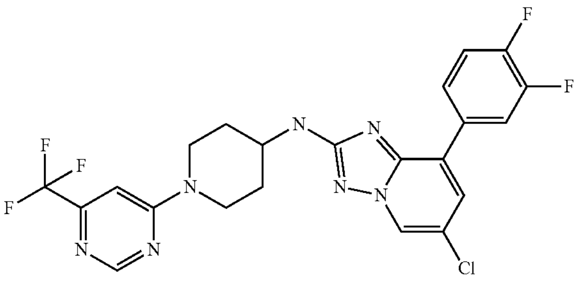 [SMILES: Fc1ccc(-c2cc(Cl)cn3nc(NC4CCN(c5cc(C(F)(F)F)ncn5)CC4)nc23)cc1F]

Prepared in analogy to example 174c, employing 2-bromo-6-chloro-8-(3,4-difluorophenyl)-[1,2,4]triazolo[1,5-a]pyridine (152 mg, 0.44 mmol) instead of 2-bromo-8-(3,4-difluorophenyl)-[1,2,4]triazolo[1,5-a]pyridine.

The title compound was obtained as an off white foam (63 mg, 31%).

MS ISP (m/e): 510.3/512.3 [$(M+H)^+$].

Example 180

8-(3,4-Difluorophenyl)-N-(1-(6-methylpyridazin-4-yl)piperidin-4-yl)-[1,2,4]triazolo[1,5-a]pyridin-2-amine

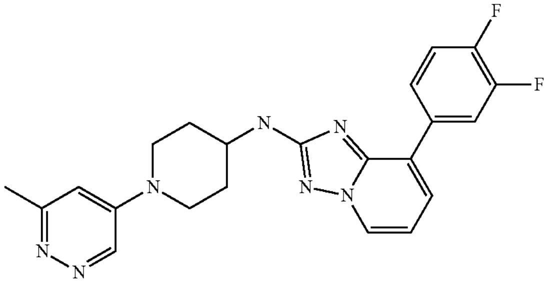 [SMILES: Cc1cc(N2CCC(Nc3nc4c(-c5ccc(F)c(F)c5)cccn4n3)CC2)cnn1]

a) tert-Butyl 1-(6-methylpyridazin-4-yl)piperidin-4-ylcarbamate

To a mixture of 5-chloro-3-methylpyridazine (1.3 g, 10.1 mmol) and Boc-4-aminopiperidine (2.63 g, 13.1 mmol) in NMP (13 mL) was added DIPEA (2.47 mL, 14.2 mmol). Argon was bubbled through the cloudy solution for 5 minutes before the reaction mixture was heated in the microwave for 30 minutes to 150° C. The mixture was then poured into water and extracted with ethyl acetate. The combined organic phases were dried over sodium sulfate, filtered and evaporated. Purification by chromatography (silica gel, 50 g, 50 to 100% ethyl acetate in heptane) afforded the title compound (2.18 g, 74%) as an off white solid.

MS ISP (m/e): 293.2 [$(M+H)^+$].

b) 1-(6-Methylpyridazin-4-yl)piperidin-4-amine dihydrochloride

To a solution tert-butyl 1-(6-methylpyridazin-4-yl)piperidin-4-ylcarbamate (2.14 g, 7.32 mmol) in dichloromethane (36 mL) was added HCl (2 M in diethylether, 18.3 mL, 36.6 mmol) and the reaction mixture was stirred at room temperature for 24 hours. The mixture was then filtered and the white precipitate was washed with dichloromethane and diethylether and dried to afford the title compound (2.35 g, 82%) as a white solid.

MS ISP (m/e): 193.2 [$(M+H)^+$].

c) 8-(3,4-Difluorophenyl)-N-(1-(6-methylpyridazin-4-yl)piperidin-4-yl)-[1,2,4]triazolo[1,5-a]pyridin-2-amine Prepared in analogy to example 173, employing 1-(6-methylpyridazin-4-yl)piperidin-4-amine dihydrochloride (14 mg, 0.053 mmol)) instead of 1-(6-ethoxypyrimidin-4-yl)piperidin-4-amine. The title compound was obtained as a yellow foam (10 mg, 45%). MS ISP (m/e): 422.3 [$(M+H)^+$].

Example 181

8-(3,4-Difluorophenyl)-N-(1-(2-methoxypyridin-4-yl)piperidin-4-yl)-[1,2,4]triazolo[1,5-a]pyridin-2-amine

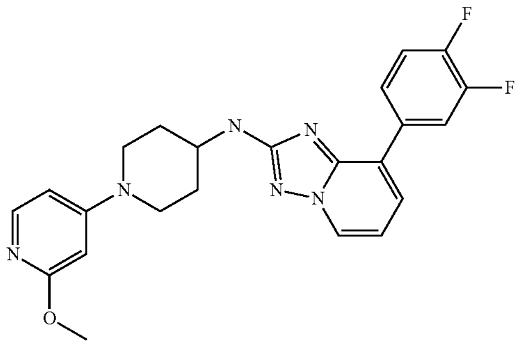 [SMILES: COc1cc(N2CCC(Nc3nc4c(-c5ccc(F)c(F)c5)cccn4n3)CC2)ccn1]

Prepared in analogy to example 173, employing 1-(2-methoxypyridin-4-yl)piperidin-4-amine dihydrochloride (101 mg, 0.36 mmol) instead of 1-(6-ethoxypyrimidin-4-yl) piperidin-4-amine. The title compound was obtained as an off white foam (66 mg, 42%).

MS ISP (m/e): 437.2 [$(M+H)^+$].

Example 182

8-(2-Chloro-4-fluorophenyl)-N-(1-(2-methoxypyridin-4-yl)piperidin-4-yl)-[1,2,4]triazolo[1,5-a]pyridin-2-amine

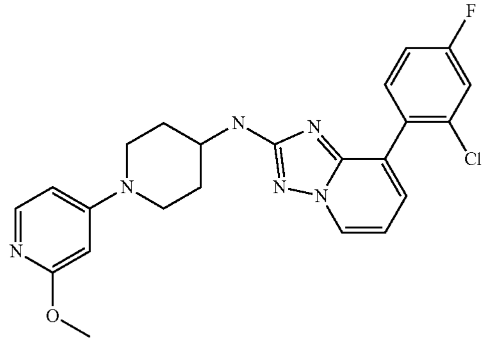 [SMILES: COc1cc(N2CCC(Nc3nc4c(-c5ccc(F)cc5Cl)cccn4n3)CC2)ccn1]

Prepared in analogy to example 181, employing 2-bromo-8-(2-chloro-4-fluorophenyl)-[1,2,4]triazolo[1,5-a]pyridine (129 mg, 0.4 mmol) instead of 2-bromo-8-(3,4-difluorophenyl)-[1,2,4]triazolo[1,5-a]pyridine. The title compound was obtained as an off white foam (57 mg, 35%). MS ISP (m/e): 453.2/455.3 [$(M+H)^+$].

Example 183

N-(1-(2-Chloropyridin-4-yl)piperidin-4-yl)-8-(3,4-difluorophenyl)-6-methyl-[1,2,4]triazolo[1,5-a]pyridin-2-amine

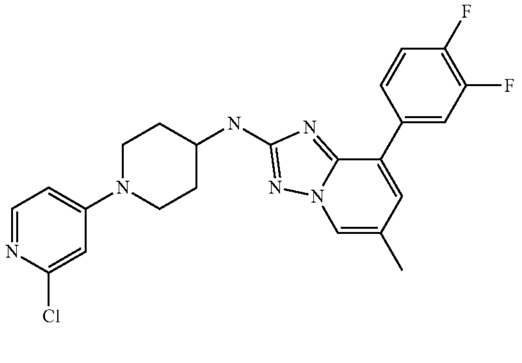 [SMILES: Cc1cc(-c2ccc(F)c(F)c2)c2nc(NC3CCN(c4ccnc(Cl)c4)CC3)nn2c1]

Prepared in analogy to example 169c, employing 2-bromo-8-(3,4-difluorophenyl)-6-methyl-[1,2,4]triazolo[1,5-a]pyridine (143 mg, 0.44 mmol) instead of 2-bromo-8-(3,4-difluorophenyl)-[1,2,4]triazolo[1,5-a]pyridine.

The title compound was obtained as a light yellow foam (73 mg, 40%).

MS ISP (m/e): 455.3 [$(M+H)^+$].

Example 184

N-(1-(2-Chloropyridin-4-yl)piperidin-4-yl)-8-(3,4-difluorophenyl)-6-fluoro-[1,2,4]triazolo[1,5-a]pyridin-2-amine

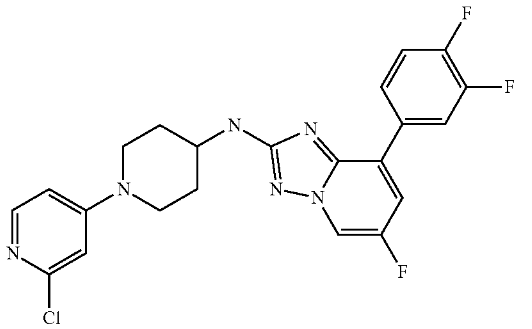 [SMILES: Fc1cc(-c2ccc(F)c(F)c2)c2nc(NC3CCN(c4ccnc(Cl)c4)CC3)nn2c1]

Prepared in analogy to example 169c, employing 2-bromo-8-(3,4-difluorophenyl)-6-fluoro-[1,2,4]triazolo[1,5-a]pyridine (145 mg, 0.44 mmol) instead of 2-bromo-8-(3,4-difluorophenyl)-[1,2,4]triazolo[1,5-a]pyridine.

The title compound was obtained as an off white solid (36 mg, 20%).

MS ISP (m/e): 459.2/461.2 [$(M+H)^+$].

Example 185

8-(2-Chloro-4-fluorophenyl)-N-(1-(2-chloropyridin-4-yl)piperidin-4-yl)-6-methyl-[1,2,4]triazolo[1,5-a]pyridin-2-amine

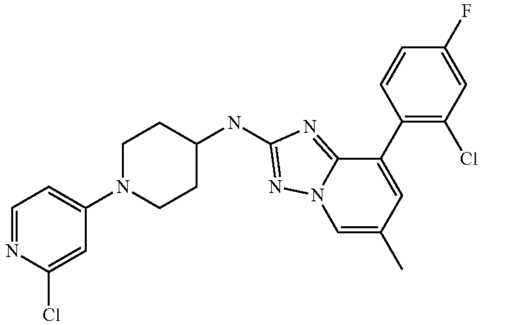 [SMILES: Cc1cc(-c2ccc(F)cc2Cl)c2nc(NC3CCN(c4ccnc(Cl)c4)CC3)nn2c1]

Prepared in analogy to example 169c, employing 2-bromo-8-(2-chloro-4-fluorophenyl)-6-methyl-[1,2,4]triazolo[1,5-a]pyridine (150 mg, 0.44 mmol) instead of 2-bromo-8-(3,4-difluorophenyl)-[1,2,4]triazolo[1,5-a]pyridine.

The title compound was obtained as a yellow foam (82 mg, 43%).

MS ISP (m/e): 471.4/473.2 [$(M+H)^+$].

Example 186

6-Chloro-N-(1-(2-chloropyridin-4-yl)piperidin-4-yl)-8-(3,4-difluorophenyl)-[1,2,4]triazolo[1,5-a]pyridin-2-amine

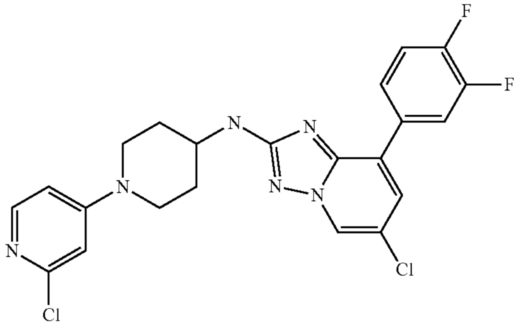 [SMILES: Fc1ccc(-c2cc(Cl)cn3nc(NC4CCN(c5ccnc(Cl)c5)CC4)nc23)cc1F]

Prepared in analogy to example 169c, employing 2-bromo-6-chloro-8-(3,4-difluorophenyl)-[1,2,4]triazolo[1,5-a]pyridine (152 mg, 0.44 mmol) instead of 2-bromo-8-(3,4-difluorophenyl)-[1,2,4]triazolo[1,5-a]pyridine.

The title compound was obtained as an off white foam (25 mg, 13%).

MS ISP (m/e): 475.1/477.1 [$(M+H)^+$].

Example 187

8-(3,4-Difluorophenyl)-N-(1-(pyrimidin-4-yl)piperidin-4-yl)-[1,2,4]triazolo[1,5-a]pyridin-2-amine

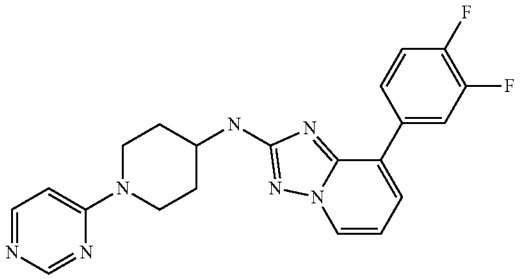 [SMILES: Fc1ccc(-c2cccn3nc(NC4CCN(c5ccncn5)CC4)nc23)cc1F]

a) 1-(Pyrimidin-4-yl)piperidin-4-amine

To a solution (1-pyrimidin-4-yl-piperidin-4-yl)-carbamic acid tert-butyl ester (1.00 g, 3.59 mmol) in dichloromethane (16 mL) was added HCl (2 M in diethylether, 8.98 mL, 18.0 mmol) and the reaction mixture was stirred at room temperature for 4 hours. The mixture was then diluted with NaOH (2 N) at 0° C. and extracted with dichloromethane. The combined organic extracts were then dried over sodium sulfate and filtered to afford the title compound (511 mg, 80%) as a light yellow solid.

MS ISP (m/e): 179.2 [$(M+H)^+$].

b) 8-(3,4-Difluorophenyl)-N-(1-(pyrimidin-4-yl)piperidin-4-yl)-[1,2,4]triazolo[1,5-a]pyridin-2-amine Prepared in analogy to example 169c, employing 1-(pyrimidin-4-yl)piperidin-4-amine (71 mg, 0.4 mmol) instead of 1-(2-chloropyridin-4-yl)piperidin-4-amine dihydrochloride.

The title compound was obtained as a white foam (63 mg, 39%).

MS ISP (m/e): 408.4 [(M+H)$^+$].

Example 188

8-(3,4-Difluorophenyl)-6-methyl-N-(1-(pyrimidin-4-yl)piperidin-4-yl)-[1,2,4]triazolo[1,5-a]pyridin-2-amine

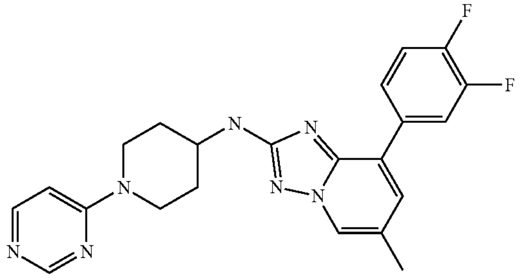 [SMILES: Cc1cc(-c2ccc(F)c(F)c2)c2nc(NC3CCN(c4ccncn4)CC3)nn2c1]

Prepared in analogy to example 187b, employing 2-bromo-8-(3,4-difluorophenyl)-6-methyl-[1,2,4]triazolo[1,5-a]pyridine (130 mg, 0.44 mmol) instead of 2-bromo-8-(3,4-difluorophenyl)-[1,2,4]triazolo[1,5-a]pyridine.

The title compound was obtained as a white foam (60 mg, 36%).

MS ISP (m/e): 422.2 [(M+H)$^+$].

Example 189

8-(2-Chloro-4-fluorophenyl)-6-methyl-N-(1-(pyrimidin-4-yl)piperidin-4-yl)-[1,2,4]triazolo[1,5-a]pyridin-2-amine

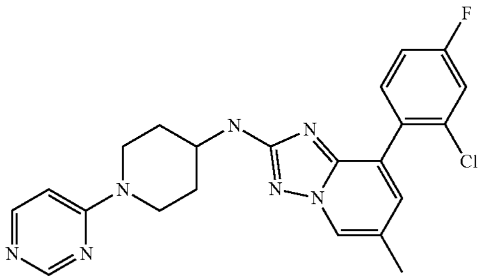 [SMILES: Cc1cc(-c2ccc(F)cc2Cl)c2nc(NC3CCN(c4ccncn4)CC3)nn2c1]

Prepared in analogy to example 187b, employing 2-bromo-8-(2-chloro-4-fluorophenyl)-6-methyl-[1,2,4]triazolo[1,5-a]pyridine (136 mg, 0.44 mmol) instead of 2-bromo-8-(3,4-difluorophenyl)-[1,2,4]triazolo[1,5-a]pyridine.

The title compound was obtained as a white foam (63 mg, 36%).

MS ISP (m/e): 438.2 [(M+H)$^+$].

Example 190

8-(2-Chloro-4-fluorophenyl)-N-(1-(2-chloropyrimidin-4-yl)piperidin-4-yl)-[1,2,4]triazolo[1,5-a]pyridin-2-amine

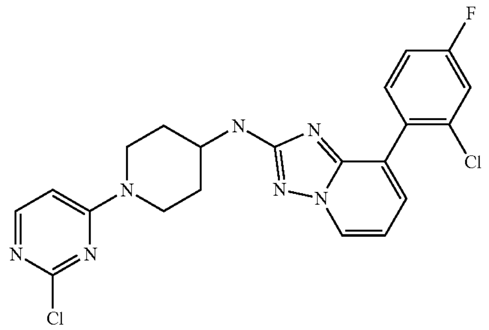 [SMILES: Fc1ccc(-c2cccn3nc(NC4CCN(c5ccnc(Cl)n5)CC4)nc23)c(Cl)c1]

a) 1-(2-Chloropyrimidin-4-yl)piperidin-4-amine dihydrochloride

To a solution 1-(2-chloro-pyrimidin-4-yl)-piperidin-4-yl)-carbamic acid tert-butyl ester (1.00 g, 3.20 mmol) in dichloromethane (18 mL) was added HCl (2 M in diethylether, 8.0 mL, 16.0 mmol) and the reaction mixture was stirred at room temperature for 18 hours. The mixture was then filtered and the white precipitate was washed with dichloromethane and diethylether and dried to afford the title compound (0.95 g, 99%) as a white solid.

MS ISP (m/e): 213.1/215.4 [(M+H)$^+$].

b) 8-(2-Chloro-4-fluorophenyl)-N-(1-(2-chloropyrimidin-4-yl)piperidin-4-yl)-[1,2,4]triazolo[1,5-a]pyridin-2-amine Prepared in analogy to example 171, employing 1-(2-chloropyrimidin-4-yl)piperidin-4-amine dihydrochloride (286 mg, 1.0 mmol) instead of 1-(6-methoxypyrimidin-4-yl)piperidin-4-amine. The title compound was obtained as a white foam (133 mg, 29%).

MS ISP (m/e): 458.3/460.2 [(M+H)$^+$].

Example 191

N-(1-(2-Chloropyridin-4-yl)piperidin-4-yl)-6,8-bis(3,4-difluorophenyl)-[1,2,4]triazolo[1,5-a]pyridin-2-amine

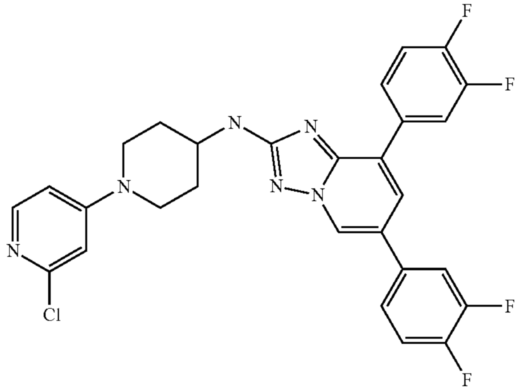 [SMILES: Fc1ccc(-c2cc(-c3ccc(F)c(F)c3)c3nc(NC4CCN(c5ccnc(Cl)c5)CC4)nn3c2)cc1F]

Prepared in analogy to example 169c, employing 2-bromo-6,8-bis(3,4-difluorophenyl)-[1,2,4]triazolo[1,5-a]pyridine (186 mg, 0.44 mmol) instead of 2-bromo-8-(3,4-difluorophenyl)-[1,2,4]triazolo[1,5-a]pyridine.

The title compound was obtained as a light yellow foam (24 mg, 11%).

MS ISP (m/e): 553.3 [$(M+H)^+$].

Example 192

8-(2-Chloro-4-ethoxyphenyl)-N-(1-(2-ethoxypyridin-4-yl)piperidin-4-yl)-[1,2,4]triazolo[1,5-a]pyridin-2-amine

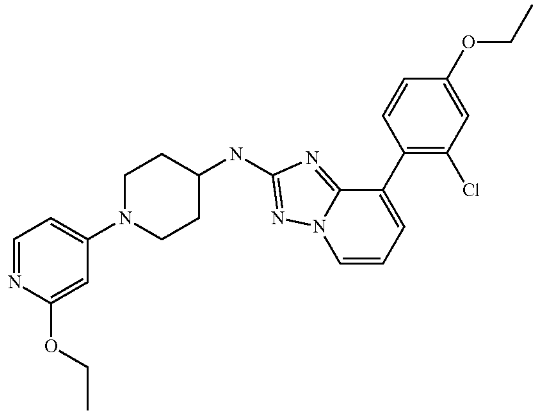 [SMILES: CCOc1ccc(-c2cccn3nc(NC4CCN(c5ccnc(OCC)c5)CC4)nc23)c(Cl)c1]

To a solution of 8-(2-chloro-4-fluorophenyl)-N-(1-(2-chloropyridin-4-yl)piperidin-4-yl)-[1,2,4]triazolo[1,5-a]pyridin-2-amine (example 58) (46 mg, 0.10 mmol) in EtOH (1 mL) was added sodium ethoxide solution (21% in ethanol, 56 L, 0.15 mmol) and the reaction mixture was stirred under Argon in a sealed tube at 60° C. for 16 h. After cooling to room temperature the mixture was heated in the microwave to 150° C. for 45 minutes and then sodium ethoxide solution (21% in ethanol, 56 uL, 0.15 mmol) was added and the mixture heated to 150° C. for another 30 in the microwave. The mixture was then evaporated and diluted with water and extracted with ethyl acetate. The combined organic phases were dried over sodium sulfate, filtered and evaporated. Purification by chromatography (silica gel, 20 g, 0 to 100% ethyl acetate in heptane) afforded the title compound (17 mg, 35%) as a white foam.

MS ISP (m/e): 493.3/495.4 [$(M+H)^+$].

Example 193

8-(2-Chloro-4-fluorophenyl)-N-(1-(2-methoxypyrimidin-4-yl)piperidin-4-yl)-[1,2,4]triazolo[1,5-a]pyridin-2-amine

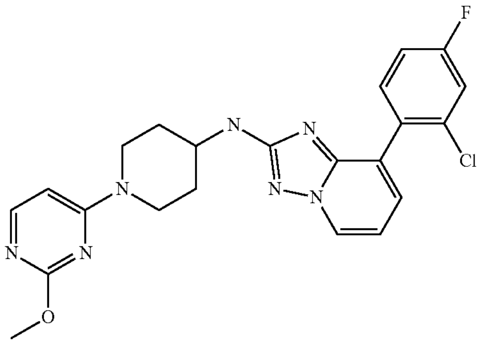 [SMILES: COc1nccc(N2CCC(Nc3nc4c(-c5ccc(F)cc5Cl)cccn4n3)CC2)n1]

To a solution of 8-(2-chloro-4-fluorophenyl)-N-(1-(2-chloropyrimidin-4-yl)piperidin-4-yl)-[1,2,4]triazolo[1,5-a]pyridin-2-amine (example 190b) (71 mg, 0.155 mmol) in MeOH (1.5 mL) was added sodium methoxide solution (30% in MeOH, 35 L, 0.186 mmol) and the reaction mixture was stirred in a sealed tube under Argon at 60° C. for 18 hours and then heated in the microwave to 150° C. for 30 minutes. The mixture was then evaporated.

Purification by chromatography (silica gel, 20 g, 0 to 100% methanol in dichloromethane) afforded the title compound (33 mg, 47%) as a light yellow foam.

MS ISP (m/e): 454.3/456.2 [$(M+H)^+$].

Example 194

8-(2-Chloro-4-methoxyphenyl)-N-(1-(2-methoxypyrimidin-4-yl)piperidin-4-yl)-[1,2,4]triazolo[1,5-a]pyridin-2-amine

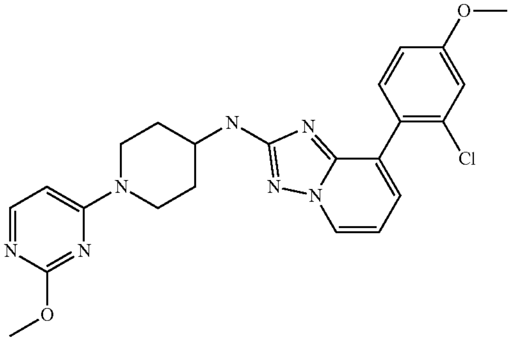 [SMILES: COc1ccc(-c2cccn3nc(NC4CCN(c5ccnc(OC)n5)CC4)nc23)c(Cl)c1]

To a solution of 8-(2-chloro-4-fluorophenyl)-N-(1-(2-chloropyrimidin-4-yl)piperidin-4-yl)-[1,2,4]triazolo[1,5-a]

pyridin-2-amine (example 190b) (71 mg, 0.155 mmol) in MeOH (1.5 mL) was added sodium methoxide solution (30% in MeOH, 35 L, 0.186 mmol) and the reaction mixture was stirred in a sealed tube under Argon at 60° C. for 18 hours and then heated in the microwave to 150° C. for 30 minutes. The mixture was then evaporated.

Purification by chromatography (silica gel, 20 g, 0 to 100% methanol in dichloromethane) afforded the title compound (5 mg, 7%) as a light yellow foam.

MS ISP (m/e): 466.3/468.3 [(M+H)$^+$].

Example 195

N-(1-(2-Chloropyrimidin-4-yl)piperidin-4-yl)-8-(3,4-difluorophenyl)-[1,2,4]triazolo[1,5-a]pyridin-2-amine

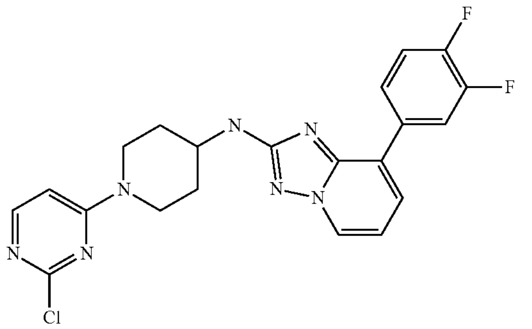 [SMILES: Fc1ccc(-c2cccn3nc(NC4CCN(c5ccnc(Cl)n5)CC4)nc23)cc1F]

Prepared in analogy to example 190b, employing 2-bromo-8-(3,4-difluorophenyl)-[1,2,4]triazolo[1,5-a]pyridine (311 mg, 1.0 mmol) instead of 2-bromo-8-(2-chloro-4-fluorophenyl)-[1,2,4]triazolo[1,5-a]pyridine.

The title compound was obtained as an off white solid (149 mg, 34%).

MS ISP (m/e): 442.2/444.3 [(M+H)$^+$].

Example 196

8-(3,4-Difluorophenyl)-N-(1-(2-ethoxypyridin-4-yl)piperidin-4-yl)-[1,2,4]triazolo[1,5-a]pyridin-2-amine

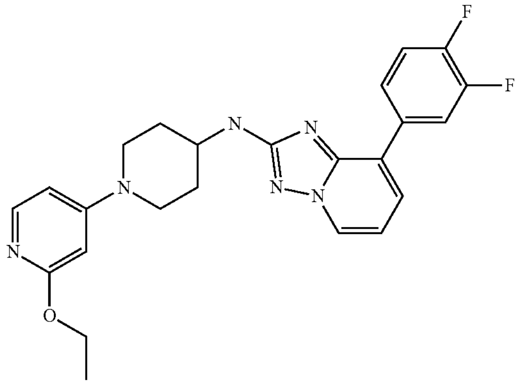 [SMILES: CCOc1cc(N2CCC(Nc3nc4c(-c5ccc(F)c(F)c5)cccn4n3)CC2)ccn1]

To a solution of N-(1-(2-chloropyridin-4-yl)piperidin-4-yl)-8-(3,4-difluorophenyl)-[1,2,4]triazolo[1,5-a]pyridin-2-amine (example 169c) (88 mg, 0.20 mmol) in EtOH (1 mL) was added sodium ethoxide solution (21% in ethanol, 75 L, 0.2 mmol) and the reaction mixture was heated in the microwave to 150° C. for 30 minutes. Again sodium ethoxide solution (21% in ethanol, 75 L, 0.2 mmol) was added and the resulting mixture heated to 150° C. for another 30 minutes. The mixture was then evaporated. Purification by chromatography (silica gel, 20 g, 0 to 100% methanol in dichloromethane) afforded the title compound (3 mg, 3%) as a colourless gum.

MS ISP (m/e): 451.3 [(M+H)$^+$].

Example 197

8-(4-Ethoxy-3-fluorophenyl)-N-(1-(pyridin-4-yl)piperidin-4-yl)-[1,2,4]triazolo[1,5-a]pyridin-2-amine

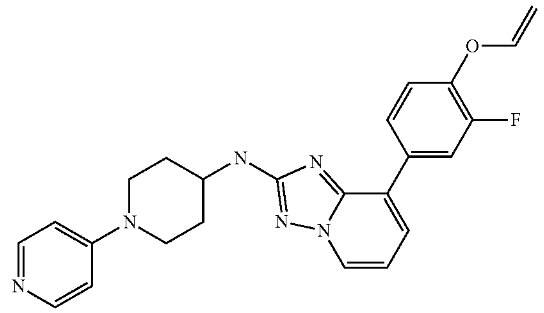 [SMILES: C=COc1ccc(-c2cccn3nc(NC4CCN(c5ccncc5)CC4)nc23)cc1F]

To a solution of N-(1-(2-chloropyridin-4-yl)piperidin-4-yl)-8-(3,4-difluorophenyl)-[1,2,4]triazolo[1,5-a]pyridin-2-amine (example 169c) (88 mg, 0.20 mmol) in EtOH (1 mL) was added sodium ethoxide solution (21% in ethanol, 75 L, 0.2 mmol) and the reaction mixture was heated in the microwave to 150° C. for 30 minutes and then sodium ethoxide solution (21% in ethanol, 75 L, 0.2 mmol) was added and the resulting mixture heated to 150° C. for another 30 minutes. The mixture was then evaporated.

Purification by chromatography (silica gel, 20 g, 0 to 100% methanol in dichloromethane) afforded the title compound (7 mg, 8%) as an off white foam.

MS ISP (m/e): 433.5 [(M+H)$^+$].

Example 198

8-(3,4-Difluorophenyl)-N-(1-(2-methoxypyrimidin-4-yl)piperidin-4-yl)-[1,2,4]triazolo[1,5-a]pyridin-2-amine

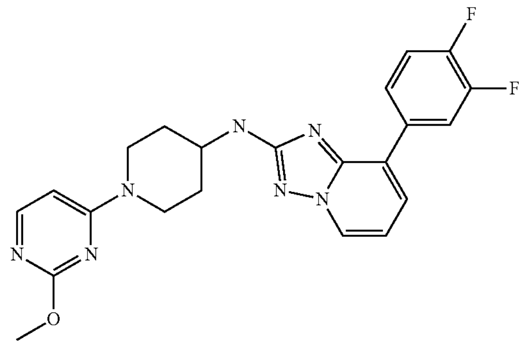 [SMILES: COc1nccc(N2CCC(Nc3nc4c(-c5ccc(F)c(F)c5)cccn4n3)CC2)n1]

To a solution of N-(1-(2-chloropyrimidin-4-yl)piperidin-4-yl)-8-(3,4-difluorophenyl)-[1,2,4]triazolo[1,5-a]pyridin-2-amine (example 195) (88 mg, 0.155 mmol) in MeOH (2.0 mL) was added sodium methoxide solution (30% in MeOH, 41 µL, 0.22 mmol) and the reaction mixture was heated in the microwave at 120° C. for 2 h. The mixture was then evaporated. Purification by chromatography (silica gel, 20 g, 0 to 100% methanol in dichloromethane) afforded the title compound (71 mg, 81%) as a white foam.

MS ISP (m/e): 438.3 [(M+H)$^+$].

Example 199

2-{8-(3,4-Difluoro-phenyl)-2-[1-(6-methyl-pyrimidin-4-yl)-piperidin-4-ylamino]-[1,2,4]triazolo[1,5-a]pyridin-5-yl}-propan-2-ol

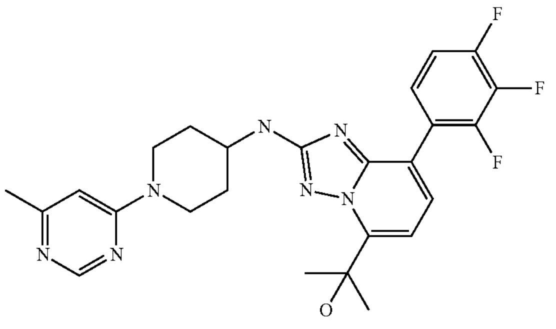 [SMILES: Cc1cc(N2CCC(Nc3nc4c(-c5ccc(F)c(F)c5F)ccc(C(C)(C)O)n4n3)CC2)ncn1]

Prepared in analogy to example 49. The title compound was obtained as an light yellow solid. MS ESI (m/z): 498.0 [(M+H)$^+$].

Example 200

8-(3,4-Difluorophenyl)-N-(1-(2-(trifluoromethyl)pyridin-4-yl)piperidin-4-yl)-[1,2,4]triazolo[1,5-a]pyridin-2-amine

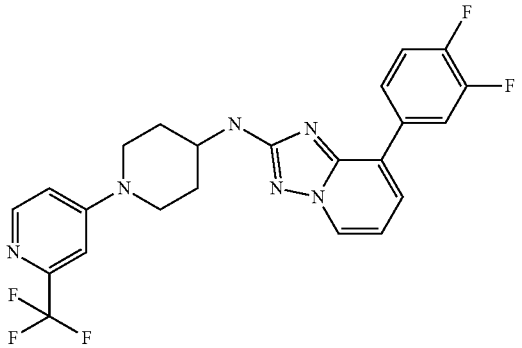 [SMILES: Fc1ccc(-c2cccn3nc(NC4CCN(c5ccnc(C(F)(F)F)c5)CC4)nc23)cc1F]

a) tert-Butyl 1-(2-(trifluoromethyl)pyridin-4-yl)piperidin-4-ylcarbamate

To a mixture of 4-iodo-2-(trifluoromethyl)pyridine (356 mg, 1.3 mmol) and Boc-4-aminopiperidine (340 mg, 1.7 mmol) in NMP (2.6 mL) was added DIPEA (319 L, 1.83 mmol). Argon was bubbled through the cloudy solution for 5 minutes before the reaction mixture was heated in the microwave for 3×30 minutes to 150° C. The mixture was then poured into water and extracted with ethyl acetate. The combined organic phases were dried over sodium sulfate, filtered and evaporated. Purification by chromatography (silica gel, 50 g, 0 to 100% ethyl acetate in heptane) afforded the title compound (343 mg, 76%) as a white solid.

MS ISP (m/e): 346.2 [(M+H)$^+$].

b) 1-(2-(Trifluoromethyl)pyridin-4-yl)piperidin-4-amine

To a solution tert-butyl 1-(2-(trifluoromethyl)pyridin-4-yl)piperidin-4-ylcarbamate (314 mg, 0.91 mmol) in dichloromethane (4.5 mL) was added HCl (2 M in diethylether, 2.27 mL, 4.55 mmol) and the reaction mixture was stirred at room temperature for 18 h. The mixture was then filtered and the white precipitate was washed with dichloromethane and diethylether and dried to afford the title compound (201 mg, 90%) as an off white solid.

MS ISP (m/e): 246.2 [(M+H)$^+$].

c) 8-(3,4-Difluorophenyl)-N-(1-(2-(trifluoromethyl)pyridin-4-yl)piperidin-4-yl)-[1,2,4]triazolo[1,5-a]pyridin-2-amine Prepared in analogy to example 169c, employing 1-(2-(trifluoromethyl)pyridin-4-yl)piperidin-4-amine (70 mg, 0.29 mmol) instead of 1-(2-chloropyridin-4-yl)piperidin-4-amine dihydrochloride. The title compound was obtained as a white foam (72 mg, 53%).

MS ISP (m/e): 475.2 [(M+H)$^+$].

Example 201

8-(2-Chloro-4-fluorophenyl)-N-(1-(2-(trifluoromethyl)pyridin-4-yl)piperidin-4-yl)-[1,2,4]triazolo[1,5-a]pyridin-2-amine

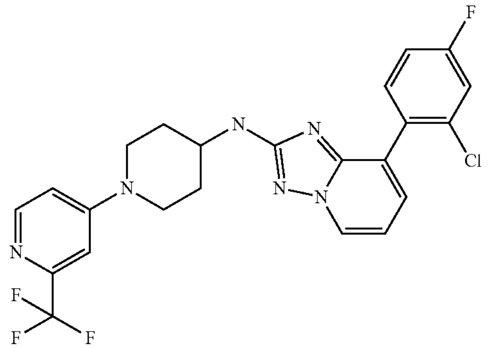 [SMILES: Fc1ccc(-c2cccn3nc(NC4CCN(c5ccnc(C(F)(F)F)c5)CC4)nc23)c(Cl)c1]

Prepared in analogy to example 200c, employing 2-bromo-8-(2-chloro-4-fluorophenyl)-[1,2,4]triazolo[1,5-a]pyridine (93 mg, 0.29 mmol) instead of 2-bromo-8-(3,4-difluorophenyl)-[1,2,4]triazolo[1,5-a]pyridine.

The title compound was obtained as a yellow foam (78 mg, 56%).

MS ISP (m/e): 491.2 [(M+H)$^+$].

Example 202

8-(3,4-Difluorophenyl)-6-fluoro-N-(1-(6-methylpyridazin-4-yl)piperidin-4-yl)-[1,2,4]triazolo[1,5-a]pyridin-2-amine

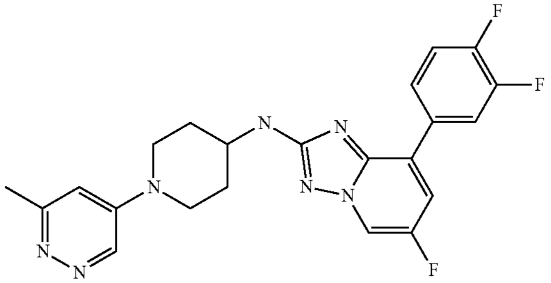 [SMILES: Cc1cc(N2CCC(Nc3nc4c(-c5ccc(F)c(F)c5)cc(F)cn4n3)CC2)cnn1]

Prepared in analogy to example 180c, employing 2-bromo-8-(3,4-difluorophenyl)-6-fluoro-[1,2,4]triazolo[1,5-a]pyridine (145 mg, 0.44 mmol)) instead of 2-bromo-8-(3,4-difluorophenyl)-[1,2,4]triazolo[1,5-a]pyridine.

The title compound was obtained as a yellow foam (87 mg, 45%).

MS ISP (m/e): 440.3 [(M+H)$^+$].

Example 203

8-(3,4-Difluorophenyl)-6-methyl-N-(1-(6-methylpyridazin-4-yl)piperidin-4-yl)-[1,2,4]triazolo[1,5-a]pyridin-2-amine

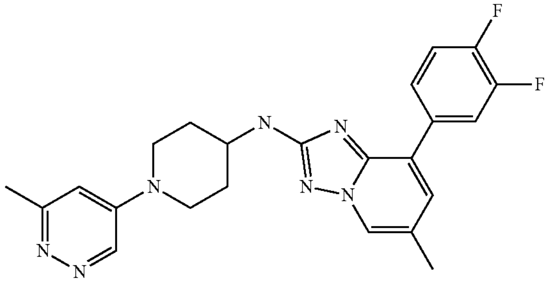 [SMILES: Cc1cc(-c2ccc(F)c(F)c2)c2nc(NC3CCN(c4cnnc(C)c4)CC3)nn2c1]

Prepared in analogy to example 180c, employing 2-bromo-8-(3,4-difluorophenyl)-6-methyl-[1,2,4]triazolo[1,5-a]pyridine (143 mg, 0.44 mmol)) instead of 2-bromo-8-(3,4-difluorophenyl)-[1,2,4]triazolo[1,5-a]pyridine.

The title compound was obtained as a yellow foam (96 mg, 50%).

MS ISP (m/e): 436.3 [(M+H)$^+$].

Example 204

8-(2-Chloro-4-fluorophenyl)-N-(1-(6-methylpyridazin-4-yl)piperidin-4-yl)-[1,2,4]triazolo[1,5-a]pyridin-2-amine

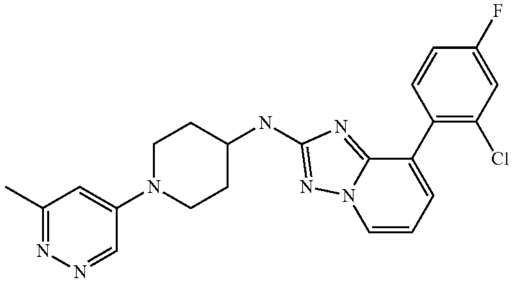 [SMILES: Cc1cc(N2CCC(Nc3nc4c(-c5ccc(F)cc5Cl)cccn4n3)CC2)cnn1]

Prepared in analogy to example 180c, employing 2-bromo-8-(2-chloro-4-fluorophenyl)-[1,2,4]triazolo[1,5-a]pyridine (144 mg, 0.44 mmol)) instead of 2-bromo-8-(3,4-difluorophenyl)-[1,2,4]triazolo[1,5-a]pyridine.

The title compound was obtained as an off white foam (73 mg, 38%).

MS ISP (m/e): 438.1 [(M+H)$^+$].

Example 205

6-Chloro-8-(3,4-difluorophenyl)-N-(1-(6-methylpyridazin-4-yl)piperidin-4-yl)-[1,2,4]triazolo[1,5-a]pyridin-2-amine

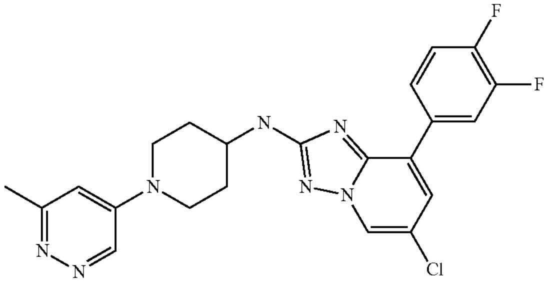 [SMILES: Cc1cc(N2CCC(Nc3nc4c(-c5ccc(F)c(F)c5)cc(Cl)cn4n3)CC2)cnn1]

Prepared in analogy to example 180c, employing 2-bromo-6-chloro-8-(3,4-difluorophenyl)-[1,2,4]triazolo[1,5-a]pyridine (152 mg, 0.44 mmol)) instead of 2-bromo-8-(3,4-difluorophenyl)-[1,2,4]triazolo[1,5-a]pyridine.

The title compound was obtained as a light yellow foam (100 mg, 50%).

MS ISP (m/e): 456.2 [(M+H)$^+$].

Example 206

8-(2-Chloro-4-fluorophenyl)-6-methyl-N-(1-(6-methylpyridazin-4-yl)piperidin-4-yl)-[1,2,4]triazolo[1,5-a]pyridin-2-amine

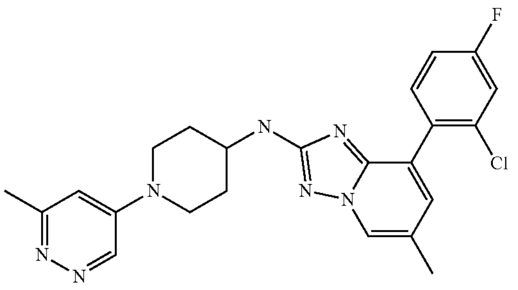 [SMILES: Cc1cc(-c2ccc(F)cc2Cl)c2nc(NC3CCN(c4cnnc(C)c4)CC3)nn2c1]

Prepared in analogy to example 180c, employing 2-bromo-6-chloro-8-(3,4-difluorophenyl)-[1,2,4]triazolo[1,5-a]pyridine (150 mg, 0.44 mmol) instead of 2-bromo-8-(3,4-difluorophenyl)-[1,2,4]triazolo[1,5-a]pyridine.

The title compound was obtained as a light yellow foam (96 mg, 48%).

MS ISP (m/e): 452.1 [(M+H)$^+$].

Example 207

4-(3-Chloro-4-fluorophenyl)-N-(1-(2-chloropyridin-4-yl)piperidin-4-yl)-6-methylbenzo[d]thiazol-2-amine

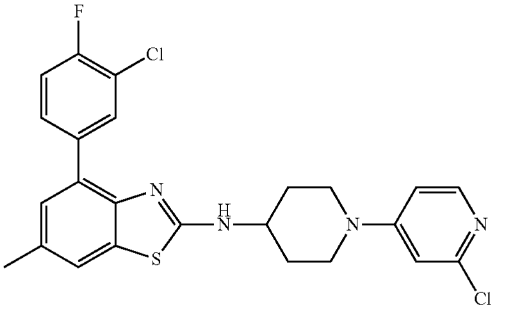 [SMILES: Cc1cc(-c2ccc(F)c(Cl)c2)c2nc(NC3CCN(c4ccnc(Cl)c4)CC3)sc2c1]

a) tert-Butyl 4-bromo-6-methylbenzo[d]thiazol-2-ylcarbamate

To a suspension of 4-bromo-6-methylbenzo[d]thiazol-2-amine (1.0 g, 4.32 mmol) in dichloromethane (30 mL) was added di-tert-butyl dicarbonate (1.0 g, 4.75 mmol) followed by 4-dimethylaminopyridine (0.6 g, 4.75 mmol) and the mixture stirred for 1 hour. The reaction was diluted with dichloromethane, Amberlite® IR120 was added, the mixture was filtered through glass wool and concentrated to give the title compound as an orange powder (1.3 g, 89%).

MS ISP (m/e): 343.2 [(M+H)$^+$]. $^1$H NMR (DMSO-$D_6$, 400 MHz): (ppm)=12.01 (s, 1H), 7.74 (s, 1H), 7.48 (s, 1H), 2.39 (s, 3H), 1.49 (s, 9H).

b) 4-(3-Chloro-4-fluorophenyl)-6-methylbenzo[d]thiazol-2-amine

To a mixture of tert-butyl 4-bromo-6-methylbenzo[d]thiazol-2-ylcarbamate (0.6 g, 1.75 mmol), 3-chloro-4-fluorophenylboronic acid (0.5 g, 2.62 mmol), palladium(II) acetate (0.08 g, 0.35 mmol), triphenylphosphine (0.3 g, 1.05 mmol) was added degassed dioxane (10 mL) and degassed 1 M aqueous sodium carbonate (5.24 mL, 5.24 mmol). The mixture was heated to 100° C. for 16 hours under argon and then diluted with ethyl acetate, washed with water, brine and concentrated. The residue was redissolved in trifluoroacetic acid (2 mL) and stirred for 15 minutes. The solvent was evaporated, the residue redissolved in dichloromethane, washed with saturated sodium hydrogen carbonate, dried with sodium sulfate and concentrated. The product was purified by column chromatography on silica gel using n-heptane:ethyl acetate (v/v=9:1-4:1) as eluent to yield the title compound as white solid (0.4 g, 80%).

MS ISP (m/e): 293.2 [(M+H)$^+$].

$^1$H NMR ($CDCl_3$, 400 MHz): (ppm)=7.82 (dd, 1H), 7.64-7.59 (m, 1H), 7.41 (brs, 1H), 7.20 (t, 1H), 7.15 (brs, 1H), 5.24 (brs, 2H), 2.44 (s, 3H).

c) 2-Bromo-4-(3-chloro-4-fluorophenyl)-6-methylbenzo[d]thiazole

To an ice-cold mixture of copper(II) bromide (0.18 g, 0.8 mmol) and tert-butyl nitrite (0.11 mL, 0.9 mmol) in acetonitrile (10 ml) was added solid 4-(3-chloro-4-fluorophenyl)-6-methylbenzo[d]thiazol-2-amine (0.2 g, 0.7 mmol). The ice bath was then removed and the reaction mixture was allowed to warm to room temperature within 0.5 hours. The reaction mixture was diluted with dichloromethane, washed with 1 M hydrochloric acid, dried with sodium sulfate and concentrated to yield the title compound as light yellow solid (0.24 g, 99%).

MS ISP (m/e): 356.0 [(M+H)$^+$].

$^1$H NMR ($CDCl_3$, 400 MHz): (ppm)=7.81 (dd, 1H), 7.70-7.65 (m, 1H), 7.59 (brs, 1H), 7.30 (brs, 1H), 7.24 (t, 1H), 2.52 (s, 3H).

d) 4-(3-Chloro-4-fluorophenyl)-N-(1-(2-chloropyridin-4-yl)piperidin-4-yl)-6-methylbenzo[d]thiazol-2-amine To a solution of 2-bromo-4-(3-chloro-4-fluorophenyl)-6-methylbenzo[d]thiazole (0.06 g, 0.2 mmol) in dimethylacetamide (1 mL) was added 1-(2-chloropyridin-4-yl)piperidin-4-amine dihydrochloride (0.05 g, 0.2 mmol) followed by triethylamine (70 L, 0.5 mmol) and the mixture was heated to 175° C. for 1 h in a microwave. The reaction was then diluted with dichloromethane, washed with water, brine, dried with sodium sulfate and concentrated. The product was purified by preparative HPLC to yield the title compound as light yellow solid (0.02 g, 24%).

MS ISP (m/e): 487.1 [(M+H)$^+$].

$^1$H NMR ($CDCl_3$, 400 MHz): (ppm)=8.06-7.98 (m, 2H), 7.65-7.61 (m, 1H), 7.41 (brs, 1H), 7.19 (apt, 2H), 6.67 (brs, 1H), 6.60 (d, 1H), 5.21 (brs, 1H), 3.93-3.82 (m, 3H), 3.10 (t, 2H), 2.44 (s, 3H), 2.02 (d, 2H), 1.71-1.55 (m, 4H).

Example 208

4-(3-Chloro-4-fluorophenyl)-6-methyl-N-(1-(6-methylpyrimidin-4-yl)piperidin-4-yl)benzo[d]thiazol-2-amine

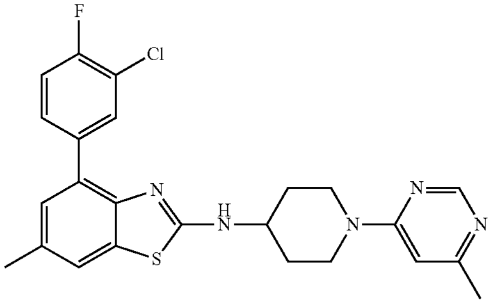

Prepared in analogy to example 207d, starting from 2-bromo-4-(3-chloro-4-fluorophenyl)-6-methylbenzo[d]thiazole and 1-(6-methyl-pyrimidin-4-yl)-piperidin-4-ylamine dihydrochloride. The title compound was obtained as a white solid.

MS ISP (m/e): 468.2 [(M+H)$^+$].

$^1$H NMR ($CDCl_3$, 400 MHz): (ppm)=7.90 (d, 1H), 7.62-7.45 (m, 2H), 7.40 (brt, 1H), 7.34 (brs, 1H), 7.14-7.08 (m, 2H), 6.36 (brs, 1H), 4.32 (d, 2H), 3.88-3.78 (m, 1H), 3.12 (t, 2H), 2.37 (s, 3H), 2.35 (s, 3H), 2.20 (d, 2H), 1.49 (q, 2H).

Example 209

4-(3,4-Difluorophenyl)-6-methyl-N-(1-(6-methylpyrimidin-4-yl)piperidin-4-yl)benzo[d]thiazol-2-amine

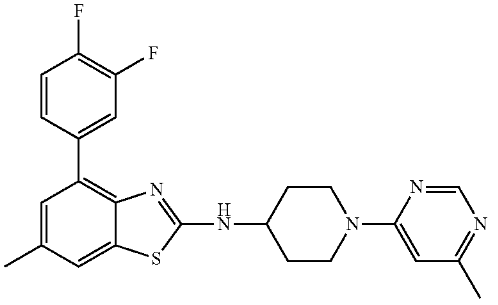

Prepared in analogy to example 207b-c then 208, starting from tert-butyl 4-bromo-6-methylbenzo[d]thiazol-2-ylcarbamate and 3,4-difluorophenylboronic acid.

The title compound was obtained as a white solid.

MS ISP (m/e): 452.1 [(M+H)$^+$].

$^1$H NMR ($CDCl_3$, 400 MHz): (ppm)=7.77-7.63 (m, 2H), 7.50-7.43 (m, 2H), 7.40 (s, 1H), 7.23-7.15 (m, 2H), 6.44 (brs, 1H), 4.38 (d, 2H), 3.96-3.87 (m, 1H), 3.27 (t, 2H), 2.46 (s, 3H), 2.44 (s, 3H), 2.27 (d, 2H), 1.62 (q, 2H).

Example 210

N-(1-(2-Chloropyridin-4-yl)piperidin-4-yl)-4-(3,4-difluorophenyl)-6-methylbenzo[d]thiazol-2-amine

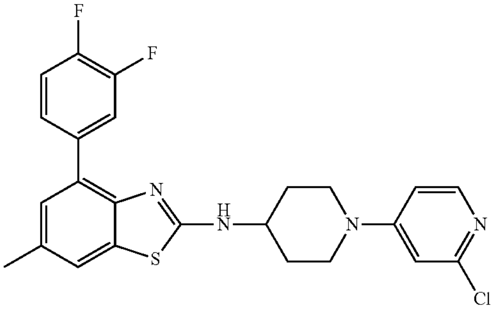

Prepared in analogy to example 207b-d, starting from tert-butyl 4-bromo-6-methylbenzo[d]thiazol-2-ylcarbamate and 3,4-difluorophenylboronic acid The title compound was obtained as a white solid.

MS ISP (m/e): 470.8 [(M+H)$^+$].

$^1$H NMR ($CDCl_3$, 400 MHz): (ppm)=8.03 (d, 1H), 7.79-7.72 (m, 2H), 7.51-7.47 (m, 1H), 7.41 (brs, 1H), 7.24-7.16 (m, 2H), 6.68 (brs, 1H), 6.60 (d, 1H), 5.23 (brs, 1H), 3.91-3.81 (m, 3H), 3.10 (t, 2H), 2.44 (s, 3H), 2.27 (d, 2H), 1.62 (q, 2H).

Example 211

4-(2-Chloro-4-fluorophenyl)-6-methyl-N-(1-(6-methylpyrimidin-4-yl)piperidin-4-yl)benzo[d]thiazol-2-amine

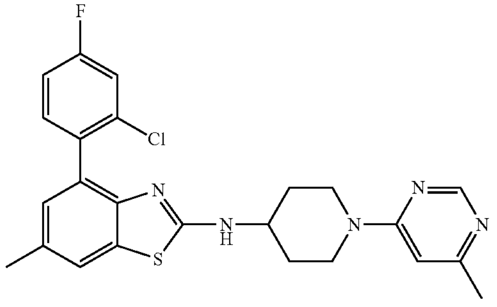

Prepared in analogy to example 207b-c then 208, starting from tert-butyl 4-bromo-6-methylbenzo[d]thiazol-2-ylcarbamate and 2-chloro-4-fluorophenylboronic acid. The title compound was obtained as a white solid.

MS ISP (m/e): 468.2 [(M+H)$^+$].

$^1$H NMR ($CDCl_3$, 400 MHz): (ppm)=8.51 (s, 1H), 7.45 (brs, 1H), 7.39 (dd, 1H), 7.23 (dd, 1H), 7.09-7.02 (m, 2H), 6.39 (brs, 1H), 5.32 (brs, 1H), 4.31 (d, 2H), 3.76-3.68 (m, 1H), 3.12 (t, 2H), 2.44 (s, 3H), 2.37 (s, 3H), 2.20 (d, 2H), 1.52 (q, 2H).

Example 212

4-(2-Chloro-4-fluorophenyl)-N-(1-(2-chloropyridin-4-yl)piperidin-4-yl)-6-methylbenzo[d]thiazol-2-amine

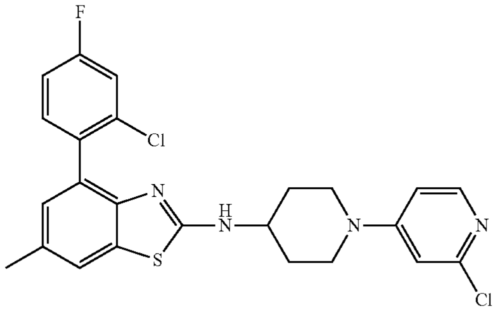 [SMILES: Cc1cc(-c2ccc(F)cc2Cl)c2nc(NC3CCN(c4ccnc(Cl)c4)CC3)sc2c1]

Prepared in analogy to example 207b-d, starting from tert-butyl 4-bromo-6-methylbenzo[d]thiazol-2-ylcarbamate and 2-chloro-4-fluorophenylboronic acid. The title compound was obtained as a white solid.

MS ISP (m/e): 487.1 [(M+H)$^+$].

$^1$H NMR ($CDCl_3$, 400 MHz): (ppm)=8.02 (d, 1H), 7.45 (brs, 1H), 7.39 (brt, 1H), 7.23 (dd, 1H), 7.07-7.01 (m, 2H), 6.66 (brs, 1H), 6.58 (dd, 1H), 5.22 (brs, 1H), 3.80 (d, 2H), 3.76-3.68 (m, 1H), 3.07 (t, 2H), 2.44 (s, 3H), 2.22 (d, 2H), 1.59 (q, 2H).

Example 213

N-(1-(2-Chloropyridin-4-yl)piperidin-4-yl)-8-(4-fluoropiperidin-1-yl)-[1,2,4]triazolo[1,5-a]pyridin-2-amine

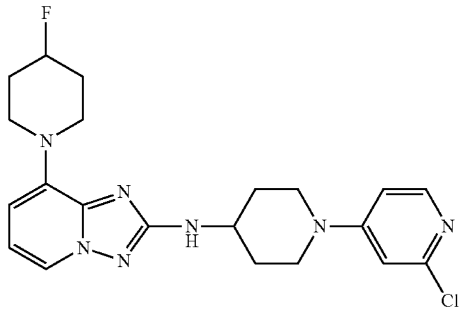 [SMILES: FC1CCN(c2cccn3nc(NC4CCN(c5ccnc(Cl)c5)CC4)nc23)CC1]

a) 2-Nitropyridin-3-yl trifluoromethanesulfonate

To an ice-cold solution of 2-nitropyridin-3-ol (10.0 g, 71 mmol) and triethylamine (14.9 mL, 107 mmol) in methylene chloride (150 mL) was added dropwise triflic anhydride (14.5 mL, 86 mmol) and the mixture was stirred for 2 hours. Water was added and the mixture extracted with methylene chloride. The organic phase was dried with sodium sulfate and the solvent was evaporated in vacuo. The residue was purified by column chromatography on silica gel using n-heptane/ethyl acetate (v/v 2:8 to 3:7) as eluent. The title compound was obtained as a light brown liquid (18.4 g, 95%).

MS ISP (m/e): 273.1 [(M+H)$^+$].

$^1$H NMR ($CDCl_3$, 400 MHz): δ (ppm)=8.65 (dd, 1H), 8.00 (dd, 1H), 7.80 (dd, 1H).

b) 3-(4-Fluoropiperidin-1-yl)-2-nitropyridine

To a solution of 4-fluoropiperidine hydrochloride (1.54 g, 11 mmol) and triethylamine (4.5 mL, 33 mmol) in dimethylacetamide (30 mL) was added 2-nitropyridin-3-yl trifluoromethanesulfonate (3.00 g, 11 mmol) and the mixture heated to 110° C. for 1 hour. Water was added and the mixture extracted with ethyl acetate. The organic phase was washed with brine and dried with sodium sulfate. The solvent was evaporated in vacuo and the product used without further purification. The title compound was obtained as a yellow oil (2.22 g, 89%).

MS ISP (m/e): 226.0 [(M+H)$^+$]. $^1$H NMR ($CDCl_3$, 400 MHz): δ (ppm)=8.10 (dd, 1H), 7.55 (dd, 1H), 7.47 (dd, 1H), 4.95-4.75 (m, 1H), 3.25-3.17 (m, 2H), 3.07-3.00 (m, 2H), 2.10-1.95 (m, 4H).

c) 3-(4-Fluoropiperidin-1-yl)pyridin-2-amine

To a solution of 3-(4-fluoropiperidin-1-yl)-2-nitropyridine (2.0 g, 8.9 mmol) in methanol (25 mL) was added a generous spoon of rainey-nickel and the mixture stirred under an atmosphere of hydrogen for 5 hours. The reaction was then filtered over Hyflo and the solvent was evaporated in vacuo to afford the product used without need for further purification. The title compound was obtained as a dark brown solid (1.7 g, 100%).

MS ISP (m/e): 196.2 [(M+H)$^+$].

d) N-(3-(4-Fluoropiperidin-1-yl)-pyridin-2-yl)-N'-ethoxycarbonyl-thiourea

Prepared in analogy to example 1e, starting from 3-(4-fluoropiperidin-1-yl)pyridin-2-amine. The residue was purified by column chromatography on silica gel using n-heptane/ethyl acetate (v/v 1:1 to 3:7) as eluent to afford the title compound as a yellow solid (yield: 73%).

MS ISP (m/e): 327.1 [(M+H)$^+$].

$^1$H NMR (DMSO-$D_6$, 400 MHz): δ (ppm)=12.0 (brs, 1H), 11.3 (bs, 1H), 8.13 (dd, 1H), 7.60 (dd, 1H), 7.34 (dd, 1H), 4.95-4.75 (m, 1H), 4.22 (q, 2H), 3.01 (t, 2H), 2.87-2.80 (m, 2H), 2.07-1.81 (m, 4H), 1.26 (t, 3H).

e) 5-(4-Fluoro-phenyl)-[1,2,4]triazolo[1,5-a]pyridin-2-ylamine

Prepared in analogy to example 1f, starting from N-(3-(4-fluoropiperidin-1-yl)-pyridin-2-yl)-N'-ethoxycarbonyl-thiourea affording the title compound without need for purification as a light yellow solid (yield: 100%).

MS ISP (m/e): 236.2 [(M+H)$^+$].

$^1$H NMR ($CDCl_3$, 400 MHz): δ (ppm)=7.95 (dd, 1H), 6.74-6.75 (m, 2H), 4.97-4.79 (m, 1H), 4.40 (brs, 2H), 3.54-3.43 (m, 4H), 2.87-2.80 (m, 2H), 2.21-2.02 (m, 4H).

f) N-(1-(2-chloropyridin-4-yl)piperidin-4-yl)-8-(4-fluoropiperidin-1-yl)-[1,2,4]triazolo[1,5-a]pyridin-2-amine Prepared in analogy to example 1h, starting from 5-(4-fluoro-phenyl)-[1,2,4]triazolo[1,5-a]pyridin-2-ylamine and 1-(2-chloropyridin-4-yl)piperidin-4-one affording the title compound as a colourless gum (yield: 7%).

MS ISP (m/e): 430.2 [(M+H)$^+$].

$^1$H NMR ($CDCl_3$, 400 MHz): δ (ppm)=8.02 (dd, 1H), 7.98 (dd, 1H), 6.75-6.66 (m, 3H), 6.60 (dd, 1H), 5.01-4.79 (m, 2H), 3.95-3.86 (m, 1H), 3.85-3.78 (m, 2H), 3.52-3.37 (m, 4H), 3.14 (t, 2H), 2.27-2.00 (m, 6H), 1.68-1.56 (m, 2H).

Example 214

N-(1-(2-Chloropyridin-4-yl)piperidin-4-yl)-8-(4-(trifluoromethyl)piperidin-1-yl)-[1,2,4]triazolo[1,5-a]pyridin-2-amine

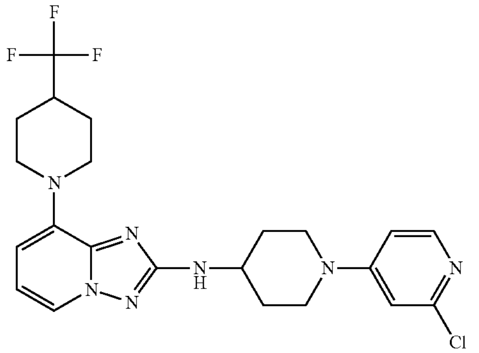 [SMILES: FC(F)(F)C1CCN(c2cccn3nc(NC4CCN(c5ccnc(Cl)c5)CC4)nc23)CC1]

Prepared in analogy to example 213, starting from 2-nitro-pyridin-3-yl trifluoro-methanesulfonate (example 213b) and 4-trifluoromethylpiperidine hydrochloride. The residue was purified by preparative HPLC to afford the title compound as a colourless gum (yield: 37%).

MS ISP (m/e): 430.2 [(M+H)$^+$].

$^1$H NMR ($CDCl_3$, 400 MHz): δ (ppm)=8.02 (dd, 1H), 7.98 (dd, 1H), 6.75-6.66 (m, 3H), 6.60 (dd, 1H), 5.01-4.79 (m, 2H), 3.95-3.86 (m, 1H), 3.85-3.78 (m, 2H), 3.52-3.37 (m, 4H), 3.14 (t, 2H), 2.27-2.00 (m, 6H), 1.68-1.56 (m, 2H).

Example 215

(S)-6-(2-(1-(2-Chloropyridin-4-yl)piperidin-4-ylamino)-[1,2,4]triazolo[1,5-a]pyridin-8-yl)-6-aza-spiro[2.5]octan-4-ol

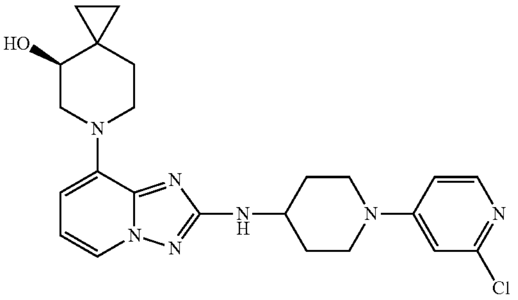 [SMILES: O[C@@H]1CN(c2cccn3nc(NC4CCN(c5ccnc(Cl)c5)CC4)nc23)CCC12CC2]

Prepared in analogy to example 213, starting from 2-nitro-pyridin-3-yl trifluoro-methanesulfonate (example 213b) and (S)-6-azaspiro[2.5]octan-4-ol hydrochloride (US2009/23713A1). The residue was purified by preparative HPLC to afford the title compound as a colourless gum (yield: 30%).

MS ISP (m/e): 454.2 [(M+H)$^+$].

$^1$H NMR ($CDCl_3$, 400 MHz): δ (ppm)=8.01 (d, 1H), 7.95 (dd, 1H), 6.75-6.70 (m, 2H), 6.66 (d, 1H), 6.58 (dd, 1H), 5.05 (bs, 1H), 4.03 (dd, 1H), 3.93-3.76 (m, 3H), 3.60 (d, 1H), 3.19-3.04 (m, 5H), 2.44 (td, 1H), 2.22 (d, 2H), 1.60 (qd, 2H), 0.98 (dt, 1H), 0.73-0.66 (m, 1H), 0.47-0.37 (m, 3H).

Example 216

N-(1-(2-Chloropyridin-4-yl)piperidin-4-yl)-8-(4,4-difluoropiperidin-1-yl)-[1,2,4]triazolo[1,5-a]pyridin-2-amine

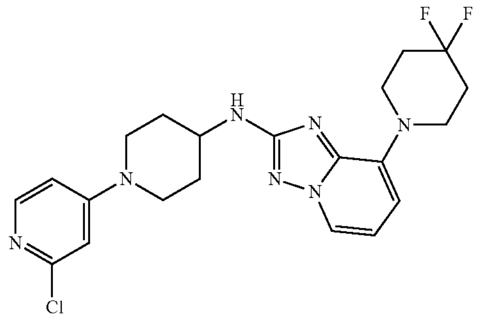 [SMILES: FC1(F)CCN(c2cccn3nc(NC4CCN(c5ccnc(Cl)c5)CC4)nc23)CC1]

Prepared in analogy to example 213, starting from 2-nitro-pyridin-3-yl trifluoro-methanesulfonate (example 213b) and 4,4-difluoropiperidine hydrochloride. The residue was purified by preparative HPLC to afford the title compound as a colourless gum (yield: 37%).

MS ISP (m/e): 488.1 [(M+H)$^+$].

$^1$H NMR ($CDCl_3$, 400 MHz): δ (ppm)=8.05-8.0 (m, 2H), 6.80-6.74 (m, 2H), 6.68 (d, 1H), 6.61 (dd, 1H), 5.82 (brs, 1H), 3.94-3.85 (m, 1H), 3.80 (dt, 2H), 3.42 (t, 4H), 3.18 (dd, 2H), 2.29-2.17 (m, 6H), 1.71-1.60 (m, 2H).

Example 217

8-(2-Chloro-4-fluorophenyl)-2-(1-(2-chloropyridin-4-yl)piperidin-4-ylamino)-5,6,7,8-tetrahydro-[1,2,4]triazolo[1,5-a]pyridin-6-ol

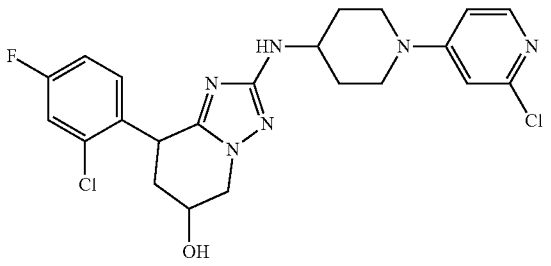 [SMILES: OC1CC(c2ccc(F)cc2Cl)c2nc(NC3CCN(c4ccnc(Cl)c4)CC3)nn2C1]

a) Methyl 2-(2-chloro-4-fluorophenyl)pent-4-enoate

To a chilled (−78° C.) solution of lithium hexamethydisilylazide (27.1 mL, 1 M in THF, 27.1 mmol) in THF (30 mL) was added methyl 2-(2-chloro-4-fluorophenyl)acetate (5 g, 24.7 mmol) in THF (10 mL). After stirring for 0.5 hour, allyl bromide (2.4 mL, 27.1 mmol) was added in a single portion, the cooling bath removed and the reaction allowed to warm to room temperature (0.5 hour). The reaction was diluted with ethyl acetate, washed with water, brine, and the organic phase was dried with sodium sulfate and the solvent was evaporated in vacuo. The residue was purified by column chromatography on silica gel using n-heptane/ethyl acetate (v/v 1:0 to 9:1) as eluent. The title compound was obtained as a colourless liquid (6.0 g, 100%).

MS ISP (m/e): 264.3 [(M+Na)$^+$].

$^1$H NMR ($CDCl_3$, 400 MHz): δ (ppm)=7.36 (dd, 1H), 7.13 (dd, 1H), 6.97 (td, 1H), 5.77-5.67 (m, 1H), 5.05 (d, 1H), 5.01 (d, 1H), 4.20 (t, 1H), 3.68 (s, 3H), 2.83-2.74 (m, 1H), 2.54-2.46 (qn, 1H).

b) Methyl 2-(2-chloro-4-fluorophenyl)-3-(oxiran-2-yl)propanoate

To an ice-cold solution of methyl 2-(2-chloro-4-fluorophenyl)pent-4-enoate (6.0 g, 24.7 mmol) in methylene chloride (50 mL) was added meta-chloroperbenzoic acid (6.7 g, 70% purity, 27.2 mmol). The cooling bath removed and the reaction stirred for 16 hours. The reaction was filtered, the filtrate washed repeatedly with 1 N sodium hydroxide, dried with sodium sulfate and the solvent was evaporated in vacuo. The residue was purified by column chromatography on silica gel using n-heptane/ethyl acetate (v/v 1:9 to 2:8) as eluent. The title compound was obtained as a colourless liquid (5.1 g, 80%).

MS ISP (m/e): 259.1 [(M+H)$^+$].

$^1$H NMR ($CDCl_3$, 400 MHz): δ (ppm)=7.37-7.30 (m, 1H), 7.17-7.13 (m, 1H), 7.02-6.96 (m, 1H), 4.34-4.28 (m, 1H), 3.70 (s, 3H), 3.01-2.96 (m, 0.5H), 2.86-2.80 (m, 0.5H), 2.76 (t, 0.5H), 2.70 (t, 0.5H), 2.51 (dd, 0.5H), 2.41 (dd, 0.5H), 2.37 (dt, 0.5H), 2.25 (dt, 0.5H), 2.06 (dt, 0.5H), 1.85 (dt, 0.5H).

c) tert-Butyl (3SR,5SR)-3-(2-chloro-4-fluorophenyl)-5-hydroxy-2-oxopiperidin-1-ylcarbamate To a solution of methyl 2-(2-chloro-4-fluorophenyl)-3-(oxiran-2-yl)propanoate (4.56 g, 17.6 mmol) in 2-propanol (20 mL) was added tert-butyl carbazate (2.3 g, 17.6 mmol) and the reaction heated to reflux for 16 hours. The reaction was then concentrated to dryness, redissolved in toluene (20 mL) and 1,5,7-triazobicylo(4.4.0)dec-5-ene (0.6 g, 4.4 mmol) was added and the mixture heated to reflux for 3 hours. The reaction was then diluted with ethylacetate, washed with 1 N HCl, dried with sodium sulfate and the solvent was evaporated in vacuo. The residue was recystallised from hot ethyl acetate to afford the title compound was obtained as a colourless solid (1.7 g, 26%). The mother liquor contained the trans isomer.

MS ISP (m/e): 359.1 [(M+H)$^+$].

$^1$H NMR ($CDCl_3$, 400 MHz): δ (ppm)=7.23 (dd, 1H), 7.12 (dd, 1H), 6.98 (td, 1H), 6.90 (br, 1H), 4.39-4.35 (m, 2H), 4.05 (dd, 1H), 3.67 (d, 1H), 2.32-2.27 (m, 1H), 2.17-2.05 (m, 1H), 1.48 (s, 9H).

d) (3SR,5SR)-1-Amino-3-(2-chloro-4-fluorophenyl)-5-hydroxypiperidin-2-one

To tert-butyl (3SR,5SR)-3-(2-chloro-4-fluorophenyl)-5-hydroxy-2-oxopiperidin-1-ylcarbamate (1.67 g, 4.7 mmol) was added HCl (10 mL, 4 N in dioxane) and the reaction stirred for 1 hour. The reaction was then concentrated to dryness, redissolved in dichloromethane, washed with sodium hydrogen carbonate, dried with sodium sulfate and the solvent was evaporated in vacuo afford the title compound was obtained as a light yellow crystalline solid (1.11 g, 92%). MS ISP (m/e): 259.1 [(M+H)$^+$].

$^1$H NMR ($CDCl_3$, 400 MHz): δ (ppm)=7.19-7.12 (m, 2H), 6.99-6.94 (m, 1H), 4.36-4.30 (m, 2H), 3.89 (dd, 1H), 3.62 (dd, 1H), 2.23-2.17 (m, 2H).

e) tert-Butyl 4-(3-((3SR,5SR)-3-(2-chloro-4-fluorophenyl)-5-hydroxy-2-oxopiperidin-1-yl)thioureido)piperidine-1-carboxylate To a solution of (3SR,5SR)-1-amino-3-(2-chloro-4-fluorophenyl)-5-hydroxypiperidin-2-one (0.8 g, 2.9 mmol) in dimethylacetamide (1 mL) was added 4-isothiocyanatopiperidine-1-carboxylic acid tert-butyl ester (0.8 g, 3.2 mmol, US2006/14958A1) and the reaction stirred for 2 hours at 80° C. The reaction was diluted with ethyl acetate, washed with water, brine, dried with sodium sulfate and the solvent was evaporated in vacuo. The product was triturated from dichloromethane by addition of heptane to afford the title compound as a colourless powder (1.2 g, 83%). MS ISP (m/e): 501.2 [(M+H)$^+$].

$^1$H NMR (DMSO-$D_6$, 400 MHz): δ (ppm)=7.45-40 (m, 2H), 7.20 (td, 1H), 4.30-4.15 (m, 4H), 3.92-3.79 (m, 3H), 2.93-2.82 (m, 2H), 2.16-2.00 (m, 2H), 1.90-1.80 (m, 2H), 1.41 (s, 9H), 1.37-1.27 (m, 2H).

f) tert-Butyl 4-(((3SR,5SR)-3-(2-chloro-4-fluorophenyl)-5-hydroxy-2-oxopiperidin-1-ylimino)(methylthio)methylamino)piperidine-1-carboxylate To a solution of tert-butyl 4-(3-((3SR,5SR)-3-(2-chloro-4-fluorophenyl)-5-hydroxy-2-oxopiperidin-1-yl)thioureido) piperidine-1-carboxylate (1.2 g, 2.4 mmol) in DMF (5 mL) was added iodomethane (0.2 mL, 3.6 mmol) and the reaction heated to 90° C. for 15 minutes. The reaction was evaporated to dryness, redissolved in ethyl acetate, washed with saturated sodium hydrogen carbonate, water, brine, dried with sodium sulfate and the solvent was evaporated in vacuo. The title compound, a mixture of geometrical isomers, was used crude in the next step (1.2 g, 99%).

MS ISP (m/e): 515.2 [(M+H)$^+$].

g) tert-Butyl 4-(8-(2-chloro-4-fluorophenyl)-6-hydroxy-5,6,7,8-tetrahydro-[1,2,4]triazolo[1,5-a]pyridin-2-ylamino)piperidine-1-carboxylate To a solution of tert-butyl 4-(((3SR,5SR)-3-(2-chloro-4-fluorophenyl)-5-hydroxy-2-oxopiperidin-1-ylimino)(methylthio)methylamino)piperidine-1-carboxylate (1.1 g, 2.1 mmol) in DMF (5.5 mL) was added sodium azide (0.2 g, 3.2 mmol) and the reaction heated to 100° C. for 48 hours. The reaction was then concentrated to dryness, redissolved in ethyl acetate, washed with water, brine, dried with sodium sulfate and the solvent was evaporated. The residue was redissolved in THF, trimethylphosphine added (2.1 mL, 1 M in toluene, 2.1 mmol) and the reaction heated to 160° C. in a micowave for 12 hours. The reaction was then concentrated in vacuo and the residue was purified by column chromatography on silica gel using ethyl acetate/MeOH (v/v 1:0 to 9:1) as eluent. The title compound was obtained as a light yellow foam (0.2 g, 20%), an inseparable 1:1 mixture of diasteriomers.

MS ISP (m/e): 466.2 [(M+H)$^+$]. $^1$H NMR ($CDCl_3$, 400 MHz): δ (ppm)=7.15-7.06 (m, 2H), 6.97-6.93 (m, 1H), 4.77-3.53 (m, 8H), 2.95-2.89 (m, 2H), 2.55-2.36 (m, 1H), 2.03-1.99 (m, 2H), 1.45 (s, 9H), 1.37-1.27 (m, 2H).

h) 8-(2-Chloro-4-fluorophenyl)-2-(1-(2-chloropyridin-4-yl)piperidin-4-ylamino)-5,6,7,8-tetrahydro-[1,2,4]triazolo[1,5-a]pyridin-6-ol To tert-butyl 4-(8-(2-chloro-4-fluorophenyl)-6-hydroxy-5,6,7,8-tetrahydro-[1,2,4]triazolo[1,5-a]pyridin-2-ylamino)piperidine-1-carboxylate (0.05 g, 0.1 mmol) was added HCl (3 mL, 4 N in dioxane) and the reaction stirred for 0.5 hour. The reaction was then concentrated to dryness, the residue redissolved in dimethylacetamide (0.5 mL), triethylamine added until the mixture was basic, followed by the addition of 2-chloro-4-fluoropyridine (0.04 g, 0.3 mmol) and the mixture heated to 80° C. for 1 hour. The reaction was evaporated to dryness, redissolved in ethyl acetate, washed with saturated sodium hydrogen carbonate, water, brine, dried with sodium sulfate and the solvent was evaporated in vacuo. The residue was purified by column chromatography on silica gel using ethyl acetate/MeOH (v/v 1:0 to 95:5) as eluent. The title compound was obtained as a light yellow gum (0.04 g, 76%), an inseparable 1:1 mixture of diasteriomers. MS ISP (m/e): 477.1 [(M+H)$^+$].

$^1$H NMR ($CDCl_3$, 400 MHz): δ (ppm)=7.98 (d, 1H), 7.15-7.06 (m, 2H), 6.98-6.92 (m, 1H), 6.64 (d, 1H), 6.56 (dd, 1H), 4.78-3.65 (m, 8H), 3.12-3.03 (m, 2H), 2.56-2.38 (m, 1H), 2.20-2.12 (m, 2H), 1.55-1.43 (m, 2H).

Example 218

8-(3-tert-Butylphenyl)-N-(1-(2-chloropyridin-4-yl)piperidin-4-yl)-[1,2,4]triazolo[1,5-a]pyridin-2-amine

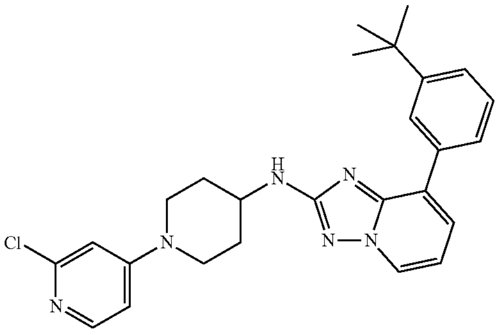 [SMILES: CC(C)(C)c1cccc(-c2cccn3nc(NC4CCN(c5ccnc(Cl)c5)CC4)nc23)c1]

Prepared in analogy to example 1 step h) starting from 1-(2-chloropyridin-4-yl)piperidin-4-one (see example 232b) and 8-(3-tert-butylphenyl)-[1,2,4]triazolo[1,5-a]pyridin-2-amine. The latter compound can be prepared in analogy to example 1 steps d-f) starting from 2-amino-6-bromo-pyridine and 3-tert-butylphenylboronic acid (EP2243785A1). The title compound was obtained as a colourless foam. MS ISP (m/e): 461.2 [(M+H)$^+$].

$^1$H NMR ($CDCl_3$, 400 MHz): (ppm)=8.30 (dd, 1H), 8.02-7.99 (m, 2H), 7.75 (dt, 1H), 7.53 (d, 1H), 7.45-7.40 (m, 2H), 6.90 (t, 1H), 6.68 (d, 1H), 6.60 (dd, 1H), 4.52 (d, 1H), 4.01-3.91 (m, 1H), 3.84 (dt, 2H), 3.12 (td, 2H), 2.30-2.22 (m, 2H), 1.63-1.55 (m, 2H), 1.39 (s, 9H).

Example 219

[4-(3,4-Difluoro-phenyl)-4,5,6,7-tetrahydro-[1,2,4]triazolo[1,5-a]pyrimidin-2-yl]-[1-(6-methyl-pyrimidin-4-yl)-piperidin-4-yl]-amine

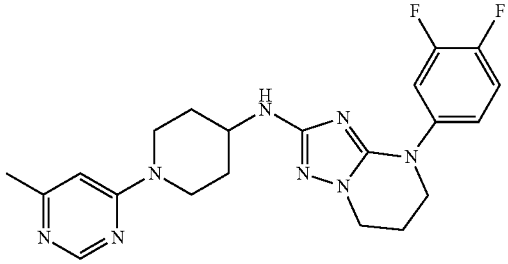 [SMILES: Cc1cc(N2CCC(Nc3nc4n(n3)CCCN4c3ccc(F)c(F)c3)CC2)ncn1]

a) (Z)-Phenyl N'-cyano-N-(3,4-difluorophenyl)carbamimidate

To a solution of 3,4-difluoroaniline (646 mg, 5 mmol) in isopropanol (10 mL) was added diphenyl cyanocarbonimidate (1.19 g, 5 mmol) and the suspension was stirred at room temperature over night. The precipitate was filtered off, washed with isopropanol and dried under reduced pressure to yield the title compound as a white solid (1.18 g, 86%).

MS ISP (m/e): 274.1 (100) [(M+H)$^+$].

$^1$H NMR (DMSO-$D_6$, 300 MHz): δ (ppm)=10.92 (s, 1H), 7.65 (m, 1H), 7.43 (m, 3H), 7.29 (m, 4H).

b) (Z)-Phenyl N'-cyano-N-(3,4-difluorophenyl)-N-(3-(tetrahydro-2H-pyran-2-yloxy)propyl)carbamimidate To a solution of (Z)-phenyl N'-cyano-N-(3,4-difluorophenyl)carbamimidate (286 mg, 1.05 mmol) and 2-(3-bromopropoxy)tetrahydro-2H-pyran (369 mg, 277 μL, 1.57 mmol) in DMF (10.5 mL) was added at room temperature under an atmosphere of nitrogen potassium carbonate (289 mg, 2.09 mmol). The suspension was heated to 85° C. over night. Additional 2-(3-bromopropoxy)tetrahydro-2H-pyran (140 μL, 0.8 mmol) and potassium carbonate (145 mg, 1.05 mmol) were added and the reaction was heated for 5 hours to 85° C. Water was added and the reaction was extracted twice with diethyl ether. The combined organic layers were washed with water and with saturated aqueous sodium chloride solution, dried over sodium sulfate, filtered and the solvent was evaporated under reduced pressure. The title compound was obtained as a light yellow viscous oil (202 mg, 46%) after column chromatography on silica gel using a gradient of heptane/ethyl acetate 4:1 to 1:1 (v/v) as eluent.

MS ISP (m/e): 332.1 (100) [(M−THP+H)$^+$], 416.3 (5) [(M+H)$^+$].

$^1$H NMR (DMSO-$D_6$, 300 MHz): δ (ppm)=7.38 (t, 2H), 7.26-7.16 (m, 3H), 7.05 (m, 3H), 4.52 (t, 1H), 3.97 (t, 2H), 3.85 (m, 2H), 3.48 (m, 2H), 2.00 (pent, 2H), 1.79 (m, 1H), 1.68 (m, 1H), 1.55 (m, 4H)).

c) N3-(3,4-Difluorophenyl)-N3-(3-(tetrahydro-2H-pyran-2-yloxy)propyl)-4H-1,2,4-triazole-3,5-diamine To a solution of (Z)-phenyl N'-cyano-N-(3,4-difluorophenyl)-N-(3-(tetrahydro-2H-pyran-2-yloxy)propyl)carbamimidate (73 mg, 176 μmol) in methanol (0.5 mL) was added hydrazine hydrate 25% in water (35.2 mg, 34.8 μl, 176 μmol). The reaction was stirred at room temperature over night. The solvent was evaporated under reduced pressure and the residue purified by column chromatography on silica gel using methylene chloride/methanol 19:1 (v/v) as eluent. The title compound was obtained as a light yellow viscous oil (46 mg, 74%).

MS ISP (m/e): 354.2 (25) [$(M+H)^+$], 270.3 (100) [$(M-THP+H)^+$].

$^1$H NMR (DMSO-$D_6$, 300 MHz): δ (ppm)=7.56 (m, 1H), 7.26 (q, 1H), 7.16 (m, 1H), 5.96 (br s, 2H), 4.49 (t, 1H), 3.87 (m, 2H), 3.37 (m, 2H), 1.84 (m, 2H), 1.74 (m, 1H), 1.62 (m, 2H), 1.45 (m, 4H).

d) 3-((5-Amino-4H-1,2,4-triazol-3-yl)(3,4-difluorophenyl)amino)propan-1-ol

To a solution of N3-(3,4-difluorophenyl)-N3-(3-(tetrahydro-2H-pyran-2-yloxy)propyl)-4H-1,2,4-triazole-3,5-diamine (43 mg, 122 μmol) in methanol (1 mL) was added 2 N aqueous hydrogen chloride solution. The solution was stirred at room temperature over night. The solvent was evaporated under reduced pressure and the residue was taken up in saturated aqueous sodium hydrogen carbonate solution. It was extracted twice with ethyl acetate. The combined organic layers were washed with saturated aqueous sodium hydrogen carbonate solution and with saturated aqueous sodium chloride solution, dried over sodium sulfate, filtered and the solvent was evaporated under reduced pressure to yield the title compound as a white solid (34 mg, quant) without further purification. MS ISP (m/e): 270.3 (100) [$(M+H)^+$].

$^1$H NMR (DMSO-$D_6$, 300 MHz): δ (ppm)=7.56 (m, 1H), 7.26 (q, 1H), 7.15 (m, 1H), 6.00 (br s, 2H), 4.67 (t, 1H), 3.87 (t, 1H), 3.42 (q, 2H), 1.71 (t, 2H).

e) 4-(3,4-Difluoro-phenyl)-4,5,6,7-tetrahydro-[1,2,4]triazolo[1,5-a]pyrimidin-2-ylamine To a solution of 3-((5-amino-4H-1,2,4-triazol-3-yl)(3,4-difluorophenyl)amino)propan-1-ol (31 mg, 115 μmol) in tetrahydrofurane (1.15 mL) was added at 0° C. under an atmosphere of nitrogen triphenylphosphine (45.3 mg, 173 μmol). The reaction was stirred for 15 minutes and then DEAD (31.0 mg, 28.2 μL, 173 μmol) was added. The reaction was stirred for 30 minutes at 0° C. and then at room temperature over night. The same procedure was repeated with additional triphenylphosphine (45.3 mg, 173 μmol) and DEAD (31.0 mg, 28.2 μL, 173 μmol). Water was added and the reaction was extracted twice with ethyl acetate. The combined organic layers were washed with saturated aqueous sodium hydrogen carbonate solution and with saturated aqueous sodium chloride solution, dried over sodium sulfate, filtered and the solvent was evaporated under reduced pressure. The title compound was obtained as a colorless solid (14 mg, 48%) after column chromatography on silica gel using a gradient from methylene chloride to methylene chloride/methanol 19:1 (v/v) as eluent. MS ISP (m/e): 252.3 (100) [$(M+H)^+$].

$^1$H NMR ($CDCl_3$, 300 MHz): δ (ppm)=7.82 (m, 1H), 7.41-7.33 (m, 2H), 4.00 (t, 2H), 3.93 (b s, 2H), 3.72 (t, 2H), 2.30 (pent, 2H).

f) 4-(3,4-Difluorophenyl)-N-(1-(6-methylpyrimidin-4-yl)piperidin-4-yl)-4,5,6,7-tetrahydro-[1,2,4]triazolo[1,5-a]pyrimidin-2-amine To a solution of 4-(3,4-difluorophenyl)-4,5,6,7-tetrahydro-[1,2,4]triazolo[1,5-a]pyrimidin-2-amine (41 mg, 163 μmol) in tetrahydrofurane (1 mL) was added under an atmosphere of nitrogen hexachloroethane (61.0 mg, 245 μmol), triethylamine (49.5 mg, 68.2 μL, 490 μmol) and a 1 M solution of trimethylphosphine in toluene (245 μL, 245 μmol). The suspension was stirred for 30 minutes at room temperature. 1-(6-Methylpyrimidin-4-yl)piperidin-4-one (see example 93b, 46.8 mg, 245 μmol) dissolved in tetrahydrofurane (0.5 mL) was added and the yellow suspension was heated to 150° C. for 30 minutes. A 1 M solution of borane tetrahydrofurane complex in methylene chloride (490 μL, 490 μmol) was added and the reaction was heated to 100° C. for one hour. The reaction was diluted with water and extracted twice with ethyl acetate. The combined organic layers were washed with saturated aqueous sodium chloride solution, dried over sodium sulfate, filtered and the solvent was evaporated. The title compound was obtained as a colorless solid (14 mg, 20%) after column chromatography on silica gel using a gradient from methylene chloride to methylene chloride/methanol 19:1 (v/v) as eluent and subsequent purification with preparative HPCL. MS ISP (m/e): 427.3 (100) [$(M+H)^+$], 176.3 (81).

$^1$H NMR ($CDCl_3$, 300 MHz): δ (ppm)=8.50 (s, 1H), 7.38 (m, 1H), 7.14-7.09 (m, 2H), 6.38 (s, 1H), 4.30 (br d, 2H), 4.03 (t, 2H), 3.91 (d, 1H), 3.73 (t, 2H), 3.71 (m, 1H), 3.14 (mt, 2H), 2.35 (s, 3H), 2.32 (m, 2H), 2.15 (br d, 2H), 1.41 (mq, 2H).

Example 220

N-(1-(2-Methoxypyridin-4-yl)piperidin-4-yl)-8-(2,3,4-trifluorophenyl)-5,6,7,8-tetrahydro-[1,2,4]triazolo[1,5-a]pyridin-2-amine

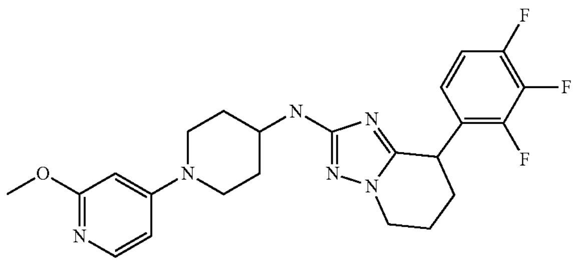 [SMILES: COc1cc(N2CCC(Nc3nc4n(n3)CCCC4c3ccc(F)c(F)c3F)CC2)ccn1]

a) 8-(2-Methoxypyridin-4-yl)-1,4-dioxa-8-azaspiro[4.5]decane

A solution of palladium(II) acetate (62.5 mg, 279 μmol) and 2-(dicyclohexylphosphino) biphenyl (201 mg, 557 μmol) in dioxane (1.5 mL) was stirred under argon at room temperature for 10 minutes, then added to a solution of 4-chloro-2-methoxypyridine (500 mg, 3.48 mmol), 1,4-dioxa-8-azaspiro[4.5]decane (499 mg, 446 μL, 3.48 mmol) and sodium tert-butoxide (502 mg, 5.22 mmol) in dioxane (1.5 mL), degassed and argon bubbled through the reaction during 5 minutes. The reaction mixture was heated in the microwave to 130° C. for 30 minutes. The reaction mixture was filtered through dicalite, water was added to the filtrate and the aqueous phase was extracted three times with ethyl acetate. The combined organic layers were dried over $Na_2SO_4$ and the solvent was evaporated. The residue was purified by flash chromatography (silica gel, 70 g, 80% to 100% ethyl acetate in heptane). The title compound was obtained as brown oil (700 mg, 80%).

MS ISP (m/e): 251.2 (100) [$(M+H)^+$].

$^1H$ NMR ($CDCl_3$, 300 MHz): δ (ppm)=7.88-7.86 (m, 1H), 6.41-6.39 (m, 1H), 6.07-6.06 (m, 1H), 3.99 (s, 4H), 3.89 (s, 3H), 3.47-3.43 (m, 4H), 1.77-1.74 (m, 4H).

b) N-(1-(2-Methoxypyridin-4-yl)piperidin-4-yl)-8-(2,3,4-trifluorophenyl)-5,6,7,8-tetrahydro-[1,2,4]triazolo[1,5-a]pyridin-2-amine Prepared in analogy to example 93b-c employing 8-(2-methoxypyridin-4-yl)-1,4-dioxa-8-azaspiro[4.5]decane. The title compound was obtained as light yellow foam.

MS ISP (m/e): 459.4 (83) [$(M+H)^+$].

$^1H$ NMR ($CDCl_3$, 300 MHz): δ (ppm)=7.88-7.86 (m, 1H), 6.96-6.87 (m, 1H), 6.77-6.70 (m, 1H), 6.40-6.37 (m, 1H), 6.06-6.05 (m, 1H), 4.38-4.34 (m, 1H), 4.11-4.07 (m, 2H), 4.01-3.98 (m, 1H), 3.89 (s, 3H), 3.77-3.62 (m, 3H), 3.07-2.98 (m, 2H), 2.33-2.24 (m, 1H), 2.16-1.90 (m, 5H), 1.56-1.42 (m, 2H).

Example 221

[8-(2-Chloro-phenyl)-[1,2,4]triazolo[1,5-a]pyridin-2-yl]-[1-(3-methyl-[1,2,4]thiadiazol-5-yl)-piperidin-4-yl]-amine

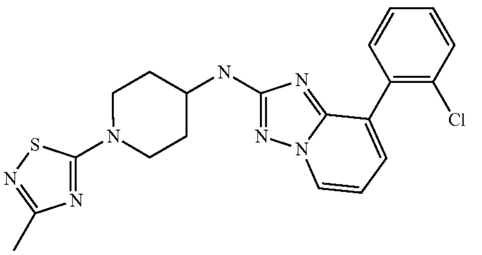 [SMILES: Cc1nsc(N2CCC(Nc3nc4c(-c5ccccc5Cl)cccn4n3)CC2)n1]

Prepared in analogy to example 66. The title compound was obtained as yellow foam.

MS ISP (m/e): 426.1/428.2 (100/47) [$(M+H)^+$].

$^1H$ NMR ($CDCl_3$, 300 MHz): δ (ppm)=8.38-8.35 (m, 1H), 7.54-7.49 (m, 2H), 7.42-7.35 (m, 3H), 6.93-6.88 (m, 1H), 4.63-4.60 (m, 1H), 3.94-3.85 (m, 3H), 3.39-3.30 (m, 2H), 2.41 (s, 3H), 2.27-2.22 (m, 2H), 1.70-1.61 (m, 2H).

Example 222

[8-(3-Dimethylamino-phenyl)-[1,2,4]triazolo[1,5-a]pyridin-2-yl]-[1-(3-methyl-[1,2,4]thiadiazol-5-yl)-piperidin-4-yl]-amine

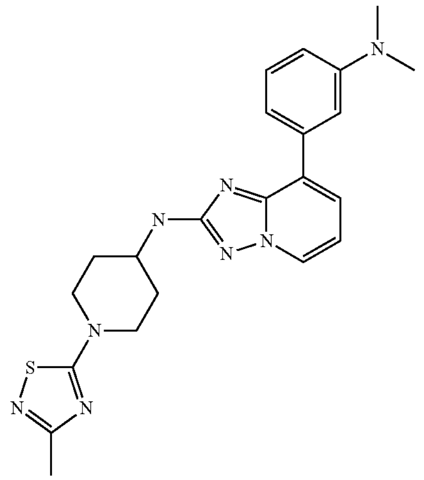 [SMILES: Cc1nsc(N2CCC(Nc3nc4c(-c5cccc(N(C)C)c5)cccn4n3)CC2)n1]

Prepared in analogy to example 1h employing 1-(3-methyl-[1,2,4]thiadiazol-5-yl)-piperidin-4-one (see example 1c) and 8-(3-dimethylamino-phenyl)-[1,2,4]triazolo[1,5-a]pyridin-2-ylamine (prepared in analogy to example 66a-c). The title compound was obtained as light yellow foam. MS ISP (m/e): 435.3 (100) [$(M+H)^+$].

$^1H$ NMR ($CDCl_3$, 300 MHz): δ (ppm)=8.30-8.28 (m, 1H), 7.55-7.52 (m, 1H), 7.36-7.32 (m, 2H), 7.22 (m, 1H), 6.91-6.86 (m, 1H), 6.80-6.78 (m, 1H), 4.57-4.54 (m, 1H), 4.00-3.87 (m, 3H), 3.38-3.30 (m, 2H), 3.01 (s, 6H), 2.42 (s, 3H), 2.29-2.23 (m, 2H), 1.72-1.62 (m, 2H).

Example 223

[8-(2-Fluoro-pyridin-4-yl)-[1,2,4]triazolo[1,5-a]pyridin-2-yl]-[1-(3-methyl-[1,2,4]thiadiazol-5-yl)-piperidin-4-yl]-amine

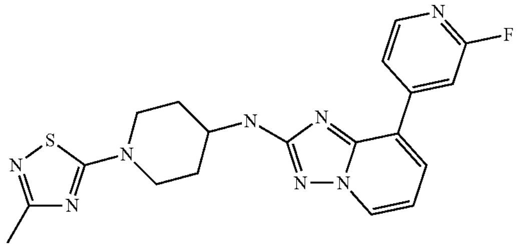 [SMILES: Cc1nsc(N2CCC(Nc3nc4c(-c5ccnc(F)c5)cccn4n3)CC2)n1]

Prepared in analogy to example 66. The title compound was obtained as light brown foam. MS ISP (m/e): 411.2 (100) [$(M+H)^+$].

$^1H$ NMR ($CDCl_3$, 300 MHz): δ (ppm)=8.43-8.40 (m, 1H), 8.34-8.32 (m, 1H), 7.84-7.81 (m, 1H), 7.73 (m, 1H), 7.70-7.67 (m, 1H), 6.98-6.94 (m, 1H), 4.62-4.60 (m, 1H), 4.01-3.90 (m, 3H), 3.42-3.32 (m, 2H), 2.42 (s, 3H), 2.31-2.25 (m, 2H), 1.75-1.66 (m, 2H).

Example 224

[8-(3,5-Bis-trifluoromethyl-phenyl)-5,6,7,8-tetrahydro-[1,2,4]triazolo[1,5-a]pyridin-2-yl]-[1-(6-methyl-pyrimidin-4-yl)-piperidin-4-yl]-amine

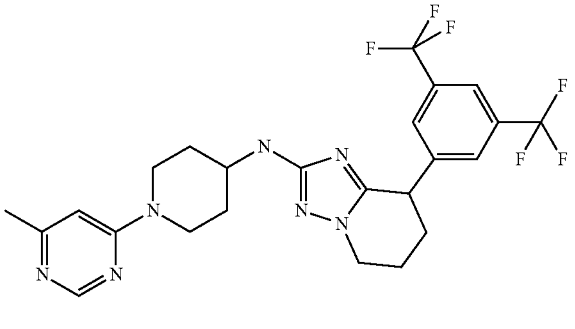 [SMILES: Cc1cc(N2CCC(Nc3nc4n(n3)CCCC4c3cc(C(F)(F)F)cc(C(F)(F)F)c3)CC2)ncn1]

Prepared in analogy to example 93. The title compound was obtained as light yellow foam. MS ISP (m/e): 526.4 (100) $[(M+H)^+]$.

$^1H$ NMR ($CDCl_3$, 300 MHz): δ (ppm)=8.49 (m, 1H), 7.79 (s, 1H), 7.65 (s, 2H), 6.38 (m, 1H), 4.28-4.23 (m, 3H), 4.16-4.00 (m, 3H), 3.79-3.68 (m, 1H), 3.17-3.07 (m, 2H), 2.35 (s, 3H), 2.41-2.32 (m, 1H), 2.17-1.92 (m, 5H), 1.51-1.34 (m, 2H).

Example 225

(8-Benzo[1,3]dioxol-5-yl-[1,2,4]triazolo[1,5-a]pyridin-2-yl)-[1-(3-methyl-[1,2,4]thiadiazol-5-yl)-piperidin-4-yl]-amine

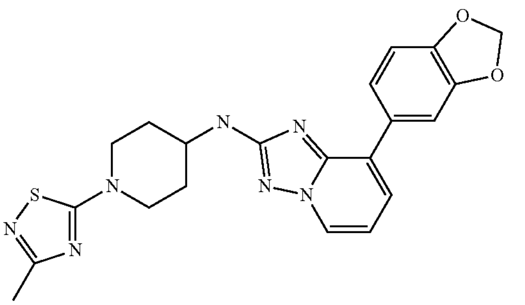 [SMILES: Cc1nsc(N2CCC(Nc3nc4c(-c5ccc6c(c5)OCO6)cccn4n3)CC2)n1]

Prepared in analogy to example 66. The title compound was obtained as yellow foam.

MS ISP (m/e): 436.3 (100) $[(M+H)^+]$.

$^1H$ NMR ($CDCl_3$, 300 MHz): δ (ppm)=8.29-8.27 (m, 1H), 7.49 (m, 1H), 7.46-7.41 (m, 2H), 6.94-6.91 (m, 1H), 6.89-6.85 (m, 1H), 6.02 (s, 2H), 4.51-4.49 (m, 1H), 4.00-3.88 (m, 3H), 3.41-3.32 (m, 2H), 2.42 (s, 3H), 2.29-2.24 (m, 2H), 1.72-1.59 (m, 2H).

Example 226

[8-(2-Chloro-5-trifluoromethyl-phenyl)-[1,2,4]triazolo[1,5-a]pyridin-2-yl]-[1-(3-methyl-[1,2,4]thiadiazol-5-yl)-piperidin-4-yl]-amine

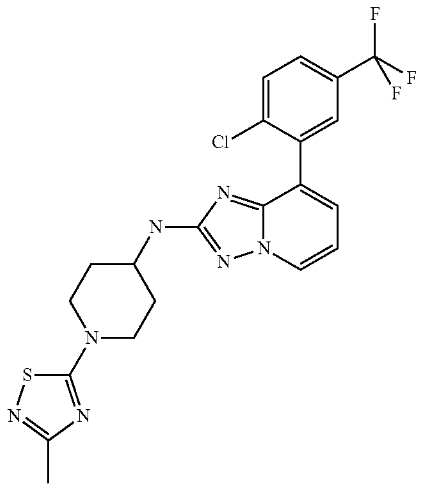 [SMILES: Cc1nsc(N2CCC(Nc3nc4c(-c5cc(C(F)(F)F)ccc5Cl)cccn4n3)CC2)n1]

a) (8-Bromo-[1,2,4]triazolo[1,5-a]pyridin-2-yl)-[1-(3-methyl-[1,2,4]thiadiazol-5-yl)-piperidin-4-yl]-amine To a suspension of 8-bromo-[1,2,4]triazolo[1,5-a]pyridin-2-amine (see example 66b, 80 mg, 376 μmol) and hexachloroethane (133 mg, 563 μmol) under argon in dry THF (3 mL) was added triethylamine (114 mg, 157 μL, 1.13 mmol) followed by trimethylphosphine (1 M in THF, 563 μL, 563 μmol). The reaction mixture was stirred at room temperature for 0.5 hours, then 1-(3-methyl-1,2,4-thiadiazol-5-yl)piperidin-4-one (88.9 mg, 451 μmol) was added and the mixture was heated in the microwave to 150° C. for 30 minutes. Further 1-(3-methyl-1,2,4-thiadiazol-5-yl)piperidin-4-one (40 mg, 188 μmol) was added and heated to 150° C. for another 30 minutes. To the reaction mixture $NaBH_4$ (56.8 mg, 1.5 mmol) and EtOH (2.0 mL) were added and heated to 65° C. for 1 hour. Further $NaBH_4$ (56.8 mg, 1.5 mmol) was added and stirred at 65° C. for another hour. Further $NaBH_4$ (56.8 mg, 1.5 mmol) was added and the reaction was stirred at 65° C. for 1 hour. The reaction mixture was extracted with $CH_2Cl_2$ and water, the organic layers were combined, dried over $Na_2SO_4$, filtered and the solvents were evaporated.

The residue was purified by flash chromatography (silica gel, 50 g, 0% to 15% $MeOH/NH_4OH$ (9:1) in dichloromethane). The title compound was obtained as white foam (140 mg, 95%).

MS ISP (m/e): 394.1/395.9 (100/98) $[(M+H)^+]$.

$^1H$ NMR ($CDCl_3$, 300 MHz): δ (ppm)=8.30-8.27 (m, 1H), 7.62-7.59 (m, 1H), 6.73-6.69 (m, 1H), 4.61-4.59 (m, 1H), 3.98-3.87 (m, 3H), 3.40-3.31 (m, 2H), 2.42 (s, 3H), 2.27-2.22 (m, 2H), 1.73-1.59 (m, 2H).

b) [8-(2-Chloro-5-trifluoromethyl-phenyl)-[1,2,4]triazolo[1,5-a]pyridin-2-yl]-[1-(3-methyl-[1,2,4]thiadiazol-5-yl)-piperidin-4-yl]-amine Prepared in analogy to example 66c employing (8-bromo-[1,2,4]triazolo[1,5-a]pyridin-2-yl)-[1-(3-methyl-[1,2,4]thiadiazol-5-yl)-piperidin-4-yl]-amine and 2-chloro-5-(trifluoromethyl)-phenyl boronic acid. The title compound was obtained as light yellow foam.

MS ISP (m/e): 494.3/496.2 (100/41) $[(M+H)^+]$.

$^1H$ NMR ($CDCl_3$, 300 MHz): δ (ppm)=8.41-8.38 (m, 1H), 7.81 (m, 1H), 7.67-7.60 (m, 2H), 7.44-7.41 (m, 1H), 6.95-6.90 (m, 1H), 4.55-4.52 (m, 1H), 3.92-3.85 (m, 3H), 3.39-3.29 (m, 2H), 2.41 (s, 3H), 2.28-2.22 (m, 2H), 1.72-1.59 (m, 2H).

Example 227

[1-(3-Methyl-[1,2,4]thiadiazol-5-yl)-piperidin-4-yl]-(6-phenyl-[1,2,4]triazolo[1,5-a]pyridin-2-yl)-amine

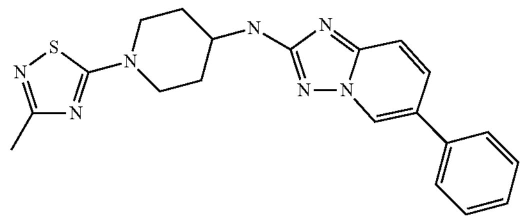 [SMILES: Cc1nsc(N2CCC(Nc3nc4ccc(-c5ccccc5)cn4n3)CC2)n1]

Prepared in analogy to example 66 starting with 5-bromopyridin-2-amine in step a). The title compound was obtained as orange solid.

MS ISP (m/e): 392.2 (40) [(M+H)$^+$].

$^1$H NMR ($CDCl_3$, 300 MHz): δ (ppm)=8.53 (m, 1H), 7.67-7.63 (m, 1H), 7.57-7.40 (m, 6H), 4.50-4.47 (m, 1H), 4.03-3.89 (m, 3H), 3.41-3.32 (m, 2H), 2.42 (s, 3H), 2.31-2.25 (m, 2H), 1.74-1.61 (m, 2H).

Example 228

[8-(3,5-Bis-trifluoromethyl-phenyl)-5,6,7,8-tetrahydro-[1,2,4]triazolo[1,5-a]pyridin-2-yl]-(2'-methoxy-3,4,5,6-tetrahydro-2H-[1,4']bipyridinyl-4-yl)-amine

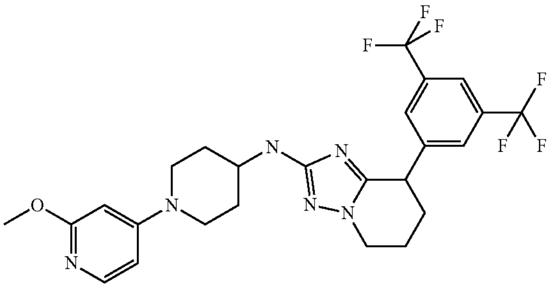 [SMILES: COc1cc(N2CCC(Nc3nc4n(n3)CCCC4c3cc(C(F)(F)F)cc(C(F)(F)F)c3)CC2)ccn1]

Prepared in analogy to example 220. The title compound was obtained as light yellow foam. MS ISP (m/e): 541.3 (100) [(M+H)$^+$].

$^1$H NMR ($CDCl_3$, 300 MHz): δ (ppm)=7.90-7.88 (m, 1H), 7.81 (s, 1H), 7.63 (s, 2H), 6.42-6.39 (m, 1H), 6.05-6.04 (m, 1H), 4.27-4.22 (m, 1H), 4.16-4.12 (m, 2H), 3.90 (s, 3H), 3.78-3.65 (m, 3H), 3.12-3.02 (m, 2H), 2.40-2.33 (m, 1H), 2.21-1.92 (m, 5H), 1.61-1.46 (m, 2H).

Example 229

[8-(3,5-Bis-trifluoromethyl-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine

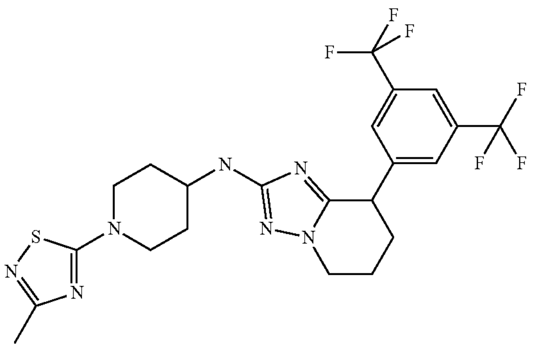 [SMILES: Cc1nsc(N2CCC(Nc3nc4n(n3)CCCC4c3cc(C(F)(F)F)cc(C(F)(F)F)c3)CC2)n1]

Prepared in analogy to example 1. The title compound was obtained as white foam.

MS ISP (m/e): 532.0 (57) [(M+H)$^+$].

$^1$H NMR ($CDCl_3$, 300 MHz): (ppm)=7.80 (m, 1H), 7.64 (m, 2H), 4.32 (br, 1H), 4.27-4.23 (m, 1H), 4.16-4.12 (m, 2H), 3.87-3.81 (m, 2H), 3.76-3.67 (m, 1H), 3.35-3.25 (m, 2H), 2.40 (s, 3H), 2.38-2.33 (m, 1H), 2.19-1.91 (m, 5H), 1.67-1.52 (m, 2H).

Example 230

[8-(4-Dimethylamino-phenyl)-[1,2,4]triazolo[1,5-a]pyridin-2-yl]-[1-(3-methyl-[1,2,4]thiadiazol-5-yl)-piperidin-4-yl]-amine

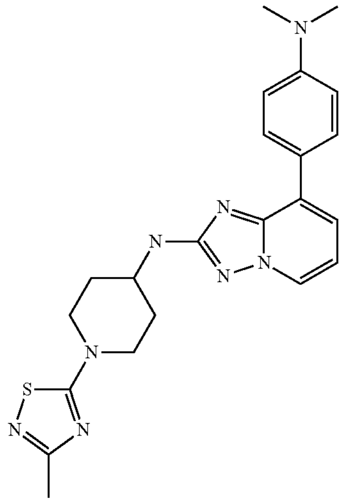 [SMILES: Cc1nsc(N2CCC(Nc3nc4c(-c5ccc(N(C)C)cc5)cccn4n3)CC2)n1]

Prepared in analogy to example 1h employing 1-(3-methyl-[1,2,4]thiadiazol-5-yl)-piperidin-4-one (see example 1c) and 8-(4-dimethylamino-phenyl)-[1,2,4]triazolo[1,5-a]pyridin-2-ylamine (prepared in analogy to example 66a-c). The title compound was obtained as white foam. MS ISP (m/e): 435.3 (100) [(M+H)$^+$].

$^1$H NMR ($CDCl_3$, 300 MHz): δ (ppm)=8.23-8.21 (m, 1H), 7.91-7.88 (m, 2H), 7.48-7.45 (m, 1H), 6.88-6.81 (m, 3H), 4.52-4.49 (m, 1H), 3.98-3.87 (m, 3H), 3.41-3.32 (m, 2H), 3.01 (s, 6H), 2.42 (s, 3H), 2.30-2.24 (m, 2H), 1.73-1.60 (m, 2H).

Example 231

4-(8-(3,4-Difluorophenyl)-[1,2,4]triazolo[1,5-a]pyridin-2-ylamino)-1-(6-methylpyrimidin-4-yl)piperidine-4-carbonitrile

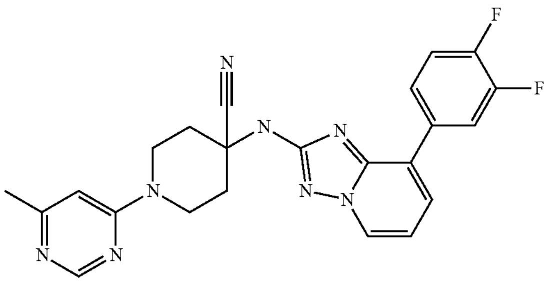 [SMILES: Cc1cc(N2CCC(C#N)(Nc3nc4c(-c5ccc(F)c(F)c5)cccn4n3)CC2)ncn1]

To a solution of 1-(6-methylpyrimidin-4-yl)piperidin-4-one (see example 93b, 100 mg, 0.523 mmol) and 8-(3,4-difluorophenyl)-[1,2,4]triazolo[1,5-a]pyridin-2-amine (129 mg, 0.523 mmol) in AcOH was added dropwise trimethylsilyl cyanide (196 μL, 1.57 mmol) and the resulting mixture stirred at room temperature for 88 hours. The mixture was then poured onto NaOH (6 M, 6 mL) and stirred for 10 minutes. The precipitate was then filtered off and dried. Purification by chromatography (silica gel, 20 g, 30 to 100% ethyl acetate in heptane) afforded the title compound (20 mg, 9%) as a yellow solid. MS ISP (m/e): 447.4 [(M+H)$^+$].

Example 232

1-(2-Chloropyridin-4-yl)-4-(8-(3,4-difluorophenyl)-[1,2,4]triazolo[1,5-a]pyridin-2-ylamino)piperidine-4-carbonitrile

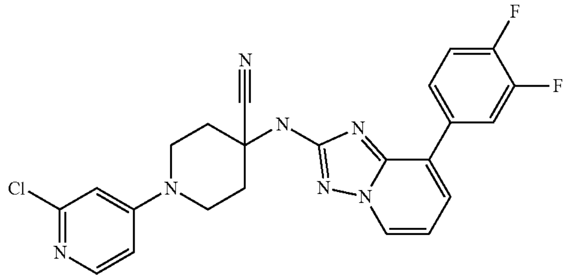 [SMILES: N#CC1(Nc2nc3c(-c4ccc(F)c(F)c4)cccn3n2)CCN(c2ccnc(Cl)c2)CC1]

a) 8-(2-Chloropyridin-4-yl)-1,4-dioxa-8-azaspiro[4.5]decane

To a solution of 1,4-dioxa-8-azaspiro[4.5]decane (895 μL, 6.98 mmol) and 2-chloro-4-fluoropyridine (1.01 g, 7.68 mmol) in dioxane (15 mL) was added N,N-diisopropylethylamine (1.83 mL, 10.5 mmol). Argon was bubbled through the reaction mixture for 5 minutes before it was heated to 120° C. in microwave for 3 hours. After evaporation, purification by chromatography (silica gel, 20 g, 30 to 10% ethyl acetate in heptane) afforded the title compound (1.3 g, 73%) as a yellow solid.

MS ISP (m/e): 255.3 [(M+H)$^+$].

b) 1-(2-Chloropyridin-4-yl)piperidin-4-one

To a solution of 8-(2-chloropyridin-4-yl)-1,4-dioxa-8-azaspiro[4.5]decane (1.26 g, 4.95 mmol) in acetone (11 mL) was added HCl (2 N, 39.6 mL, 79.1 mmol) and the resulting mixture stirred at 50° C. for 2 hours, then cooled to room temperature. The pH was set to ~8 by adding solid sodium hydrogen carbonate and then extracted with dichloromethane. The combined organic layers were washed with brine, dried over sodium sulfate, filtered and evaporated to give the title product (1.03 g, 99%) as a white solid.

MS ISP (m/e): 211.1 [(M+H)$^+$].

c) 1-(2-Chloropyridin-4-yl)-4-(8-(3,4-difluorophenyl)-[1,2,4]triazolo[1,5-a]pyridin-2-ylamino)piperidine-4-carbonitrile Prepared in analogy to example 231, employing 1-(2-chloropyridin-4-yl)piperidin-4-one (150 mg, 0.44 mmol) instead of 1-(6-methylpyrimidin-4-yl)piperidin-4-one.

The title compound was obtained as a light yellow solid (31 mg, 14%).

MS ISP (m/e): 466.3 [(M+H)$^+$].

Example 233

8-(3,4-Difluorophenyl)-N-((3S,4R)-3-methoxy-1-(6-methylpyrimidin-4-yl)piperidin-4-yl)-[1,2,4]triazolo[1,5-a]pyridin-2-amine

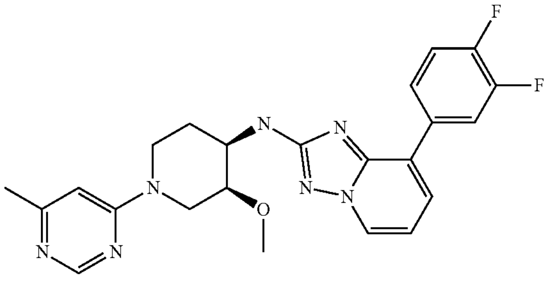 [SMILES: CO[C@H]1CN(c2cc(C)ncn2)CC[C@H]1Nc1nc2c(-c3ccc(F)c(F)c3)cccn2n1]

a) (3S,4R)-tert-Butyl 4-(8-(3,4-difluorophenyl)-[1,2,4]triazolo[1,5-a]pyridin-2-ylamino)-3-methoxypiperidine-1-carboxylate Prepared in analogy to example 169c, employing (3S,4R)-4-Amino-1-Boc-3-methoxy-pyridine (100 mg, 0.43 mmol) instead of 1-(2-chloropyridin-4-yl)piperidin-4-amine.

The title compound was obtained as a yellow gum (40 mg, 20%).

MS ISP (m/e): 460.3 [(M+H)$^+$].

b) 8-(3,4-Difluorophenyl)-N43S,4R)-3-methoxypiperidin-4-yl)-[1,2,4]triazolo[1,5-a]pyridin-2-amine dihydrochloride To a solution (3S,4R)-tert-butyl 4-(8-(3,4-difluorophenyl)-[1,2,4]triazolo[1,5-a]pyridin-2-ylamino)-3-methoxypiperidine-1-carboxylate (37 mg, 80.5 mol) in dichloromethane (1 mL) was added HCl (2 M in diethylether, 201 L, 403 mol) and the reaction mixture was stirred at room temperature for 18 hours. The mixture was then filtered and the white precipitate was washed with dichloromethane and diethylether and dried to afford the title compound (32 mg, 92%) as an off white solid.

MS ISP (m/e): 360.2 [(M+H)$^+$].

c) 8-(3,4-Difluorophenyl)-N-((3S,4R)-3-methoxy-1-(6-methylpyrimidin-4-yl)piperidin-4-yl)-[1,2,4]triazolo[1,5-a]pyridin-2-amine 8-(3,4-Difluorophenyl)-N-((3S,4R)-3-methoxypiperidin-4-yl)-[1,2,4]triazolo[1,5-a]pyridin-2-amine dihydrochloride (28 mg, 64.8 μmol) was extracted with dichloromethane/2 M NaOH. The organic layers were washed with brine, dried over sodium sulfate and evaporated. The residue was dissolved in dioxane (0.5 mL) and to this solution 4-chloro-6-methylpyrimidine (9.2 mg, 71.2 μmol) and DIPEA (17.0 μL, 97.2 μmol) were added. Argon was bubbled through the solution for 5 minutes, and then heated in the microwave at 130° C. for 2×30 minutes. After evaporation, purification by chromatography (silica gel, 10 g, 0 to 10% methanol in dichloromethane) afforded the title compound (18 mg, 62%) as an off white foam.

MS ISP (m/e): 452.3 [(M+H)$^+$].

Example 234

8-(3,4-Difluorophenyl)-N-(4-methyl-1-(6-methylpyrimidin-4-yl)piperidin-4-yl)-[1,2,4]triazolo[1,5-a]pyridin-2-amine

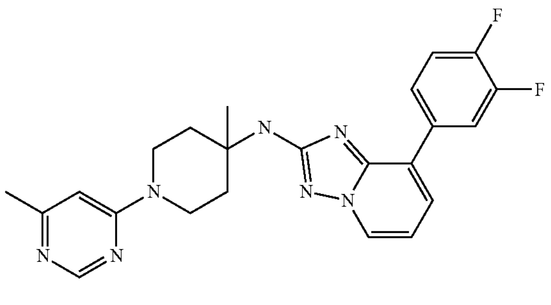 [SMILES: Cc1cc(N2CCC(C)(Nc3nc4c(-c5ccc(F)c(F)c5)cccn4n3)CC2)ncn1]

To a solution of 4-(8-(3,4-difluorophenyl)-[1,2,4]triazolo[1,5-a]pyridin-2-ylamino)-1-(6-methylpyrimidin-4-yl)piperidine-4-carbonitrile (Example 231) (50 mg, 112 μmol) in THF (2 mL) was added methylmagnesium bromide (1.4 M in toluene:THF, 240 μL, 336 μmol) dropwise at 0° C., and the resulting mixture was allowed to warm up to room temperature and stirred for 3 hours. Then the mixture was quenched with saturated aqueous ammonium chloride solution and extracted with ethyl acetate. The organic layers were washed with brine, dried over sodium sulfate, filtered and evaporated. Purification by chromatography (silica gel, 10 g, 0 to 10% methanol in dichloromethane) afforded the title compound (9 mg, 19%) as a light yellow solid.

MS ISP (m/e): 436.3 $[(M+H)^+]$.

Example 235

8-(3,4-Difluorophenyl)-N-(4-methyl-1-(6-methylpyrimidin-4-yl)piperidin-4-yl)-5,6,7,8-tetrahydro-[1,2,4]triazolo[1,5-a]pyridin-2-amine

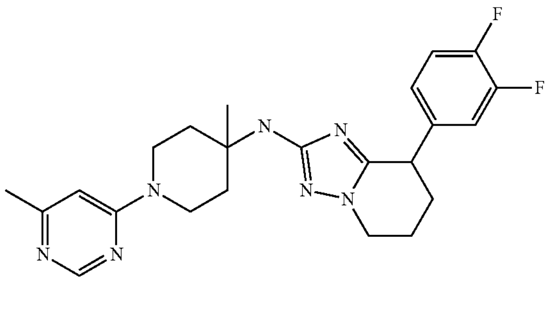 [SMILES: Cc1cc(N2CCC(C)(Nc3nc4n(n3)CCCC4c3ccc(F)c(F)c3)CC2)ncn1]

a) tert-Butyl 4-carbamoyl-4-methylpiperidine-1-carboxylate

To a solution of 1-(tert-butoxycarbonyl)-4-methylpiperidine-4-carboxylic acid (2.85 g, 11.7 mmol) in DMF (57 mL) was added CDI (2.28 g, 14.1 mmol). The mixture was stirred at 60° C. for 30 minutes, then cooled to room temperature. Ammonium hydroxide (18.2 mL, 117 mmol) was added cautiously and stirring continued for 1 hour. The mixture was then evaporated to give a colourless oil. It was extracted with ethyl acetate and the organic layer washed with HCl (1 M), with water, sodium hydrogen carbonate solution, brine, dried over sodium sulfate, filtered and evaporated. The residue was taken up in toluene, then hexane was added and the mixture was stirred at room temperature for 15 minutes. The precipitate was filtered, washed with hexane and dried to give the title compound (2.55 g, 90%) as a white solid.

MS ISP (m/e): 243.3 $[(M+H)^+]$.

b) tert-Butyl 4-amino-4-methylpiperidine-1-carboxylate

To a suspension of tert-butyl 4-carbamoyl-4-methylpiperidine-1-carboxylate (2.52 g, 10.4 mmol) in acetonitrile (7.6 mL) and water (23.4 mL) was added KOH (2.63 g, 46.8 mmol) at 0° C. Then 1,3-dibromo-5,5-dimethylhydantoin (1.64 g, 5.72 mmol) was added in one portion at 0° C. and after stirring at 0° C. for 30 minutes the solution was allowed to warm up to room temperature and stirred for 1 hour. Sodium sulfite (131 mg, 1.04 mmol) was added and the mixture was stirred for 15 minutes at room temperature, then ethyl acetate was added and the reaction was cooled to 10° C. $K_3PO_4$ (2.34 g, 11.0 mmol) was added and the mixture was warmed up to room temperature and extracted with ethyl acetate. The organic layers were washed with brine, dried over sodium sulfate, filtered and evaporated to give the title compound (2.1 g, 94%) as a colourless oil. MS ISP (m/e): 215.3 $[(M+H)^+]$.

c) 4-Methylpiperidin-4-amine bis(4-methylbenzenesulfonate)

A solution of tert-butyl 4-amino-4-methylpiperidine-1-carboxylate (1.96 g, 9.15 mmol) in MeOH (15.2 mmol) was added dropwise over 30 minutes to a solution of p-toluenesulfonic acid monohydrate (4.00 g, 21.0 mmol) in 2-propanol (7.9 mL) at 60° C. The reaction mixture was then heated to 60° C. for 16 h. After cooling to 0° C. the precipitate was filtered off and washed with 2-propanol and dried to give the title compound (3.91 g, 93%) as a white solid.

MS ISP (m/e): 115.1 $[(M+H)^+]$.

d) 4-Methyl-1-(6-methylpyrimidin-4-yl)piperidin-4-amine

To a mixture of 4-methylpiperidin-4-amine bis(4-methylbenzenesulfonate) (3.91 g, 8.53 mmol) and 4-chloro-6-methylpyrimidine (1.10 g, 8.53 mmol) in NMP (35 mL) was added $K_3PO_4$ (3.12 g, 17.9 mmol) and the reaction mixture was stirred at 80° C. for 18 hours. After cooling to room temperature, 0.5 M aqueous $K_3PO_4$ was added and the mixture extracted twice with dichloromethane. The combined organic layers were extracted twice with HCl (1 N). The combined aqueous layers were made alkaline with NaOH (6 N), extracted twice with dichloromethane and the organic layers washed with brine, dried over sodium sulfate, filtered and evaporated. Purification by chromatography (silica gel, 70 g, 0 to 100% ethyl acetate in heptane; then 0 to 50% methanol in ethyl acetate, containing 10% triethylamine) afforded the title compound (1.09 g, 62%) as a light yellow semisolid.

MS ISP (m/e): 207.2 $[(M+H)^+]$.

e) 4-(4-Isothiocyanato-4-methylpiperidin-1-yl)-6-methylpyrimidine

To a solution of 4-methyl-1-(6-methylpyrimidin-4-yl)piperidin-4-amine (1.09 g, 5.28 mmol) in dichloromethane (17.2 mL) was added 1,1'-thiocarbonyldipyridin-2(1H)-one (1.84 g, 7.92 mmol) and the reaction mixture was stirred at room temperature for 16 hours. After cooling to room temperature the mixture was evaporated. Purification by chromatography (silica gel, 3×70 g, 50 to 100% ethyl acetate in heptane) afforded the title compound (1.2 g, 91%) as a light yellow solid. MS ISP (m/e): 249.1 [(M+H)$^+$].

f) 1-(4-Methyl-1-(6-methylpyrimidin-4-yl)piperidin-4-yl)thiourea

A solution of 4-(4-isothiocyanato-4-methylpiperidin-1-yl)-6-methylpyrimidine (1.18 g, 0.53 mmol) in ammonia (7 M in MeOH, 13.6 mL, 95.0 mmol) was stirred in a sealed tube at room temperature for 3 h and then heated at 50° C. for 18 h. After cooling to room temperature the mixture was evaporated. Purification by chromatography (silica gel, 50 g, 0 to 20% methanol in dichloromethane) afforded the title compound (1.2 g, 100%) as a white foam.

MS ISP (m/e): 266.2 [(M+H)$^+$].

gi) Methyl 4-methyl-1-(6-methylpyrimidin-4-yl)piperidin-4-ylcarbamimidothioate hydroiodide To a solution of 1-(4-methyl-1-(6-methylpyrimidin-4-yl)piperidin-4-yl)thiourea (1.28 g, 4.82 mmol) in EtOH (11.7 mL) was added MeI (332 L, 5.31 mmol) and the reaction mixture was stirred under Argon at 75° C. for 3 hours. The reaction mixture was then evaporated and the residue (white foam) stirred with diethylether (15 mL) at room temperature for 1 hour. The solid was then washed with diethylether and dried to afford the title compound (1.89 g, 96%) as a white solid. MS ISP (m/e): 190.3 [(M+H)$^+$].

gii) 5-Chloro-2-(3,4-difluorophenyl)pentanoic acid

To a solution of 3,4-difluorophenylacetic acid (5.00 g, 29.0 mmol) in THF (58 mL) was added NaHMDS (1 M in THF, 58.1 mL, 58.1 mmol) dropwise at 0° C. The reaction mixture was then stirred at 0° C. for 20 min, then 1-chloro-3-iodopropane (3.12 mL, 29.0 mmol) was added dropwise at 0° C. and the reaction mixture was stirred at room temperature for 16 hours. The mixture was then quenched under ice bath cooling with water (3 mL) and evaporated. To the residue was added NaOH (1 N, 150 mL) and the resulting solution was extracted with diethylether (2×100 mL). The aqueous layer was acidified with HCl (1 N, 200 mL) and extracted with diethylether (2×100 mL). The combined organic layers were then dried over sodium sulfate, filtered and evaporated. Purification by chromatography (silica gel, 2×50 g, 0 to 50% ethyl acetate in heptane) afforded the title compound (2.02 g, 28%) as a light yellow oil.

MS ISP (m/e): 247.0/249.1 [(M−H)$^+$].

h) 8-(3,4-Difluorophenyl)-N-(4-methyl-1-(6-methylpyrimidin-4-yl)piperidin-4-yl)-5,6,7,8-tetrahydro-[1,2,4]triazolo[1,5-a]pyridin-2-amine To a solution of methyl 4-methyl-1-(6-methylpyrimidin-4-yl)piperidin-4-ylcarbamimidothioate hydroiodide (1.85, 4.54 mmol) containing 5-chloro-2-(3,4-difluorophenyl)pentanoic acid (1.24, 5.00 mmol), EDC (0.87, 4.54 mmol) and 1-hydroxybenzotriazole hydrate (1.39 g, 9.08 mmol) in DMF (22.3 mL) was added DIPEA (1.98 mL, 11.4 mmol) and the reaction mixture was stirred at room temperature for 18 hours. Hydrazine monoydrate (0.57 mL, 18.2 mmol) was then added and the reaction mixture stirred at 70° C. for 5 h. The reaction mixture was then poured into water, extracted twice with ethyl acetate, and the combined organic layers washed with brine, dried over sodium sulfate, filtered and evaporated. Purification by chromatography (silica gel, 2×50 g, 0 to 20% methanol in dichloromethane) afforded the title compound (14 mg, 1%) as a light red foam.

MS ISP (m/e): 440.3 [(M+H)$^+$].

Example 236

N-(1-(2-Chloropyridin-4-yl)-4-methylpiperidin-4-yl)-8-(3,4-difluorophenyl)-[1,2,4]triazolo[1,5-a]pyridin-2-amine

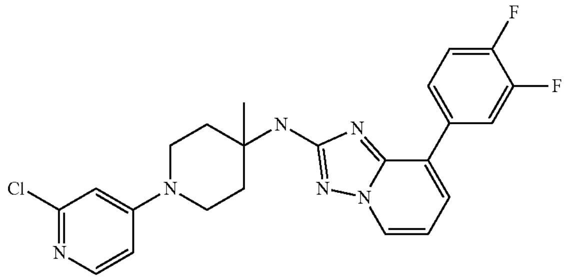 [SMILES: CC1(Nc2nc3c(-c4ccc(F)c(F)c4)cccn3n2)CCN(c2ccnc(Cl)c2)CC1]

Prepared in analogy to example 234, employing 1-(2-chloropyridin-4-yl)-4-(8-(3,4-difluorophenyl)-[1,2,4]triazolo[1,5-a]pyridin-2-ylamino)piperidine-4-carbonitrile (18 mg, 36 mol) instead of 4-(8-(3,4-difluorophenyl)-[1,2,4]triazolo[1,5-a]pyridin-2-ylamino)-1-(6-methylpyrimidin-4-yl)piperidine-4-carbonitrile.

The title compound was obtained as an off white solid (2.5 mg, 14%).

MS ISP (m/e): 455.2 [(M+H)$^+$].

Example 237

8-(3,4-Difluorophenyl)-N-(2-methyl-1-(6-methylpyrimidin-4-yl)piperidin-4-yl)-[1,2,4]triazolo[1,5-a]pyridin-2-amine

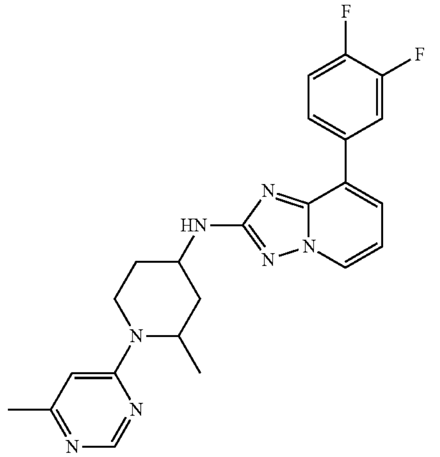 [SMILES: Cc1cc(N2CCC(Nc3nc4c(-c5ccc(F)c(F)c5)cccn4n3)CC2C)ncn1]

Prepared in analogy to example 57c) employing 4-chloro-6-methylpyrimidine instead of 4-bromo-2-methylpyridine and 8-(3,4-difluorophenyl)-N-(2-methylpiperidin-4-yl)-[1,2,4]triazolo[1,5-a]pyridin-2-amine instead of 8-(2-chloro-4-fluorophenyl)-N-(piperidin-4-yl)-[1,2,4]triazolo[1,5-a]pyridin-2-amine. The title compound was obtained as a light brown foam.

MS ISP (m/e): 436.3 [$(M+H)^+$]. $^1$H NMR ($CDCl_3$, 300 MHz): δ (ppm)=8.50 (s, 1H), 8.32 (s, 1H), 7.95 (m, 1H), 7.70 (m, 1H), 7.50 (d, 1H), 7.23 (m, 1H), 6.89 (dd, 1H), 6.33 (s, 1H), 4.70 (d, 1H), 4.50 (m, 1H), 4.30 (m, 1H), 4.00 (m, 1H), 3.35-3.25 (m, 2H), 2.60 (m, 1H), 2.40 (s, 3H), 2.10-2.00 (m, 2H), 1.34 (d, 3H).

Example 238

(cis, rac)-N-(3-Fluoro-1-(3-methyl-1,2,4-thiadiazol-5-yl)piperidin-4-yl)-8-(2,3,4-trifluorophenyl)-[1,2,4]triazolo[1,5-a]pyridin-2-amine

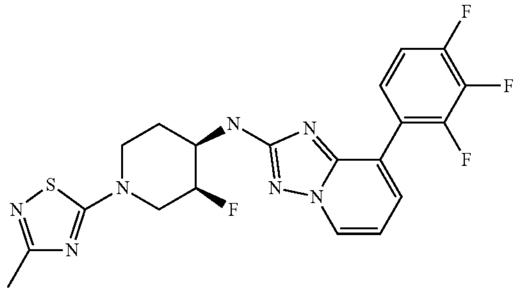 [SMILES: Cc1nsc(N2CC[C@@H](Nc3nc4c(-c5ccc(F)c(F)c5F)cccn4n3)[C@@H](F)C2)n1]

a) 4-Trimethylsilyloxy-3,6-dihydro-2H-pyridine-1-carboxylic acid tert-butyl ester tert-Butyl 4-oxopiperidine-1-carboxylate (10 g, 48.7 mmol) was dissolved in dry DMF (12.0 mL). Trimethylsilyl chloride (6.35 g, 7.39 mL, 58.4 mmol) and triethylamine (11.8 g, 16.2 mL, 117 mmol) were added under argon and the reaction mixture was stirred at 80° C. for 16 hours. The reaction mixture was cooled to room temperature, saturated $NaHCO_3$ solution was added and the aqueous phase was extracted with ethyl acetate. The combined organic layers were dried over $Na_2SO_4$ and the solvent was evaporated. The residue was purified by flash chromatography (1 drop $Et_3N$ was added during conditioning of the column) (silica gel, 100 g, 0% to 100% pentane in $Et_2O$, 45 minutes). The title compound was obtained as a colorless liquid (13.2 g, 99%).

MS ISP (m/e): 272.2/216.3 (41/100) [$(M+H)^+/(M-tBu)^+$]. $^1$H NMR ($CDCl_3$, 300 MHz): δ (ppm)=4.80 (m, 1H), 3.88-3.87 (m, 2H), 3.55-3.51 (m, 2H), 2.11 (m, 2H), 1.47 (s, 9H), 0.20 (s, 9H).

b) tert-Butyl 3-fluoro-4-oxopiperidine-1-carboxylate

4-Trimethylsilyloxy-3,6-dihydro-2H-pyridine-1-carboxylic acid tert-butyl ester (13.2 g, 48.6 mmol) was dissolved in acetonitrile (250 mL). 1-Chloromethyl-4-fluoro-1,4-diazoniabicyclo[2.2.2]octane bis(tetrafluoroborate) (19.0 g, 53.5 mmol) was added and the reaction mixture was stirred at room temperature for 2 hours. Brine was added to the reaction mixture and the aqueous phase extracted ethyl acetate. The combined organic layers were dried over $Na_2SO_4$ and the solvent was evaporated. The residue was purified by flash chromatography (silica gel, 100 g, 0% to 100% EtOAc in heptane). The title compound was obtained as white solid (5.66 g, 53%).

MS ISP (m/e): 161.2 (100) [$(M-tBu)^+$].

$^1$H NMR ($CDCl_3$, 300 MHz): δ (ppm)=4.94-4.73 (m, 1H), 4.47 (m, 1H), 4.22-4.16 (m, 1H), 3.29-3.20 (m, 2H), 2.64-2.52 (m, 2H), 1.50 (s, 9H).

c) (cis, rac)-tert-Butyl 4-(benzylamino)-3-fluoropiperidine-1-carboxylate

A mixture of tert-butyl 3-fluoro-4-oxopiperidine-1-carboxylate (1.255 g, 5.78 mmol), sodium triacetoxyborohydride (1.89 g, 8.67 mmol) and benzylamine (681 mg, 695 μL, 6.35 mmol) in 1,2-dichloroethane (15 mL) was kept at room temperature for 3 hours. An aqueous solution of sodium carbonate (2 M) was added to the reaction mixture and the aqueous phase extracted ethyl acetate. The combined organic layers were dried over $Na_2SO_4$ and the solvent was evaporated. The residue was purified by flash chromatography (silica gel, 100 g, 0% to 100% EtOAc in heptane). The title compound was obtained as yellow oil (982 mg, 55%), besides trans isomer (yellow oil, 200 mg, 11%).

MS ISP (m/e): 309.3/253.2 (50/100) [$(M+H)^+/(M-tBu)^+$]. $^1$H NMR ($CDCl_3$, 300 MHz): δ (ppm)=7.35-7.27 (m, 5H), 4.85-4.67 (br, 1H), 4.33 br, 1H), 4.11 (br, 1H), 3.87 (s, 2H), 3.04-2.88 (m, 1H), 2.78-2.64 (m, 2H), 1.77-1.50 (m, 3H), 1.46 (s, 9H).

d) (cis, rac)-4-Amino-3-fluoro-piperidine-1-carboxylic acid tert-butyl ester

A suspension of (cis)-tert-butyl 4-(benzylamino)-3-fluoropiperidine-1-carboxylate, Pd/C (102 mg, 95.5 μmol) in MeOH (20 mL) was hydrogenated at room temperature for 6 hours. The catalyst was filtered off, washed thoroughly with MeOH and the solvents evaporated. The title compound was obtained as light yellow foam (690 mg, 99%).

MS ISP (m/e): 219.2/163.3 (3/100) [$(M+H)^+/(M-tBu)^+$]. $^1$H NMR ($CDCl_3$, 300 MHz): δ (ppm)=4.63-4.47 (br, 1H), 4.31 (br, 1H), 4.07 (br, 1H), 3.08-2.79 (m, 3H), 1.77-1.63 (m, 2H), 1.49 (bs, 2H), 1.46 (s, 9H).

e) (cis, rac)-tert-Butyl 3-fluoro-4-(8-(2,3,4-trifluorophenyl)-[1,2,4]triazolo[1,5-a]pyridin-2-ylamino)piperidine-1-carboxylate Through a suspension of cis-tert-butyl 4-amino-3-fluoropiperidine-1-carboxylate (350 mg, 1.6 mmol), 2-bromo-8-(2,3,4-trifluorophenyl)-[1,2,4]triazolo[1,5-a]pyridine (prepared in analogy to example 66a-d, 579 mg, 1.76 mmol), tris(dibenzylideneacetone)dipalladium(0) chloroform adduct (66.4 mg, 64.1 μmol), sodium phenoxide (279 mg, 2.41 mmol) and 4,5-bis(diphenylphosphino)-9,9-dimethylxanthene (74.2 mg, 128 μmol) in dry dioxane (12 mL) was bubbled argon for 5 minutes, then heated to 150° C. for 60 minutes. The crude material was purified by flash chromatography (silica gel, 100 g, 0% to 100% EtOAc in heptane). The title compound was obtained as light yellow oil (231 mg, 31%).

MS ISP (m/e): 466.3/410.3 (58/100) [$(M+H)^+/(M-tBu)^+$]. $^1$H NMR ($CDCl_3$, 300 MHz): δ (ppm)=8.35-8.33 (m, 1H), 7.62-7.54 (m, 1H), 7.51-7.49 (m, 1H), 7.14-7.05 (m, 1H), 6.94-6.89 (m, 1H), 4.93-4.76 (br, 1H), 4.86-4.83 (m, 1H), 4.45 (br, 1H), 4.26 (br, 1H), 4.02-3.83 (m, 1H), 3.15-2.79 (m, 2H), 1.97-1.91 (m, 1H), 1.88-1.74 (m, 1H), 1.47 (s, 9H).

f) (cis, rac)-N-(3-fluoropiperidin-4-yl)-8-(2,3,4-trifluorophenyl)-[1,2,4]triazolo[1,5-a]pyridin-2-amine To a solution of (cis)-tert-butyl 3-fluoro-4-(8-(2,3,4-trifluorophenyl)-[1,2,4]triazolo[1,5-a]pyridin-2-ylamino)piperidine-1-carboxylate (462 mg, 993 μmol) in $CH_2Cl_2$ (10 mL) at 0° C. was added TFA (792 mg, 535 μL, 6.95 mmol) and stirred at room temperature for 18 hours. The reaction mixture was extracted with saturated $NaHCO_3$ solution and ethyl acetate, the organic layers combined, dried over $Na_2SO_4$, filtered and the solvents evaporated. The product was twice coevaporated with toluene. The title compound was obtained as light yellow foam (363 mg, 100%). The crude product was used for the next step without further purification.

MS ISP (m/e): 366.2/346.1 (58/100) $[(M+H)^+/(M-HF)^+]$.

$^1$H NMR ($CDCl_3$, 300 MHz): δ (ppm)=8.35-8.33 (m, 1H), 7.63-7.56 (m, 1H), 7.50-7.48 (m, 1H), 7.14-7.05 (m, 1H), 6.93-6.88 (m, 1H), 4.88 (bs, 1H), 4.85-4.72 (br, 1H), 4.01-3.81 (m, 1H), 3.41-3.33 (m, 1H), 3.19-3.13 (m, 1H), 2.95-2.70 (m, 2H), 1.99-1.94 (m, 1H), 1.74-1.65 (m, 1H), 1.60 (s, 1H).

g) (cis, rac)-N-(3-fluoro-1-(3-methyl-1,2,4-thiadiazol-5-yl)piperidin-4-yl)-8-(2,3,4-trifluorophenyl)-[1,2,4]triazolo[1,5-a]pyridin-2-amine A degassed solution of 2-(dicyclohexylphosphino)biphenyl (9.21 mg, 26.3 μmol) and palladium(II) acetate (2.95 mg, 13.1 μmol) in dioxane (2 mL) was stirred for 10 minutes at room temperature, then added to a solution of (cis)-N-(3-fluoropiperidin-4-yl)-8-(2,3,4-trifluorophenyl)-[1,2,4]triazolo[1,5-a]pyridin-2-amine (60 mg, 164 μmol), 5-chloro-3-methyl-1,2,4-thiadiazole (24.3 mg, 181 μmol) and sodium tert-butylate (23.7 mg, 246 μmol) in dioxane (2 mL). Through the solution was bubbled argon for 5 minutes, then heated to 140° C. in the microwave for 30 minutes. Again a degassed solution of 2-(dicyclohexylphosphino)biphenyl (9.21 mg, 26.3 μmol) and palladium(II) acetate (2.95 mg, 13.1 μmol) in dioxane (2 mL) was added, followed by 5-chloro-3-methyl-1,2,4-thiadiazole (24.3 mg, 181 μmol) and heated to 140° C. for further 30 minutes and then to 150° C. for further 30 minutes. The reaction mixture was directly purified by flash chromatography (silica gel, 70 g, 0% to 15% $MeOH/NH_4OH$ (9:1) in dichloromethane). The title compound was obtained as light yellow foam (19.7 mg, 26%).

MS ISP (m/e): 464.2 (100) $[(M+H)^+]$. $^1$H NMR ($CDCl_3$, 300 MHz): δ (ppm)=8.36-8.34 (m, 1H), 7.60-7.55 (m, 1H), 7.52-7.50 (m, 1H), 7.15-7.05 (m, 1H), 6.96-6.91 (m, 1H), 5.08-4.92 (m, 1H), 4.88-4.85 (m, 1H), 4.40-4.32 (m, 1H), 4.17-3.93 (m, 2H), 3.53-3.29 (m, 1H), 3.19-3.13 (m, 1H), 2.42 (s, 3H), 2.10-2.00 (m, 2H).

Example 239 and 240

(3S,4R)— and (3R,4S)—N-(3-Fluoro-1-(3-methyl-1,2,4-thiadiazol-5-yl)piperidin-4-yl)-8-(2,3,4-trifluorophenyl)-[1,2,4]triazolo[1,5-a]pyridin-2-amine

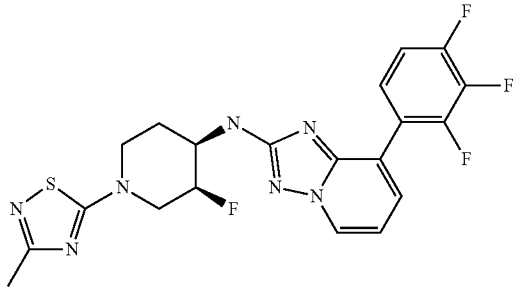

-continued

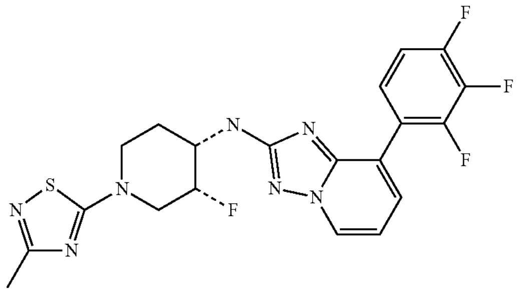

Separation of racemic (cis)-N-(3-fluoro-1-(3-methyl-1,2,4-thiadiazol-5-yl)piperidin-4-yl)-8-(2,3,4-trifluorophenyl)-[1,2,4]triazolo[1,5-a]pyridin-2-amine (example 238, 52 mg) by chiral HPLC (Chiralpak AD) using isopropanol/n-heptane 2:3 as eluent provided both enantiomers (without assignment of absolute configuration to the enantiomers).

Example 239: Enantiomer 1(−), retention time 15.76 minutes (19 mg)

Example 240: Enantiomer 2(+), retention time 26.72 minutes (16 mg)

Example 241

(cis, rac)-[3-Fluoro-1-(3-methyl-[1,2,4]thiadiazol-5-yl)-piperidin-4-yl]-[8-(4-fluoro-phenyl)-[1,2,4]triazolo[1,5-a]pyridin-2-yl]-amine

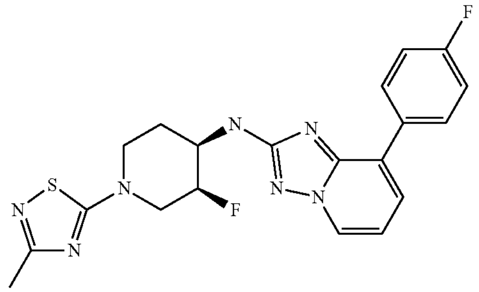 [SMILES: Cc1nsc(N2CC[C@@H](Nc3nc4c(-c5ccc(F)cc5)cccn4n3)[C@@H](F)C2)n1]

Prepared in analogy to example 238. The title compound was obtained as light yellow oil.

MS ISP (m/e): 428.0 (100) $[(M+H)^+]$.

$^1$H NMR ($CDCl_3$, 300 MHz): δ (ppm)=8.31-8.29 (m, 1H), 7.97-7.92 (m, 2H), 7.52-7.49 (m, 1H), 7.21-7.15 (m, 2H), 6.94-6.90 (m, 1H), 5.11-4.94 (m, 1H), 4.91-4.88 (m, 1H), 4.41-4.32 (m, 1H), 4.21-3.95 (m, 2H), 3.54-3.31 (m, 2H), 2.42 (s, 3H), 2.11-2.02 (m, 2H).

Example 242

(cis, rac)-[8-(3,4-Difluoro-phenyl)-[1,2,4]triazolo[1,5-a]pyridin-2-yl]-[3-fluoro-1-(6-methyl-pyrimidin-4-yl)-piperidin-4-yl]-amine

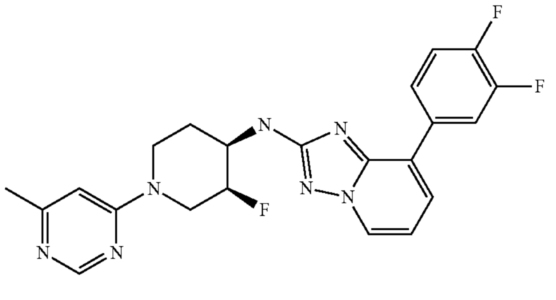 [SMILES: Cc1cc(N2CC[C@@H](Nc3nc4c(-c5ccc(F)c(F)c5)cccn4n3)[C@@H](F)C2)ncn1]

A solution of 8-(3,4-difluorophenyl)-N-(cis-3-fluoropiperidin-4-yl)-[1,2,4]triazolo[1,5-a]pyridin-2-amine (prepared in analogy to example 238a-f, 60.0 mg, 173 μmol), 4-chloro-6-methylpyrimidine (24.4 mg, 190 μmol) and N,N-diisopropylamine (33.5 mg, 44.1 μL, 259 μmol) in dioxane (4 mL) was heated to 150° C. in the microwave for 2 hours. The reaction mixture was directly purified by flash chromatography (silica gel, 70 g, 0% to 15% MeOH/$NH_4OH$ (9:1) in dichloromethane). The title compound was obtained as orange foam (52 mg, 69%).

MS ISP (m/e): 440.4 (100) [$(M+H)^+$]. $^1H$ NMR ($CDCl_3$, 300 MHz): δ (ppm)=8.53 (m, 1H), 8.33-8.31 (m, 1H), 7.96-7.89 (m, 1H), 7.74-7.68 (m, 1H), 7.53-7.50 (m, 1H), 7.32-7.23 (m, 1H), 6.95-6.90 (m, 1H), 6.46 (m, 1H), 5.11-4.94 (m, 1H), 4.89-4.86 (m, 2H), 4.60-4.55 (m, 1H), 4.21-4.02 (m, 1H), 3.29-3.02 (m, 2H), 2.38 (s, 3H), 2.13-2.08 (m, 1H), 1.97-1.83 (m, 1H).

Example 243

(cis, rac)-[3,4-Difluoro-1-(3-methyl-[1,2,4]thiadiazol-5-yl)-piperidin-4-yl]-[8-(4-fluoro-phenyl)-[1,2,4]triazolo[1,5-a]pyridin-2-yl]-amine

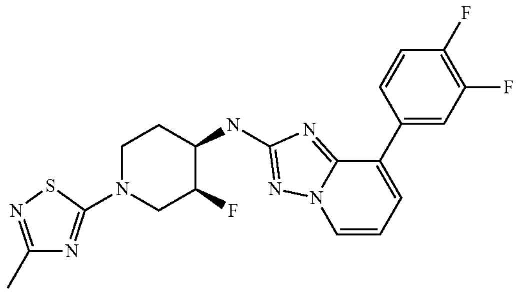 [SMILES: Cc1nsc(N2CC[C@@H](Nc3nc4c(-c5ccc(F)c(F)c5)cccn4n3)[C@@H](F)C2)n1]

Prepared in analogy to example 238. The title compound was obtained as white foam.

MS ISP (m/e): 446.1 (100) [$(M+H)^+$].

$^1H$ NMR ($CDCl_3$, 300 MHz): δ (ppm)=8.33-8.30 (m, 1H), 7.95-7.88 (m, 1H), 7.72-7.68 (m, 1H), 7.53-7.50 (m, 1H), 7.32-7.23 (m, 1H), 6.95-6.91 (m, 1H), 5.11-4.95 (m, 1H), 4.92-4.89 (m, 1H), 4.41-4.33 (m, 1H), 4.21-3.95 (m, 2H), 3.55-3.31 (m, 2H), 2.42 (s, 3H), 2.12-2.03 (m, 2H).

Example 244

(cis, rac)-N-(1-(2-Chloropyridin-4-yl)-3-fluoropiperidin-4-yl)-8-(3,4-difluorophenyl)-[1,2,4]triazolo[1,5-a]pyridin-2-amine

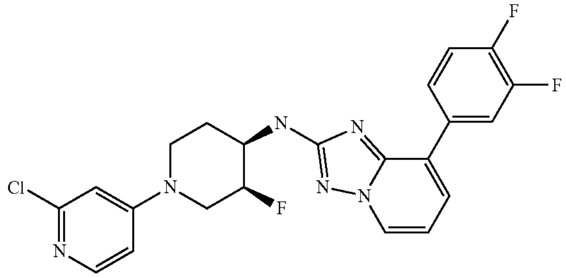 [SMILES: Fc1ccc(-c2cccn3nc(N[C@@H]4CCN(c5ccnc(Cl)c5)C[C@@H]4F)nc23)cc1F]

To a mixture of 8-(3,4-difluorophenyl)-N-(cis-3-fluoropiperidin-4-yl)-[1,2,4]triazolo[1,5-a]pyridin-2-amine (prepared in analogy to example 238a-f, 60 mg, 173 μmol) and 2-chloro-4-fluoropyridine (22.7 mg, 173 μmol) in NMP (3 mL) was added DIPEA (31.3 mg, 42.2 μL, 242 mmol). Argon was bubbled through the cloudy solution for 5 minutes before it was heated to 150° C. in the microwave oven for 60 minutes. Further 2-chloro-4-fluoropyridine (22.7 mg, 173 mmol) and DIPEA (31.3 mg, 42.2 μL, 242 μmol) were added and heated to 150° C. for another 30 minutes. The reaction mixture was poured into $H_2O$, the aqueous phase was extracted with EtOAc, the combined organic phases washed with brine, dried over $Na_2SO_4$ and the solvent was evaporated. The residue was purified by flash chromatography (silica gel, 70 g, 0% to 15% MeOH/$NH_4OH$ (9:1) in dichloromethane). The title compound was obtained as white foam (26 mg, 33%).

MS ISP (m/e): 459.4 (100) [$(M+H)^+$].

$^1H$ NMR ($CDCl_3$, 300 MHz): δ (ppm)=8.33-8.30 (m, 1H), 8.05-8.03 (m, 1H), 7.95-7.89 (m, 1H), 7.73-7.68 (m, 1H), 7.53-7.51 (m, 1H), 7.32-7.23 (m, 1H), 6.95-6.90 (m, 1H), 6.72-6.71 (m, 1H), 6.64-6.61 (m, 1H), 5.11-4.95 (m, 1H), 4.90-4.86 (m, 1H), 4.29-3.95 (m, 3H), 3.32-3.06 (m, 2H), 2.14-1.94 (m, 2H).

Example 245

(cis, rac)-N-(3-Fluoro-1-(6-methylpyrimidin-4-yl)piperidin-4-yl)-8-(2,3,4-trifluorophenyl)-[1,2,4]triazolo[1,5-a]pyridin-2-amine

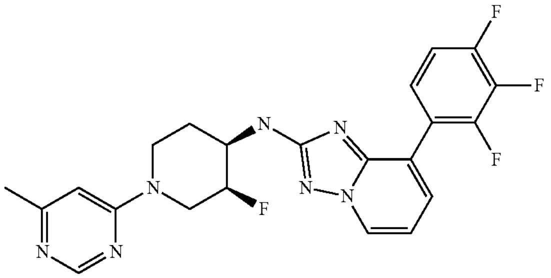 [SMILES: Cc1cc(N2CC[C@@H](Nc3nc4c(-c5ccc(F)c(F)c5F)cccn4n3)[C@@H](F)C2)ncn1]

Prepared in analogy to example 242. The title compound was obtained as orange foam.

MS ISP (m/e): 458.4 (100) [(M+H)$^+$].

$^1$H NMR ($CDCl_3$, 300 MHz): δ (ppm)=8.52 (m, 1H), 8.37-8.34 (m, 1H), 7.62-7.54 (m, 1H), 7.52-7.49 (m, 1H), 7.15-7.05 (m, 1H), 6.95-6.91 (m, 1H), 6.45 (m, 1H), 5.08-4.92 (m, 1H), 4.89-4.84 (m, 2H), 4.58-4.53 (m, 1H), 4.18-4.00 (m, 1H), 3.27-3.00 (m, 2H), 2.37 (s, 3H), 2.11-2.06 (m, 1H), 1.94-1.80 (m, 1H).

Example 246

(cis, rac)-N-(3-Fluoro-1-(2-methoxypyridin-4-yl) piperidin-4-yl)-8-(2,3,4-trifluorophenyl)-[1,2,4]triazolo[1,5-a]pyridin-2-amine

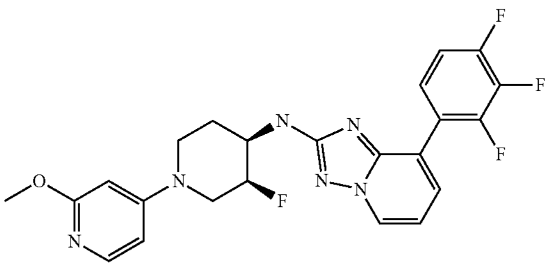 [SMILES: COc1cc(N2CC[C@@H](Nc3nc4c(-c5ccc(F)c(F)c5F)cccn4n3)[C@@H](F)C2)ccn1]

A degassed solution of 2-(dicyclohexylphosphino)biphenyl (9.21 mg, 26.3 μmol) and palladium(II) acetate (2.95 mg, 13.1 μmol) in dioxane (2 mL) was stirred for 10 minutes at room temperature, then added to a solution of (cis, rac)-N-(3-fluoropiperidin-4-yl)-8-(2,3,4-trifluorophenyl)-[1,2,4]triazolo[1,5-a]pyridin-2-amine (60 mg, 164 μmol), 4-chloro-2-methoxypyridine (see example 238f, 25.9 mg, 181 μmol) and sodium tert-butoxide (23.7 mg, 246 μmol) in dioxane (2 mL). Through the solution was bubbled argon for 5 minutes, then heated to 140° C. in the microwave for 30 minutes. Again a degassed solution of 2-(dicyclohexylphosphino)biphenyl (9.21 mg, 26.3 μmol) and palladium(II) acetate (2.95 mg, 13.1 μmol) in dioxane (2 mL) was added, followed by 4-chloro-2-methoxypyridine (25.9 mg, 181 mmol) and heated to 140° C. in the microwave for further 30 minutes. The reaction mixture was directly purified by flash chromatography (silica gel, 70 g, 0% to 15% MeOH/$NH_4OH$ (9:1) in dichloromethane) and then by preparative HPLC. The title compound was obtained as off-white foam (25 mg, 32%).

MS ISP (m/e): 473.6 (100) [(M+H)$^+$].

$^1$H NMR ($CDCl_3$, 300 MHz): δ (ppm)=8.38-8.36 (m, 1H), 7.93-7.91 (m, 1H), 7.51-7.44 (m, 2H), 7.14-7.05 (m, 1H), 6.98-6.93 (m, 1H), 6.46-6.43 (m, 1H), 6.10-6.09 (m, 1H), 5.60-5.57 (m, 1H), 5.08-4.92 (m, 1H), 4.25-3.95 (m, 3H), 3.91 (s, 3H), 3.29-3.02 (m, 2H), 2.10-1.92 (m, 2H).

Example 247

N-(3,3-difluoro-1-(3-methyl-1,2,4-thiadiazol-5-yl) piperidin-4-yl)-8-(2,3,4-trifluorophenyl)-[1,2,4]triazolo[1,5-a]pyridin-2-amine

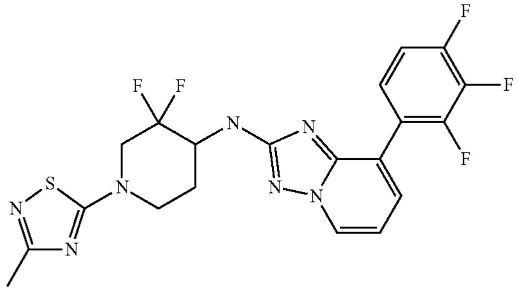 [SMILES: Cc1nsc(N2CCC(Nc3nc4c(-c5ccc(F)c(F)c5F)cccn4n3)C(F)(F)C2)n1]

a) 3-(Benzotriazol-1-ylmethyl-benzyl-amino)-propionic acid ethyl ester

To a solution of 1H-benzo[d][1,2,3]triazole (5.46 g, 45.8 mmol) in MeOH (32 mL) at 0° C. were added ethyl 3-(benzylamino)propanoate (10 g, 45.8 mmol) and an aqueous solution of formaldehyde (36%, 4.56 mL, 59.6 mmol). The reaction mixture was warmed to room temperature and stirred for 12 hours. The solvent was evaporated and the residue was purified by flash-chromatography over 330 g flash pack using gradient EtOAc/Heptane 5-50% over 40 minutes. The title compound was obtained as colorless oil (12.62 g, 81%).

b) Ethyl 3-(benzyl(3-ethoxy-3-oxopropyl)amino)-2,2-difluoropropanoate

To a suspension of activated zinc dust (4.13 g, 63.2 mmol) in dry THF (100 mL) under argon was added TMS-Cl (3.60 g, 4.24 mL, 33.2 mmol). After 10 minutes ethyl bromodifluoroacetate (7.05 g, 4.49 mL, 34.7 mmol) was added slowly, whereby the temperature was kept below 30° C. (cooling with a waterbath). Then a solution of 3-(benzotriazol-1-ylmethyl-benzyl-amino)-propionic acid ethyl ester (10.69 g, 31.6 mmol) in dry THF (100 mL) was added. The exothermic reaction was kept between 20 and 25° C. with a waterbath. The reaction mixture was stirred at room temperature for 12 hours. The reaction mixture was poured on 5% aqueous $NaHCO_3$ solution and filtered over dicalite. The filtrate was extracted three times with ethyl acetate. The organic layers were washed with water and 1 N HCl, then dried over $Na_2SO_4$, filtered and the solvents were evaporated. The residue was purified by flash chromatography (silica gel, 100 g, 0% to 50% EtOAc in heptane) to give the title compound as colorless liquid (10.78 g, 99%).

MS ISP (m/e): 344.1 (100) [(M+H)$^+$].

$^1$H NMR ($CDCl_3$, 300 MHz): δ (ppm)=7.34-7.22 (m, 5H), 4.32-4.25 (q, 2H), 4.12-4.05 (q, 2H), 3.75 (s, 2H), 3.21-3.13 (t, 2H), 2.93-2.88 (t, 2H), 2.45-2.40 (t, 2H), 1.34-1.29 (t, 3H), 1.24-1.20 (t, 3H).

c) Ethyl 1-benzyl-5,5-difluoro-4-oxopiperidine-3-carboxylate

To a solution of ethyl 3-(benzyl(3-ethoxy-3-oxopropyl)amino)-2,2-difluoropropanoate (10.78 g, 31.4 mmol) in NMP (100 mL) at 0° C. was added potassium tert-butoxide (5.64 g, 50.2 mmol) and the reaction mixture stirred at room temperature for 2 days. The reaction mixture was cooled to 0° C. and aqueous $NH_4Cl$ solution was added. The aqueous phase was extracted with EtOAc. The combined organic layers were dried over $Na_2SO_4$ and the solvent was evaporated. The residue was purified by flash chromatography using a gradient EtOAc/Heptane 0-70% over 40 minutes to give the title compound as white solid (5.56 g, 60%).

MS ISP (m/e): 298.4/316.2 (19/100) $[(M+H)^+/(M+H_2O)^+]$.

$^1H$ NMR ($CDCl_3$, 300 MHz): δ (ppm)=11.59 (s, 1H), 7.38-7.27 (m, 5H), 4.30-4.23 (q, 2H), 3.71 (s, 2H), 3.32-3.29 (m, 2H), 2.98-2.90 (m, 2H), 1.33-1.28 (t, 3H).

d) 1-Benzyl-3,3-difluoropiperidine-4,4-diol

A solution of ethyl 1-benzyl-5,5-difluoro-4-oxopiperidine-3-carboxylate (4.272 g, 14.4 mmol) dissolved in 3 N HCl (175 mL) was heated at reflux for 14 hours. The reaction mixture was cooled to room temperature, then solid $NaHCO_3$ was added until pH 8 and extracted three times with ethyl acetate, the combined organic layers were dried over $Na_2SO_4$ and the solvents were evaporated. The title compound was obtained as white solid (3.5 g, 100%).

MS ISP (m/e): 244.3 (100) $[(M+H)^+]$.

$^1H$ NMR ($CDCl_3$, 300 MHz): δ (ppm)=7.33-7.30 (m, 5H), 3.62 (s, 2H), 2.85-2.77 (m, 4H), 2.62-2.58 (m, 2H), 1.99-1.96 (m, 2H).

e) tert-Butyl 3,3-difluoro-4,4-dihydroxypiperidine-1-carboxylate

A suspension of 1-benzyl-3,3-difluoropiperidine-4,4-diol (3.5 g, 14.4 mmol), di-tert-butyl dicarbonate (3.45 g, 3.64 mL, 15.8 mmol) and palladium on carbon (10%) (459 mg, 432 μmol) in ethanol (75 mL) was hydrogenated at room temperature over night. The catalyst was filtered off, washed thoroughly with MeOH and the solvents were evaporated to yield title compound as light yellow oil (4.3 g, 100%; purity: 85%).

MS ISN (m/e): 294.3/312.2 (46/100)$[(M-H_2O+AcO)^-/(M+AcO)^-]$.

f) 4-Benzylamino-3,3-difluoro-piperidine-1-carboxylic acid tert-butyl ester

A mixture of tert-butyl 3,3-difluoro-4,4-dihydroxypiperidine-1-carboxylate (1 g, 3.36 mmol), and benzylamine (539 mg, 550 μL, 5.03 mmol) in dry toluene (70 mL) was heated to reflux with dean stark apparatus for 12 hours. Further benzyl amine (20 μL, 185 μmol) was added and heated to reflux with dean stark apparatus for another 12 hours. About 50 mL of toluene were distilled off, the residue was cooled to 55° C., ethanol (35 mL) and $NaBH_4$ (508 mg, 13.4 mmol) were added and the reaction mixture stirred at 55° C. for 2 hours. Further $NaBH_4$ (508 mg, 13.4 mmol) was added and stirred for another hour. Further $NaBH_4$ (508 mg, 13.4 mmol) was added. After 2 hours the reaction mixture was concentrated, then 2 N $Na_2CO_3$ solution was added and the aqueous phase was extracted with ethyl acetate. The combined organic layers were dried over $Na_2SO_4$ and the solvents were evaporated. The residue was purified by flash chromatography (70 g, 0% to 100% EtOAc in hexanes). The title compound was obtained as colorless oil (875 mg, 80%).

MS ISP (m/e): 327.3/271.3 (18/100) $[(M+H)^+/(M-tBu)^+]$.

$^1H$ NMR ($CDCl_3$, 300 MHz): δ (ppm)=7.34-7.24 (m, 5H), 4.03 (b, 1H), 3.92 (s, 2H), 3.77 (b, 1H), 3.39-3.25 (m, 1H), 3.15-3.07 (m, 1H), 3.03-2.91 (m, 1H), 1.92-1.86 (m, 1H), 1.67-1.60 (m, 1H), 1.55 (b, 1H), 1.46 (s, 9H).

g) 4-Amino-3,3-difluoro-piperidine-1-carboxylic acid tert-butyl ester

A suspension of 4-benzylamino-3,3-difluoro-piperidine-1-carboxylic acid tert-butyl ester (830 mg, 2.54 mmol), Pd/C (81.2 mg, 76.3 μmol) in MeOH (30 mL) was hydrogenated at room temperature for 14 hours. The catalyst was filtered off, washed thoroughly with MeOH and the solvents were evaporated. The title compound was obtained as colorless oil (601 mg, 100%).

MS ISP (m/e): 181.1 (61) $[(M-tBu)^+]$.

h) 3,3-Difluoro-4-[8-(2,3,4-trifluoro-phenyl)-[1,2,4]triazolo[1,5-a]pyridin-2-ylamino]-piperidine-1-carboxylic acid tert-butyl ester Through a suspension of 4-amino-3,3-difluoro-piperidine-1-carboxylic acid tert-butyl ester (90 mg, 381 μmol), 2-bromo-8-(2,3,4-trifluorophenyl)-[1,2,4]triazolo[1,5-a]pyridine (prepared in analogy to example 66a-d, 162 mg, 495 μmol), tris(dibenzylideneacetone)dipalladium(0) chloroform adduct (15.8 mg, 15.2 μmol), sodium phenoxide (65.2 mg, 533 μmol) and 4,5-bis(diphenylphosphino)-9,9-dimethylxanthene (17.6 mg, 30.5 μmol) in dry dioxane (5.0 mL) was bubbled argon for 5 minutes, then heated to 160° C. in the microwave for 60 minutes. The catalyst was filtered off, washed with $CH_2Cl_2$ and the solvents evaporated. The residue was purified by flash chromatography (silica gel, 70 g, 0% to 100% EtOAc in heptane). The title compound was obtained as orange solid (27 mg, 15%).

MS ISP (m/e): 484.2/428.2 (45/100) $[(M+H)^+/(M-tBu)^+]$.

$^1H$ NMR ($CDCl_3$, 300 MHz): δ (ppm)=8.36-8.33 (m, 1H), 7.64-7.55 (m, 1H), 7.52-7.49 (m, 1H), 7.15-7.05 (m, 1H), 6.94-6.90 (m, 1H), 4.82-4.78 (d, 1H), 4.48-4.11 (m, 3H), 3.23-2.91 (m, 2H), 2.17-2.12 (m, 1H), 1.80-1.60 (m, 1H), 1.48 (s, 9H).

i) N-(3,3-Difluoropiperidin-4-yl)-8-(2,3,4-trifluorophenyl)-[1,2,4]triazolo[1,5-a]pyridin-2-amine To a solution of 3,3-difluoro-4-[8-(2,3,4-trifluoro-phenyl)-[1,2,4]triazolo[1,5-a]pyridin-2-ylamino]-piperidine-1-carboxylic acid tert-butyl ester (110 mg, 228 μmol) in $CH_2Cl_2$ (4 mL) at 0° C. was added TFA (182 mg, 123 μl, 1.59 mmol) and stirred at room temperature for 18 hours. Further TFA (182 mg, 123 μl, 1.59 mmol) was added and stirred at 50° C. for 6 hours. The reaction mixture was extracted with saturated $NaHCO_3$ solution and ethyl acetate, the organic layers were combined, dried over $Na_2SO_4$, filtered and the solvents were evaporated. The product was coevaporated four times with toluene. The title compound was obtained as light yellow foam (87 mg, 100%).

MS ISP (m/e): 384.2 (100) $[(M+H)^+]$.

$^1H$ NMR ($CDCl_3$, 300 MHz): δ (ppm)=8.36-8.34 (m, 1H), 7.64-7.56 (m, 1H), 7.51-7.49 (m, 1H), 7.15-7.06 (m, 1H), 6.94-6.90 (m, 1H), 4.87-4.84 (d, 1H), 4.33-4.16 (m, 1H), 3.35-3.25 (m, 1H), 3.14-3.09 (m, 1H), 2.99-2.72 (m, 2H), 2.25-2.18 (m, 1H), 1.66-1.61 (m, 2H).

j) N-(3,3-Difluoro-1-(3-methyl-1,2,4-thiadiazol-5-yl)piperidin-4-yl)-8-(2,3,4-trifluorophenyl)-[1,2,4]triazolo[1,5-a]pyridin-2-amine A degassed solution of 2-(dicyclohexylphosphino)biphenyl (12.7 mg, 36.3 μmol) and palladium(II) acetate (4.08 mg, 18.2 μmol) in dioxane (2 mL) was stirred for 10 minutes at room temperature, then a solution of N-(3,3-difluoropiperidin-4-yl)-8-(2,3,4-trifluorophenyl)-[1,2,4]triazolo[1,5-a]pyridin-2-amine (87 mg, 227 μmol), 5-chloro-3-methyl-1,2,4-thiadiazole (30.5 mg, 227 μmol) and sodium tert-butoxide (32.7 mg, 340 μmol) in dioxane (2 mL) was added. Through the solution was bubbled argon for 5 minutes, then heated to 150° C. in the microwave for 60 minutes. Again a degassed solution of 2-(dicyclohexylphosphino)biphenyl (12.7 mg, 36.3 μmol) and palladium(II) acetate (4.08 mg, 18.2 μmol) in dioxane (2 mL) was added, followed by 5-chloro-3-methyl-1,2,4-thiadiazole (30.5 mg, 227 μmol) and heated to 150° C. in the microwave for further 60 minutes. Again a degassed solution of 2-(dicyclohexylphosphino)biphenyl (12.7 mg, 36.3 μmol) and palladium(II) acetate (4.08 mg, 18.2 mmol) in dioxane (2 mL) was added, followed by 5-chloro-3-methyl-1,2,4-thiadiazole (30.5 mg, 227 μmol) and heated to 150° C. in the microwave for further 60 minutes. The crude material was purified by flash chromatography (silica gel, 70 g, 0% to 15% MeOH/$NH_4OH$ (9:1) in dichloromethane) and then by preparative HPLC. The title compound was obtained as white foam (42 mg, 38%).

MS ISP (m/e): 482.2 (100) [$(M+H)^+$].

$^1$H NMR ($CDCl_3$, 300 MHz): δ (ppm)=8.37-8.35 (m, 1H), 7.62-7.55 (m, 1H), 7.53-7.51 (m, 1H), 7.15-7.06 (m, 1H), 6.97-6.92 (m, 1H), 4.87-4.84 (d, 1H), 4.46-4.32 (m, 2H), 3.90-3.85 (m, 1H), 3.60-3.37 (m, 2H), 2.42 (s, 3H), 2.34-2.27 (m, 1H), 2.04-1.90 (m, 1H).

Example 248

N-(1-(2-Chloropyridin-4-yl)-4-phenylpiperidin-4-yl)-8-(3,4-difluorophenyl)-[1,2,4]triazolo[1,5-a]pyridin-2-amine

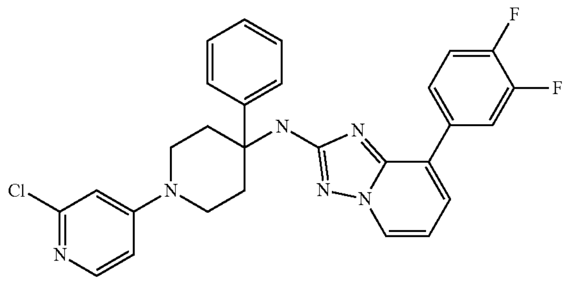 [SMILES: Fc1ccc(-c2cccn3nc(NC4(c5ccccc5)CCN(c5ccnc(Cl)c5)CC4)nc23)cc1F]

Prepared in analogy to example 236, employing phenylmagnesium bromide (1 M in THF, 0.625 mL, 0.625 mmol) instead of methylmagnesiumbromide.

The title compound was obtained as an off white solid (21 mg, 20%) after purification by HPLC.

MS ISP (m/e): 517.2 [$(M+H)^+$].

Example 249

8-(3,4-Difluorophenyl)-N-(1-(6-methylpyrimidin-4-yl)-4-phenylpiperidin-4-yl)-[1,2,4]triazolo[1,5-a]pyridin-2-amine

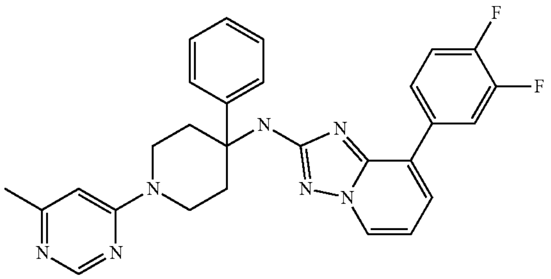 [SMILES: Cc1cc(N2CCC(Nc3nc4c(-c5ccc(F)c(F)c5)cccn4n3)(c3ccccc3)CC2)ncn1]

Prepared in analogy to example 234, employing phenylmagnesium bromide (1 M in THF, 0.625 mL, 0.625 mmol) instead of methylmagnesiumbromide.

The title compound was obtained as a white solid (27 mg, 27%) after purification by HPLC.

MS ISP (m/e): 498.3 [$(M+H)^+$].

Example 250

2-{8-(4-Fluoro-phenyl)-2-[1-(6-methyl-pyrimidin-4-yl)-piperidin-4-ylamino]-[1,2,4]triazolo[1,5-a]pyridin-5-yl}-propan-2-ol

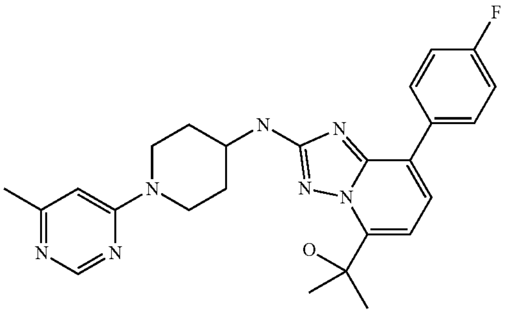 [SMILES: Cc1cc(N2CCC(Nc3nc4c(-c5ccc(F)cc5)ccc(C(C)(C)O)n4n3)CC2)ncn1]

Prepared in analogy to example 49. The title compound was obtained as an off-white solid. MS ESI (m/z): 462.0 [$(M+H)^+$].

$^1$H NMR (DMSO, 400 MHz): δ (ppm)=8.36 (s, 1H), 8.15-8.11 (m, 2H), 7.75 (d, J=7.84 Hz, 1H), 7.32 (t, J=8.88 Hz, 2H), 7.13 (d, J=7.84 Hz, 1H), 6.87 (d, J=7.36 Hz, 1H), 6.74 (s, 1H), 5.81 (s, 1H), 4.28 (d, J=12.52 Hz, 2H), 3.16 (t, J=11.28 Hz, 2H), 2.25 (s, 3H), 2.01 (d, J=2.49 Hz, 2H), 1.72 (s, 6H), 1.54-1.46 (m, 2H).

Example 251

2-{8-(3,4-Difluoro-phenyl)-2-[1-(6-methyl-pyrimidin-4-yl)-piperidin-4-ylamino]-[1,2,4]triazolo[1,5-a]pyridin-5-yl}-propan-2-ol

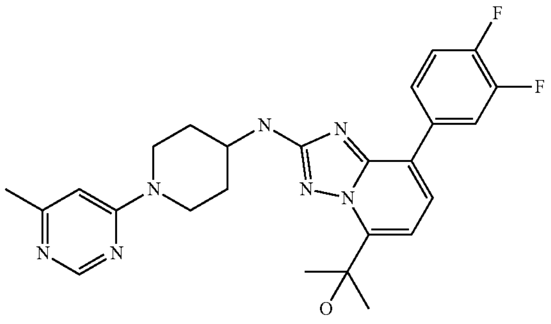 [SMILES: Cc1cc(N2CCC(Nc3nc4c(-c5ccc(F)c(F)c5)ccc(C(C)(C)O)n4n3)CC2)ncn1]

Prepared in analogy to example 49. The title compound was obtained as an off-white solid. MS ESI (m/z): 480.0 [(M+H)+].

Example 252

8-(2-Chloro-4-fluorophenyl)-6-methyl-N-(1-(2-(trifluoromethyl)pyridin-4-yl)piperidin-4-yl)-[1,2,4]triazolo[1,5-a]pyridin-2-amine

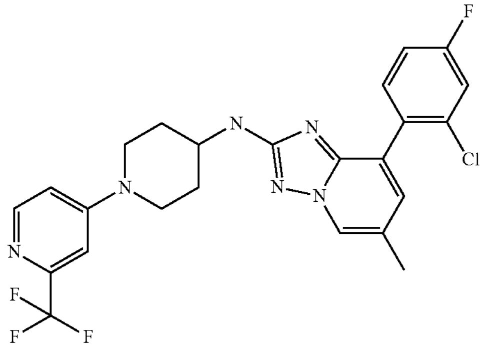 [SMILES: Cc1cc(-c2ccc(F)cc2Cl)c2nc(NC3CCN(c4ccnc(C(F)(F)F)c4)CC3)nn2c1]

Prepared in analogy to example 200c, employing 2-bromo-8-(2-chloro-4-fluorophenyl)-6-methyl-[1,2,4]triazolo[1,5-a]pyridine (102 mg, 0.3 mmol) instead of 2-bromo-8-(3,4-difluorophenyl)-[1,2,4]triazolo[1,5-a]pyridine.

The title compound was obtained as a light yellow foam (88 mg, 58%).

MS ISP (m/e): 505.3/507.2 [(M+H)+].

Example 253

N-(1-(2-(Trifluoromethyl)pyridin-4-yl)piperidin-4-yl)-8-(2,3,4-trifluorophenyl)-[1,2,4]triazolo[1,5-a]pyridin-2-amine

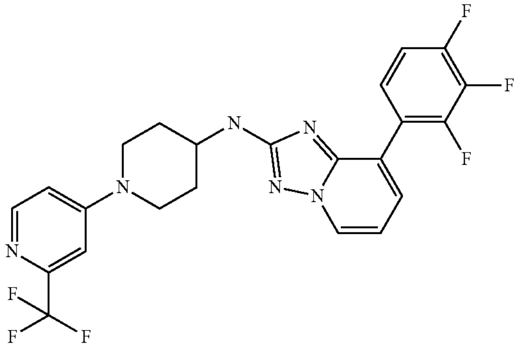 [SMILES: Fc1ccc(-c2cccn3nc(NC4CCN(c5ccnc(C(F)(F)F)c5)CC4)nc23)c(F)c1F]

Prepared in analogy to example 200c, employing 2-bromo-8-(2,3,4-trifluorophenyl)-[1,2,4]triazolo[1,5-a]pyridine (98 mg, 0.3 mmol) instead of 2-bromo-8-(3,4-difluorophenyl)-[1,2,4]triazolo[1,5-a]pyridine.

The title compound was obtained as a yellow foam (72 mg, 49%).

MS ISP (m/e): 499.3 [(M+H)+].

Example 254

8-(2,4-Difluorophenyl)-N-(1-(2-(trifluoromethyl)pyridin-4-yl)piperidin-4-yl)-[1,2,4]triazolo[1,5-a]pyridin-2-amine

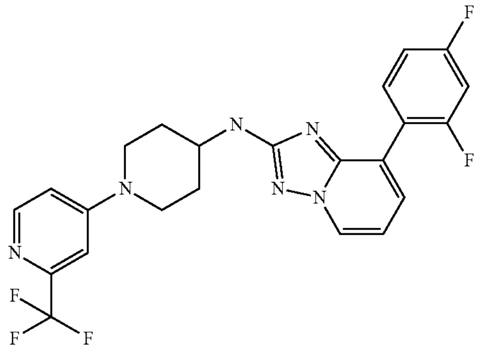 [SMILES: Fc1ccc(-c2cccn3nc(NC4CCN(c5ccnc(C(F)(F)F)c5)CC4)nc23)c(F)c1]

Prepared in analogy to example 200c, employing 2-bromo-8-(2,4-difluorophenyl)-[1,2,4]triazolo[1,5-a]pyridine (93 mg, 0.3 mmol) instead of 2-bromo-8-(3,4-difluorophenyl)-[1,2,4]triazolo[1,5-a]pyridine.

The title compound was obtained as a yellow foam (81 mg, 57%).

MS ISP (m/e): 475.3 [(M+H)+].

Example 255

6-Chloro-8-(2-chloro-4-fluorophenyl)-N-(1-(2-(trifluoromethyl)pyridin-4-yl)piperidin-4-yl)-[1,2,4]triazolo[1,5-a]pyridin-2-amine

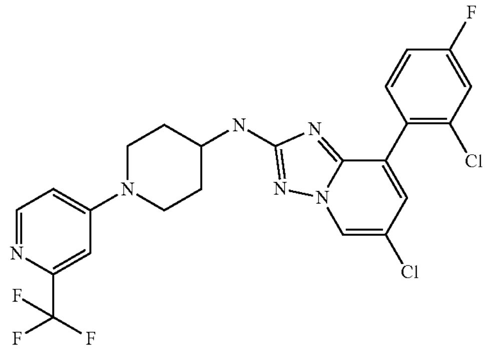 [SMILES: Fc1ccc(-c2cc(Cl)cn3nc(NC4CCN(c5ccnc(C(F)(F)F)c5)CC4)nc23)c(Cl)c1]

Prepared in analogy to example 200c, employing 2-bromo-6-chloro-8-(2-chloro-4-fluorophenyl)-[1,2,4]triazolo[1,5-a]pyridine (108 mg, 0.3 mmol) instead of 2-bromo-8-(3,4-difluorophenyl)-[1,2,4]triazolo[1,5-a]pyridine.

The title compound was obtained as a yellow foam (50 mg, 32%).

MS ISP (m/e): 525.2/527.1 [(M+H)$^+$].

Example 256

8-(3,5-Bis(trifluoromethyl)phenyl)-N-(1-(2-(trifluoromethyl)pyridin-4-yl)piperidin-4-yl)-[1,2,4]triazolo[1,5-a]pyridin-2-amine

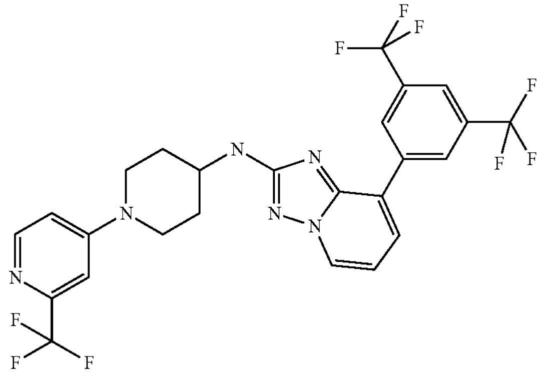 [SMILES: FC(F)(F)c1cc(-c2cccn3nc(NC4CCN(c5ccnc(C(F)(F)F)c5)CC4)nc23)cc(C(F)(F)F)c1]

Prepared in analogy to example 200c, employing 8-(3,5-bis(trifluoromethyl)phenyl)-2-bromo-[1,2,4]triazolo[1,5-a]pyridine (123 mg, 0.3 mmol) instead of 2-bromo-8-(3,4-difluorophenyl)-[1,2,4]triazolo[1,5-a]pyridine.

The title compound was obtained as a yellow foam (94 mg, 54%).

MS ISP (m/e): 575.2 [(M+H)$^+$].

Example 257

8-(2-Chloro-4-fluorophenyl)-6-fluoro-N-(1-(2-(trifluoromethyl)pyridin-4-yl)piperidin-4-yl)-[1,2,4]triazolo[1,5-a]pyridin-2-amine

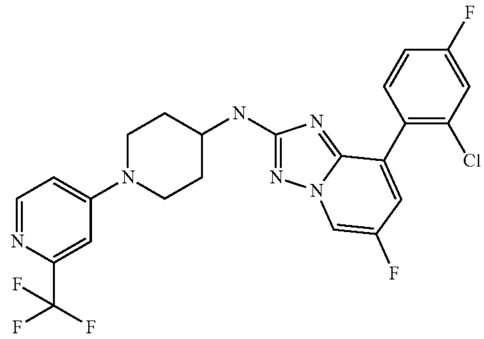 [SMILES: Fc1ccc(-c2cc(F)cn3nc(NC4CCN(c5ccnc(C(F)(F)F)c5)CC4)nc23)c(Cl)c1]

Prepared in analogy to example 200c, employing 2-bromo-8-(2-chloro-4-fluorophenyl)-6-fluoro-[1,2,4]triazolo[1,5-a]pyridine (103 mg, 0.3 mmol) instead of 2-bromo-8-(3,4-difluorophenyl)-[1,2,4]triazolo[1,5-a]pyridine.

The title compound was obtained as an off white foam (61 mg, 40%).

MS ISP (m/e): 509.2/511.2 [(M+H)$^+$].

Example 258

4-Chloro-3-(2-(1-(3-methyl-1,2,4-thiadiazol-5-yl)piperidin-4-ylamino)-[1,2,4]triazolo[1,5-a]pyridin-8-yl)benzonitrile

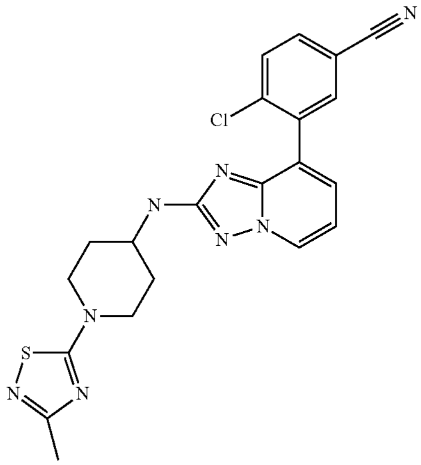 [SMILES: Cc1nsc(N2CCC(Nc3nc4c(-c5cc(C#N)ccc5Cl)cccn4n3)CC2)n1]

Prepared in analogy to example 226. The title compound was obtained as an white foam.

MS ISP (m/e): 451.2/453.2 (100/35) [(M+H)$^+$].

$^1$H NMR ($CDCl_3$, 300 MHz): δ (ppm)=8.42-8.39 (m, 1H), 7.86 (m, 1H), 7.65 (m, 2H), 7.44-7.41 (m, 1H), 6.96-6.91 (m, 1H), 4.64-4.61 (m, 1H), 3.92-3.85 (m, 3H), 3.40-3.31 (m, 2H), 2.41 (s, 3H), 2.27-2.22 (m, 2H), 1.72-1.59 (m, 2H).

Example 259

(3,4-Difluorophenyl)-N-((3RS,4SR)-3-fluoro-1-(2-(trifluoromethyl)pyridin-4-yl)piperidin-4-yl)-[1,2,4]triazolo[1,5-a]pyridin-2-amine

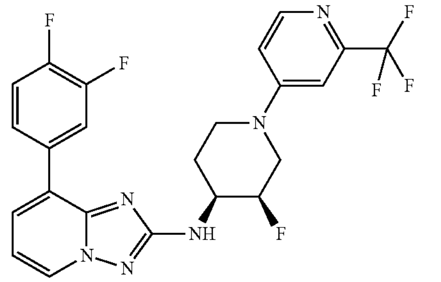 [SMILES: Fc1ccc(-c2cccn3nc(N[C@H]4CCN(c5ccnc(C(F)(F)F)c5)C[C@H]4F)nc23)cc1F]

(cis, rac)-8-(3,4-Difluorophenyl)-N-(3-fluoropiperidin-4-yl)-[1,2,4]triazolo[1,5-a]pyridin-2-amine (prepared in analogy to example 238a-f) was reacted with 4-iodo-2-(trifluoromethyl)pyridine in analogy to example 242 affording the title compound as a light brown foam (yield: 35%). MS ISP (m/e): 493.2 [(M+H)$^+$].

$^1$H NMR ($CDCl_3$, 400 MHz): δ (ppm)=8.36 (d, 1H), 8.32 (d, 1H), 7.96-7.90 (m, 1H), 7.73-7.68 (m, 1H), 7.52 (d, 1H), 7.32-7.23 (m, 1H), 7.07 (d, 1H), 6.93 (t, 1H), 6.81 (dd, 1H), 5.06 (d, 1H), 4.88 (d, 1H), 4.33 (tt, 1H), 4.21-4.02 (m, 2H), 3.29 (dd, 1H), 3.16 (td, 1H), 2.18-2.11 (m, 1H), 1.98 (qd, 1H).

Example 260

[1-(3-Methyl-[1,2,4]thiadiazol-5-yl)-piperidin-4-yl]-(6-phenoxy-[1,2,4]triazolo[1,5-a]pyridin-2-yl)-amine

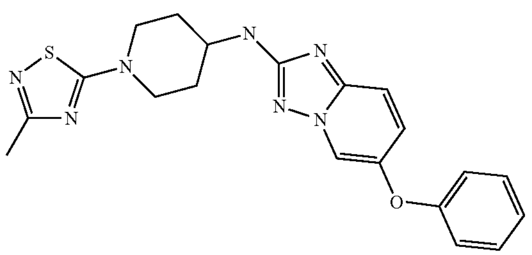 [SMILES: Cc1nsc(N2CCC(Nc3nc4ccc(Oc5ccccc5)cn4n3)CC2)n1]

To a mixture (6-bromo-[1,2,4]triazolo[1,5-a]pyridin-2-yl)-[1-(3-methyl-[1,2,4]thiadiazol-5-yl)-piperidin-4-yl]-amine (prepared in analogy to example 226a employing 6-bromo-[1,2,4]triazolo[1,5-a]pyridin-2-ylamine which was prepared in analogy to example 66a-b) (78 mg, 198 μmol), phenol (37.2 mg, 34.8 μL, 396 μmol), copper(I) iodide (1.77 mg, 19.8 μmol), picolinic acid (4.87 mg, 39.6 μmol) and potassium phosphate tribasic (126 mg, 593 μmol) was added DMSO (1 mL) and heated to 120° C. for 12 hours. Further phenol (37.2 mg, 34.8 μl, 396 mmol), picolinic acid (4.87 mg, 39.6 μmol), copper(I) iodide (1.77 mg, 19.8 μmol) and potassium phosphate tribasic (126 mg, 593 μmol) in DMSO (1 mL) were added and stirred at 120° C. another 16 hours. Water was added to the reaction mixture and the aqueous phase was extracted three times with ethyl acetate. The combined organic phases were dried over $Na_2SO_4$ and the solvent was evaporated. The residue was purified by flash chromatography (silica gel, 50 g, 0% to 15% MeOH/$NH_4$OH (9:1) in dichloromethane, 45 minutes) and then by preparative HPLC.

The title compound was obtained as off-white foam (15 mg, 18%).

MS ISP (m/e): 408.3 (100) [(M+H)$^+$].

$^1$H NMR ($CDCl_3$, 300 MHz): δ (ppm)=8.12-8.11 (m, 1H), 7.39-7.34 (m, 3H), 7.28-7.24 (m, 1H), 7.17-7.12 (m, 1H), 7.02-7.00 (m, 2H), 4.41-4.39 (m, 1H), 3.93-3.88 (m, 3H), 3.38-3.29 (m, 2H), 2.42 (s, 3H), 2.28-2.23 (m, 2H), 1.72-1.58 (m, 2H).

Example 261

N-(1-(3-methyl-1,2,4-thiadiazol-5-yl)piperidin-4-yl)-7-phenyl-[1,2,4]triazolo[1,5-a]pyridin-2-amino

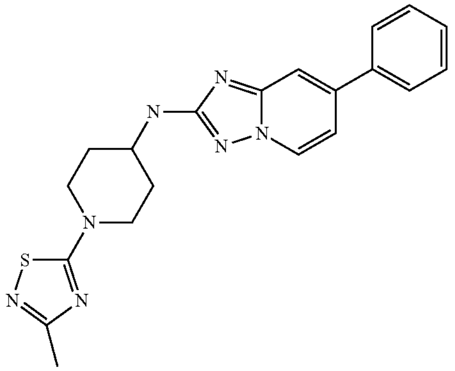 [SMILES: Cc1nsc(N2CCC(Nc3nc4cc(-c5ccccc5)ccn4n3)CC2)n1]

a) (7-Bromo-[1,2,4]triazolo[1,5-a]pyridin-2-yl)-[1-(3-methyl-[1,2,4]thiadiazol-5-yl)-piperidin-4-yl]-amine To a suspension of 7-bromo-[1,2,4]triazolo[1,5-a]pyridin-2-amine (prepared in analogy to example 66a-b starting from 4-bromo-pyridin-2-ylamine) (250 mg, 1.17 mmol) and hexachloroethane (333 mg, 1.41 mmol) under argon in dry THF (12.5 mL) was added triethylamine (356 mg, 491 μL, 3.52 mmol) and the mixture was heated to 50° C. for 10 minutes. Trimethylphosphine (1 M in THF, 1.41 mL, 1.41 mmol) was added. The reaction mixture was stirred at room temperature for 0.5 h, then 1-(3-methyl-1,2,4-thiadiazol-5-yl)piperidin-4-one (278 mg, 1.41 mmol) was added and the mixture heated in the microwave to 150° C. for 30 minutes. To the reaction mixture a solution of decaborane (143 mg, 153 μL, 1.17 mmol) in dry methanol (3 mL) was added and stirred at for 3 hours at room temperature. Further decaborane (34.4 mg, 36.6 μL, 282 μmol) in dry methanol (1.00 mL) was added. The reaction mixture was heated to 60° C. for 12 hours. Further decaborane (17 mg) dissolved in methanol (1 mL) was added and heated to 70° C. for 3 hours. Aqueous $NaHCO_3$ solution was added and the aqueous phase was extracted with $CH_2Cl_2$, the organic layers were combined, dried over $Na_2SO_4$, filtered and the solvents were evaporated. The residue was purified by flash chromatography (silica gel, 70 g, 0% to 15% MeOH/$NH_4$OH (9:1) in dichloromethane). The title compound was obtained as off-white solid (300 mg, 65%).

MS ISP (m/e): 394.0/396.0 (96/100) [(M+H)$^+$].

$^1$H NMR ($CDCl_3$, 300 MHz): δ (ppm)=8.16-8.14 (m, 1H), 7.56 (m, 1H), 6.94-6.91 (m, 1H), 4.49-4.46 (m, 1H), 3.93-3.87 (m, 3H), 3.39-3.30 (m, 2H), 2.42 (s, 3H), 2.27-2.22 (m, 2H), 1.72-1.60 (m, 2H).

b) N-(1-(3-Methyl-1,2,4-thiadiazol-5-yl)piperidin-4-yl)-7-phenyl-[1,2,4]triazolo[1,5-a]pyridin-2-amine Prepared in analogy to example 66c from (7-bromo-[1,2,4]triazolo[1,5-a]pyridin-2-yl)-[1-(3-methyl-[1,2,4]thiadiazol-5-yl)-piperidin-4-yl]-amine and phenyl boronic acid. The title compound was obtained as off-white foam.

MS ISP (m/e): 392.2 (100) [(M+H)$^+$].

$^1$H NMR ($CDCl_3$, 300 MHz): δ (ppm)=8.35-8.33 (m, 1H), 7.56-7.60 (m, 3H), 7.52-7.44 (m, 3H), 7.10-7.07 (m, 1H), 4.55-4.52 (m, 1H), 3.99-3.90 (m, 3H), 3.41-3.32 (m, 2H), 2.42 (s, 3H), 2.31-2.25 (m, 2H), 1.74-1.60 (m, 2H).

Example 262 and 263

(4-Fluorophenyl)(2-(1-(3-methyl-1,2,4-thiadiazol-5-yl)piperidin-4-ylamino)-[1,2,4]triazolo[1,5-a]pyridin-8-yl)methanol and {8-[(4-Fluoro-phenyl)-methoxy-methyl]-[1,2,4]triazolo[1,5-a]pyridin-2-yl}-[1-(3-methyl-[1,2,4]thiadiazol-5-yl)-piperidin-4-yl]-amine

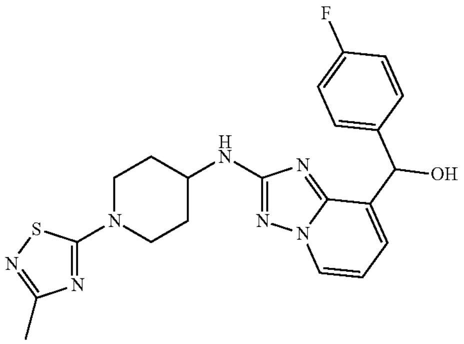

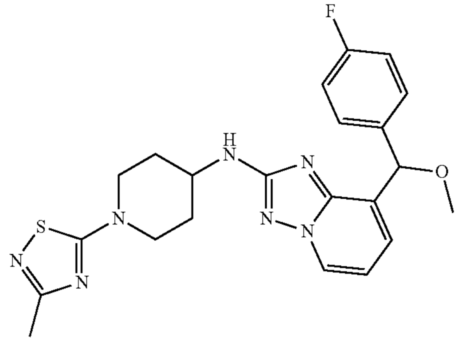

N-{3-[(4-Fluoro-phenyl)-hydroxy-methyl]-pyridin-2-yl}pivalamide

To a solution of N-(pyridin-2-yl)pivalamide (1.84 g, 10 mmol) in tetrahydrofurane (100 mL) was added at −78° C. under an atmosphere of nitrogen 1.6 M butyl lithium in hexane (13.1 mL, 21 mmol). The reaction is slighly exothermic and a yellow color appears. The reaction is warmed to 0° C. within 15 minutes and stirred at 0° C. for 2 hours. A white suspension is formed. The reaction is cooled to −78° C. and 4-fluorobenzaldehyde (1.52 g, 1.29 mL, 12.0 mmol) was added in tetrahydrofurane (6.55 mL). The reaction was warmed to room temperature over night to yield an orange suspension. Saturated aqueous ammonium chloride solution was added and the reaction was extracted twice with ethyl acetate and once with methylene chloride. The combined organic layers were washed with saturated aqueous sodium chloride solution, dried over sodium sulfate, filtered and the solvent was evaporated under reduced pressure. The title compound was obtained as a yellow viscous oil (1.058 g, 35%) after purification by column chromatography on silica gel using a gradient from $CH_2Cl_2$ to $CH_2Cl_2$/MeOH 19:1 (v/v) as eluent. MS ISP (m/e): 303.1 (100) [(M+H)$^+$].

b) (2-Amino-pyridin-3-yl)-(4-fluoro-phenyl)-methanol

To a solution of N-{3-[(4-fluoro-phenyl)-hydroxy-methyl]-pyridin-2-yl}pivalamide (890 mg, 2.94 mmol) in ethanol (44 mL) was added 2 N aqueous sodium hydroxide solution (7.36 mL, 14.7 mmol). The reaction was heated to 100° C. for 5 hours. Water was added and the reaction was extracted twice with ethyl acetate. The combined organic layers were washed with saturated aqueous sodium chloride solution, dried over sodium sulfate, filtered and the solvent was evaporated under reduced pressure to yield the title compound as a as a light yellow solid (548 mg, 85%) without further purification.

MS ISP (m/e): 219.2 (61) [(M+H)$^+$], 201.2 (100) [(M−$H_2O$+H)$^+$].

c) (2-Amino-[1,2,4]triazolo[1,5-a]pyridin-8-yl)-(4-fluoro-phenyl)-methanol

Prepared in analogy to example 1e-f), starting from (2-amino-pyridin-3-yl)-(4-fluoro-phenyl)-methanol. The title compound was obtained on pouring the reaction on water, washing and drying as a white solid (yield: 63% over 2 steps).

MS ISP (m/e): 259.1 (19) [(M+H)$^+$], 241.2 (100).

$^1$H NMR (DMSO-$D_6$, 300 MHz): (ppm)=8.42 (d, 1H), 7.52 (d, 1H), 7.46 (dd, 2H), 6.89 (t, 2H), 6.08 (m, 2H), 6.02 (br s, 2H).

d) (4-Fluorophenyl)(2-(1-(3-methyl-1,2,4-thiadiazol-5-yl)piperidin-4-ylamino)-[1,2,4]triazolo[1,5-a]pyridin-8-yl)methanol and {8-[4-fluoro-phenyl)-methoxy-methyl]-[1,2,4]triazolo[1,5-a]pyridin-2-yl}-[1-(3-methyl-[1,2,4]thiadiazol-5-yl)-piperidin-4-yl]-amine Prepared in analogy to example 219f), starting from (2-amino-[1,2,4]triazolo[1,5-a]pyridin-8-yl)(4-fluorophenyl)methanol and 1-(3-methyl-1,2,4-thiadiazol-5-yl)piperidin-4-one. As a reducing agent 1 eq decaborane in methanol was used at 50° C. over night. The crude product was purified by column chromatography on silica gel using a gradient from $CH_2Cl_2$ to $CH_2Cl_2$/MeOH 19:1 (v/v) as eluent to yield eluting first {8-[(4-fluoro-phenyl)-methoxy-methyl]-[1,2,4]triazolo[1,5-a]pyridin-2-yl}-[1-(3-methyl-[1,2,4]thiadiazol-5-yl)-piperidin-4-yl]-amine (yield: 4%) as a colorless oil.

MS ISP (m/e): 454.3 (100) [(M+H)$^+$], 422.2 (98), 241.2 (98).

$^1$H NMR ($CDCl_3$, 300 MHz): δ (ppm)=8.22 (d, 1H), 7.48 (m, 3H), 7.00 (t, 2H), 6.83 (t, 1H), 5.76 (br s, 1H), 4.52 (m, 1H), 3.89 (m, 3H), 3.43 (s, 3H), 3.35 (br t, 2H), 2.42 (s, 3H), 2.23 (br d, 2H), 1.64 (m, 2H).

(4-Fluorophenyl)(2-(1-(3-methyl-1,2,4-thiadiazol-5-yl)piperidin-4-ylamino)-[1,2,4]triazolo[1,5-a]pyridin-8-yl)methanol eluted second and was further purified with preparative HPCL. The title compound was obtained as a white solid (yield: 42%).

MS ISP (m/e): 440.2 (100) [(M+H)$^+$], 422.1 (69).

$^1$H NMR ($CDCl_3$, 300 MHz): δ (ppm)=8.50 (d, 1H), 7.55 (d, 1H), 7.46 (dd, 2H), 7.11 (t, 2H), 6.91 (t, 1H), 6.75 (d, 1H), 6.10 (br s, 1H), 6.07 (br s, 1H), 3.77 (m, 3H), 3.32 (m, 2H), 2.28 (s, 3H), 2.00 (br d, 2H), 1.57 (m, 2H).

Example 264

N-(1-(3-Methyl-1,2,4-thiadiazol-5-yl)piperidin-4-yl)-8-phenyl-6,8-dihydro-5H-[1,2,4]triazolo[5,1-c][1,4]oxazin-2-amine

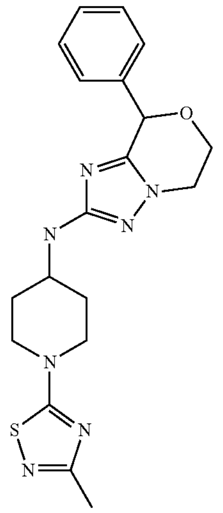 [SMILES: Cc1nsc(N2CCC(Nc3nc4n(n3)CCOC4c3ccccc3)CC2)n1]

a) (2-Oxo-ethoxy)-phenyl-acetic acid methyl ester

Allyloxy-phenyl-acetic acid methyl ester (described in EJOC 2000, 3145-3163; 3 g, 14.5 mmol) was dissolved in dichloromethane (300 mL) and cooled to −75° C. $O_3$ was blubbled through the solution for 6 hours until the solution turned blue. Argon was blubbled through the solution for 1 hour, then dimethyl sulfide (9.04 g, 10.8 mL, 145 mmol) was added to the reaction mixture and kept at room temperature for 12 hours. The reaction mixture was evaporated and the residue purified by flash chromatography over 50 g $SiO_2$-flash pack using gradient 10-100% EtOAc in heptane over 60 minutes to give the title compound as light yellow oil (2.72 g, 90%).

$^1$H NMR ($CDCl_3$, 300 MHz): δ (ppm)=9.75 (s, 1H), 7.47-7.36 (m, 5H), 5.03 (s, 1H), 4.13 (s, 2H), 3.74 (s, 3H).

b) tert-Butyl 2-(2-(2-methoxy-2-oxo-1-phenylethoxy)ethylidene)hydrazinecarboxylate (2-Oxo-ethoxy)-phenyl-acetic acid methyl ester (2.7 g, 13.0 mmol) and tert-butyl carbazate (1.75 g, 13.0 mmol) were dissolved in toluene (290 mL) and heated to 65° C. over night. The reaction mixture was concentrated in vacuo and the residue was purified by flash chromatography (silica gel, 100 g, 0% to 100% EtOAc in heptane over 60 minutes) to give the title compound as yellow viscous oil (2.81 g, 67%).

MS ISP (m/e): 323.3 (42) [(M+H)$^+$], 267.1 (100)) [(M−tBu)$^+$].

$^1$H NMR ($CDCl_3$, 300 MHz): δ (ppm)=7.85 (bs, 1H), 7.44-7.34 (m, 5H), 4.94 (s, 1H), 4.23-4.21 (m, 2H), 3.71 (s, 3H), 1.50 (s, 9H).

c) tert-Butyl 2-(2-(2-methoxy-2-oxo-1-phenylethoxy)ethyl)hydrazinecarboxylate tert-Butyl 2-(2-(2-methoxy-2-oxo-1-phenylethoxy)ethylidene)hydrazinecarboxylate (4.7 g, 14.6 mmol) in MeOH (175 mL) was hydrogenated at 3.5 bar and 30° C. for 20 hours in a Parr bottle in the presence of Raney-nickel (4.69 g, 37.2 mmol). The reaction mixture was filtered and washed with MeOH. The solvent was evaporated to give the title compound as brown oil (4.5 g, 95%) that was used crude for the next reaction.

$^1$H NMR ($CDCl_3$, 300 MHz): δ (ppm)=7.47-7.33 (m, 5H), 6.30 (bs, 1H), 4.93 (s, 1H), 4.20 (bs, 1H), 3.72 (s, 3H), 3.70-3.57 (m, 2H), 3.12-3.07 (m, 2H), 1.46 (s, 9H).

d) 4-Amino-2-phenylmorpholin-3-one tert-Butyl 2-(2-(2-methoxy-2-oxo-1-phenylethoxy)ethyl)hydrazinecarboxylate (390 mg, 1.2 mmol) in water (85 mL) was heated to 95° C. for 12 h. The reaction mixture was extracted with dichloromethane, the organic layers were combined, dried over $Na_2SO_4$ and the solvent was evaporated to give the title compound as light yellow oil (183 mg, 79%).

MS ISP (m/e): 193.2 (100) [(M+H)$^+$].

$^1$H NMR ($CDCl_3$, 300 MHz): δ (ppm)=7.45-7.33 (m, 5H), 5.24 (s, 1H), 4.54 (bs, 2H), 4.12-4.05 (m, 1H), 3.99-3.91 (m, 1H), 3.83-3.75 (m, 1H), 3.65-3.58 (m, 1H).

e) 8-Phenyl-6,8-dihydro-5H-[1,2,4]triazolo[5,1-c][1,4]oxazin-2-amine

4-Amino-2-phenylmorpholin-3-one (175 mg, 910 μmol) and cyanamide (230 mg, 179 μL, 5.46 mmol) were dissolved in ethanol (4 mL). p-Toluenesulfonic acid monohydrate (260 mg, 209 μL, 1.37 mmol) was added and the mixture was heated under reflux at 80° C. for 24 hours. After cooling to room temperature, triethylamine (461 mg, 634 μL, 4.55 mmol) was added and the mixture was heated under reflux at 80° C. for 3 days.

The reaction mixture was extracted with saturated sodium bicarbonate solution and EtOAc. The combined organic layers were washed with brine, dried over $Na_2SO_4$ and the solvent was evaporated. The residue was purified by chromatography over 10 g $NH_2$-flash pack using gradient 0-15% MeOH/$NH_3$ (9:1) in dichloromethane to give the title compound as off-white solid (41 mg, 21%). MS ISP (m/e): 217.3 (100) [(M+H)$^+$].

$^1$H NMR ($CDCl_3$, 300 MHz): δ (ppm)=7.40-7.37 (m, 5H), 5.75 (s, 1H), 4.31-4.16 (m, 2H), 4.13-4.06 (m, 4H).

f) N-(1-(3-Methyl-1,2,4-thiadiazol-5-yl)piperidin-4-yl)-8-phenyl-6,8-dihydro-5H-[1,2,4]triazolo[5,1-c][1,4]oxazin-2-amine Prepared in analogy to example 261a employing 8-phenyl-6,8-dihydro-5H-[1,2,4]triazolo[5,1-c][1,4]oxazin-2-amine and 1-(3-methyl-1,2,4-thiadiazol-5-yl)piperidin-4-one (see example 1d). The title compound was obtained as an white foam.

MS ISP (m/e): 398.2 (100) [(M+H)$^+$].

$^1H$ NMR ($CDCl_3$, 300 MHz): δ (ppm)=7.42-7.37 (m, 5H), 5.76 (s, 1H), 4.30-4.08 (m, 5H), 3.87-3.83 (m, 2H), 3.78-3.67 (m, 1H), 3.35-3.26 (m, 2H), 2.40 (s, 3H), 2.22-2.16 (m, 2H), 1.64-1.53 (m, 2H).

Example 265

N-(1-(6-Methylpyrimidin-4-yl)piperidin-4-yl)-8-phenyl-6,8-dihydro-5H-[1,2,4]triazolo[5,1-c][1,4]oxazin-2-amine

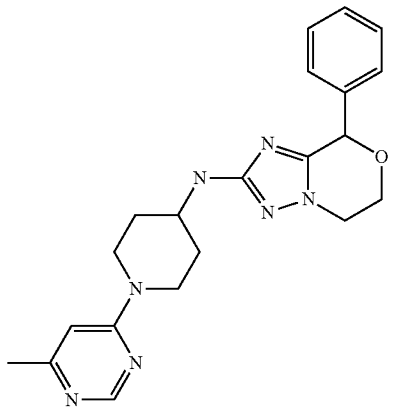 [SMILES: Cc1cc(N2CCC(Nc3nc4n(n3)CCOC4c3ccccc3)CC2)ncn1]

Prepared in analogy to example 264 employing 1-(6-methyl-pyrimidin-4-yl)-piperidin-4-one (see example 93b) in step f). The title compound was obtained as light yellow foam.

MS ISP (m/e): 392.2 (100) [$(M+H)^+$].

$^1H$ NMR ($CDCl_3$, 300 MHz): δ (ppm)=8.43 (s, 1H), 7.41-7.36 (m, 5H), 6.41 (s, 1H), 5.75 (s, 1H), 4.33-4.19 (m, 4H), 4.14-4.07 (m, 3H), 3.82-3.71 (m, 1H), 3.23-3.15 (m, 2H), 2.37 (s, 3H), 2.21-2.16 (m, 2H), 1.54-1.47 (m, 2H).

Example 266 & 267

N-((3R,4S,5S)-3,5-Dimethyl-1-(3-methyl-1,2,4-thiadiazol-5-yl)piperidin-4-yl)-8-(2,3,4-trifluorophenyl)-[1,2,4]triazolo[1,5-a]pyridin-2-amine & N-((3S,5S)-3,5-dimethyl-1-(3-methyl-1,2,4-thiadiazol-5-yl)piperidin-4-yl)-8-(2,3,4-trifluorophenyl)-[1,2,4]triazolo[1,5-a]pyridin-2-amine

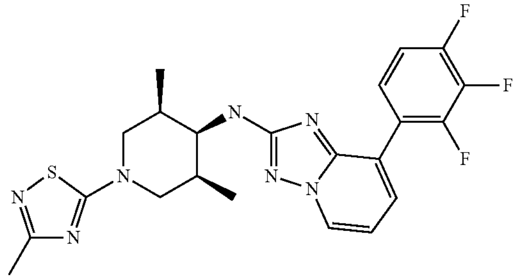

-continued

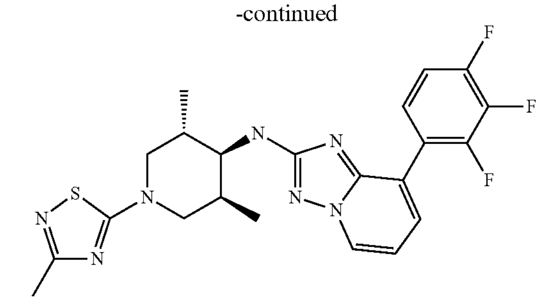

a) (3S,5R)-3,5-Dimethyl-4-oxo-piperidine-1-carboxylic acid tert-butyl ester

A suspension of (3R,5S)-1-benzyl-3,5-dimethylpiperidin-4-one (prepared according to A. A. Calabrese et al., US20050176772, preparation 12-14) (2.08 g, 9.57 mmol), di-tert-butyl dicarbonate (2.3 g, 2.42 mL, 10.5 mmol) and palladium on carbon (10%) (306 mg, 287 μmol) in ethanol (47.5 mL) was hydrogenated at room temperature for 12 hours. The catalyst was filtered off, washed thoroughly with MeOH and the solvents were evaporated to yield the title compound as white solid (2.38 g). MS ISP (m/e): 172.2 (100) [$(M-tBu)^+$].

$^1H$ NMR ($CDCl_3$, 300 MHz): δ (ppm)=4.36 (bs, 2H), 2.70-2.51 (m, 4H), 1.50 (s, 9H), 1.03-1.01 (d, 6H).

b) 3,5-Dimethyl-4-[8-(2,3,4-trifluoro-phenyl)-[1,2,4]triazolo[1,5-a]pyridin-2-ylamino]-piperidine-1-carboxylic acid tert-butyl ester To a solution of 8-(2,3,4-trifluorophenyl)-[1,2,4]triazolo[1,5-a]pyridin-2-amine (prepared in analogy to example 66a-c) (300 mg, 1.14 mmol) and hexachloroethane (296 mg, 1.25 mmol) in dry THF (8 mL) was added triethylamine (287 mg, 396 μL, 2.84 mmol) under an argon atmosphere followed by trimethylphosphine (1 M in THF, 1.25 mL, 1.25 mmol). The reaction mixture was stirred at room temperature for 45 minutes, then (3R,5S)-tert-butyl 3,5-dimethyl-4-oxopiperidine-1-carboxylate (315 mg, 1.25 mmol) added and the mixture heated to 150° C. in the microwave for 3 hours. A solution of decaborane (139 mg, 148 μL, 1.14 mmol) in MeOH (3 mL) was added to the reaction mixture and stirred at 50° C. for 2 hours. Further decaborane (139 mg, 148 μl, 1.14 mmol) in MeOH (3 mL) was added and stirred at 50° C. for another 2 hours. The reaction mixture was poured in water and extracted with dichloromethane. The organic layers were combined, dried over $Na_2SO_4$ and evaporated. The residue was purified by flash-chromatography over 70 g $SiO_2$-flash pack using gradient 0-100% EtOAc in heptane over 35 minutes to give the title compound as off-white foam (208 mg, 39%) as a mixture of cis- and trans-isomers. MS ISP (m/e): 476.2/420.2/376.3 (13/40/62) [$(M+H)^+$/$(M-tBu)^+$/$(M-Boc)^+$].

c) 3,5-Dimethyl-piperidin-4-yl)-[8-(2,3,4-trifluoro-phenyl)-[1,2,4]triazolo[1,5-a]pyridin-2-yl]-amine To a solution of tert-butyl 3,5-dimethyl-4-(8-(2,3,4-trifluorophenyl)-[1,2,4]triazolo[1,5-a]pyridin-2-ylamino)piperidine-1-carboxylate (200 mg, 421 μmol) in $CH_2Cl_2$ (5 mL) was added trifluoroacetic acid (336 mg, 227 μL, 2.94 mmol) at 0° C. and then stirred at room temperature for 18 hours. Further trifluoroacetic acid was added at 0° C. (336 mg, 227 μL, 2.94 mmol) and stirred at room temperature for another 2 hours. Saturated $NaHCO_3$ solution was added to the reaction mixture and the aqueous phase was extracted with EtOAc. The organic layers were combined, dried over $Na_2SO_4$, filtered and the solvents evaporated. The product was coevaporated with toluene. The title compound was isolated as white solid (106 mg, 67%) as a mixture of cis- and trans-isomers.

MS ISP (m/e): 376.5 (100) [$(M+H)^+$].

d) N-((3R,4S,5S)-3,5-Dimethyl-1-(3-methyl-1,2,4-thiadiazol-5-yl)piperidin-4-yl)-8-(2,3,4-trifluorophenyl)-[1,2,4]triazolo[1,5-a]pyridin-2-amine & N-((3S,5S)-3,5-Dimethyl-1-(3-methyl-1,2,4-thiadiazol-5-yl)piperidin-4-yl)-8-(2,3,4-trifluorophenyl)-[1,2,4]triazolo[1,5-a]pyridin-2-amine A degassed solution of 2-(dicyclohexylphosphino)biphenyl (14.9 mg, 42.6 μmol) and palladium(II) acetate (4.78 mg, 21.3 μmol) in dioxane (2 mL) was stirred for 10 minutes at room temperature, then added to a solution of N-(3,5-dimethylpiperidin-4-yl)-8-(2,3,4-trifluorophenyl)-[1,2,4]triazolo[1,5-a]pyridin-2-amine (100 mg, 266 μmol), 5-chloro-3-methyl-1,2,4-thiadiazole (39.4 mg, 293 μmol) and sodium tert-butoxide (38.4 mg, 400 μmol) in dioxane (2 mL). Through the solution was bubbled argon for 5 minutes, then heated to 150° C. in the microwave for 30 minutes. The crude material was purified by flash chromatography (silica gel, 70 g, 0% to 15% $MeOH/NH_4OH$ (9:1) in dichloromethane) and again purified by flash-chromatography (silica gel, 20 g, 0-100% EtOAc in Heptane) to yield:

Example 266

N-((3R,4S,5S)-3,5-Dimethyl-1-(3-methyl-1,2,4-thiadiazol-5-yl)piperidin-4-yl)-8-(2,3,4-trifluorophenyl)-[1,2,4]triazolo[1,5-a]pyridin-2-amine as off-white solid (45 mg, 36%). MS ISP (m/e): 474.1 (100) [$(M+H)^+$].

$^1H$ NMR ($CDCl_3$, 300 MHz): δ (ppm)=8.34-8.31 (m, 1H), 7.62-7.55 (m, 1H), 7.49-7.47 (m, 1H), 7.15-7.06 (m, 1H), 6.92-6.88 (m, 1H), 4.59-4.56 (d, 1H), 4.24-4.19 (dt, 1H), 3.67-3.61 (m, 2H), 2.95-2.86 (m, 2H), 2.42 (s, 3H), 2.20-2.11 (m, 2H), 1.03-1.00 (d, 6H) and Example 267

N-((3S,5S)-3,5-Dimethyl-1-(3-methyl-1,2,4-thiadiazol-5-yl)piperidin-4-yl)-8-(2,3,4-trifluorophenyl)-[1,2,4]triazolo[1,5-a]pyridin-2-amine as off-white foam (23 mg, 18%). MS ISP (m/e): 474.2 (100) [$(M+H)^+$].

$^1H$ NMR ($CDCl_3$, 300 MHz): δ (ppm)=8.36-8.34 (m, 1H), 7.61-7.53 (m, 1H), 7.50-7.47 (m, 1H), 7.15-7.05 (m, 1H), 6.93-6.88 (m, 1H), 4.57-4.54 (d, 1H), 3.97-3.91 (m, 1H), 3.76-3.68 (m, 1H), 3.56-3.55 (m, 2H), 3.01-2.93 (m, 1H), 2.54-2.48 (m, 1H), 2.40 (s, 3H), 2.09-1.99 (m, 1H), 1.09-1.07 (d, 3H), 1.02-1.00 (d, 3H).

Example 268

N-(1-(3-Methyl-1,2,4-thiadiazol-5-yl)piperidin-4-yl)-7-phenoxy-[1,2,4]triazolo[1,5-a]pyridin-2-amine

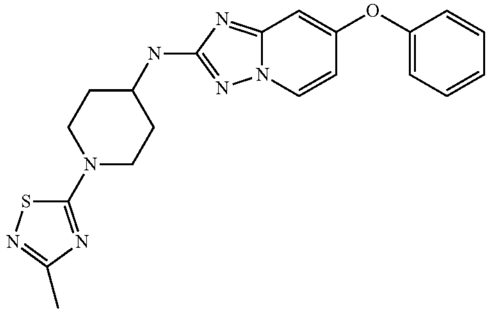 [SMILES: Cc1nsc(N2CCC(Nc3nc4cc(Oc5ccccc5)ccn4n3)CC2)n1]

Prepared in analogy to example 260 employing (7-bromo-[1,2,4]triazolo[1,5-a]pyridin-2-yl)-[1-(3-methyl-[1,2,4]thiadiazol-5-yl)-piperidin-4-yl]-amine (see example 261a) in stead of (6-bromo-[1,2,4]triazolo[1,5-a]pyridin-2-yl)-[1-(3-methyl-[1,2,4]thiadiazol-5-yl)-piperidin-4-yl]-amine. The title compound was obtained as off-white foam.

MS ISP (m/e): 408.4 (100) [$(M+H)^+$].

$^1H$ NMR ($CDCl_3$, 300 MHz): δ (ppm)=8.21-8.18 (m, 1H), 7.45-7.40 (m, 2H), 7.28-7.23 (m, 1H), 7.13-7.10 (m, 2H), 6.69-6.68 (m, 1H), 6.63-6.60 (m, 1H), 4.59-4.56 (m, 1H), 3.91-3.87 (m, 3H), 3.38-3.28 (m, 2H), 2.41 (s, 3H), 2.26-2.20 (m, 2H), 1.71-1.58 (m, 2H).

Example 269 & 270 & 271

(3SR,4SR), (3R,4S) and (3S,4R)-[8-(3,5-Bis-trifluoromethyl-phenyl)-[1,2,4]triazolo[1,5-a]pyridin-2-yl]-[3-fluoro-1-(3-methyl-[1,2,4]thiadiazol-5-yl)-piperidin-4-yl]-amine

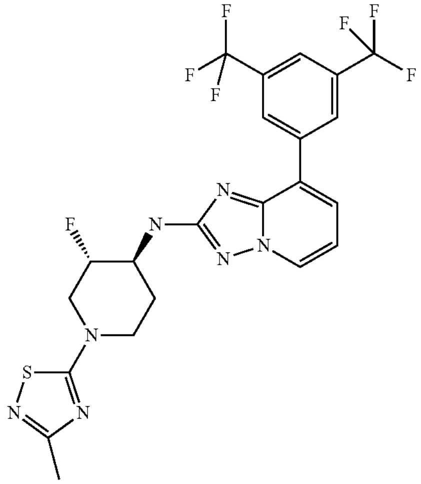

-continued

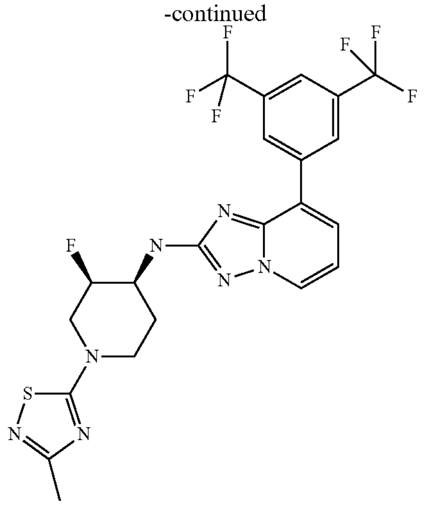

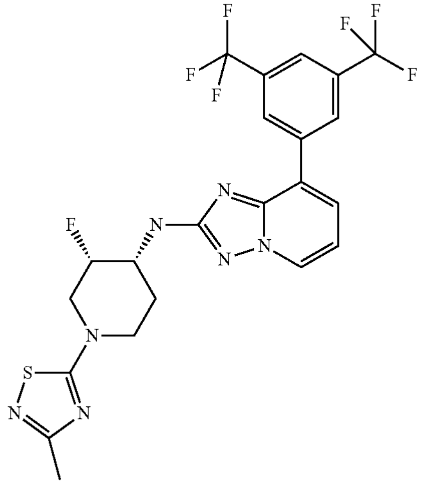

a) 4-[8-(3,5-Bis-trifluoromethyl-phenyl)-[1,2,4]triazolo[1,5-a]pyridin-2-ylamino]-3-fluoro-piperidine-1-carboxylic acid tert-butyl ester To a suspension of 8-(3,5-bis(trifluoromethyl)phenyl)-[1,2,4]triazolo[1,5-a]pyridin-2-amine (prepared in analogy to example 66a-c) (80 mg, 231 μmol) and hexachloroethane (65.6 mg, 277 μmol) under argon in dry THF (4 mL) was added triethylamine (70.1 mg, 96.6 μL, 693 mmol) followed by trimethylphosphine (1 M in THF, 277 μL, 277 μmol). The reaction mixture was stirred at room temperature for 0.5 hours, then tert-butyl 3-fluoro-4-oxopiperidine-1-carboxylate (example 238b, 60.2 mg, 277 μmol) was added and the mixture heated to 150° C. for 30 minutes in the microwave. A solution of decaborane (28.2 mg, 30.0 μL, 231 μmol) in dry methanol (1 mL) was added to the reaction mixture and stirred at room temperature for 3 hours. Aqueous $NaHCO_3$ solution was added to the reaction mixture, the aqueous phase was extracted with $CH_2Cl_2$, the organic layers were combined, dried over $Na_2SO_4$, filtered and the solvents evaporated. The residue was purified by flash chromatography (silica gel, 50 g, 0% to 15% $MeOH/NH_4OH$ (9:1) in dichloromethane). The title compound was obtained as off-white foam (107 mg, 85%) as a mixture of cis- and trans-isomers.

MS ISP (m/e): 548.3/492.2 (33/100) $[(M+H)^+/(M-tBu)^+]$.

b) 8-(3,5-Bis-trifluoromethyl-phenyl)-[1,2,4]triazolo[1,5-a]pyridin-2-yl]-(3-fluoro-piperidin-4-yl)-amine To solution of 4-[8-(3,5-bis-trifluoromethyl-phenyl)-[1,2,4]triazolo[1,5-a]pyridin-2-ylamino]-3-fluoro-piperidine-1-carboxylic acid tert-butyl ester (180 mg, 329 μmol) in $CH_2Cl_2$ (3 mL) at 0° C. was added trifluoroacetic acid (262 mg, 177 μL, 2.3 mmol) and then stirred at room temperature for 18 hours. Further trifluoroacetic acid (262 mg, 177 μL, 2.3 mmol) was added and stirred at 40° C. for 6 hours. Aqueous saturated $NaHCO_3$ solution was added to the reaction mixture and the aqueous phase was extracted with ethyl acetate, the organic layers were combined, dried over $Na_2SO_4$, filtered and the solvents were evaporated. The product was coevaporated twice with toluene. The title compound was obtained as light yellow foam (142 mg, 96%) as a mixture of cis- and trans-isomers.

MS ISP (m/e): 448.2/428.2 (32/100) $[(M+H)^+/(M-HF)^+]$.

c) [8-(3,5-Bis-trifluoromethyl-phenyl)-[1,2,4]triazolo[1,5-a]pyridin-2-yl]-[3-fluoro-1-(3-methyl-[1,2,4]thiadiazol-5-yl)-piperidin-4-yl]-amine A degassed solution of palladium(II) acetate (2.73 mg, 12.2 μmol) and 2-(dicyclohexylphosphino)biphenyl (8.52 mg, 24.3 μmol) in dioxane (1 mL) was stirred for 10 minutes at room temperature, then added to a solution of 8-(3,5-bis(trifluoromethyl)phenyl)-N-(3-fluoropiperidin-4-yl)-[1,2,4]triazolo[1,5-a]pyridin-2-amine (68 mg, 152 μmol), 5-chloro-3-methyl-1,2,4-thiadiazole (24.5 mg, 182 μmol) and sodium tert-butoxide (21.9 mg, 228 μmol) in dioxane (2 mL). Through the solution was bubbled argon for 5 minutes, then heated to 150° C. in the microwave for 45 minutes. Again a degassed solution of palladium(II) acetate (3.1 mg, 13.8 mmol) and 2-(dicyclohexylphosphino)biphenyl (9.69 mg, 27.6 μmol) in dioxane (1 mL) was added, followed by 5-chloro-3-methyl-1,2,4-thiadiazole (24.5 mg, 182 μmol) and heated for further 45 minutes to 150° C. The crude material was purified by flash chromatography (silica gel, 70 g, 0% to 15% $MeOH/NH_4OH$ (9:1) in dichloromethane). The title compound was obtained as colorless oil (30 mg, 36%) as a mixture of cis- and trans-isomers.

MS ISP (m/e): 546.7 (100) $[(M+H)^+]$.

d) (3SR,4SR)-, (3R,4S)- and (3S,4R)-[8-(3,5-Bis-trifluoromethyl-phenyl)-[1,2,4]triazolo[1,5-a]pyridin-2-yl]-[3-fluoro-1-(3-methyl-[1,2,4]thiadiazol-5-yl)-piperidin-4-yl]-amine The mixture of cis- and trans-isomers was separated by Supercritical Fluid Chromatography (SFC) over a Chiralpak AD-H column using ethanol and $CO_2$ as eluent to provide the trans-isomer as racemate (example 269) and the two cis-enantiomers (example 270 and 271) without assignment of absolute configuration to the enantiomers.

Example 269

(3SR,4SR)-[8-(3,5-Bis-trifluoromethyl-phenyl)-[1,2,4]triazolo[1,5-a]pyridin-2-yl]-[3-fluoro-1-(3-methyl-[1,2,4]thiadiazol-5-yl)-piperidin-4-yl]-amine Retention time: 4.00/4.33 minutes. $^1H$ NMR ($CDCl_3$, 300 MHz): δ (ppm)=8.55 (s, 2H), 8.42-8.39 (m, 1H), 7.91 (s, 1H), 7.68-7.66 (m, 1H), 7.02-6.97 (m, 1H), 4.88-4.66 (m, 1H), 4.79-4.77 (m, 1H), 4.23-4.02 (m, 2H), 3.78-3.68 (m, 1H), 3.59-3.44 (m, 2H), 2.60-1.80 (m, 2H), 2.43 (s, 3H).

Example 270

(3R,4S)-[8-(3,5-Bis-trifluoromethyl-phenyl)-[1,2,4]triazolo[1,5-a]pyridin-2-yl]-[3-fluoro-1-(3-methyl-[1,2,4]thiadiazol-5-yl)-piperidin-4-yl]-amine or enantiomer Retention time: 5.06 minutes. $^{1}$H NMR ($CDCl_3$, 300 MHz): δ (ppm)=8.55 (s, 2H), 8.40-8.38 (m, 1H), 7.91 (s, 1H), 7.69-7.66 (m, 1H), 7.02-6.97 (m, 1H), 5.11-4.98 (m, 1H), 4.93-4.90 (m, 1H), 4.44-3.96 (m, 3H), 3.53-3.30 (m, 2H), 2.43 (s, 3H), 2.15-2.06 (m, 2H).

Example 271

(3S,4R)-[8-(3,5-Bis-trifluoromethyl-phenyl)-[1,2,4]triazolo[1,5-a]pyridin-2-yl]-[3-fluoro-1-(3-methyl-[1,2,4]thiadiazol-5-yl)-piperidin-4-yl]-amine or enantiomer Retention time: 6.33 minutes.

$^{1}$H NMR ($CDCl_3$, 300 MHz): δ (ppm)=8.55 (s, 2H), 8.40-8.37 (m, 1H), 7.91 (s, 1H), 7.68-7.66 (m, 1H), 7.02-6.97 (m, 1H), 5.14-4.98 (m, 1H), 4.93-4.90 (m, 1H), 4.44-3.97 (m, 3H), 3.53-3.30 (m, 2H), 2.43 (s, 3H), 2.15-2.06 (m, 2H).

Example 272 & 273 & 274

(3SR,4SR), (3R,4S) and (3S,4R)-[8-(3,5-Bis-trifluoromethyl-phenyl)-[1,2,4]triazolo[1,5-a]pyridin-2-yl]-[3-fluoro-1-(5-methyl-[1,3,4]oxadiazol-2-yl)-piperidin-4-yl]-amine

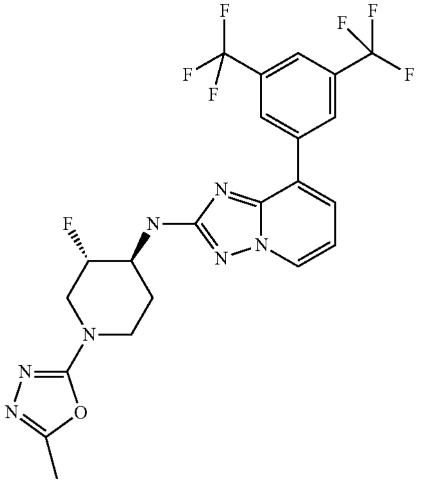

-continued

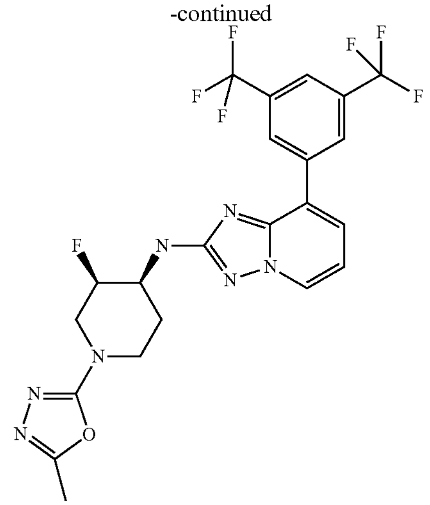

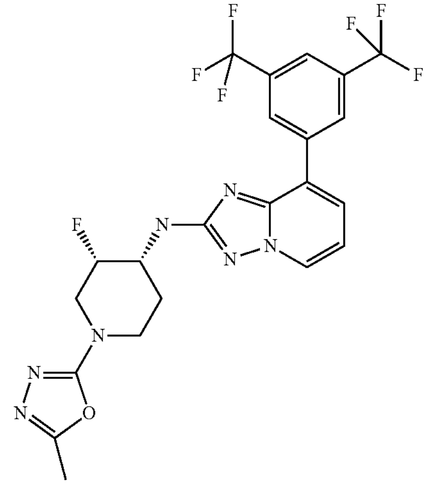

a) [8-(3,5-Bis-trifluoromethyl-phenyl)-[1,2,4]triazolo[1,5-a]pyridin-2-yl]-[3-fluoro-1-(5-methyl-[1,3,4]oxadiazol-2-yl)-piperidin-4-yl]-amine A solution of 8-(3,5-bis(trifluoromethyl)phenyl)-N-(3-fluoropiperidin-4-yl)-[1,2,4]triazolo[1,5-a]pyridin-2-amine (example 269b, 68 mg, 152 μmol), 2-bromo-5-methyl-1,3,4-oxadiazole (32.2 mg, 198 μmol) and diisopropylethylamine (39.3 mg, 53.1 μL, 304 μmol) dissolved in dry dioxane (2 mL) was stirred at 70° C. for 12 hours and then at 110° C. for 1 hour. Further diisopropylethylamine (39.3 mg, 53.1 μL, 304 μmol) and 2-bromo-5-methyl-1,3,4-oxadiazole (32.2 mg, 198 μmol) were added and heated to 110° C. for another hour. The solvent was evaporated and the residue directly purified by flash chromatography (silica gel, 70 g, 0% to 15% MeOH/$NH_4OH$ (9:1) in dichloromethane). The title compound was obtained as colorless oil (46 mg, 57%) as a mixture of cis- and trans-isomers.

MS ISP (m/e): 530.1/510.3 (100/27) [$(M+H)^+$/$(M-HF)^+$].

b) (3SR,4SR), (3R,4S) and (3S,4R)-[8-(3,5-Bis-trifluoromethyl-phenyl)-[1,2,4]triazolo[1,5-a]pyridin-2-yl]-[3-fluoro-1-(5-methyl-[1,3,4]oxadiazol-2-yl)-piperidin-4-yl]-amine The mixture of cis- and trans-isomers was separated by Supercritical Fluid Chromatography (SFC) over a Chiralpak AD-H column using ethanol and $CO_2$ as eluent to provide the trans-isomer as racemate (example 272) and the two cis-enantiomers (example 273 and 274) without assignment of absolute configuration to the enantiomers.

Example 272

(3SR,4SR)-[8-(3,5-Bis-trifluoromethyl-phenyl)-[1,2,4]triazolo[1,5-a]pyridin-2-yl]-[3-fluoro-1-(5-methyl-[1,3,4]oxadiazol-2-yl)-piperidin-4-yl]-amine Retention time: 4.11/4.37 minutes. $^1H$ NMR ($CDCl_3$, 300 MHz): δ (ppm)=8.55 (s, 2H), 8.42-8.38 (m, 1H), 7.91 (s, 1H), 7.68-7.65 (m, 1H), 7.01-6.96 (m, 1H), 5.11-4.64 (m, 2H), 4.40-4.01 (m, 2H), 3.86-3.71 (m, 1H), 3.49-3.15 (m, 2H), 2.57-1.77 (m, 2H), 2.41 (s, 3H).

Example 273

(3R,4S)-[8-(3,5-Bis-trifluoromethyl-phenyl)-[1,2,4]triazolo[1,5-a]pyridin-2-yl]-[3-fluoro-1-(5-methyl-[1,3,4]oxadiazol-2-yl)-piperidin-4-yl]-amine Retention time: 5.72 minutes. $^1H$ NMR ($CDCl_3$, 300 MHz): δ (ppm)=8.55 (s, 2H), 8.40-8.37 (m, 1H), 7.91 (s, 1H), 7.68-7.65 (m, 1H), 7.01-6.96 (m, 1H), 5.11-4.94 (m, 1H), 4.93-4.90 (m, 1H), 4.40-3.98 (m, 3H), 3.41-3.14 (m, 2H), 2.41 (s, 3H), 2.11-2.04 (m, 2H).

Example 274

(3S,4R)-[8-(3,5-Bis-trifluoromethyl-phenyl)-[1,2,4]triazolo[1,5-a]pyridin-2-yl]-[3-fluoro-1-(5-methyl-[1,3,4]oxadiazol-2-yl)-piperidin-4-yl]-amine Retention time: 8.18 minutes. $^1H$ NMR ($CDCl_3$, 300 MHz): δ (ppm)=8.55 (s, 2H), 8.40-8.37 (m, 1H), 7.91 (s, 1H), 7.68-7.65 (m, 1H), 7.01-6.96 (m, 1H), 5.11-4.94 (m, 1H), 4.92-4.89 (m, 1H), 4.40-3.98 (m, 3H), 3.41-3.14 (m, 2H), 2.41 (s, 3H), 2.11-2.04 (m, 2H).

Example 275

N-(3,3-Difluoro-1-(6-methylpyrimidin-4-yl)piperidin-4-yl)-8-(2,3,4-trifluorophenyl)-[1,2,4]triazolo[1,5-a]pyridin-2-amine

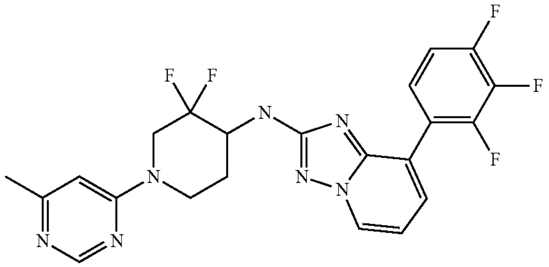 [SMILES: Cc1cc(N2CCC(Nc3nc4c(-c5ccc(F)c(F)c5F)cccn4n3)C(F)(F)C2)ncn1]

a) 3,3-Difluoro-4-[8-(2,3,4-trifluoro-phenyl)-[1,2,4]triazolo[1,5-a]pyridin-2-ylamino]-piperidine-1-carboxylic acid tert-butyl ester To a suspension of 8-(2,3,4-trifluorophenyl)-[1,2,4]triazolo[1,5-a]pyridin-2-amine (prepared in analogy to example 66a-c, 200 mg, 757 μmol) and hexachloroethane (215 mg, 908 mmol) under argon in dry THF (10 mL) was added triethylamine (230 mg, 317 μL, 2.27 mmol) followed by trimethylphosphine (1 M in THF, 908 μl, 908 μmol). The reaction mixture was stirred at room temperature for 0.5 hous, then tert-butyl 3,3-difluoro-4,4-dihydroxypiperidine-1-carboxylate (see example 247e, 230 mg, 908 μmol) was added and the mixture was heated to 150° C. in the microwave for 30 minutes. A solution of decaborane (92.5 mg, 98.4 μL, 757 μmol) in MeOH (1 mL) was added to the reaction mixture, then stirred at room temperature for 12 hours. Again a solution of decaborane (92.5 mg, 98.4 μL, 757 μmol) in MeOH (5 mL) was added and heated to 70° C. for 18 hours. Aqueous $NaHCO_3$ solution was added to the reaction mixture, the aqueous phase was extracted with $CH_2Cl_2$, the organic layers were combined, dried over $Na_2SO_4$, filtered and the solvents evaporated. The residue was purified by flash chromatography (silica gel, 50 g, 0% to 15% MeOH/$NH_4OH$ (9:1) in dichloromethane), whereby 85 mg of intermediate imine, 3,3-difluoro-4-[(E)-8-(2,3,4-trifluoro-phenyl)-[1,2,4]triazolo[1,5-a]pyridin-2-ylimino]-piperidine-1-carboxylic acid tert-butyl ester, was isolated, which was again dissolved in dry MeOH (3 mL). Decaborane (21.6 mg, 23.0 μL, 177 μmol) was added and heated to 70° C. for 30 minutes. Aqueous $NaHCO_3$ solution was added to the reaction mixture, the aqueous phase was extracted with $CH_2Cl_2$, the organic layers were combined, dried over $Na_2SO_4$, filtered and the solvents evaporated. The residue was purified (together with impure product fractions from first chromatography) by flash chromatography (silica gel, 50 g, 0% to 15% MeOH/$NH_4OH$ (9:1) in dichloromethane) to yield title compound as white foam (300 mg, 82%). MS ISP (m/e): 484.3/428.1/384.2 (13/100/41) $[(M+H)^+/(M-tBu)^+/(M-Boc)^+]$.

b) N-(3,3-Difluoropiperidin-4-yl)-8-(2,3,4-trifluorophenyl)-[1,2,4]triazolo[1,5-a]pyridin-2-amine To solution of 3,3-difluoro-4-[8-(2,3,4-trifluoro-phenyl)-[1,2,4]triazolo[1,5-a]pyridin-2-ylamino]-piperidine-1-carboxylic acid tert-butyl ester (110 mg, 228 μmol) in $CH_2Cl_2$ (4 mL) at 0° C. was added TFA (182 mg, 123 μl, 1.59 mmol) and stirred at room temperature for 18 hours. Further TFA (182 mg, 123 μl, 1.59 mmol) was added and stirred at 50° C. for 6 hours. The reaction mixture was extracted with saturated $NaHCO_3$ solution and ethyl acetate, the organic layers combined, dried over $Na_2SO_4$, filtered and the solvents evaporated. The product was coevaporated four times with toluene. The title compound was obtained as light yellow foam (87 mg, 100%). MS ISP (m/e): 384.2 (100) $[(M+H)^+]$.

$^1H$ NMR ($CDCl_3$, 300 MHz): δ (ppm)=8.36-8.34 (m, 1H), 7.64-7.56 (m, 1H), 7.51-7.49 (m, 1H), 7.15-7.06 (m, 1H), 6.94-6.90 (m, 1H), 4.87-4.84 (d, 1H), 4.33-4.16 (m, 1H), 3.35-3.25 (m, 1H), 3.14-3.09 (m, 1H), 2.99-2.72 (m, 2H), 2.25-2.18 (m, 1H), 1.66-1.61 (m, 2H).

c) N-(3,3-Difluoro-1-(6-methylpyrimidin-4-yl)piperidin-4-yl)-8-(2,3,4-trifluorophenyl)-[1,2,4]triazolo[1,5-a]pyridin-2-amine A solution of N-(3,3-difluoropiperidin-4-yl)-8-(2,3,4-trifluorophenyl)-[1,2,4]triazolo[1,5-a]pyridin-2-amine (75 mg, 196 μmol), 4-chloro-6-methylpyrimidine (27.7 mg, 215 μmol) and N,N-diisopropylethylamine (37.9 mg, 49.9 μL, 293 μmol) in dioxane (4 mL) was heated to 150° C. in the microwave for 1 hour. Further 4-chloro-6-methylpyrimidine (27.7 mg, 215 μmol) and N,N-diisopropylethylamine (37.9 mg, 49.9 μL, 293 μmol) were added and heated to 150° C. in the microwave for another hour. Further 4-chloro-6-methylpyrimidine (27.7 mg, 215 μmol) and N,N-diisopropylethylamine (37.9 mg, 49.9 μL, 293 μmol) were added and heated to 110° C. for 12 hours. The crude material was directly purified by flash chromatography (silica gel, 70 g, 0% to 15% MeOH/$NH_4OH$ (9:1) in dichloromethane). The title compound was obtained as light yellow foam (25 mg, 22%). MS ISP (m/e): 476.1 (100) [$(M+H)^+$].

$^1H$ NMR ($CDCl_3$, 300 MHz): δ (ppm)=8.55 (s, 1H), 8.37-8.35 (m, 1H), 7.62-7.55 (m, 1H), 7.53-7.50 (m, 1H), 7.15-7.06 (m, 1H), 6.96-6.91 (m, 1H), 6.47 (s, 1H), 4.94-4.91 (d, 1H), 4.85-4.75 (m, 1H), 4.48-4.32 (m, 2H), 3.39-3.11 (m, 2H), 2.39 (s, 3H), 2.30-2.25 (m, 1H), 1.84-1.76 (m, 1H).

Example 276

N-(3,3-Difluoro-1-(5-methyl-1,3,4-oxadiazol-2-yl)piperidin-4-yl)-8-(2,3,4-trifluorophenyl)-[1,2,4]triazolo[1,5-a]pyridin-2-amine

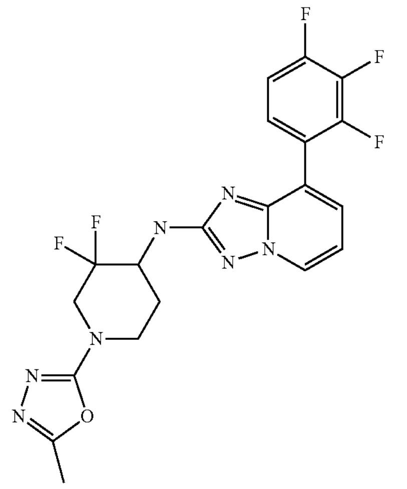 [SMILES: Cc1nnc(N2CCC(Nc3nc4c(-c5ccc(F)c(F)c5F)cccn4n3)C(F)(F)C2)o1]

A solution of N-(3,3-difluoropiperidin-4-yl)-8-(2,3,4-trifluorophenyl)-[1,2,4]triazolo[1,5-a]pyridin-2-amine (see example 275b, 75 mg, 196 μmol), 2-bromo-5-methyl-1,3,4-oxadiazole (41.5 mg, 254 μmol) and diisopropylethylamine (50.6 mg, 68.3 μL, 391 μmol) dissolved in dry dioxane (4 mL) was stirred at 110° C. for 3 hours. Further diisopropylethylamine (50.6 mg, 68.3 μL, 391 μmol) and 2-bromo-5-methyl-1,3,4-oxadiazole (41.5 mg, 254 μmol) were added and heated to 110° C. for 12 hours. The solvent was evaporated and the residue was purified by flash chromatography (silica gel, 70 g, 0% to 15% MeOH/$NH_4OH$ (9:1) in dichloromethane). The title compound was as white foam (36 mg, 40%).

MS ISP (m/e): 466.0 (100) [$(M+H)^+$].

$^1H$ NMR ($CDCl_3$, 300 MHz): δ (ppm)=8.37-8.34 (m, 1H), 7.63-7.55 (m, 1H), 7.53-7.50 (m, 1H), 7.15-7.06 (m, 1H), 6.96-6.91 (m, 1H), 4.83-4.80 (m, 1H), 4.43-4.17 (m, 2H), 4.14-4.07 (m, 1H), 3.48-3.23 (m, 2H), 2.41 (s, 3H), 2.31-2.24 (m, 1H), 2.03-1.89 (m, 1H).

Example 277

4-(8-(2-Chloro-4-fluorophenyl)-[1,2,4]triazolo[1,5-a]pyridin-2-ylamino)-1-(2-(trifluoromethyl)pyridin-4-yl)piperidine-4-carbonitrile

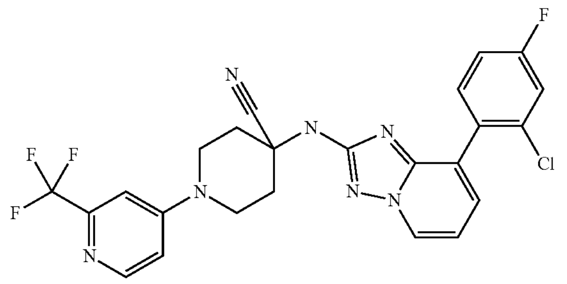 [SMILES: N#CC1(Nc2nc3c(-c4ccc(F)cc4Cl)cccn3n2)CCN(c2ccnc(C(F)(F)F)c2)CC1]

To a suspension of the 8-(2-chloro-4-fluorophenyl)-[1,2,4]triazolo[1,5-a]pyridin-2-amine (50 mg, 0.19 mmol) and hexachloroethane (54 mg, 0.226 mmol) in THF (1.5 mL) was added triethylamine (79 μL, 0.57 mmol) followed by trimethylphosphine (1 M in THF, 0.226 mL, 0.23 mmol) and the resulting mixture was stirred under Argon for 30 min. Then the ketone 1-(2-(trifluoromethyl)pyridin-4-yl)piperidin-4-one (46 mg, 0.19 mmol) was added and the resulting mixture heated in the microwave at 120° C. for 30 minutes. Then trimethylsilyl cyanide (48 μL, 0.38 mmol) was added, followed by MeOH (1.5 mL) followed by acetic acid (44 μL, 0.75 mmol) and the resulting mixture heated to 70° C. for 24 hours. After cooling to room temperature the mixture was evaporated and the residue was extracted with dichloromethane and washed with a saturated solution of sodium hydrogen carbonate. The organic layers were washed with brine, dried over sodium sulfate, filtered and evaporated. Purification by chromatography (silica gel, 50 g, 0 to 20% ethylacetate in heptane) afforded the title compound (20 mg, 21%) as a white foam.

MS ISP (m/e): 516.2 [$(M+H)^+$].

Example 278

N-((3RS,4SR)-3-Fluoro-1-(2-(trifluoromethyl)pyridin-4-yl)piperidin-4-yl)-8-(2,3,4-trifluorophenyl)-[1,2,4]triazolo[1,5-a]pyridin-2-amine

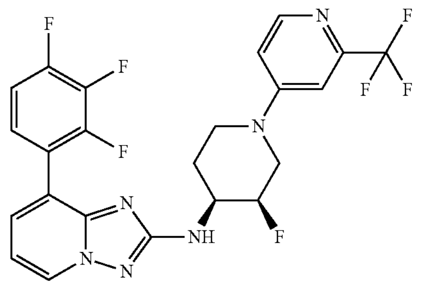 [SMILES: Fc1ccc(-c2cccn3nc(N[C@H]4CCN(c5ccnc(C(F)(F)F)c5)C[C@H]4F)nc23)c(F)c1F]

(cis, rac)-N-(3-Fluoropiperidin-4-yl)-8-(2,3,4-trifluorophenyl)-[1,2,4]triazolo[1,5-a]pyridin-2-amine (example 238f) was reacted with 4-iodo-2-(trifluoromethyl)pyridine in analogy to example 242 affording the title compound was obtained as an off white foam (yield: 33%). MS ISP (m/e): 511.1 [(M+H)+].

$^1$H NMR ($CDCl_3$, 400 MHz): δ (ppm)=8.36 (d, 2H), 7.60-7.51 (m, 2H), 7.14-7.05 (m, 2H), 6.94 (t, 1H), 6.80 (dd, 1H), 5.04 (d, 1H), 4.88 (d, 1H), 4.31 (tt, 1H), 4.17-4.02 (m, 2H), 3.27 (dd, 1H), 3.14 (td, 1H), 2.16-2.09 (m, 1H), 1.96 (qd, 1H).

Example 279

8-(2-Chloro-4-fluorophenyl)-N-(4-methyl-1-(2-(trifluoromethyl)pyridin-4-yl)piperidin-4-yl)-[1,2,4]triazolo[1,5-a]pyridin-2-amine

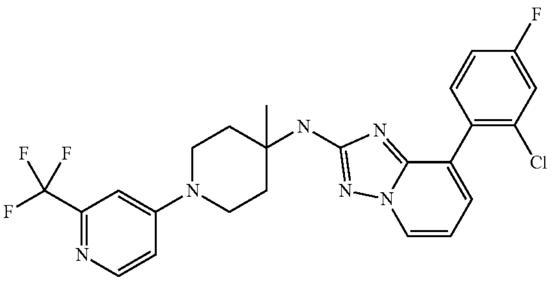 [SMILES: CC1(Nc2nc3c(-c4ccc(F)cc4Cl)cccn3n2)CCN(c2ccnc(C(F)(F)F)c2)CC1]

Prepared in analogy to example 234, employing 4-(8-(2-chloro-4-fluorophenyl)-[1,2,4]triazolo[1,5-a]pyridin-2-ylamino)-1-(2-(trifluoromethyl)pyridin-4-yl)piperidine-4-carbonitrile (100 mg, 0.19 mmol) instead of 4-(8-(3,4-difluorophenyl)-[1,2,4]triazolo[1,5-a]pyridin-2-ylamino)-1-(6-methylpyrimidin-4-yl)piperidine-4-carbonitrile.

The title compound was obtained as a white foam (25 mg, 26%).

MS ISP (m/e): 505.2 [(M+H)+].

Example 280

8-(2-Chloro-4-fluorophenyl)-N-(4-phenyl-1-(2-(trifluoromethyl)pyridin-4-yl)piperidin-4-yl)-[1,2,4]triazolo[1,5-a]pyridin-2-amine

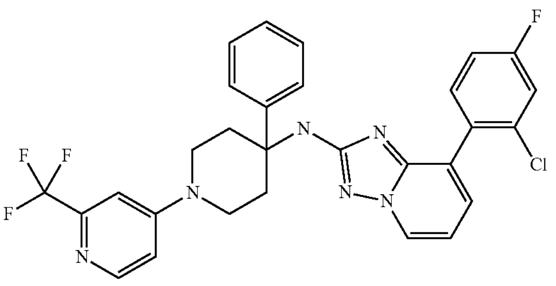 [SMILES: Fc1ccc(-c2cccn3nc(NC4(c5ccccc5)CCN(c5ccnc(C(F)(F)F)c5)CC4)nc23)c(Cl)c1]

Prepared in analogy to example 279, employing phenylmagnesium bromide (1 M in THF, 0.582 mL, 0.582 mmol) instead of methylmagnesiumbromide.

The title compound was obtained as a white foam (19 mg, 17%).

MS ISP (m/e): 567.2 [(M+H)+].

Example 281

N-(1-(3-Methyl-1,2,4-thiadiazol-5-yl)piperidin-4-yl)-8-(4-(trifluoromethyl)cyclohex-1-enyl)-[1,2,4]triazolo[1,5-a]pyridin-2-amine

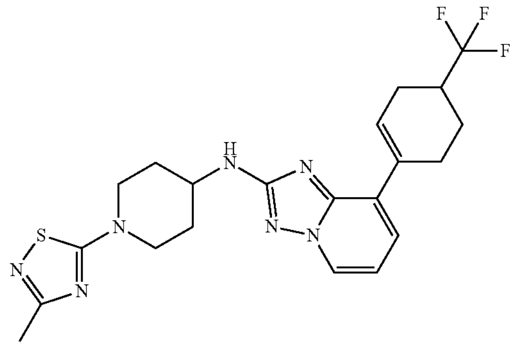 [SMILES: Cc1nsc(N2CCC(Nc3nc4c(C5=CCC(C(F)(F)F)CC5)cccn4n3)CC2)n1]

1-(2-Aminopyridin-3-yl)-4-(trifluoromethyl)cyclohexanol and 3-(4-trifluoromethyl-cyclohex-1-enyl)-pyridin-2-ylamine Prepared in analogy to example 262 step a-b), starting from N-(pyridin-2-yl)pivalamide and 4-(trifluoromethyl)cyclohexanone. 3-(4-Trifluoromethyl-cyclohex-1-enyl)-pyridin-2-ylamine was obtained after column chromatography on silica gel using a gradient from $CH_2Cl_2$ to $CH_2Cl_2$/MeOH 19:1 (v/v) as eluent as a white solid (yield: 26% over 2 steps). MS ISP (m/e): 243.3 (100) [(M+H)+], 226.3 (14).

1-(2-Aminopyridin-3-yl)-4-(trifluoromethyl)cyclohexanol eluted second as a white solid (yield: 15% over 2 steps). MS ISP (m/e): 261.1 (100) [(M+H)+], 243.3 (52).

b) 8-(4-(Trifluoromethyl)cyclohex-1-enyl)-[1,2,4]triazolo[1,5-a]pyridin-2-amine Prepared in analogy to example 1e-f), starting from 3-(4-trifluoromethyl-cyclohex-1-enyl)-pyridin-2-ylamine. The title compound was obtained as a white solid (yield: 84% over 2 steps) after column chromatography on silica gel using ethyl acetate as eluent.

MS ISP (m/e): 283.1 (100) [(M+H)+].

c) N-(1-(3-Methyl-1,2,4-thiadiazol-5-yl) piperidin-4-yl)-8-(4-trifluoromethyl)cyclohex-1-enyl)-[1,2,4]triazolo[1,5-a]pyridin-2-amine Prepared in analogy to example 219f), starting from 8-(4-(trifluoromethyl)cyclohex-1-enyl)-[1,2,4]triazolo[1,5-a]pyridin-2-amine and 1-(3-methyl-1,2,4-thiadiazol-5-yl)piperidin-4-one. As a reducing agent 4 equivalent sodium borohydride in ethanol was used at 70° C. over night. The title compound was obtained after column chromatography on silica gel using ethyl acetate as eluent as a light yellow solid (yield: 44%).

MS ISP (m/e): 464.2 (100) [(M+H)+], 243.2 (26).

$^1$H NMR (DMSO-$D_6$, 300 MHz): δ (ppm)=8.51 (d, 1H), 7.38 (d, 2H), 7.29 (br s, 1H), 6.88 (t, 1H), 6.79 (d, 1H), 3.78

(m, 3H), 3.33 (m, 2H), 2.79-2.45 (m, 4H), 2.31 (m, 1H), 2.28 (s, 3H), 2.20-1.99 (m, 3H), 1.59 (m, 3H).

Example 282

1-(2-(1-(3-Methyl-1,2,4-thiadiazol-5-yl)piperidin-4-ylamino)-[1,2,4]triazolo[1,5-a]pyridin-8-yl)-4-(trifluoromethyl)cyclohexanol

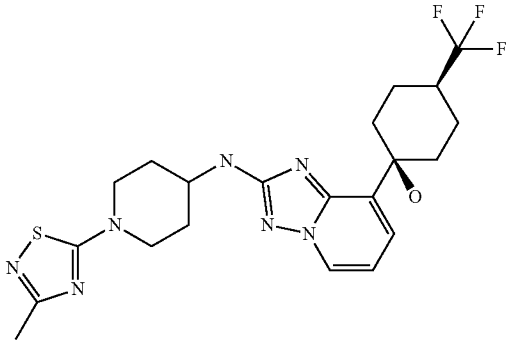 [SMILES: Cc1nsc(N2CCC(Nc3nc4c([C@]5(O)CC[C@@H](C(F)(F)F)CC5)cccn4n3)CC2)n1]

a) 1-(2-Amino-[1,2,4]triazolo[1,5-a]pyridin-8-yl)-4-(trifluoromethyl)cyclohexanol Prepared in analogy to example 1e-f), starting from 1-(2-aminopyridin-3-yl)-4-(trifluoromethyl)cyclohexanol. The title compound was obtained as a white solid (yield: 81% over 2 steps) after column chromatography on silica gel using ethyl acetate as eluent.

MS ISP (m/e): 301.2 (40) [$(M+H)^+$], 283.1 (100).

b) 1-(2-(1-(3-Methyl-1,2,4-thiadiazol-5-yl)piperidin-4-ylamino)-[1,2,4]-triazolo[1,5-a]pyridin-8-yl)-4-(trifluoromethyl)cyclohexanol Prepared in analogy to example 219f), starting from 1-(2-amino-[1,2,4]triazolo[1,5-a]pyridin-8-yl)-4-(trifluoromethyl)cyclohexanol and 1-(3-methyl-1,2,4-thiadiazol-5-yl) piperidin-4-one. As a reducing agent 4 equivalent sodium borohydride in ethanol was used at 70° C. over night. The title compound was obtained after column chromatography on silica gel using ethyl acetate as eluent as a white solid (yield: 46%).

MS ISP (m/e): 482.3 (100) [$(M+H)^+$], 464.2 (29), 243.2 (37).

$^1$H NMR (DMSO-$D_6$, 300 MHz): δ (ppm)=8.51 (d, 1H), 7.56 (d, 2H), 6.91 (t, 1H), 6.68 (d, 1H), 5.28 (s, 1H), 3.77 (m, 3H), 3.33 (m, 2H), 2.68-2.42 (m, 4H), 2.28 (s, 3H), 2.05 (m, 2H), 1.75 (m, 4H), 1.61 (m, 3H).

Example 283

8-(Fluoro(4-fluorophenyl)methyl)-N-(1-(3-methyl-1,2,4-thiadiazol-5-yl)piperidin-4-yl)-[1,2,4]triazolo[1,5-a]pyridin-2-amine

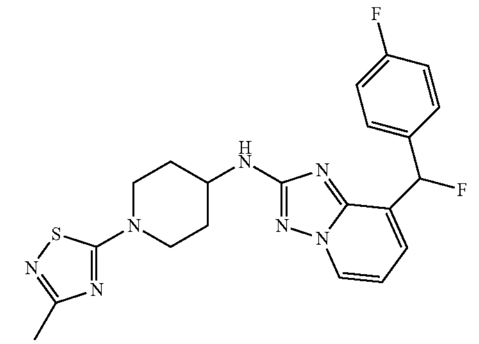 [SMILES: Cc1nsc(N2CCC(Nc3nc4c(C(F)c5ccc(F)cc5)cccn4n3)CC2)n1]

To a solution of (4-fluorophenyl)(2-(1-(3-methyl-1,2,4-thiadiazol-5-yl)piperidin-4-ylamino)-[1,2,4]triazolo[1,5-a] pyridin-8-yl)methanol (72 mg, 164 μmol) in dichloromethane (0.82 mL) was added under an atmosphere of nitrogen diethylaminosulfurtrifluoride (DAST) (58.7 mg, 48.1 μL, 328 μmol). The reaction turned yellow and was stirred at room temperature for 3 hours. Water was added and the reaction was extracted twice with dichloromethane. The combined organic layers were washed with saturated aqueous sodium hydrogen carbonate solution, dried over sodium sulfate, filtered and the solvent was removed under reduced pressure. The title compound was obtained as a white solid (20.1 mg, 27%) after purification by column chromatography on silica gel using ethyl acetate as eluent.

MS ISP (m/e): 442.4 (44) [$(M+H)^+$], 422.1 (100). $^1$H NMR (DMSO-$D_6$, 300 MHz): δ (ppm)=8.29 (d, 1H), 7.49-7.43 (m, 3H), 7.06 (t, 2H), 6.90 (d, J=44.7 Hz, 1H), 6.85 (t, 1H), 4.49 (d, 1H), 3.89 (m, 3H), 3.35 (br t, 2H), 2.42 (s, 3H), 2.22 (br d, 2H), 1.65 (m, 2H).

The invention claimed is:

1. A compound of formula I

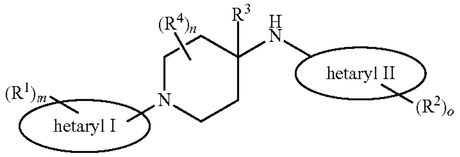

I wherein hetaryl I is 1,2,4-thiadiazole;

hetaryl II is a [1,2,4]triazolo1,5-a]pyridine ring or a 5,6,7,8-tetrahydro-[1,2,4]triazolo[1,5-a]pyridine ring;

$R^1$ is lower alkyl, lower alkoxy, lower alkyl substituted by halogen, or halogen;

$R^2$ is halogen, lower alkyl, lower alkoxy, hydroxy, lower alkyl substituted by halogen, lower alkyl substituted by hydroxy or benzo[1,3]dioxolyl, or is —$(CHR)_p$-phenyl, optionally substituted by halogen, lower alkyl, lower alkoxy, $S(O)_2$-lower alkyl, cyano, nitro, lower alkoxy substituted by halogen, dimethylamino, —$(CH_2)$p-NHC(O)O-lower alkyl, or lower alkyl substituted by halogen, R is hydrogen, halogen, hydroxy or lower alkoxy, or is cycloalkenyl or cycloalkyl, each of which is optionally substituted by hydroxy or lower alkyl substituted by halogen, or is a five or six membered heteroaryl group, containing 1 to 3 heteroatoms, selected from O, S and N, which is optionally substituted by halogen, lower alkyl, lower alkoxy or dimethylamino, or is O-phenyl, optionally substituted by halogen, or is heterocycloalkyl, optionally substituted by halogen, hydroxy, lower alkyl substituted by halogen or C(O)O-lower alkyl;

$R^3$ is hydrogen, lower alkyl, cyano or phenyl;

$R^4$ is lower alkoxy, lower alkyl or halogen;

p is 0 or 1;

n is 0, 1 or 2; when n is 2 then each $R^4$ is the same or different;

m is 0, 1 or 2; when m is 2 then each $R^1$ is the same or different;

o is 0, 1, 2 or 3, when o is 2 or 3 then each $R^2$ is the same or different;

or a pharmaceutically active acid addition salt thereof.

2. The compound of claim 1, selected from the group consisting of

[8-(4-fluoro-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(4-fluoro-phenyl)-[1,2,4]triazolo[1,5-a]pyridin-2-yl]-[1-(3-methyl-[1,2,4]thiadiazol-5-yl)-piperidin-4-yl]-amine;

[5-(4-fluoro-phenyl)-[1,2,4]triazolo[1,5-a]pyridin-2-yl]-[1-(3-methyl-[1,2,4]thiadiazol-5-yl)-piperidin-4-yl]-amine;

[8-(2-chloro-4-fluoro-phenyl)-[1,2,4]triazolo[1,5-a]pyridin-2-yl]-[1-(3-methyl-[1,2,4]thiadiazol-5-yl)-piperidin-4-yl]-amine;

[8-(2,4-difluoro-phenyl)-[1,2,4]triazolo[1,5-a]pyridin-2-yl]-[1-(3-methyl-[1,2,4]thiadiazol-5-yl)-piperidin-4-yl]-amine;

[8-(4-chloro-phenyl)-[1,2,4]triazolo[1,5-a]pyridin-2-yl]-[1-(3-methyl-[1,2,4]thiadiazol-5-yl)-piperidin-4-yl]-amine;

[8-(3-chloro-4-fluoro-phenyl)-6-methyl-[1,2,4]triazolo[1,5-a]pyridin-2-yl]-[1-(3-methyl-[1,2,4]thiadiazol-5-yl)-piperidin-4-yl]-amine;

[8-(2-chloro-4-fluoro-phenyl)-6-methyl-[1,2,4]triazolo[1,5-a]pyridin-2-yl]-[1-(3-methyl-[1,2,4]thiadiazol-5-yl)-piperidin-4-yl]-amine; and

[8-(3,4-difluoro-phenyl)-6-methyl-[1,2,4]triazolo[1,5-a]pyridin-2-yl]-[1-(3-methyl-[1,2,4]thiadiazol-5-yl)-piperidin-4-yl]-amine.

3. The compound of claim 1, selected from the group consisting of

[8-(3,4-difluoro-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(4-fluoro-2-methoxy-phenyl)-[1,2,4]triazolo[1,5-a]pyridin-2-yl]-[1-(3-methyl-[1,2,4]thiadiazol-5-yl)-piperidin-4-yl]-amine;

[8-(4-fluoro-3-trifluoromethyl-phenyl)-[1,2,4]triazolo[1,5-a]pyridin-2-yl]-[1-(3-methyl-[1,2,4]thiadiazol-5-yl)-piperidin-4-yl]-amine;

[8-(2,4-difluoro-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(4-fluoro-3-trifluoromethyl-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(2-fluoro-4-methanesulfonyl-phenyl)-[1,2,4]triazolo[1,5-a]pyridin-2-yl]-[1-(3-methyl-[1,2,4]thiadiazol-5-yl)-piperidin-4-yl]-amine;

[8-(3,4-difluoro-phenyl)-6-fluoro-[1,2,4]triazolo[1,5-a]pyridin-2-yl]-[1-(3-methyl-[1,2,4]thiadiazol-5-yl)-piperidin-4-yl]-amine;

[8-(2,4-dichloro-phenyl)-[1,2,4]triazolo[1,5-a]pyridin-2-yl]-[1-(3-methyl-[1,2,4]thiadiazol-5-yl)-piperidin-4-yl]-amine;

[8-(2-fluoro-4-trifluoromethyl-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine; and

[1-(3-methyl-[1,2,4]thiadiazol-5-yl)-piperidin-4-yl]-[8-(2,3,4-trifluoro-phenyl)-[1,2,4]triazolo[1,5-a]pyridin-2-yl]-amine.

4. The compound of claim 1, selected from the group consisting of

[8-(3,4-difluoro-phenyl)-6-fluoro-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[8-(3,4-difluoro-phenyl)-5-trifluoromethyl-[1,2,4]triazolo[1,5-a]pyridin-2-yl]-[1-(3-methyl-[1,2,4]thiadiazol-5-yl)-piperidin-4-yl]-amine;

[8-(6-methoxy-pyridin-3-yl)-[1,2,4]triazolo[1,5-a]pyridin-2-yl]-[1-(3-methyl-[1,2,4]thiadiazol-5-yl)-piperidin-4-yl]-amine;

[8-(3-chloro-4-fluoro-phenyl)-6-fluoro-[1,2,4]triazolo[1,5-a]pyridin-2-yl]-[1-(3-methyl-[1,2,4]thiadiazol-5-yl)-piperidin-4-yl]-amine;

[8-(6-fluoro-pyridin-3-yl)-[1,2,4]triazolo[1,5-a]pyridin-2-yl]-[1-(3-methyl-[1,2,4]thiadiazol-5-yl)-piperidin-4-yl]-amine;

[8-(2-fluoro-pyridin-3-yl)-[1,2,4]triazolo[1,5-a]pyridin-2-yl]-[1-(3-methyl-[1,2,4]thiadiazol-5-yl)-piperidin-4-yl]-amine;

[1-(3-methyl-[1,2,4]thiadiazol-5-yl)-piperidin-4-yl]-[8-(3,4,5-trifluoro-phenyl)-[1,2,4]triazolo[1,5-a]pyridin-2-yl]-amine;

[1-(3-methyl-[1,2,4]thiadiazol-5-yl)-piperidin-4-yl]-[8-(2,3,4-trifluoro-phenyl)-5,6,7,8-tetrahydro-[1,2,4]triazolo[1,5-a]pyridin-2-yl]-amine;

[8-(3,4-difluoro-phenyl)-6-trifluoromethyl-[1,2,4]triazolo[1,5-a]pyridin-2-yl]-[1-(3-methyl-[1,2,4]thiadiazol-5-yl)-piperidin-4-yl]-amine; and

[8-(3,4-difluoro-phenyl)-5-trifluoromethyl-5,6,7,8-tetrahydro-[1,2,4]triazolo[1,5-a]pyridin-2-yl]-[1-(3-methyl-[1,2,4]thiadiazol-5-yl)-piperidin-4-yl]-amine.

5. The compound of claim 1, selected from the group consisting of

[8-(3,4-difluoro-phenyl)-6-trifluoromethyl-5,6,7,8-tetrahydro-[1,2,4]triazolo[1,5-a]pyridin-2-yl]-[1-(3-methyl-[1,2,4]thiadiazol-5-yl)-piperidin-4-yl]-amine;

[1-(3-methyl-[1,2,4]thiadiazol-5-yl)-piperidin-4-yl]-(8-phenoxy-[1,2,4]triazolo[1,5-a]pyridin-2-yl)-amine;

N-(1-(3-methyl-1,2,4-thiadiazol-5-yl)piperidin-4-yl)-8-(3-(trifluoromethoxy)phenyl)-[1,2,4]triazolo[1,5-a]pyridin-2-amine;

8-(2,3-dichlorophenyl)-N-(1-(3-methyl-1,2,4-thiadiazol-5-yl)piperidin-4-yl)-[1,2,4]triazolo[1,5-a]pyridin-2-amine;

8-(3,4-dichlorophenyl)-N-(1-(3-methyl-1,2,4-thiadiazol-5-yl)piperidin-4-yl)-[1,2,4]triazolo[1,5-a]pyridin-2-amine;

8-(3-chlorophenyl)-N-(1-(3-methyl-1,2,4-thiadiazol-5-yl)piperidin-4-yl)-[1,2,4]triazolo[1,5-a]pyridin-2-amine;

[8-(5-dimethylamino-2-nitro-phenyl)-[1,2,4]triazolo[1,5-a]pyridin-2-yl]-[1-(3-methyl-[1,2,4]thiadiazol-5-yl)-piperidin-4-yl]-amine;

[8-(3,5-bis-trifluoromethyl-phenyl)-[1,2,4]triazolo[1,5-a]pyridin-2-yl]-[1-(3-methyl-[1,2,4]thiadiazol-5-yl)-piperidin-4-yl]-amine; and N-(1-(3-methyl-1,2,4-thiadiazol-5-yl)piperidin-4-yl)-8-(4-(trifluoromethoxy)phenyl)-[1,2,4]triazolo[1,5-a]pyridin-2-amine.

6. The compound of claim 1, selected from the group consisting of

[8-(3-methoxy-phenyl)-[1,2,4]triazolo[1,5-a]pyridin-2-yl]-[1-(3-methyl-[1,2,4]thiadiazol-5-yl)-piperidin-4-yl]-amine;

[8-(3-chloro-phenoxy)-[1,2,4]triazolo[1,5-a]pyridin-2-yl]-[1-(3-methyl-[1,2,4]thiadiazol-5-yl)-piperidin-4-yl]-amine;

[8-(5-chloro-2-fluoro-phenyl)-[1,2,4]triazolo[1,5-a]pyridin-2-yl]-[1-(3-methyl-[1,2,4]thiadiazol-5-yl)-piperidin-4-yl]-amine;

[8-(2-chloro-phenyl)-[1,2,4]triazolo[1,5-a]pyridin-2-yl]-[1-(3-methyl-[1,2,4]thiadiazol-5-yl)-piperidin-4-yl]-amine;

[8-(3-dimethylamino-phenyl)-[1,2,4]triazolo[1,5-a]pyridin-2-yl]-[1-(3-methyl-[1,2,4]thiadiazol-5-yl)-piperidin-4-yl]-amine;

[8-(2-fluoro-pyridin-4-yl)-[1,2,4]triazolo[1,5-a]pyridin-2-yl]-[1-(3-methyl-[1,2,4]thiadiazol-5-yl)-piperidin-4-yl]-amine;

(8-benzo[1,3]dioxol-5-yl-[1,2,4]triazolo[1,5-a]pyridin-2-yl)-[1-(3-methyl-[1,2,4]thiadiazol-5-yl)-piperidin-4-yl]-amine;

[8-(2-chloro-5-trifluoromethyl-phenyl)-[1,2,4]triazolo[1,5-a]pyridin-2-yl]-[1-(3-methyl-[1,2,4]thiadiazol-5-yl)-piperidin-4-yl]-amine;

[8-(3,5-bis-trifluoromethyl-phenyl)-5,6,7,8-tetrahydro-[1,2,4]triazolo[1,5-a]pyridin-2-yl]-[1-(3-methyl-[1,2,4]thiadiazol-5-yl)-piperidin-4-yl]-amine; and

[8-(4-dimethylamino-phenyl)-[1,2,4]triazolo[1,5-a]pyridin-2-yl]-[1-(3-methyl-[1,2,4]thiadiazol-5-yl)-piperidin-4-yl]-amine.

7. The compound of claim 1, selected from the group consisting of (cis, rac)-N-(3-fluoro-1-(3-methyl-1,2,4-thiadiazol-5-yl)piperidin-4-yl)-8-(2,3,4-trifluorophenyl)-[1,2,4]triazolo[1,5-a]pyridin-2-amine;

(3S,4R)— and (3R,4S)—N-(3-fluoro-1-(3-methyl-1,2,4-thiadiazol-5-yl)piperidin-4-yl)-8-(2,3,4-trifluorophenyl)-[1,2,4]triazolo[1,5-a]pyridin-2-amine;

(cis, rac)-[3-fluoro-1-(3-methyl-[1,2,4]thiadiazol-5-yl)-piperidin-4-yl]-[8-(4-fluoro-phenyl)-[1,2,4]triazolo[1,5-a]pyridin-2-yl]-amine;

(cis, rac)-[3,4-difluoro-1-(3-methyl-[1,2,4]thiadiazol-5-yl)-piperidin-4-yl]-[8-(4-fluoro-phenyl)-[1,2,4]triazolo[1,5-a]pyridin-2-yl]-amine;

N-(3,3-difluoro-1-(3-methyl-1,2,4-thiadiazol-5-yl)piperidin-4-yl)-8-(2,3,4-trifluorophenyl)-[1,2,4]triazolo[1,5-a]pyridin-2-amine;

4-chloro-3-(2-(1-(3-methyl-1,2,4-thiadiazol-5-yl)piperidin-4-ylamino)-[1,2,4]triazolo[1,5-a]pyridin-8-yl)benzonitrile;

(4-fluorophenyl)(2-(1-(3-methyl-1,2,4-thiadiazol-5-yl)piperidin-4-ylamino)-[1,2,4]triazolo[1,5-a]pyridin-8-yl)methanol; and N-((3S,5S)-3,5-dimethyl-1-(3-methyl-1,2,4-thiadiazol-5-yl)piperidin-4-yl)-8-(2,3,4-trifluorophenyl)-[1,2,4]triazolo[1,5-a]pyridin-2-amine.

8. A pharmaceutical composition comprising a compound of formula I

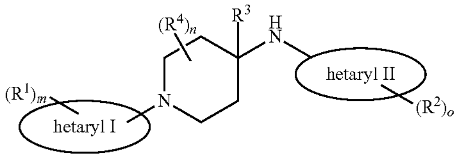

I wherein hetaryl I is 1,2,4-thiadiazole;

hetaryl II is a [1,2,4]triazolo1,5-a]pyridine ring or a 5,6,7,8-tetrahydro-[1,2,4]triazolo[1,5-a]pyridine ring;

$R^1$ is lower alkyl, lower alkoxy, lower alkyl substituted by halogen, or halogen;

$R^2$ is halogen, lower alkyl, lower alkoxy, hydroxy, lower alkyl substituted by halogen, lower alkyl substituted by hydroxy or benzo[1,3]dioxolyl, or is —$(CHR)_p$-phenyl, optionally substituted by halogen, lower alkyl, lower alkoxy, $S(O)_2$-lower alkyl, cyano, nitro, lower alkoxy substituted by halogen, dimethylamino, —$(CH_2)$p-NHC(O)O-lower alkyl, or lower alkyl substituted by halogen, R is hydrogen, halogen, hydroxy or lower alkoxy, or is cycloalkenyl or cycloalkyl, each of which is optionally substituted by hydroxy or lower alkyl substituted by halogen, or is a five or six membered heteroaryl group, containing 1 to 3 heteroatoms, selected from O, S and N, which is optionally substituted by halogen, lower alkyl, lower alkoxy or dimethylamino, or is O-phenyl, optionally substituted by halogen, or is heterocycloalkyl, optionally substituted by halogen, hydroxy, lower alkyl substituted by halogen or C(O)O-lower alkyl;

$R^3$ is hydrogen, lower alkyl, cyano or phenyl;

$R^4$ is lower alkoxy, lower alkyl or halogen;

p is 0 or 1;

n is 0, 1 or 2; when n is 2 then each $R^4$ is the same or different;

m is 0, 1 or 2; when m is 2 then each $R^1$ is the same or different;

o is 0, 1, 2 or 3, when o is 2 or 3 then each $R^2$ is the same or different;

or a pharmaceutically active acid addition salt thereof and a pharmaceutically acceptable carrier.

* * * * *